US012161680B2

(12) United States Patent
Norman et al.

(10) Patent No.: US 12,161,680 B2
(45) Date of Patent: Dec. 10, 2024

(54) METHODS OF DECREASING DYSBIOSIS AND RESTORING A MICROBIOME

(71) Applicant: Vedanta Biosciences, Inc., Cambridge, MA (US)

(72) Inventors: Jason Norman, North Weymouth, MA (US); Bernat Olle, Cambridge, MA (US); Bruce Roberts, Framingham, MA (US); Rajita Menon, Brighton, MA (US)

(73) Assignee: Vedanta Biosciences, Inc., Cambridge, MA (US)

( * ) Notice: Subject to any disclaimer, the term of this patent is extended or adjusted under 35 U.S.C. 154(b) by 421 days.

(21) Appl. No.: 17/268,781

(22) PCT Filed: Aug. 16, 2019

(86) PCT No.: PCT/US2019/046926
§ 371 (c)(1),
(2) Date: Feb. 16, 2021

(87) PCT Pub. No.: WO2020/037271
PCT Pub. Date: Feb. 20, 2020

(65) Prior Publication Data
US 2022/0143108 A1 May 12, 2022

Related U.S. Application Data

(60) Provisional application No. 62/829,959, filed on Apr. 5, 2019, provisional application No. 62/829,513, filed on Apr. 4, 2019, provisional application No. 62/815,395, filed on Mar. 8, 2019, provisional application No. 62/724,185, filed on Aug. 29, 2018, provisional application No. 62/765,165, filed on Aug. 17, 2018.

(51) Int. Cl.
*A61K 35/742* (2015.01)
(52) U.S. Cl.
CPC ................... *A61K 35/742* (2013.01)
(58) Field of Classification Search
None
See application file for complete search history.

(56) References Cited

U.S. PATENT DOCUMENTS

| | | | |
|---|---|---|---|
| 6,635,260 B1 | 10/2003 | Gerding | |
| 8,460,648 B2 | 6/2013 | Borody | |
| 9,386,793 B2 | 7/2016 | Blaser et al. | |
| 9,642,881 B2 | 5/2017 | Honda et al. | |
| 9,649,345 B2 | 5/2017 | Honda et al. | |
| 9,999,641 B2 | 6/2018 | Schneider et al. | |
| 10,064,904 B2 | 9/2018 | Schneider et al. | |
| 10,350,250 B2 | 7/2019 | Schneider et al. | |
| 10,456,431 B2 | 10/2019 | Schneider et al. | |
| 10,555,980 B2 | 2/2020 | Schneider et al. | |
| 11,701,396 B2 | 7/2023 | Schneider et al. | |
| 2004/0028689 A1* | 2/2004 | Borody | A61K 36/062 424/184.1 |
| 2009/0269321 A1 | 10/2009 | Sashihara et al. | |
| 2010/0074872 A1 | 3/2010 | Blaser et al. | |
| 2013/0045274 A1* | 2/2013 | Hlavka | A61K 35/74 424/93.4 |
| 2013/0195804 A1 | 8/2013 | Borody | |
| 2014/0199281 A1 | 7/2014 | Henn et al. | |
| 2014/0328803 A1 | 11/2014 | McKenzie et al. | |
| 2014/0341921 A1 | 11/2014 | Honda et al. | |
| 2015/0037476 A1 | 2/2015 | Dhingra et al. | |
| 2015/0079209 A1 | 3/2015 | Kameyama et al. | |
| 2016/0022745 A1 | 1/2016 | Wang | |
| 2016/0022746 A1 | 1/2016 | Lawley et al. | |
| 2016/0040215 A1 | 2/2016 | Henn et al. | |
| 2016/0113971 A1 | 4/2016 | Kaplan et al. | |
| 2016/0193256 A1 | 7/2016 | Honda et al. | |
| 2016/0193257 A1 | 7/2016 | Honda et al. | |
| 2016/0228476 A1 | 8/2016 | Cutcliffe et al. | |
| 2017/0143772 A1 | 5/2017 | Mulder et al. | |
| 2017/0209502 A1 | 7/2017 | Honda et al. | |
| 2017/0216378 A1 | 8/2017 | Honda et al. | |
| 2017/0290889 A1 | 10/2017 | Loke et al. | |
| 2017/0354697 A1 | 12/2017 | Schneider et al. | |

(Continued)

FOREIGN PATENT DOCUMENTS

| | | |
|---|---|---|
| EP | 3052111 B1 | 12/2020 |
| JP | 2015-500792 A | 1/2015 |

(Continued)

OTHER PUBLICATIONS

Stackebrandt et al., "Authors need to be prudent when assigning names to microbial isolates", Antonie van Leeuwenhoek, vol. 115, pp. 1-5 (Year: 2022).*
EP 17814024.0, Feb. 3, 2020, Extended European Search Report.
PCT/US2017/037498, Aug. 30, 2017, Invitation to Pay Additional Fees.
PCT/US2017/037498, Oct. 27, 2017, International Search Report and Written Opinion.
PCT/US2017/037498, Dec. 18, 2018, International Preliminary Report on Patentability.

(Continued)

*Primary Examiner* — Michelle F. Paguio Frising

(74) *Attorney, Agent, or Firm* — Wolf, Greenfield & Sacks, P.C.

(57) ABSTRACT

Provided herein are methods for decreasing dysbiosis, restoring the microbiome, and/or increasing recovery of a healthy microbiome (e.g. following a dysbiosis inducing event), by administering pharmaceutical compositions to a subject. Also provided are methods for protecting the microbiome of a subject and/or colonizing the microbiome of a subject by administering pharmaceutical compositions to the subject.

20 Claims, 210 Drawing Sheets

Specification includes a Sequence Listing.

(56) References Cited

U.S. PATENT DOCUMENTS

| | | | |
|---|---|---|---|
| 2018/0169153 | A1 | 6/2018 | Berry et al. |
| 2018/0169157 | A1 | 6/2018 | Schneider et al. |
| 2018/0221286 | A1 | 8/2018 | Kabadi et al. |
| 2018/0264056 | A1 | 9/2018 | Schneider et al. |
| 2019/0030098 | A1 | 1/2019 | Schneider et al. |
| 2019/0134106 | A1 | 5/2019 | Borody |
| 2019/0275090 | A1 | 9/2019 | Schneider et al. |
| 2020/0206284 | A1 | 7/2020 | Schneider et al. |
| 2024/0100103 | A1 | 3/2024 | Olle et al. |
| 2024/0123000 | A1 | 4/2024 | Schneider et al. |

FOREIGN PATENT DOCUMENTS

| | | | | |
|---|---|---|---|---|
| JP | 2016-509002 | A | 3/2016 | |
| WO | WO 2002/007741 | A1 | 1/2002 | |
| WO | WO 2006/050479 | A1 | 5/2006 | |
| WO | WO-2011033310 | A1 * | 3/2011 | ............ A61K 35/38 |
| WO | WO 2011/152566 | A1 | 12/2011 | |
| WO | WO 2013/037067 | A1 | 3/2013 | |
| WO | WO 2013/037068 | A1 | 3/2013 | |
| WO | WO 2013/080561 | A1 | 6/2013 | |
| WO | WO 2013/182038 | A1 | 12/2013 | |
| WO | WO 2014/082050 | A1 | 5/2014 | |
| WO | WO 2014/121298 | A1 | 8/2014 | |
| WO | WO 2014/121301 | A1 | 8/2014 | |
| WO | WO 2014/121302 | A1 | 8/2014 | |
| WO | WO 2014/145958 | A2 | 9/2014 | |
| WO | WO 2014/153194 | A2 | 9/2014 | |
| WO | WO 2015/006355 | A2 | 1/2015 | |
| WO | WO 2015/051323 | A1 | 4/2015 | |
| WO | WO 2015/077794 | A1 | 5/2015 | |
| WO | WO 2015/095241 | A2 | 6/2015 | |
| WO | WO 2015/156419 | A1 | 10/2015 | |
| WO | WO 2015/164555 | A1 | 10/2015 | |
| WO | WO 2015/179437 | A1 | 11/2015 | |
| WO | WO 2016/086161 | A1 | 6/2016 | |
| WO | WO 2016/086205 | A2 | 6/2016 | |
| WO | WO 2016/086206 | A1 | 6/2016 | |
| WO | WO 2016/086208 | A1 | 6/2016 | |
| WO | WO 2016/086209 | A1 | 6/2016 | |
| WO | WO 2016/086210 | A1 | 6/2016 | |
| WO | WO 2016/185469 | A1 | 11/2016 | |
| WO | WO 2016/201053 | A1 | 12/2016 | |
| WO | WO 2016/203217 | A1 | 12/2016 | |
| WO | WO 2016/203218 | A1 | 12/2016 | |
| WO | WO 2016/203220 | A1 | 12/2016 | |
| WO | WO 2016/203221 | A1 | 12/2016 | |
| WO | WO 2016/203223 | A1 | 12/2016 | |
| WO | WO 2016/209806 | A1 | 12/2016 | |
| WO | WO 2017/008026 | A1 | 1/2017 | |
| WO | WO 2017/035188 | A1 | 3/2017 | |
| WO | WO 2017/075098 | A1 | 5/2017 | |
| WO | WO 2017/085518 | A1 | 5/2017 | |
| WO | WO 2017/085520 | A1 | 5/2017 | |
| WO | WO 2017/089794 | A1 | 6/2017 | |
| WO | WO 2017/089795 | A1 | 6/2017 | |
| WO | WO 2017/091783 | A2 | 6/2017 | |
| WO | WO 2017/148596 | A1 | 9/2017 | |
| WO | WO-2017218680 | A1 * | 12/2017 | ........... A23L 33/135 |
| WO | WO 2018/005606 | A1 | 1/2018 | |
| WO | 2018/080477 | A1 | 5/2018 | |
| WO | WO 2019/227085 | A1 | 11/2019 | |
| WO | WO 2020/037271 | A1 | 2/2020 | |

OTHER PUBLICATIONS

PCT/US2019/046926, Dec. 2, 2019, International Search Report and Written Opinion.

PCT/US2019/046926, Mar. 4, 2021, International Preliminary Report on Patentability.

Alang et al., Weight gain after fecal microbiota transplantation. Open Forum Infect Dis. Feb. 4, 2015;2(1):ofv004. doi: 10.1093/ofid/ofv004. eCollection Jan. 2015.

Apisarnthanarak et al., Adjunctive intracolonic vancomycin for severe *Clostridium difficile* colitis: case series and review of the literature. Clin Infect Dis. Sep. 15, 2002;35(6):690-6. Epub Aug. 26, 2002.

Blaser, The microbiome revolution. J Clin Invest. Oct. 2014;124(10):4162-5. doi: 10.1172/JCI78366. Epub Oct. 1, 2014.

Bobilev et al., 1953. VE303, a Rationally Designed Bacterial Consortium for Prevention of Recurrent Clostridioides difficile (C. Difficile) infection (rCDI), Stably Restores the Gut Microbiota After Vancomycin (vanco)-Induced Dysbiosis in Adult Healthy Volunteers (HV). Open Forum Infect Dis. Oct. 2019; 6(Suppl 2): S60. EPub Oct. 23, 2019. doi: 10.1093/ofid/ofz359.130.

Borody et al., Therapeutic faecal microbiota transplantation: current status and future developments. Curr Opin Gastroenterol.Jan. 2014;30(1):97-105. doi: 10.1097/MOG.0000000000000027.

Bucci et al., MDSINE: Microbial Dynamical Systems INference Engine for microbiome time-series analyses. Genome Biol. Jun. 3, 2016;17(1):121. doi: 10.1186/s13059-016-0980-6.

Buffie et al., Precision microbiome reconstitution restores bile acid mediated resistance to *Clostridium difficile*. Nature. Jan. 8, 2015;517(7533):205-8. doi: 10.1038/nature13828. Epub Oct. 22, 2014.

Burns et al., Donor Recruitment and Eligibility for Fecal Microbiota Transplantation: Results From an International Public Stool Bank. Gastro. Apr. 2015;148(4):S96-S97.

Cammarota et al., Randomised clinical trial: faecal microbiota transplantation by colonoscopy vs. vancomycin for the treatment of recurrent *Clostridium difficile* infection. Aliment Pharmacol Ther. May 2015;41(9):835-43. doi: 10.1111/apt.13144. Epub Mar. 1, 2015.

Drancourt et al., 16S ribosomal DNA sequence analysis of a large collection of environmental and clinical unidentifiable bacterial isolates. J Clin Microbiol. Oct. 2000;38(10):3623-30.

Eyre et al., Whole-genome sequencing demonstrates that fidaxomicin is superior to vancomycin for preventing reinfection and relapse of infection with *Clostridium difficile*. J Infect Dis. May 1, 2014;209(9):1446-51. doi:10.1093/infdis/jit598. Epub Nov. 11, 2013.

Genbank Accession No. NR_104687.1. NCBI. Sakamoto. Feb. 3, 2015.

Hooper et al., Interactions between the microbiota and the immune system. Science. Jun. 8, 2012;336(6086):1268-73. doi:10.1126/science.1223490. Epub Jun. 6, 2012.

Hughes et al., Immune activation in irritable bowel syndrome: can neuroimmune interactions explain symptoms? Am J Gastroenterol. Jul. 2013;108(7):1066-74. doi: 10.1038/ajg.2013.120. Epub May 7, 2013.

Kakihana et al., Fecal microbiota transplantation for patients with steroid-resistant acute graft-versus-host disease of the gut. Blood. Oct. 20, 2016;128(16):2083-2088. doi: 10.1182/blood-2016-05-717652. Epub Jul. 26, 2016.

Kassam et al., Fecal microbiota transplantation for *Clostridium difficile* infection: systematic review and meta-analysis. Am J Gastroenterol. Apr. 2013;108(4):500-8. doi: 10.1038/ajg.2013.59. Epub Mar. 19, 2013.

Khoruts et al., Emergence of fecal microbiota transplantation as an approach to repair disrupted microbial gut ecology. Immunol Lett. Dec. 2014;162(2 Pt A):77-81. doi: 10.1016/j.imlet.2014.07.016. Epub Aug. 10, 2014.

Leblanc et al., Bacteria as vitamin suppliers to their host: a gut microbiota perspective. Curr Opin Biotechnol. Apr. 2013;24(2):160-8. doi: 10.1016/j.copbio.2012.08.005. Epub Aug. 30, 2012.

Lessa et al., Burden of *Clostridium difficile* infection in the United States. N Engl J Med. Feb. 26, 2015;372(9):825-34. doi:10.1056/NEJMoa1408913.

Louie et al., Fidaxomicin preserves the intestinal microbiome during and after treatment of *Clostridium difficile* infection (CDI) and reduces both toxin reexpression and recurrence of CDI. Clin Infect Dis. Aug. 2012;55 Suppl 2:S132-42. doi: 10.1093/cid/cis338.

Marvola et al., Enteric polymers as binders and coating materials in multiple-unit site-specific drug delivery systems. Eur J Pharm Sci. Feb. 1999;7(3):259-67.

(56) References Cited

OTHER PUBLICATIONS

Miller, Fidaxomicin (OPT-80) for the treatment of *Clostridium difficile* infection. Expert Opin Pharmacother. Jun. 2010;11(9):1569-78. doi:10.1517/14656566.2010.485614.

Mullane, Fidaxomicin in *Clostridium difficile* infection: latest evidence and clinical guidance. Ther Adv Chronic Dis. Mar. 2014;5(2):69-84. doi: 10.1177/2040622313511285.

Narushima et al., Characterization of the 17 strains of regulatory T cell-inducing human-derived Clostridia. Gut Microbes. May-Jun. 2014;5(3):333-9. doi: 10.4161/gmic.28572. Epub Mar. 18, 2014.

Paramsothy et al., Donor Recruitment for Fecal Microbiota Transplantation. Inflamm Bowel Dis. Jul. 2015;21(7):1600-6. doi: 10.1097/MIB.0000000000000405.

Rossi-Tamisier et al., Cautionary tale of using 16S rRNA gene sequence similarity values in identification of human-associated bacterial species. Int J Syst Evol Microbiol. Jun. 2015;65(Pt 6):1929-34. doi:10.1099/ijs.0.000161. Epub Mar. 3, 2015.

Shannon-Lowe et al., Prevention and medical management of *Clostridium difficile* infection. BMJ. Mar. 12, 2010;340:c1296. doi:10.1136/bmj.c1296.

Surawicz, Fecal microbiota transplantation: what we know and what we need to know. Ann Intern Med. May 5, 2015;162(9):662-3. doi: 10.7326/M15-0609.

Tannock et al., A new macrocyclic antibiotic, fidaxomicin (OPT-80), causes less alteration to the bowel microbiota of *Clostridium difficile*-infected patients than does vancomycin. Microbiology. Nov. 2010;156(Pt 11):3354-9. doi: 10.1099/mic.0.042010-0. Epub Aug. 19, 2010.

Van Nood et al., Duodenal infusion of donor feces for recurrent *Clostridium difficile*. N Engl J Med. Jan. 31, 2013;368(5):407-15. doi: 10.1056/NEJMoa1205037. Epub Jan. 16, 2013.

Wei et al., Fecal microbiota transplantation restores dysbiosis in patients with methicillin resistant *Staphylococcus aureus* enterocolitis. BMC Infect Dis. Jul. 11, 2015;15:265. doi: 10.1186/s12879-015-0973-1.

Youngster et al., Fecal microbiota transplant for relapsing *Clostridium difficile* infection using a frozen inoculum from unrelated donors: a randomized, open-label, controlled pilot study. Clin Infect Dis. Jun. 2014;58(11):1515-22. doi: 10.1093/cid/ciu135. Epub Apr. 23, 2014.

[No Author Listed], [Clostridium] innocuum strain 146 16S ribosomal RNA gene, partial sequence. GenBank Accession No. KR364751.1. Nov. 28, 2016. 2 pages.

[No Author Listed], [Clostridium] symbiosum gene for 16S ribosomal RNA, partial sequence, strain: JCM 1297. GenBank Accession No. LC036311.1. Mar. 20, 2015. 1 page.

Calfee, *Clostridium difficile*: a reemerging pathogen. Geriatrics. Sep. 1, 2008;63(9):10-21.

Janda et al., 16S rRNA gene sequencing for bacterial identification in the diagnostic laboratory: pluses, perils, and pitfalls. J Clin Microbiol. Sep. 2007;45(9):2761-4. doi: 10.1128/JCM.01228-07. Epub Jul. 11, 2007.

Xiao et al., Bacterial diversity and community structure of supragingival plaques in adults with dental health or caries revealed by 16S pyrosequencing. Frontiers in microbiology. Jul. 22, 2016;7:1145. 15 pages.

Dsouza et al., Colonization of the live biotherapeutic product VE303 and modulation of the microbiota and metabolites in healthy volunteers. Cell Host Microbe. Apr. 13, 2022;30(4):583-598.e8. doi: 10.1016/j.chom.2022.03.016.

Martiny et al., Phylogenetic conservatism of functional traits in microorganisms. ISME J. Apr. 2013;7(4):830-8. doi: 10.1038/ismej.2012.160. Epub Dec. 13, 2012.

Wang et al., Microbiota-derived butyrate dynamically regulates intestinal homeostasis through regulation of actin-associated protein synaptopodin. Proc Natl Acad Sci U S A. May 26, 2020;117(21):11648-11657. doi: 10.1073/pnas.1917597117. Epub May 12, 2020.

\* cited by examiner

| Strain ID | Vancomycin | Sentinel/Cohort 1 | Cohort 2 | Cohort 3 | Cohort 4 | Cohort 5 |
|---|---|---|---|---|---|---|
| VE303-01 | 0 of 5 | 2 of 3 | 1 of 3 | 2 of 3 | 6 of 6* | 8 of 8* |
| VE303-02 | 0 of 5 | 1 of 3 | 1 of 3 | 0 of 3 | 6 of 6* | 8 of 8* |
| VE303-03 | 0 of 5 | 1 of 3 | 3 of 3* | 3 of 3* | 6 of 6* | 8 of 8* |
| VE303-04 | 0 of 5 | 2 of 3 | 1 of 3 | 2 of 3 | 6 of 6* | 8 of 8* |
| VE303-05 | 0 of 5 | 1 of 3 | 2 of 3 | 2 of 3 | 6 of 6* | 8 of 8* |
| VE303-06 | 0 of 5 | 1 of 3 | 1 of 3 | 0 of 3 | 6 of 6* | 7 of 8 |
| VE303-07 | 0 of 5 | 1 of 3 | 2 of 3 | 2 of 3 | 5 of 6 | 8 of 8* |
| VE303-08 | 0 of 5 | 1 of 3 | 3 of 3* | 3 of 3* | 5 of 6 | 8 of 8* |

FIG. 8

Mean VE303 Abundance (Total %)

| Cohort | Screening | Week 6 | Week 8 | Week 12 |
|---|---|---|---|---|
| Vanco | 0.14 | 1.19 | 1.49 | 1.50 |
| Sentinel/Cohort1 | 0.34 | 6.04 | 9.75 | 3.84 |
| Cohort 2 | 0.44 | 3.14 | 5.24 | 7.36 |
| Cohort 3 | 0.58 | 1.68 | 0.51 | 0.62 |
| Cohort 4 | 0.29 | 3.68 | 4.08 | 5.37 |
| Cohort 5 | 0.25 | 6.72 | 6.93 | 7.86 |

FIG. 9C

| | Total | VE303-01 | VE303-02 | VE303-03 | VE303-04 | VE303-05 | VE30306 | VE30307 | VE303-08 |
|---|---|---|---|---|---|---|---|---|---|
| Cohort 4 (week 4) | 5.37 | 0.61 | 0.11 | 0.62 | 0.63 | 0.23 | 1.57 | 0.54 | 1.05 |
| Cohort 5 (day 26) | 10.38 | 2.23 | 0.37 | 0.93 | 0.71 | 1.75 | 2.08 | 1.19 | 1.12 |
| Diff. | 5.01 | 1.62 | 0.25 | 0.31 | 0.09 | 1.52 | 0.51 | 0.65 | 0.07 |

Mean VE303 Strain Abundance at ~4 weeks (%)

FIG. 11C

| Strain ID | Day 10 | | Week 4 | | Week 12 | |
|---|---|---|---|---|---|---|
| | Cohort 4 | Cohort 5 | Cohort 4 | Cohort 5 | Cohort 4 | Cohort 5 |
| VE303-01 | 83.3 | 87.5 | 66.7 | 87.5 | 100 | 87.5 |
| VE303-02 | 66.7 | 75 | 66.7 | 87.5 | 66.7 | 75 |
| VE303-03 | 100 | 87.5 | 66.7 | 100 | 83.3 | 62.5 |
| VE303-04 | 100 | 75 | 83.3 | 100 | 83.3 | 37.5 |
| VE303-05 | 83.3 | 75 | 50 | 75 | 66.7 | 62.5 |
| VE303-06 | 66.7 | 62.5 | 83.3 | 75 | 83.3 | 75 |
| VE303-07 | 66.7 | 87.5 | 66.7 | 75 | 83.3 | 50 |
| VE303-08 | 66.7 | 75 | 66.7 | 87.5 | 50 | 62.5 |

FIG. 17B

| Strain ID | Day 10 | | Week 4 | | Week 12 | |
|---|---|---|---|---|---|---|
| | Cohort 4 | Cohort 5 | Cohort 4 | Cohort 5 | Cohort 4 | Cohort 5 |
| VE303-01 | 1.43% | 1.17% | 0.26% | 0.78% | 0.11% | 0.02% |
| VE303-02 | 0.10% | 0.08% | 0.07% | 0.31% | 0.04% | 0.11% |
| VE303-03 | 0.62% | 0.62% | 0.11% | 0.48% | 0.56% | 0.19% |
| VE303-04 | 0.58% | 0.24% | 0.29% | 0.52% | 0.58% | 0.00% |
| VE303-05 | 0.51% | 0.35% | 0.13% | 1.60% | 0.05% | 0.00% |
| VE303-06 | 0.61% | 0.10% | 0.26% | 2.02% | 1.55% | 1.28% |
| VE303-07 | 1.19% | 3.16% | 0.18% | 1.12% | 0.48% | 0.20% |
| VE303-08 | 2.37% | 1.37% | 0.67% | 0.48% | 0.51% | 0.89% |

FIG. 17D

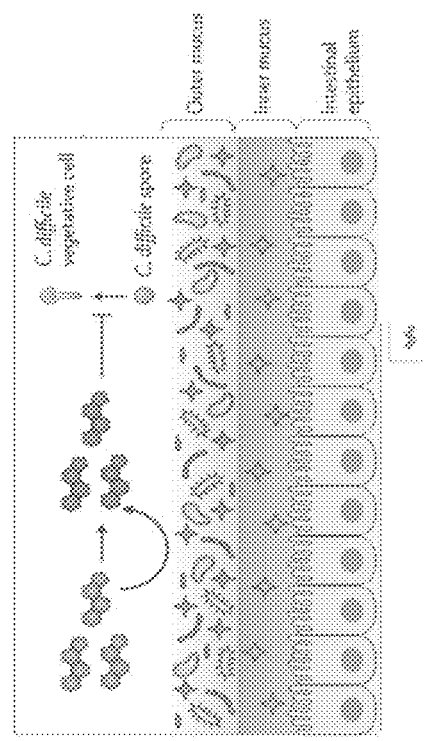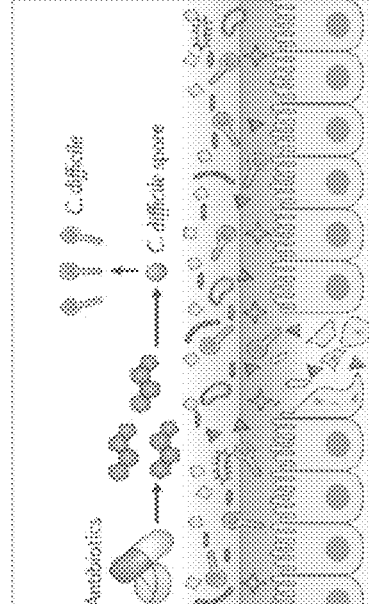
FIG. 28

| | | P-Value | | | Association | | |
|---|---|---|---|---|---|---|---|
| | Type | [a] during vanco | [b] post vanco (baseline) | [c] VE303 | [a] during vanco | [b] post vanco (baseline) | [c] VE303 |
| Cholic Acid | PBA | 1.92E-01 | | | | | 416.82 |
| Glycocholic Acid | PBA | | 4.09E-01 | | | 285.61 | 394.22 |
| Glycochenodeoxycholic Acid | PBA | | 3.35E-01 | | 749.18 | 275.01 | 388.24 |
| Chenodeoxycholic Acid | PBA | 1.09E-01 | | | 360.26 | 415.35 | -141.85 |
| Taurocholic Acid | PBA | | 1.88E-01 | 1.88E-01 | 196.07 | 95.03 | -28.37 |
| Taurochenodeoxycholic Acid | PBA | | 6.35E-01 | 3.78E-01 | 118.02 | 23.47 | -12.80 |
| Glycodeoxycholic Acid | SBA | | 5.45E-01 | | 290.82 | 67.42 | -115.97 |
| Glycoursodeoxycholic Acid | SBA | 1.57E-01 | 7.55E-01 | | 39.19 | 7.39 | -11.26 |
| Taurodeoxycholic Acid | SBA | 1.88E-01 | 7.11E-01 | 6.35E-01 | 103.56 | -30.10 | -10.54 |
| Taurolithocholic Acid | SBA | 6.29E-03 | NA | | -0.30 | NA | -0.36 |
| Glycolithocholic Acid | SBA | 1.89E-01 | 2.47E-01 | 9.94E-01 | -0.62 | -0.73 | 0.00 |
| Tauroursodeoxycholic Acid | SBA | 9.95E-02 | 3.78E-02 | 7.08E-02 | 3.93 | -2.04 | 1.11 |
| Ursodeoxycholic Acid | SBA | 9.30E-01 | 3.47E-01 | | 4.71 | 45.39 | 22.44 |
| Lithocholic Acid | SBA | | | | | | 161.10 |
| Deoxycholic Acid | SBA | | | | | | 204.40 |

[a] Vanco treatment vs baseline
[b] Post Vanco without VE303
[c] Post Vanco with VE303

VE303 significantly associated with the recovery of 2° BA and reduction of 1° BA

FIG. 34A $$BileAcid \sim Treatment + ve303_{tot} + \frac{pID}{CohortID}$$

$Treatment$ = baseline, during, or post-vancomycin

| | During Vancomycin | | | Post Vancomycin (No VE303) | | | Post Vancomycin (With VE303) | | |
|---|---|---|---|---|---|---|---|---|---|
| | d | | p | d | | p | β | | p |
| Cholic Acid | 6.463E+02 | + | 1.476E-01 | 1.974E+03 | + | *1.875E-06 | -3.633E+02 | * | *1.109E-04* |
| Chenodeoxycholic Acid | 2.716E+02 | + | 9.926E-02 | 3.095E+02 | + | *6.597E-03 | -1.308E+02 | * | *3.992E-04* |
| Taurocholic Acid | 1.887E+02 | + | 1.374E-01 | 6.966E+01 | | 4.343E-01 | -3.328E+01 | | 1.824E-01 |
| Glycocholic Acid | 1.357E+03 | * | 7.775E-04 | 2.973E+02 | + | 4.135E-01 | -3.848E+02 | * | *4.240E-05* |
| Glycochenodeoxycholic Acid | 8.523E+02 | * | 1.054E-02 | 4.011E+02 | | 2.007E-01 | -3.546E+02 | * | *1.497E-05* |
| Taurochenodeoxycholic Acid | 7.431E+01 | * | 2.876E-01 | 2.219E+01 | | 7.271E-01 | -2.177E+01 | | 1.904E-01 |
| Lithocholic Acid | -6.119E+02 | - | 3.512E-04 | -1.180E+03 | * | *1.325E-10 | +1.785E+02 | * | *1.785E-05* |
| Deoxycholic Acid | -9.509E+02 | - | 2.244E-04 | -1.578E+03 | * | *1.875E-10 | +2.019E+02 | * | *7.540E-04* |
| Glycoursodeoxycholic Acid | 5.441E+01 | | 8.691E-02 | 2.687E+01 | | 3.385E-01 | -9.978E+00 | | 1.033E-01 |
| Ursodeoxycholic Acid | 8.403E+00 | | 9.413E-01 | 8.975E+01 | | 2.700E-01 | 2.276E+01 | | 2.127E-01 |

Linear Mixed Effects Model of the changes in Bile Acids with Vancomycin and Recovery +/-VE303

Vancomycin:
- Increases Primary BAs
- Decreases Secondary BAs

Recovery without VE303:
- Primary BAs remain elevated
- Secondary BAs remain low Recovery with VE303:
- Primary BAs decline
- Secondary BAs increase d = Distance from baseline
β = Regression coefficient

* $p < 0.05$
+ increasing
- decreasing

FIG. 34B

| | P-value | | | Association | | |
|---|---|---|---|---|---|---|
| | a during vanco | b post vanco (baseline) | c VE303 | a during vanco – pre vanco | b post vanco (baseline) – pre vanco | c VE303 |
| Acetate | 2.26E-03 | 2.46E-03 | 6.93E-03 | 802.91 | 896.2 | 497.4 |
| Butyrate | 4.08E-04 | 8.04E-06 | 8.22E-04 | -535.38 | -406.73 | 161.73 |
| Isobutyrate | 1.80E-01 | 1.19E-05 | 2.39E-05 | -23.42 | -76.22 | 19.25 |
| Propionate | 1.21E-04 | 4.65E-05 | 1.15E-05 | -466.46 | -520.33 | 152.61 |
| 2-Methylbutyrate | 2.54E-01 | 1.27E-05 | 4.05E-05 | -17.49 | -65.08 | 16.14 |
| Isovalerate | 2.94E-01 | 1.04E-05 | 1.63E-04 | -20.09 | -79.16 | 19.17 | a Vanco treatment vs baseline
b Post Vanco without VE303
c Post Vanco with VE303

VE303 significantly associated with the recovery of Acetate, Butyrate and Propionate

FIG. 39A $$SCFA \sim Treatment + ve303_{tot} + \frac{pID}{CohortID}$$

$Treatment$ = baseline, during, or post-vancomycin

Linear Mixed Effects Model of the changes in SCFAs with Vancomycin and Recovery +/- VE303

Vancomycin:
• Significantly reduces SCFA levels

Recovery without VE303:
• SCFAs remain low

Recovery with VE303:
• SCFAs significantly recover

| SCFAs | During Vancomycin | | | Post Vancomycin (No VE303) | | | Post Vancomycin (With VE303) | | |
|---|---|---|---|---|---|---|---|---|---|
| | d | | p | d | | p | β | | p |
| Butyrate | -8.035E+02 | * | 2.325E-09 | -1.185E+03 | * | 5.235E-11 | 1.274E+00 | + | 2.540E-03 |
| Acetate | -1.104E+02 | * | 9.789E-04 | -8.984E+02 | * | 9.314E-03 | 4.186E+02 | + | 9.283E-02 |
| Propionate | -5.768E+02 | * | 3.349E-03 | -4.661E+02 | * | 2.320E-04 | 1.094E+02 | + | 7.006E-04 |
| Isobutyrate | -4.929E+01 | * | 3.314E-03 | -8.278E+01 | * | 3.283E-07 | 1.531E+01 | * | 1.199E-04 |
| Methylbutyrate | -4.088E+01 | * | 6.913E-03 | -7.189E+01 | * | 7.473E-07 | 1.305E+01 | * | 2.939E-04 |
| Isovalerate | -5.593E+01 | * | 3.314E-03 | -8.635E+01 | * | 9.893E-07 | 1.392E+01 | * | 1.392E-03 |
| Valerate | -7.774E-01 | | 6.220E-02 | -1.589E+02 | * | 2.349E-03 | 9.636E+00 | | 3.953E-01 |
| Hexanoate | -5.165E-01 | | 9.722E-01 | -4.137E+01 | | 6.702E-03 | 6.148E+00 | | 1.730E-01 | d = Distance from baseline
β = Regression coefficient

*P <0.05
+ increasing
- decreasing

FIG. 39B

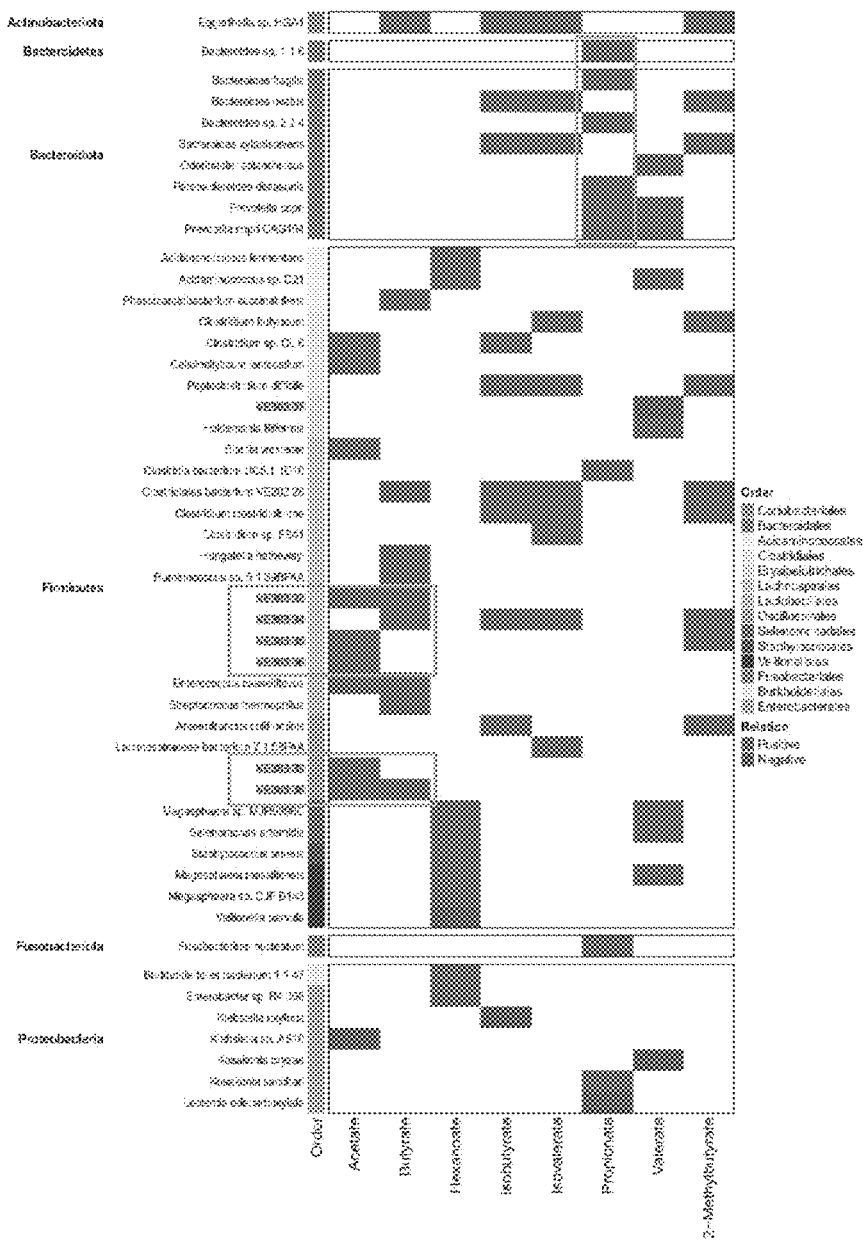

FIG. 41C

Identify Species Important for the Recovery of SCFAs by Random Forest Regression and ALE VE303 Directly associated with the recovery of Acetate and Butyrate, plus other less abundant SCFAs
• Consistent with *in vitro* phenotypes VE303 Indirectly Associated – via expedited recovery of commensal species:
• Commensal Bacteroidetes species mostly associated with Propionate recovery Proteobacteria species negatively associated with the recovery of several SCFAs

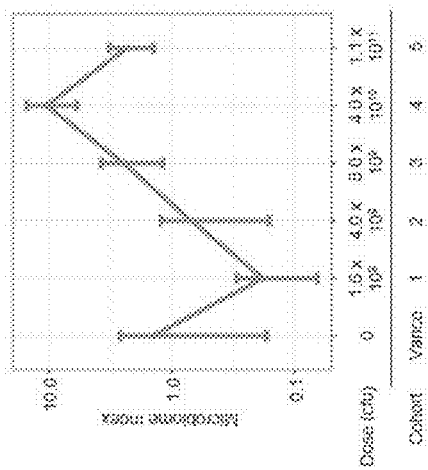
FIG. 46D
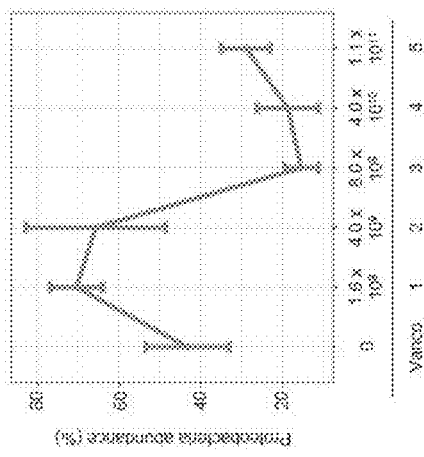
FIG. 46C
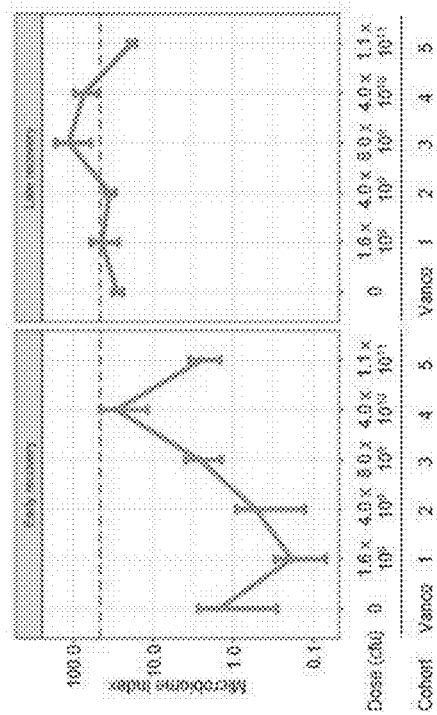
FIG. 46E
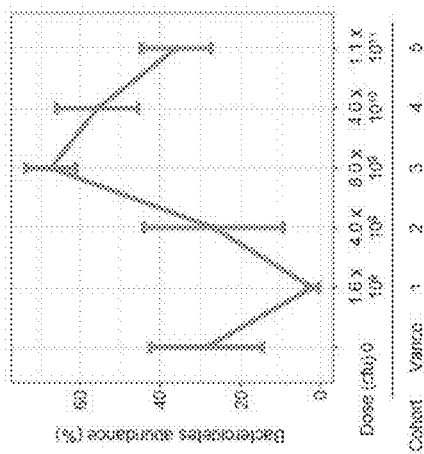

Timepoint

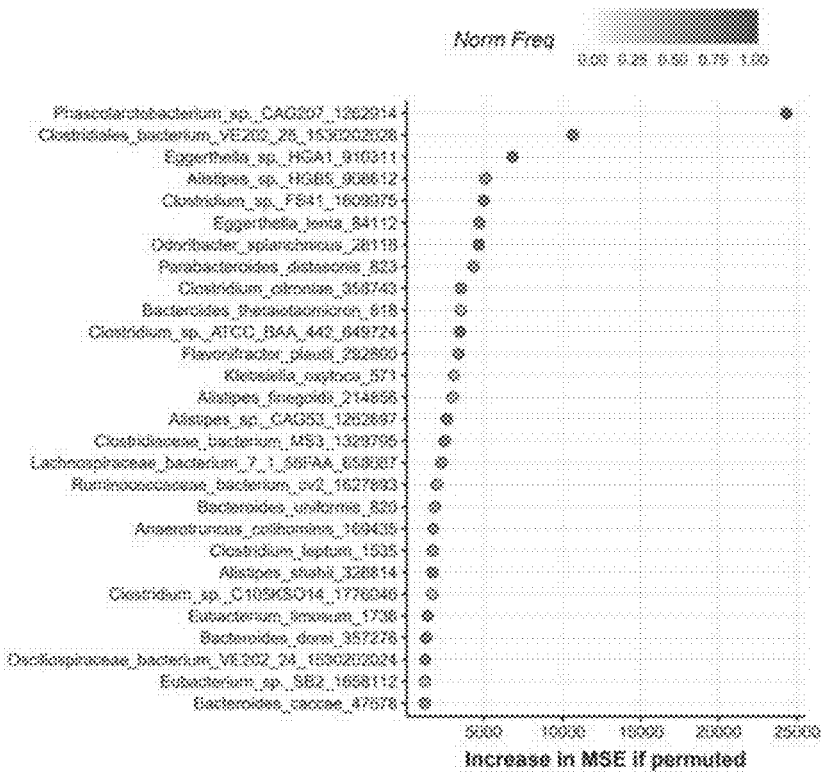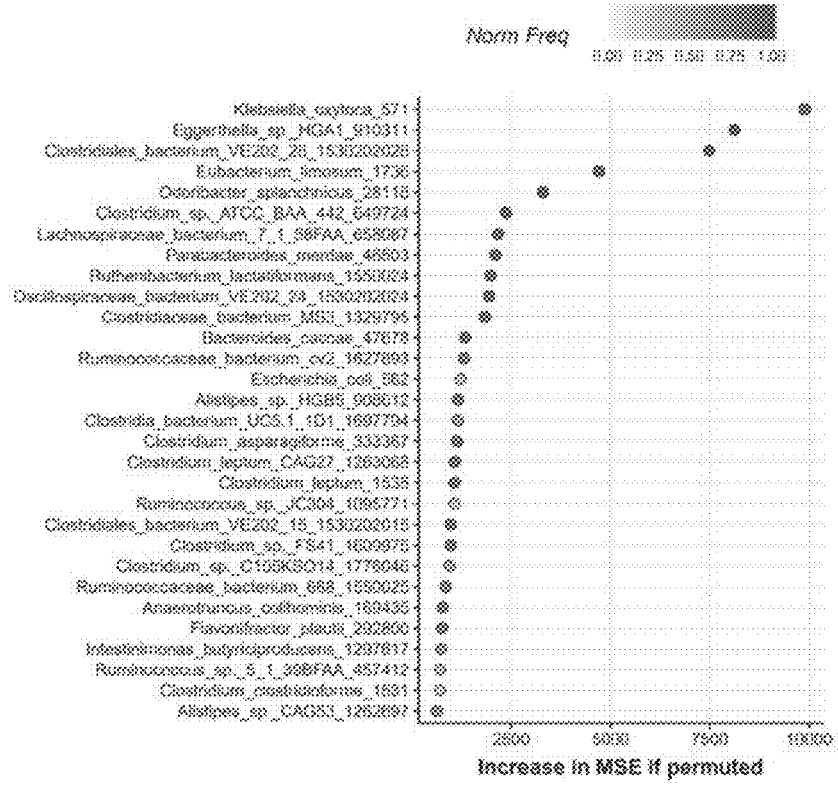
FIG. 57G

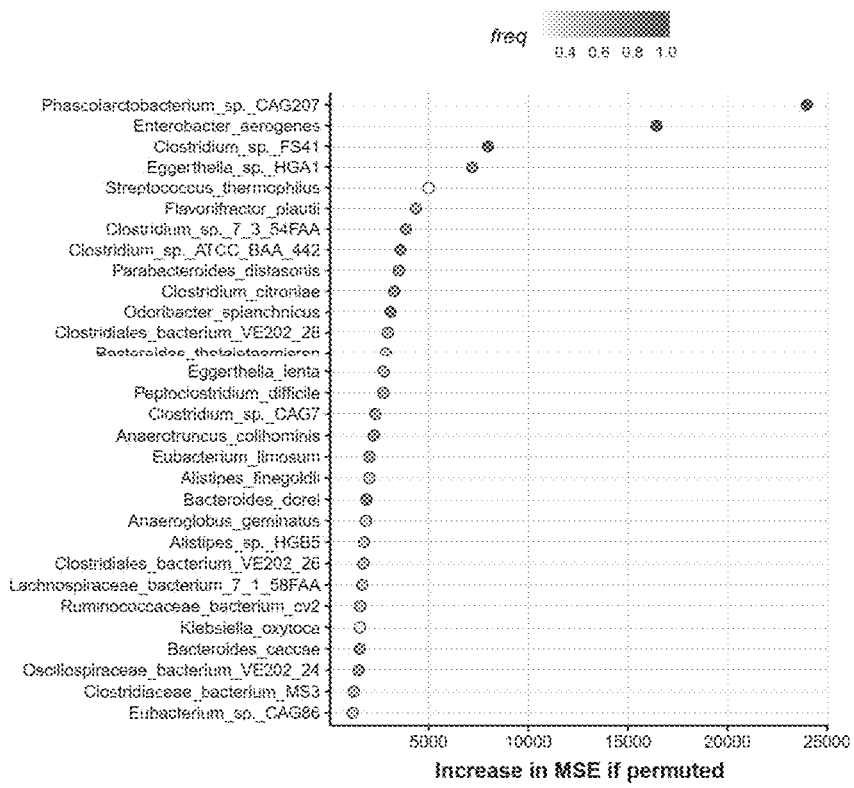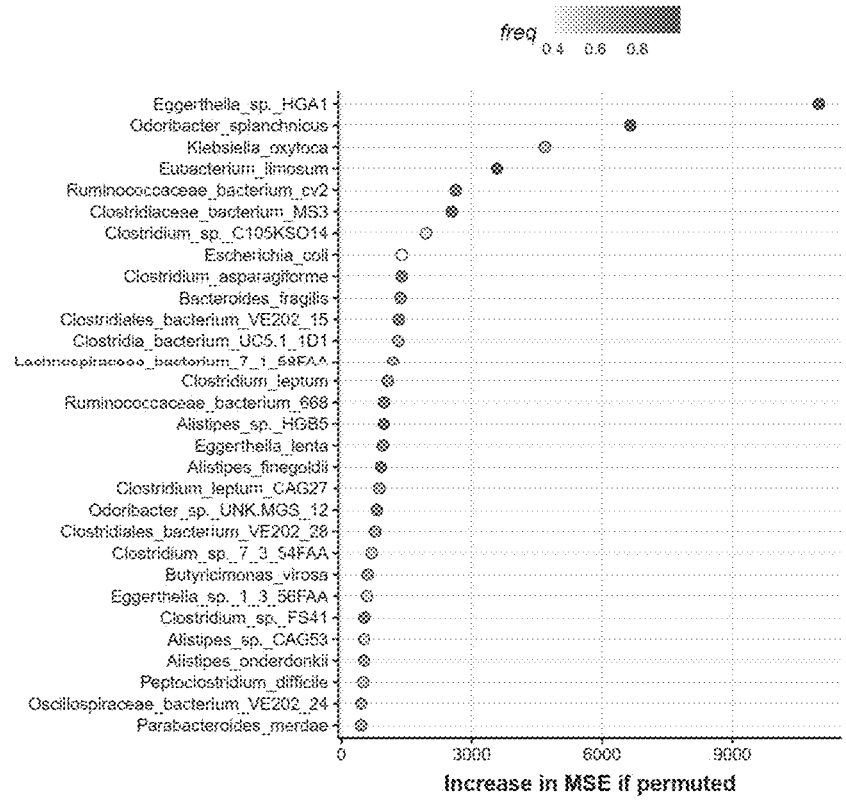
FIG. 57Q

| Common Path | | Indication-specific Path |
|---|---|---|
| LBP | Pharmacokinetics (PK) | Pharmacodynamics (PD) | CDI-associated PD |

| Genomes / Unique Marker Sequences | Metagenomics-based strain colonization | Metagenomics-based Microbiota dynamics | Fecal Short Chain Fatty Acids / Fecal Bile Acids |

FIG. 60

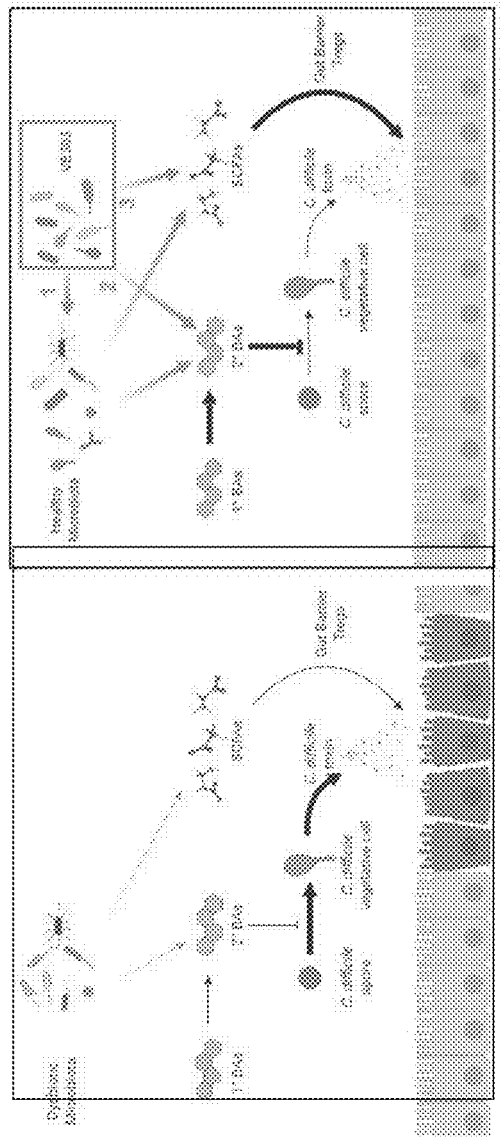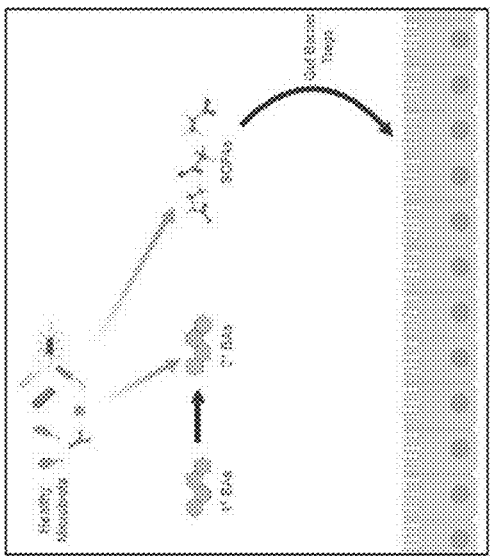
FIG. 61

SEQUENCE LISTING

```
<160> NUMBER OF SEQ ID NOS: 74

<210> SEQ ID NO 1
<211> LENGTH: 1530
<212> TYPE: DNA
<213> ORGANISM: Clostridium bolteae

<400> SEQUENCE: 1
atgagagttt gatcctggct caggatgaac gctggcggcg tgcctaacac atgcaagtcg      60
aacgaagcaa ttaaaatgaa gttttcggat ggatttttga ttgactgagt ggcggacggg     120
tgagtaacgc gtggataacc tgcctcacac tgggggataa cagttagaaa tgactgctaa     180
taccgcataa gcgcacagta ccgcatggta cggtgtgaaa aactccggtg gtgtgagatg     240
gatccgcgtc tgattagcca gttggcgggg taacggccca ccaaagcgac gatcagtagc     300
cgacctgaga gggtgaccgg ccacattggg actgagacac ggcccaaact cctacgggag     360
gcagcagtgg ggaatattgc acaatgggcg aaagcctgat gcagcgacgc cgcgtgagtg     420
aagaagtatt tcggtatgta aagctctatc agcagggaag aaaatgacgg tacctgacta     480
```

```
agaagccccg gctaactacg tgccagcagc cgcggtaata cgtaggggc aagcgttatc      540 cggatttact gggtgtaaag ggagcgtaga cggcgaagca gtctgaagt gaaaacccag      600 ggctcaaccc tgggactgct ttggaaactg ttttgctaga gtgtcggaga ggtaagtgga     660
attcctagtg tagcggtgaa atgcgtagat attaggagga acaccagtgg cgaaggcggc    720
ttactggacg ataactgacg ttgaggctcg aaagcgtggg gagcaaacag gattagatac    780
cctggtagtc cacgccgtaa acgatgaatg ctaggtgttg gggggcaaag cccttcggtg    840
ccgtcgcaaa cgcagtaagc attccacctg gggagtacgt tcgcaagaat gaaactcaaa    900
ggaattgacg gggacccgca caagcggtgg agcatgtggt ttaattcgaa gcaacgcgaa    960
gaaccttacc aagtcttgac atcctcttga ccggcgtgta acggcgcctt cccttcgggg   1020
caagagagac aggtggtgca tggttgtcgt cagctcgtgt cgtgagatgt tgggttaagt   1080
cccgcaacga gcgcaaccct tatccttagt agccagcagg taaagctggg cactctaggg   1140
agactgccag ggataacctg gaggaaggtg gggatgacg caaatcatca tgcccttat     1200 gatttgggct acacacgtgc tacaatggcg taaacaaagg gaagcaagac agtgatgtgg   1260
agcaaatccc aaaaataacg tcccagttcg gactgtagtc tgcaacccga ctacacgaag   1320
ctggaatcgc tagtaatcgc gaatcagaat gtcgcggtga atacgttccc gggtcttgta   1380
cacaccgccc gtcacaccat gggagtcagc aacgcccgaa gtcagtgacc caactcgcaa   1440
gagagggagc tgccgaaggc ggggcaggta actggggtga agtcgtaaca aggtagccgt   1500
atcggaaggt gcggctggat cacctccttt                                    1530

<210> SEQ ID NO 2
<211> LENGTH: 1522
<212> TYPE: DNA
<213> ORGANISM: Anaerotruncus colihominis

<400> SEQUENCE: 2
tcaaagagtt tgatcctggc tcaggacgaa cgctggcggc gcgcctaaca catgcaagtc     60
gaacggagct tacgttttga agttttcgga tggatgaatg taagcttagt ggcggacggg    120
tgagtaacac gtgagcaacc tgcctttcag agggggataa cagccggaaa cggctgctaa    180
taccgcatga tgttgcgggg gcacatgccc ctgcaaccaa aggagcaatc cgctgaaaga    240
tgggctcgcg tccgattagc cagttggcgg ggtaacggcc caccaaagcg acgatcggta    300
gccggactga gaggttgaac ggccacattg gactgagac acggcccaga ctcctacggg    360
aggcagcagt gggggatatt gcacaatggg cgaaagcctg atgcagcgac gccgcgtgag    420
ggaagacggt cttcggattg taaacctctg tctttgggga gaaaatgac ggtacccaaa    480 gaggaagctc cggctaacta cgtgccagca gccgcggtaa tacgtaggga gcaagcgttg    540
tccgaattac tgggtgtaa agggagcgta ggcgggatgg caagtagaat gttaaatcca    600
tcggctcaac cggtggctgc gttctaaact gccgttcttg agtgaagtag aggcaggcgg    660
aattcctagt gtagcggtga aatgcgtaga tattaggagg aacaccagtg gcgaaggcgg    720
cctgctgggc tttaactgac gctgaggctc gaaagcgtgg ggagcaaaca ggattagata    780
ccctggtagt ccacgccgta aacgatgatt actaggtgtg ggggactga cccccttccgt    840 gccgcagtta acacaataag taatccacct ggggagtacg ccgcaaggt tgaaactcaa     900 aggaattgac gggggcccgc acaagcagtg gagtatgtgg tttaattcga agcaacgcga    960
agaaccttac caggtcttga catcggatgc atagcctaga gataggtgaa gcccttcggg    1020
```

-continued

| | |
|---|---|
| gcatccagac aggtggtgca tggttgtcgt cagctcgtgt cgtgagatgt tgggttaagt | 1080 |
| cccgcaacga gcgcaaccct tattattagt tgctacgcaa gagcactcta atgagactgc | 1140 |
| cgttgacaaa acggaggaag gtggggatga cgtcaaatca tcatgcccct tatgacctgg | 1200 |
| gctacacacg tactacaatg gcactaaaac agagggcggc gacaccgcga ggtgaagcga | 1260 |
| atcccgaaaa agtgtctcag ttcagattgc aggctgcaac ccgcctgcat gaagtcggaa | 1320 |
| ttgctagtaa tcgcggatca gcatgccgcg gtgaatacgt tcccgggcct tgtacacacc | 1380 |
| gcccgtcaca ccatgggagt cggtaacacc cgaagccagt agcctaaccg caaggggggc | 1440 |
| gctgtcgaag gtgggattga tgactggggt gaagtcgtaa caaggtagcc gtatcggaag | 1500 |
| gtgcggctgg atcacctcct tt | 1522 |

<210> SEQ ID NO 3
<211> LENGTH: 1529
<212> TYPE: DNA
<213> ORGANISM: Ruminococcus torques

<400> SEQUENCE: 3

| | |
|---|---|
| tacgagagtt tgatcctggc tcaggatgaa cgctggcggc gtgcctaaca catgcaagtc | 60 |
| gagcgaagcg ctgtttcag aatcttcgga ggaagaggac agtgactgag cggcggacgg | 120 |
| gtgagtaacg cgtgggcaac ctgcctcata caggggata acagttagaa atgactgcta | 180 |
| ataccgcata agcgcacagg accgcatggt gtagtgtgaa aaactccggt ggtatgagat | 240 |
| ggacccgcgt ctgattaggt agttggtggg gtaaaggcct accaagccga cgatcagtag | 300 |
| ccgacctgag agggtgaccg gccacattgg gactgagaca cggcccaaac tcctacggga | 360 |
| ggcagcagtg gggaatattg cacaatgggg gaaaccctga tgcagcgacg ccgcgtgaag | 420 |
| gaagaagtat tcggtatgt aaacttctat cagcagggaa gaaaatgacg gtacctgagt | 480 |
| aagaagcacc ggctaaatac gtgccagcag ccgcggtaat acgtatggtg caagcgttat | 540 |
| ccggatttac tgggtgtaaa gggagcgtag acggataggc aagtctggag tgaaaaccca | 600 |
| gggctcaacc ctgggactgc tttggaaact gcagatctgg agtgccggag aggtaagcgg | 660 |
| aattcctagt gtagcggtga aatgcgtaga tattaggagg aacaccagtg gcgaaggcgg | 720 |
| cttactggac ggtgactgac gttgaggctc gaaagcgtgg ggagcaaaca ggattagata | 780 |
| ccctggtagt ccacgccgta aacgatgact actaggtgtc ggtgtgcaaa gcacatcggt | 840 |
| gccgcagcaa acgcaataag tagtccacct ggggagtacg ttcgcaagaa tgaaactcaa | 900 |
| aggaattgac ggggacccgc acaagcggtg gagcatgtgg tttaattcga agcaacgcga | 960 |
| agaaccttac ctggtcttga catccggatg acgggcgagt aatgtcgccg tcccttcggg | 1020 |
| gcgtccgaga caggtggtgc atggttgtcg tcagctcgtg tcgtgagatg ttgggttaag | 1080 |
| tcccgcaacg agcgcaaccc ttatcttcag tagccagcat ataaggtggg cactctggag | 1140 |
| agactgccag ggagaacctg gaggaaggtg gggatgacgt caaatcatca tgccccttat | 1200 |
| ggccagggct acacacgtgc tacaatggcg taaacaaagg gaagcgagag ggtgacctgg | 1260 |
| agcgaatccc aaaaataacg tctcagttcg gattgtagtc tgcaactcga ctacatgaag | 1320 |
| ctggaatcgc tagtaatcgc ggatcagcat gccgcggtga atacgttccc gggtcttgta | 1380 |
| cacaccgccc gtcacaccat gggagtcagt aacgcccgaa gccagtgacc caaccttaga | 1440 |
| ggagggagct gtcgaaggcg ggacggataa ctgggtgaa gtcgtaacaa ggtagccgta | 1500 |
| tcggaaggtg cggctggatc acctcctttt | 1529 |

```
<210> SEQ ID NO 4
<211> LENGTH: 1527
<212> TYPE: DNA
<213> ORGANISM: Clostridium symbiosum

<400> SEQUENCE: 4
atgagagttt gatcctggct caggatgaac gctggcggcg tgcctaacac atgcaagtcg      60
aacgaagcga tttaacggaa gttttcggat ggaagttgaa ttgactgagt ggcggacggg     120
tgagtaacgc gtgggtaacc tgccttgtac tggggacaa cagttagaaa tgactgctaa     180
taccgcataa gcgcacagta tcgcatgata cagtgtgaaa actccggtg gtacaagatg     240 gacccgcgtc tgattagcta gttggtaagg taacggctta ccaaggcgac gatcagtagc     300
cgacctgaga gggtgaccgg ccacattggg actgagacac ggcccaaact cctacgggag     360
gcagcagtgg ggaatattgc acaatgggcg aaagcctgat gcagcgacgc cgcgtgagtg     420
aagaagtatt tcggtatgta aagctctatc agcagggaag aaaatgacgg tacctgacta     480 agaagcccg gctaactacg tgccagcagc cgcggtaata cgtaggggc aagcgttatc       540 cggatttact gggtgtaaag ggagcgtaga cggtaaagca gtctgaagt gaaagcccgc      600 ggctcaactg cgggactgct ttggaaactg tttaactgga gtgtcggaga ggtaagtgga     660
attcctagtg tagcggtgaa atgcgtagat attaggagga acaccagtgg cgaaggcgac     720
ttactggacg ataactgacg ttgaggctcg aaagcgtggg gagcaaacag gattagatac     780
cctggtagtc cacgccgtaa acgatgaata ctaggtgttg gggagcaaag ctcttcggtg     840
ccgtcgcaaa cgcagtaagt attccacctg gggagtacgt tcgcaagaat gaaactcaaa     900
ggaattgacg gggacccgca caagcggtgg agcatgtggt ttaattcgaa gcaacgcgaa     960
gaaccttacc aggtcttgac atcgatccga cggggagta acgtcccctt cccttcgggg    1020
cggagaagac aggtggtgca tggttgtcgt cagctcgtgt cgtgagatgt tgggttaagt    1080
cccgcaacga gcgcaaccct tattctaagt agccagcggt tcggccggga actcttggga    1140
gactgccagg gataacctgg aggaaggtgg ggatgacgtc aaatcatcat gccccttatg    1200
atctgggcta cacacgtgct acaatggcgt aaacaaagag aagcaagacc gcgaggtgga    1260
gcaaatctca aaataacgt ctcagttcgg actgcaggct gcaactcgcc tgcacgaagc     1320
tggaatcgct agtaatcgcg aatcagaatg tcgcggtgaa tacgttcccg ggtcttgtac    1380
acaccgcccg tcacaccatg ggagtcagta acgcccgaag tcagtgaccc aaccgcaagg    1440
agggagctgc cgaaggcggg accgataact ggggtgaagt cgtaacaagg tagccgtatc    1500
ggaaggtgcg gctggatcac ctccttt                                        1527

<210> SEQ ID NO 5
<211> LENGTH: 1531
<212> TYPE: DNA
<213> ORGANISM: Blautia producta

<400> SEQUENCE: 5
atcagagagt ttgatcctgg ctcaggatga acgctggcgg cgtgcttaac acatgcaagt      60
cgagcgaagc acttaagtgg atctcttcgg attgaagctt atttgactga gcggcggacg     120
ggtgagtaac gcgtgggtaa cctgcctcat acaggggat aacagttaga aatggctgct      180
aataccgcat aagcgcacag gaccgcatgg tctggtgtga aaaactccgg tggtatgaga     240
tggacccgcg tctgattagc tagttggagg ggtaacggcc caccaaggcg acgatcagta     300
gccggcctga gagggtgaac ggccacattg ggactgagac acggcccaga ctcctacggg     360
```

```
aggcagcagt ggggaatatt gcacaatggg ggaaaccctg atgcagcgac gccgcgtgaa      420
ggaagaagta tctcggtatg taaacttcta tcagcaggga agaaaatgac ggtacctgac      480
taagaagccc cggctaacta cgtgccagca gccgcggtaa tacgtagggg caagcgtta       540 tccggattta ctgggtgtaa agggagcgta gacggaagag caagtctgat gtgaaaggct      600
ggggcttaac cccaggactg cattggaaac tgttttcta gagtgccgga gaggtaagcg       660
gaattcctag tgtagcggtg aaatgcgtag atattaggag gaacaccagt ggcgaaggcg      720
gcttactgga cggtaactga cgttgaggct cgaaagcgtg gggagcaaac aggattagat      780
accctggtag tccacgccgt aaacgatgaa tactaggtgt cgggtggcaa agccattcgg      840
tgccgcagca aacgcaataa gtattccacc tggggagtac gttcgcaaga atgaaactca      900
aaggaattga cggggacccg cacaagcggt ggagcatgtg gtttaattcg aagcaacgcg      960 aagaaccta ccaagtcttg acatccctct gaccggcccg taacggggcc ttcccttcgg       1020
ggcagaggag acaggtggtg catggttgtc gtcagctcgt gtcgtgagat gttgggttaa      1080
gtcccgcaac gagcgcaacc cctatcctta gtagccagca ggtgaagctg gcactctag       1140 ggagactgcc ggggataacc ggaggaagg cggggacgac gtcaaatcat catgccctt       1200 atgatttggg ctacacacgt gctacaatgg cgtaaacaaa gggaagcgag acagcgatgt      1260
tgagcaaatc ccaaaaataa cgtcccagtt cggactgcag tctgcaactc gactgcacga      1320
agctggaatc gctagtaatc gcgaatcaga atgtcgcggt gaatacgttc ccgggtcttg      1380
tacacaccgc ccgtcacacc atgggagtca gtaacgcccg aagtcagtga cccaaccta       1440 caggagggag ctgccgaagg cgggaccgat aactggggtg aagtcgtaac aaggtagccg      1500
tatcggaagg tgcggctgga tcacctcctt t                                     1531

<210> SEQ ID NO 6
<211> LENGTH: 1529
<212> TYPE: DNA
<213> ORGANISM: Dorea longicatena

<400> SEQUENCE: 6
aacgagagtt tgatcctggc tcaggatgaa cgctggcggc gtgcttaaca catgcaagtc       60
gagcgaagca cttaagtttg attcttcgga tgaagacttt tgtgactgag cggcggacgg      120
gtgagtaacg cgtgggtaac ctgcctcata caggggata acagtagaa atgactgcta        180 ataccgcata agaccacggt accgcatggt acagtggtaa aaactccggt ggtatgagat      240
ggacccgcgt ctgattaggt agttggtggg gtaacggcct accaagccga cgatcagtag      300
ccgacctgag agggtgaccg gccacattgg gactgagaca cggcccagac tcctacggga      360
ggcagcagtg gggaatattg cacaatggag gaaactctga tgcagcgacg ccgcgtgaag      420
gatgaagtat ttcggtatgt aaacttctat cagcaggaa gaaaatgacg gtacctgact       480
aagaagcccc ggctaactac gtgccagcag ccgcggtaat acgtaggggg caagcgttat      540
ccggatttac tgggtgtaaa gggagcgtag acggcacggc aagccagatg tgaaagcccg      600
gggctcaacc ccgggactgc atttggaact gctgagctag agtgtcggag aggcaagtgg      660
aattcctagt gtagcggtga aatgcgtaga tattaggagg aacaccagtg gcgaaggcgg      720
cttgctggac gatgactgac gttgaggctc gaaagcgtgg ggagcaaaca ggattagata      780
ccctggtagt ccacgccgta aacgatgact gctaggtgtc gggtggcaaa gccattcgt       840 gccgcagcta acgcaataag cagtccacct ggggagtacg ttcgcaagaa tgaaactcaa      900
aggaattgac ggggacccgc acaagcggtg gagcatgtgg tttaattcga agcaacgcga      960
```

| | |
|---|---|
| agaaccttac ctgatcttga catcccgatg accgcttcgt aatgaaagct tttcttcgga | 1020 |
| acatcggtga caggtggtgc atggttgtcg tcagctcgtg tcgtgagatg ttgggttaag | 1080 |
| tcccgcaacg agcgcaaccc ctatcttcag tagccagcag gttaagctgg cactctgga | 1140 |
| gagactgcca gggataacct ggaggaaggt ggggatgacg tcaaatcatc atgcccctta | 1200 |
| tgaccagggc tacacacgtg ctacaatggc gtaaacaaag agaagcgaac tcgcgagggt | 1260 |
| aagcaaatct caaaaataac gtctcagttc ggattgtagt ctgcaactcg actacatgaa | 1320 |
| gctggaatcg ctagtaatcg cagatcagaa tgctgcggtg aatacgttcc cgggtcttgt | 1380 |
| acacaccgcc cgtcacacca tgggagtcag taacgcccga agtcagtgac caaccgtaa | 1440 |
| ggagggagct gccgaaggtg ggaccgataa ctggggtgaa gtcgtaacaa ggtagccgta | 1500 |
| tcggaaggtg cggctggatc acctccttt | 1529 |

<210> SEQ ID NO 7
<211> LENGTH: 1537
<212> TYPE: DNA
<213> ORGANISM: Erysipelotrichaceae bacterium

<400> SEQUENCE: 7

| | |
|---|---|
| atggagagtt tgatcctggc tcaggatgaa cgctggcggc atgcctaata catgcaagtc | 60 |
| gaacgaagtt tcgaggaagc ttgcttccaa agagacttag tggcgaacgg gtgagtaaca | 120 |
| cgtaggtaac ctgcccatgt gtccgggata actgctggaa acggtagcta aaccggata | 180 |
| ggtatacaga gcgcatgctc agtatattaa agcgcccatc aaggcgtgaa catggatgga | 240 |
| cctgcggcgc attagctagt tggtgaggta acggcccacc aaggcgatga tgcgtagccg | 300 |
| gcctgagagg gtaaacggcc acattgggac tgagacacgg cccaaactcc tacgggaggc | 360 |
| agcagtaggg aattttcgtc aatgggggaa accctgaacg agcaatgccg cgtgagtgaa | 420 |
| gaaggtcttc ggatcgtaaa gctctgttgt aagtgaagaa cggctcatag aggaaatgct | 480 |
| atgggagtga cggtagctta ccagaaagcc acggctaact acgtgccagc agccgcggta | 540 |
| atacgtaggt ggcaagcgtt atccggaatc attgggcgta aagggtgcgt aggtggcgta | 600 |
| ctaagtctgt agtaaaaggc aatggctcaa ccattgtaag ctatggaaac tggtatgctg | 660 |
| gagtgcagaa gagggcgatg gaattccatg tgtagcggta aaatgcgtag atatatggag | 720 |
| gaacaccagt ggcgaaggcg tcgcctggtc tgtaactga cactgaggca cgaaagcgtg | 780 |
| gggagcaaat aggattagat accctagtag tccacgccgt aaacgatgag aactaagtgt | 840 |
| tggaggaatt cagtgctgca gttaacgcaa taagttctcc gcctggggag tatgcacgca | 900 |
| agtgtgaaac tcaaaggaat tgacgggggc ccgcacaagc ggtggagtat gtggtttaat | 960 |
| tcgaagcaac gcgaagaacc ttaccaggcc ttgacatgga acaaatacc ctagagatag | 1020 |
| ggggataatt atggatcaca caggtggtgc atggttgtcg tcagctcgtg tcgtgagatg | 1080 |
| ttgggttaag tcccgcaacg agcgcaaccc ttgtcgcatg ttaccagcat caagttgggg | 1140 |
| actcatgcga gactgccggt gacaaaccgg aggaaggtgg ggatgacgtc aaatcatcat | 1200 |
| gccccttatg gcctgggcta cacacgtact acaatggcgg ccacaaagag cagcgacaca | 1260 |
| gtgatgtgaa gcgaatctca taaggtcgt ctcagttcgg attgaagtct gcaactcgac | 1320 |
| ttcatgaagt cggaatcgct agtaatcgca gatcagcatg ctgcggtgaa tacgttctcg | 1380 |
| ggccttgtac acaccgcccg tcaaaccatg ggagtcagta atacccgaag ccggtggcat | 1440 |
| aaccgtaagg agtgagccgt cgaaggtagg accgatgact ggggttaagt cgtaacaagg | 1500 |

```
tatccctacg ggaacgtggg gatggatcac ctcctttt                    1537
```

<210> SEQ ID NO 8
<211> LENGTH: 1530
<212> TYPE: DNA
<213> ORGANISM: Subdoligranulum spp

<400> SEQUENCE: 8

```
tattgagagt tgatcctgg ctcaggatga acgctggcgg cgtgcttaac acatgcaagt    60
cgaacggggt gctcatgacg gaggattcgt ccaacggatt gagttaccta gtggcggacg   120
ggtgagtaac gcgtgaggaa cctgccttgg agagggaat aacactccga aaggagtgct   180
aataccgcat gatgcagttg ggtcgcatgg ctctgactgc caaagattta cgctctgag   240
atggcctcgc gtctgattag ctagtaggcg gggtaacggc ccacctaggc gacgatcagt   300
agccggactg agaggttgac cggccacatt gggactgaga cacggcccag actcctacgg   360
gaggcagcag tggggaatat tgggcaatgg gcgcaagcct gacccagcaa cgccgcgtga   420
aggaagaagg ctttcgggtt gtaaacttct tttgtcgggg acgaaacaaa tgacggtacc   480
cgacgaataa gccacggcta actacgtgcc agcagccgcg gtaatacgta ggtggcaagc   540
gttatccgga tttactgggt gtaaaggggg tgtaggcggg attgcaagtc agatgtgaaa   600
actgggggct caacctccag cctgcatttg aaactgtagt tcttgagtgc tggagaggca   660
atcggaattc cgtgtgtagc ggtgaaatgc gtagatatac ggaggaacac cagtggcgaa   720
ggcggattgc tggacagtaa ctgacgctga ggcgcgaaag cgtggggagc aaacaggatt   780
agataccctg gtagtccacg ccgtaaacga tggatactag gtgtggggg tctgaccccc   840
tccgtgccgc agttaacaca ataagtatcc cacctgggga gtacgatcgc aaggttgaaa   900
ctcaaaggaa ttgacggggg cccgcacaag cggtggagta tgtggttaa ttcgaagcaa   960
cgcgaagaac cttaccaggg cttgacatcc cactaacgaa gcagagatgc attaggtgcc  1020
cttcggggaa agtggagaca ggtggtgcat ggttgtcgtc agctcgtgtc gtgagatgtt  1080
gggttaagtc ccgcaacgag cgcaacccct attgttagtt gctacgcaag agcactctag  1140
cgagactgcc gttgacaaaa cggaggaagg tggggacgac gtcaaatcat catgccccct  1200
atgtcctggg ccacacacgt actacaatgg tggttaacag agggaggcaa taccgcgagg  1260
tggagcaaat ccctaaaagc catcccagtt cggattgcag gctgaaaccc gcctgtatga  1320
agttggaatc gctagtaatc gcggatcagc atgccgcggt gaatacgttc ccgggccttg  1380
tacacaccgc ccgtcacacc atgagagtcg gaacacccg aagtccgtag cctaaccgca  1440
aggagggcgc ggccgaaggt gggttcgata ttggggtga agtcgtaaca aggtagccgt  1500
atcggaaggt gcggctggat cacctccttt                                  1530
```

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9

```
tgcagccggt attctgattt                                                20
```

<210> SEQ ID NO 10
<211> LENGTH: 22
<212> TYPE: DNA
<213> ORGANISM: Artificial Sequence

```
<220> FEATURE:
<223> OTHER INFORMATION: Synthetic polynucleotide

<400> SEQUENCE: 10
gcgaatggta gtccggtata at                                              22

<210> SEQ ID NO 11
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (21)..(21)
<223> OTHER INFORMATION: may be modified by a 3IABkFQ quencher

<400> SEQUENCE: 11
tgggctgatc ccgttccgtt t                                               21

<210> SEQ ID NO 12
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 12
ttgtactgtt cccaatgagt atcaa                                           25

<210> SEQ ID NO 13
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 13
gaatataatc aagatcctcc agcgg                                           25

<210> SEQ ID NO 14
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (23)..(23)
<223> OTHER INFORMATION: may be modified by a 3IABkFQ quencher

<400> SEQUENCE: 14
aaaaatattt gggttatgca acc                                             23
```

```
<210> SEQ ID NO 15
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 15
cgaaccctta aacctcttcc tt                                              22

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
tccggcttgt gatgtcttgt                                                 20

<210> SEQ ID NO 17
<211> LENGTH: 28
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (28)..(28)
<223> OTHER INFORMATION: may be modified by a 3IABkFQ quencher

<400> SEQUENCE: 17
ccctccttct tgatattcgg ttgttcca                                        28

<210> SEQ ID NO 18
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 18
cccgaaaccc tttgatttac tg                                              22

<210> SEQ ID NO 19
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 19
cttggccggt ggatatgtt                                                  19

<210> SEQ ID NO 20
<211> LENGTH: 24
<212> TYPE: DNA
<213> ORGANISM: Artificial Sequence
<220> FEATURE:
<223> OTHER INFORMATION: Synthetic polynucleotide
```

```
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (24)..(24)
<223> OTHER INFORMATION: may be modified by a 3IABkFQ quencher

<400> SEQUENCE: 20
agcaacacca ccgtttcaac atgc                                          24

<210> SEQ ID NO 21
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 21
acacgcatat cgtttgacac tgtt                                          24

<210> SEQ ID NO 22
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 22
caattatgat tgccgttct                                                19

<210> SEQ ID NO 23
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (17)..(17)
<223> OTHER INFORMATION: may be modified by a 3IABkFQ quencher

<400> SEQUENCE: 23
acggaactta tgaaccc                                                  17

<210> SEQ ID NO 24
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 24
tattcagatc gtatttggat gtacc                                         25

<210> SEQ ID NO 25
```

```
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 25
cccttgcaag ctctgtcgtc ataag                                              25

<210> SEQ ID NO 26
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (15)..(15)
<223> OTHER INFORMATION: may be modified by a 3IABkFQ quencher

<400> SEQUENCE: 26
actgctcgct tcagg                                                         15

<210> SEQ ID NO 27
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 27
aatgccagaa agcatgtgat ccgtc                                              25

<210> SEQ ID NO 28
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 28
tcctgccatt ccgtgatgta aggt                                               24

<210> SEQ ID NO 29
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (21)..(21)
<223> OTHER INFORMATION: may be modified by a 3IABkFQ quencher

<400> SEQUENCE: 29
```
cattgaaaga tatccggaac t                                              21

<210> SEQ ID NO 30
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 30
ctctgtaacc agacaggagt tg                                             22

<210> SEQ ID NO 31
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 31
ccggtgatac ccaaagaaga a                                              21

<210> SEQ ID NO 32
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (24)..(24)
<223> OTHER INFORMATION: may be modified by a 3IABkFQ quencher

<400> SEQUENCE: 32
cgtcgtgctg gatcggttga atct                                           24

<210> SEQ ID NO 33
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 33
gaaatcttac acacctattc agacc                                          25

<210> SEQ ID NO 34
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 34
atcatccatc tgctgttcca ggctc                                          25

<210> SEQ ID NO 35
<211> LENGTH: 19
<212> TYPE: DNA

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (19)..(19)
<223> OTHER INFORMATION: may be modified by a 3IABkFQ quencher

<400> SEQUENCE: 35
cataattatc cgcgtggcc                                                  19

<210> SEQ ID NO 36
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 36
ggcttgtgag ccctgatta                                                  19

<210> SEQ ID NO 37
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 37
gctatttggg agaatgtcct ttg                                             23

<210> SEQ ID NO 38
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (24)..(24)
<223> OTHER INFORMATION: may be modified by a 3IABkFQ quencher

<400> SEQUENCE: 38
aatctccaca ctttccgcag gtca                                            24

<210> SEQ ID NO 39
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 39
tttaatccat gggcctcctt ag                                              22
```

```
<210> SEQ ID NO 40
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 40
atgaggcaga gacggaaatg                                               20

<210> SEQ ID NO 41
<211> LENGTH: 25
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (25)..(25)
<223> OTHER INFORMATION: may be modified by a 3IABkFQ quencher

<400> SEQUENCE: 41
ccctttctgg cctgttctat tgcct                                         25

<210> SEQ ID NO 42
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 42
ctgatagacg aagaaggcgc atact                                         25

<210> SEQ ID NO 43
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 43
ttctccattt tccatcatcc tttca                                         25

<210> SEQ ID NO 44
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (18)..(18)
```

<223> OTHER INFORMATION: may be modified by a 3IABkFQ quencher

<400> SEQUENCE: 44
ctgtatggaa gggctgtt                                        18

<210> SEQ ID NO 45
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 45
ctgatagacg aagaaggcgc atact                                25

<210> SEQ ID NO 46
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 46
ttctccattt tccatcatcc tttca                                25

<210> SEQ ID NO 47
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (18)..(18)
<223> OTHER INFORMATION: may be modified by a 3IABkFQ quencher

<400> SEQUENCE: 47
ctgtatggaa gggctgtt                                        18

<210> SEQ ID NO 48
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 48
ccaaagcaaa tgttaacgga acta                                 24

<210> SEQ ID NO 49
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 49
tacagcagga gtttgtgtga tt                                   22

```
<210> SEQ ID NO 50
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (24)..(24)
<223> OTHER INFORMATION: may be modified by a 3IABkFQ quencher

<400> SEQUENCE: 50
actgccaatc tccaatcaat gcca                                          24

<210> SEQ ID NO 51
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 51
gttaacggaa ctacaatgct agaaa                                         25

<210> SEQ ID NO 52
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 52
tgtggaatct cagaccatta act                                           23

<210> SEQ ID NO 53
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (24)..(24)
<223> OTHER INFORMATION: may be modified by a 3IABkFQ quencher

<400> SEQUENCE: 53
actgccaatc tccaatcaat gcca                                          24

<210> SEQ ID NO 54
<211> LENGTH: 22
<212> TYPE: DNA
<213> ORGANISM: Artificial Sequence
<220> FEATURE:
<223> OTHER INFORMATION: Synthetic polynucleotide
```

```
<400> SEQUENCE: 54
atcaatccca tgactctctc cc                                              22

<210> SEQ ID NO 55
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 55
cctactgatg aaataataga aggaactc                                        28

<210> SEQ ID NO 56
<211> LENGTH: 29
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (29)..(29)
<223> OTHER INFORMATION: may be modified by a 3IABkFQ quencher

<400> SEQUENCE: 56
tcctccacgt aagtcatgac taagaagct                                       29

<210> SEQ ID NO 57
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 57
atcatccgct actccaaacc cgatt                                           25

<210> SEQ ID NO 58
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 58
gtgcgatggg gaggacgatt atgcc                                           25

<210> SEQ ID NO 59
<211> LENGTH: 13
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
```

```
<220> FEATURE:
<221> NAME/KEY: misc_feature
<222> LOCATION: (13)..(13)
<223> OTHER INFORMATION: may be modified by a 3IABkFQ quencher

<400> SEQUENCE: 59
cccgcataat tgc                                                         13

<210> SEQ ID NO 60
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 60
ctaccttctt tccgcctatt gt                                               22

<210> SEQ ID NO 61
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 61
ttgaggcggt tctcgtaaat aa                                               22

<210> SEQ ID NO 62
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (24)..(24)
<223> OTHER INFORMATION: may be modified by a 3IABkFQ quencher

<400> SEQUENCE: 62
tctgattcgg aataacggct ggcc                                             24

<210> SEQ ID NO 63
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 63
ctggttccgt gggcattta                                                   19

<210> SEQ ID NO 64
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 64
```
cgatgcctac catatcacat cc                                             22

<210> SEQ ID NO 65
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (24)..(24)
<223> OTHER INFORMATION: may be modified by a 3IABkFQ quencher

<400> SEQUENCE: 65
cggcatcgtt catcgcaaat tcca                                           24

<210> SEQ ID NO 66
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 66
ctgcgttctg ggtcagataa a                                              21

<210> SEQ ID NO 67
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 67
ccaaagcagt aagaggagga taaa                                           24

<210> SEQ ID NO 68
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (24)..(24)
<223> OTHER INFORMATION: may be modified by a 3IABkFQ quencher

<400> SEQUENCE: 68
tgtttcgcca ggctgttctg tact                                           24

<210> SEQ ID NO 69
<211> LENGTH: 25
<212> TYPE: DNA
<213> ORGANISM: Artificial Sequence

```
<220> FEATURE:
<223> OTHER INFORMATION: Synthetic polynucleotide

<400> SEQUENCE: 69
agggtgaagt ccaatgaaga tctcc                                              25

<210> SEQ ID NO 70
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 70
atacctccag aagcacacaa gggcc                                              25

<210> SEQ ID NO 71
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (17)..(17)
<223> OTHER INFORMATION: may be modified by a 3IABkFQ quencher

<400> SEQUENCE: 71
atcatggctc tgctacc                                                       17

<210> SEQ ID NO 72
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 72
ccgaatattg cgtccgtagt t                                                  21

<210> SEQ ID NO 73
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 73
taggtatatc acagccgtct ctc                                                23

<210> SEQ ID NO 74
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by 56-FAM fluorescent dye
<220> FEATURE:
```

```
<221> NAME/KEY: misc_feature
<222> LOCATION: (9)..(10)
<223> OTHER INFORMATION: may be modified by a ZEN moiety
<220> FEATURE:
<221> NAME/KEY: misc_feature
<222> LOCATION: (24)..(24)
<223> OTHER INFORMATION: may be modified by a 3IABkFQ quencher

<400> SEQUENCE: 74
tgttaatcac tcttgcgctc ggct                                              24
```

METHODS OF DECREASING DYSBIOSIS AND RESTORING A MICROBIOME

RELATED APPLICATIONS

This application is a national stage filing under 35 U.S.C. § 371 of international application number PCT/US2019/046926, filed Aug. 16, 2019, which was published under PCT Article 21(2) in English and claims the benefit under 35 U.S.C. § 119(e) of U.S. provisional application No. 62/765,165, filed Aug. 17, 2018; U.S. provisional application No. 62/724,185, filed Aug. 29, 2018; U.S. provisional application No. 62/815,395, filed Mar. 8, 2019; U.S. provisional application No. 62/829,513, filed Apr. 4, 2019; and U.S. provisional application No. 62/829,959, filed Apr. 5, 2019. The entire contents of each of these referenced applications are incorporated by reference herein.

GOVERNMENT SUPPORT

This invention was made with government support under Grant No. 4500002475 awarded by the U.S. Department of Health and Human Services Office of the Assistant Secretary for Preparedness and Response (HHS/ASPR). The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Feb. 16, 2021, is named P074570017US04-SEQ-CEW, and is 36,613 bytes in size.

FIELD OF INVENTION

The disclosure relates to methods for decreasing dysbiosis, restoring the microbiome, and/or increasing recovery of a microbiome (e.g., following a dysbiosis inducing event), by administering pharmaceutical compositions to a subject. Also provided are methods for protecting the microbiome of a subject and/or colonizing the microbiome of a subject by administering pharmaceutical compositions to the subject.

BACKGROUND OF THE INVENTION

The human intestinal microbiome comprises tens of trillions of bacteria from over 1000 identified species. The composition of an individual's microbiome is as unique as a fingerprint, with wide variety existing between even close relatives. The vast majority of species present in the human microbiome are commensals, which neither harm nor hurt the host. Numerous bacterial species which inhabit the human intestinal tract, including members of the taxa *Lactobacillus*, Firmicutes, and Bacteriodetes are symbionts which perform functions which benefit the human, such as the metabolism of food by-products into nutrients which can be absorbed. However, pathogenic bacterial species, such as strains of *Escherichia coli*, may also inhabit the human intestinal tract and may cause disease if allowed to overpopulate the human microbiome. Thus, the balance of bacterial species within the human microbiome is critical to maintaining overall human health.

Perturbations in the abundance of bacterial species within the human microbiome, reduction in bacterial diversity, and changes in the functional capacity of bacteria are indicative of microbiome dysbiosis, which may result from events such as infectious disease, recurrent and inappropriate treatment with antibiotics, and inflammation. Dysbioses occur when commensal or symbiotic bacterial species become underrepresented in the human microbiome, thereby allowing opportunistic, pathogenic species to become overrepresented. Conventional therapies for reversing dysbioses and restoring a microbiome include fecal matter transplants (FMTs). Although FMT may be effective for treating dysbioses, it lacks a standardized method for administering treatment and may poses a potential risk of in transplanting pathogens or allowing pathogen overgrowth before recovery occurs.

SUMMARY OF THE INVENTION

Aspects of the present disclosure provide methods for decreasing dysbiosis in a subject comprising administering to the subject a therapeutically effective amount of a pharmaceutical composition comprising one or more purified bacterial strains to decrease dysbiosis in a subject. In some embodiments, decreasing dysbiosis comprises an increase in the abundance of Bacteroides relative to the abundance of Bacteroides prior to administering the pharmaceutical composition. In some embodiments, the pharmaceutical composition does not include Bacteroides.

In some embodiments, decreasing dysbiosis comprises an increase in the abundance of Firmicutes relative to the abundance of Firmicutes prior to administering the pharmaceutical composition. In some embodiments, decreasing dysbiosis comprises an increase in the abundance of bacterial strains belonging to *Clostridium* cluster IV and/or XIVa relative to the abundance of bacterial strains belonging to *Clostridium* cluster IV and/or XIVa prior to administering the pharmaceutical composition. In some embodiments, decreasing dysbiosis comprises an increase in the abundance of bacterial strains belonging to *Clostridium* cluster XVII relative to the abundance of bacterial strains belonging to *Clostridium* cluster XVII prior to administering the pharmaceutical composition.

In some embodiments, decreasing dysbiosis comprises a decrease in the abundance of microorganisms associated with inflammation relative to the abundance of microorganisms associated with inflammation prior to administering the pharmaceutical composition. In some embodiments, decreasing dysbiosis comprises a decrease in the abundance of Proteobacteria relative to the abundance of Proteobacteria prior to administering the pharmaceutical composition. In some embodiments, decreasing dysbiosis is not correlated with a proportional increase in microbiome diversity of the subject.

Aspects of the present disclosure provide methods for restoring the microbiome in a subject comprising administering to the subject a therapeutically effective amount of a pharmaceutical composition comprising one or more purified bacterial strains to restore the microbiome in the subject. In some embodiments, the subject has not undergone a dysbiosis inducing event. In some embodiments, the subject has not had an infectious disease. In some embodiments, the subject has not had a *Clostridium difficile* infection. In some embodiments, the subject has not been treated with an antibiotic.

Aspects of the present disclosure provide methods for increasing the recovery of a healthy microbiome in a subject after a dysbiosis inducing event comprising administering to the subject a therapeutically effective amount of a pharmaceutical composition comprising one or more purified bacterial strains to increase the recovery of a healthy microbiome.

In some embodiments, the dysbiosis inducing event is treatment with one or more antibiotics. In some embodiments, the dysbiosis inducing even is treatment with one or more antibiotics in connection with surgery. In some embodiments, the antibiotic is vancomycin.

In some embodiments, the dysbiosis inducing even is an infectious disease. In some embodiments, the dysbiosis inducing event is infection by *Clostridium difficile*. In some embodiments, the dysbiosis inducing event is a primary infection by *Clostridium difficile*. In some embodiments, the dysbiosis inducing even is a secondary or recurring infection by *Clostridium difficile*. In some embodiments, the dysbiosis inducing event is traveler's diarrhea.

In some embodiments, the recovery of a microbiome in a subject occurs without detectable colonization of the bacterial strains of the pharmaceutical composition. In some embodiments, the recovery of the microbiome is increased relative to recovery of the healthy microbiome in the absence of administration of the pharmaceutical composition. In some embodiments, the recovery of the microbiome is increased relative to the recovery of the microbiome in a subject who has undergone a fecal matter transplant.

Aspects of the present disclosure provide methods for protecting a microbiome in a subject comprising administering to the subject a therapeutically effective amount of a pharmaceutical composition comprising one or more purified bacterial strains to protect the microbiome. In some embodiments, the microbiome is protected against antibiotic treatment. In some embodiments, the microbiome is protected against attack by an infectious agent. In some embodiments, the microbiome is protected against *Clostridium difficile* infection. In some embodiments, the microbiome is protect against a secondary or recurring *Clostridium difficile* infection.

Aspects of the present disclosure provide methods for colonizing a microbiome of a subject comprising administering to the subject a therapeutically effective amount of a pharmaceutical composition comprising one or more purified bacterial strains to colonize the microbiome. In some embodiments, at least 25% of the bacterial strains of the pharmaceutical composition colonize the microbiome of the subject. In some embodiments, at least 50% of the bacterial strains of the pharmaceutical composition colonize the microbiome of the subject. In some embodiments, 100% of the bacterial strains of the pharmaceutical composition colonize the microbiome of the subject.

In some embodiments, after administration, at least 25% of bacterial strains in the microbiome of the subject are the bacterial strains of the pharmaceutical composition. In some embodiments, after administration, at least 50% of bacterial strains in the microbiome of the subject are the bacterial strains of the pharmaceutical composition.

In some embodiments, one or more bacterial strains are detected in the microbiome at least four weeks after initial administration of the pharmaceutical composition. In some embodiments, one or more bacterial strains are detected in the microbiome at least six weeks after initial administration of the pharmaceutical composition. In some embodiments, one or more bacterial strains are detected in the microbiome at least twelve weeks after initial administration of the pharmaceutical composition. In some embodiments, one or more bacterial strains are detected in the microbiome at least six months after initial administration of the pharmaceutical composition. In some embodiments, one or more bacterial strains are detected in the microbiome at least twelve months after initial administration of the pharmaceutical composition.

Aspects of the present disclosure provide methods for colonizing a microbiome in a subject comprising administering to the subject an antibiotic followed by the administration of a therapeutically effective amount of a pharmaceutical composition comprising one or more bacterial strains to colonize the microbiome. In some embodiments, each of the bacterial strains of the bacterial composition colonizes the microbiome.

Aspects of the present disclosure provide methods for treating *C. difficile* infection in a subject, comprising administering to the subject a therapeutically effective amount of a pharmaceutical composition comprising one or more purified bacterial strains to treat the *C. difficile* infection. In some embodiments, wherein the *C. difficile* infection is a primary *C. difficile* infection or a recurrent *C. difficile* infection.

Aspects of the present disclosure provide methods for treating a food allergy in a subject, comprising administering to the subject a therapeutically effective amount of a pharmaceutical composition comprising one or more purified bacterial strains to treat the food allergy. In some embodiments, the composition suppresses the production of IgE antibodies. In some embodiments, the composition suppresses one or more Th2 immune response. In some embodiments, the composition suppresses one or more mast cell function and/or mast cell degranulation. In some embodiments, the composition modulates an immune response associated with a food allergy.

In some embodiments, the bacterial strains of the pharmaceutical composition colonize the microbiome over an extended period of time. In some embodiments, the antibiotic is vancomycin. In some embodiments, the pharmaceutical composition is administered as a single dose. In some embodiments, the pharmaceutical composition is administered in multiple doses. In some embodiments, the one or more bacterial strains comprise on or more *Clostridium difficile*-suppressing strains. In some embodiments, the pharmaceutical composition is administered to a subject in a therapeutically effective amount comprising one or more bacterial strains to colonize the microbiome to treat Graft versus Host Disease (GvHD).

In some embodiments, the pharmaceutical composition comprises one or more bacterial strains belonging to *Clostridium* clusters IV, XIVa, and XVII. In some embodiments, the pharmaceutical composition comprises one or more bacterial strains belonging to each of *Clostridium* clusters IV, XIVa, and XVII. In some embodiments, the pharmaceutical composition comprises the bacterial strain *Dorea longicatena*. In some embodiments, the pharmaceutical composition consists of the bacterial strain *Dorea longicatena*. In some embodiments, the pharmaceutical composition comprises a 16S rDNA sequence of at least 97% sequence identity to the nucleic acid sequence set forth as SEQ ID NO: 6. In some embodiments, the pharmaceutical composition consists of a single bacterial strain comprising a 16S rDNA sequence of at least 97% sequence identity to the nucleic acid sequence set forth as SEQ ID NO: 6. In some embodiments, the pharmaceutical composition comprises at least 50% bacterial strains belonging to *Clostridium* cluster XIVa. In some embodiments, the pharmaceutical composition comprises at least 75% bacterial strains belonging to *Clostridium* clusters IV and/or XIVa. In some embodiments, the pharmaceutical composition comprises *Clostridium bolteae, Anaerotruncus colihominis, Eubacterium fissicatena, Clostridium symbiosum, Blautia producta,*

*Dorea longicatena*, *Clostridium innocuum*, and *Flavonifractor plautii*. In some embodiments, the pharmaceutical composition consists of *Clostridium bolteae*, *Anaerotruncus colihominis*, *Eubacterium fissicatena*, *Clostridium symbiosum*, *Blautia producta*, *Dorea longicatena*, *Clostridium innocuum*, and *Flavonifractor plautii*. In some embodiments, the pharmaceutical composition comprises a purified bacterial mixture consisting of bacterial strains that comprise 16S rDNA sequences of at least 97% sequence identity to the sequence set forth as SEQ ID NO:1, SEQ ID NO:2, SEQ ID NO:3, SEQ ID NO:4, SEQ ID NO:5, SEQ ID NO:6, SEQ ID NO:7, and SEQ ID NO:8. In some embodiments, the pharmaceutical composition consists of a purified bacterial mixture consisting of bacterial strains that comprises 16S rDNA sequences of at least 97% sequence identity to the nucleic acid sequences set forth as SEQ ID NO:1, SEQ ID NO:2, SEQ ID NO:3, SEQ ID NO:4, SEQ ID NO:5, SEQ ID NO:6, SEQ ID NO:7, and SEQ ID NO:8.

In some embodiments, the pharmaceutical composition comprises *Clostridium bolteae*, *Anaerotruncus colihominis*, *Eubacterium fissicatena*, *Clostridium symbiosum*, *Blautia producta*, *Clostridium innocuum*, and *Flavonifractor plautii*. In some embodiments, the pharmaceutical composition consists of *Clostridium bolteae*, *Anaerotruncus colihominis*, *Eubacterium fissicatena*, *Clostridium symbiosum*, *Blautia producta*, *Clostridium innocuum*, and *Flavonifractor plautii*. In some embodiments, the pharmaceutical composition comprises a purified bacterial mixture consisting of bacterial strains that comprise 16S rDNA sequences of at least 97% sequence identity to the nucleic acid sequences set forth as SEQ ID NO:1, SEQ ID NO:2, SEQ ID NO:3, SEQ ID NO:4, SEQ ID NO:5, SEQ ID NO:7, and SEQ ID NO:8. In some embodiments, the pharmaceutical composition consists of a purified bacterial mixture consisting of bacterial strains that comprise 16S rDNA sequences of at least 97% sequence identity to the nucleic acid sequences set forth as SEQ ID NO:1, SEQ ID NO:2, SEQ ID NO:3, SEQ ID NO:4, SEQ ID NO:5, SEQ ID NO:7, and SEQ ID NO:8.

In some embodiments, the pharmaceutical composition comprises a purified bacterial mixture comprising *Clostridium saccharogumia* (*Clostridium ramosum* JCM 1298), *Flavonifractor plautii* (*Pseudoflavonifractor capillosus* ATCC 29799), *Clostridium hathewayi* (*Clostridium saccharolyticum* WM1), *Blautia coccoides* (*Lachnospiraceae bacterium* 6_1_63FAA), *Clostridium spp.* (*Clostridium bolteae* ATCC BAA-613), cf. *Clostridium sp.* MLG055 (*Erysipelotrichaceae bacterium* 2_2_44A), *Clostridium indolis* (*Anaerostipes caccae* DSM 14662), *Anaerotruncus colihominis* (*Anaerotruncus colihominis* DSM 17241), *Ruminococcus* sp. ID8 (*Lachnospiraceae bacterium* 2_1_46FAA), *Clostridium lavalense* (*Clostridium asparagiforme* DSM 15981), *Clostridium symbiosum* (*Clostridium symbiosum* WAL-14163), *Clostridium ramosum*, *Eubacterium contortum* (*Clostridium sp.* D5), *Clostridium scindens* (*Lachnospiraceae bacterium* 5_1_57FAA), *Lachnospiraceae bacterium* A4 (*Lachnospiraceae bacterium* 3_1_57FAA_CT1), *Clostridium* sp. 316002/08 (*Clostriales bacterium* 1_7_47FAA), *Lachnospiraceae bacterium* A4 (*Lachnospiraceae bacterium* 3_1_57FAA_CT1). In some embodiments, the pharmaceutical composition consists of a purified bacterial mixture comprising *Clostridium saccharogumia* (*Clostridium ramosum* JCM 1298), *Flavonifractor plautii* (*Pseudoflavonifractor capillosus* ATCC 29799), *Clostridium hathewayi* (*Clostridium saccharolyticum* WM1), *Blautia coccoides* (*Lachnospiraceae bacterium* 6_1_63FAA), *Clostridium spp.* (*Clostridium bolteae* ATCC BAA-613), cf. *Clostridium sp.* MLG055 (*Erysipelotrichaceae bacterium* 2_2_44A), *Clostridium indolis* (*Anaerostipes caccae* DSM 14662), *Anaerotruncus colihominis* (*Anaerotruncus colihominis* DSM 17241), *Ruminococcus* sp. ID8 (*Lachnospiraceae bacterium* 2_1_46FAA), *Clostridium lavalense* (*Clostridium asparagiforme* DSM 15981), *Clostridium symbiosum* (*Clostridium symbiosum* WAL-14163), *Clostridium ramosum*, *Eubacterium contortum* (*Clostridium sp.* D5), *Clostridium scindens* (*Lachnospiraceae bacterium* 5_1_57FAA), *Lachnospiraceae bacterium* A4 (*Lachnospiraceae bacterium* 3_1_57FAA_CT1), *Clostridium* sp. 316002/08 (*Clostriales bacterium* 1_7_47FAA), *Lachnospiraceae bacterium* A4 (*Lachnospiraceae bacterium* 3_1_57FAA_CT1).

In some embodiments, the pharmaceutical composition comprises at least $1.6 \times 10^9$ CFUs (colony forming units). In some embodiments, the pharmaceutical composition comprises at least $4.0 \times 10^9$ CFUs (colony forming units). In some embodiments, the pharmaceutical composition comprises at least $8.0 \times 10^9$ CFUs (colony forming units). In some embodiments, the pharmaceutical composition comprises at least $4.0 \times 10^{10}$ CFUs (colony forming units). In some embodiments, the pharmaceutical composition comprises at least $1.1 \times 10^{11}$ CFUs (colony forming units). In some embodiments, the pharmaceutical composition comprises at least $1.1 \times 10^{17}$ CFUs (colony forming units).

In some embodiments, the pharmaceutical composition is administered as one dose. In some embodiments, the pharmaceutical composition is administered as multiple doses. In some embodiments, each dose comprises the administration of multiple capsules. In some embodiments, each capsule comprises at least $8.0 \times 10^8$ CFUs (colony forming units). In some embodiments, each capsule comprises at least $1.6 \times 10^9$ CFUs (colony forming units).

In some embodiments, the pharmaceutical composition comprises at least $1.6 \times 10^9$ CFUs (colony forming units) and is administered as a single dose. In some embodiments, the pharmaceutical composition comprises at least $4.0 \times 10^{10}$ CFUs (colony forming units) and is administered as a single dose. In some embodiments, the pharmaceutical composition comprises at least $8.0 \times 10^9$ CFUs (colony forming units) and is administered as a single dose. In some embodiments, the pharmaceutical composition comprises at least $4.0 \times 10^{10}$ CFUs (colony forming units) and is administered as multiple doses. In some embodiments, the pharmaceutical composition comprises at least $4.0 \times 10^{10}$ CFUs (colony forming units) and is administered as five doses. In some embodiments, the pharmaceutical composition comprises at least $2.8 \times 10^{10}$ CFUs (colony forming units) and is administered as multiple doses. In some embodiments, the pharmaceutical composition comprises at least $2.8 \times 10^{10}$ CFUs (colony forming units) and is administered as seven doses. In some embodiments, the pharmaceutical composition comprises at least $5.6 \times 10^{10}$ CFUs (colony forming units) and is administered as multiple doses. In some embodiments, the pharmaceutical composition comprises at least $5.6 \times 10^{10}$ CFUs (colony forming units) and is administered as fourteen doses. In some embodiments, the pharmaceutical composition comprises at least $1.1 \times 10^{11}$ CFUs (colony forming units) and is administered as multiple doses. In some embodiments, the pharmaceutical composition comprises at least $1.1 \times 10^{11}$ CFUs (colony forming units) and is administered as fourteen doses. In some embodiments, the pharmaceutical composition comprises at least $1.1 \times 10^{17}$ CFUs (colony forming units) and is administered as multiple doses. In some embodiments, the pharmaceutical composition comprises at least $1.1 \times 10^{17}$ CFUs (colony forming units) and is administered as fourteen doses.

In some embodiments, the multiple doses are administered on consecutive days. In some embodiments, the method comprises one or more additional administrations of the pharmaceutical composition. In some embodiments, the one or more additional administrations of the pharmaceutical compositions comprises fewer CFUs (colony forming units) as compared to the initial administration of the pharmaceutical composition.

In some embodiments, the one or more additional administrations of the pharmaceutical composition are performed on consecutive days following the initial administration of the pharmaceutical composition. In some embodiments, the one or more additional administrations of the pharmaceutical composition are performed at least six weeks following the initial administration of the pharmaceutical composition. In some embodiments, the one or more additional administrations of the pharmaceutical composition are performed at least twelve weeks following the initial administration of the pharmaceutical composition.

In some embodiments, the pharmaceutical composition comprises at least $2.1 \times 10^{10}$ CFUs (colony forming units). In some embodiments, the pharmaceutical composition is administered in multiple doses. In some embodiments, the pharmaceutical composition is administered in five doses.

In some embodiments, the pharmaceutical composition is administered on five consecutive days. In some embodiments, the pharmaceutical composition is administered as two high doses followed by three low doses. In some embodiments, the high dose is $8.0 \times 10^9$ CFUs (colony forming units). In some embodiments, the low dose is $1.6 \times 10^9$ CFUs (colony forming units). In some embodiments, the pharmaceutical composition is administered as two doses of $8.0 \times 10^9$ CFUs (colony forming units) followed by three doses of $1.6 \times 10^9$ CFUs (colony forming units). In some embodiments, administration of the pharmaceutical composition is not preceded by administration of an antibiotic. In some embodiments, administration of the pharmaceutical composition is not preceded by administration of vancomycin.

In some embodiments, the method further comprises administering an antibiotic to the subject prior to administration of the pharmaceutical composition. In some embodiments, the antibiotic is vancomycin, metronidazole, fidaxomycin, or ridinilazole. In some embodiments, the antibiotic is vancomycin. In some embodiments, the vancomycin is administered at 500 mg per day. In some embodiments, the vancomycin is administered in 4 doses of 125 mg per day. In some embodiments, the vancomycin is administered at 250 mg per day. In some embodiments, the vancomycin is administered in 2 doses of 125 mg per day. In some embodiments, the vancomycin is administered at 125 mg per day.

In some embodiments, the vancomycin is administered for five consecutive days. In some embodiments, the vancomycin is administered for three consecutive days. In some embodiments, the vancomycin is administered for one day. In some embodiments, the vancomycin is administered one day immediately prior to the administration of the pharmaceutical composition.

In some embodiments, 250 mg of vancomycin is administered two days prior to the day of the administration of the pharmaceutical composition, wherein the method includes a washout day prior to the day of administration of the pharmaceutical composition. In some embodiments, 250 mg of vancomycin is administered on three consecutive days immediately prior to the day of the administration of the pharmaceutical composition.

In some embodiments, 500 mg of vancomycin is administered on five consecutive days immediately prior to the day of the administration of the pharmaceutical composition. In some embodiments, 500 mg of vancomycin is administered on five consecutive days up to two days prior to the day of the administration of the pharmaceutical compositions, wherein the method includes a washout day one day prior to the day of administration of the pharmaceutical composition.

In some embodiments, the one or more bacterial strains are lyophilized. In some embodiments, the one or more bacterial strains are spray-dried. In some embodiments, the one or more bacterial strains are in spore form. In some embodiments, each of the one or more bacterial strains are in spore form. In some embodiments, the one or more bacterial strains are in vegetative form. In some embodiments, each of the one or more bacterial strains are in vegetative form.

In some embodiments, the pharmaceutical composition further comprises one or more enteric polymers. In some embodiments, the administration is oral administration. In some embodiments, the pharmaceutical composition is formulation for oral delivery. In some embodiments, the pharmaceutical composition is formulated for rectal delivery. In some embodiments, the pharmaceutical composition is formulated for delivery to the intestine. In some embodiments, the pharmaceutical composition is formulated for delivery to the colon.

Aspects of the present disclosure provide methods for reducing the levels of primary bile acids comprising administering to a subject in need thereof a therapeutically effective amount of the pharmaceutical compositions described herein. In some embodiments, the primary bile acid is the primary bile acid is glycochenodeoxycholic acid, glycocholic acid or taurocholic acid. In some embodiments, the levels of primary bile acids are reduced by 10-fold to 100,000-fold. In some embodiments, the subject has a *Clostridium difficile* infection, optionally wherein the *Clostridium difficile* infection is recurrent. In some embodiments, the methods further comprise administering an antibiotic to the subject prior to the administration of the pharmaceutical composition by any of the methods described herein.

Aspects of the present disclosure provide methods for increasing the levels of secondary bile acids comprising administering to a subject in need thereof a therapeutically effective amount of the pharmaceutical compositions described herein. In some embodiments, the secondary bile acid is deoxycholic acid, litocholic acid or ursodeoxycholic acid. In some embodiments, the levels of secondary bile acids are increased by 10-fold to 1,000-fold. In some embodiments, the subject has a *Clostridium difficile* infection, optionally wherein the *Clostridium difficile* infection is recurrent. In some embodiments, the subject has a disease characterized by increased levels of primary bile acids or decreased levels of secondary bile acids. In some embodiments, the disease characterized by increased levels of primary bile acids or decreased levels of secondary bile acids is selected from the group consisting of IBD, IBS, infection by a pathogen, food allergy, a metabolic disease, and cardiovascular disease. In some embodiments, the methods further comprise administering an antibiotic to the subject prior to the administration of the pharmaceutical composition by any of the methods described herein.

Aspects of the present disclosure provide methods for increasing the levels of short chain fatty acids comprising administering to a subject in need thereof a therapeutically effective amount of the pharmaceutical compositions described herein. In some embodiments, the short chain fatty acids is acetate, propionate, butyrate or valerate. In some embodiments, the levels of short chain fatty acids are increased by 2-fold to 500-fold. In some embodiments, the subject has a *Clostridium difficile* infection, optionally wherein the *Clostridium difficile* infection is recurrent. In some embodiments, the subject has a disease characterized by decreased levels of short chain fatty amino acids. In some embodiments, the disease characterized by decreased levels of short chain fatty amino acids is selected from the group consisting of IBD, IBS, infection by a pathogen, food allergy, a metabolic disease, and cardiovascular disease. In some embodiments, the methods further comprise administering an antibiotic to the subject prior to the administration of the pharmaceutical composition by any of the methods described herein.

Aspects of the present disclosure provide methods for assessing colonization of one or more bacterial strains of a bacterial composition in a microbiome of a subject. In some embodiments, the methods comprise isolating nucleic acid from a sample of the microbiome of the subject, sequencing the isolated nucleic acid to obtain a plurality of nucleotide sequences of the isolated nucleic acid, and determining the presence of at least one bacterial strain of the bacterial composition by comparing the plurality of nucleotide sequences to a plurality of genomic markers for each bacterial strain of the bacterial composition. In some embodiments, if a genomic marker for a bacterial strain is present in the plurality of nucleotide sequences, the microbiome is colonized with the bacterial strain. In some embodiments, when the one or more of the bacterial strains of the bacterial composition is not present in the plurality of nucleotides sequences, the method further comprises administering one or more additional doses of the bacterial composition to the subject.

In some embodiments, the subject was previously administered one or more doses of the bacterial composition. In some embodiments, the sample of the microbiome is a fecal sample obtained from the subject. In some embodiments, the sequencing is DNA sequencing.

In some embodiments, the plurality of genomic markers comprises between 200 to 1000 nucleotide sequences for each bacterial strain of the bacterial composition. In some embodiments, the plurality of genomic markers comprises about 50 nucleotides.

In some embodiments, the bacterial composition comprises a purified bacterial mixture consisting of bacterial strains that comprise 16S rDNA sequences of at least 97% sequence identity to the nucleic acid sequences set forth as SEQ ID NO:1, SEQ ID NO:2, SEQ ID NO:3, SEQ ID NO:4, SEQ ID NO:5, SEQ ID NO:6, SEQ ID NO:7, and SEQ ID NO:8. In some embodiments, the bacterial composition comprises *Clostridium bolteae, Anaerotruncus colihominis, Eubacterium fissicatena, Clostridium symbiosum, Blautia producta, Dorea longicatena, Clostridium innocuum,* and *Flavonifractor plautii.*

In some embodiments, if a genomic marker for a bacterial strain is absent in the plurality of nucleotide sequences, the method further comprises administering one or more additional doses of the bacterial composition to the subject.

Aspects of the present disclosure provide methods for assessing colonization of one or more bacterial strains of a bacterial composition in a microbiome of a subject comprising isolating nucleic acid from a sample of the microbiome of the subject and determining the presence of at least one bacterial strain of the bacterial composition by amplifying a nucleotide sequence of a genomic marker for the at least one the bacterial strains in the isolated nucleic acid. In some embodiments, if a genomic marker for a bacterial strain is present in the amplified nucleotide sequences, the microbiome is colonized with the bacterial strain.

In some embodiments, amplifying comprises performing one or more quantitative polymerase chain reactions (qPCR). In some embodiments, the qPCR is performed using one or more pair of primers, wherein each pair of primers comprises a forward primer and a reverse primer for amplifying the nucleotide sequence of the genomic marker of bacterial strain.

In some embodiments, the methods further comprise selecting a pair of primers comprising a forward primer and a reverse primer for amplifying the nucleotide sequence of the genomic marker of bacterial strain. In some embodiments, the pair of primers for amplifying the nucleotide sequence of the genomic marker of comprises the forward primer set forth in SEQ ID NO: 9 and the reverse primer set forth in SEQ ID NO: 10. In some embodiments, the pair of primers for amplifying the nucleotide sequence of the genomic marker of comprises the forward primer set forth in SEQ ID NO: 12 and the reverse primer set forth in SEQ ID NO: 13. In some embodiments, the pair of primers for amplifying the nucleotide sequence of the genomic marker of comprises the forward primer set forth in SEQ ID NO: 15 and the reverse primer set forth in SEQ ID NO: 16. In some embodiments, the pair of primers for amplifying the nucleotide sequence of the genomic marker of comprises the forward primer set forth in SEQ ID NO: 18 and the reverse primer set forth in SEQ ID NO: 19. In some embodiments, the pair of primers for amplifying the nucleotide sequence of the genomic marker of comprises the forward primer set forth in SEQ ID NO: 21 and the reverse primer set forth in SEQ ID NO: 22. In some embodiments, the pair of primers for amplifying the nucleotide sequence of the genomic marker of comprises the forward primer set forth in SEQ ID NO: 24 and the reverse primer set forth in SEQ ID NO: 25. In some embodiments, the pair of primers for amplifying the nucleotide sequence of the genomic marker of comprises the forward primer set forth in SEQ ID NO: 27 and the reverse primer set forth in SEQ ID NO: 28. In some embodiments, the pair of primers for amplifying the nucleotide sequence of the genomic marker of comprises the forward primer set forth in SEQ ID NO: 30 and the reverse primer set forth in SEQ ID NO: 31.

In some embodiments, the qPCR reaction further comprises a DNA probe. In some embodiments, the DNA probe comprises a fluorophore and at least one quencher. In some embodiments, the DNA probe comprises a sequence set forth in SEQ ID NO: 11, SEQ ID NO: 14, SEQ ID NO: 17, SEQ ID NO: 20, SEQ ID NO: 23, SEQ ID NO: 26, SEQ ID NO: 29, and/or SEQ ID NO: 32.

In some embodiments, if a genomic marker for a bacterial strain is absent in the amplified nucleotide sequences, the method further comprises administering one or more additional doses of the bacterial composition to the subject.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing. In the drawings:

FIG. 2A shows the abundance of bacterial taxa belonging to Clostridium clusters IV and XIVa after fecal matter transplant (FMT) transfer (see, van Nood, et al., N. Engl. J. Med. (2013) 368: 407-415). "rCDI-pre" refers to recurrent C. difficile infection prior to FMT transfer, "rCDI-post" refers to recurrent C. difficile infection after FMT transfer. FIG. 2B shows the abundance of bacterial strains belonging to Clostridium clusters IV, XIVa, and XVII following administration of composition VE303. For each time point the data are presented, from left to right: vancomycin ("Vanco"), Sentinel/Cohort 1, Cohort 2, Cohort 3, Cohort 4, and Cohort 5.

FIG. 3A shows the relative abundance of bacterial phyla prior to and following FMT transfer (see, Smilie, et al., Cell Host Microbe (2018) 23(2): 229-240). FIG. 3B shows the relative abundance of bacterial phyla prior to (baseline), after administration of vancomycin, and after administration of composition VE303. FIGS. 3C and 3D show the abundance of Bacteriodetes (FIG. 3C) and Proteobacteria (FIG. 3D) in each cohort ("Coh") or vancomycin control ("Vanco") either less than one week following administration with composition VE303 or greater than one week administration with composition VE303.

FIG. 4A shows microbial communities for all cohorts at baseline, following administration of vancomycin, less than one week following administration of composition VE303 (recovery), and greater than one week following administration of composition VE303. FIG. 4B shows microbial communities for Cohort 5 at baseline, following administration of vancomycin, less than one week following administration of composition VE303 (recovery), and greater than one week following administration of composition VE303. FIG. 4C shows the change in bacterial species present in the microbiota at baseline, following administration of vancomycin, less than one week following administration of composition VE303 (recovery), and greater than one week following administration of composition VE303 (recovery).

FIGS. 7A-7B show the number of bacterial strains of composition VE303 detected in the microbiota of subjects (A-N) in Cohorts 4 and 5. FIG. 7C shows the number of bacterial strains of composition VE303 detected in the microbiota of subjects (O-S) in the control cohort that did not receive vancomycin. For each time point, the bacterial strains of composition VE303 are shown, from top to bottom: VE303-1, VE303-2, VE303-3, VE303-4, VE303-5, VE303-6, VE303-7, VE303-8. The shaded region indicated by "*" shows the time of vancomycin administration. The region indicated by "#" shows the time of composition VE303 administration.

FIG. 8 summarizes the bacterial strains of composition VE303 detected in the microbiota of the total number of subjects one week following administration of composition VE303 (e.g., in Cohort 3, the VE303-01 strain is found in 2 out of 3 subjects). An asterisk (*) indicates strains detected in each subject are after background levels were subtracted.

FIGS. 9A-9E show the relative abundance and durability of engraftment of bacterial strains of composition VE303 in the microbiome of each individual subject in each cohort. FIG. 9A shows the overall abundance of each of the bacterial strains of composition VE303 in each individual subject in each cohort. For each subject, the bacterial strains of composition VE303 are shown, from top to bottom: VE303-1, VE303-2, VE303-3, VE303-4, VE303-5, VE303-6, VE303-7, VE303-8. FIGS. 9B-9C show the total abundance of bacterial strains of composition VE303 per cohort and over time and a summary table. FIGS. 9D-9E show durable engraftment (See also FIGS. 6A-6D).

FIGS. 11A-11C show the relative abundance of bacterial strains of composition VE303 strains in subjects in cohorts 4 and 5. FIGS. 11A-11B present plots showing the relative abundance of bacterial strains of composition VE303 in Cohorts 4 and 5 over time. FIG. 11C shows a summary table of the relative abundance of bacterial strains of composition VE303 at about 4 weeks.

FIG. 13A shows a clustered heatmap of the top bacterial genera associated with recurrent Clostridium difficile infection (rCDI) recovery post fecal microbiota transplantation (FMT). Healthy donor and rCDI patient stools were collected in collaboration with the Leiden University Medical Center (LUMC) and the Netherlands Donor Feces Bank (NDFB). Response to FMT is associated with transfer of Clostridium clusters IV and XIVa. FIG. 13B shows Kaplan-Meyer plots illustrating the survival of mice that were administered the VE303 composition, human FMT, or vancomycin. For comparison, mice administered phosphate-buffered saline (PBS) or negative live biotherapeutic products (Neg. LBPs) died of Clostridium difficile infection.

FIGS. 17A-17D show the pharmacokinetics (PK) of VE303 in normal healthy volunteers. FIG. 17A shows the number of VE303 strains detected in each normal healthy volunteer subject over time. FIG. 17B shows the percent of subjects colonized with each strain is indicated, with values greater than the median highlighted. All 8 VE303 strains were detected in nearly all Cohort 4 and 5 subjects. FIG. 17C shows the total abundance of the VE303 consortium in each subject over time for all data points (top panel) and a subset of the data points (bottom panel). FIG. 17D shows the median abundance per VE303 strain, with values greater than the median highlighted.

FIG. 19A shows the number of VE303 strains detected in the microbiota of a subject treated with vancomycin (vanco) only and a subject treated with vancomycin followed by VE303. FIG. 19B shows the percent abundance of each VE303 strain detected in the microbiota of the subject treated with vancomycin only and the subject treated with vancomycin followed by VE303. For each time point, the bacterial strains of composition VE303 are shown, from top to bottom: VE303-1, VE303-2, VE303-3, VE303-4, VE303-5, VE303-6, VE303-7, VE303-8. The shaded region indicated by "*" shows the time of vancomycin administration. The region indicated by "#" shows the time of composition VE303 administration.

FIG. 28 illustrates how an antibiotic-disturbed gut can be returned to health by treatment with VE303.

FIGS. 34A and 34B show the results of a linear mixed effects model analysis for the association of VE303 treatment with bile acid production. VE303 is significantly associated with the recovery of secondary bile acids and the reduction of primary bile acids.

FIGS. 39A and 39B show the results of a linear mixed effects model analysis for the association of VE303 treatment with short chain fatty acid (SCFA) recovery. VE303 is significantly associated with the recovery of acetate, butyrate and propionate.

FIGS. 41A-41C show the VE303 species and resident microbes that are important for short chain fatty acid (SCFA) recovery. VE303 group A strains (VE303-01, VE303-02, VE303-06, VE303-07) are positively associated with hexanoate recovery and VE303 group B strains (VE303-03, VE303-04, VE303-08) are positively associated with propionate recovery.

FIG. 45A depicts the total number of bacterial strains of composition VE303 detected in the microbiota of the subject populations. FIG. 45B depicts the relative abundance of the total VE303 strains in the microbiota of the subject population. The top row in FIG. 45B includes all data points and the bottom row is zoomed in to the points below the dashed line in the top row. Vancomycin ("Vanco"): 0 CFU; Cohort 1: $1.6 \times 10^9$ CFU (1 day); Cohort 2: $4.0 \times 10^9$ CFU (1 day); Cohort 3: $8.0 \times 10^9$ CFU (1 day); Cohort 4: $4.0 \times 10^{10}$ CFU (5 days); Cohort 5: $1.1 \times 10^{11}$ CFU (14 days); Cohort 6: $1.7 \times 10^{11}$ CFU (21 days). D6 is day 6; D6-D11 is days 6-11; D0-20 is days 0-20 of VE303 treatment. The median (+/−interquartile range and 95% confidence) is plotted for each cohort. The day of VE303 administration is indicated for each cohort with an arrow.

FIGS. 46A-46E show the microbiota pharmacodynamics of VE303 administration. FIG. 46A shows the relative abundance of bacterial phyla at baseline (to the left of the dashed box), after administration of vancomycin (dashed box), and during recovery after vancomycin administration (to the right of the dashed box). Each bar corresponds to the bacterial relative abundance at a single time point in one subject and are increasing order by time. D6 is day 6; D6-D11 is days 6-11; D0-20 is days 0-20 of VE303 treatment. FIG. 46B shows the microbiome index (MI) according to the time point in treatment (see Equation 4 in Example 11). "Baseline" corresponds to the starting community, "Vanco" corresponds to days 4-6; "Early recovery" corresponds to days 7-13 of the study (or 1 week post-vancomycin treatment with or without VE303); "Late recovery" corresponds to days greater than or equal to 14; "Early no vanco" corresponds to days 1-7 (or 1 week post VE303 for Cohort 6 only); and "Late no vanco" corresponds to days greater than or equal to 8 for Cohort 6 only. The MI is plotted on a log$_{10}$ scale. FIG. 46C shows the abundance (%) of Bacteroidetes (left panel) and Proteobacteria (right panel) in each cohort or vancomycin control during the "early recovery" time points for each cohort. FIG. 46D shows the microbiota response (as measured by MI) at increasing VE303 doses during "early recovery" time points. FIG. 46E shows the microbiota response (as measured by MI) at increasing VE303 doses during "early recovery" and "late recovery" time points. The mean+/−standard error is indicated.

FIG. 47A shows the relative abundance of bile acids measured in the stool of healthy volunteers at baseline, after vancomycin administration (inside dashed box), or during the recovery period after vancomycin administration. Each bar corresponds to the relative bile acid abundance at a single time point in one subject. "Vanco" is vancomycin; "BA" is bile acid; D6 is day 6; D6-D11 is days 6-11; and D0-20 is days 0-20 of VE303 treatment. FIG. 47B shows the bile acid index (BAI) (see Equation 3 5 in Example 11). "Baseline" is the starting community; "Vanco" is days 4-6; "Early recovery" corresponds to days 7-13 of the study (or 1 week post vancomycin treatment with or without VE303 administration); "Late recovery" corresponds to days greater than or equal to 14; "Early no vanco" corresponds to study days 1-7 (or 1 week post VE303 for Cohort 6 only); and "Late no vanco" corresponds to study days greater than or equal to 8 for Cohort 6 only. The latest day a sample was collected in each cohort is indicated in the lower right corner of each panel. FIGS. 47C-47E show the reduction and recovery of the indicated BAs at baseline and following treatment with antibiotics and administration of VE303. Different primary and secondary BAs (chenodeoxycholic acid, cholic acid, glycochenodeoxycholic acid, glycocholic acid, taurocholic acid, deoxycholic acid, lithocholic acid, and ursodeoxycholic acid) from subjects in the "vanco" cohort, cohort 4, and cohort 5, from left to right for each time point, were quantified from samples taken at the indicated time points. FIGS. 47F-47K show the predicted measured bile acid abundance as a function of measured microbial abundances as predicted by Random Forest Regression. 100 different Random Forest Regressions were built by selecting at random a single sample per patient. This process was repeated 30 different times corresponding to different random seed initializations. Microbes with a permutated importance p-value less than 0.05 in at least 50% of the 30×100 iterations are evaluated with accumulated local effect (ALE) analysis. A linear model was fit to the resulting ALE plots to qualitatively determine positive/negative contribution of each microbe to each measured bile acid.

FIGS. 48A and 48B show the concentration of short chain fatty acids (SCFAs) measured in the stool of healthy volunteers at baseline, after administration of vancomycin, and during recovery after vancomycin administration. "B" is baseline; "V" is vancomycin; and "R" is recovery. FIG. 48C shows the concentration of the indicated SCFAs in stool samples (mean+/−sem) over time for subjected that received vancomycin only as compared to subjects who received multiple doses of VE303 (Cohorts 4 and 5). FIGS. 48D-48G show the predicted measured SCFA abundance as a function of measured microbial abundances. 100 different random forest regressions were built by selecting at random a single sample per patient. This process was repeated 30 different times corresponding to different random seed initializations. Microbes with a permutated importance p-value less than 0.05 in at least 50% of the 30×100 iterations are evaluated with accumulated local effect (ALE) analysis. A linear model was fit to the resulting ALE plots to qualitatively determine positive/negative contribution of each microbe to each measured SCFA.

FIG. 50A shows the number of bacterial strains of composition VE303 detected in the microbiota of the indicated subjects in the cohort that received vancomycin only ("Vanco"). FIGS. 50B-50D show the number of bacterial strains of composition VE303 detected in the microbiota of the indicated subjects Cohorts 1-3. FIGS. 50E-50H show the number of bacterial strains of composition VE303 detected in the microbiota of the indicated subjects in Cohorts 4 and 5. FIG. 50I shows the number of bacterial strains of composition VE303 detected in the microbiota of the indicated subjects in Cohort 6. For each column for each time point, the bacterial strains of composition VE303 are shown, from top to bottom: VE303-1, VE303-2, VE303-3, VE303-4, VE303-5, VE303-6, VE303-7, and VE303-8.

FIG. 51A shows the mean VE303 marker depth for each cohort. FIG. 51B shows the coverage of VE303 markers (proportion of VE303 markers detected) for each cohort. Each data point represents the mean depth or coverage of a VE303 strain detected in a subject's fecal stool sample metagenome across all time points. The maximum number of strains detected is 8.

FIG. 52A shows the abundance of bacterial strains of composition VE303 detected in the microbiota of the indicated subjects in the cohort that received vancomycin only ("Vanco"). FIGS. 52B-52D show the abundance of bacterial strains of composition VE303 detected in the microbiota of the indicated subjects in Cohorts 1-3. FIGS. 52E-52F show the abundance of bacterial strains of composition VE303 detected in the microbiota of the indicated subjects in Cohort 4. FIGS. 52G-52I show the abundance of bacterial strains of composition VE303 detected in the microbiota of the indicated subjects in Cohort 5. FIGS. 52J-52K show the abundance of bacterial strains of composition VE303 detected in the microbiota of the indicated subjects in Cohort 6. For each column for each time point, the bacterial strains of composition VE303 are shown, from top to bottom: VE303-1, VE303-2, VE303-3, VE303-4, VE303-5, VE303-6, VE303-7, and VE303-8. In FIGS. 52E-52K the top row includes all data points and the bottom row is zoomed in to the points below the dashed line in the top row.

FIG. 53A depicts the species richness as assessed by the number of bacterial species detected in the microbiota of each cohort. FIG. 53B depicts the bacterial species diversity index (Shannon) in the microbiota of each cohort. FIG. 53C depicts the bacterial species diversity (Inv Simpson) in the microbiota of each cohort. "Shannon" is the Shannon diversity index; and "Inv Simpson" is the inverse of the Simpson diversity index.

FIG. 54A shows a quantification of the bacterial DNA for each of the indicated bacterial phyla prior to vancomycin administration (baseline), after administration of vancomycin, and after administration of composition VE303. FIG. 54B shows the total VE303 strain abundance in fecal samples of the indicated cohorts In FIGS. 54A and 54B, the top row includes all data points and the bottom row is zoomed in to the points below the dashed line in the top row. "B" indicates the quantity of each bacterial phyla detected at baseline, "V" indicates the quantity of each bacterial phyla detected during vancomycin treatment, and "R" indicates the quantity of each bacterial phyla detected during recovery from vancomycin treatment.

FIG. 60 shows a summary of an exemplary method described herein for defining the pharmacokinetics (PK) and pharmacodynamics (PD) of live biotherapeutic products (LBPs). The genome sequence of each LBP consortium member and unique marker sequences for each are identified, the bacterial strains are used to colonize a subject, and the impacts of the LBP on the commensal microbiota of subjects may be performed during LBP development. Fecal short chain fatty acids (SCFAs) and bile acids (BAs) may be useful in characterizing the PD of LBPs designed for the treatment of specific indications.

FIG. 61 shows a model of microbiota and metabolite associations with VE303 administration. A simplified model of interactions between commensal microbiota, BAs, SCFAs, and the intestinal epithelium in a healthy human gut (left panel), in the context of a *Clostridium difficile* infection (middle panel), and in healthy human gut following administration of VE303, resulting in restoration of the microbiota, bile acids, and SCFA homeostasis (right panel).

FIG. 72A shows results using 25 PCR cycles. FIG. 72B shows results using 30 PCR cycles. FIG. 72C shows results using 35 PCR cycles.

FIG. 73A shows results using 25 PCR cycles. FIG. 73B shows results using 30 PCR cycles. FIG. 73C shows results using 35 PCR cycles.

DETAILED DESCRIPTION OF THE INVENTION

Figure 1:
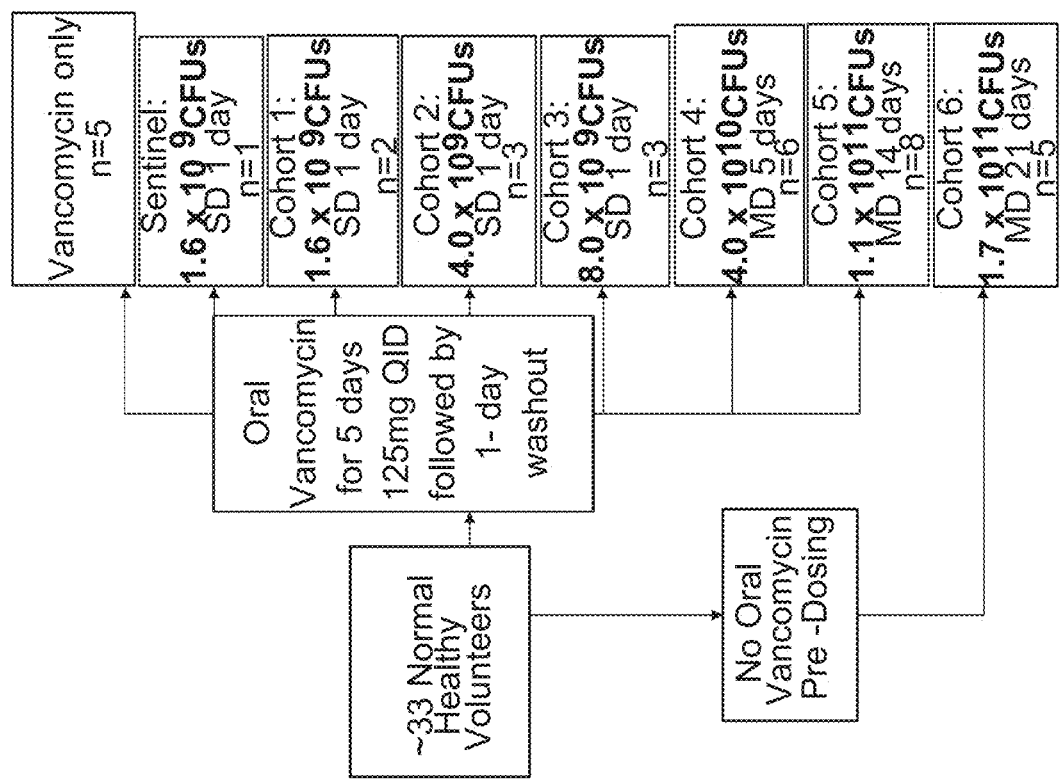
FIG. 1 presents a diagram illustrating the various treatment cohorts for the present disclosure.

Provided herein methods for decreasing dysbiosis in a subject involving administering pharmaceutical compositions comprising one or more purified bacterial strains. Provided herein methods for restoring the microbiome in a subject involving administering pharmaceutical compositions comprising one or more purified bacterial strains. Also provided herein are methods for increasing the recovery of a microbiome in a subject involving administering pharmaceutical compositions comprising one or more purified bacterial strains to a subject. Also provided herein are methods for protecting the microbiome of a subject involving administering pharmaceutical compositions comprising one or more purified bacterial strains to a subject. Also provided herein are methods for colonizing the microbiome of a subject involving administering pharmaceutical compositions comprising one or more purified bacterial strains to a subject.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Aspects of the present disclosure relate to methods for decreasing dysbiosis in a subject comprising administering to the subject a therapeutically effective amount of a pharmaceutical composition comprising one or more purified bacterial strains. In some embodiments, the pharmaceutical composition is administered to decrease dysbiosis of the intestinal microbiome of the subject. In some embodiments, the method further comprises administering one or more additional doses or amounts of the pharmaceutical compositions described herein. In some embodiments, the method further comprises administering vancomycin to the subject prior to administration of the pharmaceutical compositions.

As used herein, "dysbiosis" refers to an imbalance in the microbiome within a subject or on the surface of the subject. Microbiomes are present, for example in mammalian subjects, on the skin, within the gastrointestinal tract (i.e., the gut), within the oral cavity, and within the vaginal tract of female subjects, and comprise bacteria, archaea, protists, fungi, and viruses. In some instances, the species present in a microbiome benefit the subject by performing useful or necessary functions, such as aiding in the digestion of food in the intestinal tract of the subject, protecting the body from penetration by pathogenic microbes, and promoting immunological development. Organisms within the microbiota that perform these functions may be referred to as symbiotic or commensal organisms because they exist in the subject without harming, and, in some cases, actually benefit the host. In dysbiosis, the normal microbiome of the subject is perturbed or damaged, which may lead to a variety of diseases and/or disorders. Dysbiosis may result, for example, from a loss of beneficial species, loss of microbial diversity, increase in pathogenic organism(s), and/or change in metabolic capacity. In some embodiments, the species that normally dominate the microbiome become underrepresented (e.g., commensal or symbiotic species) and species which are normally underrepresented (e.g., opportunistic species) become overrepresented. See also Petersen et al., "Defining dysbiosis and its influence on host immunity and disease." *Cell Microbiol* 2014, July 16 (7), 1024-1033. It should be appreciated that the compositions and methods of the present disclosure, in some embodiments, can reduce dysbiosis in various aspects. Thus, for instance, in some embodiments, the compositions and methods provide for an increase in the abundance of bacterial species beneficial to the microbiome. In some embodiments, the compositions and methods provide for a decrease in the abundance of pathogenic bacterial species. However, it should also be appreciated that the compositions and methods provide herein do not necessarily have to reduce all characteristics of dysbiosis. For example, in some embodiments, the compositions and methods provide for an increase in the abundance of bacterial species beneficial to the microbiome, but do not at the same time increase the diversity of the microbiome. Aspects of the present disclosure relate to methods of decreasing dysbiosis in a subject. As used herein, "decreasing dysbiosis" refers to restoring the microbiota community composition and homeostasis.

Disruptions in the microbiome may allow pathogens within the microbiome or from other sources to colonize, overpopulate, and/or cause disease in the subject. Dysbiosis is associated with many diseases and/or disorders, including *Clostridium difficile* infection, cancer, inflammatory bowel disease (IBD), obesity, colitis, chronic fatigue syndrome, periodontitis, and bacterial vaginosis.

Dysbiosis may be detected and/or monitored by many of a variety of methods, such as stool tests (e.g., identification and/or quantification of microbial populations, enzyme assays, metabolite assays, immune function), hydrogen/methane breath tests.

In some embodiments, decreasing dysbiosis involves a change (increase or decrease) in the abundance of one or more population of bacteria. The abundance of bacteria, including the abundance of specific species or strains of bacteria and abundance of a population of bacteria (e.g., bacteria belonging to a particular phylum) may be assessed using any method known in the art. In general, the abundance of bacteria may be assessed directly or indirectly. Examples of methods for directly assessing the abundance of bacteria in a sample (e.g., a microbiome or sample thereof) include identifying and quantifying bacterial strains in a fecal sample from the subject. Examples of methods for indirectly assessing the abundance of bacteria in a sample (e.g., a microbiome or sample thereof) include sequencing of nucleic acid samples (e.g., 16S rRNA gene for a given bacterial species or other bacterial genes) obtained from a fecal or biopsy sample, and detecting and quantifying metabolites associated with specific bacteria (e.g., phospholipid fatty acid metabolism, microbial biomass carbon analysis) in a fecal sample from the subject.

The abundance of one or more populations of bacteria in a sample from a subject may be compared to the abundance of the populations of bacteria in a sample from the same subject obtained at another time (e.g., obtained previously or subsequently). Alternatively, the abundance of one or more populations of bacteria in a sample from a subject may be compared to the abundance of the populations of bacteria in a sample from a different subject (e.g., a reference subject).

In some embodiments, dysbiosis of the microbiota (e.g., of the gastrointestinal microbiota) of a subject is characterized by an increase in the abundance of microorganisms associated with inflammation and/or disease. In some embodiments, the dysbiosis is characterized by an increase in the abundance of Proteobacteria. In some embodiments, the increase in the abundance of microorganisms associated with inflammation and/or disease is relative to the abundance of microorganisms associated with inflammation prior to exposure to an event, referred to as a dysbiosis-inducing event, as described herein.

In some embodiments, dysbiosis of the microbiota (e.g., of the gastrointestinal microbiota) of a subject is characterized by a decrease in the abundance of microorganisms considered to provide one or more beneficial effects to the subject. In some embodiments, dysbiosis of the microbiota (e.g., of the gastrointestinal microbiota) of a subject is characterized by a decrease in the abundance of bacteria of the phylum Bacteroidetes. In some embodiments, dysbiosis of the microbiota (e.g., of the gastrointestinal microbiota) of a subject is characterized by a decrease in the abundance of bacteria of the phylum Firmicutes. In some embodiments, dysbiosis of the microbiota (e.g., of the gastrointestinal microbiota) of a subject is characterized by a decrease in the abundance of bacteria belonging to *Clostridium* clusters IV and/or XIVa. In some embodiments, dysbiosis of the microbiota (e.g., of the gastrointestinal microbiota) of a subject is characterized by a decrease in the abundance of bacteria belonging to *Clostridium* cluster XVII. In some embodiments, the decrease in the abundance of beneficial microorganisms is relative to the abundance of microorganisms associated with inflammation prior to exposure to an event, referred to as a dysbiosis-inducing event, as described herein.

In some embodiments, decreasing dysbiosis results in an increase in the abundance of bacteria of the phylum Bacteroidetes (e.g., bacteria of the genus Bacteroides) relative to the abundance of Bacteroides in the subject (or microbiome thereof) prior to administering the pharmaceutical composition. In some embodiments, decreasing dysbiosis results in an increase in the abundance of bacteria of the phylum Bacteroidetes (e.g., bacteria of the genus Bacteroides) relative to the abundance of Bacteroides in a subject (e.g., a reference subject) (or microbiome thereof) who did not receive the pharmaceutical composition. In some embodiments, decreasing dysbiosis results in an increase in the abundance of one or more bacterial species belonging to the genus Bacteroides. In some embodiments, decreasing dysbiosis results in an increase in the abundance overall of bacterial species belonging to the genus Bacteroides.

In some embodiments, the methods described herein result in an increase in the abundance of Bacteroides. Interestingly, in some embodiments, the pharmaceutical compositions described herein do not comprise Bacteroides species. Without wishing to be bound by any particular theory, in some embodiments, the pharmaceutical compositions described herein may promote colonization and/or proliferation of Bacteroides species, e.g, by providing a favorable environment for Bacteroides species to engraft and/or proliferate.

In some embodiments, administration of the pharmaceutical compositions described herein results in an increase in the abundance of bacteria of the phylum Bacteroidetes in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of bacteria of the phylum Bacteroidetes in the subject (or microbiome thereof) prior to administering the pharmaceutical compositions. In some embodiments, the abundance of bacteria of the phylum Bacteroidetes in the subject prior to the administration of the pharmaceutical compositions was lower because of treatment with an antibiotic. In some embodiments, administration of the pharmaceutical compositions described herein results in an increase in the abundance of bacteria of the phylum Bacteroidetes in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of bacteria of the phylum Bacteroidetes in another subject (e.g., a reference subject) (or microbiome thereof) who did not receive the pharmaceutical compositions. In some embodiments, the abundance of bacteria of the phylum Bacteroidetes in the reference subject was lower because of treatment with an antibiotic.

In some embodiments, administration of the pharmaceutical compositions described herein results in an increase in the abundance of Bacteroides in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of Bacteroides in the subject (or microbiome thereof) prior to administering the pharmaceutical compositions. In some embodiments, the abundance of bacteria of Bacteroides in the subject prior to the administration of the pharmaceutical compositions was lower because of treatment with an antibiotic. In some embodiments, administration of the pharmaceutical compositions described herein results in an increase in the abundance of Bacteroides in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of Bacteroides in another subject (e.g., a reference subject) (or microbiome thereof) who did not receive the pharmaceutical compositions. In some embodiments, the abundance of bacteria of Bacteroides in the reference subject was lower because of treatment with an antibiotic.

In some embodiments, administration of the pharmaceutical compositions described herein results in an increase in the abundance of bacteria of the phylum Bacteroidetes in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the abundance of bacteria of the phylum Bacteroidetes in the subject (or microbiome thereof) prior to administering the pharmaceutical compositions. In some embodiments, the abundance of bacteria of the phylum Bacteroidetes in the subject prior to the administration of the pharmaceutical compositions was lower because of treatment with an antibiotic. In some embodiments, administration of the pharmaceutical compositions described herein results in an increase in the abundance of bacteria of the phylum Bacteroidetes in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the abundance of Bacteroides in a subject (e.g., a reference subject) (or microbiome thereof) who did not receive the compositions. In some embodiments, the abundance of bacteria of the phylum Bacteroidetes in the reference subject was lower because of treatment with an antibiotic.

In some embodiments, administration of the pharmaceutical compositions described herein results in an increase in the abundance of Bacteroides in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the abundance of Bacteroides in the subject (or microbiome thereof) prior to administering the pharmaceutical compositions. In some embodiments, the abundance of bacteria of Bacteroides in the subject prior to the administration of the pharmaceutical compositions was lower because of treatment with an antibiotic. In some embodiments, administration of the pharmaceutical compositions described herein results in an increase in the abundance of Bacteroides in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the abundance of Bacteroides in a subject (e.g., a reference subject) (or microbiome thereof) who did not receive the compositions. In some embodiments, the abundance of bacteria of Bacteroides in the reference subject was lower because of treatment with an antibiotic.

In some embodiments, decreasing dysbiosis results in an increase in the abundance of Firmicutes relative to the abundance of Firmicutes in the subject (or microbiome thereof) prior to administering the pharmaceutical composition. In some embodiments, decreasing dysbiosis results in an increase in the abundance of Firmicutes relative to the abundance of Firmicutes in a subject (e.g., reference subject) (or microbiome thereof) who did not receive the pharmaceutical composition. In some embodiments, decreasing dysbiosis results in an increase in the abundance of one or more bacterial species belonging to the phylum Firmicutes. In some embodiments, decreasing dysbiosis results in an increase in the abundance overall of bacterial species belonging to the phylum Firmicutes. It should be appreciated that the increase in abundance of bacterial species belonging the phylum Firmicutes can also occur even if the pharmaceutical composition does not include any bacterial species belonging the phylum Firmicutes. If the pharmaceutical composition includes bacterial species belonging the phylum Firmicutes, the increase in abundance may include both bacterial species belonging the phylum Firmicutes that were present in the bacterial composition and bacterial species belonging the phylum Firmicutes that were not present in the composition.

In some embodiments, administration of the pharmaceutical compositions described herein results in an increase in the abundance of Firmicutes in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of Firmicutes in the subject (or microbiome thereof) prior to administering the pharmaceutical compositions. In some embodiments, the abundance of bacteria of the phylum Firmicutes in the subject prior to the administration of the pharmaceutical compositions was lower because of treatment with an antibiotic. In some embodiments, administration of the pharmaceutical compositions described herein results in an increase in the abundance of Firmicutes in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of Firmicutes in another subject (e.g., a reference subject) (or microbiome thereof) who did not receive the pharmaceutical compositions. In some embodiments, the abundance of bacteria of the phylum Firmicutes in the reference subject was lower because of treatment with an antibiotic.

In some embodiments, administration of the pharmaceutical compositions described herein results in an increase in the abundance of Firmicutes in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the abundance of Firmicutes in the subject (or microbiome thereof) prior to administering the pharmaceutical compositions. In some embodiments, the abundance of bacteria of the phylum Firmicutes in the subject prior to the administration of the pharmaceutical compositions was lower because of treatment with an antibiotic. In some embodiments, administration of the pharmaceutical compositions described herein results in an increase in the abundance of Firmicutes in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the abundance of Firmicutes in a subject (e.g., a reference subject) (or microbiome thereof) who did not receive the compositions. In some embodiments, the abundance of bacteria of the phylum Firmicutes in the reference subject was lower because of treatment with an antibiotic.

In some embodiments, according to the methods provided herein, the administration of the pharmaceutical compositions described herein results in an increase in the abundance of bacterial species of the phylum Firmicutes and increase in bacterial species of the phylum Bacteroidetes.

In some embodiments, decreasing dysbiosis results in an increase in the abundance of bacteria belonging to *Clostridium* cluster IV and/or XIVa relative to the abundance of bacteria belonging to *Clostridium* cluster IV and/or XIVa in the subject (or microbiome thereof) prior to administering the pharmaceutical composition. In some embodiments, decreasing dysbiosis results in an increase in the abundance of bacteria belonging to *Clostridium* cluster IV, XIVa and/or XVII relative to the abundance of bacteria belonging to *Clostridium* cluster IV, XIVa and/or XVII in the subject (or microbiome thereof) prior to administering the pharmaceutical composition. In some embodiments, decreasing dysbiosis results in an increase in the abundance of bacteria belonging to *Clostridium* cluster IV and/or XIVa relative to the abundance of bacteria belonging to *Clostridium* cluster IV and/or XIVa in a subject (e.g., reference subject) (or microbiome thereof) who did not receive the pharmaceutical composition. In some embodiments, decreasing dysbiosis results in an increase in the abundance of one or more bacterial species bacteria belonging to *Clostridium* cluster IV and/or XIVa. In some embodiments, decreasing dysbiosis results in an increase in the abundance overall of bacterial species belonging to *Clostridium* cluster IV and/or XIVa. In some embodiments, the abundance of bacteria belonging to *Clostridium* cluster IV, XIVa and/or XVII in the subject prior to the administration was lower because of treatment with an antibiotic.

In some embodiments, administration of the pharmaceutical compositions described herein results in an increase in the abundance of bacterial strains belonging to *Clostridium* cluster IV and/or XIVa in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of *Clostridium* cluster IV and/or XIVa in the subject (or microbiome thereof) prior to administering the pharmaceutical compositions. In some embodiments, the abundance of *Clostridium* cluster IV and/or XIVa in the subject prior to the administration of the pharmaceutical compositions was lower because of treatment with an antibiotic. In some embodiments, administration of the pharmaceutical compositions described herein results in an increase in the abundance of *Clostridium* cluster IV and/or XIVa in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of *Clostridium* cluster IV and/or XIVa in another subject (e.g., a reference subject) (or microbiome thereof) who did not receive the pharmaceutical compositions.

In some embodiments, administration of the pharmaceutical compositions described herein results in an increase in the abundance of *Clostridium* cluster IV and/or XIVa in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the abundance of *Clostridium* cluster IV and/or XIVa in the subject (or microbiome thereof) prior to administering the pharmaceutical compositions. In some embodiments, the abundance of *Clostridium* cluster IV and/or XIVa in the subject prior to the administration of the pharmaceutical compositions was lower because of treatment with an antibiotic. In some embodiments, administration of the pharmaceutical compositions described herein results in an increase in the abundance of *Clostridium* cluster IV and/or XIVa in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the abundance of *Clostridium* cluster IV and/or XIVa in a subject (e.g., a reference subject) (or microbiome thereof) who did not receive the compositions.

In some embodiments, decreasing dysbiosis results in an increase in the abundance of bacteria belonging to *Clostridium* cluster XVII relative to the abundance of bacteria belonging to *Clostridium* cluster XVII in the subject (or microbiome thereof) prior to administering the pharmaceutical composition. In some embodiments, decreasing dysbiosis results in an increase in the abundance of bacteria belonging to *Clostridium* cluster XVII relative to the abundance of bacteria belonging to *Clostridium* cluster XVII in a subject (e.g., reference subject) (or microbiome thereof) who did not receive the pharmaceutical composition. In some embodiments, decreasing dysbiosis results in an increase in the abundance of one or more bacterial species belonging to *Clostridium* cluster XVII. In some embodiments, decreasing dysbiosis results in an increase in the abundance overall of bacterial species belonging to *Clostridium* cluster XVII.

In some embodiments, administration of the pharmaceutical compositions described herein results in an increase in the abundance of bacterial strains belonging to *Clostridium* cluster XVII in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of *Clostridium* cluster XVII in the subject (or microbiome thereof) prior to administering the pharmaceutical compositions. In some embodiments, the abundance of *Clostridium* cluster XVII in the subject prior to the administration of the pharmaceutical compositions was lower because of treatment with an antibiotic. In some embodiments, administration of the pharmaceutical compositions described herein results in an increase in the abundance of *Clostridium* cluster XVII in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of *Clostridium* cluster XVII in another subject (e.g., a reference subject) (or microbiome thereof) who did not receive the pharmaceutical compositions.

In some embodiments, administration of the pharmaceutical compositions described herein results in an increase in the abundance of *Clostridium* cluster XVII in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the abundance of *Clostridium* cluster XVII in the subject (or microbiome thereof) prior to administering the pharmaceutical compositions. In some embodiments, the abundance of *Clostridium* cluster XVII in the subject prior to the administration of the pharmaceutical compositions was lower because of treatment with an antibiotic. In some embodiments, administration of the pharmaceutical compositions described herein results in an increase in the abundance of *Clostridium* cluster XVII in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the abundance of *Clostridium* cluster XVII in a subject (e.g., a reference subject) (or microbiome thereof) who did not receive the compositions.

In some embodiments, administration of the pharmaceutical compositions described herein results in a decrease in the abundance of microorganisms associated with inflammation. In some embodiments, administration of the pharmaceutical compositions described herein results in a decrease in the abundance of one or more microorganisms associated with inflammation. As used, herein, the term "microorganisms associated with inflammation" refers to microorganisms that induce pro-inflammatory responses upon colonization or infection of a subject. Microorganisms associated with inflammation are described for instance in Zechner: "Inflammatory disease caused by intestinal pathobionts," *Current Opinion in Microbiology* (2017) 35: 64-69; and in numerous publications describing the role of the microorganisms in IBD (See eg., Hoffmann et al., ISME J. 2016 February; 10(2): 460-477.) In some embodiments, the microorganisms associated with inflammation induce acute inflammation characterized, for example, by the presence of pro-inflammatory cytokines and/or infiltration of inflammatory immune cells to the site of colonization or infection. In some embodiments, the microorganisms associated with inflammation induce chronic inflammation. In some embodiments, the microorganisms associated with inflammation are Proteobacteria. In some embodiments, decreasing dysbiosis results in a decrease in the abundance of one or more bacterial species that are associated with inflammation. In some embodiments, decreasing dysbiosis results in a decrease in the abundance overall of bacterial species that are associated with inflammation. In some embodiments, the abundance of bacterial species that are associated with inflammation (e.g., Proteobacteria) in the subject prior to the administration was increased because of treatment with an antibiotic.

In some embodiments, administration of the pharmaceutical compositions described herein results in a decrease in abundance of microorganisms associated with inflammation in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of microorganisms associated with inflammation in the subject (or microbiome thereof) prior to administering the pharmaceutical compositions. In some embodiments, the abundance of microorganisms associated with inflammation in the subject prior to the administration of the pharmaceutical compositions was higher because of treatment with an antibiotic. In some embodiments, administration of the pharmaceutical compositions described herein results in a decrease in abundance of microorganisms associated with inflammation in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of microorganisms associated with inflammation in another subject (e.g., a reference subject) (or microbiome thereof) who did not receive the pharmaceutical compositions.

In some embodiments, administration of the pharmaceutical compositions described herein results in a decrease in abundance of microorganisms associated with inflammation in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%, as compared to the abundance of microorganisms associated with inflammation in the subject (or microbiome thereof) prior to administering the pharmaceutical compositions. In some embodiments, the abundance of microorganisms associated with inflammation in the subject prior to the administration of the pharmaceutical compositions was higher because of treatment with an antibiotic. In some embodiments, administration of the pharmaceutical compositions described herein results in decrease in the abundance of microorganisms associated with inflammation in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the abundance of microorganisms associated with inflammation in a subject (e.g., a reference subject) (or microbiome thereof) who did not receive the compositions.

In some embodiments, administration of the pharmaceutical compositions described herein results in a decrease in the abundance of Proteobacteria. In some embodiments, administration of the pharmaceutical compositions described herein results in a decrease in the abundance of one or more bacterial strain that belongs to the phylum Proteobacteria. Proteobacteria is a phylum of Gram-negative bacteria that includes a number of pathogens, such as *Escherichia coli*, *Salmonella* sp., *Campylobacter* sp., and *Pseudomonas* sp. In some embodiments, decreasing dysbiosis results in a decrease in the abundance of one or more bacterial species belonging to the phylum Proteobacteria. In some embodiments, decreasing dysbiosis results in a decrease in the abundance overall of bacterial species belonging to the phylum Proteobacteria.

In some embodiments, administration of the pharmaceutical compositions described herein results in a decrease in abundance of Proteobacteria in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of Proteobacteria in the subject (or microbiome thereof) prior to administering the pharmaceutical compositions. In some embodiments, the abundance of Proteobacteria in the subject prior to the administration of the pharmaceutical compositions was higher because of treatment with an antibiotic. In some embodiments, the abundance of Proteobacteria in the subject prior to the administration of the pharmaceutical compositions was higher because of treatment with an antibiotic. In some embodiments, administration of the pharmaceutical compositions described herein results in a decrease in abundance of Proteobacteria in the subject (or microbiome thereof) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the abundance of Proteobacteria in another subject (e.g., a reference subject) (or microbiome thereof) who did not receive the pharmaceutical compositions.

In some embodiments, administration of the pharmaceutical compositions described herein results in a decrease in abundance of Proteobacteria in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%, as compared to the abundance of Proteobacteria in the subject (or microbiome thereof) prior to administering the pharmaceutical compositions. In some embodiments, administration of the pharmaceutical compositions described herein results in decrease in the abundance of Proteobacteria in the subject (or microbiome thereof) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the abundance of Proteobacteria in a subject (e.g., a reference subject) (or microbiome thereof) who did not receive the compositions.

In some embodiments, according to the methods provided herein, the administration of the pharmaceutical compositions described herein results in an increase in the abundance of bacterial species of the phylum Firmicutes an increase in bacterial species of the phylum Bacteroidetes, and a decrease in the abundance of bacterial species of the phylum Proteobacteria.

In some embodiments, according to the methods provided herein, the administration of the pharmaceutical compositions described herein results in an increase in the abundance of bacterial species of the phylum Firmicutes and an increase in bacterial species of the phylum Bacteroidetes.

In some embodiments, according to the methods provided herein, the administration of the pharmaceutical compositions described herein results in an increase in the abundance of bacterial species of the phylum Firmicutes and a decrease in the abundance of bacterial species of the phylum Proteobacteria.

In some embodiments, according to the methods provided herein, the administration of the pharmaceutical compositions described herein results in an increase in the abundance of bacterial species of the phylum Bacteroidetes, and a decrease in the abundance of bacterial species of the phylum Proteobacteria.

In some embodiments, the decreasing dysbiosis is not correlated with a proportional increase in microbiome diversity of the subject. While generally the diversity of the microbiome is associated with a healthy microbiome, it was found remarkably herein that the compositions and methods provided herein restore the strength of the microbiome without restoring the diversity. While not being limited to a particular mechanism, it is thought that the microbiome is restored by the make-up of the pharmaceutical compositions provided herein. Thus, for instance, a limited number of bacterial strains of *Clostridium* cluster XIVa in the composition can take over the role of a larger group of *Clostridium* cluster XIVa strains found in an untreated healthy microbiome. Thus, a microbiome treated with the compositions provided herein and according to the methods provided herein may show all the hallmarks of a healthy microbiome (including the presence of Bacteroidetes and Firmicutes and the absence of Proteobacteria) but may not have the high diversity sometimes associated with a healthy microbiome.

Aspects of the present disclosure relate to methods for restoring the microbiome of a subject comprising administering a therapeutically effective amount of a pharmaceutical composition comprising one or more purified bacterial strains. In some embodiments, the method further comprises administering one or more additional administrations of the pharmaceutical compositions described herein. In some embodiments, the method further comprises administering an antibiotic to the subject prior to administration of the pharmaceutical compositions. In some embodiments, the method further comprises administering vancomycin to the subject prior to administration of the pharmaceutical compositions.

As used herein, "restoring the microbiome" of a subject refers to re-establishing or recovering the relative abundance of bacterial populations and/or microbial diversity of the gastrointestinal microbiome of the subject. In some embodiments, the microbiome of the subject is restored to a microbiome of a healthy subject (a healthy microbiome). In some embodiments, the microbiome of the subject is restored to the microbiome of the same subject at a previous time. In some embodiments, the subject whose microbiome is being restored may have an inflammatory condition, such as irritable bowel syndrome, ulcerative colitis, or Crohn's disease. In some embodiments, the subject whose microbiome is being restored may have an allergy (e.g., food allergy). In some embodiments, the microbiome of the subject is restored to the microbiome of the same subject prior to the inflammatory condition. Thus, it should be appreciated that a microbiome that is need of restoring may have not undergone a dysbiosis inducing event. According to the methods provided herein, in some embodiments, the subject whose microbiome is in need of restoring may have not undergone a dysbiosis inducing event. In some embodiment, the subject whose microbiome is in need of restoring has not had a *Clostridium difficile* infection. In some embodiment, the subject whose microbiome is in need of restoring has not been treated with an antibiotic.

A microbiome that is in need of restoration may be characterized, for example, by the presence of a signature associated with a damaged microbiome. In general, a microbiome may be characterized based on the presence or absence of populations of bacteria or specific bacterial species. For example, a damaged microbiome may be overpopulated with pathogens and/or have reduced presence of commensal bacteria. A damage microbiome may also be characterized by its biological function. For example, a damaged microbiome may not be able to maintain the mucosal barrier and healthy immune function, and/or a damaged microbiome may not be able to fight of infections as well as a healthy microbiome.

In some embodiments, restoring the microbiome of a subject results in a microbiome that is substantially similar to a healthy microbiome (e.g., a microbiome of a healthy subject). In some embodiments, restoring the microbiome of a subject results in a microbiome that is more similar to a healthy microbiome than a damaged microbiome. In some embodiments, restoring the microbiome of a subject results in a restoration or increased presence of one or more populations of bacteria or specific bacterial species. In some embodiments, restoring the microbiome of a subject results in a restoration or decreased presence of one or more populations of bacteria or specific bacterial species. In some embodiments, restoring the microbiome of a subject results in an increase of one or more functions of the microbiome. In some embodiments, restoring the microbiome of a subject results in a decrease of one or more functions of the microbiome.

In some embodiments, the pharmaceutical compositions described herein can restore the microbiome without restoring the full diversity of the microbiome. While generally the diversity of the microbiome is associated with a healthy microbiome, it was found remarkably herein that the compositions and methods provided herein restore the strength of the microbiome without restoring the diversity (e.g., as defined by the Shannon index). Without wishing to be limited to a particular theory, it is thought that the microbiome is restored by the make-up of the specific bacterial strains administered in the compositions and the methods of treatment and dosing regimens provided herein. Thus, for instance, a limited number of bacterial strains belonging to *Clostridium* cluster XIVa in the composition may perform the role of a larger group of XIVa strains found in an untreated healthy microbiome. Thus, a microbiome treated with the compositions described herein may show a signature of a healthy microbiome (including the presence of Bacteroidetes and Firmicutes and the absence of Proteobacteria) but may not have the high diversity that may be typically associated with a healthy microbiome.

As used herein, a "healthy microbiome," refers to a microbiome from a subject who does not have overt disease (e.g., a healthy subject). Although the microbial composition of healthy microbiomes can vary widely, several trends have emerged which characterized healthy microbiomes. For example, the gastrointestinal microbiome may perform a number of metabolic and/or other molecular functions, including the metabolism of carbohydrates, lipids, and other nutrients which are performed by healthy microbiomes, regardless of the specific species composition. In some instances, the metabolic and molecular functions carried out by a healthy microbiome cannot be performed by the host subject, resulting in a symbiotic host-microbial relationship. Additionally, healthy microbiomes tend to be resilient to external (e.g., dietary or pharmaceutical) and/or internal (e.g., age, disease-state, stress, inflammation) changes in the subject. The resilience of a healthy microbiome can also be characterized by the ability and the rate at which a healthy state is restored after occurrence of a perturbation. Alternatively, or in addition, a healthy microbiome may be characterized by a high (e.g., greater than 75%) relative abundance of bacterial species from the phylum Firmicutes and genus Bacteroides relative to species from the phylum Proteobacteria.

In some embodiments, a subject with a restored microbiome or healthy microbiome has an increased abundance of bacteria from the phylum Firmicutes and/or genus Bacteroides as compared to bacteria from the phylum Proteobacteria.

In some embodiments, a subject with a restored microbiome or healthy microbiome has an increased abundance of bacteria from the phylum Firmicutes and/or Bacteroidetes as compared to bacteria from the phylum Proteobacteria.

In some embodiments, the subject has not undergone or experienced a dysbiosis inducing event. In some embodiments, the subject has not undergone a dysbiosis or experienced a dysbiosis inducing event within 1 week, 2 weeks, 3 weeks, 4 weeks, 5 weeks, 6 weeks, 7 weeks, 8 weeks, 9 weeks, 10 weeks, 12 weeks, 6 months, 7 months, 8 months, 9 months, 10 months, 11 months, 12 months or longer prior to administration of the pharmaceutical compositions described herein. In some embodiments, the subject has not had an infectious disease. In some embodiments, the subject has not had an infectious disease within 1 week, 2 weeks, 3 weeks, 4 weeks, 5 weeks, 6 weeks, 7 weeks, 8 weeks, 9 weeks, 10 weeks, 12 weeks, 6 months, 7 months, 8 months, 9 months, 10 months, 11 months, 12 months or longer prior to administration of the pharmaceutical compositions described herein. In some embodiments, the subject has not had a *Clostridium difficile* infection. In some embodiments, the subject has not had a *Clostridium difficile* infection within 1 week, 2 weeks, 3 weeks, 4 weeks, 5 weeks, 6 weeks, 7 weeks, 8 weeks, 9 weeks, 10 weeks, 12 weeks, 6 months, 7 months, 8 months, 9 months, 10 months, 11 months, 12 months or longer prior to administration of the pharmaceutical compositions described herein. In some embodiments, the subject has not been treated with an antibiotic. In some embodiments, the subject has not been treated with an antibiotic within 1 week, 2 weeks, 3 weeks, 4 weeks, 5 weeks, 6 weeks, 7 weeks, 8 weeks, 9 weeks, 10 weeks, 12 weeks, 6 months, 7 months, 8 months, 9 months, 10 months, 11 months, 12 months or longer prior to administration of the pharmaceutical compositions described herein. In some embodiments, the subject has not been treated with vancomycin. In some embodiments, the subject has not been treated with vancomycin within 1 week, 2 weeks, 3 weeks, 4 weeks, 5 weeks, 6 weeks, 7 weeks, 8 weeks, 9 weeks, 10 weeks, 12 weeks, 6 months, 7 months, 8 months, 9 months, 10 months, 11 months, 12 months or longer prior to administration of the pharmaceutical compositions described herein.

Aspects of the present disclosure relate to methods for increasing the recovery of a healthy microbiome in a subject after a dysbiosis inducing event, comprising administering a therapeutically effective amount of a pharmaceutical composition comprising one or more purified bacterial strains. In some embodiments, the method further comprises administering one or more additional administrations of the pharmaceutical compositions described herein. In some embodiments, the method further comprises administering an antibiotic to the subject prior to administration of the pharmaceutical compositions. In some embodiments, the method further comprises administering vancomycin to the subject prior to administration of the pharmaceutical compositions As used herein, the term "increasing the recovery" of a healthy microbiome refers to an increase in the rate of recovery or the overall extent of the recovery (e.g., the microbiome of the subject is more similar to a healthy microbiome following administration of the pharmaceutical compositions). In some embodiments, increasing the recovery of a healthy microbiome refers to an increase in the rate of recovery. In some embodiments, increasing the recovery of a healthy microbiome refers to an increase in the overall extent of the recovery (e.g., the microbiome of the subject is more similar to a healthy microbiome following administration of the pharmaceutical compositions). In some embodiments, "increasing the recovery" of a healthy microbiome refers to an increase in the rate of recovery and an increase in the overall extent of the recovery. In some embodiments, a healthy microbiome is recovered in a subject more quickly following administration of any of the pharmaceutical compositions described herein as compared to recovery of a healthy microbiome in a subject who was not administered the pharmaceutical compositions. In some embodiments, a healthy microbiome is recovered in a subject more quickly following administration of any of the pharmaceutical compositions described herein as compared to recovery of a healthy microbiome in a subject who has undergone a fecal matter transplant. In some embodiments, the increased recovery of a healthy microbiome occurs at least one day, two days, three days, four days, five days, six days, one week, two weeks, three weeks, four weeks, five weeks, or six weeks more quickly than recovery of a healthy microbiome in a subject who was not administered the pharmaceutical compositions. In some embodiments, the increased recovery of a healthy microbiome occurs at least one day, two days, three days, four days, five days, six days, one week, two weeks, three weeks, four weeks, five weeks, or six weeks more quickly than recovery of a healthy microbiome in a subject who has undergone a fecal matter transplant.

In some embodiments, increasing the recovery of a healthy microbiome refers to an increase in the rate of recovery. In some embodiments, recovery of a healthy microbiome occurs within one day, two days, three days, four days, five days, six days, one week, two weeks, three weeks, four weeks, five weeks, or six weeks following administration of the pharmaceutical compositions described herein. In some embodiments, recovery of a healthy microbiome occurs twice as fast, three times as fast, four times as fast, five as fast, six times as fast, seven times as fast, eight times as fast, nine times as fast, ten times as fast, twenty times as fast, one hundred times as fast, or faster, compared to subjects who were not treated with the pharmaceutical compositions according to the methods provided herein.

In some embodiments, increasing the recovery of a healthy microbiome refers to an increase in the overall extent of the recovery. In some embodiments, recovery of a healthy microbiome is better by 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more compared to subjects who were not treated with the pharmaceutical compositions according to the methods provided herein.

In some embodiments, the recovery occurs without detectable colonization of one or more bacterial strains of the pharmaceutical compositions. In some embodiments, the recovery of the healthy microbiome is associated with colonization of one or more bacterial strains of the pharmaceutical compositions.

In some embodiments of the methods provided herein, the subject has experienced a dysbiosis inducing event. In some embodiments of the methods provided herein, the subject has experienced a dysbiosis inducing event prior to the administration of a single does or multiple doses of the pharmaceutical compositions provided herein. As used herein, the term "dysbiosis inducing event" refers to an event or events that disrupt the microbiome of a subject. In some embodiments, a subject who has experienced a dysbiosis inducing event is in need of administration of any of the pharmaceutical compositions described herein. In some embodiments, a subject who has experienced a dysbiosis inducing event is administered any of the pharmaceutical compositions described herein to recover or restore the microbiome to a healthy microbiome. In some embodiments, the microbiome of the subject has one or more characteristics (signatures) of a damaged microbiome following the dysbiosis inducing event. Examples of dysbiosis inducing events include, without limitation, antibiotic exposure (e.g., treatment with vancomycin), infectious disease, *Clostridium difficile* infection, alcohol misuse, surgery, treatment with a chemotherapeutic, treatment with immunosuppressants, traveler's diarrhea, and inappropriate diet.

In addition, it has been appreciated that exposure to any of a variety of classes of therapeutics may modulate the microbiota and that members of the gut microbiota metabolize structurally diverse drug molecules (see, e.g., Zimmermann et al. *Nature* (2019) 570: 462-471). In some embodiments, the dysbiosis inducing event involves exposure of the subject to one or more therapeutic that may be metabolized by the microbiota.

Examples of classes of drug molecules that may be metabolized by the microbiota include, without limitation, steroids and hormone agonists (e.g., norethindrone acetate, levonorgestrel, megestrol acetate, betamethasone acetate, dexamethasone, drospirenone, norgestimate, finasteride); hormone antagonists (e.g., cyproterone acetate, bromocriptine mseylate, naloxone, mifepristone, bicalutamide); anti-depressants and drugs associated with mental health (e.g., vilazodone, fluoxetine, olanzapine, thiothixene, fluvoxamine maleate, paroxetine, sulpiride, metitepine maleate, bupropion, ziprasidone mesylate, pimozide, fluoxetine, periciazine, paliperidone, risperidone); anti-viral agents (e.g., famciclovir, ritonavir, zidovudine [azt], nevirapine, amantadine); anti-allergy/anti-histamines (e.g., roxatidine actetate, clemastine fumarate, cetirizine, nizatidine, diphenylpyraline, tranilast); anti-diarrheal agents (e.g., racecadotril, trimebutine maleate, loperamide); immunosuppressive agents (e.g., mycophenolate mofetil, deflazacort, tacrolimus); anti-hypertensive agents (e.g., olmesatran medoxomil, diltiazem fluphenazine, telmisaratan, quinapril, trandolapril, benazepril, irbesartan, losartan, valsartan, enalapril maleate, benzthiazide, doxazosin mesylate, papaverine, lofexidine, verampimil, penbutolol sulfate, ramipril, carvedilol, nitrendipine); diabetic medications (e.g., linagliptin, tolazamide, nateglinide, glipizide, gliclazide, repaglinide); anti-itch agents (e.g., diflorasone diacetate, betamethasone valerate); cholesterol medications (e.g., fenofibrate, bezafibrate, ezetimibe, mevastatin, lovastatin); non-steroidal anti-inflammatory agents (e.g., famprofazone, pranoprofen, oxaprozin, etodolac, ketorolac tromethamine, colchicine, naproxen, celecoxib, diacetamate); muscle relaxants (e.g., carisoprodol, oxybutynin chloride, metaxalone, naftopidil, sumatriptan succinate, orphenadrine citrate, clemizole, trihexyphnidyl, alfuzosin, alprenolol, camylofine, chlormezanone, carbapentane citrate, phenazopyridine); anti-fungal agents (e.g., griseoulvin, mebendazole, voliconazole, fluconazole, itraconazole); sedatives (e.g., ramelteon, zaleplon, clonidine, eszopiclone); central nervous system drugs (e.g., riluzole, galantamine, ergotamine tartrate, nicergoline, ethopropazine, methylphenidate, methsiximide, oxcarbazepine, memantine, biperiden, methysergide maleate, ethozolamide, phenytoin sodium, idebenone, entacapone); blood thinners (e.g., clopidrogrel sulfate, sulfinpyrazone, warfarin, dipyridamole, anagrelide, trimetazidine, nafronyl oxalate); blood pressure enhancement drugs (e.g., digitoxin, digoxin, sotalol, acecainide); respiratory disease drugs (e.g., fenspiride); anti-parasitic (e.g., primaquine phosphate, mefloquine, levamisole, artemisinin); chemotherapeutic agents (e.g., dasatinib, procarbaine, cyclophosphamide, anastrozole, imiatinib, paclitaxel, capecitabine, melphalan); muscle stiffeners/strengtheners (e.g., ergonovine maleate, neostigmine bromide); agents associated with gastric/mucosal defense (e.g., rebamipide, metoprolol tartrate, ranitidine, pantoprazole, tenatoprazole); bowel disorder agents (e.g., budesonide, dicyclomine, sulfasalazine, bisacodyl); uric acid reducers (e.g., febuxostate, indomethacin); anti-acids (e.g., cimetidine, benzbromarone, omeprazole); erectile dysfunction agents (e.g., tadalafil, sildenafil citrate); pain reduction agents (e.g., noscapine, rizatriptan benzoate); natural products (e.g. vinpocetine); skin disease treatment (e.g., methoxsaline); immunostimulants (e.g., pidotimod); antibiotics; reproductive disorder treatments (e.g., danazol).

In some embodiments, the subject has experienced or undergone a dysbiosis inducing event within 1 week, 2 weeks, 3 weeks, 4 weeks, 5 weeks, 6 weeks, 7 weeks, 8 weeks, 9 weeks, 10 weeks, 12 weeks, 6 months, 7 months, 8 months, 9 months, 10 months, 11 months, 12 months or longer prior to administration of the pharmaceutical compositions described herein.

Antibiotic administration has been associated with gastrointestinal dysbiosis due to killing of commensal and/or symbiotic bacteria thereby allowing opportunistic bacteria to overpopulate, which may cause disease. In some embodiments, antibiotics are administered to treat or prevent a bacterial infection or a suspected bacterial infection. In some embodiments, antibiotics are administered in connection with surgery on the subject. In some embodiments, antibiotics are administered to the subject prior to (prophylactically) or subsequent to a surgical procedure.

Non-limiting examples of antibiotics that may induce dysbiosis include cephalosporin antibiotics cephalexin, cefuroxime, cefadroxil, cefazolin, cephalothin, cefaclor, cefamandole, cefoxitin, cefprozil, ceftobiprole, clindamycin, ceftriaxone, cefotaxime, cefazolin, cefoperazone, cefuroxime, cefmetazole, fluoroquinolone, ciprofloxacin, Levaquin, floxin, tequin, avelox, norflox, tetracycline, minocycline, oxytetracycline, doxycycline, amoxicillin, ampicillin, penicillin V, dicloxacillin, benzylpenicillin, carbenicillin, vancomycin, and methicillin), ertapenem, doripenem, imipenem/cilastatin, meropenem, clavulanate, tazobactam, piperacillin, ceftriaxone, cefotaxime, cefazolin, fluoroquinolone, imipenem, meropenem, metronidazole, fidaxomyxin, ridinilazole, trimethoprim/sulfamexthoxazole, ceftobioprole, ceftaroline, dalbavancin, daptomycin, fusidic acid, linezolid, mupirocin, omadacycline, oritavancin, tedizolid, telavancin, tigecycline, ceftadizime, cefepime, ceftolozane/tazobactam, piperacillin/tazobactam, ticarcillin/clavulanic acid, streptogramins, daptomycin, amikacin, kanamycin, neomycin, netilimicin, tobramycin, paromycin, spectinomycin, geldanamycin, herbimycin, rifamixin, loracarbef, cefrodoxil, cephardine, cephadrine, cephapirin, cephalexin, cefotetan, cefmetazole, cefonicid, cefprozil, cefuroxime, cefiximine, cefdinir, cefditoren, cefoperazone, cefotaxime, cefpodoxime, ceftazidime, ceftibuten, ceftizoxime, moxalactam, ceftriaxone, cefepime, ceftaroline fosamil, teicoplanin, telvancin, dalbavancin, oritavancin, lincomycin, daptomycin, azithromycin, clarithromycin, erythromycin, roxithromycin, telithromycin, spiramycin, fidaxomicin, azetrenoma, furazolidone, nitrofurantoin, posizolid, radezolid, torezolid, azlocillin, dicloxacillin, flucloxacillin, mezlocillin, nafcillin, oxacillin, piperacillin, temocillin, ticarcillin, bacitracin, colistin, polymyxin B, enoxacin, gatifloxacin, gemifloxacin, gemifloxacin, levofloxacin, lomefloxacin, moxifloxacin, nadifloxacin, naldixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilamide, sulfasalazine, sulfisoxazole, sulfoamindochrysoidine, demeclocycline, metacycline, minocycline, clofazimine, dapsone, capreomycine, cycloserine, ethambutol, ethionamide, isoniazid, pyrazinamide, rifampicin, rifubutin, rifapentine, arsphenamine, fosfomycin, fusidic acid, mupirocin, platensimycin, quinupristin/dalfopristin, thiamphenicol, tigecycline, and tinidazole.

In some embodiments, the dysbiosis inducing event is treatment with an antibiotic. In some embodiments, the dysbiosis inducing event is treatment with an antibiotic in connection with surgery. In some embodiments, the antibiotic is vancomycin.

In some embodiments, the dysbiosis inducing event is an infectious disease, such as an infectious disease caused by a virus, bacterium, fungus, yeast, parasite, or combination thereof. In some embodiments, the subject is administered one or more therapeutic agents (e.g., anti-virals, antibiotics, anti-fungals, anti-parasitics, etc.) to treat the infectious disease. In some embodiments, the dysbiosis inducing event is *Clostridium difficile* infection. Antibiotics typically used to treat *Clostridium difficile* infection include metronidazole, vancomycin, and fidaxomicin.

In some embodiments, the dysbiosis inducing event is a gastrointestinal infection. In some embodiments, the subject has experienced a gastrointestinal infection, for example with *Clostridium perfringens, Staphylococcus, Enterococcus faecium, Roseburia hominis, Raecalibacterium prausnitzii, Clostridioides difficile, Escherichia coli, Salmonella typhii, Vibrio cholerae, Shigella flexneri, Campylobacter, Peptostreptococcus, Yersinia*, or Proteobacteria. In some embodiments, the dysbiosis inducing event is traveler's diarrhea. In general, traveler's diarrhea is a gastrointestinal disorder characterized by diarrhea, abdominal cramps, nausea, vomiting, and/or fever that is caused by exposure to an infectious agent while traveling (e.g., typically eating contaminated foods, drinking contaminated water).

In some embodiments, administration of one or more therapeutic agents to treat the infectious disease, *C. difficile* infection, or traveler's diarrhea, as described herein, may contribute to gastrointestinal dysbiosis.

In some embodiments, the dysbiosis-inducing event is exposure to an anti-fungal agent. In some embodiments, the subject is administered one or more anti-fungals agent, for example to treat fungal infection. Examples of anti-fungal agents include, without limitation, clotrimazole, econazole, micronazole, fluconazole, terbinafine, ketoconazole, amphotericin, tioconazole, itraconazole, posaconazole, voriconazole, isavuconazonium, casopfungin, anidulafungin, micafungin, griseofulvin, flucytosine, terbinafine, nyastin, amphotericin B, candidicin, filipin, hamycin, natamycin, rimocidin, bifonazole, butoconazole, fenticonazole, isoconazole, luciloconazole, omoconazole, oxiconazole, sertaconazole, sulconazole, albaconazole, efinaconazole, epoxiconazole, isavuconazole, propiconazole, ravuconazole, terconazole, and voriconazole.

In some embodiments, the dysbiosis-inducing event is exposure to an anti-parasitic agent. In some embodiments, the subject is administered one or more anti-parasitic agent, for example to treat a parasite infection. Examples of anti-parasitic agents include, without limitation, nitazonxanide, melarsoprol, eflornithine, metronidazole, tinidazole, meltefosine, mebenzaole, pyrantel pamoate, thiabendazole, diethylcarbamzine, ivermectin, niclosamide, praziquantel, albenzaole, praziquantel, rifampin, amphotericin B, fumagillin, bephenium, diethylcarbamazine, niclosamide, piperazine, pyantel, pyrvinium, flubenazole, benzyl benzoate/disulfiram, lindane, malathion, permethrin, benzyl alcohol, piperonyl butoxide/pyrethrins, spinosad, and crotamiton.

In some embodiments, the dysbiosis-inducing event is exposure to one or more immunosuppressants. Examples of immunosuppressants include, without limitation, prednisone, dexamethasone, hydrocortisone, methotrexate, azathipurine, mecaptopurine, fluorouracil, dactinomycin, anthracyclines, mitomycin C, bleomycin, mithramycin, cyclosporine, tacrolimus, everolimus, sirolimus, rapamycin, infliximab, etanercept, adaluminab, mycophenolic acid, fingolimond, myriocin, hydroxychloroquine, pexidaratinib, darolutamide, ferric maltol, glucagon, rilonacept, benralizumab, canakinumab, brodalumab, anakinra, reslizumab, ustekinumab, mepolizumab, tocilizumab, dupilumab, ixekizumab, guselkumab, secukinumab, srilumab, tildrakizumab, basiliximab, risankizumab, siltuximab, daclizumab, thalidomide.

In some embodiments, the dysbiosis-inducing event is exposure to one or more chemotherapeutic agents. Examples of chemotherapeutic agents include, without limitation, cyclophosphamide, methotrexate, 5-fluorouracil, vinorelbine, doxorubicin, docetaxel, bleomycin, vinblastine, dacarbazine, mustine, vincristine, procarbazine, prednisolone, etoposide, cisplatin, epirubicin, cisplatin, capecitabine, folinic acid, oxaliplatin, melphalan, chlorambucil, ifosfamide, busulfan, N-Nitroso-N-methylurea, carmustine, lomustine, semustine, fotemustine, streptozotocin, dacarbazine, mitozolomide, temozolomide, thiotepa, mytomycin, diaziquone, procarbazine, hexamethylmelamine, pemetrexed, capecitabine, cytarabine, gemcitabine, decitabine, azacitidine, fludarabine, nelarabine, cladribine, clofabine, pentostatin, thioguanine, mecaptopurine, vinblastine, vinorelbine, vindesine, vinflunine, paclitaxel, docetaxel, podophyllotoxin, teniposide, camptothecin, nobobiocin, merbarone, aclarubicin, daunorubicin, epirubicin, idarubicin, pirarubicin, and mitoxantrone.

In some embodiments, the dysbiosis inducing event is bowel lavage.

Aspects of the present disclosure relate to methods for protecting the microbiome of a subject comprising administering a therapeutically effective amount of a pharmaceutical composition comprising one or more purified bacterial strains. In some embodiments, the method further comprises administering one or more additional administrations of the pharmaceutical compositions described herein. In some embodiments, the method further comprises administering an antibiotic to the subject prior to administration of the pharmaceutical compositions. In some embodiments, the method further comprises administering vancomycin to the subject prior to administration of the pharmaceutical compositions.

A number of a factors may affect the composition (e.g., diversity, abundance of specific populations) of the gastrointestinal microbiome. The compositions described herein may be used to protect the microbiome from such factors. As used herein, the term "protecting the microbiome" refers to preventing or minimizing disruption of the microbiome of a subject. In some embodiments, the compositions described herein aid in maintaining a subject's normal gastrointestinal microbiome. In some embodiments, the compositions described herein aid in maintaining a healthy gastrointestinal microbiome. In some embodiments, protecting the microbiome may treat or prevent a microbiome-mediated disorder, such as an antibiotic-induced adverse effect, *Clostridium difficile* infection, ulcerative colitis, Crohn's disease, and irritable bowel syndrome.

In some embodiments, the microbiome is considered to be protected, if following an event, the composition (e.g., diversity, abundance of specific populations) of the gastrointestinal microbiome does not substantially change. In some embodiments, the microbiome is considered to be protected, if following an event, the composition (e.g., diversity, abundance of specific populations) of the gastrointestinal microbiome does not detectably change. In some embodiments, the composition of the gastrointestinal microbiome (e.g., diversity, abundance of specific populations) changes by less than 10% (e.g., 9%, 8%, 7%, 6%, 5%, 4%, 3%, 2%, 1% or less) following an event. In some embodiments, the event that may affect the composition of the microbiome is antibiotic treatment, attack by an infectious agent (e.g., an infectious disease), and/or *C. difficile* infection.

In some embodiments, administration of the pharmaceutical compositions described herein protects the microbiome of the subject against antibiotic treatment. Thus, for instance, according to the methods provided herein, a subject may be administered an antibiotic for an infection or to prevent an infection, wherein the administration of the antibiotic (e.g., vancomycin) does not result in significant dysbiosis. In some embodiments, administration of the pharmaceutical compositions described herein protects the microbiome of the subject against attack by an infectious agent (e.g., an infectious disease). In some embodiments, administration of the pharmaceutical compositions described herein protects the microbiome of the subject against *C. difficile* infection. In some embodiments, pharmaceutical compositions described herein protect the microbiome of the subject against *C. difficile* infection by increasing the rate of recovery of the microbiome following administration of an antibiotic (e.g., vancomycin) for treating the *C. difficile* infection. While not wishing to be bound by any particular theory, it is thought that an increased rate of recovery of the microbiome following administration of an antibiotic prevents *C. difficile* colonization (grafting) in preferred niches of the gastrointestinal tract. In some embodiments, the *C. difficile* preferred niches of the gastrointestinal tract are colonized by one or more bacterial strains of the pharmaceutical compositions or bacterial strains associated with bacterial strains of the pharmaceutical compositions, thereby preventing colonization with *C. difficile*.

Aspects of the present disclosure relate to methods for colonizing the microbiome of a subject comprising administering a therapeutically effective amount of a pharmaceutical composition comprising one or more purified bacterial strains. In some embodiments, the method further comprises administering one or more additional doses or amounts of the pharmaceutical compositions described herein. In some embodiments, the method further comprises administering an antibiotic to the subject prior to administration of the pharmaceutical compositions. In some embodiments, the method further comprises administering vancomycin to the subject prior to administration of the pharmaceutical compositions.

In some embodiments, the one or more of the bacterial strains of the pharmaceutical compositions provided herein colonize or recolonize the gastrointestinal tract or parts thereof (e.g., the colon or the cecum) of the subject. Such colonization may also be referred to as grafting or engraftment. In some embodiments, the one or more of the bacterial strains of the compositions recolonize the intestinal tract (e.g., the colon or the cecum) of the subject after the naturally present microbiome has been partially or completely removed, e.g., due to a dysbiosis inducing event. In some embodiments, the one or more of the bacterial strains of the compositions recolonize the intestinal tract (e.g., the colon or the cecum) of the subject after the naturally present microbiome has been partially or completely removed by antibiotic (e.g., vancomycin) treatment. In some embodiments, the one or more of the bacterial strains of the compositions colonize a dysbiotic gastrointestinal tract (e.g., a gastrointestinal tract that has undergone antibiotic treatment). In some embodiments, all of the bacterial strains of the composition colonize the gastrointestinal tract. In some embodiments, all of the bacterial strains of the compositions colonize a dysbiotic gastrointestinal tract. In some embodiments, multiple doses of the bacterial compositions are administered to allow for all of the bacterial strains of the composition colonize the gastrointestinal tract. In some embodiments, multiple doses of the bacterial compositions are administered to allow for all of the bacterial strains of the compositions colonize a dysbiotic gastrointestinal tract.

In some embodiments, the one or more bacterial strains of the pharmaceutical compositions colonize the microbiome because they can "outgrow" other bacterial strains (e.g., pathogens). In some embodiments, the subject has been treated with an antibiotic resulting in a removal of most of the microbiome, providing a "clean slate" environment for both the one or more bacterial strains of compositions and any other bacterial strains (e.g., pathogens). Thus, without being limited to a specific mechanism, if a pathogen and one or more bacterial strains of compositions provided herein are both present in the intestinal tract (e.g., the colon or the cecum), the one or more bacterial strains of compositions provided herein grow faster (e.g., have a shorter doubling time) than the pathogen, thereby preventing the pathogen from accumulating in the intestinal tract (e.g., the colon or the cecum) and allowing the one or more bacterial strains of the compositions to colonize. In some embodiments, the faster growth results because the one or more bacterial strains of the compositions provided herein are better at grafting in the intestinal tract (e.g., the colon or the cecum). In some embodiments, the faster growth results because the one or more bacterial strains of the compositions provided herein are better at metabolizing nutrients present in the intestinal tract (e.g., the colon or the cecum). In some embodiments, the compositions of bacterial strains provided herein prevent or inhibit production of bacterial toxins by an infectious agent, or prevent or inhibit the cytopathic or cytotoxic effects of such toxins. In some embodiments, the bacterial strains of the compositions provided herein can treat pathogenic infections, because of the synergy between the bacterial strains. Thus, without being limiting, in some embodiments, the combination of the bacterial strains of the compositions provided herein act synergistically because the combination of the strains is particularly well-suited to use nutrients in the intestinal tract (e.g., the colon or the cecum), or instance through metabolic interactions, and/or because the combination is superior in grafting (e.g., by providing a favorable microenvironment). In some embodiments, the one or more bacterial strains of the compositions described herein are able to colonize specific niches in the intestinal tract (e.g., the colon or the cecum). In some embodiments, the one or more bacterial strains of the compositions described herein are able to colonize specific niches in the intestinal tract (e.g., the colon or the cecum) that became available after antibiotic treatment.

In some embodiments, the pharmaceutical composition contains seven bacterial strains and at least two bacterial strains colonize the microbiome of the subject. In some embodiments, the pharmaceutical composition contains seven bacterial strains and at least four bacterial strains colonize the microbiome of the subject. In some embodiments, the pharmaceutical composition contains seven bacterial strains and each of the seven bacterial strains colonize the microbiome of the subject.

The extent of colonization of one or more of the bacterial strains may be determined, for example by detecting the presence of one or more bacterial strains and/or by quantifying the abundance of the one or more bacterial strains. In some embodiments, at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the bacterial strains of the pharmaceutical compositions colonize the microbiome of the subject. In some embodiments, at least 25% of the bacterial strains of the pharmaceutical compositions colonize the microbiome of the subject. In some embodiments, at least 50% of the bacterial strains of the pharmaceutical compositions colonize the microbiome of the subject. In some embodiments, 100% of the bacterial strains of the pharmaceutical compositions colonize the microbiome of the subject. In some embodiments, the percentage of the bacterial strains of the pharmaceutical compositions that colonize the microbiome of the subject is increased by administering additional doses of the pharmaceutical compositions.

It should be appreciated that in one aspect, the methods provided herein provide better colonization (e.g., engraftment of a higher number/percentage and/or higher abundance) of the bacterial strains of the pharmaceutical compositions when compared to the colonization of the same pharmaceutical compositions administered according to different methods. Thus, in one aspect, the colonization is better because the pharmaceutical compositions are administered according to the specific dose regimens, amounts and/or antibiotic treatment regimens provided herein.

In some embodiments, the pharmaceutical composition contains eight bacterial strains and at least two bacterial strains colonize the microbiome of the subject. In some embodiments, the pharmaceutical composition contains eight bacterial strains and at least four bacterial strains colonize the microbiome of the subject. In some embodiments, the pharmaceutical composition contains eight bacterial strains and each of the eight bacterial strains colonize the microbiome of the subject.

The extent of colonization of the microbiome by the one or more bacterial strains of the pharmaceutical compositions described herein may be based on the relative abundance of the bacterial strains of the pharmaceutical compositions in the microbiome. For example, in some embodiments, at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the bacterial strains of the microbiome of the subject are the bacterial strains of the pharmaceutical compositions. In some embodiments, at least 25% of the bacterial strains detected in the microbiome of the subject are the bacterial strains of the pharmaceutical compositions. In some embodiments, at least 50% of the bacterial strains detected in the microbiome of the subject are the bacterial strains of the pharmaceutical compositions. In some embodiments, the percentage of the bacterial strains of the bacterial compositions in the microbiome of the subject is increased by administering additional doses of the pharmaceutical compositions.

In some embodiments, the pharmaceutical compositions described herein result in durable colonization by one or more bacterial strains in the composition. In some embodiments, one or more bacterial strains of the pharmaceutical compositions described herein are detected in the microbiome of the subject for an extended period of time. In some embodiments, one or more bacterial strains of the pharmaceutical compositions described herein colonize the microbiome of the subject for an extended period of time. In some embodiments, one or more bacterial strains of the pharmaceutical compositions described herein are detected in the microbiome of the subject at least one week, two weeks, three weeks, four weeks, five weeks, or six weeks, seven weeks, eight weeks, nine weeks, ten weeks, eleven weeks, twelve weeks, three months, four months, five months, six months, seven months, eight months, nine months, ten months, eleven months, or one year following administration of the pharmaceutical composition.

It should be appreciated that in one aspect, the methods provided herein provide better colonization (e.g., engraftment of a higher number/percentage and/or higher abundance) and more durable colonization of the bacterial strains of the pharmaceutical compositions when compared to the colonization of the same pharmaceutical compositions administered according to different methods. Thus, in one aspect, the colonization is more better and more durable because the pharmaceutical compositions are administered according to the specific dose regimens, amounts and/or antibiotic treatment regimens provided herein.

It should be appreciated that in one aspect, the methods provided herein provide more durable colonization of the bacterial strains of the pharmaceutical compositions when compared to the colonization of the same pharmaceutical compositions administered according to different methods. Thus, in one aspect, the colonization is more durable because the pharmaceutical compositions are administered according to the specific dose regimens, amounts and/or antibiotic treatment regimens provided herein.

The methods described herein involve administering any of the pharmaceutical compositions described herein to a subject in need thereof. As used herein, "subject," "individual," and "patient" are used interchangeably, and refer to a vertebrate, preferably a mammal such as a human. Mammals include, but are not limited to, human primates, non-human primates or murine, bovine, equine, canine or feline species. In some embodiments, the subject is a human. In some embodiments, the human subject is a neonatal subject, a pediatric subject, an adolescent subject, an adult subject, or a geriatric subject. In some embodiments, the subject has or is at risk of having dysbiosis or has undergone or is at risk of undergoing a dysbiosis inducing event. In some embodiments, the subject has a risk factor associated with dysbiosis. In some embodiments, the subject has a risk factor associated with perturbation of the microbiome.

Any of the compositions described herein may be administered to a subject in a therapeutically effective amount or a dose of a therapeutically effective amount. In some embodiments, the therapeutically effective amount is an amount sufficient to treat or prevent a disease or disorder. The terms "treat" or "treatment" refer to reducing or alleviating one or more of the symptoms associated with a disease or disorder (e.g., dysbiosis).

In some embodiments, a therapeutically effective amount of any of the compositions described herein may be administered to prevent a disease or disorder (e.g., dysbiosis), prevent perturbation of the microbiome, and/or prevent colonization by pathogens. The terms "prevent" or "prevention" encompass prophylactic administration and may reduce the incidence or likelihood of the occurrence, for example, of the disease or disorder. In some embodiments, the composition reduces the incidence or likelihood of the occurrence of perturbation of the microbiome. In some embodiments, the composition reduces the incidence or likelihood of the occurrence of prevent colonization by pathogens. For instance, in some embodiments, administration of the compositions provided herein result in a healthy microbiome in the subject that provides an effect in a subject that reduces the incidence or likelihood of a disease or disorder. In some embodiments, administration of the composition provided herein result in a reduction or alleviation of one or more symptom associated with disease or disorder.

As used herein, the term "therapeutically effective amount" may be used interchangeably with the term "effective amount." A therapeutically effective amount or an effective amount of a composition, such as a pharmaceutical composition, as described herein, is any amount that results in a desired response or outcome in a subject, such as those described herein, including but not limited to delay the manifestation, arrest the progression, relieve or alleviate at least one symptom of a disease or disorder (e.g., dysbiosis), perturbation of the microbiome, and/or colonization of the microbiome by pathogens. In some embodiments, the therapeutically effective amount is an amount sufficient to restore the microbiome, increase recovery of the microbiome after a dysbiosis inducing event, protect the microbiome, and/or colonize the microbiome of a subject. In some embodiments, the therapeutically effective amount is an amount sufficient to treat primary and/or secondary (recurrent) *Clostridium difficile* infection. In some embodiments, the therapeutically effective amount is an amount sufficient to treat or suppress food allergy.

It should be appreciated that the term "effective amount," in reference to a composition comprising bacterial strains, may be expressed as the number of bacteria or CFUs to be administered. It should further be appreciated that the bacteria can multiply once administered. Thus, administration of even a relatively small amount of bacteria may have therapeutic effects.

Also within the scope of the present disclosure are methods involving determining whether a subject has or is at risk of having dysbiosis, *Clostridium difficile* infection or food allergy, or in need of administration of any of the pharmaceutical compositions described herein.

Aspects of the disclosure relate to bacterial strains with 16S rDNA sequences that have sequence identity to a nucleic acid sequence of any one of the sequences of the bacterial strains or species described herein. As will be appreciated by one of ordinary skill in the art, the 16S rDNA sequences represent DNA sequences corresponding to the 16S rRNA sequence. The terms "identical," or percent "identity," in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% sequence identity) over a specified region of a nucleic acid or amino acid sequence or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

In some embodiments, the bacterial strain has at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% sequence identity relative to any of the strains or bacterial species described herein over a specified region or over the entire sequence. It would be appreciated by one of skill in the art that the term "sequence identity" or "percent sequence identity," in the context of two or more nucleic acid sequences or amino acid sequences, refers to a measure of similarity between two or more sequences or portion(s) thereof.

In some embodiments, the pharmaceutical composition includes one or more (e.g., 1, 2, 3, 4, 5, 6, 7, 8, 9, 10, 11, 12, 13, 14, 15, 16, 17, 18, 19, or 20) bacterial strains, wherein the one or more bacterial strains contain 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:6, SEQ ID NO:7, and SEQ ID NO:8. In some embodiments, the pharmaceutical composition includes two or more (e.g., 3, 4, 5, 6, 7, 8, 9, 10, 11, 12, 13, 14, 15, 16, 17, 18, 19, or 20) bacterial strains, wherein the one or more bacterial strains contain 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:6, SEQ ID NO:7, and SEQ ID NO:8. In some embodiments, the pharmaceutical composition includes three or more (e.g., 3, 4, 5, 6, 7, 8, 9, 10, 11, 12, 13, 14, 15, 16, 17, 18, 19, or 20) bacterial strains, wherein the three or more bacterial strains contain 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO: 6, SEQ ID NO:7, and SEQ ID NO:8. In some embodiments, the pharmaceutical composition includes four or more (e.g., 4, 5, 6, 7, 8, 9, 10, 11, 12, 13, 14, 15, 16, 17, 18, 19, or 20) bacterial strains, wherein the four or more bacterial strains contain 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:6, SEQ ID NO: 7, and SEQ ID NO:8. In some embodiments, the pharmaceutical composition includes five or more (e.g., 5, 6, 7, 8, 9, 10, 11, 12, 13, 14, 15, 16, 17, 18, 19, or 20) bacterial strains, wherein the five or more bacterial strains contain 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:6, SEQ ID NO: 7, and SEQ ID NO:8. In some embodiments, the pharmaceutical composition includes six or more (e.g., 6, 7, 8, 9, 10, 11, 12, 13, 14, 15, 16, 17, 18, 19, or 20) bacterial strains, wherein the six or more bacterial strains contain 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:6, SEQ ID NO: 7, and SEQ ID NO:8. In some embodiments, the pharmaceutical composition includes seven or more (e.g., 7, 8, 9, 10, 11, 12, 13, 14, 15, 16, 17, 18, 19, or 20) bacterial strains, wherein the seven or more bacterial strains contain 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:6, SEQ ID NO: 7, and SEQ ID NO:8. In some embodiments, the pharmaceutical composition includes eight or more (e.g., 8, 9, 10, 11, 12, 13, 14, 15, 16, 17, 18, 19, or 20) bacterial strains, wherein the eight or more bacterial strains contain 16S rDNA sequences having at least 97% sequence identity with nucleic acid sequences selected from SEQ ID NO:1, SEQ ID NO:2, SEQ ID NO:3, SEQ ID NO:4, SEQ ID NO:5, SEQ ID NO:6, SEQ ID NO: 7, and SEQ ID NO:8.

In some embodiments, the pharmaceutical composition includes eight bacterial strains, wherein the bacterial strains include 16S rDNA sequences having at least 97% sequence identity to the nucleic acid sequences set forth by SEQ ID NO:1, SEQ ID NO:2, SEQ ID NO:3, SEQ ID NO:4, SEQ ID NO:5, SEQ ID NO: 6, SEQ ID NO:7, and SEQ ID NO:8. In some embodiments, the pharmaceutical composition consists of eight bacterial strains, wherein the bacterial strains include 16S rDNA sequences having at least 97% sequence identity to the nucleic acid sequences set forth by SEQ ID NO:1, SEQ ID NO:2, SEQ ID NO:3, SEQ ID NO:4, SEQ ID NO:5, SEQ ID NO: 6, SEQ ID NO:7, and SEQ ID NO:8.

In some embodiments, the pharmaceutical composition includes seven bacterial strains, wherein the bacterial strains include 16S rDNA sequences having at least 97% sequence identity to the nucleic acid sequences set forth by SEQ ID NO:1, SEQ ID NO:2, SEQ ID NO:3, SEQ ID NO:4, SEQ ID NO:5, SEQ ID NO:7, and SEQ ID NO:8. In some embodiments, the pharmaceutical composition consists of seven bacterial strains, wherein the bacterial strains include 16S rDNA sequences having at least 97% sequence identity to the nucleic acid sequences set forth by SEQ ID NO:1, SEQ ID NO:2, SEQ ID NO:3, SEQ ID NO:4, SEQ ID NO:5, SEQ ID NO:7, and SEQ ID NO:8. A composition comprising bacterial strains having 16S rRNA sequences having at 97% identity to the nucleic acid sequences set forth by SEQ ID NO:1, SEQ ID NO:2, SEQ ID NO:3, SEQ ID NO:4, SEQ ID NO:5, SEQ ID NO:7, and SEQ ID NO:8 may be referred to as "composition VE416" or "VE416". Additional aspects of the composition comprising bacterial strains having 16S rRNA sequences having at 97% identity to the nucleic acid sequences set forth by SEQ ID NO:1, SEQ ID NO:2, SEQ ID NO:3, SEQ ID NO:4, SEQ ID NO:5, SEQ ID NO:7, and SEQ ID NO:8 are described in PCT Publication Nos. WO2019/094837.

A composition comprising bacterial strains having 16S rRNA sequences having at 97% identity to the nucleic acid sequences set forth by SEQ ID NO:1, SEQ ID NO:2, SEQ ID NO:3, SEQ ID NO:4, SEQ ID NO:5, SEQ ID NO: 6, SEQ ID NO:7, and SEQ ID NO:8 may be referred to as "composition VE303" or "VE303". Additional aspects of the composition comprising bacterial strains having 16S rRNA sequences having at 97% identity to the nucleic acid sequences set forth by SEQ ID NO:1, SEQ ID NO:2, SEQ ID NO:3, SEQ ID NO:4, SEQ ID NO:5, SEQ ID NO: 6, SEQ ID NO:7, and SEQ ID NO:8 are described in PCT Publication Nos. WO2017/218680, WO2018/081550 and WO2018/112371.

In some embodiments, the pharmaceutical composition includes one or more (e.g., 1, 2, 3, 4, 5, 6, 7, 8, 9, 10, 11, 12, 13, 14, 15, 16, 17, 18, 19, or 20) bacterial strains, wherein at least one of the bacterial strains contains 16S rDNA sequences having at least 97% sequence identity with nucleic acid sequence provided by SEQ ID NO: 6. In some embodiments, the pharmaceutical composition includes two or more (e.g., 1, 2, 3, 4, 5, 6, 7, 8, 9, 10, 11, 12, 13, 14, 15, 16, 17, 18, 19, or 20) bacterial strains, wherein at least one of the bacterial strains contains 16S rDNA sequences having at least 97% sequence identity with nucleic acid sequence provided by SEQ ID NO: 6. In some embodiments, the pharmaceutical composition includes three or more (e.g., 1, 2, 3, 4, 5, 6, 7, 8, 9, 10, 11, 12, 13, 14, 15, 16, 17, 18, 19, or 20) bacterial strains, wherein at least one of the bacterial strains contains 16S rDNA sequences having at least 97% sequence identity with nucleic acid sequence provided by SEQ ID NO: 6. In some embodiments, the pharmaceutical composition includes four or more (e.g., 1, 2, 3, 4, 5, 6, 7, 8, 9, 10, 11, 12, 13, 14, 15, 16, 17, 18, 19, or 20) bacterial strains, wherein at least one of the bacterial strains contains 16S rDNA sequences having at least 97% sequence identity with nucleic acid sequence provided by SEQ ID NO: 6. In some embodiments, the pharmaceutical composition includes five or more (e.g., 1, 2, 3, 4, 5, 6, 7, 8, 9, 10, 11, 12, 13, 14, 15, 16, 17, 18, 19, or 20) bacterial strains, wherein at least one of the bacterial strains contains 16S rDNA sequences having at least 97% sequence identity with nucleic acid sequence provided by SEQ ID NO: 6. In some embodiments, the pharmaceutical composition includes six or more (e.g., 1, 2, 3, 4, 5, 6, 7, 8, 9, 10, 11, 12, 13, 14, 15, 16, 17, 18, 19, or 20) bacterial strains, wherein at least one of the bacterial strains contains 16S rDNA sequences having at least 97% sequence identity with nucleic acid sequence provided by SEQ ID NO: 6. In some embodiments, the pharmaceutical composition includes seven or more (e.g., 1, 2, 3, 4, 5, 6, 7, 8, 9, 10, 11, 12, 13, 14, 15, 16, 17, 18, 19, or 20) bacterial strains, wherein at least one of the bacterial strains contains 16S rDNA sequences having at least 97% sequence identity with nucleic acid sequence provided by SEQ ID NO: 6. In some embodiments, the pharmaceutical composition includes eight or more (e.g., 1, 2, 3, 4, 5, 6, 7, 8, 9, 10, 11, 12, 13, 14, 15, 16, 17, 18, 19, or 20) bacterial strains, wherein at least one of the bacterial strains contains 16S rDNA sequences having at least 97% sequence identity with nucleic acid sequence provided by SEQ ID NO: 6.

In some embodiments, the pharmaceutical composition consists of a bacterial strain comprising a 16S rDNA sequence having at least 97% sequence identity with nucleic acid sequence provided by SEQ ID NO: 6. In some embodiments, the pharmaceutical composition consists of a single bacterial strain comprising a 16S rDNA sequence having at least 97% sequence identity with nucleic acid sequence provided by SEQ ID NO: 6.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) *Adv. Appl. Math.* 2:482c, by the homology alignment algorithm of Needleman and Wunsch, *J. Mol. Biol.* 48:443, 1970, by the search for similarity method of Pearson and Lipman. *Proc. Natl. Acad. Sci. USA* 85:2444, 1988, by computerized implementations of these algorithms (GAP, BESTFIT, FASTA, and TFASTA in the Wisconsin Genetics Software Package, Genetics Computer Group. Madison. WI), or by manual alignment and visual inspection (see. e.g., Brent et al., *Current Protocols in Molecular Biology*, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., *Nuc. Acids Res.* 25:3389-3402, 1977; and Altschul et al., *J. Mol. Biol.* 215:403-410, 1990, respectively.

It should be appreciated that the terms "bacteria" and "bacterial strains" as used herein are interchangeable. The compositions described herein containing multiple purified bacterial strains may also be referred to as "live bacterial products."

In some embodiments, the pharmaceutical compositions described herein contain one or more bacterial strains belonging to the class Clostridia. In some embodiments, the pharmaceutical compositions described herein contain one or more bacterial strains belonging to the family Clostridiaceae. In some embodiments, the pharmaceutical compositions described herein contain one or more bacterial strains belonging to the genus *Clostridium*. In some embodiments, the pharmaceutical compositions described herein contain one or more bacterial strains belonging to *Clostridium* cluster IV, XIVa, and/or XVII. In some embodiments, the pharmaceutical compositions contain one or more bacterial strains belonging to *Clostridium* cluster XVII. In some embodiments, the compositions described herein contain one or more bacterial strains belonging to *Clostridium* cluster IV and/or XIVa.

In some embodiments, the compositions described herein comprise at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% bacterial strains belonging to *Clostridium* cluster XIVa, IV, and/or XVII. In some embodiments, the compositions described herein comprise at least 50% bacterial strains belonging to *Clostridium* cluster IV and/or XIVa. In some embodiments, the compositions described herein comprise at least 75% bacterial strains belonging to *Clostridium* cluster IV and/or XIVa.

In some embodiments, the pharmaceutical compositions described herein contain one or more of the following bacterial strains: *Clostridium bolteae, Anaerotruncus colihominis, Eubacterium fissicatena, Clostridium symbiosum, Blautia producta, Dorea longicatena, Clostridium*

*innocuum*, and *Flavonifractor plautii*. In some embodiments, the composition includes one or more (e.g., 2, 3, 4, 5, 6, 7, or 8) of the following bacterial strains: *Clostridium bolteae, Anaerotruncus colihominis, Eubacterium fissicatena, Clostridium symbiosum, Blautia producta, Dorea longicatena, Clostridium innocuum*, and *Flavonifractor plautii*.

In some embodiments, the pharmaceutical compositions described herein contain one or more of the following bacterial strains: *Clostridium bolteae, Anaerotruncus colihominis, Eubacterium fissicatena* or *Dracourtella massiliensis* or *Sellimonas intestinalis, Clostridium symbiosum, Blautia producta, Dorea longicatena, Clostridium innocuum* or *Erysipelotrichaceae bacterium*, and *Flavonifractor plautii* or *Subdolino granulum* species. In some embodiments, the composition includes one or more (e.g., 2, 3, 4, 5, 6, 7, or 8) of the following bacterial strains: *Clostridium bolteae, Anaerotruncus colihominis, Eubacterium fissicatena* or *Dracourtella massiliensis* or *Sellimonas intestinalis, Clostridium symbiosum, Blautia producta, Dorea longicatena, Clostridium innocuum* or *Erysipelotrichaceae bacterium*, and *Flavonifractor plautii* or *Subdolino granulum* species.

In some embodiments, the pharmaceutical composition consists of the following eight bacterial strains: *Clostridium bolteae, Anaerotruncus colihominis, Eubacterium fissicatena, Clostridium symbiosum, Blautia producta, Dorea longicatena, Clostridium innocuum*, and *Flavonifractor plautii*.

In some embodiments, the pharmaceutical composition consists of the following eight bacterial strains: *Clostridium bolteae, Anaerotruncus colihominis, Eubacterium fissicatena* or *Dracourtella massiliensis* or *Sellimonas intestinalis, Clostridium symbiosum, Blautia producta, Dorea longicatena, Clostridium innocuum* or *Erysipelotrichaceae bacterium*, and *Flavonifractor plautii* or *Subdolino granulum* species.

In some embodiments, the pharmaceutical composition is "VE303".

In some embodiments, the pharmaceutical compositions described herein contain one or more of the following bacterial strains: *Clostridium bolteae, Anaerotruncus colihominis, Eubacterium fissicatena, Clostridium symbiosum, Blautia producta, Clostridium innocuum*, and *Flavonifractor plautii*. In some embodiments, the pharmaceutical compositions described herein contain one or more of the following bacterial strains: *Clostridium bolteae, Anaerotruncus colihominis, Eubacterium fissicatena* or *Dracourtella massiliensis* or *Sellimonas intestinalis, Clostridium symbiosum, Blautia producta, Clostridium innocuum* or *Erysipelotrichaceae bacterium*, and *Flavonifractor plautii* or *Subdolino granulum* species. In some embodiments, the composition includes one or more (e.g., 2, 3, 4, 5, 6, or 7) of the following bacterial strains: *Clostridium bolteae, Anaerotruncus colihominis, Eubacterium fissicatena, Clostridium symbiosum, Blautia producta, Clostridium innocuum*, and *Flavonifractor plautii*. In some embodiments, the composition includes one or more (e.g., 2, 3, 4, 5, 6, or 7) of the following bacterial strains: *Clostridium bolteae, Anaerotruncus colihominis, Eubacterium fissicatena* or *Dracourtella massiliensis* or *Sellimonas intestinalis, Clostridium symbiosum, Blautia producta, Clostridium innocuum* or *Erysipelotrichaceae bacterium*, and *Flavonifractor plautii* or *Subdolino granulum* species.

In some embodiments, the compositions described herein contain two or more of the following bacterial strains: *Clostridium bolteae, Anaerotruncus colihominis, Eubacterium fissicatena, Clostridium symbiosum, Blautia producta, Clostridium innocuum*, and *Flavonifractor plautii*; and the composition does not contain *Dorea longicatena*. In some embodiments, the compositions described herein contain two or more of the following bacterial strains: *Clostridium bolteae, Anaerotruncus colihominis, Eubacterium fissicatena* or *Dracourtella massiliensis* or *Sellimonas intestinalis, Clostridium symbiosum, Blautia producta, Clostridium innocuum* or *Erysipelotrichaceae bacterium*, and *Flavonifractor plautii* or *Subdolino granulum* species and the composition does not contain *Dorea longicatena*.

In some embodiments, the compositions contain 7 bacterial strains. In some embodiments, the compositions consist of the following bacterial strains: *Clostridium bolteae, Anaerotruncus colihominis, Eubacterium fissicatena, Clostridium symbiosum, Blautia producta, Clostridium innocuum*, and *Flavonifractor plautii*. In some embodiments, the compositions consist of the following bacterial strains: *Clostridium bolteae, Anaerotruncus colihominis, Eubacterium fissicatena* or *Dracourtella massiliensis* or *Sellimonas intestinalis, Clostridium symbiosum, Blautia producta, Clostridium innocuum* or *Erysipelotrichaceae bacterium*, and *Flavonifractor plautii* or *Subdolino granulum*.

In some embodiments, the pharmaceutical composition is "VE416".

In some embodiments, the composition includes one or more (e.g., 2, 3, 4, 5, 6, 7, 8 or more) bacterial strains, wherein at least one of the bacterial strain is *Dorea longicatena*. In some embodiments, the composition consists of *Dorea longicatena*. In some embodiments, the composition consists of a single bacterial strain that is *Dorea longicatena*.

In one aspect, the 16S rDNA sequences of purified bacterial strains were compared to 16S rDNA sequences of known bacterial species/strains in a bacterial genome database to identify the closest known related bacterial species to the bacterial strains disclosed herein. It should be appreciated that multiple bacterial strains of the compositions disclosed herein may have the same closest related bacterial species.

In one aspect, as shown herein (e.g., in the Examples) the compositions and methods provided herein include the following bacteria *Clostridium bolteae, Anaerotruncus colihominis, Eubacterium fissicatena, Clostridium symbiosum, Blautia producta, Dorea longicatena, Clostridium innocuum*, and *Flavonifractor plautii*. The exemplary bacterial strains of the compositions disclosed herein can also be identified by their 16S rRNA sequences (SEQ ID NOs: 1-8). Identifying bacteria by their sequences furthermore allows for the identification of additional bacterial strains that are identical or highly similar to the exemplified bacteria. For instance, the 16S rRNA sequences of bacterial strains were used to identify the closest relative (based on percent identity) through whole genome sequencing and by comparing these sequences with 16S databases (Table 1). In addition, based on whole genome sequencing and comparing of the whole genome to whole genome databases, the bacterial strains having 16S rRNA sequences provided by SEQ ID NOs: 1-8 are most closely related to the following bacterial species: *Clostridium bolteae* 90A9, *Anaerotruncus colihominis* DSM 17241, *Dracourtella massiliensis* GD1, *Clostridium symbiosum* WAL-14163, *Clostridium* bacterium UC5.1-1D4, *Dorea longicatena* CAG:42, *Erysipelotrichaceae bacterium* 213, and *Clostridium orbiscindens* 1_3_50AFAA (see, e.g., Table 1). Thus, in one aspect, it should be appreciated that each row of Table 1, the bacterial strains are highly similar and/or are identical. In some embodiments, in context of the instant disclosure the names of bacterial strains within a row of Table 1 can be used interchangeably.

Thus, for example, in some embodiments, the disclosure provides methods and compositions including the following bacteria, which may be referred to as "composition VE303": *Clostridium bolteae, Anaerotruncus colihominis, Sellimonas intestinalis, Clostridium symbiosum, Blautia producta, Dorea longicatena, Erysipelotrichaceae bacterium*, and *Subdolino granulum* spp. See also PCT Publication No. WO2017/218680.

In some embodiments, the disclosure provides methods and compositions consisting of the following bacteria: *Clostridium bolteae, Anaerotruncus colihominis, Sellimonas intestinalis, Clostridium symbiosum, Blautia producta, Dorea longicatena, Erysipelotrichaceae bacterium*, and *Subdolino granulum* spp.

Homologies based on whole genome analysis are presented in Table 1.

1_7_47FAA), and *Lachnospiraceae bacterium* A4 (*Lachnospiraceae bacterium* 3_1_57FAA_CT1). Such bacterial strains are described, for example, in PCT Publication No. WO 2013/080561, which is incorporated herein by reference in its entirety. See for instance, Table 4, which also provides the OTU and 16S sRNA sequences. Such bacterial compositions are also described, for example in Atarashi et al. *Science* (2011) 331(6015): 337-341 and Atarashi et al. *Nature* (2013) 500(7361): 232-236. Sequences of the bacterial strains of VE202 are also presented in PCT Publication No. WO 2013/080561. It should be appreciated that alternative names of the bacterial strains may be used.

In some embodiments, disclosure provides compositions consisting of a purified bacterial mixture comprising *Clostridium saccharogumia* (*Clostridium ramosum* JCM 1298), *Flavonifractor plautii* (*Pseudoflavonifractor capillosus* ATCC 29799), *Clostridium hathewayi* (*Clostridium saccharolyticum* WM1), *Blautia coccoides* (*Lachnospiraceae bacterium* 6_1_63FAA), *Clostridium* spp. (*Clostridium bol-*

TABLE 1

Bacterial strains

| Strain number | SEQ ID NO: | Closest species based on Sanger sequencing of 16S region | Closest species based on Consensus SEQ ID # of 16S region as compared with 16S database | Closest species based on WGS compared versus WG databases | Additional closely related sequences | *Clostridium* cluster |
|---|---|---|---|---|---|---|
| 1 | 1 | *Clostridium bolteae* | *Clostridium bolteae* | *Clostridium bolteae* 90A9 | | XIVa |
| 2 | 2 | *Anaerotruncus colihominis* | *Anaerotruncus colihominis* | *Anaerotruncus colihominis* DSM 17241 | | IV |
| 3 | 3 | *Eubacterium fissicatena* | *Dracourtella massiliensis* | *Dracourtella massiliensis* GD1 | *Ruminococcus torques; Sellimonas intestinalis* | XIVa |
| 4 | 4 | *Clostridium symbiosum* | *Clostridium symbiosum* | *Clostridium symbiosum* WAL-14163 | | XIVa |
| 5 | 5 | *Blautia producta* | *Blautia producta* | *Clostridium bacterium* UC5.1-1D4 | *Blautia product* ATCC 27340 | XIVa |
| 6 | 6 | *Dorea longicatena* | *Dorea longicatena* | *Dorea longicatena* CAG:42 | | XIVa |
| 7 | 7 | *Clostridium innocuum* | *Clostridium innocuum* | *Erysipelotrichaceae bacterium* 21_3 | | XVII |
| 8 | 8 | *Flavinofractor plautii* | *Flavinofractor plautii* | *Clostridium orbiscindens* 1_3_50AFAA | *Subdolinogranulum* | IV |

In some embodiments, disclosure provides methods and compositions including the following bacterial strains, which may be referred to as "composition VE202": *Clostridium saccharogumia* (*Clostridium ramosum* JCM 1298), *Flavonifractor plautii* (*Pseudoflavonifractor capillosus* ATCC 29799), *Clostridium hathewayi* (*Clostridium saccharolyticum* WM1), *Blautia coccoides* (*Lachnospiraceae bacterium* 6_1_63FAA), *Clostridium* spp. (*Clostridium bolteae* ATCC BAA-613), cf. *Clostridium* sp. MLG055 (*Erysipelotrichaceae bacterium* 2_2_44A), *Clostridium indolis* (*Anaerostipes caccae* DSM 14662), *Anaerotruncus colihominis* (*Anaerotruncus colihominis* DSM 17241), *Ruminococcus* sp. ID8 (*Lachnospiraceae bacterium* 2_1_46FAA), *Clostridium lavalense* (*Clostridium asparagiforme* DSM 15981), *Clostridium symbiosum* (*Clostridium symbiosum* WAL-14163), *Clostridium ramosum, Eubacterium contortum* (*Clostridium* sp. D5), *Clostridium scindens* (*Lachnospiraceae bacterium* 5_1_57FAA), *Lachnospiraceae bacterium* A4 (*Lachnospiraceae bacterium* 3_1_57FAA_CT1), *Clostridium* sp. 316002/08 (*Clostriales bacterium* 1_7_47FAA), and *Lachnospiraceae bacterium* A4 (*Lachnospiraceae bacterium* 3_1_57FAA_CT1).

teae ATCC BAA-613), cf. *Clostridium* sp. MLG055 (*Erysipelotrichaceae bacterium* 2_2_44A), *Clostridium indolis* (*Anaerostipes caccae* DSM 14662), *Anaerotruncus colihominis* (*Anaerotruncus colihominis* DSM 17241), *Ruminococcus* sp. ID8 (*Lachnospiraceae bacterium* 2_1_46FAA), *Clostridium lavalense* (*Clostridium asparagiforme* DSM 15981), *Clostridium symbiosum* (*Clostridium symbiosum* WAL-14163), *Clostridium ramosum, Eubacterium contortum* (*Clostridium* sp. D5), *Clostridium scindens* (*Lachnospiraceae bacterium* 5_1_57FAA), *Lachnospiraceae bacterium* A4 (*Lachnospiraceae bacterium* 3_1_57FAA_CT1), *Clostridium* sp. 316002/08 (*Clostriales bacterium* 1_7_47FAA), and *Lachnospiraceae bacterium* A4 (*Lachnospiraceae bacterium* 3_1_57FAA_CT1).

In one aspect, the disclosure provides compositions and methods for the treatment of infectious pathogens. In some embodiments, the disclosure provides compositions and methods for the treatment of *Clostridium difficile* infection. *Clostridium difficile* was renamed as *Clostridioides difficile* (see, e.g., Lawson et al., Anaerobe. 2016 August; 40:95-9.

doi: 10.1016/j.anaerobe.2016.06.008. Epub 2016 Jun. 28). *Clostridium difficile* and *Clostridioides difficile* are used interchangeably herein. In some embodiments, the disclosure provides compositions and methods for the treatment of primary *Clostridium difficile* infection. In some embodiments, the disclosure provides compositions and methods for the treatment of recurring *Clostridium difficile* infection. Any of the pharmaceutical compositions described herein may comprise one or more *Clostridium difficile*-suppressing strains. As used herein, a "*Clostridium difficile*-suppressing strains" or strain "capable of suppressing *C. difficile*" refers to a bacterial strain that (directly or indirectly) suppresses the presence and/or quantity of *C. difficile* in the microbiome of the subject. In some embodiments, the *Clostridium difficile*-suppressing strain directly suppresses the presence and/or quantity of *C. difficile* in the microbiome of the subject. In some embodiments, the *Clostridium difficile*-suppressing strain indirectly suppresses the presence and/or quantity of *C. difficile* in the microbiome of the subject. The *C. difficile*-suppressing strain may suppress the presence and/or quantity of *C. difficile* in the microbiome of the subject by any of a variety of mechanisms. For example, the *C. difficile*-suppressing strain may kill *C. difficile*, inhibit growth/replication of *C. difficile*, and/or prevent colonization by *C. difficile*. Examples of *Clostridium difficile*-suppressing strains, and compositions comprising such strains are provided for instance in PCT Publication No. WO2017/218680.

In some embodiments, the presence and/or quantity of *C. difficile* in the microbiome of the subject is reduced by at least 10%, 20%, 30%, 40%, 50%, 60%, 70%, 80%, 90%, or 100% in the presence of a *C. difficile*-suppressing strain(s) as compared to the presence and/or quantity of *C. difficile* in the microbiome of the subject in the absence of a *C. difficile*-suppressing strain(s).

In one aspect, the disclosure provides compositions and methods for the treatment or suppression of food allergy.

In some embodiments, one or more of the bacterial strains are human-derived bacteria, meaning the one or more bacterial strains were obtained from or identified from a human or a sample therefrom (e.g., a human donor). In some embodiments, all of the bacterial strains are human-derived bacteria. In some embodiments, the bacterial strains are derived from more than one human donor.

The bacterial strains used in the pharmaceutical compositions provided herein generally are isolated from the microbiome of healthy individuals. In some embodiments, the pharmaceutical compositions include strains originating from a single individual. In some embodiments, the pharmaceutical compositions include strains originating from multiple individuals. In some embodiments, the pharmaceutical compositions are obtained from multiple individuals, isolated, and grown up individually. The bacterial compositions that are grown up individually may subsequently be combined to provide the pharmaceutical compositions of the disclosure. It should be appreciated that the origin of the bacterial strains of the pharmaceutical compositions provided herein is not limited to the human microbiome from a healthy individual. In some embodiments, the bacterial strains originate from a human with a microbiome in dysbiosis. In some embodiments, the bacterial strains originate from non-human animals or the environment (e.g., soil or surface water). In some embodiments, the combinations of bacterial strains provided herein originate from multiple sources (e.g., human and non-human animals).

In some embodiments, the pharmaceutical composition includes one or more anaerobic bacteria. In some embodiments, the pharmaceutical composition includes only anaerobic bacteria. In some embodiments, the pharmaceutical composition includes one or more facultative anaerobic bacteria. In some embodiments, the pharmaceutical composition includes only facultative anaerobic bacteria. In some embodiments, the pharmaceutical composition includes one or more obligate anaerobic bacteria. In some embodiments, the pharmaceutical composition includes only obligate anaerobic bacteria.

In some embodiments, at least one (e.g., 1, 2, 3, 4, 5, 6, 7, 8, or more) of the bacterial strains in the pharmaceutical composition is a spore former. In some embodiments, at least one (e.g., 1, 2, 3, 4, 5, 6, 7, 8, or more) of the bacterial strains in the pharmaceutical composition is in spore form. In some embodiments, at least one (e.g., 1, 2, 3, 4, 5, 6, 7, 8, or more) of the bacterial strains in the pharmaceutical composition is a non-spore former. In some embodiments, at least one (e.g., 1, 2, 3, 4, 5, 6, 7, 8, or more) of the bacterial strains in the pharmaceutical composition is in vegetative form. As discussed above, spore forming bacteria can also be in vegetative form. In some embodiments, at least one (e.g., 1, 2, 3, 4, 5, 6, 7, 8, or more) of the bacterial strains in the pharmaceutical composition is in spore form and at least one (e.g., 1, 2, 3, 4, 5, 6, 7, 8, or more) of the bacterial strains in the pharmaceutical composition is in vegetative form. In some embodiments, at least one bacterial strain that is considered able to form spores (i.e., a spore-former) but is present in the composition in vegetative form. In some embodiments, at least one bacterial strain that is considered able to form spores is present in the pharmaceutical composition both in spore form and in vegetative form. In some embodiments, each of the bacterial strains are in vegetative form.

It is envisioned that the bacterial strains of the pharmaceutical compositions provided herein are alive and will be alive when they reach the target area (e.g., the intestines). Bacterial spores are considered to be alive in this regard. In some embodiments, bacteria that are administered as spores may germinate in the target area (e.g., the intestines). It should further be appreciated that not all of the bacteria are alive and the compositions can include a percentage (e.g., by weight) that is not alive. In addition, in some embodiments, the compositions include bacterial strains that are not alive when administered or at the time when the composition reaches the target area (e.g., the intestines). It is envisioned that non-living bacteria may still be useful by providing some nutrients and metabolites for the other bacterial strains in the composition.

In any of the live bacterial products provided herein, in some embodiments, the bacterial strains are purified. In any of the live bacterial products provided herein, in some embodiments, the bacterial strains are isolated. Any of the bacterial strains described herein may be isolated and/or purified, for example, from a source such as a culture or a microbiota sample (e.g., fecal matter). The bacterial strains used in the compositions provided herein generally are isolated from the microbiome of healthy individuals. However, bacterial strains can also be isolated from individuals that are considered not to be healthy. In some embodiments, the compositions include strains originating from multiple individuals. As used herein, the term "isolated" in the bacteria refers to bacteria that have been separated from one or more undesired component, such as another bacterium or bacterial strain, one or more component of a growth medium, and/or one or more component of a sample, such as a fecal sample. In some embodiments, the bacteria are substantially isolated from a source such that other components of the source are not detected (e.g., below the level of detection). As also used herein, the term "purified" refers to a bacterial strain or composition comprising such that has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

In some embodiments, the specific combination of one or more bacterial strains of the compositions described herein provides a synergistic effect that promotes decreasing dysbiosis, restoring the microbiome, recovery of a healthy microbiome following a dysbiosis inducing event, protecting the microbiome, and/or colonizing the microbiome of the subject. In some embodiments, the synergistic effect is provided by the capacity of the combination to metabolize specific nutrients. In some embodiments, the synergistic effect is provided by the capacity of the combination to provide specific metabolites to the environment. Such specific metabolites may suppress growth of the pathogen and/or stimulate growth of non-pathogens. In some embodiments, the synergistic effect is provided by the capacity of the combination to provide short-chain fatty acids to the environment. In some embodiments, the synergistic effect is provided by the capacity of the combination to provide specific short-chain fatty acids to the environment. In some embodiments, the synergistic effect is provided by the capacity of the combination to produce butyrate. In some embodiments, the synergistic effect is provided by the capacity of the combination to produce acetate. In some embodiments, the synergistic effect is provided by the capacity of the combination to produce lactate. In some embodiments, the synergistic effect is provided by the capacity of the combination to produce propionate. In some embodiments, the synergistic effect is provided by the capacity of the combination to produce succinate. In some embodiments, the synergistic effect is provided by the capacity of the combination to produce multiple metabolites. In some embodiments, the synergistic effect is provided by the capacity of the combination to produce multiple short-chain fatty acids. In some embodiments, the synergistic effect is provided by the capacity of the combination to produce both butyrate and acetate. In some embodiments, the synergistic effect is provided by the capacity of the combination to produce both butyrate and lactate. In some embodiments, the synergistic effect is provided by the capacity of the combination to produce both butyrate and propionate. In some embodiments, the synergistic effect is provided by the capacity of the combination to produce both butyrate and succinate. In some embodiments, the synergistic effect is provided by the capacity of the combination to produce butyrate, acetate and additional short-chain fatty acids.

In some embodiments, the specific combination of one or more bacterial strains of the compositions provided herein is superior in the use of nutrients and in grafting when compared to other strains (e.g., pathogens), thereby protecting and or restoring the microbiome, for instance through suppressing the growth of the pathogen. In some embodiments, the specific combination of one or more bacterial strains of the compositions provided herein induces an immune response in the subject that promotes decreasing dysbiosis, restoring the microbiome, recovery of a healthy microbiome following a dysbiosis inducing event, protecting the microbiome, and/or colonizing the microbiome of the subject with one of or of the bacterial strains of the pharmaceutical compositions.

Also within the scope of the present disclosure are compositions, e.g., compositions for administering to a subject, such as pharmaceutical compositions. In some embodiments, the composition comprises any of the bacterial strains described herein.

In one aspect, the disclosure provides pharmaceutical compositions comprising any of the bacterial strains described herein. In some embodiments, the pharmaceutical composition comprises a pharmaceutical acceptable excipient. In some embodiments, the pharmaceutical composition is formulated for oral administration. In some embodiments, the pharmaceutical composition is formulated for rectal administration. In some embodiments, the pharmaceutical composition is formulated for delivery to the intestine. In some embodiments, the pharmaceutical composition is formulated for delivery to the colon.

In some embodiments, the pharmaceutical compositions described herein contain one or more bacterial strains. In some embodiments, the pharmaceutical compositions may be lyophilized. In some embodiments, the pharmaceutical composition is in the form of a capsule. In some embodiments, the pharmaceutical composition further comprises a pH sensitive composition comprising one or more enteric polymers.

In some embodiments, one of or more of the bacterial strains of the pharmaceutical compositions has been spray-dried. The process of spray-drying refers to production of a dry powder from a liquid comprising bacterial compositions. (See e.g., Ledet et al., Spray-Drying of Pharmaceuticals in "*Lyophilized Biologics and Vaccines*" pages 273-194, Springer). In general, the process involves rapidly drying the bacterial compositions with a hot gas.

Any of the compositions described herein, including the pharmaceutical compositions and food products comprising bacterial strains, the bacterial strains in any form, for example in an aqueous form, such as a solution or a suspension, embedded in a semi-solid form, in a powdered form, or freeze-dried form. In some embodiments, the composition or the bacterial strains are lyophilized. In some embodiments, a subset of the bacterial strains is lyophilized. Methods of lyophilizing compositions, specifically compositions comprising bacteria, are well known in the art. See, e.g., U.S. Pat. Nos. 3,261,761; 4,205,132; PCT Publications WO 2014/029578 and WO 2012/098358, herein incorporated by reference in their entirety. The bacteria may be lyophilized as a combination and/or the bacteria may be lyophilized separately and combined prior to administration. A bacterial strain may be combined with a pharmaceutical excipient prior to combining it with the other bacterial strain or multiple lyophilized bacteria may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake.

In some embodiments, one or more of the bacterial strains of the compositions, including pharmaceutical compositions and food products, has been spray-dried. In some embodiments, a subset of the bacterial strains is spray-dried. The process of spray-drying refers to production of dry powder from a liquid comprising bacterial compositions (See, e.g., Ledet, et al., Spray Draying of Pharmaceuticals in "*Lyophilized Biologics and Vaccines*" pages 273-294, Springer). In general, the process involves rapidly drying the bacterial compositions with a hot gas. A bacterial strain may be combined with a pharmaceutical excipient prior to combining it with the other bacterial strains or multiple spray-dried bacterial strains may be combined while in spray-dried form and the mixture of bacterial strains, once combined, may be subsequently combined with a pharmaceutical excipient.

The bacterial strains can be manufactured using fermentation techniques well known in the art. In some embodiments, the bacteria are propagated or manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

In some embodiments, the live bacterial product may be formulated for administration as a pharmaceutical composition. The term "pharmaceutical composition" as used herein means a product that results from the mixing or combining of at least one active ingredient, such as any of the bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions of the invention can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution. Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like. In some embodiments, the pharmaceutical compositions can be used by injection, such as by intravenous, intramuscular, subcutaneous, or intradermal administration.

In some embodiments, the compositions comprising bacterial strains are formulated for oral delivery. In some embodiments, the compositions comprising bacterial strains are formulated for delivery to the intestines (e.g., the small intestine and/or the colon). In some embodiments, the composition comprising bacterial strains may be formulated with an enteric coating that increases the survival of the bacteria through the harsh environment in the stomach. The enteric coating is one which resists the action of gastric juices in the stomach so that the bacteria of the composition therein will pass through the stomach and into the intestines. The enteric coating may readily dissolve when in contact with intestinal fluids, so that the bacteria enclosed in the coating will be released in the intestinal tract. Enteric coatings may consist of polymers and copolymers well known in the art, such as commercially available EUDRAGIT (Evonik Industries). (See e.g., Zhang, AAPS PharmSciTech, 2016, 17 (1), 56-67).

The compositions comprising bacterial strains may also be formulated for rectal delivery to the intestine (e.g., the colon). Thus, in some embodiments, compositions comprising bacterial strains may be formulated for delivery by suppository, colonoscopy, endoscopy, sigmoidoscopy or enema. A pharmaceutical preparation or formulation and particularly a pharmaceutical preparation for oral administration, may include an additional component that enables efficient delivery of the compositions of the disclosure to the intestine (e.g., the colon). A variety of pharmaceutical preparations that allow for the delivery of the compositions to the intestine (e.g., the colon) can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon. It should further be appreciated that each part of the intestine (e.g., the duodenum, jejunum, ileum, cecum, colon and rectum), has different biochemical and chemical environment. For instance, parts of the intestines have different pHs, allowing for targeted delivery by compositions that have a specific pH sensitivity. Thus, the compositions provided herein may be formulated for delivery to the intestine or specific parts of the intestine (e.g., the duodenum, jejunum, ileum, cecum, colon and rectum) by providing formulations with the appropriate pH sensitivity. (See e.g., Villena et al., *Int J Pharm* 2015, 487 (1-2): 314-9).

Also within the scope of the present disclosure are pharmaceutical compositions for administration by additional or alternative routes. In some embodiments, the pharmaceutical compositions are formulated for sublingual administration. In some embodiments, the pharmaceutical compositions are formulated for administration by injection.

In some embodiments, a pharmaceutical composition may include an additional component that enables efficient delivery of the compositions of the disclosure to a desired site, such as the gastrointestinal tract (e.g., the colon).

In some embodiments, the pharmaceutical composition includes an adjuvant associated with providing a benefit in the treatment of allergy. In some embodiments, the pharmaceutical composition includes one or more components of an oral immunotherapeutic, an epicutaneous immunotherapeutic, or a sublingual immunotherapeutic.

Another embodiment of a pharmaceutical preparation useful for delivery of the compositions to the intestine (e.g., the colon) is one that ensures the delivery to the colon by delaying the release of the contents (e.g., the bacterial strains) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Additional examples of pharmaceutical compositions that allow for the delivery to the intestine (e.g., the colon) include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

Another example of a system enabling the delivery to the intestine (e.g., the colon) is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

A further example of a system enabling the delivery of a composition to the intestine (e.g., the colon), is a composition that includes a coating that can be removed by an enzyme present in the gut (e.g., the colon), such as, for example, a carbohydrate hydrolase or a carbohydrate reductase. Such a system is not particularly limited, and more specific examples thereof include systems which use food components such as non-starch polysaccharides, amylose, xanthan gum, and azopolymers.

The compositions provided herein can also be delivered to specific target areas, such as the intestine, by delivery through an orifice (e.g., a nasal tube) or through surgery. In addition, the compositions provided herein that are formulated for delivery to a specific area (e.g., the cecum or the colon), may be administered by a tube (e.g., directly into the small intestine). Combining mechanical delivery methods such as tubes with chemical delivery methods such as pH specific coatings, allow for the delivery of the compositions provided herein to a desired target area (e.g., the cecum or the colon).

The compositions comprising bacterial are formulated into pharmaceutically acceptable dosage forms by conventional methods known to those of skill in the art. Dosage regimens are adjusted to provide the optimum desired response (e.g., the prophylactic or therapeutic effect). In some embodiments, the dosage form of the composition is a tablet, pill, capsule, powder, granules, solution, or suppository. In some embodiments, the pharmaceutical composition is formulated for oral administration. In some embodiments, the pharmaceutical composition comprises bacterial strains and is formulated such that the bacteria, or a portion thereof, remain viable after passage through the stomach of the subject. In some embodiments, the pharmaceutical composition is formulated for rectal administration, e.g., as a suppository. In some embodiments, the pharmaceutical composition is formulated for delivery to the intestine or a specific area of the intestine (e.g., the colon) by providing an appropriate coating (e.g., a pH specific coating, a coating that can be degraded by target area specific enzymes, or a coating that can bind to receptors that are present in a target area).

Dosages of the active ingredients in the pharmaceutical compositions of the present invention can be varied so as to obtain an amount of the active ingredient which is effective to achieve the desired pharmaceutical response for a particular subject, composition, and mode of administration, without being toxic or having an adverse effect on the subject. The selected dosage level depends upon a variety of factors including the activity of the particular compositions of the present invention employed, the route of administration, the time of administration, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the pharmaceutical composition at levels lower than that required to achieve the desired therapeutic effect and gradually increase the dosage until the desired effect (e.g., treatment of *Clostridium difficile* infection, treatment of allergy, modulation of one or more immune responses associated with allergy) is achieved. In general, effective doses of the compositions of the present invention, for the prophylactic treatment of groups of people as described herein vary depending upon many different factors, including routes of administration, physiological state of the subject, whether the subject is human or an animal, other medications administered, and the therapeutic effect desired. Dosages need to be titrated to optimize safety and efficacy. In some embodiments, the dosing regimen entails oral administration of a dose of any of the compositions described herein. In some embodiments, the dosing regimen entails oral administration of multiple doses of any of the compositions described herein. In some embodiments, any of the compositions described herein are administered the subject once, twice, 3 times, 4 times, 5 times, 6 times, 7 times, 8 times, 9 times, at least 10 times, at least 11 times, at least 12 times, at least 13 times, at least 14 times, or more. In some embodiments, any of the compositions described herein are administered the subject in multiple doses at a regular interval, such as every day, every 2 days, every 3 days, every 4 days, every 5 days, every 6 days, every week, every 2 weeks, every month, every 2 months, every 3 months, every 4 months, every 5 months, every 6 months, or more. In some embodiments, one dose of any of the compositions described herein is administered and a second dose of the composition is administered the following day (e.g., consecutive day). In some embodiments, one dose of any of the compositions described herein is administered and each of the additional doses of the composition are administered on consecutive days (e.g., first dose on day 1, second dose of day 2, third dose on day 3, etc.).

In one aspect, the disclosure provides methods comprising administration of multiple doses of the pharmaceutical compositions. In some embodiments, the disclosure provides methods comprising administration of antibiotic (e.g., vancomycin) followed by multiple doses of the pharmaceutical compositions. In some embodiments, administration of multiple doses of the pharmaceutical compositions described herein provides enhanced colonization (engraftment) of one or more bacterial strains of the pharmaceutical compositions as compared to administration of a single dose of the pharmaceutical composition. In some embodiments, administration of multiple doses of the pharmaceutical compositions described herein provides enhanced recovery of one or more bacterial strains of the pharmaceutical compositions as compared to administration of a single dose of the pharmaceutical composition. In some embodiments, administration of multiple doses of the pharmaceutical compositions described herein provides increased abundance of one or more bacterial strains of the pharmaceutical compositions as compared to administration of a single dose of the pharmaceutical composition. In some embodiments, administration of multiple doses of the pharmaceutical compositions described herein provides an increase in the number of subjects that were colonized with of all of bacterial strains of the pharmaceutical compositions as compared to administration of a single dose of the pharmaceutical composition. In some embodiments, administration of multiple doses of the pharmaceutical compositions described herein provides durable colonization (e.g., up to 6 months) of one or more bacterial strains of the pharmaceutical compositions as compared to administration of a single dose of the pharmaceutical composition. In some embodiments, administration of multiple doses of the pharmaceutical compositions described herein provides durable colonization (e.g., up to 6 months) of all of the bacterial strains of the pharmaceutical compositions as compared to administration of a single dose of the pharmaceutical composition. It should further be appreciated that administration of multiple dose my results in a combination of the results described. Thus, for example, in some embodiments, administration of multiple doses of the pharmaceutical compositions described herein provides enhanced colonization (engraftment) and increased rate of recovery of one or more bacterial strains of the pharmaceutical compositions as compared to administration of a single dose of the pharmaceutical composition.

Figure 7A:
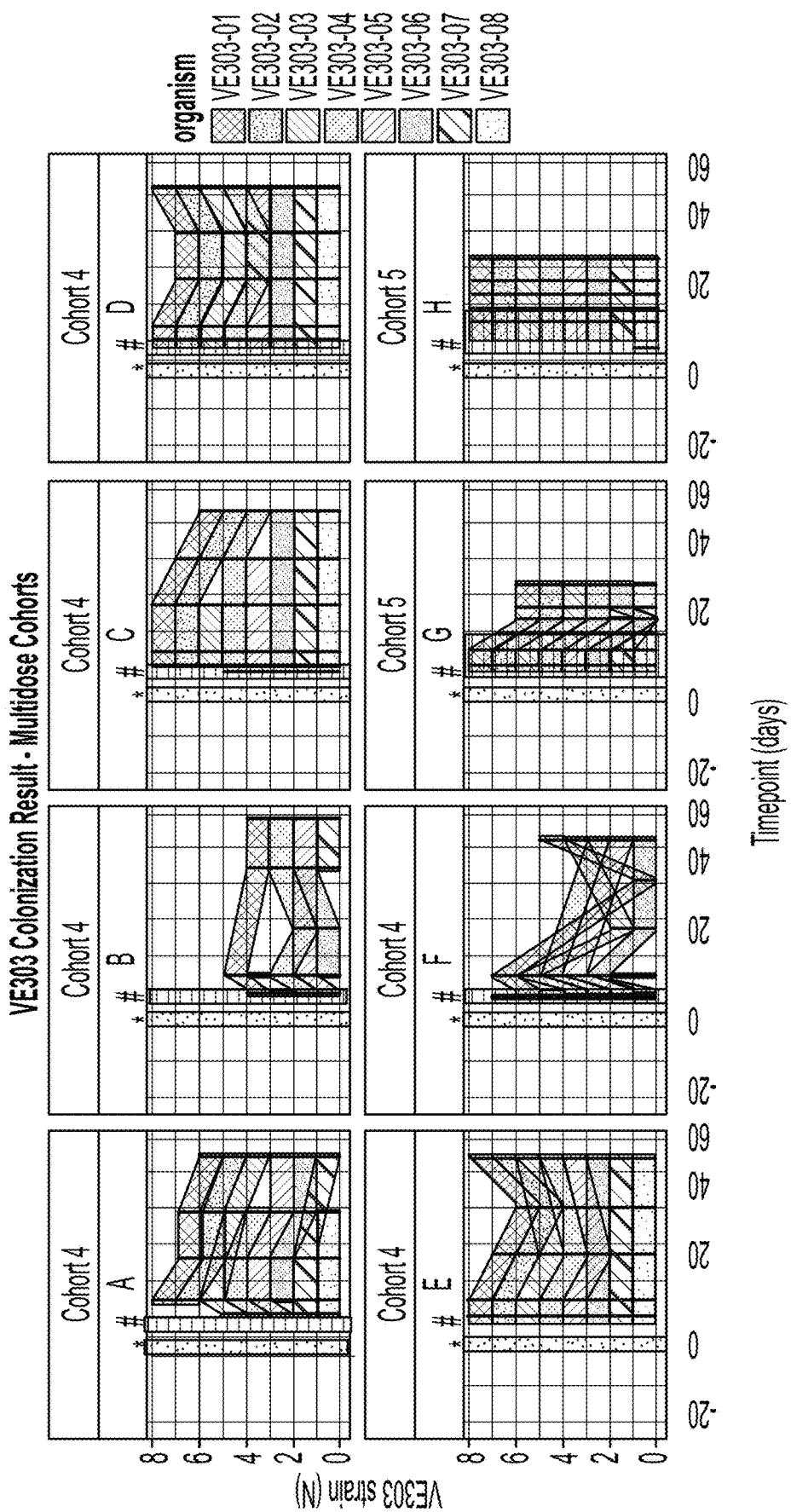
FIGS. 7A-7C present graphs showing the number of bacterial strains of composition VE303 detected in the microbiota of individual subjects.
Figure 7B:
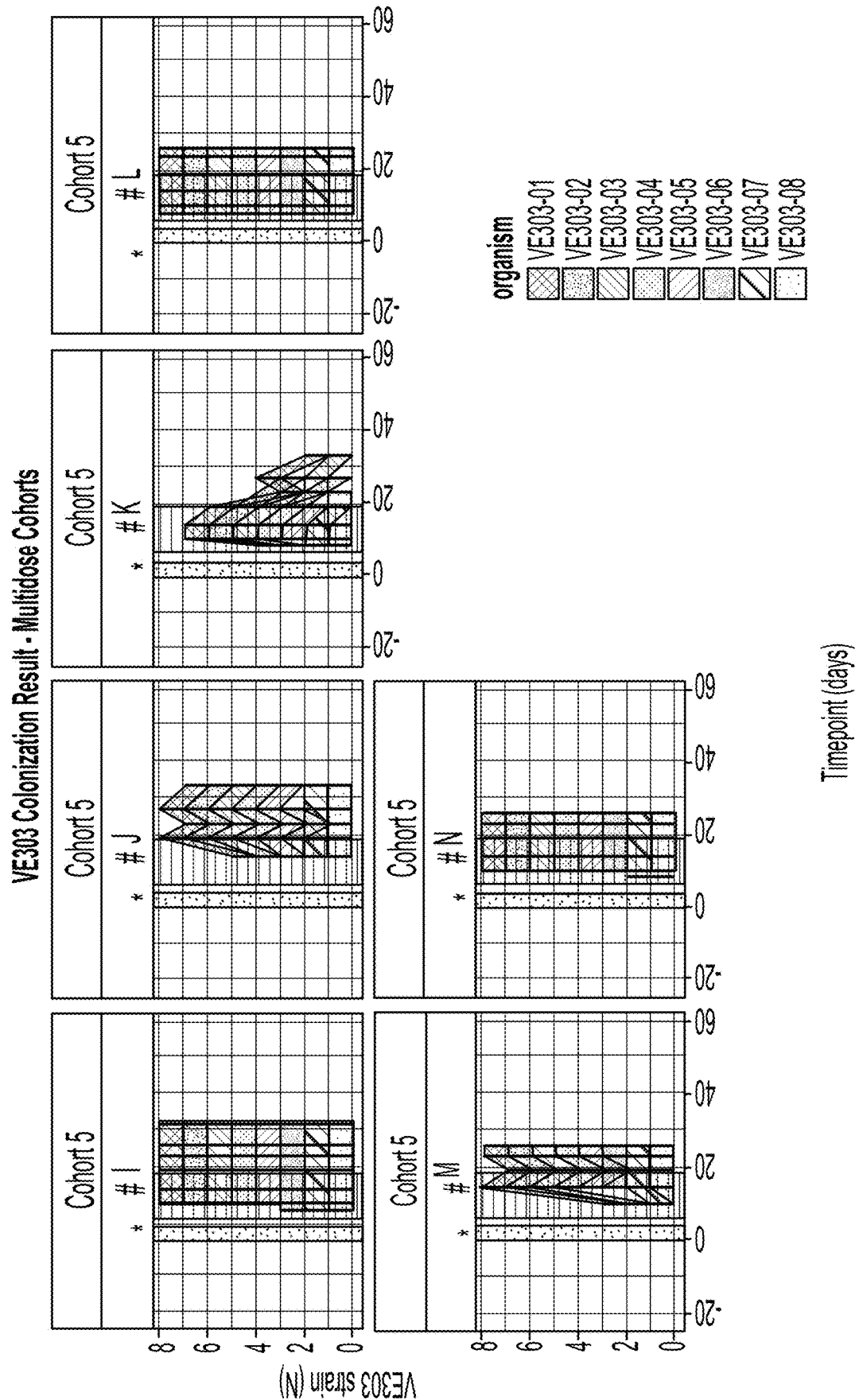
Figure 7C:
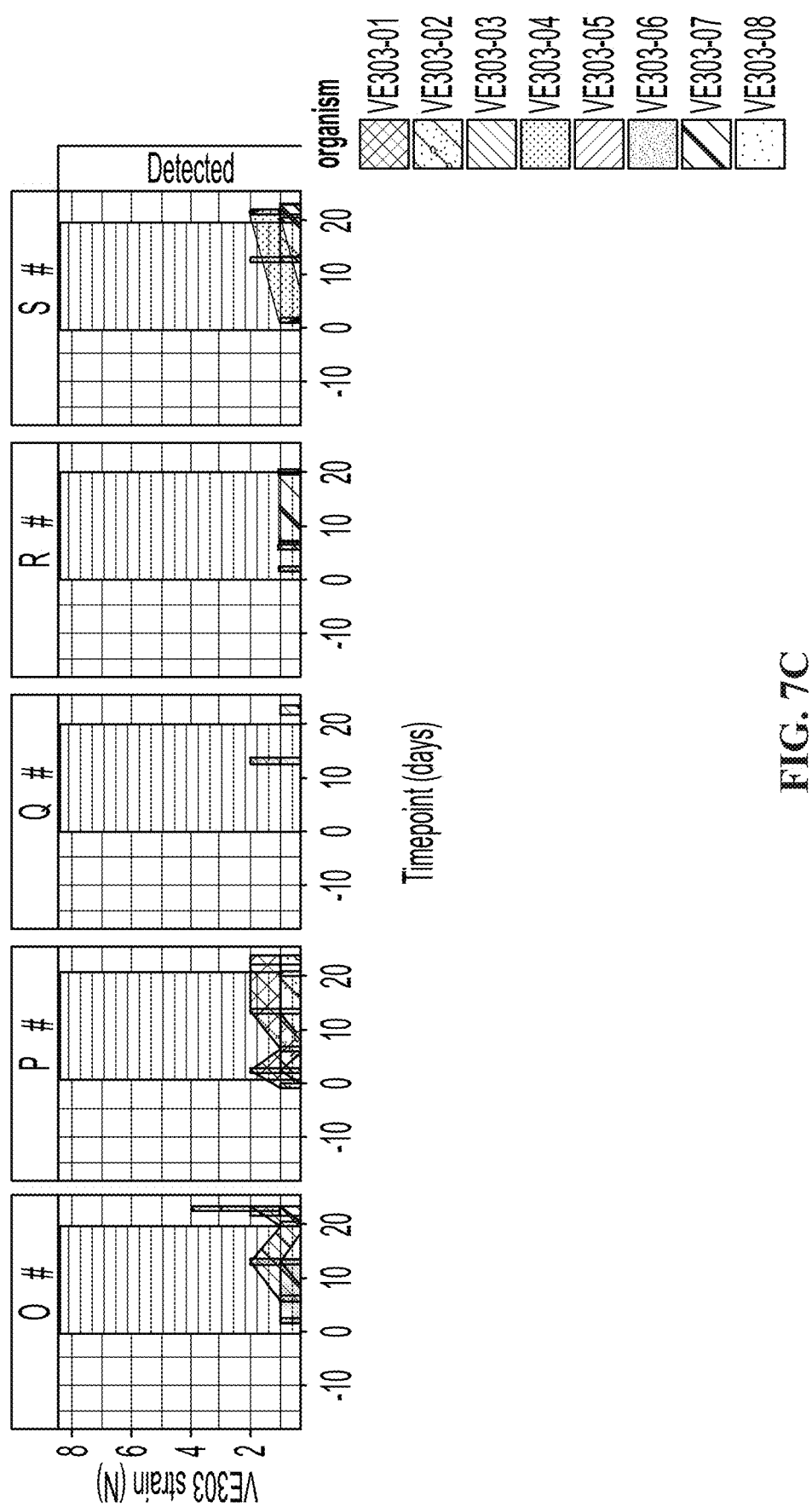
Figure 9A:
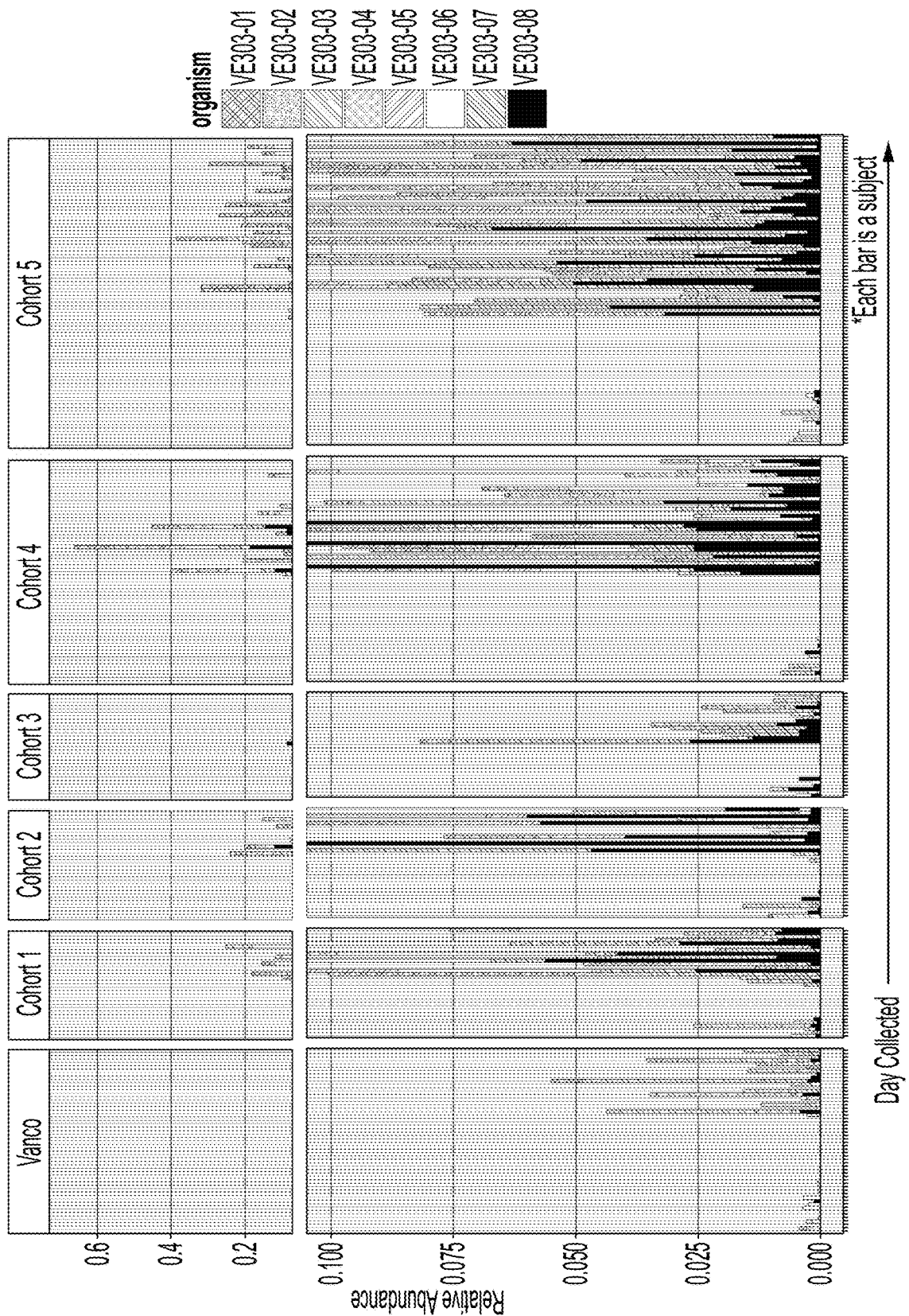
Figure 9B:
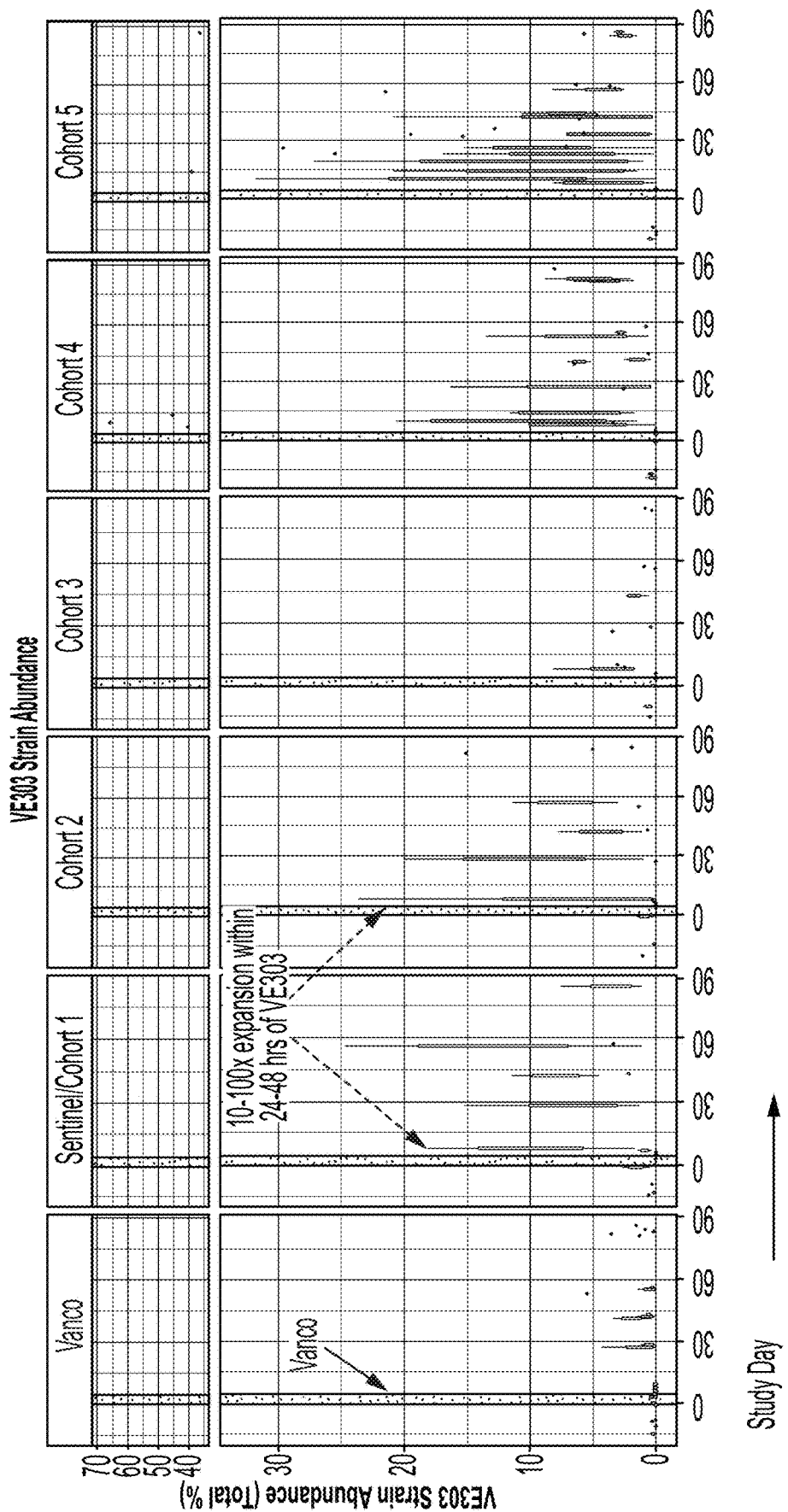
Figure 9D:
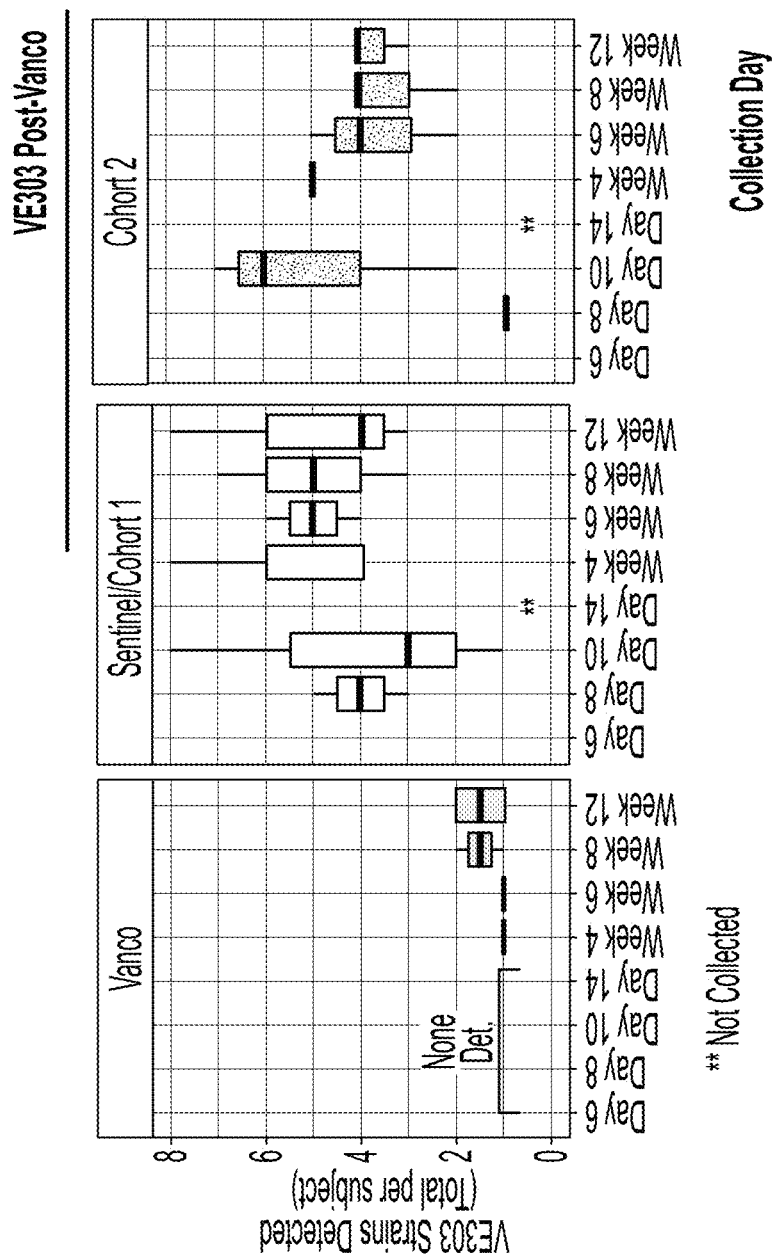
Figure 9E:
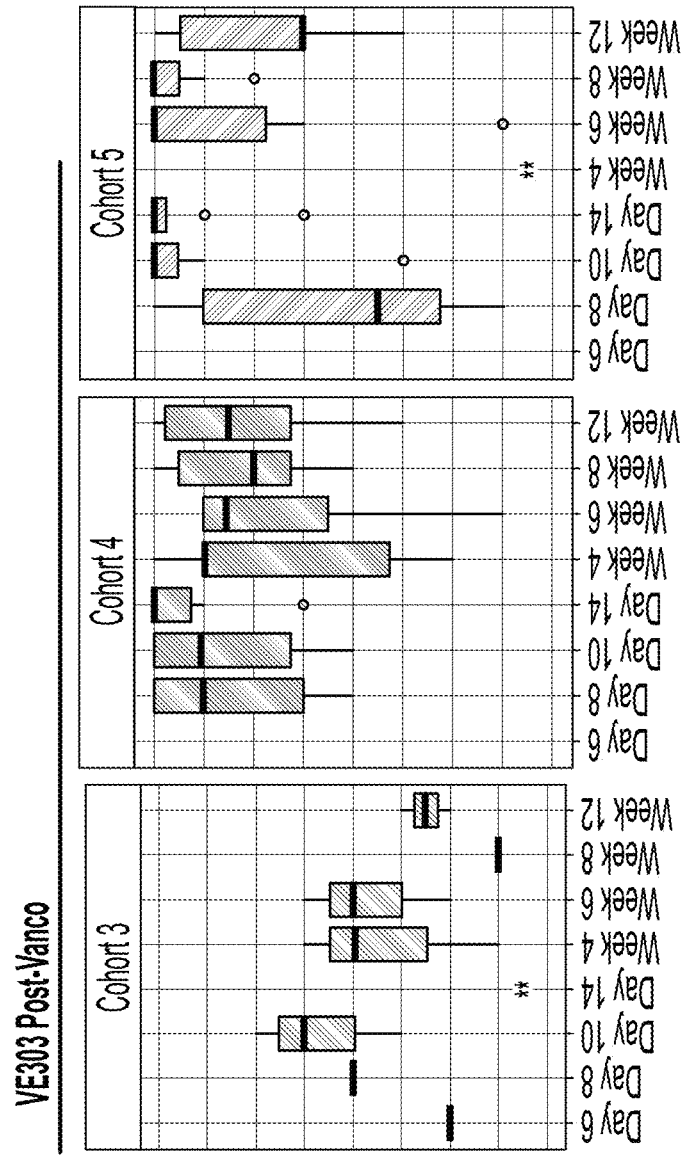
Figure 10A:
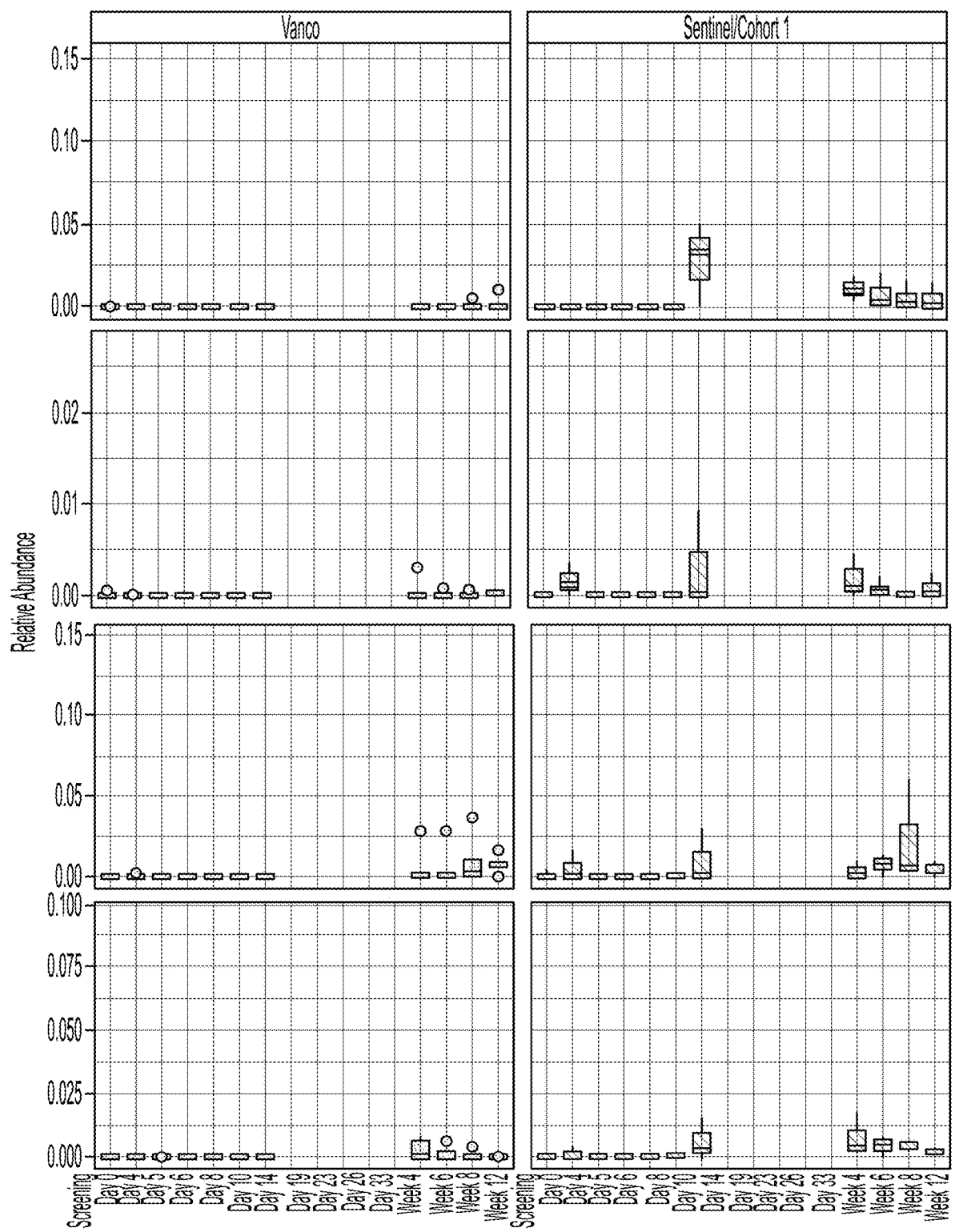
FIGS. 10A-10F show the relative abundance of each bacterial strains of composition VE303 in the microbiome within each cohort over time.
Figure 10B:
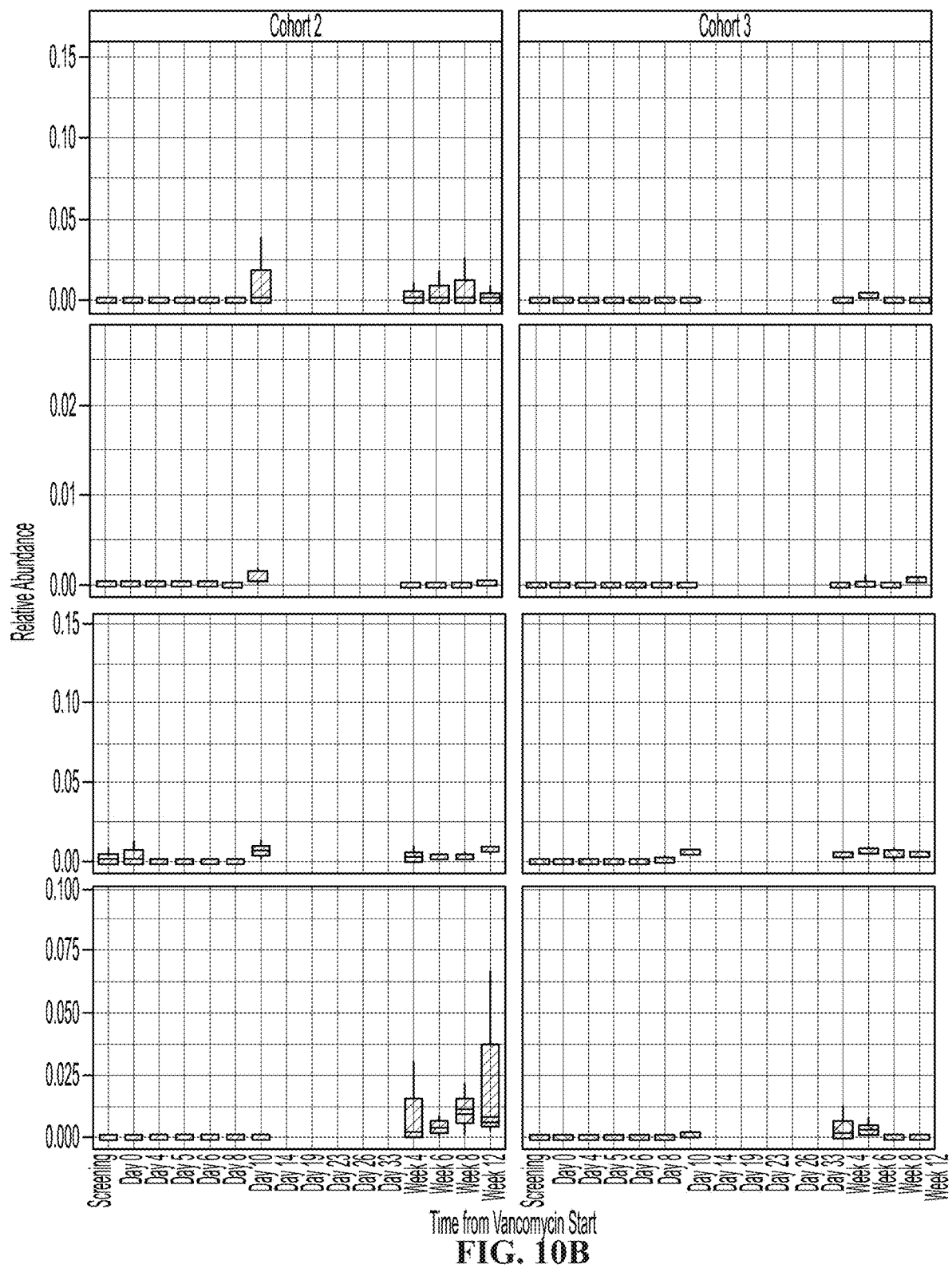
Figure 10C:
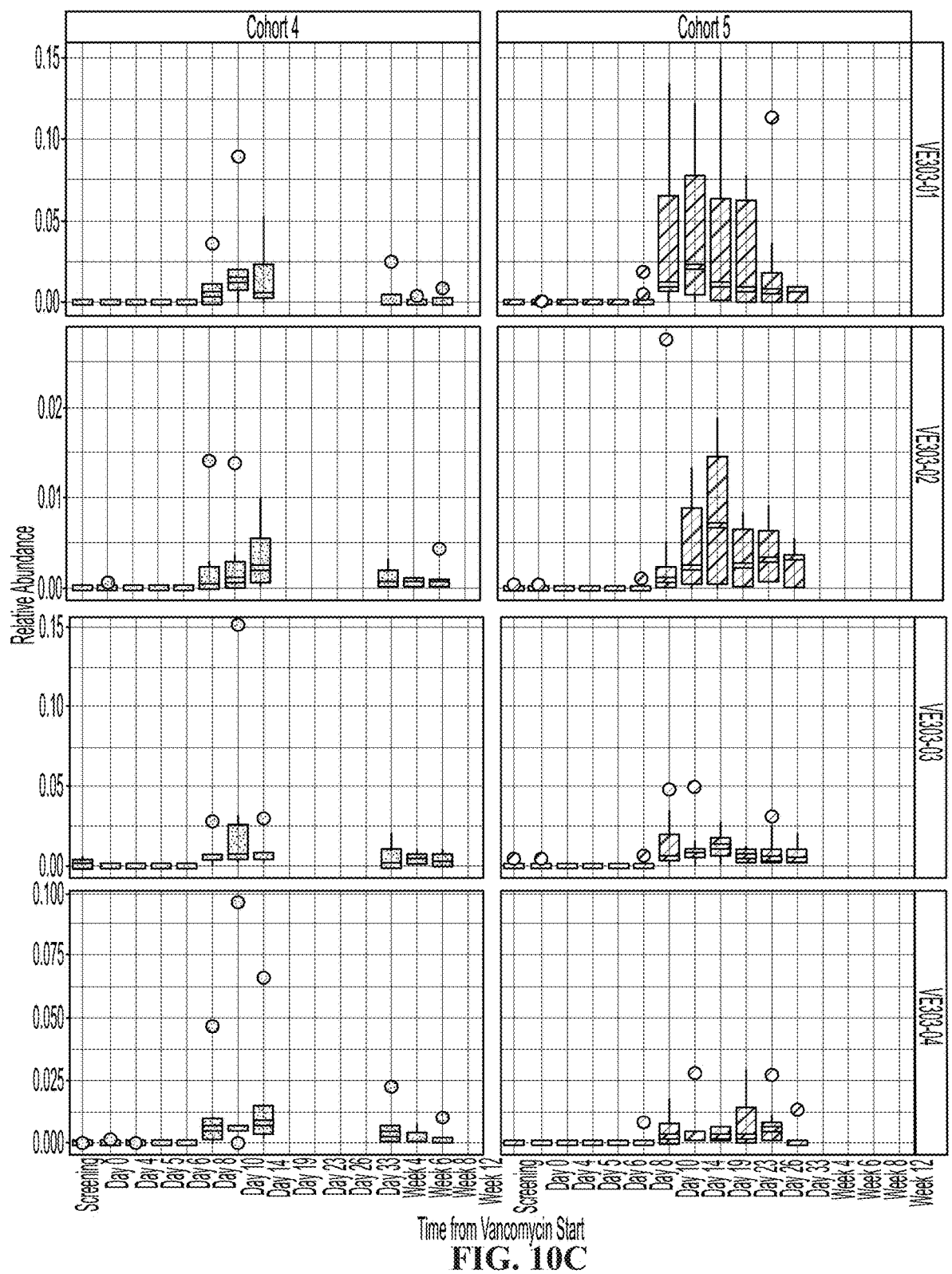
Figure 10D:
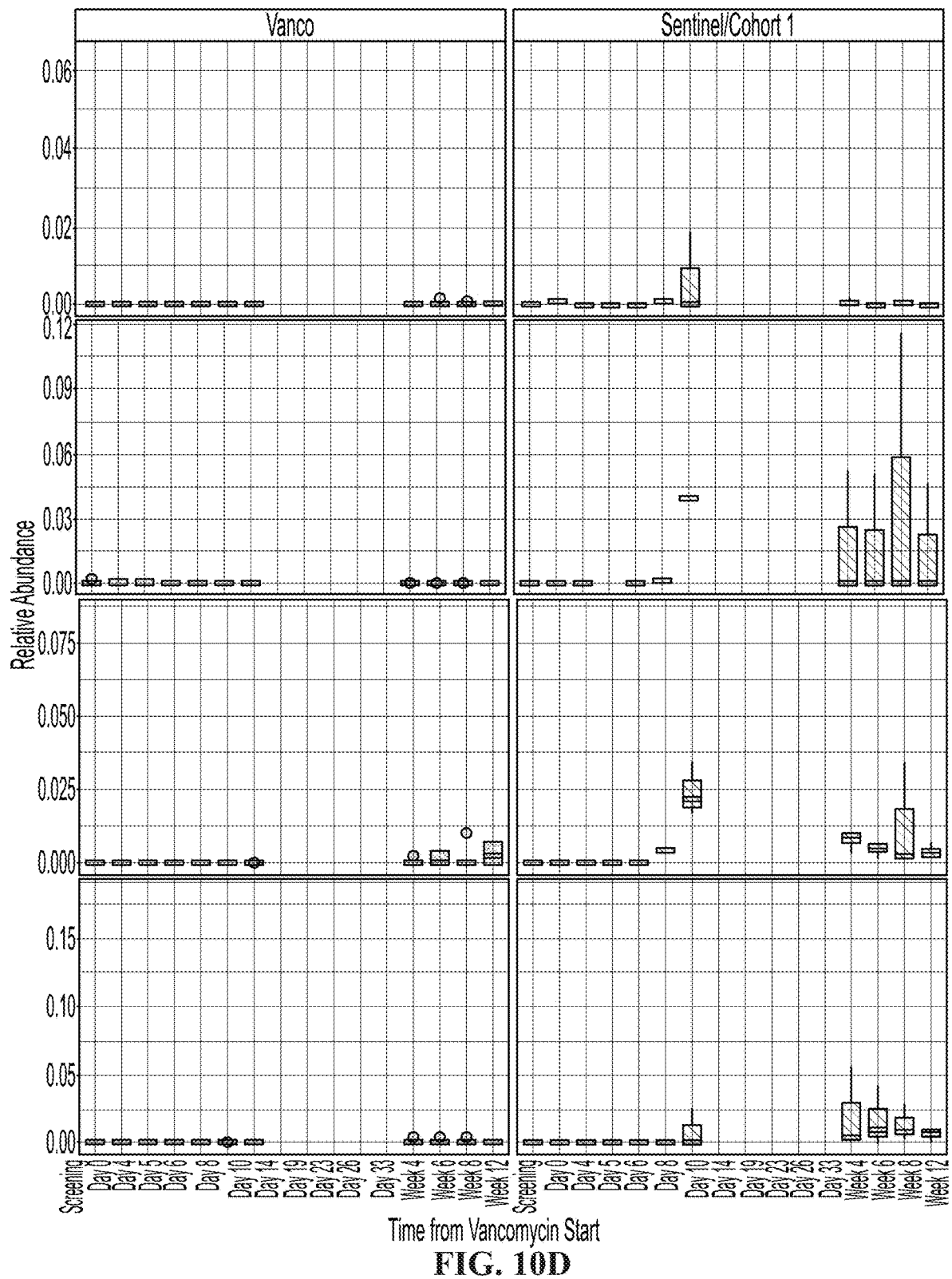
Figure 10E:
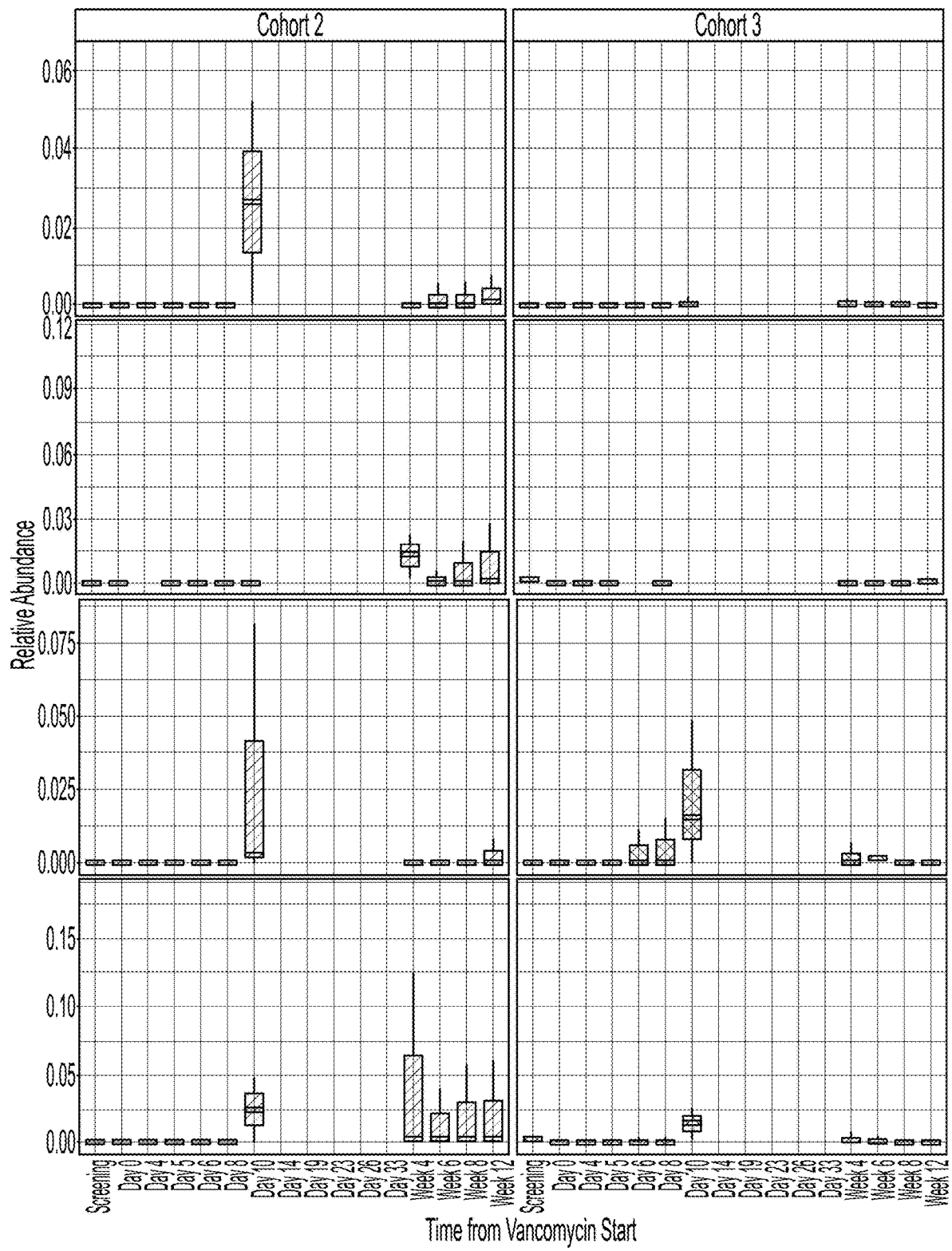
Figure 10F:
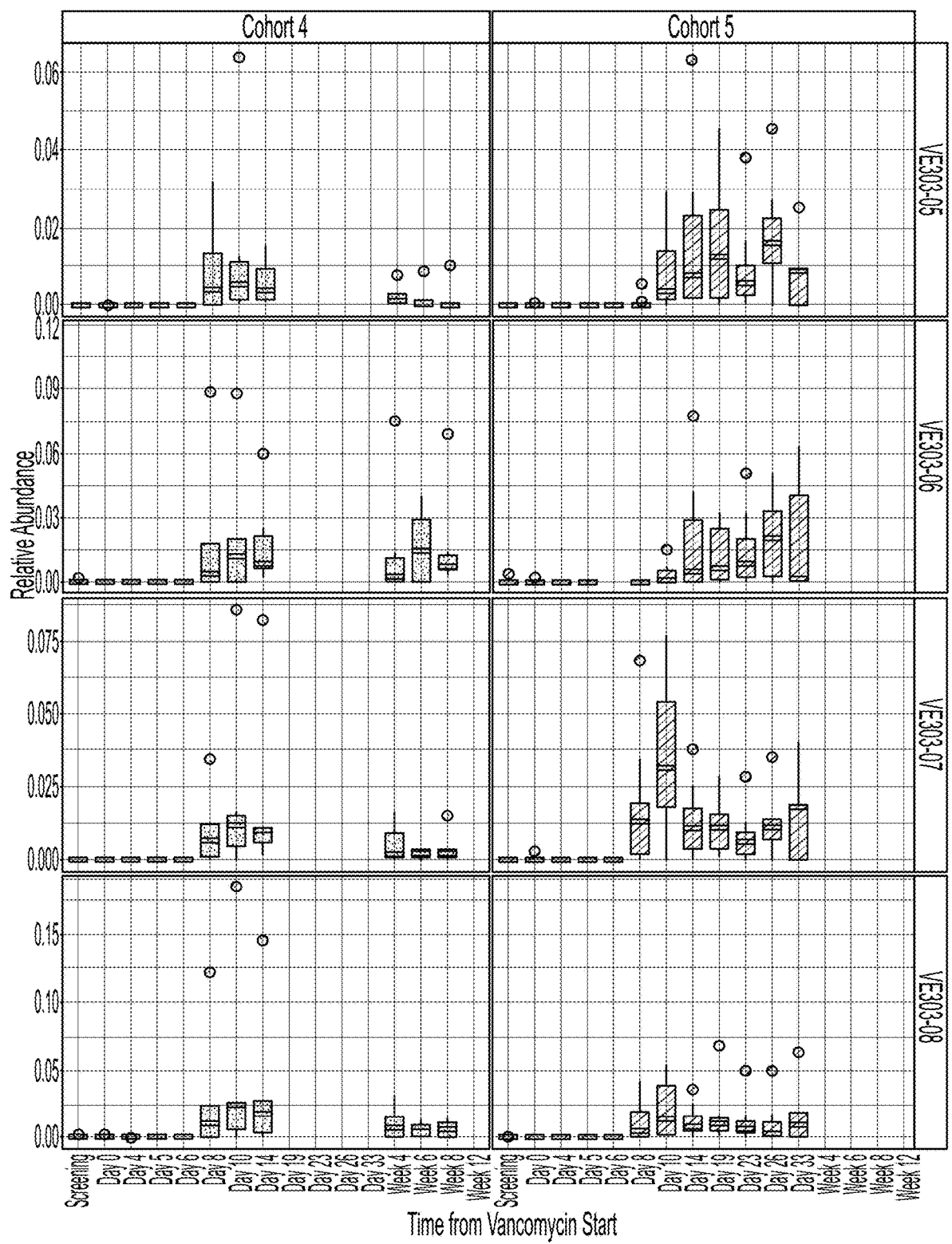

In some embodiments, administration of multiple doses of the pharmaceutical compositions described herein provides enhanced colonization (engraftment) of one or more bacterial strains of the pharmaceutical compositions as compared to administration of a single dose of the pharmaceutical composition. As shown in FIGS. 6 and 7, administration of multiple doses of the pharmaceutical composition results in enhanced colonization (engraftment) and an increased abundance of each of the bacterial strains of the pharmaceutical composition. In some embodiments, administration of a single dose of the pharmaceutical composition results in the same or a similar level of engraftment (e.g., total bacteria) as administration of multiple doses of the pharmaceutical composition, however the engraftment may be dominated by one bacterial strain or only a subset of the bacterial strains of the pharmaceutical compositions.

Any of the methods described herein may further comprise administering an antibiotic to the subject prior to administration of the pharmaceutical compositions described herein. In some embodiments, the antibiotic is vancomycin, fidaxomycin or ridinilazole. Non-limiting examples of antibiotics that may be used in any of the methods provided herein include cephalosporin antibiotics cephalexin, cefuroxime, cefadroxil, cefazolin, cephalothin, cefaclor, cefamandole, cefoxitin, cefprozil, ceftobiprole, clindamycin, ceftriaxone, cefotaxime, cefazolin, cefoperazone, cefuroxime, cefmetazole, fluoroquinolone, ciprofloxacin, Levaquin, floxin, tequin, avelox, norflox, tetracycline, minocycline, oxytetracycline, doxycycline, amoxicillin, ampicillin, penicillin V, dicloxacillin, benzylpenicillin, carbenicillin, vancomycin, and methicillin), ertapenem, doripenem, imipenem/cilastatin, meropenem, clavulanate, tazobactam, piperacillin, ceftriaxone, cefotaxime, cefazolin, fluoroquinolone, imipenem, meropenem, metronidazole, fidaxomyxin or ridinilazole. In some embodiments, any of the methods described herein may further comprise administering vancomycin to the subject prior to administration of the pharmaceutical compositions described herein. In some embodiments, the method does not comprise administering vancomycin to the subject prior to administration of the pharmaceutical compositions described herein. Vancomycin administration has been found to alter the composition of human gut microbiota. See, e.g., Reijnders et al. *Cell Metabolism* (2016) 24(1): 63-72. Without wishing to be bound by any particular theory, it is thought that administration of vancomycin may aid engraftment of the bacterial strain(s) of the pharmaceutical compositions described herein, for example by removing other microbes present in the gastrointestinal tract.

In some embodiments, the vancomycin is administered to the subject once, as a single dose. In some embodiments, the vancomycin is administered to the subject in multiple doses. In some embodiments, the vancomycin is administered to the subject in at least 2, 3, 4, 5, 6, 7, 8, 9, 10, 11, 12, 13, 14, 15 or more doses. The multiple doses of vancomycin may be administered to the subject at regular intervals prior to administering any of the pharmaceutical compositions described herein. In some embodiments, each of the multiple doses of vancomycin are administered on consecutive days (e.g., first dose on day 1, second dose of day 2, third dose on day 3, etc.). In some embodiments, the vancomycin is administered to the subject for 2, 3, 4, 5, 6, 7, 8, 9, 10, 11, 12, 13, 14, 15, or more consecutive days. In some embodiments, vancomycin is administered to the subject each day for three consecutive days. In some embodiments, vancomycin is administered to the subject each day for five consecutive days. In some embodiments, vancomycin is administered to the subject for one day. In some embodiments, the vancomycin is administered to the subject each day for seven consecutive days. In any of the embodiments described herein, a subject may be administered one or more doses of a first antibiotic followed by one or more doses of a second antibiotic.

In some embodiments, a single dose, or the first dose in a treatment regimen of multiple doses, is administered, the same day as the administration of the final dose of vancomycin. In some embodiments, a single dose, or the first dose in a treatment regimen of multiple doses, is administered, the day after administration of the final dose of vancomycin. In some embodiments, a single dose, or the first dose in a treatment regimen of multiple doses, is administered, two days after administration of the final dose of vancomycin. In some embodiments, the methods provided herein allow for a wash out day between the final dose of vancomycin and the first dose of the pharmaceutical composition. In some embodiments, a single dose, or the first dose in a treatment regimen of multiple doses, is administered, three days, four days, five days, six days, ten days or more, after administration of the final dose of vancomycin. In some embodiments, the methods provided herein allow for multiple wash out days between the final dose of vancomycin and the first dose of the pharmaceutical composition.

Each dose of the vancomycin may be the same amount of vancomycin or may be a different amount of vancomycin. In some embodiments, the vancomycin is administered in an amount sufficient to allow for colonization of one or more of the bacterial strains of the pharmaceutical compositions described herein. In some embodiments, the subject is administered between about 50 mg and 1 g, 100 mg and 750 mg, 100 mg and 500 mg, 200 mg and 750 mg, 200 mg and 500 mg, 300 mg and 750 mg, 300 mg and 500 mg, 100 mg and 400 mg, 100 mg and 300 mg, 100 mg and 200 mg, 200 mg and 400 mg, 200 mg and 300 mg, or 450 mg to 550 mg vancomycin per day. As will be appreciated by one of skill in the art, the total amount of vancomycin administered to the subject per day may be administered in a single dose or between multiple doses, which in sum results in the total amount of vancomycin per day.

In some embodiments, the subject is administered about 500 mg vancomycin per day prior to administration of any of the pharmaceutical compositions described herein. In some embodiments, 500 mg vancomycin per day is administered in a single dose (e.g., 500 mg). In some embodiments, 500 mg vancomycin per day is administered in multiple doses (e.g., 2, 3, 4, 5 or more), which in sum results in 500 mg vancomycin per day. In some embodiments, 500 mg vancomycin is administered in 4 doses of 125 mg vancomycin per day. In some embodiments, 500 mg vancomycin is administered to the subject for one day. In some embodiments, 500 mg vancomycin is administered to the subject per day for two days. In some embodiments, 500 mg vancomycin is administered to the subject per day for three days. In some embodiments, 500 mg vancomycin is administered to the subject per day for four days. In some embodiments, 500 mg vancomycin is administered to the subject per day for five days. In some embodiments, 500 mg vancomycin is administered to the subject per day for six days. In some embodiments, 500 mg vancomycin is administered to the subject per day for seven days. In some embodiments, 500 mg vancomycin is administered to the subject per day for eight days. In some embodiments, 500 mg vancomycin is administered to the subject per day for nine days. In some embodiments, 500 mg vancomycin is administered to the subject per day for ten days.

In some embodiments, the subject is administered about 250 mg vancomycin per day prior to administration of any of the pharmaceutical compositions described herein. In some embodiments, 250 mg vancomycin per day is administered in a single dose (e.g., 250 mg). In some embodiments, 250 mg vancomycin per day is administered in multiple doses (e.g., 2, 3, 4, 5 or more), which in sum results in 250 mg vancomycin per day. In some embodiments, 250 mg vancomycin is administered in 2 doses of 125 mg vancomycin per day. In some embodiments, 250 mg vancomycin is administered to the subject for one day. In some embodiments, 250 mg vancomycin is administered to the subject per day for two days. In some embodiments, 250 mg vancomycin is administered to the subject per day for three days. In some embodiments, 250 mg vancomycin is administered to the subject per day for four days. In some embodiments, 250 mg vancomycin is administered to the subject per day for five days. In some embodiments, 250 mg vancomycin is administered to the subject per day for six days. In some embodiments, 250 mg vancomycin is administered to the subject per day for seven days. In some embodiments, 250 mg vancomycin is administered to the subject per day for eight days. In some embodiments, 250 mg vancomycin is administered to the subject per day for nine days. In some embodiments, 250 mg vancomycin is administered to the subject per day for ten days.

In some embodiments, the subject is administered about 125 mg vancomycin per day prior to administration of any of the pharmaceutical compositions described herein. In some embodiments, the 125 mg vancomycin per day is administered in a single dose (e.g., 125 mg). In some embodiments, the 125 mg vancomycin per day is administered in multiple doses (e.g., 2, 3, 4, 5 or more), which in sum results in 125 mg vancomycin per day. In some embodiments, 125 mg vancomycin is administered to the subject for one day. In some embodiments, 125 mg vancomycin is administered to the subject per day for two days. In some embodiments, 125 mg vancomycin is administered to the subject per day for three days. In some embodiments, 125 mg vancomycin is administered to the subject per day for four days. In some embodiments, 125 mg vancomycin is administered to the subject per day for five days. In some embodiments, 125 mg vancomycin is administered to the subject per day for six days. In some embodiments, 125 mg vancomycin is administered to the subject per day for seven days. In some embodiments, 125 mg vancomycin is administered to the subject per day for eight days. In some embodiments, 125 mg vancomycin is administered to the subject per day for nine days. In some embodiments, 125 mg vancomycin is administered to the subject per day for ten days.

In some embodiments, the vancomycin is administered according to a pulse tapered-regime. See e.g., Sirbu et al., *Clinical Infectious Diseases* (2017) 65: 1396-1399.

In some embodiments, the vancomycin is administered to the subject at least 1, 2, 3, 4, 5, 6, 7 days or more prior to administration of the pharmaceutical compositions described herein. In some embodiments, administration of vancomycin is terminated at least one day (e.g., 1, 2, 3, 4, 5, or more) prior to administration of any of the pharmaceutical compositions described herein.

In some embodiments, additional antibiotics are administered in combination with the vancomycin regimes provided herein.

It should be appreciated, in some embodiments, that any of the vancomycin doses or administration regimens may be combined with any of the pharmaceutical composition doses or administration regimens provided herein.

In some embodiments, the disclosure provides methods comprising administering one or more antibiotics to the subject and subsequently administering any of the bacterial compositions to the subject once, twice, 3 times, 4 times, 5 times, 6 times, 7 times, 8 times, 9 times, or at least 10 times or more. In some embodiments, the disclosure provides methods comprising administering one or more antibiotics to the subject and subsequently administering any of the bacterial compositions described herein to the subject in multiple doses at a regular interval, such as every 2 weeks, every month, every 2 months, every 3 months, every 4 months, every 5 months, every 6 months, or more. In some embodiments, one dose of any of the compositions described herein is administered and a second dose of the composition is administered the following day (e.g., consecutive day). In some embodiments, one dose of any of the compositions described herein is administered and each of the additional doses of the composition are administered on consecutive days (e.g., first dose on day 1, second dose on day 2, third dose on day 3, etc.).

In one aspect, the disclosure provides methods comprising administering one or more antibiotics to the subject and subsequently administering any of the bacterial compositions as multiple daily doses of the pharmaceutical compositions. In some embodiments, the pharmaceutical compositions are administered on a daily basis for 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, 12 months, or more.

In one aspect the disclosure provides methods comprising the administration of an antibiotic (e.g., vancomycin) followed by the administration of a pharmaceutical composition provided herein, wherein the administration of an antibiotic (e.g., vancomycin) is followed by the administration of a single dose or multiple doses of the pharmaceutical composition. In some embodiments, administration of an antibiotic (e.g., vancomycin) followed by the administration of a single dose or multiple doses of the pharmaceutical composition results in an increase in the abundance of bacterial strains of the pharmaceutical compositions in the microbiome of the subject (engraftment) compared to the administration of a pharmaceutical composition without the administration of the antibiotic. In some embodiments, administration of an antibiotic (e.g., vancomycin) followed by the administration of a single dose or multiple doses of the pharmaceutical composition results in an increase in the duration of the colonization of bacterial strains of the pharmaceutical composition in the microbiome of the subject (e.g., up to 6 months) compared to the administration of a pharmaceutical composition without the administration of the antibiotic.

In some embodiments, administration of an antibiotic (e.g., vancomycin) followed by the administration of a single dose or multiple doses of the pharmaceutical composition results in an increase in the rate of engraftment of the initial amount of the bacterial strains of the pharmaceutical composition in the microbiome of the subject by between ten- to one hundred-fold (e.g., within the first 48 hours) compared to the administration of a pharmaceutical composition without the administration of the antibiotic.

In some embodiments, administration of an antibiotic (e.g., vancomycin) followed by the administration of a single dose or multiple doses of the pharmaceutical composition results in a greater number (amount) of subjects having all of the bacterial strains of the pharmaceutical composition present in their microbiome as compared to compared to the administration of a pharmaceutical composition without the administration of the antibiotic.

In some embodiments, administration of an antibiotic (e.g., vancomycin) followed by the administration of multiple doses of the pharmaceutical composition results in an increase in the abundance of bacterial strains of the pharmaceutical composition in the microbiome of the subject (engraftment) compared to the administration of a single dose of the pharmaceutical composition. In some embodiments, the disclosure provides methods comprising the administration of a pharmaceutical composition provided herein, wherein the administration of multiple doses of the pharmaceutical composition increases the abundance of bacterial strains in the microbiota of the subject (engraftment) of the pharmaceutical composition in the microbiome of the subject compared to the administration of a single dose of the pharmaceutical composition.

In some embodiments, administration of an antibiotic (e.g., vancomycin) followed by the administration of multiple doses of the pharmaceutical composition results in an increase in the rate of engraftment of the initial amount of the bacterial strains of the pharmaceutical composition in the microbiome of the subject as compared to the administration of a single dose of the pharmaceutical composition. In some embodiments, the disclosure provides methods comprising the administration of a pharmaceutical composition provided herein, wherein the administration of multiple doses of the pharmaceutical composition increases the rate of engraftment of the initial amount of the bacterial strains of the pharmaceutical composition in the microbiome of the subject compared to the administration of a single dose of the pharmaceutical composition.

In some embodiments, administration of an antibiotic (e.g., vancomycin) followed by the administration of multiple doses of the pharmaceutical composition results in a higher abundance of the bacterial strains of the pharmaceutical composition in the microbiome of the subject as compared to the administration of a single dose of the pharmaceutical composition. In some embodiments, the disclosure provides methods comprising the administration of a pharmaceutical composition provided herein, wherein the administration of multiple doses of the pharmaceutical composition results in higher abundance of the bacterial strains of the pharmaceutical composition in the microbiome of the subject compared to the administration of a single dose of the pharmaceutical composition.

In some embodiments, administration of an antibiotic (e.g., vancomycin) followed by the administration of multiple doses of the pharmaceutical composition results in a greater number (amount) of subjects having all of the bacterial strains of the pharmaceutical composition present in their microbiome as compared to the administration of a single dose of the pharmaceutical composition. In some embodiments, the disclosure provides methods comprising the administration of a pharmaceutical composition provided herein, wherein the administration of multiple doses of the pharmaceutical results in a greater number (amount) of subject having all of the bacterial strains of the pharmaceutical composition in their microbiome as compared to the administration of a single dose of the pharmaceutical composition.

In some embodiments, administration of an antibiotic (e.g., vancomycin) followed by the administration of multiple doses of the pharmaceutical composition results in an accelerated recovery of the microbiome (e.g., increase in bacterial species of Bacteroidetes and/or Firmicutes, and/or decrease in Proteobacteria) as compared to the administration of a single dose of the pharmaceutical composition. In some embodiments, the disclosure provides methods comprising the administration of a pharmaceutical composition provided herein, wherein the administration of multiple doses of the pharmaceutical results in an accelerated recovery of the microbiome (e.g., increase in bacterial species of Bacteroidetes and/or Firmicutes, and/or decrease in Proteobacteria) as compared the administration of a single dose of the pharmaceutical composition.

In some embodiments, administration of an antibiotic (e.g., vancomycin) followed by the administration of a single dose or multiple doses of the pharmaceutical composition results in an accelerated recovery of the microbiome (e.g., increase in bacterial species of Bacteroidetes and/or Firmicutes, and/or decrease in Proteobacteria) as compared to the administration of an antibiotic (e.g., vancomycin) without the administration of a pharmaceutical composition.

The compositions, including the pharmaceutical compositions disclosed herein, include compositions that contain selected bacterial strains. The amount of bacteria, including the amount of bacteria of each of the bacterial strains, in the compositions, including pharmaceutical compositions, may be expressed in weight, number of bacteria and/or CFUs (colony forming units). In some embodiments, the compositions, including pharmaceutical compositions, comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the bacterial strains per dosage amount. In some embodiments, the compositions, including pharmaceutical compositions, comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total bacteria per dosage amount. It should further be appreciated that bacteria of each of the bacterial strains may be present in different amounts. Thus, for instance, as a non-limiting example, composition may include $10^3$ of bacteria A, $10^4$ of bacteria B and $10^6$ of bacteria C. In some embodiments, compositions, including pharmaceutical composition, comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs of each of the bacterial strains per dosage amount. In some embodiments, compositions, including pharmaceutical compositions, comprise about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs in total for all of the bacterial strains combined per dosage amount. As discussed above, bacteria of each of the bacterial strains may be present in different amounts. In some embodiments, the compositions, including pharmaceutical compositions, contain about $10^{-7}$, about $10^{-6}$, about $10^{-5}$, about $10^{-4}$, about $10^{-3}$, about $10^{-2}$, about $10^{-1}$ or more grams of bacteria of each of the bacterial strains in the composition per dosage amount. In some embodiments, the compositions, including pharmaceutical compositions, contain about $10^{-7}$, about $10^{-6}$, about $10^{-5}$, about $10^{-4}$, about $10^{-3}$, about $10^{-2}$, about $10^{-1}$ or more grams of bacteria in total for all of the bacterial strains combined per dosage amount.

In some embodiments, the dosage amount is one administration device (e.g., one table, pill or capsule). In some embodiments, the dosage amount is the amount administered at one time, which may be in the form of more than one administration device (e.g., more than one table, pill or capsule). In some embodiment, the dosage amount is the amount that is administered in a particular period (e.g., one day or one week).

As described herein, any of the pharmaceutical compositions described herein may be administered once, as a single dose. In some embodiments, the pharmaceutical compositions described herein are administered in multiple doses. In some embodiments, each dose is administered in the form of one or more capsules. In some embodiments, each dose comprises administration of multiple capsules. In some embodiments, each dose is administered in the form of 1, 2, 3, 4, 5, 6, 7, 8, 9, 10, 11, 12, 13, 14, 15, or more capsules.

In some embodiments, each capsule contains between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^{13}$, between $10^2$ and $10^{13}$, or between 10 and $10^2$ of each of the bacterial strains per capsule.

In some embodiments, each capsule contains between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^{13}$, between $10^2$ and $10^{13}$, or between 10 and $10^2$ total bacteria per capsule. In some embodiments, each capsule contains between $10^7$ and $10^9$, between $10^7$ and $10^8$, or between $10^8$ and $10^9$ total bacteria. In some embodiments, each capsule contains about $1.0 \times 10^7$, $2.0 \times 10^7$, $3.0 \times 10^7$, $4.0 \times 10^7$, $5.0 \times 10^7$, $6.0 \times 10^7$, $7.0 \times 10^7$, $8.0 \times 10^7$, $9.0 \times 10^7$, $1.0 \times 10^8$, $2.0 \times 10^8$, $3.0 \times 10^8$, $4.0 \times 10^8$, $5.0 \times 10^8$, $6.0 \times 10^8$, $7.0 \times 10^9$, $1.7 \times 10^9$, $1.8 \times 10^9$, $1.9 \times 10^9$, $2.0 \times 10^9$, $2.1 \times 10^9$, $2.2 \times 10^9$, $2.3 \times 10^9$, $2.4 \times 10^9$, $2.5 \times 10^9$, $2.6 \times 10^9$, $2.7 \times 10^9$, $2.8 \times 10^9$, $2.9 \times 10^9$, $3.0 \times 10^9$, $3.1 \times 10^9$, $3.2 \times 10^9$, $3.3 \times 10^9$, $3.4 \times 10^9$, $3.5 \times 10^9$, $3.6 \times 10^9$, $3.7 \times 10^9$, $3.8 \times 10^9$, $3.9 \times 10^9$, $4.0 \times 10^9$, $4.1 \times 10^9$, $4.2 \times 10^9$, $4.3 \times 10^9$, $4.4 \times 10^9$, $4.5 \times 10^9$, $4.6 \times 10^9$, $4.7 \times 10^9$, $4.8 \times 10^9$, $4.9 \times 10^9$, $5.0 \times 10^9$ total bacteria. In some embodiments, each capsule contains about $8.0 \times 10^8$ total bacteria. In some embodiments, each capsule contains about $1.6 \times 10^9$ total bacteria. In some embodiments, each capsule contains about $8.0 \times 10^8$ CFUs. In some embodiments, each capsule contains about $1.6 \times 10^9$ CFUs.

In some embodiments, each capsule contains between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^{13}$, between $10^2$ and $10^{13}$, or between 10 and $10^2$ of each bacterial strain per capsule.

In some embodiments, the pharmaceutical compositions contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^{13}$, between $10^2$ and $10^{13}$, or between 10 and $10^2$ CFUs of each of the bacterial strains per dosage amount. In some embodiments, the pharmaceutical compositions contain between 10 and $10^{13}$, between $10^2$ and $10^3$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^{13}$, between $10^2$ and $10^{13}$, or between 10 and $10^2$ total CFUs per dosage amount.

In some embodiments, the pharmaceutical compositions contain at least about $1.0 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2.0 \times 10^8$, $2.1 \times 10^8$, $2.2 \times 10^8$, $2.3 \times 10^8$, $2.4 \times 10^8$, $2.5 \times 10^8$, $2.6 \times 10^8$, $2.7 \times 10^8$, $2.8 \times 10^8$, $2.9 \times 10^8$, $3.0 \times 10^8$, $3.1 \times 10^8$, $3.2 \times 10^8$, $3.3 \times 10^8$, $3.4 \times 10^8$, $3.5 \times 10^8$, $3.6 \times 10^8$, $3.7 \times 10^8$, $3.8 \times 10^8$, $3.9 \times 10^8$, $4.0 \times 10^8$, $4.1 \times 10^8$, $4.2 \times 10^8$, $4.3 \times 10^8$, $4.4 \times 10^8$, $4.5 \times 10^8$, $4.6 \times 10^8$, $4.7 \times 10^8$, $4.8 \times 10^8$, $4.9 \times 10^8$, $5.0 \times 10^8$, $5.1 \times 10^8$, $5.2 \times 10^8$, $5.3 \times 10^8$, $5.4 \times 10^8$, $55 \times 10^8$, $5.6 \times 10^8$, $5.7 \times 10^8$, $5.8 \times 10^8$, $5.9 \times 10^8$, $6.0 \times 10^8$, $6.1 \times 10^8$, $6.2 \times 10^8$, $6.3 \times 10^8$, $6.4 \times 10^8$, $6.5 \times 10^8$, $6.6 \times 10^8$, $6.7 \times 10^8$, $6.8 \times 10^8$, $6.9 \times 10^8$, $7.0 \times 10^8$, $7.1 \times 10^8$, $7.2 \times 10^8$, $7.3 \times 10^8$, $7.4 \times 10^8$, $7.5 \times 10^8$, $7.6 \times 10^8$, $7.7 \times 10^8$, $7.8 \times 10^8$, $7.9 \times 10^8$, $8.0 \times 10^8$, $8.1 \times 10^8$, $8.2 \times 10^8$, $8.3 \times 10^8$, $8.4 \times 10^8$, $8.5 \times 10^8$, $8.6 \times 10^8$, $8.7 \times 10^8$, $8.8 \times 10^8$, $8.9 \times 10^8$, $9.0 \times 10^8$, $9.1 \times 10^8$, $9.2 \times 10^8$, $9.3 \times 10^8$, $9.4 \times 10^8$, $9.5 \times 10^8$, $9.6 \times 10^8$, $9.7 \times 10^8$, $9.8 \times 10^8$, $9.9 \times 10^8$, $1.0 \times 10^9$, $1.1 \times 10^9$, $1.2 \times 10^9$, $1.3 \times 10^9$, $1.4 \times 10^9$, $1.5 \times 10^9$, $1.6 \times 10^9$, $1.7 \times 10^9$, $1.8 \times 10^9$, $1.9 \times 10^9$, $2.0 \times 10^9$, $2.1 \times 10^9$, $2.2 \times 10^9$, $2.3 \times 10^9$, $2.4 \times 10^9$, $2.5 \times 10^9$, $2.6 \times 10^9$, $2.7 \times 10^9$, $2.8 \times 10^9$, $2.9 \times 10^9$, $3.0 \times 10^9$, $3.1 \times 10^9$, $3.2 \times 10^9$, $3.3 \times 10^9$, $3.4 \times 10^9$, $3.5 \times 10^9$, $3.6 \times 10$, $3.7 \times 10^9$, $3.8 \times 10^9$, $3.9 \times 10^9$, $4.0 \times 10^9$, $4.1 \times 10^9$, $4.2 \times 10^9$, $4.3 \times 10^9$, $4.4 \times 10^9$, $4.5 \times 10^9$, $4.6 \times 10^9$, $4.7 \times 10^9$, $4.8 \times 10^9$, $4.9 \times 10^9$, $5.0 \times 10^9$, $5.1 \times 10^9$, $5.2 \times 10^9$, $5.3 \times 10^9$, $5.4 \times 10^9$, $5.5 \times 10^9$, $5.6 \times 10^9$, $5.7 \times 10^9$, $5.8 \times 10^9$, $5.9 \times 10^9$, $6.0 \times 10^9$, $6.1 \times 10^9$, $6.2 \times 10^9$, $6.3 \times 10^9$, $6.4 \times 10^9$, $6.5 \times 10^9$, $6.6 \times 10^9$, $6.7 \times 10^9$, $6.8 \times 10^9$, $6.9 \times 10^9$, $7.0 \times 10^9$, $7.1 \times 10^9$, $7.2 \times 10^9$, $7.3 \times 10^9$, $7.4 \times 10^9$, $7.5 \times 10^9$, $7.6 \times 10^9$, $7.7 \times 10^9$, $7.8 \times 10^9$, $7.9 \times 10^9$, $8.0 \times 10^9$, $8.1 \times 10^9$, $8.2 \times 10^9$, $8.3 \times 10^9$, $8.4 \times 10^9$, $8.5 \times 10^9$, $8.6 \times 10^9$, $8.7 \times 10^9$, $8.8 \times 10^9$, $8.9 \times 10^9$, $9.0 \times 10^9$, $9.1 \times 10^9$, $9.2 \times 10^9$, $9.3 \times 10^9$, $9.4 \times 10^9$, $9.5 \times 10^9$, $9.6 \times 10^9$, $9.7 \times 10^9$, $9.8 \times 10^9$, $9.9 \times 10^9$, $1.0 \times 10^{10}$, $1.1 \times 10^{10}$, $1.2 \times 10^{10}$, $1.3 \times 10^{10}$, $1.4 \times 10^{10}$, $1.5 \times 10^{10}$, $1.6 \times 10^{10}$, $1.7 \times 10^{10}$, $1.8 \times 10^{10}$, $1.9 \times 10^{10}$, $2.0 \times 10^{10}$, $2.1 \times 10^{10}$, $2.2 \times 10^{10}$, $2.3 \times 10^{10}$, $2.4 \times 10^{10}$, $2.5 \times 10^{10}$, $2.6 \times 10^{10}$, $2.7 \times 10^{10}$, $2.8 \times 10^{10}$, $2.9 \times 10^{10}$, $3.0 \times 10^{10}$, $3.1 \times 10^{10}$, $3.2 \times 10^{10}$, $3.3 \times 10^{10}$, $3.4 \times 10^{10}$, $3.5 \times 10^{10}$, $3.6 \times 10^{10}$, $3.7 \times 10^{10}$, $3.8 \times 10^{10}$, $3.9 \times 10^{10}$, $4.0 \times 10^{10}$, $4.1 \times 10^{10}$, $4.2 \times 10^{10}$, $4.3 \times 10^{10}$, $4.4 \times 10^{10}$, $4.5 \times 10^{10}$, $4.6 \times 10^{10}$, $4.7 \times 10^{10}$, $4.8 \times 10^{10}$, $4.9 \times 10^{10}$, $5.0 \times 10^{10}$, $5.1 \times 10^{10}$, $5.2 \times 10^{10}$, $5.3 \times 10^{10}$, $5.4 \times 10^{10}$, $5.5 \times 10^{10}$, $5.6 \times 10^{10}$, $5.7 \times 10^{10}$, $5.8 \times 10^{10}$, $5.9 \times 10^{10}$, $6.0 \times 10^{10}$, $6.1 \times 10^{10}$, $6.2 \times 10^{10}$, $6.3 \times 10^{10}$, $6.4 \times 10^{10}$, $6.5 \times 10^{10}$, $6.6 \times 10^{10}$, $6.7 \times 10^{10}$, $6.8 \times 10^{10}$, $6.9 \times 10^{10}$, $7.0 \times 10^{10}$, $7.1 \times 10^{10}$, $7.2 \times 10^{10}$, $7.3 \times 10^{10}$, $7.4 \times 10^{10}$, $7.5 \times 10^{10}$, $7.6 \times 10^{10}$, $7.7 \times 10^{10}$, $7.8 \times 10^{10}$, $7.9 \times 10^{10}$, $8.0 \times 10^{10}$, $8.1 \times 10^{10}$, $8.2 \times 10^{10}$, $8.3 \times 10^{10}$, $8.4 \times 10^{10}$, $8.5 \times 10^{10}$, $8.6 \times 10^{10}$, $8.7 \times 10^{10}$, $8.8 \times 10^{10}$, $8.9 \times 10^{10}$, $9.0 \times 10^{10}$, $9.1 \times 10^{10}$, $9.2 \times 10^{10}$, $9.3 \times 10^{10}$, $9.4 \times 10^{10}$, $9.5 \times 10^{10}$, $9.6 \times 10^{10}$, $9.7 \times 10^{10}$, $9.8 \times 10^{10}$, $9.9 \times 10^{10}$, $1.0 \times 10^{11}$, $1.1 \times 10^{11}$, $1.2 \times 10^{11}$, $1.3 \times 10^{11}$, $1.4 \times 10^{11}$, $1.5 \times 10^{11}$, $1.6 \times 10^{11}$, $1.7 \times 10^{11}$, $1.8 \times 10^{11}$, $1.9 \times 10^{11}$, $2.0 \times 10^{11}$, $2.1 \times 10^{11}$, $2.2 \times 10^{11}$, $2.3 \times 10^{11}$, $2.4 \times 10^{11}$, $2.5 \times 10^{11}$, $2.6 \times 10^{11}$, $2.7 \times 10^{11}$, $2.8 \times 10^{11}$, $2.9 \times 10^{11}$, $3.0 \times 10^{11}$, $3.1 \times 10^{11}$, $3.2 \times 10^{11}$, $3.3 \times 10^{11}$, $3.4 \times 10^{11}$, $3.5 \times 10^{11}$, $3.6 \times 10^{11}$, $3.7 \times 10^{11}$, $3.8 \times 10^{11}$, $3.9 \times 10^{11}$, $4.0 \times 10^{11}$, $4.1 \times 10^{11}$, $4.2 \times 10^{11}$, $4.3 \times 10^{11}$, $4.4 \times 10^{11}$, $4.5 \times 10^{11}$, $4.6 \times 10^{11}$, $4.7 \times 10^{11}$, $4.8 \times 10^{11}$, $4.9 \times 10^{11}$, $5.0 \times 10^{11}$, $5.1 \times 10^{11}$, $5.2 \times 10^{11}$, $5.3 \times 10^{11}$, $5.4 \times 10^{11}$, $5.5 \times 10^{11}$, $5.6 \times 10^{11}$, $5.7 \times 10^{11}$, $5.8 \times 10^{11}$, $5.9 \times 10^{11}$, $6.0 \times 10^{11}$, $6.1 \times 10^{11}$, $6.2 \times 10^{11}$, $6.3 \times 10^{11}$, $6.4 \times 10^{11}$, $6.5 \times 10^{11}$, $6.6 \times 10^{11}$, $6.7 \times 10^{11}$, $6.8 \times 10^{11}$, $6.9 \times 10^{11}$, $7.0 \times 10^{11}$, $7.1 \times 10^{11}$, $7.2 \times 10^{11}$, $7.3 \times 10^{11}$, $7.4 \times 10^{11}$, $7.5 \times 10^{11}$, $7.6 \times 10^{11}$, $7.7 \times 10^{11}$, $7.8 \times 10^{11}$, $7.9 \times 10^{11}$, $8.0 \times 10^{11}$, $8.1 \times 10^{11}$, $8.2 \times 10^{11}$, $8.3 \times 10^{11}$, $8.4 \times 10^{11}$, $8.5 \times 10^{11}$, $8.6 \times 10^{11}$, $8.7 \times 10^{11}$, $8.8 \times 10^{11}$, $8.9 \times 10^{11}$, $9.0 \times 10^{11}$, $9.1 \times 10^{11}$, $9.2 \times 10^{11}$, $9.3 \times 10^{11}$, $9.4 \times 10^{11}$, $9.5 \times 10^{11}$, $9.6 \times 10^{11}$, $9.7 \times 10^{11}$, $9.8 \times 10^{11}$, $9.9 \times 10^{11}$, or $1.0 \times 10^{11}$ total CFUs.

In some embodiments, the pharmaceutical composition comprises at least $1.6 \times 10^9$ total CFUs. In some embodiments, the pharmaceutical composition comprises at least $1.6 \times 10^9$ total CFUs and is administered as a single dose. In some embodiments, the pharmaceutical composition comprises at least $1.6 \times 10^9$ total CFUs and is administered as multiple (e.g., 2, 3, 4, 5, or more) doses. In some embodiments, the pharmaceutical composition comprises at least $1.6 \times 10^9$ total CFUs and is administered as two, three, four, five, six, seven, eight, nine, ten, eleven, twelve, thirteen, fourteen, fifteen or more doses. In some embodiments, each of the multiple doses are administered at regular intervals. In some embodiments, each of the multiple doses are on consecutive days (e.g., first dose on day 1, second dose of day 2, third dose on day 3, etc.).

In some embodiments, the pharmaceutical composition comprises at least $4.0 \times 10^9$ total CFUs. In some embodiments, the pharmaceutical composition comprises at least $4.0 \times 10^9$ total CFUs and is administered as a single dose. In some embodiments, the pharmaceutical composition comprises at least $4.0 \times 10^9$ total CFUs and is administered as multiple (e.g., 2, 3, 4, 5, or more) doses. In some embodiments, the pharmaceutical composition comprises at least $4.0 \times 10^{10}$ total CFUs and is administered as two, three, four, five, six, seven, eight, nine, ten, eleven, twelve, thirteen, fourteen, fifteen or more doses. In some embodiments, each of the multiple doses are administered at regular intervals. In some embodiments, each of the multiple doses are on consecutive days (e.g., first dose on day 1, second dose of day 2, third dose on day 3, etc.).

In some embodiments, the pharmaceutical composition comprises at least $8.0 \times 10^9$ total CFUs. In some embodiments, the pharmaceutical composition comprises at least $8.0 \times 10^9$ total CFUs and is administered as a single dose. In some embodiments, the pharmaceutical composition comprises at least $8.0 \times 10^9$ total CFUs and is administered as multiple (e.g., 2, 3, 4, 5, or more) doses. In some embodiments, the pharmaceutical composition comprises at least $8.0 \times 10^9$ total CFUs and is administered as two, three, four, five, six, seven, eight, nine, ten, eleven, twelve, thirteen, fourteen, fifteen or more doses. In some embodiments, each of the multiple doses are administered at regular intervals. In some embodiments, each of the multiple doses are on consecutive days (e.g., first dose on day 1, second dose of day 2, third dose on day 3, etc.).

In some embodiments, the pharmaceutical composition comprises at least $2.8 \times 10^{10}$ total CFUs. In some embodiments, the pharmaceutical composition comprises at least $2.8 \times 10^{10}$ total CFUs and is administered as a single dose. In some embodiments, the pharmaceutical composition comprises at least $2.8 \times 10^{10}$ total CFUs and is administered as multiple (e.g., 2, 3, 4, 5, or more) doses. In some embodiments, the pharmaceutical composition comprises at least $2.8 \times 10^{10}$ total CFUs and is administered as two, three, four, five, six, seven, eight, nine, ten, eleven, twelve, thirteen, fourteen, fifteen or more doses. In some embodiments, the pharmaceutical composition comprises at least $2.8 \times 10^{10}$ total CFUs and is administered as seven doses. In some embodiments, each of the multiple doses are administered at regular intervals. In some embodiments, each of the multiple doses are on consecutive days (e.g., first dose on day 1, second dose of day 2, third dose on day 3, etc.).

In some embodiments, the pharmaceutical composition comprises at least $4.0 \times 10^{10}$ total CFUs. In some embodiments, the pharmaceutical composition comprises at least $4.0 \times 10^{10}$ total CFUs and is administered as a single dose. In some embodiments, the pharmaceutical composition comprises at least $4.0 \times 10^{10}$ total CFUs and is administered as multiple (e.g., 2, 3, 4, 5, or more) doses. In some embodiments, the pharmaceutical composition comprises at least $4.0 \times 10^{10}$ total CFUs and is administered as two, three, four, five, six, seven, eight, nine, ten, eleven, twelve, thirteen, fourteen, fifteen or more doses. In some embodiments, the pharmaceutical composition comprises at least $4.0 \times 10^{10}$ total CFUs and is administered as five doses. In some embodiments, each of the multiple doses are administered at regular intervals. In some embodiments, each of the multiple doses are on consecutive days (e.g., first dose on day 1, second dose of day 2, third dose on day 3, etc.). In some embodiments, the pharmaceutical composition comprises at least $4.0 \times 10^{10}$ total CFUs and is administered as five doses, each of which are administered on five consecutive days.

In some embodiments, the pharmaceutical composition comprises at least $5.6 \times 10^{10}$ total CFUs. In some embodiments, the pharmaceutical composition comprises at least $5.6 \times 10^{10}$ total CFUs and is administered as a single dose. In some embodiments, the pharmaceutical composition comprises at least $5.6 \times 10^{10}$ total CFUs and is administered as multiple (e.g., 2, 3, 4, 5, or more) doses. In some embodiments, the pharmaceutical composition comprises at least $5.6 \times 10^{10}$ total CFUs and is administered as two, three, four, five, six, seven, eight, nine, ten, eleven, twelve, thirteen, fourteen, fifteen or more doses. In some embodiments, the pharmaceutical composition comprises at least $5.6 \times 10^{10}$ total CFUs and is administered as fourteen doses. In some embodiments, each of the multiple doses are administered at regular intervals. In some embodiments, each of the multiple doses are on consecutive days (e.g., first dose on day 1, second dose of day 2, third dose on day 3, etc.). In some embodiments, the pharmaceutical composition comprises at least 5.6×10¹⁰ total CFUs and is administered as fourteen doses, each of which are administered on fourteen consecutive days.

In some embodiments, the pharmaceutical composition comprises at least 1.1×10¹¹ total CFUs. In some embodiments, the pharmaceutical composition comprises at least 1.1×10¹¹ total CFUs and is administered as a single dose. In some embodiments, the pharmaceutical composition comprises at least 1.1×10¹¹ total CFUs and is administered as multiple (e.g., 2, 3, 4, 5, or more) doses. In some embodiments, the pharmaceutical composition comprises at least 1.1×10¹¹ total CFUs and is administered as two, three, four, five, six, seven, eight, nine, ten, eleven, twelve, thirteen, fourteen, fifteen or more doses. In some embodiments, the pharmaceutical composition comprises at least 1.1×10¹¹ total CFUs and is administered as fourteen doses. In some embodiments, each of the multiple doses are administered at regular intervals. In some embodiments, each of the multiple doses are on consecutive days (e.g., first dose on day 1, second dose of day 2, third dose on day 3, etc.). In some embodiments, the pharmaceutical composition comprises at least 1.1×10¹¹ total CFUs and is administered as fourteen doses, each of which are administered on fourteen consecutive days.

In some embodiments, the pharmaceutical composition comprises at least 2.1×10¹⁰ total CFUs. In some embodiments, the pharmaceutical composition comprises at least 2.1×10¹⁰ total CFUs and is administered as a single dose. In some embodiments, the pharmaceutical composition comprises at least 2.1×10¹⁰ total CFUs and is administered as multiple (e.g., 2, 3, 4, 5, or more) doses. In some embodiments, the pharmaceutical composition comprises at least 2.1×10¹⁰ total CFUs and is administered as two, three, four, five, six, seven, eight, nine, ten, eleven, twelve, thirteen, fourteen, fifteen or more doses. In some embodiments, the pharmaceutical composition comprises at least 2.1×10¹⁰ total CFUs and is administered as five doses. In some embodiments, each of the multiple doses are administered at regular intervals. In some embodiments, each of the multiple doses are on consecutive days (e.g., first dose on day 1, second dose of day 2, third dose on day 3, etc.). In some embodiments, the pharmaceutical composition comprises at least 2.1×10¹⁰ total CFUs and is administered as five doses, each of which are administered on five consecutive days.

As described herein, any of the pharmaceutical compositions described herein may be administered to a subject in one dose or in multiple doses (e.g., initial administration), which may be followed by one or more additional doses of any of the pharmaceutical compositions described herein. In some embodiments, any of pharmaceutical composition described herein may be administered to a subject in one dose or in multiple doses in an initial administration, followed by one or more additional doses of a pharmaceutical composition comprising the same one or more bacterial strains as the pharmaceutical composition of the initial administration. In some embodiments, any of pharmaceutical composition described herein may be administered to a subject in one dose or in multiple doses in an initial administration, followed by one or more additional doses of a pharmaceutical composition comprising more total bacteria (colony-forming units) relative to the initial administration of the pharmaceutical composition. In some embodiments, any of pharmaceutical composition described herein may be administered to a subject in one dose or in multiple doses in an initial administration, followed by one or more additional doses of a pharmaceutical composition comprising fewer total bacteria (colony-forming units) relative to the initial administration of the pharmaceutical composition. In some embodiments, the initial administration includes at least 1, 2, 3, 4, 5, 6, 7, 8, 9, 10, 11, 12, 13, 14, 15 or more doses of any of the pharmaceutical compositions described herein. In some embodiments, the additional administration includes at least 1, 2, 3, 4, 5, 6, 7, 8, 9, 10, 11, 12, 13, 14, 15 or more doses of any of the pharmaceutical compositions described herein. In some embodiments, the initial administration comprises two doses of any of the pharmaceutical composition and the additional administration comprises three doses of any of the pharmaceutical compositions described herein.

In some embodiments, any of pharmaceutical composition described herein may be administered to a subject in one dose or in multiple doses in an initial administration, followed by one or more additional doses of a pharmaceutical composition comprising fewer total bacteria (colony-forming units) relative to the initial administration of the pharmaceutical composition. In such embodiments, the dose(s) of the initial administration may be referred to as a "high dose" and the dose(s) of the additional administration may be referred to as a "low dose. In some embodiments, the high dose is at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold or more higher than the low dose. In some embodiments, the high dose is 8.0×10⁹ CFUs. In some embodiments, the low dose is 1.6×10⁹ CFUs. In some embodiments, the initial administration comprises multiple doses (e.g., 2, 3, 4, 5 or more) of 8.0×10⁹ CFUs and the additional administration comprises multiple doses (e.g., 2, 3, 4, 5 or more) of 1.6×10⁹ CFUs. In some embodiments, the low dose is 1.6×10⁹ CFUs. In some embodiments, the initial administration comprises two doses of 8.0×10⁹ CFUs and the additional administration comprises three doses of 1.6×10⁹ CFUs.

In some embodiments, the one or more additional administrations is performed on the day following the initial administration (e.g., consecutive days). In some embodiments, the one or more additional administrations is performed at least 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks or longer following the initial administration. In some embodiments, the one or more additional administrations is performed at least 6 weeks after the initial administration. In some embodiments, the one or more additional administrations is performed at least 12 weeks after the initial administration.

In some embodiments, the compositions, including pharmaceutical compositions, contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$ between $10^{-6}$ and $10^{-5}$, or between $10^{-7}$ and $10^{-6}$ grams of bacteria of each of the bacterial strains in the composition per dosage amount. In some embodiments, the compositions, including pharmaceutical compositions, disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of all of the bacteria combined (total) per dosage amount.

In one aspect the disclosure provides methods comprising the administration of an antibiotic (e.g., vancomycin) followed by the administration of a pharmaceutical composition provided herein, wherein the administration of an antibiotic (e.g., vancomycin) is followed by the administration of a single dose or multiple doses of the pharmaceutical composition. In some embodiments, administration of an antibiotic (e.g., vancomycin) followed by the administration of a single dose or multiple doses of the pharmaceutical composition results in an increase in the abundance of bacterial strains of the pharmaceutical compositions in the microbiome of the subject (engraftment) compared to the administration of a pharmaceutical composition without the administration of the antibiotic. In some embodiments, administration of an antibiotic (e.g., vancomycin) followed by the administration of a single dose or multiple doses of the pharmaceutical composition results in an increase in the duration of the colonization of bacterial strains of the pharmaceutical composition in the microbiome of the subject (e.g., up to 6 months) compared to the administration of a pharmaceutical composition without the administration of the antibiotic.

In some embodiments, administration of an antibiotic (e.g., vancomycin) followed by the administration of a single dose or multiple doses of the pharmaceutical composition results in an increase in the rate of engraftment of the initial amount of the bacterial strains of the pharmaceutical composition in the microbiome of the subject by between ten- to one hundred-fold (e.g., within the first 48 hours) compared to the administration of a pharmaceutical composition without the administration of the antibiotic.

In some embodiments, administration of an antibiotic (e.g., vancomycin) followed by the administration of a single dose or multiple doses of the pharmaceutical composition results in a greater number (amount) of subjects having all of the bacterial strains of the pharmaceutical composition present in their microbiome as compared to the administration of a pharmaceutical composition without the administration of the antibiotic.

In some embodiments, administration of an antibiotic (e.g., vancomycin) followed by the administration of multiple doses of the pharmaceutical composition results in an increase in the abundance of bacterial strains of the pharmaceutical composition in the microbiome of the subject (engraftment) compared to the administration of a single dose of the pharmaceutical composition. In some embodiments, the disclosure provides methods comprising the administration of a pharmaceutical composition provided herein, wherein the administration of multiple doses of the pharmaceutical composition increases the abundance of bacterial strains in the microbiota of the subject (engraftment) of the pharmaceutical composition in the microbiome of the subject compared to the administration of a single dose of the pharmaceutical composition.

In some embodiments, administration of an antibiotic (e.g., vancomycin) followed by the administration of multiple doses of the pharmaceutical composition results in an increase in the rate of engraftment of the initial amount of the bacterial strains of the pharmaceutical composition in the microbiome of the subject as compared to the administration of a single dose of the pharmaceutical composition. In some embodiments, the disclosure provides methods comprising the administration of a pharmaceutical composition provided herein, wherein the administration of multiple doses of the pharmaceutical composition increases the rate of engraftment of the initial amount of the bacterial strains of the pharmaceutical composition in the microbiome of the subject compared to the administration of a single dose of the pharmaceutical composition.

In some embodiments, administration of an antibiotic (e.g., vancomycin) followed by the administration of multiple doses of the pharmaceutical composition results in a higher abundance of the bacterial strains of the pharmaceutical composition in the microbiome of the subject as compared to the administration of a single dose of the pharmaceutical composition. In some embodiments, the disclosure provides methods comprising the administration of a pharmaceutical composition provided herein, wherein the administration of multiple doses of the pharmaceutical composition results in higher abundance of the bacterial strains of the pharmaceutical composition in the microbiome of the subject compared to the administration of a single dose of the pharmaceutical composition.

In some embodiments, administration of an antibiotic (e.g., vancomycin) followed by the administration of multiple doses of the pharmaceutical composition results in a greater number (amount) of subjects having all of the bacterial strains of the pharmaceutical composition present in their microbiome as compared to the administration of a single dose of the pharmaceutical composition. In some embodiments, the disclosure provides methods comprising the administration of a pharmaceutical composition provided herein, wherein the administration of multiple doses of the pharmaceutical results in a greater number (amount) of subject having all of the bacterial strains of the pharmaceutical composition in their microbiome as compared to the administration of a single dose of the pharmaceutical composition.

In some embodiments, administration of an antibiotic (e.g., vancomycin) followed by the administration of multiple doses of the pharmaceutical composition results in an accelerated recovery of the microbiome (e.g., increase in bacterial species of Bacteroidetes and/or Firmicutes, and/or decrease in Proteobacteria) as compared to the administration of a single dose of the pharmaceutical composition. In some embodiments, the disclosure provides methods comprising the administration of a pharmaceutical composition provided herein, wherein the administration of multiple doses of the pharmaceutical results in an accelerated recovery of the microbiome (e.g., increase in bacterial species of Bacteroidetes and/or Firmicutes, and/or decrease in Proteobacteria) as compared the administration of a single dose of the pharmaceutical composition.

In some embodiments, administration of an antibiotic (e.g., vancomycin) followed by the administration of a single dose or multiple doses of the pharmaceutical composition results in an accelerated recovery of the microbiome (e.g., increase in bacterial species of Bacteroidetes and/or Firmicutes, and/or decrease in Proteobacteria) as compared to the administration of an antibiotic (e.g., vancomycin) without the administration of a pharmaceutical composition.

In some embodiments, the methods described herein may involve subjecting the subject to a bowel lavage (bowel irrigation, whole bowel irrigation, gastrointestinal lavage, gastric lavage) prior to administration of the compositions described herein. In some embodiments, a bowel lavage may remove or aid in removing microbiota from the gastrointestinal tract of the subject, creating a niche for the bacterial strains of the compositions described herein. In some embodiments, the bowel lavage may be an oral bowel lavage or a rectal bowel lavage.

Methods of performing a bowel lavage are known in the art, and generally involve the rapid administration of large volumes of a solution, such as polyethylene glycol or a balanced electrolyte solution. A rectal bowel lavage can involve the administration of a solution or a suppository containing the pharmaceutical composition. A bowel lavage may be performed under doctor supervision, hospitalization, or at home.

Aspects of the present disclosure relate to methods of treating an infection by a pathogen comprising administering any of the pharmaceutical compositions according to any of the methods described herein.

Aspects of the present disclosure relate to methods of treating *C. difficile* infection comprising administering any of the pharmaceutical compositions according to any of the methods described herein. In some embodiments, the *C. difficile* infection is a primary *C. difficile* infection. In some embodiments, the *C. difficile* infection is a recurrent *C. difficile* infection. In some embodiments, the method comprises administering a single dose or multiple doses of any of the pharmaceutical compositions described herein. In some embodiments, the method further comprises administering one or more additional doses or amounts of the pharmaceutical compositions described herein. In some embodiments, the method further comprises administering an antibiotic (e.g., vancomycin) to the subject prior to administration of the pharmaceutical compositions.

The compositions and methods described herein are effective in the treatment of *C. difficile* infection. The methods described herein may be effective in suppressing the pathogenic effects of *C. difficile* infection. In some embodiments, administration of the compositions provided herein reduce the amount of *C. difficile* after infection and thereby provide an effective method for eliminating *C. difficile* from the body (e.g., the gut). In some embodiments, administration of the compositions provided herein induce the proliferation and/or accumulation of regulatory T cells (Tregs), for example when administered to a subject. In some embodiments, administration of the compositions disclosed may reduce or inhibit production or activity of *C. difficile* Toxin B and thereby represent effective compositions for the treatment or prevention of *C. difficile* infection. The compositions disclosed herein have also been found to inhibit the growth and/or survival of *C. difficile*.

The present disclosure provides methods of administering the pharmaceutical compositions to subjects experiencing or having experienced a pathogenic infection to treat the infection. In some embodiments, the compositions may be administered to subjects who may be at risk for a pathogenic infection. Such subjects include subjects who previously had pathogenic infections, subjects who have been treated with antibiotics and subjects who will undergo a procedure that will put them at an increased risk for a pathogenic infection (e.g., surgery and/or hospitalization). In some embodiments, the pathogenic infection, is infection by a pathogen that is present predominantly in the gut or the intestine. In some embodiments, the pathogen that is present predominantly in the gut or the intestine is *Clostridium difficile*.

In some embodiments, a pathogenic infection such as *C. difficile* is treated because the combination of bacterial strains of the compositions provided herein is superior in the use of nutrients when compared to the pathogen such as *C. difficile*, thereby suppressing the growth of the pathogen such as *C. difficile*. In some embodiments, a pathogenic infection such as *C. difficile* is treated because the combination of bacterial strains of the compositions provided herein is superior in grafting when compared to the pathogen such as *C. difficile*, thereby suppressing the growth of the pathogen such as *C. difficile*. In some embodiments, a pathogenic infection such as *C. difficile* is treated because the combination of bacterial strains of the compositions provided herein is superior in the use of nutrients and in grafting when compared to the pathogen such as *C. difficile*, thereby suppressing the growth of the pathogen such as *C. difficile*. In some embodiments, a pathogenic infection such as *C. difficile* is treated because the combination of bacterial strains of the compositions provided herein inhibits the growth and/or survival of the pathogen such as *C. difficile*. In some embodiments, a pathogenic infection such as *C. difficile* is treated because the combination of bacterial strains of the compositions provided herein induces regulatory T cells (Tregs) in the subject that results in reduction or elimination of the pathogen such as *C. difficile*. In some embodiments, a pathogenic infection such as *C. difficile* is treated because the combination of bacterial strains of the compositions provided herein inhibits the growth and/or survival of the pathogen and induces regulatory T cells (Tregs) in the subject that results in reduction or elimination of the pathogen such as *C. difficile*.

In some embodiments, the subject is a carrier of a pathogenic organism and is suffering from the effects of the infection (e.g., diarrhea caused by *C. difficile* toxins). In some embodiments the subject is an asymptomatic carrier of a pathogen. In some embodiments, the subject is a carrier of *C. difficile*. In some embodiments the subject is an asymptomatic *C. difficile* carrier. In some embodiments, the subject has experienced recurrent or chronic pathogenic infections. In some embodiments, the subject is suffering from a first occurrence of a particular pathogenic infection. In some embodiments, the subject has been treated with antibiotics which resulted in the recurrence of the pathogenic infection. In some embodiments, the subject has been treated with antibiotics which resulted in a first occurrence of a pathogenic infection. In some embodiments, the subject is to undergo a procedure that puts the subject at a higher risk of infection. In some embodiments, the compositions provided herein are administered to a subject to lower the risk of becoming infected by a pathogen.

Any of the compositions described herein may be administered to a subject in a therapeutically effective amount or a dose of a therapeutically effective amount to treat or prevent a pathogenic infection (e.g., one or more pathogenic infections). The terms "treat" or "treatment" refer to reducing or alleviating one or more of the symptoms associated with a pathogenic infection, reducing the amount of bacterial toxin produced by the pathogenic infection, and/or reducing the bacterial load of the pathogenic infection. The terms "prevent" or "prevention" encompass prophylactic administration and may reduce the incidence or likelihood of pathogenic infection or a recurrent or chronic pathogenic infection. For instance, in some embodiments, administration of the compositions provided herein result in a healthy microbiome that is refractory to pathogenic infection, thereby preventing the pathogenic infection.

In some embodiments, the therapeutically effective amount of any of the compositions described herein is an amount sufficient to enhance survival of the subject, reduce the bacterial burden of the pathogenic infection in the subject, and/or reduce or inhibit toxin production by the pathogenic infection. In some embodiments, the therapeutically effective amount is an amount sufficient to reduce the bacterial burden of the pathogenic infection in a fecal sample from the subject by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the bacterial burden in a subject with a pathogenic infection that has not received any of the compositions described herein, or as compared to a fecal sample from the same subject that was collected prior to administration of any of the compositions.

In some embodiments, the compositions provided herein inhibit the production of a bacterial toxin, e.g., *C. difficile* Toxin B. In some embodiments, the therapeutically effective amount is an amount sufficient to reduce or inhibit the amount of bacterial toxin (e.g., *C. difficile* Toxin B) produced by pathogenic infection in a fecal sample from the subject by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 150-fold, 200-fold, 500-fold or more, as compared to the amount of the bacterial toxin in a subject with a pathogenic infection that has not received any of the compositions described herein or as compared to a fecal sample from the same subject that was collected prior to administration of any of the compositions.

In some embodiments, the compositions provided herein induce the proliferation and/or accumulation of regulatory T cells in the subject. As will be evident to one of ordinary skill in the art, regulatory T cells, also referred to as "Tregs," are a subset of T lymphocytes that are generally thought to suppress an abnormal or excessive immune response and play a role in immune tolerance. Regulatory T cells may be identified based expression of the markers Foxp3 and CD4 (Foxp3+ CD4+). The term regulatory T cells may also include Foxp3-negative regulatory T cells that are IL-10-producing CD4-positive T cells.

In some embodiments, the therapeutically effective amount is an amount sufficient to induce the proliferation and/or accumulation of Tregs in the subject (or in a sample obtained from a subject) by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 150-fold, 200-fold, 500-fold or more, as compared to the amount of Tregs in a subject (e.g., a subject with a pathogenic infection) that has not received any of the compositions described herein or as compared to a fecal sample from the same subject that was collected prior to administration of any of the compositions.

As used herein, the phrase "induces proliferation and/or accumulation of regulatory T cells" refers to an effect of inducing the differentiation of immature T cells into regulatory T cells, which differentiation leads to the proliferation and/or the accumulation of regulatory T cells. Further, the meaning of "induces proliferation and/or accumulation of regulatory T cells" includes in vivo effects, in vitro effects, and ex vivo effects. In some embodiments, the proliferation and/or accumulation of regulatory T cells may be assessed by detecting and/or quantifying the number of cells that express markers of regulatory T cells (e.g., Foxp3 and CD4), for example by flow cytometry. In some embodiments, the proliferation and/or accumulation of regulatory T cells may be assessed by determining the activity of the regulatory T cells, such as the production of cytokines (e.g., IL-10).

Aspects of the present disclosure relate to compositions and methods for treating a food allergy in a subject. Also provided are compositions and methods for modulating immune responses associated with a food allergy and/or inducing immune tolerance or desensitization to a food allergy. In some embodiments, the method comprises administering a single dose or multiple doses of any of the pharmaceutical compositions described herein. In some embodiments, the method further comprises administering one or more additional doses or amounts of the pharmaceutical compositions described herein. In some embodiments, the method further comprises administering antibiotics (e.g., vancomycin) to the subject prior to administration of the pharmaceutical compositions.

Allergy is characterized by an undesired immune response upon contact or exposure to a (non-self) substance that is typically considered harmless, referred to as an allergen. In the general population, contact or exposure to allergens does not elicit a substantial immune response and individuals are considered to be tolerant or not sensitive to the allergens. Accordingly, allergy may be referred to a hypersensitivity reaction to an allergen. As used herein, the term "food allergy" refers to an undesired allergic immune response to a food, or specifically, to an allergen present in the food. In some embodiments, an allergic reaction associated with a food allergy is induced following contact, for example through ingestion, of a food or foods containing the same or similar allergens. As will be evident to one of skill in the art, the symptoms associated with the food allergy may manifest in the gastrointestinal tract of the subject, for example, following ingestion with food containing the allergen; however, the allergic reaction may affect other sites, such as the respiratory tract or skin.

Food allergies are generally considered to be IgE-mediated immune reactions, however non-IgE-mediated food allergies as well as mixed IgE-mediated/non-IgE-mediated food allergies. See, e.g., Fiocchi et al. "Food Allergy" World Allergy Organization: March 2017. IgE-mediated food allergies tend to occur immediately or within about 2 hours following contact with the allergen and include hives (acute uticaria), angioedema, swelling, anaphylaxis, food-associated exercise-induced anaphylaxis, oral allergy syndrome, and/or immediate gastrointestinal hypersensitivity involving vomiting and pain. Non-IgE-mediated immune responses involved in food allergy, also referred to as cell-mediated responses, are delayed hypersensitivity reactions and may involve food protein-induced enterocolitis syndrome, food protein-induced allergic proctocolitis, allergic contact dermatitis, and Heiner syndrome. Mixed or combined IgE-mediated/non-IgE-mediated immune responses involved in food allergy are associated with both IgE and T cell mediated effects and may include atopic dermatitis, eosinophilic esophagitis, and/or eosinophilic gastroenteritis.

In contrast to food allergies, food intolerance is not generally considered to be mediated by the immune system and onset occurs between about 30 mins after exposure to within 48 hours after exposure.

In some embodiments, the compositions and methods described herein are used to treat an IgE-mediated food allergy. In some embodiments, the compositions and methods described herein are used to modulate an immune response associated with an IgE-mediated food allergy. In some embodiments, the compositions and methods described herein are used to induce immune tolerance or desensitization to an IgE-mediated food allergy. The compositions and methods described herein may also be used in the context of non-IgE mediated food allergies and/or mixed or combined IgE-mediated/non-IgE-mediated food allergies.

Examples of food allergies include, without limitation, peanut allergy, tree nut allergy, egg allergy, corn allergy, fruit allergy, milk allergy, garlic allergy, soy allergy, wheat allergy, seafood allergy, fish allergy (e.g., shellfish allergy), and seed allergy (e.g., sesame seed allergy).

Non-limiting examples of foods containing allergens to which a food allergy may occur include abalone (perlemoen), acerola, Alaska pollock, almond, aniseed, apple, apricot, avocado, banana, barley, bell pepper, Brazil nut, buckwheat, cabbage, carp, carrot, cashew, caster bean, celery, celeriac, cherry, chestnut, chickpea (garbanzo, bengal gram), cocoa, coconut, cod, cotton seed, courgette (zucchini), crab, date, egg, fig, fish, flax seed (linseed), frog, garden plum, garlic, grape, hazelnut, kiwi fruit (Chinese gooseberry), lentil, lettuce, lobster, lupin (lupine), lychee, mackerel, maize (corn), mango, melon, milk, mustard, oat oyster, peach, peanut (ground nuts, monkey nuts), pear, pecan, persimmon, pine nut, pineapple, pomegranate, poppy seed, potato, pumpkin, rice, rye, salmon, sesame, sesame seed, shrimp (black tiger shrimp, brown shrimp, greasyback shrimp, Indian prawn, Neptune rose shrimp, white shrimp), snail, soybean (soya), squid, strawberry, sunflower seed, tomato, tuna, turnip, walnut, and wheat (bread-making wheat, pasta wheat, kamut, spelt).

In some embodiments, the compositions and methods described herein are used to induce immune tolerance to an allergen associated with a food allergy or desensitize an immune response to an allergen associated with a food allergy. As used herein, the terms "tolerance" and "immune tolerance" in the context of allergy refer to a reduced responsiveness or non-responsiveness of the immune response to one or more stimuli, such as an allergen associated with allergy. In particular, tolerance or immune tolerance refer to reduced responsiveness or non-responsiveness of the immune response to one or more stimuli over a sustained or long term period of time. In contrast, the term "desensitize" in the context of allergy refers a reversible state of reduced responsiveness or non-responsiveness of the immune response to one or more stimuli, for example during the course of a desensitization regimen.

In some embodiments, the compositions and methods described herein are used to modulate an immune response associated with a food allergy. As will be evident to one of skill in the art, the compositions and methods described herein may enhance one or more immune response(s) associated with an allergy and reduce or suppress one or more other immune response(s) associated with the allergy.

In some embodiments, administration of the compositions described herein results in an increase the proliferation and/or accumulation of regulatory T cells (e.g., total Tregs or allergen-specific Tregs) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, 104-fold, 105-fold or more, as compared to the quantity of regulatory T cells in the subject (or particular site in the subject) prior to administration of the compositions. In some embodiments, administration of the compositions described herein results in an increase the proliferation and/or accumulation of regulatory T cells (e.g., total Tregs or allergen-specific Tregs) by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, 104-fold, 105-fold or more, as compared to the quantity of regulatory T cells in another subject (e.g., a reference subject) who did not receive the compositions.

In some embodiments, administration of the compositions described herein results in an increase the proliferation and/or accumulation of regulatory T cells (e.g., total Tregs or allergen-specific Tregs) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the quantity of regulatory T cells in the subject (or particular site in the subject) prior to administration of the compositions. In some embodiments, administration of the compositions described herein results in an increase the proliferation and/or accumulation of regulatory T cells (e.g., total Tregs or allergen-specific Tregs) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the quantity of regulatory T cells in another subject (e.g., a reference subject) who did not receive the compositions.

The induction of Treg cells and corresponding allergy treatment are intricately related. In some embodiments, in the treatment of one or more allergies, it is desired to have a Treg induction that is a range associated with efficacy for the one more allergies. In some embodiments, for a particular allergy treatment regimen it is desired to have a Treg response that is significantly strong to induce the desired allergy treatment effect, but not so strong as to result in undesired immunological events. In some embodiments, administration of the compositions described herein results in an increase the proliferation and/or accumulation of regulatory T cells (e.g., total Tregs or allergen-specific Tregs) by between 1% and 20%, 2% and 19%, 3% and 17%, 4% and 16%, 4% and 15%, 5% and 15%, 6% and 14%, 7% and 13%, 8% and 12%, 5% and 10%, 5% and 15%, 10% and 15%, or 8% and 15% as compared to the quantity of regulatory T cells in the subject (or particular site in the subject) prior to administration of the compositions. In some embodiments, administration of the compositions described herein results in an increase the proliferation and/or accumulation of regulatory T cells (e.g., total Tregs or allergen-specific Tregs) by between 1% and 20%, 2% and 19%, 3% and 17%, 4% and 16%, 4% and 15%, 5% and 15%, 6% and 14%, 7% and 13%, 8% and 12%, 5% and 10%, 5% and 15%, 10% and 15%, or 8% and 15% as compared to the quantity of regulatory T cells in another subject (e.g., a reference subject) who did not receive the compositions.

In some embodiments, administration of the compositions described herein results in an increase in activity of regulatory T cells (e.g., total Tregs or allergen-specific Tregs) at a particular site (e.g., the gastrointestinal tract) in the subject. In some embodiments, administration of the compositions described herein results in an increase in activity of regulatory T cells (e.g., total Tregs or allergen-specific Tregs) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, 104-fold, 105-fold or more, as compared to the activity of regulatory T cells in the subject (or particular site in the subject) prior to administration of the compositions. In some embodiments, administration of the compositions described herein results in an increase in activity of regulatory T cells (e.g., total Tregs or allergen-specific Tregs) by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, 104-fold, 105-fold or more, as compared to the activity of regulatory T cells in another subject (e.g., a reference subject) who did not receive the compositions.

In some embodiments, administration of the compositions described herein results in an increase in the activity of regulatory T cells (e.g., total Tregs or allergen-specific Tregs) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the activity of regulatory T cells in the subject (or particular site in the subject) prior to administration of the compositions. In some embodiments, administration of the compositions described herein results in an increase in the activity of regulatory T cells (e.g., total Tregs or allergen-specific Tregs) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the activity of regulatory T cells in another subject (e.g., a reference subject) who did not receive the compositions.

The abundance of regulatory T cells (e.g., total Tregs or allergen-specific Tregs) can be assessed by any method known in the art, for example by detecting a cellular marker indicative of regulatory T cells (e.g., FoxP3), assessing a direct or indirect activity of regulatory T cells, and/or by measuring the production of one or more cytokines produced by regulatory T cells (e.g., IL-10).

In some embodiments, the compositions described herein suppress the production of IgE antibodies. In some embodiments, the composition suppresses the production of total IgE antibodies in the subject. In some embodiments, the composition suppresses the production of IgE antibodies that are specific to an allergen (e.g., allergen-specific IgE antibodies) associated with an allergy, e.g., a food allergen associated with a food allergy. In some embodiments, administration of the compositions described herein results in levels of IgE antibodies (e.g., total IgE antibodies or allergen-specific IgE antibodies) that are reduced by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the level of IgE antibodies (e.g., total IgE antibodies or allergen-specific IgE antibodies) in the subject (or a sample thereof) prior to administration of the compositions. In some embodiments, administration of the compositions described herein results in levels of IgE antibodies (e.g., total IgE antibodies or allergen-specific IgE antibodies) that are reduced by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the level of IgE antibodies in another subject (e.g., a reference subject) who did not receive the compositions.

In some embodiments, administration of the compositions described herein results in levels of IgE antibodies (e.g., total IgE antibodies or allergen-specific IgE antibodies) that are reduced by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100% as compared to the level of IgE antibodies (e.g., total IgE antibodies or allergen-specific IgE antibodies) in the subject (or a sample thereof) prior to administration of the compositions. In some embodiments, administration of the compositions described herein results in levels of IgE antibodies (e.g., total IgE antibodies or allergen-specific IgE antibodies) that are reduced by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100% as compared to the level of IgE antibodies in another subject (e.g., a reference subject) who did not receive the compositions.

In some embodiments, administration of the compositions described herein results in levels of IgE antibodies (e.g., total IgE antibodies or allergen-specific IgE antibodies) that are reduced by between 30% and 50%, 30% and 45%, 35% and 45%, 30% and 40%, 35% and 40%, 40% and 50%, 40% and 45%, 45% and 50% as compared to the level of IgE antibodies (e.g., total IgE antibodies or allergen-specific IgE antibodies) in the subject (or a sample thereof) prior to administration of the compositions. In some embodiments, administration of the compositions described herein results in levels of IgE antibodies (e.g., total IgE antibodies or allergen-specific IgE antibodies) that are reduced by between 30% and 50%, 30% and 45%, 35% and 45%, 30% and 40%, 35% and 40%, 40% and 50%, 40% and 45%, 45% and 50% as compared to the level of IgE antibodies in another subject (e.g., a reference subject) who did not receive the compositions.

The presence and/or quantity of IgE antibodies in a subject, including the presence and/or quantity of allergen-specific IgE antibodies, can be assessed by methods known in the art. For example, a sample, such as a blood or plasma sample, may be obtained from a subject and subjected to analysis, for example by immunoassays (e.g., radio allergosorbent test (RAST), fluorescent allergosorbant test (FAST), enzyme-linked immunosorbent assays (ELISA)) and protein arrays (see e.g., Fall et al. Methods Mol Biol (2009) 509: 107-122). The presence of allergen-specific IgE antibodies may, additionally or alternatively, be assessed using a skin test (e.g., skin prick test).

In some embodiments, the compositions described herein suppress one or more Th2 immune responses. In some embodiments, the compositions described herein suppress the development or differentiation of Th2 cells (also referred to as type 2 helper T cells). In some embodiments, the compositions described herein suppress the activity of Th2 cells. As will be evident by one of ordinary skill in the art, Th2 cells are a subject of CD4+ cells that produce IL-4, IL-5, IL-6, IL-10, and/or IL-13 and may be involved in promoting IgE antibody responses and/or eosinophil activity. The differentiation of CD4+ cells to Th2 cells is promoted by the presence of IL-4 and/or IL-12 and activation of the transcription factors STAT6 and GATA3 (see, e.g., Wan Trends Immunol. (2014) 35(6): 233-242; Zhu et al. J. Immunol. (2001) 166: 7276-7281). In some embodiments, the amount of IgE antibodies may be assessed as a marker of Th2 immune responses in a subject.

In some embodiments, administration of the compositions described herein results in levels of Th2 immune responses that are reduced by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to Th2 immune response in the subject (or a sample thereof) prior to administration of the compositions. In some embodiments, administration of the compositions described herein results in Th2 immune responses that are reduced by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to Th2 immune responses in another subject (e.g., a reference subject) who did not receive the compositions.

In some embodiments, administration of the compositions described herein results in levels of Th2 immune responses that are reduced by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%, as compared to Th2 immune response in the subject (or a sample thereof) prior to administration of the compositions. In some embodiments, administration of the compositions described herein results in Th2 immune responses that are reduced by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%, as compared to Th2 immune responses in another subject (e.g., a reference subject) who did not receive the compositions.

The presence or level of a Th2 immune response may be assessed using any method known in the art. The presence or level of a Th2 immune response may be assessed, for example, by detecting and/or quantifying the number of Th2 cells in a sample obtained from the subject, such as by detecting a cellular marker indicative of the Th2 cells; assessing transcription profile associated with Th2 cells; assessing a direct or indirect activity of Th2 cells; and/or by measuring the production of one or more cytokines produced by Th2 cells (e.g., IL-4, IL-5, IL-6, IL-10, IL-13). In some embodiments, administration of the compositions provided herein results in a healthy microbiome that modulates an immune response associated with allergy (e.g., a food allergy) in a subject. In some embodiments, administration of the compositions provided herein results in a healthy microbiome that modulates an immune response associated with allergy (e.g., a food allergy) in a subject. In some embodiments, administration of the compositions provided herein results in a healthy microbiome that induces the accumulation and/or proliferation of regulatory T cells in a subject. In some embodiments, administration of the compositions provided herein results in a healthy microbiome that suppresses production of IgE antibodies in a subject. In some embodiments, administration of the compositions provided herein results in a healthy microbiome that suppresses Th2 immune responses in a subject.

In some embodiments, the compositions described herein suppress one or more mast cell functions. In some embodiments, the compositions described herein suppress mast cell degranulation. As will be evident by one of ordinary skill in the art, mast cells are characterized by the presence of granules of containing histamine, heparin, cytokines, chondroitin sulfate, and neutral proteases in the cytoplasm of the cells. Mast cells are thought to be involved in regulating a range of physiological functions, such as vasodilation, vascular homeostasis, innate and adaptive immune responses, angiogenesis, and venom detoxification, as well as play a role in the pathophysiology of many diseases (see, e.g., Krystel-Whittemore et al. Front. Immunol. (2015) 6:620). In some embodiments, the mast cells are mucosal mast cells.

In some embodiments, administration of the compositions described herein results in levels of mast cell function and/or mast cell degranulation that are reduced by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to mast cell function and/or mast cell degranulation in the subject (or a sample thereof) prior to administration of the compositions. In some embodiments, administration of the compositions described herein results in mast cell function and/or mast cell degranulation that are reduced by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to mast cell function and/or mast cell degranulation in another subject (e.g., a reference subject) who did not receive the compositions.

In some embodiments, administration of the compositions described herein results in levels of mast cell function and/or mast cell degranulation that are reduced by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%, as compared to mast cell function and/or mast cell degranulation in the subject (or a sample thereof) prior to administration of the compositions. In some embodiments, administration of the compositions described herein results in mast cell function and/or mast cell degranulation that are reduced by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%, as compared to mast cell function and/or mast cell degranulation in another subject (e.g., a reference subject) who did not receive the compositions.

The presence or level of a mast cell function and/or mast cell degranulation may be assessed using any method known in the art. The presence or level of a mast cell function and/or mast cell degranulation may be assessed, for example, by detecting and/or quantifying the number of mast cells in a sample obtained from the subject, such as by detecting a cellular marker indicative of the mast cells; assessing degranulation of the mast cells (e.g., release of histamine, heparin, etc.), activation of the mast cells (e.g., via antigen/IgE/FcεRI cross linking).

Aspects of the present disclosure also provide food products comprising any of the compositions provided herein and a nutrient. Also within the scope of the present disclosure are food products comprising any of the bacterial strains described herein and a nutrient. Food products are, in general, intended for the consumption of a human or an animal. Any of the compositions described herein may be formulated as a food product. In some embodiments, the bacterial strains are formulated as a food product in spore form. In some embodiments, the bacterial strains are formulated as a food product in vegetative form. In some embodiments, the food product comprises both vegetative bacteria and bacteria in spore form. The compositions disclosed herein can be used in a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed.

Non-limiting examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

Food products containing the bacterial strains described herein may be produced using methods known in the art and may contain the same amount of bacteria (e.g., by weight, amount or CFU) as the pharmaceutical compositions provided herein. Selection of an appropriate amount of bacteria in the food product may depend on various factors, including for example, the serving size of the food product, the frequency of consumption of the food product, the specific bacterial strains contained in the food product, the amount of water in the food product, and/or additional conditions for survival of the bacteria in the food product.

Examples of food products which may be formulated to contain any of the bacterial strains described herein include, without limitation, a beverage, a drink, a bar, a snack, a dairy product, a confectionery product, a cereal product, a ready-to-eat product, a nutritional formula, such as a nutritional supplementary formulation, a food or beverage additive.

Aspects of the present disclosure relate to methods of treating diseases characterized by increased levels of primary bile acids and/or decreased levels of secondary bile acids comprising administering any of the pharmaceutical compositions according to any of the methods described herein.

Aspects of the present disclosure also provide methods for reducing primary bile acids comprising administering the bacterial strains or a pharmaceutical composition as described herein to a subject in need thereof. Some aspects of the present disclosure also provide methods for increasing secondary bile acids comprising administering the bacterial strains or a pharmaceutical composition as described herein to a subject in need thereof. Some aspects of the present disclosure also provide methods for increasing short chain fatty acids comprising administering the bacterial strains or a pharmaceutical composition as described herein to a subject in need thereof. In some embodiments, the subject has a *Clostridium difficile* infection (CDI). In some embodiments, the CDI is recurrent (rCDI). rCDI is CDI that occurs more than once in the same subject and is associated with reduced short chain fatty acids (SCFAs), increased primary bile acids, and decreased secondary bile acids in the gut microbiota of the subject.

Bile acids are steroid acids that allow the digestion of dietary fats and oils by acting as surfactants that turn the fats and oils into micelles. Bile acids also act as hormones utilizing the farnesoid X receptor and GBPAR1. Primary bile acids are synthesized in the liver from cholesterol and a conjugated with either taurine or glycine prior to secretion. When the primary bile acids are secreted into the lumen of the intestine, bacteria partially dehydroxylate and remove the glycine or taurine groups, forming secondary bile acids.

Non-limiting examples of primary bile acids are cholic acid (CA), chenodeoxycholic acid (CDCA), glycocholic acid (GCA), glycochenodeoxycholic acid (GCDCA), glycodeoxycholic acid (GDCA), taurocholic acid (TCA), and turochenodeoxycholic acid (TCDCA). Non-limiting examples of secondary bile acids are deoxycholic acid (DCA), lithocholic acid (LCA), ursodeoxycholic acid (UDCA), taurodeoxycholic acid (TDCA), taurolithocholic acid (TLCA), and tauroursodeoxycholic acid (TUDCA).

Non-limiting examples of secondary bile acids include lithocholic acid (LCA), deoxycholic acid (DCA), ursodeoxycholic acid, glycolithocholic acid, glycodeoxycholic acid, glycoursodeoxycholic acid, 12-dehydrocholic acid, 7-ketodeoxycholic acid, 7-dehydrochenodeoxycholic acid, 3-dehydrocholic acid, 3-dehydrochenodeoxycholic acid, isocholic acid, isochenodeoxycholic acid, allolithocholic acid, allodeoxycholic acid, ursocholic acid, hyodeoxycholic acid, ursocholic acid, isochenodeoxycholic acid, bitocholic acid, taurolithocholic acid, taurodeoxycholic acid, tauroursodeoxycholic acid, and taurocholic acid.

*Clostridium difficile* infection and rCDI are associated with increased primary bile acids and reduced secondary bile acids. The primary bile acids are reduced and the secondary bile acids are increased following fecal matter transplant (FMT) (Seekatz, et al., 2018). In some embodiments, administration of the bacterial strains or a pharmaceutical composition as described herein reduces primary bile acids and/or increases secondary bile acids.

In some embodiments, the levels of primary bile acids are reduced by 10-fold to 100,000-fold following administration of the bacterial strains or the pharmaceutical composition. In some embodiments, the levels of primary bile acids are reduced by 10-fold to 1,000-fold following administration of the bacterial strains or the pharmaceutical composition. In some embodiments, the levels of primary bile acids are reduced 2-fold to 10,000-fold following administration of the bacterial strains or the pharmaceutical composition. In some embodiments, the levels of primary bile acids are reduced by 2-fold, 5-fold, 10-fold, 100-fold, 200-fold, 300-fold, 400-fold, 500-fold, 600-fold, 700-fold, 800-fold, 900-fold, 1,000-fold, 10,000-fold, 20,000-fold, 30,000-fold, 40,000-fold, 50,000-fold, 60,000-fold, 70,000-fold, 80,000-fold, 90,000-fold, or 100,000-fold following administration of the bacterial strains or the pharmaceutical composition.

In some embodiments, the levels of secondary bile salts are increased by 10-fold to 10,000-fold following administration of the bacterial strains or the pharmaceutical composition. In some embodiments, the levels of secondary bile acids are increased by 10-fold to 1,000-fold following administration of the bacterial strains or the pharmaceutical composition. In some embodiments, the levels of secondary bile acids are increased by 2-fold to 100-fold following administration of the bacterial strains or the pharmaceutical composition. In some embodiments, the levels of secondary bile acids are increased by 2-fold, 5-fold, 10-fold, 20-fold, 50-fold, 100-fold, 200-fold, 300-fold, 400-fold, 500-fold, 600-fold, 700-fold, 800-fold, 900-fold, 1,000-fold, 2,000-fold, 3,000-fold, 4,000-fold, 5,000-fold, 6,000-fold, 7,000-fold, 8,000-fold, 9,000-fold, or 1,000-fold following administration of the bacterial strains or the pharmaceutical composition.

In some embodiments, the compositions and methods described herein are for the treatment of a disease characterized by or associated with increased levels of primary bile acids and/or decreased levels of secondary bile acids. In some embodiments, the disease associated with increased levels of primary bile acids and/or decreased levels of secondary bile acids may be treated by reducing the levels of primary bile acids and/or increasing levels of secondary bile acids. In some embodiments, the disease is a cardiovascular disease, a metabolic disease, an autoimmune disease, a digestive disease, a liver disease, a cancer, an infectious disease, a disease of the central nervous system, or a bone disease. Examples of such diseases include, without limitation, hypercholesterolemia, diabetic dyslipidemia, hypertension, arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (Cad), peripheral artery disease (Pad), cerebrovascular disease, diabetes (including Type 1, 2 diabetes and maturity onset diabetes of the young (MODY)), obesity, weight gain, gallstones, hypertriglyceridemia, hyperfattyacidemia, hyperinsulinemia, multiple sclerosis, experimental autoimmune encephalomyelitis (EAE), inflammatory bowel disease (IBD), irritable bowel syndrome-associated constipation, irritable bowel syndrome-associated diarrhea, cirrhosis, nonalcoholic steatohepatitis (NASH), progressive familial intrahepatic cholestasis type 2 (PFIC2), non-alcoholic fatty liver disease (NAFLD), cholestasis, gastrointestinal cancer, hepatocellular carcinoma, colon cancer, vancomycin-resistant Enterococci (VRE) infection or colonization, *Salmonella* infections, *Citrobacter* infections, Alzheimer's disease, Parkinson's disease, osteopenia, and osteoporosis.

Some aspects compositions and methods described herein increase production of short chain fatty acids (e.g., in the gastrointestinal tract of the subject). In some embodiments, the methods involve administering to a subject one or more compositions containing bacterial strains that produce short chain fatty acids. SCFAs are abundant in healthy subjects (e.g., subjects not having a pathogenic organism infection) and decreased in subjects having pathogenic organism infections (e.g., *Clostridium difficile* infections and rCDIs). Fecal matter transplants (FMTs) have been shown to increase SCFA following rCDI (Seekatz, et al., 2018).

SCFA produced in the gastrointestinal tract are thought to function as signaling molecules between the gut microbiota and the host organism, with the SCFA playing a in local, intermediary and peripheral metabolism of the host. See, e.g., Morrison, et al. *Gut Microbes* (2016) 7(3): 189-200. In some embodiments, a damaged gut mucosal barrier can be repaired by providing SCFA.

Short chain fatty acids (SCFAs) are fatty acids containing six or less carbon atoms. They are produced when dietary fiber is fermented in the intestine. They are primarily absorbed in the portal vein following lipid digestion. SCFAs can affect the production of lipids, energy, and vitamins, as well as playing a critical role in maintaining intestinal epithelial cell membrane integrity for preventing *Clostridium difficile* infection.

Examples of SCFA include, without limitation, formic acid, acetic acid, butyric acid, isobutyric acid, valeric acid, or isovaleric acid. In some embodiments, the SCFA is butyric acid (butyrate).

SCFAs are abundant in healthy subjects (e.g., subjects not having a *Clostridium difficile* infection) and decreased in subjects having *Clostridium difficile* infections and rCDIs. Fecal matter transplant (FMT) increases SCFA following rCDI (Seekatz, et al., 2018).

In some embodiments, SCFAs are increased by 10-fold to 500-fold following administration of the bacterial strains or a pharmaceutical composition as described herein. In some embodiments, SCFAs are increased by 2-fold to 250-fold following administration of the bacterial strains or the pharmaceutical composition. In some embodiments, SCFAs are increased by 100-fold to 500-fold following administration of the bacterial strains or the pharmaceutical composition. In some embodiments, SCFAs are increased by 2-fold, 5-fold, 10-fold, 20-fold, 30-fold, 40-fold, 50-fold, 60-fold, 70-fold, 80-fold, 90-fold, 100-fold, 200-fold, 300-fold, 400-fold, or 500-fold following administration of the bacterial strains or the pharmaceutical composition.

In some embodiments, the compositions and methods described herein are for the treatment of a disease characterized by or associated with decreased levels of SCFAs. In some embodiments, the disease associated with decreased levels of SCFAs may be treated by increasing levels of SCFAs, for example by increasing production of SCFAs in the gastrointestinal tract of the subject. In some embodiments, the disease is a cardiovascular disease, a metabolic disease, high blood pressure, obesity, diabetes type 1, diabetes type 2, irritable bowel disease, irritable bowel syndrome, colon cancer, allergic asthma, colitis, arthritis, bronchitis, chronic kidney disease, end-stage renal disease, prostatic hyperplasia, aging, depression, anxiety, graft-versus-host disease, food allergy, colorectal cancer.

Aspects of the present disclosure provide compositions and methods for treating graft versus host disease (GvHD) comprising administering any of the compositions described herein, for example to a subject having, suspected of having, or at risk of having GvHD. In some embodiments, the methods involve administering a therapeutically effective amount of any of the compositions described herein to colonize the microbiome of the subject.

In general, a subject may experience or be at risk of experiencing GvHD after receiving a transplant, e.g., a bone marrow transplant, stem cell transplant. GvHD may occur when cells from the donor recognize histocompatibility antigens of the transplant recipient as foreign, leading to inflammatory responses, including T cell activation and cytokine production, targeting tissues of the subject and may lead to multi-organ dysfunction and destruction.

In some embodiments, a therapeutically effective amount of any of the compositions described herein is administered to a subject having or suspected of having GvHD such that one or more symptoms of GvHD are improved (e.g., as compared to the one or more symptom prior to the administration). In some embodiments, a therapeutically effective amount of any of the compositions described herein is administered to a subject at risk of having GvHD (e.g., a subject who has recently undergone a transplantation or will undergo a transplantation) such that the subject does not experience one or more symptoms of GvHD or the subject experiences one or more symptoms of GvHD to a lesser degree (e.g., as compared to subjects that do not receive the compositions).

Also provided herein are methods for assessing colonization of one or more bacterial strains of a bacterial composition in a microbiome of a subject comprising isolating nucleic acid from a sample of the microbiome of the subject and determining the presence of each least one bacterial strain of the bacterial composition by detecting one or more genomic markers for bacterial strains of the bacterial composition. In some embodiments, provided herein are methods for assessing recovery or restoration of a microbiome of a subject, for example following a dysbiosis inducing event. In some embodiments, if a genomic marker for a bacterial strain is present, the microbiome is colonized with the bacterial strain. In some embodiments, if a genomic marker for a bacterial strain is absent, the microbiome is not colonized with the bacterial strain. In some embodiments, a genomic marker for a bacterial strain that is absent indicates that the subject should be administered one or more further doses of the bacterial composition.

In some embodiments, detection of a genomic marker of one bacterial strain is used as a proxy for the presence of each of the bacterial strains of the bacterial composition.

Provided herein are methods for assessing colonization of one or more bacterial strains of a bacterial composition in a microbiome of a subject comprising isolating nucleic acid from a sample of the microbiome of the subject; sequencing the isolated nucleic acid to obtain a plurality of nucleotide sequences of the isolated nucleic acid; and determining the presence of each bacterial strain of the bacterial composition by comparing the plurality of nucleotide sequences to a plurality of genomic markers for each bacterial strain of the bacterial composition; wherein if a genomic marker for a bacterial strain is present in the plurality of nucleotide sequences, the microbiome is colonized with the bacterial strain.

Also provided herein are methods for assessing colonization of one or more bacterial strains of a bacterial composition in a microbiome of a subject comprising isolating nucleic acid from a sample of the microbiome of the subject; amplifying one or more nucleotide sequence of the bacterial strains in the isolated nucleic acid; and determining the presence of each bacterial strain of the bacterial composition by amplifying a nucleotide sequence of a genomic marker for the bacterial strains in the isolated nucleic acid; wherein if a genomic marker for a bacterial strain is present in the plurality of nucleotide sequences, the microbiome is colonized with the bacterial strain.

In some embodiments, the one or more of the bacterial strains of the bacterial compositions colonize the microbiome of the gastrointestinal tract or parts thereof (e.g., the colon or the cecum) of the subject. Such colonization may also be referred to as grafting or engraftment. The methods described herein allow for the determination of the presence of each bacterial strain of the bacterial composition within the microbiome, which indicates whether the bacterial strain has colonized the microbiome.

In some embodiments, the methods described herein may be used as a companion diagnostic for use with a bacterial composition comprising a mixture of bacterial strains. For example, the described herein may be used for identifying subjects in need of one or more (e.g., 1, 2, 3, 4, 5 or more) additional doses of a bacterial composition. In some embodiments, if one or more of the bacterial strains of the bacterial composition is not present in the plurality of nucleotides sequences, the method further comprising administering one or more additional doses of the bacterial composition to the subject.

In some embodiments, the subject was previously administered one or more doses of the bacterial composition and the methods involve determining whether the subject is in need of one or more additional doses of a bacterial composition.

In some embodiments, the methods described herein include collecting a sample that comprises the microbiome from a subject that has previously been administered one or more doses of a bacterial composition. A sample may be any biological sample that may contain the bacterial strains from the bacterial composition. In some embodiments, a sample is a fecal sample, a urine sample, a blood sample, a serum sample, a plasma sample, a lymph sample, a swab sample, a sputum sample, an aspirate sample, a saliva sample, a lavage sample, a brushing sample, and a biopsy sample. In some embodiments, the sample is a fecal sample.

In some embodiments, the bacterial compositions described herein are administered to the subject such that the bacterial strains may engraft into the gastrointestinal tract of the subject. Accordingly, in some embodiments, collecting and analyzing a biological sample of the gastrointestinal tract of the subject may indicate whether one or more of the bacterial strains of the composition engrafted in the gastrointestinal tract. In some embodiments, the sample is a sample representative of the gastrointestinal tract, or region thereof (e.g., small intestine, colon) of the subject. In some embodiments, the microbiota of the sample is representative of the microbiota of the gastrointestinal tract, or region thereof (e.g., small intestine, colon) of the subject.

In some embodiments, the methods described herein include removal of microorganism and/or cells of the subject (e.g., host cells) from the sample collected from the subject. Microbes may include bacteria, yeast, protozoa, and viruses. Microbes may be removed by any method known in the art including, but not limited to, selective lysis, centrifugation, size-based exclusion, and specific binding and removal of microorganism or cells of the subject (e.g., host cells).

In some embodiments, the methods described herein include lysing cells in the sample prior to isolating nucleic acid from the sample. Methods of lysing cells will be evident to one ordinary skill in the art and may depend on the type of cells present in the sample or type of cells for which lysis is desired. Examples of for cell lysis, include but are not limited to, contacting the cells with anionic detergents, cationic detergents, non-ionic detergents, guanadinium chloride, urea, alcohols, ethers, chloroforms, sonication, freeze-thaw cycles, electroporation, French press, manual grinding, and extrusion.

In some embodiments, specific nucleic acids or types of nucleic acids are removed from lysed cells prior to DNA sequencing or selective amplification. In some embodiments, RNA is selectively removed from the sample. RNA may be removed from lysed cells by any method known in the art including, but not limited to, addition of RNAse (RNAse A, RNAse H, etc.), centrifugation, and precipitation. In some embodiments, DNA is selectively removed from the sample. DNA may be removed from lysed cells by any method known in the art including, but not limited to, addition of DNAse, centrifugation, and precipitation.

In some embodiments, sequencing of the isolated nucleic acid from the sample of the microbiome comprises DNA sequencing. Methods for DNA sequencing will be evident to one of ordinary skill in the art. In some embodiments, the DNA sequencing is performed using high throughput DNA sequencing. In some embodiments, the DNA sequencing is performed by sequencing by synthesis, for example using DNA that has been immobilized on a surface (e.g., a flow cell) and fluorescently labelled reversible nucleotide terminators. In some embodiments, the DNA sequencing is performed using the MiSeq, iSeq, MiniSeq, NextSeq, or HiSeq platform from Illumina®. In some embodiments, the DNA sequencing is performed by translocating the DNA through a nanopore and detecting the ion flow through the nanopore, referred to a "nanopore sequencing." In some embodiments, the DNA sequencing is performed using the SmidgION, Flongle, PromethION, GriodION×5, or MinION platform from Oxford Nanopore Technologies.

In some embodiments, one or more genomic markers of a bacterial strain are determined to be present in the sample if the genomic marker is detected in a plurality of nucleotide sequences sequenced from the sample. In some embodiments, a bacterial strain is determined to be present in the sample if one or more genomic markers associated with the bacterial strain is detected in a plurality of nucleotide sequences sequenced from the sample.

In some embodiments, the one or more genomic markers of a bacterial strain are determined to be present in the sample if the abundance of the genomic marker associated with the bacterial strain represents greater than a particular percentage of the plurality of nucleotide sequences sequenced from the sample. In some embodiments, the one or more genomic markers of a bacterial strain are determined to be present in the sample if the abundance of the genomic marker associated with the bacterial strain represents greater than 0.0001%, 0.0005%, 0.001%, 0.005%, 0.01%, 0.05%, 0.1% 0.5%, 1.0%, 1.5%, 2%, 2.5%, 3%, 3.5%, 4.0%, 4.5%, or 5% of the plurality of nucleotide sequences sequenced from the sample.

As used herein, the term "genomic marker" is used to refer to a sequence that is associated with a target bacterial strain, whereby detection of the genomic marker indicates presence of the target bacterial strain. In some embodiments, the genomic marker is unique to given genome (e.g., present in the genome of target bacterial strain but not present in the genome of other non-target bacterial strains or host genome). The target genomic marker is the genomic marker for a given genome (e.g., bacterial strain 16S rDNA).

In some embodiments, the genomic marker is about 50 nucleotides-about 900 nucleotides. In some embodiments, the target amplified piece of DNA is about 500 nucleotides-about 1000 nucleotides. In some embodiments, the target amplified piece of DNA is about 50 nucleotides, 100 nucleotides, 150 nucleotides, 200 nucleotides, 250 nucleotides, 300 nucleotides, 350 nucleotides, 400 nucleotides, 450 nucleotides, 500 nucleotides, 550 nucleotides, 600 nucleotides, 650 nucleotides, 700 nucleotides, 750 nucleotides, 800 nucleotides, 850 nucleotides, 900 nucleotides, 1000 nucleotides, 1050 nucleotides, 1100 nucleotides, 1150 nucleotides, or 1200 nucleotides.

In some embodiments, the presence of one or more genomic markers of a plurality of genomic markers of a bacterial strain indicates that the bacterial strain has colonized the microbiome. In some embodiments, the plurality of genomic markers comprises between 200 to 1000 nucleotide sequences for each bacterial strain of the bacterial composition. In some embodiments, each of the genomic markers is a nucleotide sequence that is generally not present in a healthy microbiome. In some embodiments, each of the genomic markers of a bacterial strain is a nucleotide sequence that is not present in the genome of other microorganisms, including other bacterial strains of the bacterial composition. Therefore, in some embodiments, the presence of a genomic marker of a bacterial strain uniquely identifies the presence of a specific bacterial strain. In some embodiments, each genomic marker of the plurality of genomic markers comprises between 25 and 75 nucleotides. In some embodiments, each genomic marker of the plurality of genomic markers comprises about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 72, 73, 74, or 75 nucleotides. In some embodiments, each genomic marker of the plurality of genomic markers comprises about 50 nucleotides.

In some embodiments, the colonization of one or more bacterial strains from the bacterial composition is assessed in the subject by selectively amplifying the nucleotide sequence of a genomic marker for one or more of the bacterial strains. As used herein, the term "selectively amplifying" refers to amplifying a nucleotide sequence of genome marker for at least one of the bacterial strains in isolated nucleic acid. In some embodiments, selective amplification involves providing one or more DNA primers (e.g., a pair of DNA primers) that hybridize (bind) to a region of the isolated nucleic acid that is associated with the target bacterial strain. In some embodiments, the pair of DNA primers are used to amplify a genomic marker from the one or more bacterial strains in the isolated nucleic acids. Selective amplification may be by any method known in the art including, but not limited to, quantitative polymerase chain reaction (qPCR), quantitative real time polymerase chain reaction (qRT-PCR), real time polymerase chain reaction (RT-PCR), and polymerase chain reaction (PCR).

In some embodiments, selectively amplifying one or more nucleotide sequences of the bacterial strains in the isolated nucleic acid involves performing quantitative polymerase chain reactions (qPCR). In some embodiments, the qPCR comprises a pair of DNA primers that specifically hybridize to a genomic marker for a bacterial strains of the bacterial composition, thereby amplifying the genomic marker or portion thereof. In some embodiments, the method further involves selecting a pair of primers (e.g., qPCR primers) for amplifying the nucleotide sequence of the genomic marker of bacterial strain.

In some embodiments, a qPCR reaction mixture contains all components necessary to perform a qPCR reaction. In some embodiments, the qPCR reaction mixture contains isolated DNA, a pair of forward and reverse primers, a DNA probe, an enzyme (e.g., polymerase), mixture of deoxyribonucleotide triphosphates (e.g., dCTP, dATP, dTTP, dGTP), one or more buffers, and water.

In some embodiments, the qPCR reaction mixture contains about 10% isolated DNA. It should be understood that the terms "isolated DNA" and "extracted DNA" are interchangeable herein. In some embodiments, the qPCR reaction mixture contains at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 49%, or 50% isolated DNA. In some embodiments, the qPCR reaction mixture contains 10% isolated DNA.

The qPCR reaction contains a forward primer and a reverse primer that hybridize (bind) to and selectively amplify a genomic marker for a target bacterial strain. The sequences of the forward and reverse primers may be designed to specifically recognize a genomic marker for a given bacterial strain (e.g., of the bacterial composition). The sequences of the forward and reverse primers may be designed to preferentially recognize a genomic marker for a given bacterial strain (e.g., of the bacterial composition) (e.g., better than the primer pair recognizes one or more other sequences). The sequence composition and length of the forward and reverse primers are designed to bind and selectively amplify a target genomic marker. In some embodiments, the qPCR reaction contains more than one pair of primers. In some embodiments, the qPCR reaction contains at least one pair, at least two pairs, at least three pairs, at least four pairs, at least five pairs, at least six pairs, at least seven pairs, or at least eight pairs of qPCR primers. In some embodiments, the qPCR reaction contains at least eight pairs of qPCR primers.

Without wishing to be bound by any particular theory, it is generally thought that longer qPCR primers (e.g., >25 nucleotides) may have greater binding specificity for a target genomic marker as compared to short qPCR primers (e.g., <25 nucleotides). However, longer qPCR primers (e.g., >25 nucleotides) may have lower amplification of the target genomic marker as compared to shorter qPCR primers due to formation of secondary structures.

In some embodiments, the forward primer is 25-45 nucleotides in length. In some embodiments, the forward primer is 10-35 nucleotides in length. In some embodiments, the forward primer is 15-40 nucleotides in length. In some embodiments, the forward primer is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the reverse primer is 25-45 nucleotides in length. In some embodiments, the reverse primer is 10-35 nucleotides in length. In some embodiments, the reverse primer is 15-40 nucleotides in length. In some embodiments, the reverse primer is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. The forward primer and the reverse primer need not be the same length. In some embodiments, the forward primer and the reverse primer are the same length.

In general, the primers of a primer pair may not be 100% complementary to a target genomic marker in order to hybridize and selectively amplify target genomic markers in the isolated nucleic acid. In some embodiments, the forward primer is 100% complementary to a region of the target genomic marker. In some embodiments, the reverse primer is 100% complementary to a region of the target genomic marker. In some embodiments, the forward primer is at least 75%, 76%, 77%, 78%, 79%, 80%, 81%, 82%, 83%, 84%, 85%, 86,%, 87%, 88%, 89%, 90%, 91%, 92%, 93%, 94%, 95%, 96%, 97%, 98%, 99%, 99.5%, or 99.9% complementary to a region of the target genomic marker. In some embodiments, the reverse primer is at least 75%, 76%, 77%, 78%, 79%, 80%, 81%, 82%, 83%, 84%, 85%, 86,%, 87%, 88%, 89%, 90%, 91%, 92%, 93%, 94%, 95%, 96%, 97%, 98%, 99%, 99.5%, or 99.9% complementary to a region of the target genomic marker. In some embodiments, the forward primer and the reverse primer are sufficiently complementary to a region of the target genomic marker such that the genomic marker is amplified in the qPCR reaction.

In some embodiments, the qPCR reaction mixture contains about 3% primer DNA. Primer DNA may include forward primers and/or reverse primers. In some embodiments, the qPCR reaction mixture contains at least 2%, 3%, 4%, 5%, 6%, 7%, 8%, 9%, 10%, 11%, 12%, 13%, 14%, 15%, 16%, 17%, 18%, 19%, or 20% primer DNA. In some embodiments, the qPCR reaction mixture contains 3% primer DNA.

In some embodiments, the qPCR reaction mixture contains a DNA probe. A DNA probe is single-stranded DNA molecule that is complementary to a sequence on the target genomic marker. Binding of the DNA probe to the amplified genomic marker in a qPCR reaction produces a measurable signal that can be used to quantify the bacterial genomic marker present in the qPCR reaction. In some embodiments, the DNA probe contains a fluorescent molecule (e.g., fluorophore) and the measurable signal is fluorescence. In some embodiments, the qPCR reaction mixture contains about 2% DNA probe. In some embodiments the qPCR reaction mixture contains at least 1%, 2%, 3%, 4%, 5%, 6%, 7%, 8%, 9%, 10%, 11%, 12%, 13%, 14%, 15%, 16%, 17%, 18%, 19%, or 20% DNA probe. In some embodiments, the qPCR reaction mixture contains 2% DNA probe.

In some embodiments, the DNA probe is 100% complementary to a region of the target genomic marker. In some embodiments, the DNA probe is at least 75%, 76%, 77%, 78%, 79%, 80%, 81%, 82%, 83%, 84%, 85%, 86,%, 87%, 88%, 89%, 90%, 91%, 92%, 93%, 94%, 95%, 96%, 97%, 98%, 99%, 99.5%, or 99.9% complementary to a region of the target genomic marker.

In some embodiments, the DNA probe contains a fluorophore and a quencher, wherein the fluorophore produces a fluorescent signal that can be detected at a particular wavelength of light and the quencher diminishes the fluorescent signal. In some embodiments, the quencher diminishes the fluorescent signal by absorbing the energy produced by the fluorophore (e.g., fluorescence) and converting that energy to another form (e.g., heat). In some embodiments, the DNA probe contains more than one quencher. The presence of more than one quencher in a DNA probe may decrease the number of false positives in a qPCR reaction by decreasing the likelihood that a fluorescent signal will be detected on a non-target amplified DNA.

In some embodiments, the DNA probe contains one fluorophore and one quencher. In some embodiments, the DNA probe contains one fluorophore and two quenchers. In some embodiments, the DNA probe contains one fluorophore and two, three, four, five, six, seven, eight, nine, or ten quenchers.

In some embodiments, the fluorophore is present at the 5' end of the DNA probe and one quencher is present at the 3' end of the DNA probe. In some embodiments, the fluorophore is present at the 3' end of the DNA probe and one quencher is present at the 5' end of the DNA probe. In some embodiments, the fluorophore is present at the 5' end of the DNA probe, one quencher is present at the 3' end of the DNA probe, and at least one quencher is internal in the DNA probe (e.g., not at the 5' end or 3' end). In some embodiments, the fluorophore is present at the 3' end of the DNA probe, one quencher is present at the 5' end of the DNA probe, and at least one quencher is internal in the DNA probe (e.g., not at the 5' end or 3' end).

The fluorophore may be any fluorophore known in the art. Selection of the fluorophore may be based, for example, on the excitation and emission wavelengths of the fluorophore, as well as the chemical modifications required to incorporate the fluorophore into the DNA probe. Non-limiting examples of fluorophores that may be present in DNA probes of the present disclosure include: fluorescein (FAM), fluorescein dT, cyanine 3 (Cy3™), TAMRA™, 6-carboxy-4',5'-dichloro-2',7'-dimethoxyfluorescein, JOE, cyanine 5 (Cy5™), MAX, tetrachlorofluorescein (TET™), cyanine 5.5 (Cy5.5™), carboxy-X-rhodamine (ROX), TYE™ 563, Yakima Yellow®, hexachlorofluorescein (HEX), TEX 615, TYE™ 665, TYE 705, Alexa Fluor® 488, Alexa Fluor® 532, Alexa Fluor® 546, Alexa Fluor® 594, Alexa Fluor® 647, Alexa Fluor® 660, Alexa Fluor® 750, IRDye® 700, IRDye® 800, IRDye® 800 CW, ATTO™ 488, ATTO™ 532, ATTO™ 550, ATTO™ 565, ATTO™ Rho101, ATTO™ 590, ATTO™ 633, ATTO™ 674N, Rhodamine Green™-X, Rhodamine Red™-X, WellRED D4, WellRED D3, WellRED D2, Texas Red®-X, Lightcycler® 640, and Dy750. In some embodiments, the fluorophore is FAM.

The quencher(s) may be any quencher(s) known in the art. Selection of one or more quenchers may be based, for example, on the excitation and emission wavelengths of the fluorophore that the quencher is quenching, as well as the chemical modifications required to incorporate the quencher into the DNA probe. In some embodiments, when more than one quencher is present in the DNA probe, the quenchers are different. In some embodiments, when more than one quencher is present in the DNA probe, the quenchers are the same. Non-limiting examples of quenchers that may be present in DNA probes of the present disclosure include: ZEN™, TAO™, Iowa Black™, Iowa Black FQ™ (IABKFQ), Eclipse Dark Quencher, IQ4, Black Hole Quencher 1, Black Hole Quencher 2, and Black Hole Quencher 3. In some embodiments, the 3' quencher is Iowa Black FQ™. In some embodiments, the internal quencher is ZEN™. In some embodiments, the 3' quencher is Iowa Black FQ™ and the internal quencher is ZEN™.

In general, a qPCR reactions involve cycles that may comprise a denaturing step, an annealing step that allows the forward primer and reverse primer to hybridize (bind) to a region of the target genomic marker, followed by an amplification/extension step that allows the enzyme (e.g., polymerase), to synthesize a complementary strand of DNA. In some embodiments, the annealing step and the amplification/extension step are performed as a single step (e.g., at one temperature). The length and temperature of the annealing step is determined, for example, by the length and sequence composition of the primer pair and the target genomic marker. In some embodiments, primer sequences greater than 60 base pairs and/or primer sequences with a high concentration of adenine-thymine base pairs (e.g., >50%) may require a longer annealing step and/or a higher annealing temperature as compared to primer sequences less than 60 base pairs and/or primer sequences with a low concentration of adenine-thymine base pairs (e.g., <50%).

In some embodiments, the qPCR cycle(s) include a denaturing step. As will be evident to one of ordinary skill in the art, a denaturing step involves increasing the temperature of the qPCR reaction to a sufficient temperature such that the DNA is melted (e.g., separate double stranded DNA to single stranded DNA). In some embodiments, the temperature of the denaturing step is between 75° C.-115° C. In some embodiments, the denaturing step temperature is about 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., or 115° C. In some embodiments, the temperature of the denaturing step is about 95° C.

In some embodiments, the length of time of the denaturing step is between 0.5 seconds and 9.0 seconds. In some embodiments, the length of time of the denaturing step is about 0.5 seconds, 1.0 seconds, 1.5 seconds, 2.0 seconds, 2.5 seconds, 3.0 seconds, 3.5 seconds, 4.0 seconds, 4.5 seconds, 5.0 seconds, 5.5 seconds, 6.0 seconds, 6.5 seconds, 7.0 seconds, 7.5 seconds, 8.0 seconds, 8.5 seconds, or 9.0 seconds. In some embodiments, the denaturing step length is 3 seconds.

The length and temperature of the amplification/extension step of a qPCR reaction cycle may be depend, for example, on the length of the target genomic marker and/or the activity of the enzyme.

In some embodiments, the amplification step is performed at a temperature between 45° C.-75° C. In some embodiments, the amplification step is performed at a temperature of about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., or 75° C. In some embodiments, the amplification step is performed at about 60° C.

In some embodiments, the length of time of the amplification step is between 15 seconds and 1 minute. In some embodiments, the length of time of the amplification step is about 15 seconds, 16 seconds, 17 seconds, 18 seconds, 19 seconds, 20 seconds, 21 seconds, 22 seconds, 23 seconds, 24 seconds, 25 seconds, 26 seconds, 27 seconds, 28 seconds, 29 seconds, 30 seconds, 31 seconds, 32 seconds, 33 seconds, 34 seconds, 35 seconds, 36 seconds, 37 seconds, 38 seconds, 39 seconds, 40 seconds, 41 seconds, 42 seconds, 43 seconds, 44 seconds, or 45 seconds. In some embodiments, the length of time of the amplification step is about 30 seconds.

The number of cycles (e.g., denaturing, annealing, amplifying/extension) may vary based, for example, on the detection of a target amplified piece of DNA (e.g., by fluorescence of the DNA probe). In some embodiments, the number of cycles is selected for robust detection of positive sample. In some embodiments, the number of cycles is selected to minimize the number of false positives.

In some embodiments, the qPCR reaction comprises 20 cycles, 21 cycles, 22 cycles, 23 cycles, 24 cycles, 25 cycles, 26 cycles, 27 cycles, 28 cycles, 29 cycles, 30 cycles, 31 cycles, 32 cycles, 33 cycles, 34 cycles, 35 cycles, 36 cycles, 37 cycles, 38 cycles, 39 cycles, or 40 cycles, 41 cycles, 42 cycles, 43 cycles, 44 cycles, 45 cycles, 46 cycles, 47 cycles, 48 cycles, 49 cycles, or 50 cycles. In some embodiments, the qPCR reaction comprises 40 cycles An amplified piece of DNA is the DNA that is produced during a qPCR reaction after the sets of primers bind target genomic markers and are extended by enzyme (e.g., polymerase). The number of cycles in the qPCR reaction lead to amplification of the DNA.

In some embodiments, the amplified nucleotide sequence of the genomic marker is between about 50 nucleotides-about 1200 nucleotides. In some embodiments, the amplified nucleotide sequence of the genomic marker is about 50 nucleotides-about 900 nucleotides. In some embodiments, the target amplified piece of DNA is about 500 nucleotides-about 1000 nucleotides. In some embodiments, the amplified nucleotide sequence of the genomic marker is about 50 nucleotides, 100 nucleotides, 150 nucleotides, 200 nucleotides, 250 nucleotides, 300 nucleotides, 350 nucleotides, 400 nucleotides, 450 nucleotides, 500 nucleotides, 550 nucleotides, 600 nucleotides, 650 nucleotides, 700 nucleotides, 750 nucleotides, 800 nucleotides, 850 nucleotides, 900 nucleotides, 1000 nucleotides, 1050 nucleotides, 1100 nucleotides, 1150 nucleotides, or 1200 nucleotides. In some embodiments, the genomic markers are about 150 nucleotides long. In some embodiments, the genomic markers are about 100 nucleotides long. In some embodiments, the genomic markers are about 200 nucleotides long. In some embodiments, the genomic markers are about 100, 105, 110, 115, 120, 125, 130, 135, 140, 145, 150, 155, 160, 165, 170, 175, 180, 185, 190, 195, or 200 nucleotides long.

In some embodiments, determining whether a target genomic marker is present is assessed at a particular time point during the qPCR reaction. In some embodiments, determining whether a target genomic marker is present is assessed at a particular cycle number during the qPCR reaction. In some embodiments, determining whether a target genomic marker is present is assessed at a particular cycle number during the qPCR reaction, for example by analyzing the amplification plot. In some embodiments, determining whether a target genomic marker is present is assessed at cycle 25, 26, 27, 28, 29, 30, 31, 32, 33, 34, or 35. In some embodiments, determining whether a target genomic marker is present is assessed at cycle 25. In some embodiments, determining whether a target genomic marker is present is assessed at cycle 30. In some embodiments, determining whether a target genomic marker is present is assessed at cycle 35.

In some embodiments, a target genomic marker is determined to be present in a sample if a detectable amount of an amplified product corresponding to the genomic marker for the strain is detected at a particular time point during the qPCR reaction. In some embodiments, a target genomic marker is determined to be present in a sample if a fluorescent signal corresponding to the amount of an amplified product is detected at a particular time point during the qPCR reaction. In some embodiments, a target genomic marker is determined to be present in a sample if the amplification peak of the qPCR reaction crosses a threshold particular time point during the qPCR reaction. In some embodiments, the threshold cycle is cycle 25 and a target genomic marker is determined to be present in a sample if the amplification peak of the qPCR reaction crosses a threshold at cycle 25. In some embodiments, the threshold cycle is cycle 30 and a target genomic marker is determined to be present in a sample if the amplification peak of the qPCR reaction crosses a threshold at cycle 35.

As will be evident to one of ordinary skill in the art, selection of a threshold cycle at which to determine whether a genomic marker has been amplified and therefore indicating that the corresponding bacterial strain is present in the sample, depends on balancing one or more factors. For example, use of a higher cycle number for the threshold cycle may result a higher rate of false positives as increased cycles of qPCR increase the likelihood of non-specific (off-target) amplification. Alternatively, use of a higher cycle number for the threshold cycle may result aa higher rate of false negatives as fewer cycles of qPCR may not allow sufficient amplification of genomic markers that are present albeit at low abundance.

In some embodiments, the genomic marker sequence is a protein coding sequence. In some embodiments, the genomic marker sequence is a non-protein coding sequence.

In some embodiments, the target bacterial strain is *Clostridium bolteae*. Any nucleotide sequence that is capable of identifying a nucleotide sequence as belonging to *Clostridium bolteae* may be used in the methods described herein. In some embodiments, the genomic marker is a *Clostridium bolteae* 16S rDNA sequence. In some embodiments, the genomic marker is unique to *Clostridium bolteae*. In some embodiments, the genomic marker identifying *Clostridium bolteae* is a protein coding sequence, or portion thereof. In some embodiments, the genomic marker identifying *Clostridium bolteae* is a non-coding sequence. In some embodiments, the genomic marker identifying *Clostridium bolteae* is a nucleotide sequence encoding a transmembrane protein, or portion thereof. In some embodiments, the genomic marker identifying *Clostridium bolteae* is a nucleotide sequence encoding glutaconyl-CoA decarboxylase subunit beta (gcdB), or portion thereof.

In some embodiments, the presence of *Clostridium bolteae* is determined by amplifying a nucleotide sequence of a genomic marker for *Clostridium bolteae*. In some embodiments, one or more genomic marker for *Clostridium bolteae* is amplified by qPCR. In some embodiments, the genomic marker for determining the presence of *Clostridium bolteae* gcdB, or a portion thereof. In some embodiments, the genomic marker for determining the presence of *Clostridium bolteae* is amplified using a forward primer having a nucleotide sequence provided by SEQ ID NO: 9. In some embodiments, the genomic marker for determining the presence of *Clostridium bolteae* is amplified using a reverse primer having a nucleotide sequence provided by SEQ ID NO: 10. In some embodiments, the genomic marker for determining the presence of *Clostridium bolteae* is amplified using a forward primer having a nucleotide sequence provided by SEQ ID NO: 9 and a reverse primer having a nucleotide sequence provided by SEQ ID NO: 10.

In some embodiments, the genomic marker for determining the presence of *Clostridium bolteae* is amplified using a forward primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 9. In some embodiments, the genomic marker for determining the presence of *Clostridium bolteae* is amplified using a reverse primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 10. In some embodiments, the genomic marker for determining the presence of *Clostridium bolteae* is amplified using a forward primer having a nucleotide sequence provided by SEQ ID NO: 9 and a reverse primer having a nucleotide sequence provided by SEQ ID NO: 10.

In some embodiments, amplification of the *Clostridium bolteae* genomic marker GCDB, or portion thereof, is detected by a DNA probe, e.g., a DNA probe that is included in the qPCR reaction. In some embodiments, the DNA probe has the sequence as provided by SEQ ID NO: 11. In some embodiments, the DNA probe has a sequence that is at least 85%, 86%, 87%, 88%, 89%, 90%, 91%, 92%, 93%, 94%, 95%, 96%, 97%, 98%, or 99% identical to the sequence provided by SEQ ID NO: 11.

In some embodiments, the target bacterial strain is *Anaerotruncus colihominis*. Any nucleotide sequence that is capable of identifying a nucleotide sequence as belonging to *Anaerotruncus colihominis* may be used in the methods described herein. In some embodiments, the genomic marker is a *Anaerotruncus colihominis* 16S rDNA sequence. In some embodiments, the genomic marker is unique to *Anaerotruncus colihominis*. In some embodiments, the genomic marker identifying *Anaerotruncus colihominis* is a protein coding sequence, or portion thereof. In some embodiments, the genomic marker identifying *Anaerotruncus colihominis* is a non-coding sequence.

In some embodiments, the presence of *Anaerotruncus colihominis* is determined by amplifying a nucleotide sequence of a genomic marker for *Anaerotruncus colihominis*. In some embodiments, one or more genomic marker for *Anaerotruncus colihominis* is amplified by qPCR. In some embodiments, the genomic marker for determining the presence *Anaerotruncus colihominis* is amplified using a forward primer having a nucleotide sequence provided by SEQ ID NO: 12. In some embodiments, the genomic marker for determining the presence of *Anaerotruncus colihominis* is amplified using a reverse primer having a nucleotide sequence provided by SEQ ID NO: 13. In some embodiments, the genomic marker for determining the presence of *Anaerotruncus colihominis* is amplified using a forward primer having a nucleotide sequence provided by SEQ ID NO: 12 and a reverse primer having a nucleotide sequence provided by SEQ ID NO: 13.

In some embodiments, the genomic marker for determining the presence of *Anaerotruncus colihominis* is amplified using a forward primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 12. In some embodiments, the genomic marker for determining the presence of *Anaerotruncus colihominis* is amplified using a reverse primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 13. In some embodiments, the genomic marker for determining the presence of *Anaerotruncus colihominis* is amplified using a forward primer having a nucleotide sequence provided by SEQ ID NO: 12 and a reverse primer having a nucleotide sequence provided by SEQ ID NO: 13.

In some embodiments, amplification of the *Anaerotruncus colihominis* genomic marker is detected by a DNA probe, e.g., a DNA probe that is included in the qPCR reaction. In some embodiments, the DNA probe has the sequence as provided by SEQ ID NO: 14. In some embodiments, the DNA probe has a sequence that is at least 85%, 86%, 87%, 88%, 89%, 90%, 91%, 92%, 93%, 94%, 95%, 96%, 97%, 98%, or 99% identical to the sequence provided by SEQ ID NO: 14.

In some embodiments, the target bacterial strain is *Eubacterium fissicatena*. Any nucleotide sequence that is capable of identifying a nucleotide sequence as belonging to *Eubacterium fissicatena* may be used in the methods described herein. In some embodiments, the genomic marker is a *Eubacterium fissicatena* 16S rDNA sequence. In some embodiments, the genomic marker is unique to *Eubacterium fissicatena*. In some embodiments, the genomic marker identifying *Eubacterium fissicatena* is a protein coding sequence, or portion thereof. In some embodiments, the genomic marker identifying *Eubacterium fissicatena* is a non-coding sequence. In some embodiments, the genomic marker identifying *Eubacterium fissicatena* is a glycosyltransferase gene, or a portion thereof. In some embodiments, the genomic marker identifying *Eubacterium fissicatena* espJ, or a portion thereof.

In some embodiments, the presence of *Eubacterium fissicatena* is determined by amplifying a nucleotide sequence of a genomic marker for *Eubacterium fissicatena*. In some embodiments, one or more genomic marker for *Eubacterium fissicatena* is amplified by qPCR. In some embodiments, the genomic marker for determining the presence *Eubacterium fissicatena* is amplified using a forward primer having a nucleotide sequence provided by SEQ ID NO: 15. In some embodiments, the genomic marker for determining the presence of *Eubacterium fissicatena* is amplified using a reverse primer having a nucleotide sequence provided by SEQ ID NO: 16. In some embodiments, the genomic marker for determining the presence of *Eubacterium fissicatena* is amplified using a forward primer having a nucleotide sequence provided by SEQ ID NO: 15 and a reverse primer having a nucleotide sequence provided by SEQ ID NO: 16.

In some embodiments, the genomic marker for determining the presence of *Eubacterium fissicatena* is amplified using a forward primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 15. In some embodiments, the genomic marker for determining the presence of *Eubacterium fissicatena* is amplified using a reverse primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 16. In some embodiments, the genomic marker for determining the presence of *Eubacterium fissicatena* is amplified using a forward primer having a nucleotide sequence provided by SEQ ID NO: 15 and a reverse primer having a nucleotide sequence provided by SEQ ID NO: 16.

In some embodiments, amplification of the *Eubacterium fissicatena* genomic marker is detected by a DNA probe, e.g., a DNA probe that is included in the qPCR reaction. In some embodiments, the DNA probe has the sequence as provided by SEQ ID NO: 17. In some embodiments, the DNA probe has a sequence that is at least 85%, 86%, 87%, 88%, 89%, 90%, 91%, 92%, 93%, 94%, 95%, 96%, 97%, 98%, or 99% identical to the sequence provided by SEQ ID NO: 17.

In some embodiments, the target bacterial strain is *Clostridium symbiosum*. Any nucleotide sequence that is capable of identifying a nucleotide sequence as belonging to *Clostridium symbiosum* may be used in the methods described herein. In some embodiments, the genomic marker is a *Clostridium symbiosum* 16S rDNA sequence. In some embodiments, the genomic marker is unique to *Clostridium symbiosum*. In some embodiments, the genomic marker identifying *Clostridium symbiosum* is a protein coding sequence, or portion thereof. In some embodiments, the genomic marker identifying *Clostridium symbiosum* is a non-coding sequence. In some embodiments, the genomic marker identifying *Clostridium symbiosum* rimCD, or a portion thereof.

In some embodiments, the presence of *Clostridium symbiosum* is determined by amplifying a nucleotide sequence of a genomic marker for *Clostridium symbiosum*. In some embodiments, one or more genomic marker for *Clostridium symbiosum* is amplified by qPCR. In some embodiments, the genomic marker for determining the presence *Clostridium symbiosum* is amplified using a forward primer having a nucleotide sequence provided by SEQ ID NO: 18. In some embodiments, the genomic marker for determining the presence of *Clostridium symbiosum* is amplified using a reverse primer having a nucleotide sequence provided by SEQ ID NO: 19. In some embodiments, the genomic marker for determining the presence of *Clostridium symbiosum* is amplified using a forward primer having a nucleotide sequence provided by SEQ ID NO: 18 and a reverse primer having a nucleotide sequence provided by SEQ ID NO: 19.

In some embodiments, the genomic marker for determining the presence of *Clostridium symbiosum* is amplified using a forward primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 18. In some embodiments, the genomic marker for determining the presence of *Clostridium symbiosum* is amplified using a reverse primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 19. In some embodiments, the genomic marker for determining the presence of *Clostridium symbiosum* is amplified using a forward primer having a nucleotide sequence provided by SEQ ID NO: 18 and a reverse primer having a nucleotide sequence provided by SEQ ID NO: 19.

In some embodiments, amplification of the *Clostridium symbiosum* genomic marker is detected by a DNA probe, e.g., a DNA probe that is included in the qPCR reaction. In some embodiments, the DNA probe has the sequence as provided by SEQ ID NO: 20. In some embodiments, the DNA probe has a sequence that is at least 85%, 86%, 87%, 88%, 89%, 90%, 91%, 92%, 93%, 94%, 95%, 96%, 97%, 98%, or 99% identical to the sequence provided by SEQ ID NO: 20.

In some embodiments, the target bacterial strain is *Blautia producta*. Any nucleotide sequence that is capable of identifying a nucleotide sequence as belonging to *Blautia producta* may be used in the methods described herein. In some embodiments, the genomic marker is a *Blautia producta* 16S rDNA sequence. In some embodiments, the genomic marker is unique to *Blautia producta*. In some embodiments, the genomic marker identifying *Blautia producta* is a protein coding sequence, or portion thereof. In some embodiments, the genomic marker identifying *Blautia producta* is a non-coding sequence.

In some embodiments, the presence of *Blautia producta* is determined by amplifying a nucleotide sequence of a genomic marker for *Blautia producta* In some embodiments, one or more genomic marker for *Blautia producta* is amplified by qPCR. In some embodiments, the genomic marker for determining the presence *Blautia producta* is amplified using a forward primer having a nucleotide sequence provided by SEQ ID NO: 21. In some embodiments, the genomic marker for determining the presence of *Blautia producta* is amplified using a reverse primer having a nucleotide sequence provided by SEQ ID NO: 22. In some embodiments, the genomic marker for determining the presence of *Blautia producta* is amplified using a forward primer having a nucleotide sequence provided by SEQ ID NO: 21 and a reverse primer having a nucleotide sequence provided by SEQ ID NO: 22.

In some embodiments, the genomic marker for determining the presence of *Blautia producta* is amplified using a forward primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 21. In some embodiments, the genomic marker for determining the presence of *Blautia producta* is amplified using a reverse primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 22. In some embodiments, the genomic marker for determining the presence of *Blautia producta* is amplified using a forward primer having a nucleotide sequence provided by SEQ ID NO: 21 and a reverse primer having a nucleotide sequence provided by SEQ ID NO: 22.

In some embodiments, amplification of the *Blautia producta* genomic marker is detected by a DNA probe, e.g., a DNA probe that is included in the qPCR reaction. In some embodiments, the DNA probe has the sequence as provided by SEQ ID NO: 23. In some embodiments, the DNA probe has a sequence that is at least 85%, 86%, 87%, 88%, 89%, 90%, 91%, 92%, 93%, 94%, 95%, 96%, 97%, 98%, or 99% identical to the sequence provided by SEQ ID NO: 23.

In some embodiments, the target bacterial strain is *Dorea longicatena*. Any nucleotide sequence that is capable of identifying a nucleotide sequence as belonging to *Dorea longicatena* may be used in the methods described herein. In some embodiments, the genomic marker is a *Dorea longicatena* 16S rDNA sequence. In some embodiments, the genomic marker is unique to *Dorea longicatena*. In some embodiments, the genomic marker identifying *Dorea longicatena* is a protein coding sequence, or portion thereof. In some embodiments, the genomic marker identifying *Dorea longicatena* is a non-coding sequence.

In some embodiments, the presence of *Dorea longicatena* is determined by amplifying a nucleotide sequence of a genomic marker for *Dorea longicatena* In some embodiments, one or more genomic marker for *Dorea longicatena* is amplified by qPCR. In some embodiments, the genomic marker for determining the presence *Dorea longicatena* is amplified using a forward primer having a nucleotide sequence provided by SEQ ID NO: 24. In some embodiments, the genomic marker for determining the presence of *Dorea longicatena* is amplified using a reverse primer having a nucleotide sequence provided by SEQ ID NO: 25.

In some embodiments, the genomic marker for determining the presence of *Dorea longicatena* is amplified using a forward primer having a nucleotide sequence provided by SEQ ID NO: 24 and a reverse primer having a nucleotide sequence provided by SEQ ID NO: 25.

In some embodiments, the genomic marker for determining the presence of *Dorea longicatena* is amplified using a forward primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 24. In some embodiments, the genomic marker for determining the presence of *Dorea longicatena* is amplified using a reverse primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 25. In some embodiments, the genomic marker for determining the presence of *Dorea longicatena* is amplified using a forward primer having a nucleotide sequence provided by SEQ ID NO: 24 and a reverse primer having a nucleotide sequence provided by SEQ ID NO: 25.

In some embodiments, amplification of the *Dorea longicatena* genomic marker is detected by a DNA probe, e.g., a DNA probe that is included in the qPCR reaction. In some embodiments, the DNA probe has the sequence as provided by SEQ ID NO: 26. In some embodiments, the DNA probe has a sequence that is at least 85%, 86%, 87%, 88%, 89%, 90%, 91%, 92%, 93%, 94%, 95%, 96%, 97%, 98%, or 99% identical to the sequence provided by SEQ ID NO: 26.

In some embodiments, the target bacterial strain is *Clostridium innocuum*. Any nucleotide sequence that is capable of identifying a nucleotide sequence as belonging to *Clostridium innocuum* may be used in the methods described herein. In some embodiments, the genomic marker is a *Clostridium innocuum* 16S rDNA sequence. In some embodiments, the genomic marker is unique to *Clostridium innocuum*. In some embodiments, the genomic marker identifying *Clostridium innocuum* is a protein coding sequence, or portion thereof. In some embodiments, the genomic marker identifying *Clostridium innocuum* is a non-coding sequence.

In some embodiments, the presence of *Clostridium innocuum* is determined by amplifying a nucleotide sequence of a genomic marker for *Clostridium innocuum* In some embodiments, one or more genomic marker for *Clostridium innocuum* is amplified by qPCR. In some embodiments, the genomic marker for determining the presence of *Clostridium innocuum* is amplified using a forward primer having a nucleotide sequence provided by SEQ ID NO: 27. In some embodiments, the genomic marker for determining the presence of *Clostridium innocuum* is amplified using a reverse primer having a nucleotide sequence provided by SEQ ID NO: 28. In some embodiments, the genomic marker for determining the presence of *Clostridium innocuum* is amplified using a forward primer having a nucleotide sequence provided by SEQ ID NO: 27 and a reverse primer having a nucleotide sequence provided by SEQ ID NO: 28.

In some embodiments, the genomic marker for determining the presence of *Clostridium innocuum* is amplified using a forward primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 27. In some embodiments, the genomic marker for determining the presence of *Clostridium innocuum* is amplified using a reverse primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 28. In some embodiments, the genomic marker for determining the presence of *Clostridium innocuum* is amplified using a forward primer having a nucleotide sequence provided by SEQ ID NO: 27 and a reverse primer having a nucleotide sequence provided by SEQ ID NO: 28.

In some embodiments, amplification of the *Clostridium innocuum* genomic marker is detected by a DNA probe, e.g., a DNA probe that is included in the qPCR reaction. In some embodiments, the DNA probe has the sequence as provided by SEQ ID NO: 29. In some embodiments, the DNA probe has a sequence that is at least 85%, 86%, 87%, 88%, 89%, 90%, 91%, 92%, 93%, 94%, 95%, 96%, 97%, 98%, or 99% identical to the sequence provided by SEQ ID NO: 29.

In some embodiments, the target bacterial strain is *Flavonifractor plautii*. Any nucleotide sequence that is capable of identifying a nucleotide sequence as belonging to *Flavonifractor plautii* may be used in the methods described herein. In some embodiments, the genomic marker is a *Flavonifractor plautii* 16S rDNA sequence. In some embodiments, the genomic marker is unique to *Flavonifractor plautii*. In some embodiments, the genomic marker identifying *Flavonifractor plautii* is a protein coding sequence, or portion thereof. In some embodiments, the genomic marker identifying *Flavonifractor plautii* is a non-coding sequence.

In some embodiments, the presence of *Flavonifractor plautii* is determined by amplifying a nucleotide sequence of a genomic marker for *Flavonifractor plautii* In some embodiments, one or more genomic marker for *Flavonifractor plautii* is amplified by qPCR. In some embodiments, the genomic marker for determining the presence of *Flavonifractor plautii* is amplified using a forward primer having a nucleotide sequence provided by SEQ ID NO: 30. In some embodiments, the genomic marker for determining the presence of *Flavonifractor plautii* is amplified using a reverse primer having a nucleotide sequence provided by SEQ ID NO: 31. In some embodiments, the genomic marker for determining the presence of *Flavonifractor plautii* is amplified using a forward primer having a nucleotide sequence provided by SEQ ID NO: 30 and a reverse primer having a nucleotide sequence provided by SEQ ID NO: 31.

In some embodiments, the genomic marker for determining the presence of *Flavonifractor plautii* is amplified using a forward primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 30. In some embodiments, the genomic marker for determining the presence of *Flavonifractor plautii* is amplified using a reverse primer having a nucleotide sequence that is at least 85%, 86%, 87%, 88%, 89%, 90%, 91%, 92%, 93%, 94%, 95%, 96%, 97%, 98%, or 99% identical to the sequence provided by SEQ ID NO: 31. In some embodiments, the genomic marker for determining the presence of *Flavonifractor plautii* is amplified using a forward primer having a nucleotide sequence provided by SEQ ID NO: 30 and a reverse primer having a nucleotide sequence provided by SEQ ID NO: 31.

In some embodiments, amplification of the *Flavonifractor plautii* genomic marker is detected by a DNA probe, e.g., a DNA probe that is included in the qPCR reaction. In some embodiments, the DNA probe has the sequence as provided by SEQ ID NO: 32. In some embodiments, the DNA probe has a sequence that is at least 85%, 86%, 87%, 88%, 89%, 90%, 91%, 92%, 93%, 94%, 95%, 96%, 97%, 98%, or 99% identical to the sequence provided by SEQ ID NO: 32.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

```
Strain 1 16S ribosomal RNA Clostridium bolteae
                                                        SEQ ID NO: 1
ATGAGAGTTTGATCCTGGCTCAGGATGAACGCTGGCGGCGTGCCTAACACATGCAAGTCGAACGAAGC

AATTAAAATGAAGTTTTCGGATGGATTTTTGATTGACTGAGTGGCGGACGGGTGAGTAACGCGTGGAT

AACCTGCCTCACACTGGGGGATAACAGTTAGAAATGACTGCTAATACCGCATAAGCGCACAGTACCGC

ATGGTACGGTGTGAAAAACTCCGGTGGTGTGAGATGGATCCGCGTCTGATTAGCCAGTTGGCGGGGTA

ACGGCCCACCAAAGCGACGATCAGTAGCCGACCTGAGAGGGTGACCGGCCACATTGGGACTGAGACAC

GGCCCAAACTCCTACGGGAGGCAGCAGTGGGGAATATTGCACAATGGGCGAAAGCCTGATGCAGCGAC

GCCGCGTGAGTGAAGAAGTATTTCGGTATGTAAAGCTCTATCAGCAGGGAAGAAAATGACGGTACCTG

ACTAAGAAGCCCCGGCTAACTACGTGCCAGCAGCCGCGGTAATACGTAGGGGGCAAGCGTTATCCGGA

TTTACTGGGTGTAAAGGGAGCGTAGACGGCGAAGCAAGTCTGAAGTGAAACCCAGGGCTCAACCCTG
```

```
GGACTGCTTTGGAAACTGTTTTGCTAGAGTGTCGGAGAGGTAAGTGGAATTCCTAGTGTAGCGGTGAA
ATGCGTAGATATTAGGAGGAACACCAGTGGCGAAGGCGGCTTACTGGACGATAACTGACGTTGAGGCT
CGAAAGCGTGGGGAGCAAACAGGATTAGATACCCTGGTAGTCCACGCCGTAAACGATGAATGCTAGGT
GTTGGGGGGCAAAGCCCTTCGGTGCCGTCGCAAACGCAGTAAGCATTCCACCTGGGGAGTACGTTCGC
AAGAATGAAACTCAAAGGAATTGACGGGGACCCGCACAAGCGGTGGAGCATGTGGTTTAATTCGAAGC
AACGCGAAGAACCTTACCAAGTCTTGACATCCTCTTGACCGGCGTGTAACGGCGCCTTCCCTTCGGGG
CAAGAGAGACAGGTGGTGCATGGTTGTCGTCAGCTCGTGTCGTGAGATGTTGGGTTAAGTCCCGCAAC
GAGCGCAACCCTTATCCTTAGTAGCCAGCAGGTAAAGCTGGGCACTCTAGGGAGACTGCCAGGGATAA
CCTGGAGGAAGGTGGGGATGACGTCAAATCATCATGCCCCTTATGATTTGGGCTACACACGTGCTACA
ATGGCGTAAACAAAGGGAAGCAAGACAGTGATGTGGAGCAAATCCCAAAAATAACGTCCCAGTTCGGA
CTGTAGTCTGCAACCCGACTACACGAAGCTGGAATCGCTAGTAATCGCGAATCAGAATGTCGCGGTGA
ATACGTTCCCGGGTCTTGTACACACCGCCCGTCACACCATGGGAGTCAGCAACGCCCGAAGTCAGTGA
CCCAACTCGCAAGAGAGGGAGCTGCCGAAGGCGGGGCAGGTAACTGGGGTGAAGTCGTAACAAGGTAG
CCGTATCGGAAGGTGCGGCTGGATCACCTCCTTT
```

Strain 2 16S ribosomal RNA *Anaerotruncus colihominis*
                                                       SEQ ID NO: 2
```
TCAAAGAGTTTGATCCTGGCTCAGGACGAACGCTGGCGGCGCGCCTAACACATGCAAGTCGAACGGAG
CTTACGTTTTGAAGTTTTCGGATGGATGAATGTAAGCTTAGTGGCGGACGGGTGAGTAACACGTGAGC
AACCTGCCTTTCAGAGGGGGATAACAGCCGGAAACGGCTGCTAATACCGCATGATGTTGCGGGGGCAC
ATGCCCCTGCAACCAAAGGAGCAATCCGCTGAAAGATGGGCTCGCGTCCGATTAGCCAGTTGGCGGGG
TAACGGCCCACCAAAGCGACGATCGGTAGCCGGACTGAGAGGTTGAACGGCCACATTGGGACTGAGAC
ACGGCCCAGACTCCTACGGGAGGCAGCAGTGGGGGATATTGCACAATGGGCGAAAGCCTGATGCAGCG
ACGCCGCGTGAGGGAAGACGGTCTTCGGATTGTAAACCTCTGTCTTTGGGGAAGAAAATGACGGTACC
CAAAGAGGAAGCTCCGGCTAACTACGTGCCAGCAGCCGCGGTAATACGTAGGGAGCAAGCGTTGTCCG
GAATTACTGGGTGTAAAGGGAGCGTAGGCGGGATGGCAAGTAGAATGTTAAATCCATCGGCTCAACCG
GTGGCTGCGTTCTAAACTGCCGTTCTTGAGTGAAGTAGAGGCAGGCGGAATTCCTAGTGTAGCGGTGA
AATGCGTAGATATTAGGAGGAACACCAGTGGCGAAGGCGGCCTGCTGGGCTTTAACTGACGCTGAGGC
TCGAAAGCGTGGGGAGCAAACAGGATTAGATACCCTGGTAGTCCACGCCGTAAACGATGATTACTAGG
TGTGGGGGGACTGACCCCTTCCGTGCCGCAGTTAACACAATAAGTAATCCACCTGGGGAGTACGGCCG
CAAGGTTGAAACTCAAAGGAATTGACGGGGGCCCGCACAAGCAGTGGAGTATGTGGTTTAATTCGAAG
CAACGCGAAGAACCTTACCAGGTCTTGACATCGGATGCATAGCCTAGAGATAGGTGAAGCCCTTCGGG
GCATCCAGACAGGTGGTGCATGGTTGTCGTCAGCTCGTGTCGTGAGATGTTGGGTTAAGTCCCGCAAC
GAGCGCAACCCTTATTATTAGTTGCTACGCAAGAGCACTCTAATGAGACTGCCGTTGACAAAACGGAG
GAAGGTGGGGATGACGTCAAATCATCATGCCCCTTATGACCTGGGCTACACACGTACTACAATGGCAC
TAAAACAGAGGGCGGCGACACCGCGAGGTGAAGCGAATCCCGAAAAAGTGTCTCAGTTCAGATTGCAG
GCTGCAACCCGCCTGCATGAAGTCGGAATTGCTAGTAATCGCGGATCAGCATGCCGCGGTGAATACGT
TCCCGGGCCTTGTACACACCGCCCGTCACACCATGGGAGTCGGTAACACCCGAAGCCAGTAGCCTAAC
CGCAAGGGGGCGCTGTCGAAGGTGGGATTGATGACTGGGGTGAAGTCGTAACAAGGTAGCCGTATCG
GAAGGTGCGGCTGGATCACCTCCTTT
```

Strain 3 16S ribosomal RNA *Ruminococcus torques*
                                                       SEQ ID NO: 3
```
TACGAGAGTTTGATCCTGGCTCAGGATGAACGCTGGCGGCGTGCCTAACACATGCAAGTCGAGCGAAG
CGCTGTTTTCAGAATCTTCGGAGGAAGAGGACAGTGACTGAGCGGCGGACGGGTGAGTAACGCGTGGG
```

-continued

```
CAACCTGCCTCATACAGGGGGATAACAGTTAGAAATGACTGCTAATACCGCATAAGCGCACAGGACCG
CATGGTGTAGTGTGAAAAACTCCGGTGGTATGAGATGGACCCGCGTCTGATTAGGTAGTTGGTGGGGT
AAAGGCCTACCAAGCCGACGATCAGTAGCCGACCTGAGAGGGTGACCGGCCACATTGGGACTGAGACA
CGGCCCAAACTCCTACGGGAGGCAGCAGTGGGGAATATTGCACAATGGGGGAAACCCTGATGCAGCGA
CGCCGCGTGAAGGAAGAAGTATTTCGGTATGTAAACTTCTATCAGCAGGGAAGAAAATGACGGTACCT
GAGTAAGAAGCACCGGCTAAATACGTGCCAGCAGCCGCGGTAATACGTATGGTGCAAGCGTTATCCGG
ATTTACTGGGTGTAAAGGGAGCGTAGACGGATAGGCAAGTCTGGAGTGAAAACCCAGGGCTCAACCCT
GGGACTGCTTTGGAAACTGCAGATCTGGAGTGCCGGAGAGGTAAGCGGAATTCCTAGTGTAGCGGTGA
AATGCGTAGATATTAGGAGGAACACCAGTGGCGAAGGCGGCTTACTGGACGGTGACTGACGTTGAGGC
TCGAAAGCGTGGGGAGCAAACAGGATTAGATACCCTGGTAGTCCACGCCGTAAACGATGACTACTAGG
TGTCGGTGTGCAAAGCACATCGGTGCCGCAGCAAACGCAATAAGTAGTCCACCTGGGGAGTACGTTCG
CAAGAATGAAACTCAAAGGAATTGACGGGACCCGCACAAGCGGTGGAGCATGTGGTTTAATTCGAAG
CAACGCGAAGAACCTTACCTGGTCTTGACATCCGGATGACGGGCGAGTAATGTCGCCGTCCCTTCGGG
GCGTCCGAGACAGGTGGTGCATGGTTGTCGTCAGCTCGTGTCGTGAGATGTTGGGTTAAGTCCCGCAA
CGAGCGCAACCCTTATCTTCAGTAGCCAGCATATAAGGTGGGCACTCTGGAGAGACTGCCAGGGAGAA
CCTGGAGGAAGGTGGGGATGACGTCAAATCATCATGCCCCTTATGGCCAGGGCTACACACGTGCTACA
ATGGCGTAAACAAAGGGAAGCGAGAGGGTGACCTGGAGCGAATCCCAAAAATAACGTCTCAGTTCGGA
TTGTAGTCTGCAACTCGACTACATGAAGCTGGAATCGCTAGTAATCGCGGATCAGCATGCCGCGGTGA
ATACGTTCCCGGGTCTTGTACACACCGCCCGTCACACCATGGGAGTCAGTAACGCCCGAAGCCAGTGA
CCCAACCTTAGAGGAGGGAGCTGTCGAAGGCGGGACGGATAACTGGGGTGAAGTCGTAACAAGGTAGC
CGTATCGGAAGGTGCGGCTGGATCACCTCCTTT
```

Strain 4 16S ribosomal RNA *Clostridium symbiosum*
                                                                    SEQ ID NO: 4
```
ATGAGAGTTTGATCCTGGCTCAGGATGAACGCTGGCGGCGTGCCTAACACATGCAAGTCGAACGAAGC
GATTTAACGGAAGTTTTCGGATGGAAGTTGAATTGACTGAGTGGCGGACGGGTGAGTAACGCGTGGGT
AACCTGCCTTGTACTGGGGGACAACAGTTAGAAATGACTGCTAATACCGCATAAGCGCACAGTATCGC
ATGATACAGTGTGAAAAACTCCGGTGGTACAAGATGGACCCGCGTCTGATTAGCTAGTTGGTAAGGTA
ACGGCTTACCAAGGCGACGATCAGTAGCCGACCTGAGAGGGTGACCGGCCACATTGGGACTGAGACAC
GGCCCAAACTCCTACGGGAGGCAGCAGTGGGGAATATTGCACAATGGGCGAAAGCCTGATGCAGCGAC
GCCGCGTGAGTGAAGAAGTATTTCGGTATGTAAAGCTCTATCAGCAGGGAAGAAAATGACGGTACCTG
ACTAAGAAGCCCCGGCTAACTACGTGCCAGCAGCCGCGGTAATACGTAGGGGGCAAGCGTTATCCGGA
TTTACTGGGTGTAAAGGGAGCGTAGACGGTAAAGCAAGTCTGAAGTGAAAGCCCGCGGCTCAACTGCG
GGACTGCTTTGGAAACTGTTTAACTGGAGTGTCGGAGAGGTAAGTGGAATTCCTAGTGTAGCGGTGAA
ATGCGTAGATATTAGGAGGAACACCAGTGGCGAAGGCGACTTACTGGACGATAACTGACGTTGAGGCT
CGAAAGCGTGGGGAGCAAACAGGATTAGATACCCTGGTAGTCCACGCCGTAAACGATGAATACTAGGT
GTTGGGGAGCAAAGCTCTTCGGTGCCGTCGCAAACGCAGTAAGTATTCCACCTGGGGAGTACGTTCGC
AAGAATGAAACTCAAAGGAATTGACGGGACCCGCACAAGCGGTGGAGCATGTGGTTTAATTCGAAGC
AACGCGAAGAACCTTACCAGGTCTTGACATCGATCCGACGGGGAGTAACGTCCCCTTCCCTTCGGGG
CGGAGAAGACAGGTGGTGCATGGTTGTCGTCAGCTCGTGTCGTGAGATGTTGGGTTAAGTCCCGCAAC
GAGCGCAACCCTTATTCTAAGTAGCCAGCGGTTCGGCCGGGAACTCTTGGGAGACTGCCAGGGATAAC
CTGGAGGAAGGTGGGGATGACGTCAAATCATCATGCCCCTTATGATCTGGGCTACACACGTGCTACAA
```

-continued

```
TGGCGTAAACAAAGAGAAGCAAGACCGCGAGGTGGAGCAAATCTCAAAAATAACGTCTCAGTTCGGAC

TGCAGGCTGCAACTCGCCTGCACGAAGCTGGAATCGCTAGTAATCGCGAATCAGAATGTCGCGGTGAA

TACGTTCCCGGGTCTTGTACACACCGCCCGTCACACCATGGGAGTCAGTAACGCCCGAAGTCAGTGAC

CCAACCGCAAGGAGGGAGCTGCCGAAGGCGGGACCGATAACTGGGGTGAAGTCGTAACAAGGTAGCCG

TATCGGAAGGTGCGGCTGGATCACCTCCTTT
```

Strain 5 16S Ribosomal RNA *Blautia producta*

SEQ ID NO: 5

```
ATCAGAGAGTTTGATCCTGGCTCAGGATGAACGCTGGCGGCGTGCTTAACACATGCAAGTCGAGCGAA

GCACTTAAGTGGATCTCTTCGGATTGAAGCTTATTTGACTGAGCGGCGGACGGGTGAGTAACGCGTGG

GTAACCTGCCTCATACAGGGGGATAACAGTTAGAAATGGCTGCTAATACCGCATAAGCGCACAGGACC

GCATGGTCTGGTGTGAAAAACTCCGGTGGTATGAGATGGACCCGCGTCTGATTAGCTAGTTGGAGGGG

TAACGGCCCACCAAGGCGACGATCAGTAGCCGGCCTGAGAGGGTGAACGGCCACATTGGGACTGAGAC

ACGGCCCAGACTCCTACGGGAGGCAGCAGTGGGGAATATTGCACAATGGGGGAAACCCTGATGCAGCG

ACGCCGCGTGAAGGAAGAAGTATCTCGGTATGTAAACTTCTATCAGCAGGGAAGAAAATGACGGTACC

TGACTAAGAAGCCCCGGCTAACTACGTGCCAGCAGCCGCGGTAATACGTAGGGGGCAAGCGTTATCCG

GATTTACTGGGTGTAAAGGGAGCGTAGACGGAAGAGCAAGTCTGATGTGAAAGGCTGGGGCTTAACCC

CAGGACTGCATTGGAAACTGTTTTTCTAGAGTGCCGGAGAGGTAAGCGGAATTCCTAGTGTAGCGGTG

AAATGCGTAGATATTAGGAGGAACACCAGTGGCGAAGGCGGCTTACTGGACGGTAACTGACGTTGAGG

CTCGAAAGCGTGGGGAGCAAACAGGATTAGATACCCTGGTAGTCCACGCCGTAAACGATGAATACTAG

GTGTCGGGTGGCAAAGCCATTCGGTGCCGCAGCAAACGCAATAAGTATTCCACCTGGGGAGTACGTTC

GCAAGAATGAAACTCAAAGGAATTGACGGGGACCCGCACAAGCGGTGGAGCATGTGGTTTAATTCGAA

GCAACGCGAAGAACCTTACCAAGTCTTGACATCCCTCTGACCGGCCCGTAACGGGGCCTTCCCTTCGG

GGCAGAGGAGACAGGTGGTGCATGGTTGTCGTCAGCTCGTGTCGTGAGATGTTGGGTTAAGTCCCGCA

ACGAGCGCAACCCCTATCCTTAGTAGCCAGCAGGTGAAGCTGGGCACTCTAGGGAGACTGCCGGGGAT

AACCCGGAGGAAGGCGGGGACGACGTCAAATCATCATGCCCCTTATGATTTGGGCTACACACGTGCTA

CAATGGCGTAAACAAAGGGAAGCGAGACAGCGATGTTGAGCAAATCCCAAAAATAACGTCCCAGTTCG

GACTGCAGTCTGCAACTCGACTGCACGAAGCTGGAATCGCTAGTAATCGCGAATCAGAATGTCGCGGT

GAATACGTTCCCGGGTCTTGTACACACCGCCCGTCACACCATGGGAGTCAGTAACGCCCGAAGTCAGT

GACCCAACCTTACAGGAGGGAGCTGCCGAAGGCGGGACCGATAACTGGGGTGAAGTCGTAACAAGGTA

GCCGTATCGGAAGGTGCGGCTGGATCACCTCCTTT
```

Strain 6 16S ribosomal RNA *Dorea longicatena*

SEQ ID NO: 6

```
AACGAGAGTTTGATCCTGGCTCAGGATGAACGCTGGCGGCGTGCTTAACACATGCAAGTCGAGCGAAG

CACTTAAGTTTGATTCTTCGGATGAAGACTTTTGTGACTGAGCGGCGGACGGGTGAGTAACGCGTGGG

TAACCTGCCTCATACAGGGGGATAACAGTTAGAAATGACTGCTAATACCGCATAAGACCACGGTACCG

CATGGTACAGTGGTAAAAACTCCGGTGGTATGAGATGGACCCGCGTCTGATTAGGTAGTTGGTGGGGT

AACGGCCTACCAAGCCGACGATCAGTAGCCGACCTGAGAGGGTGACCGGCCACATTGGGACTGAGACA

CGGCCCAGACTCCTACGGGAGGCAGCAGTGGGGAATATTGCACAATGGAGGAAACTCTGATGCAGCGA

CGCCGCGTGAAGGATGAAGTATTTCGGTATGTAAACTTCTATCAGCAGGGAAGAAAATGACGGTACCT

GACTAAGAAGCCCCGGCTAACTACGTGCCAGCAGCCGCGGTAATACGTAGGGGGCAAGCGTTATCCGG

ATTTACTGGGTGTAAAGGGAGCGTAGACGGCACGGCAAGCCAGATGTGAAAGCCCGGGGCTCAACCCC

GGGACTGCATTTGGAACTGCTGAGCTAGAGTGTCGGAGAGGCAAGTGGAATTCCTAGTGTAGCGGTGA

AATGCGTAGATATTAGGAGGAACACCAGTGGCGAAGGCGGCTTGCTGGACGATGACTGACGTTGAGGC
```

-continued

```
TCGAAAGCGTGGGGAGCAAACAGGATTAGATACCCTGGTAGTCCACGCCGTAAACGATGACTGCTAGG

TGTCGGGTGGCAAAGCCATTCGGTGCCGCAGCTAACGCAATAAGCAGTCCACCTGGGGAGTACGTTCG

CAAGAATGAAACTCAAAGGAATTGACGGGGACCCGCACAAGCGGTGGAGCATGTGGTTTAATTCGAAG

CAACGCGAAGAACCTTACCTGATCTTGACATCCCGATGACCGCTTCGTAATGGAAGCTTTTCTTCGGA

ACATCGGTGACAGGTGGTGCATGGTTGTCGTCAGCTCGTGTCGTGAGATGTTGGGTTAAGTCCCGCAA

CGAGCGCAACCCCTATCTTCAGTAGCCAGCAGGTTAAGCTGGGCACTCTGGAGAGACTGCCAGGGATA

ACCTGGAGGAAGGTGGGGATGACGTCAAATCATCATGCCCCTTATGACCAGGGCTACACACGTGCTAC

AATGGCGTAAACAAAGAGAAGCGAACTCGCGAGGGTAAGCAAATCTCAAAAATAACGTCTCAGTTCGG

ATTGTAGTCTGCAACTCGACTACATGAAGCTGGAATCGCTAGTAATCGCAGATCAGAATGCTGCGGTG

AATACGTTCCCGGGTCTTGTACACACCGCCCGTCACACCATGGGAGTCAGTAACGCCCGAAGTCAGTG

ACCCAACCGTAAGGAGGGAGCTGCCGAAGGTGGGACCGATAACTGGGGTGAAGTCGTAACAAGGTAGC

CGTATCGGAAGGTGCGGCTGGATCACCTCCTTT
```

Strain 7 16S ribosomal RNA *Erysipelotrichaceae bacterium*
SEQ ID NO: 7

```
ATGGAGAGTTTGATCCTGGCTCAGGATGAACGCTGGCGGCATGCCTAATACATGCAAGTCGAACGAAG

TTTCGAGGAAGCTTGCTTCCAAAGAGACTTAGTGGCGAACGGGTGAGTAACACGTAGGTAACCTGCCC

ATGTGTCCGGGATAACTGCTGGAAACGGTAGCTAAAACCGGATAGGTATACAGAGCGCATGCTCAGTA

TATTAAAGCGCCCATCAAGGCGTGAACATGGATGGACCTGCGGCGCATTAGCTAGTTGGTGAGGTAAC

GGCCCACCAAGGCGATGATGCGTAGCCGGCCTGAGAGGGTAAACGGCCACATTGGGACTGAGACACGG

CCCAAACTCCTACGGGAGGCAGCAGTAGGGAATTTTCGTCAATGGGGGAAACCCTGAACGAGCAATGC

CGCGTGAGTGAAGAAGGTCTTCGGATCGTAAAGCTCTGTTGTAAGTGAAGAACGGCTCATAGAGGAAA

TGCTATGGGAGTGACGGTAGCTTACCAGAAAGCCACGGCTAACTACGTGCCAGCAGCCGCGGTAATAC

GTAGGTGGCAAGCGTTATCCGGAATCATTGGGCGTAAAGGGTGCGTAGGTGGCGTACTAAGTCTGTAG

TAAAAGGCAATGGCTCAACCATTGTAAGCTATGGAAACTGGTATGCTGGAGTGCAGAAGAGGGCGATG

GAATTCCATGTGTAGCGGTAAAATGCGTAGATATATGGAGGAACACCAGTGGCGAAGGCGGTCGCCTG

GTCTGTAACTGACACTGAGGCACGAAAGCGTGGGGAGCAAATAGGATTAGATACCCTAGTAGTCCACG

CCGTAAACGATGAGAACTAAGTGTTGGAGGAATTCAGTGCTGCAGTTAACGCAATAAGTTCTCCGCCT

GGGGAGTATGCACGCAAGTGTGAAACTCAAAGGAATTGACGGGGCCCGCACAAGCGGTGGAGTATGT

GGTTTAATTCGAAGCAACGCGAAGAACCTTACCAGGCCTTGACATGGAAACAAATACCCTAGAGATAG

GGGGATAATTATGGATCACACAGGTGGTGCATGGTTGTCGTCAGCTCGTGTCGTGAGATGTTGGGTTA

AGTCCCGCAACGAGCGCAACCCTTGTCGCATGTTACCAGCATCAAGTTGGGGACTCATGCGAGACTGC

CGGTGACAAACCGGAGGAAGGTGGGGATGACGTCAAATCATCATGCCCCTTATGGCCTGGGCTACACA

CGTACTACAATGGCGGCCAGAAAGAGCAGCGACACAGTGATGTGAAGCGAATCTCATAAAGGTCGTCT

CAGTTCGGATTGAAGTCTGCAACTCGACTTCATGAAGTCGGAATCGCTAGTAATCGCAGATCAGCATG

CTGCGGTGAATACGTTCTCGGGCCTTGTACACACCGCCCGTCAAACCATGGGAGTCAGTAATACCCGA

AGCCGGTGGCATAACCGTAAGGAGTGAGCCGTCGAAGGTAGGACCGATGACTGGGGTTAAGTCGTAAC

AAGGTATCCCTACGGGAACGTGGGGATGGATCACCTCCTTT
```

Strain 8 16S ribosomal RNA *Subdoligranulum spp*
SEQ ID NO: 8

```
TATTGAGAGTTTGATCCTGGCTCAGGATGAACGCTGGCGGCGTGCTTAACACATGCAAGTCGAACGGG

GTGCTCATGACGGAGGATTCGTCCAACGGATTGAGTTACCTAGTGGCGGACGGGTGAGTAACGCGTGA

GGAACCTGCCTTGGAGAGGGGAATAACACTCCGAAAGGAGTGCTAATACCGCATGATGCAGTTGGGTC
```

```
                        -continued
GCATGGCTCTGACTGCCAAAGATTTATCGCTCTGAGATGGCCTCGCGTCTGATTAGCTAGTAGGCGGG

GTAACGGCCCACCTAGGCGACGATCAGTAGCCGGACTGAGAGGTTGACCGGCCACATTGGGACTGAGA

CACGGCCCAGACTCCTACGGGAGGCAGCAGTGGGGAATATTGGGCAATGGGCGCAAGCCTGACCCAGC

AACGCCGCGTGAAGGAAGAAGGCTTTCGGGTTGTAAACTTCTTTTGTCGGGGACGAAACAAATGACGG

TACCCGACGAATAAGCCACGGCTAACTACGTGCCAGCAGCCGCGGTAATACGTAGGTGGCAAGCGTTA

TCCGGATTTACTGGGTGTAAAGGGCGTGTAGGCGGGATTGCAAGTCAGATGTGAAAACTGGGGCTCA

ACCTCCAGCCTGCATTTGAAACTGTAGTTCTTGAGTGCTGGAGAGGCAATCGGAATTCCGTGTGTAGC

GGTGAAATGCGTAGATATACGGAGGAACACCAGTGGCGAAGGCGGATTGCTGGACAGTAACTGACGCT

GAGGCGCGAAAGCGTGGGGAGCAAACAGGATTAGATACCCTGGTAGTCCACGCCGTAAACGATGGATA

CTAGGTGTGGGGGGTCTGACCCCCTCCGTGCCGCAGTTAACACAATAAGTATCCCACCTGGGGAGTAC

GATCGCAAGGTTGAAACTCAAAGGAATTGACGGGGCCCGCACAAGCGGTGGAGTATGTGGTTTAATT

CGAAGCAACGCGAAGAACCTTACCAGGGCTTGACATCCCACTAACGAAGCAGAGATGCATTAGGTGCC

CTTCGGGGAAAGTGGAGACAGGTGGTGCATGGTTGTCGTCAGCTCGTGTCGTGAGATGTTGGGTTAAG

TCCCGCAACGAGCGCAACCCTTATTGTTAGTTGCTACGCAAGAGCACTCTAGCGAGACTGCCGTTGAC

AAAACGGAGGAAGGTGGGGACGACGTCAAATCATCATGCCCCTTATGTCCTGGGCCACACACGTACTA

CAATGGTGGTTAACAGAGGGAGGCAATACCGCGAGGTGGAGCAAATCCCTAAAAGCCATCCCAGTTCG

GATTGCAGGCTGAAACCCGCCTGTATGAAGTTGGAATCGCTAGTAATCGCGGATCAGCATGCCGCGGT

GAATACGTTCCCGGGCCTTGTACACACCGCCCGTCACACCATGAGAGTCGGGAACACCCGAAGTCCGT

AGCCTAACCGCAAGGAGGGCGCGGCCGAAGGTGGGTTCGATAATTGGGGTGAAGTCGTAACAAGGTAG

CCGTATCGGAAGGTGCGGCTGGATCACCTCCTTT
```

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1A: Phase 1 Dose-Escalation Study of Composition VE303 in Healthy Volunteers

*C. difficile* infection is associated with alterations of the gastrointestinal microbiota. A frequently utilized therapy for *C. difficile* infection, such as fecal microbiota transplant (FMT), may prevent recurrent *C. difficile* infections (rCDI), but has limitations for routine use and unforeseen risks.

Composition VE303 is a rationally defined bacterial composition containing the bacterial strains shown in Table 1 that has been found to suppress *C. difficile* growth in vitro, and improve survival in *C. difficile* infection (CDI) models.

Methods

Figure 20:
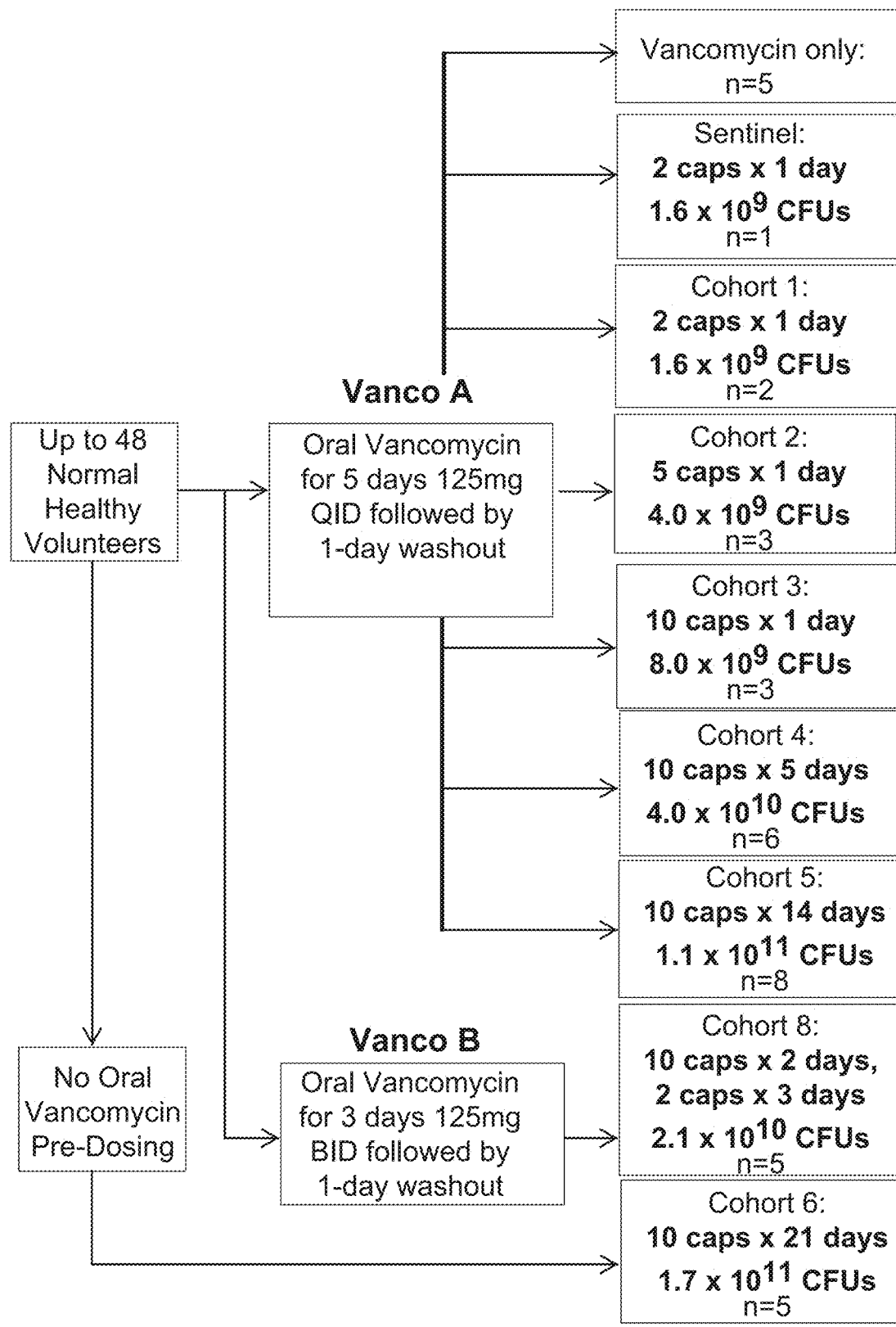
FIG. 20 presents a diagram illustrating additional various treatment cohorts for the present disclosure.
Figure 21A:
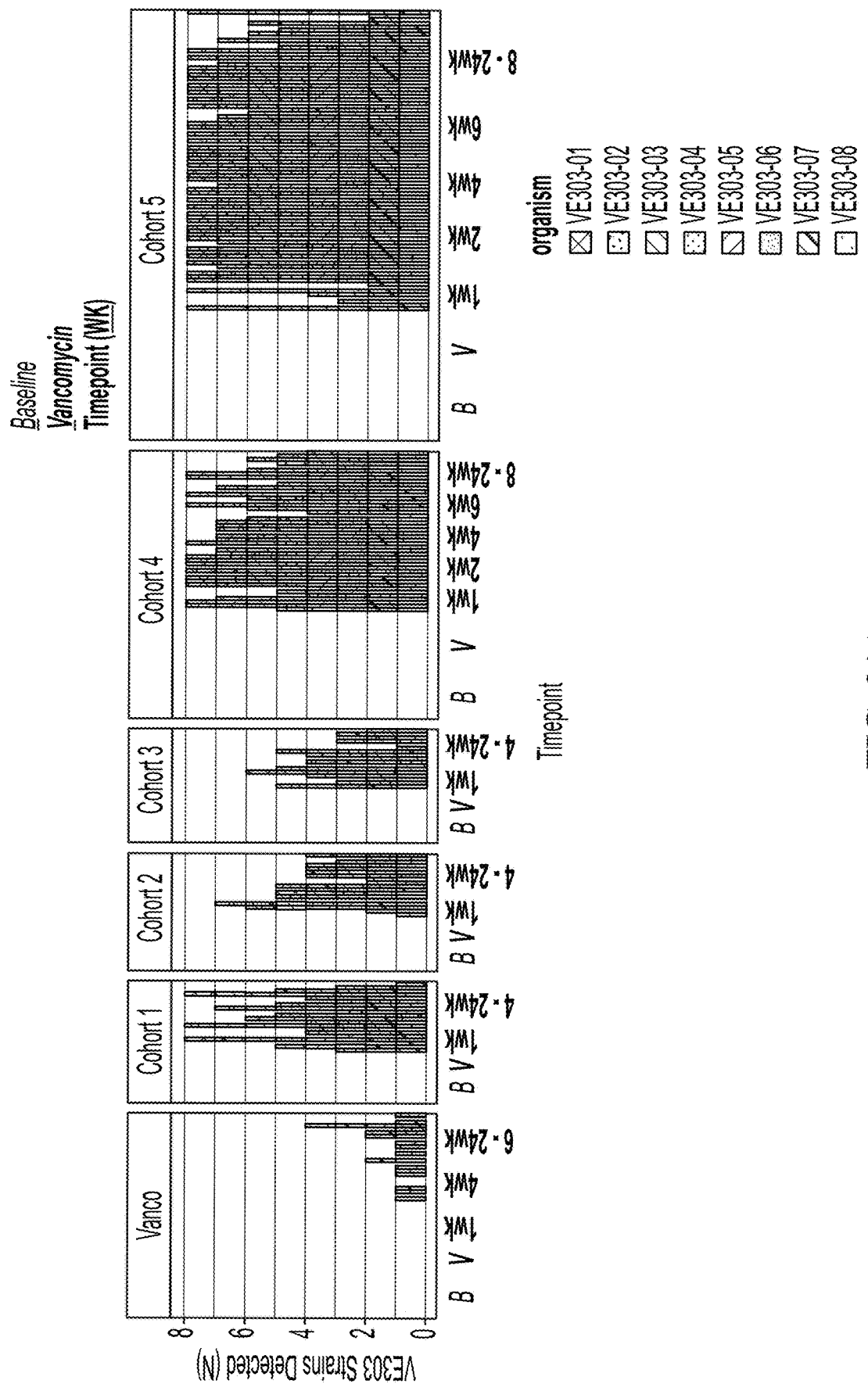
FIGS. 21A-21B present graphs showing the number of bacterial strains of composition VE303 detected in the microbiota of individual subjects. The graphs show the number of bacterial strains of composition VE303 detected in the microbiota of subjects in Cohorts 1-6 and 8. For each time point, the bacterial strains of composition VE303 are shown, from top to bottom: VE303-1, VE303-2, VE303-3, VE303-4, VE303-5, VE303-6, VE303-7, and VE303-8. "B" indicates the number of VE303 composition strains detected at baseline and "V" indicates the number of VE303 composition strains detected during vancomycin treatment.
Figure 21B:
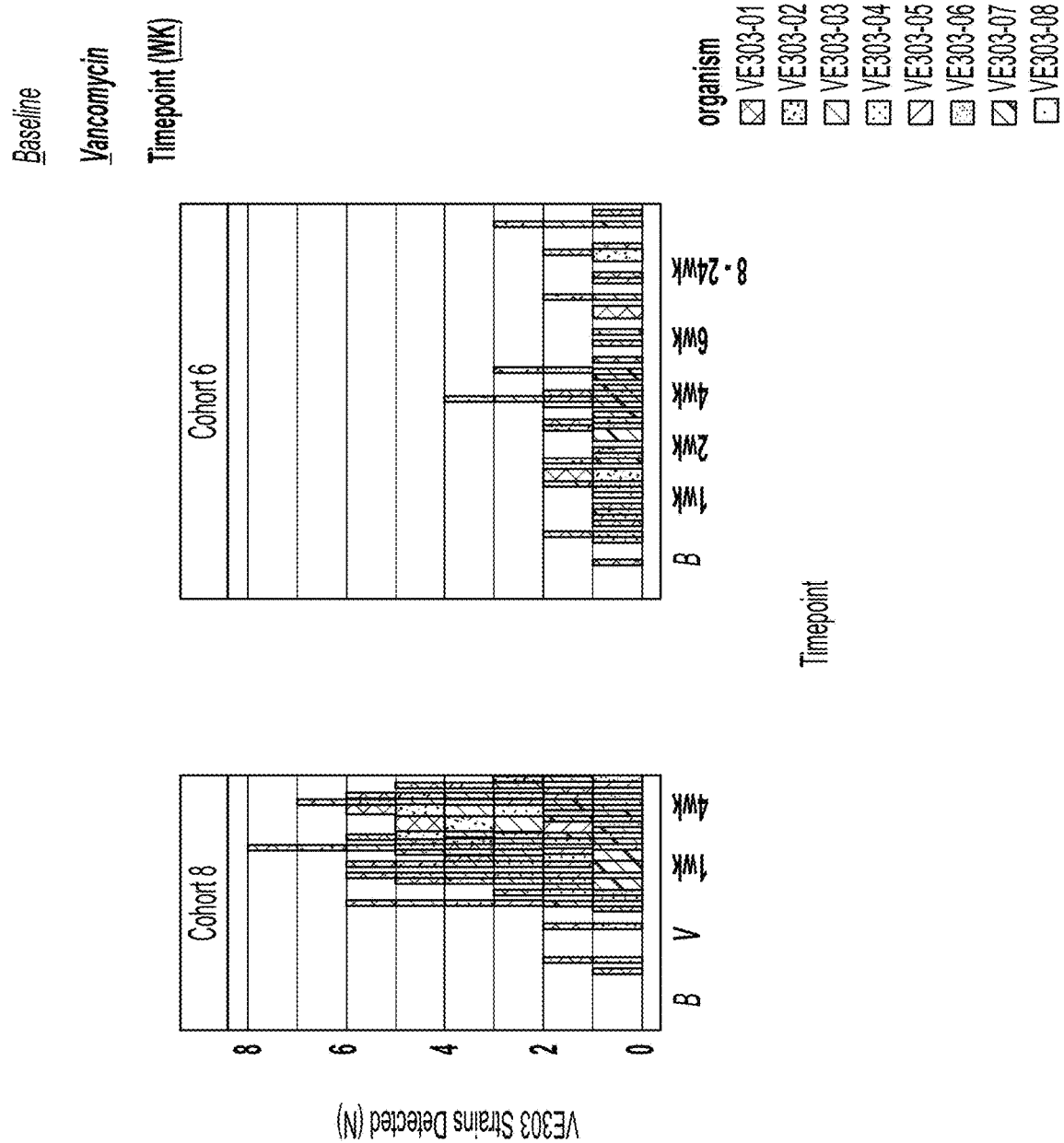

A Phase 1 dose-escalation study was conducted to assess the safety and tolerability of composition VE303 in healthy volunteers (HVs) after vancomycin-induced dysbiosis. As shown in FIG. 1 and FIG. 20, HVs were divided into seven cohorts and a vancomycin control group. Pharmacokinetics, including strain colonization and durability) and pharmacodynamics (e.g., restoration of resident microbiota) were evaluated by metagenomics sequencing of fecal bacteria collected longitudinally.

The healthy volunteers (N=48, 7 cohorts) were administered oral vancomycin (125 mg×4 times daily) for 5 days or 3 days twice daily followed by composition VE303 capsules at escalating single doses or multiple doses (dose range $1.6 \times 10^9$ to $1.1 \times 10^{11}$ total CFUs). A control group of healthy volunteers did not receive vancomycin but were administered composition VE303 ($1.7 \times 10^{11}$ total CFUs) for 21 days.

Figure 14A:
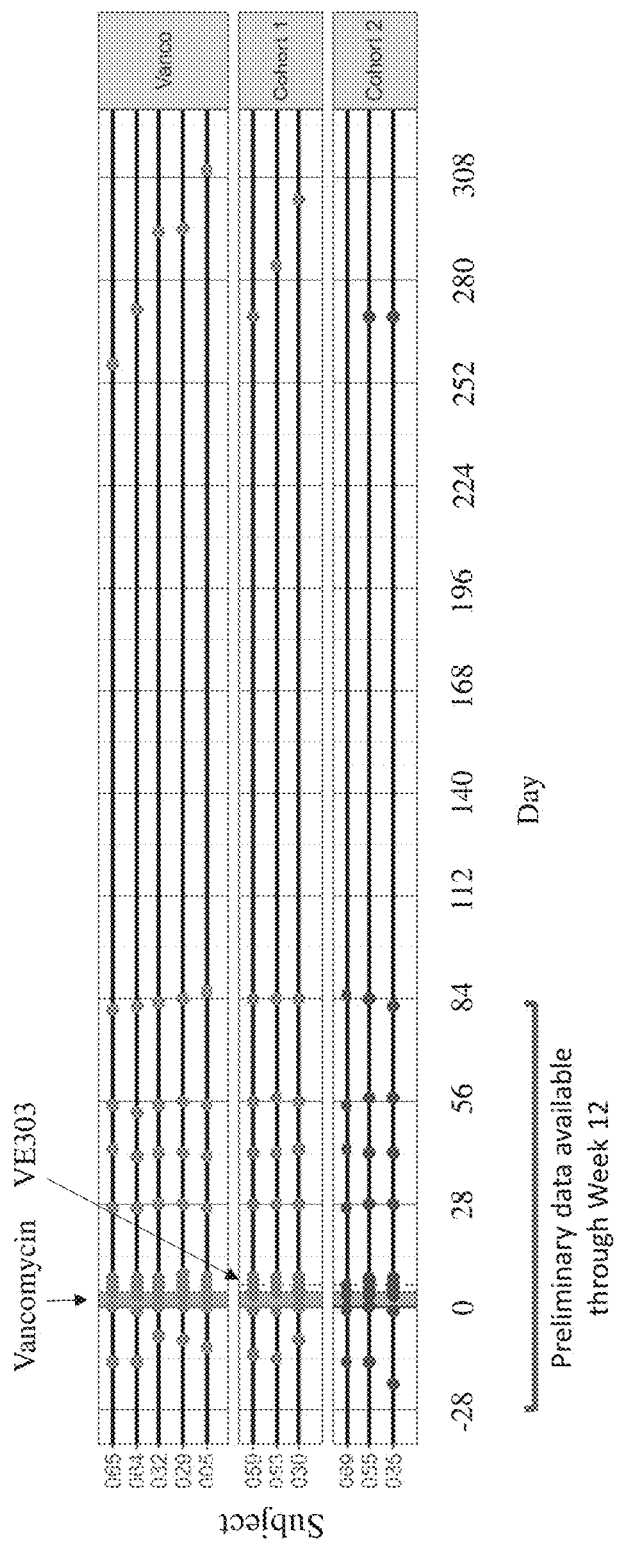
FIGS. 14A-14B show an investigational Phase 1a/b dose escalation study in normal healthy volunteers. The various cohorts were treated according to the diagram in FIG. 1. Fecal stool samples were collected longitudinally at the indicated times for each subject and analyzed by Illumina shotgun metagenomics sequencing. The first shaded region (left) indicates a daily vancomycin administration. The second shaded region (right) indicates daily VE303 administration. Each data point represents a fecal stool collection.
Figure 14B:
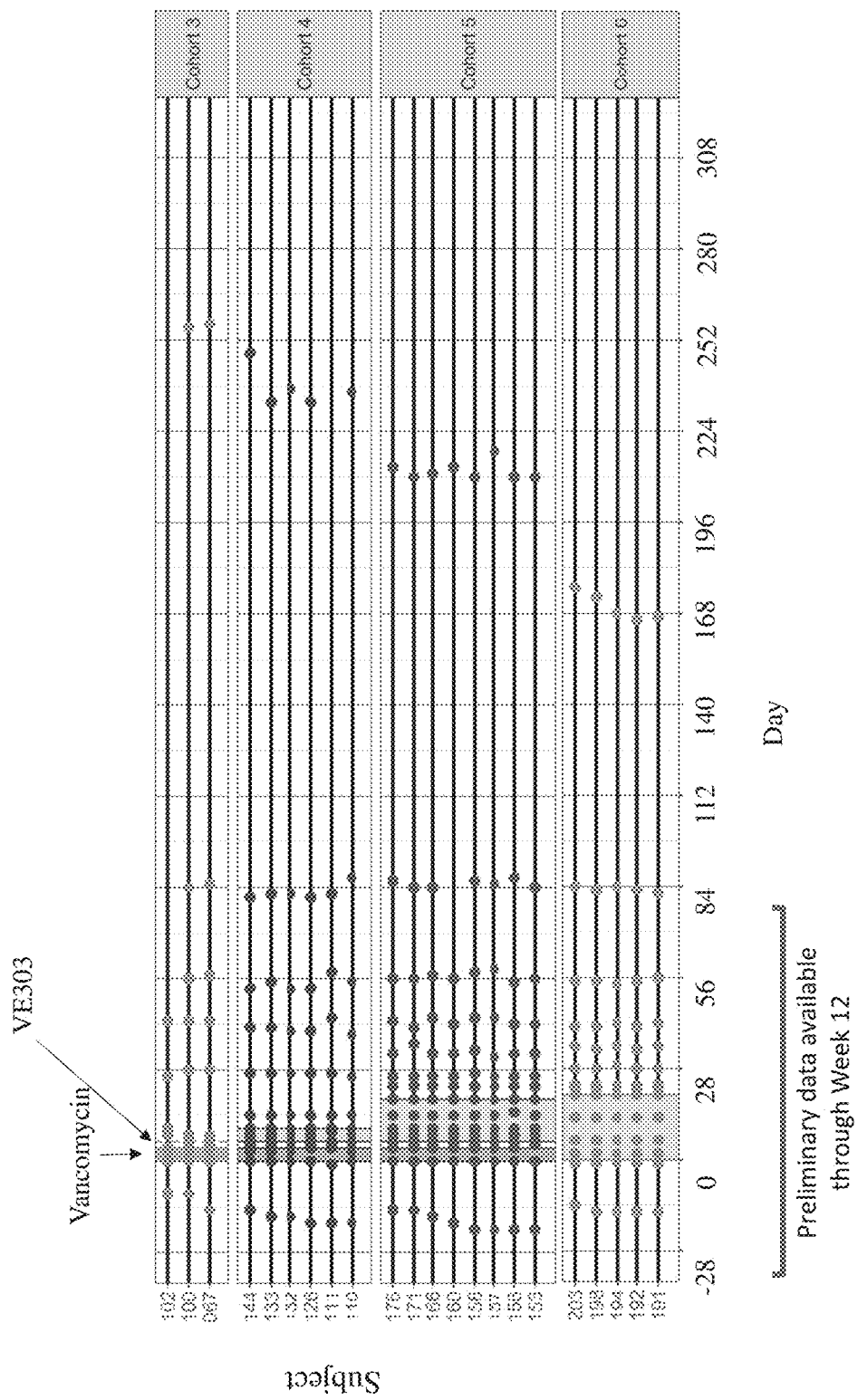

Fecal stool samples were collected from normal healthy volunteers divided into vancomycin only (vanco), Cohort 1 (single dose of $1.6 \times 10^9$ colony forming units (CFUs) VE303), Cohort 2 (single dose of $4.0 \times 10^9$ CFUs), Cohort 3 (single dose of $8.0 \times 10^9$ CFUs), Cohort 4 (multiple doses of $4.0 \times 10^{10}$ CFUs), Cohort 5 (multiple doses of $1.1 \times 10^{11}$ CFUs), Cohort 6 (multiple doses of $1.7 \times 10^{11}$ CFUs, no vancomycin pre-dosing), or Cohort 8 (multiple doses of $2.1 \times 10^{10}$ CFUs, 3 days vancomycin pre-dosing) (FIGS. 1, 14, and 20). Fecal stool samples were collected and analyzed by Illumina shotgun sequencing.

Results

Adverse events (AEs) associated with composition VE303 were observed in 16% of healthy volunteers, although all adverse events were Grade 1 ("mild adverse events," on a scale from 1-5) and transient. Of the adverse events, the majority were gastrointestinal (abdominal distention or pain, soft or hard feces, nausea, flatulence, and diarrhea). The most common Grade 2-3 laboratory abnormalities were increased cholesterol, blood in urine, and increased lipase and amylase. There were no related Grade 3-4 adverse events or serious adverse events.

Durable, abundant, dose-dependent colonization was observed in the single- and multi-dose cohorts. Each bacterial strain of composition VE303 was detectable in the stool, and the bacterial strains of composition VE303 expanded 10-100 fold within 2 days after dosing. In many healthy volunteers, the bacterial strains of composition VE303 were abundantly detected at 12 weeks and appeared to enhance subjects' microbiota recovery following administration of vancomycin. When compared with the control cohort that received vancomycin only, healthy volunteers that received composition VE303 had earlier and more complete recovery of potentially beneficial taxa (e.g., Bacteroides, Firmicutes) and a reduction in potentially inflammatory taxa (e.g., Proteobacteria).

Figure 2A:
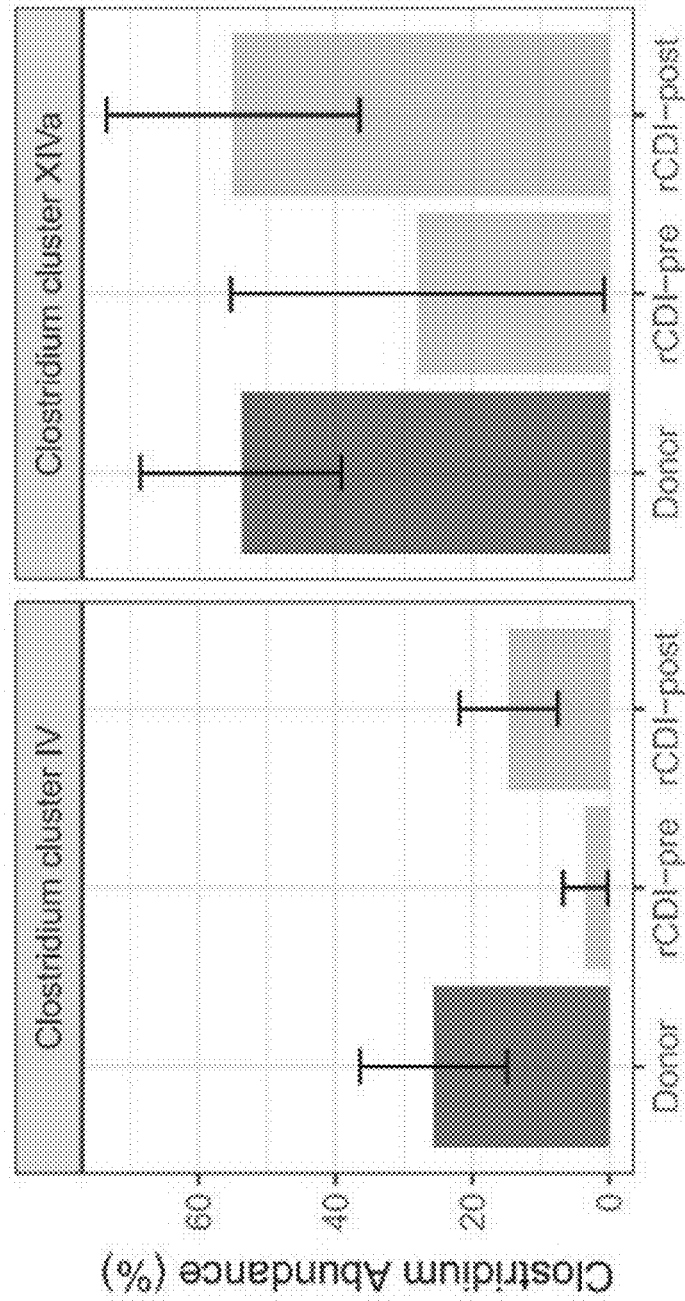
FIGS. 2A-2B present data showing the abundance of bacterial strains belonging to Clostridium clusters IV and XIVa.
Figure 2B:
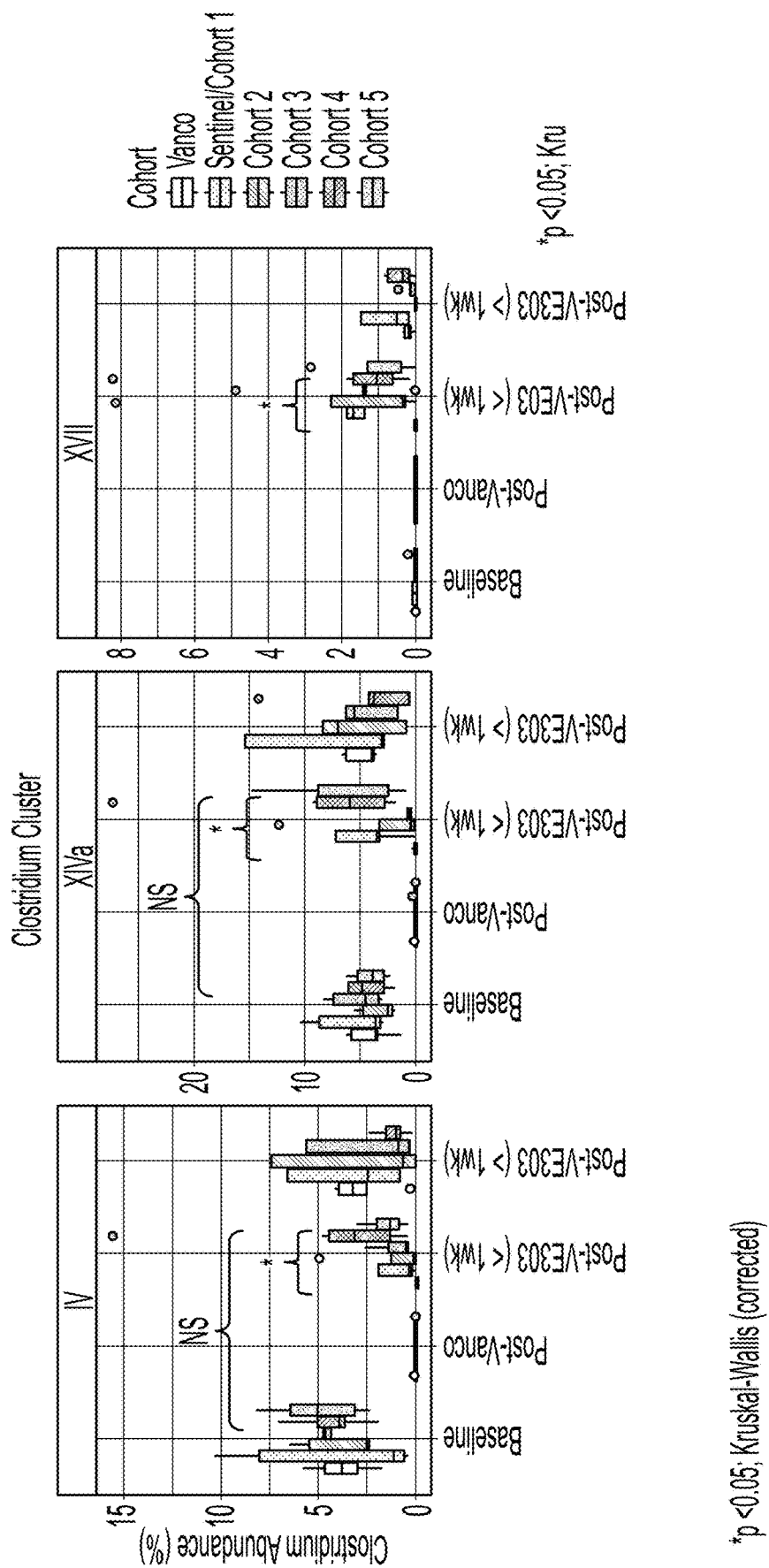

The presence of bacterial strains belonging to *Clostridium* clusters IV and XIVa has previously been found to be associated with response to FMTs in rCDI (FIG. 2A; Van Nood et al. 2013). Administration of vancomycin resulted in an almost complete disappearance of bacterial strains belonging to the *Clostridium* clusters IV, XIVa and XVII. Subsequent administration of composition VE303 was found to result in an increase in the abundance of bacterial strains belonging to *Clostridium* clusters IV, XIVa, and XVII in the microbiome of subjects from each Cohort. Interestingly, the abundance of bacterial strains belonging to *Clostridium* clusters IV and XIVa in the microbiome of the subjects recovered to levels similar baseline following administration of composition VE303 (FIG. 2B).

Figure 3A:
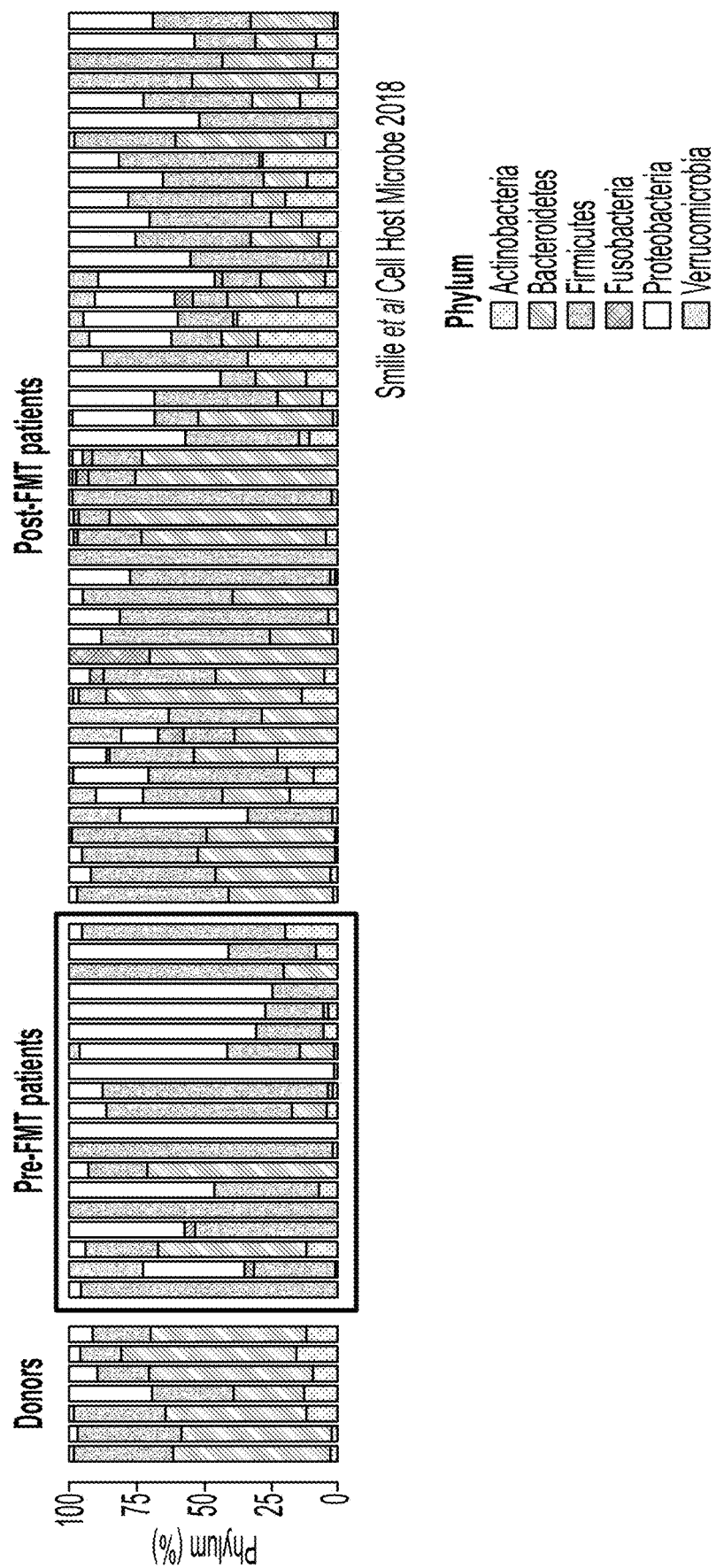
FIGS. 3A-3D present graphs depicting microbiota recovery in subjects following treatment with vancomycin.
Figure 3B:
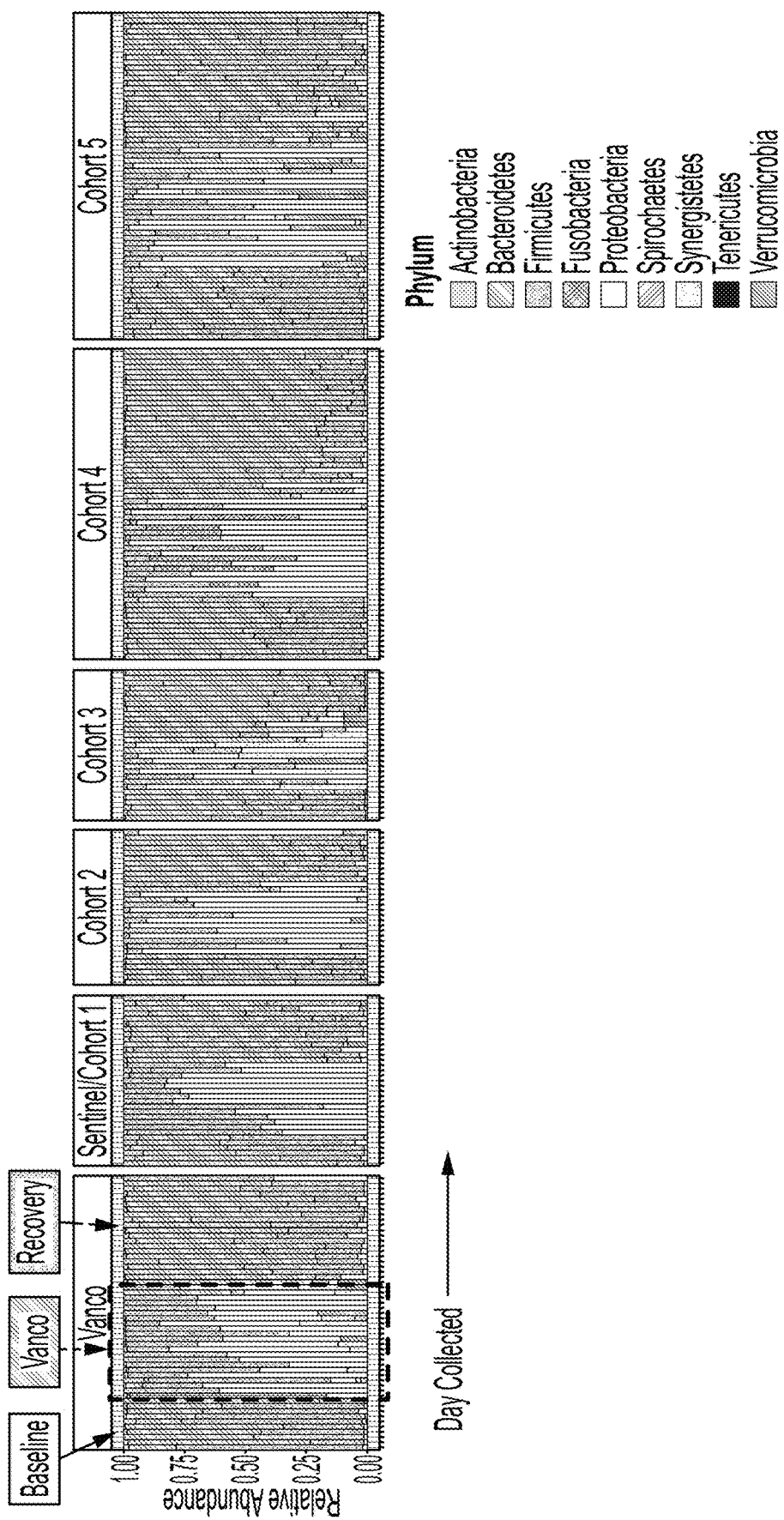
Figures 3C, 3D:
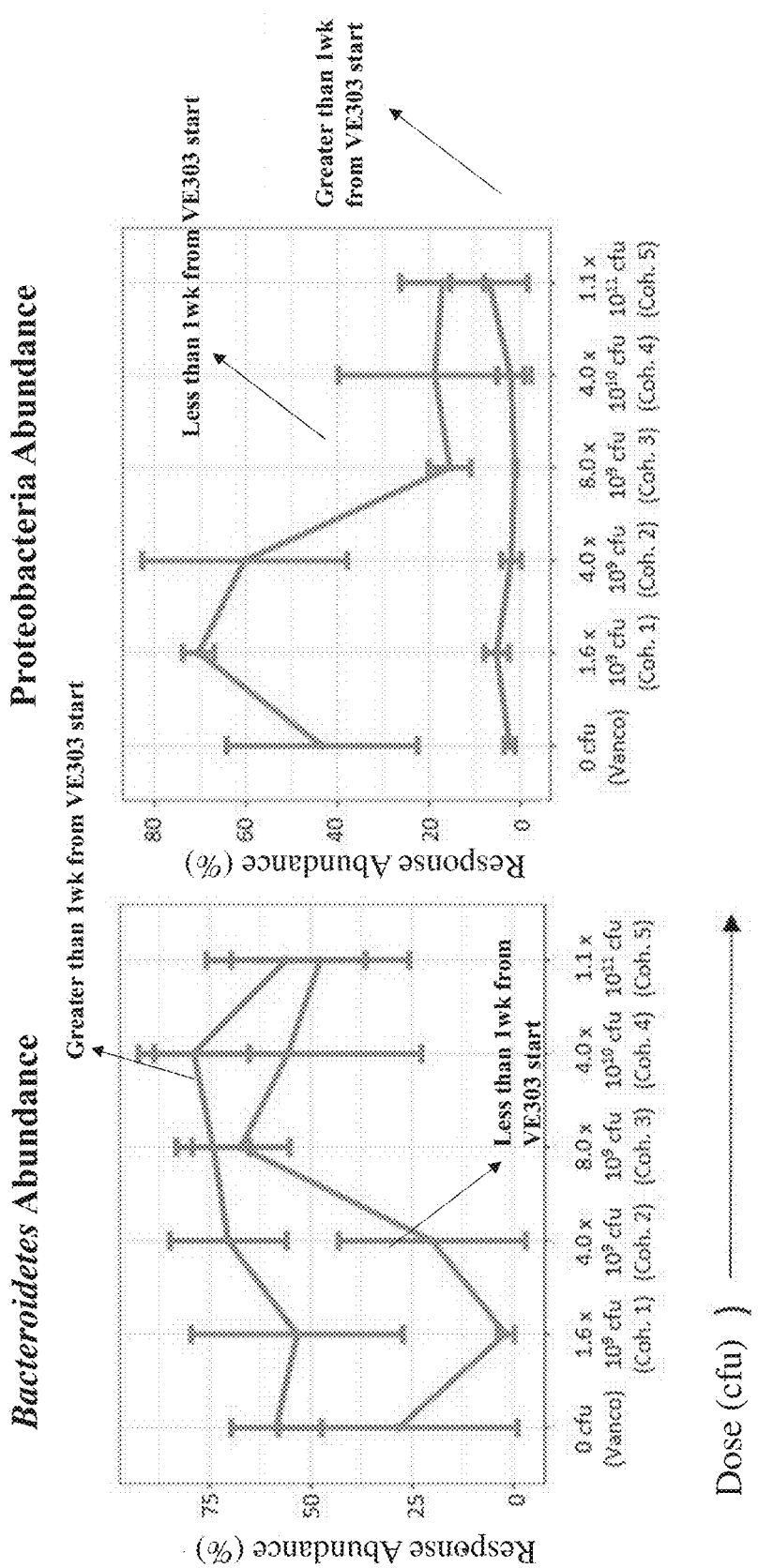
Figure 15:
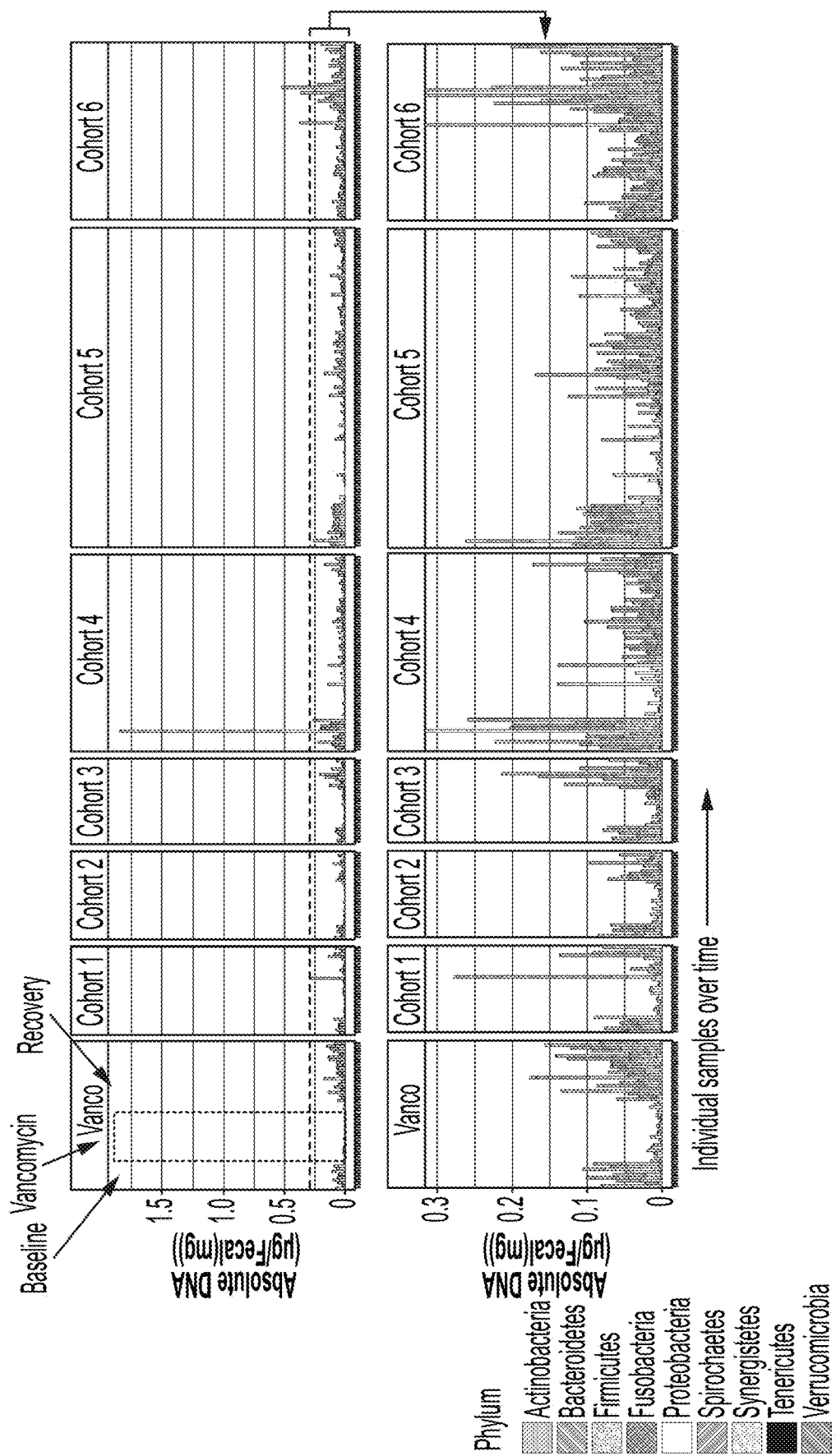
FIG. 15 shows the pharmacodynamics of VE303 in normal healthy volunteers. The changes in the absolute abundance of each bacterial phylum are based on the mass of stool extracted and the DNA yield. All data points are displayed in the top panel and a subset of data points are displayed in the bottom panel. Treatment with vancomycin significantly reduces the bacterial biomass, while the Proteobacteria DNA increases in some subjects.
Figure 16:
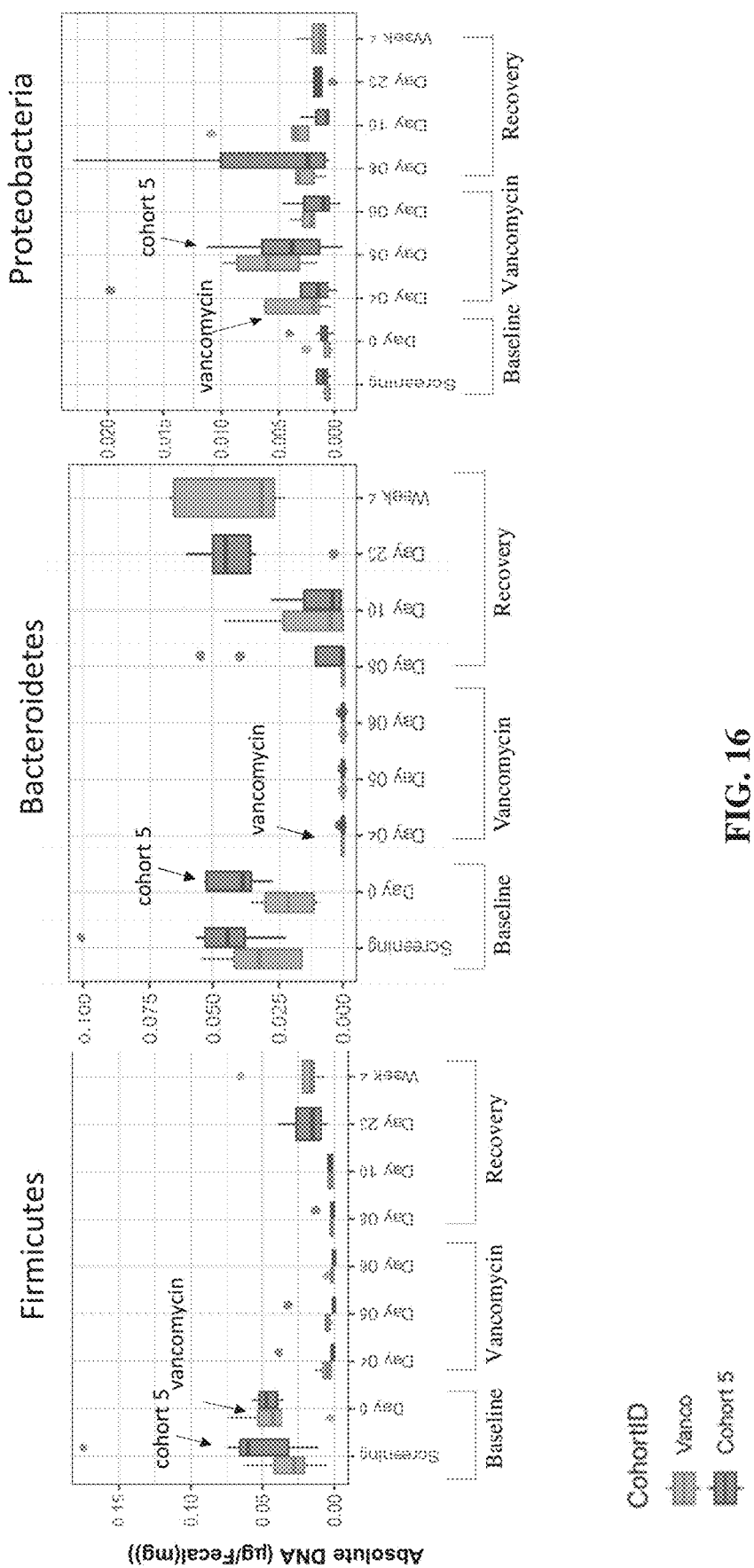
FIG. 16 shows changes in the absolute abundance of Firmicutes, Bacteroidetes, and Proteobacteria at the selected time points. Arrows indicate VE303-associated recovery trends within the first week after vancomycin treatment.
Figure 25:
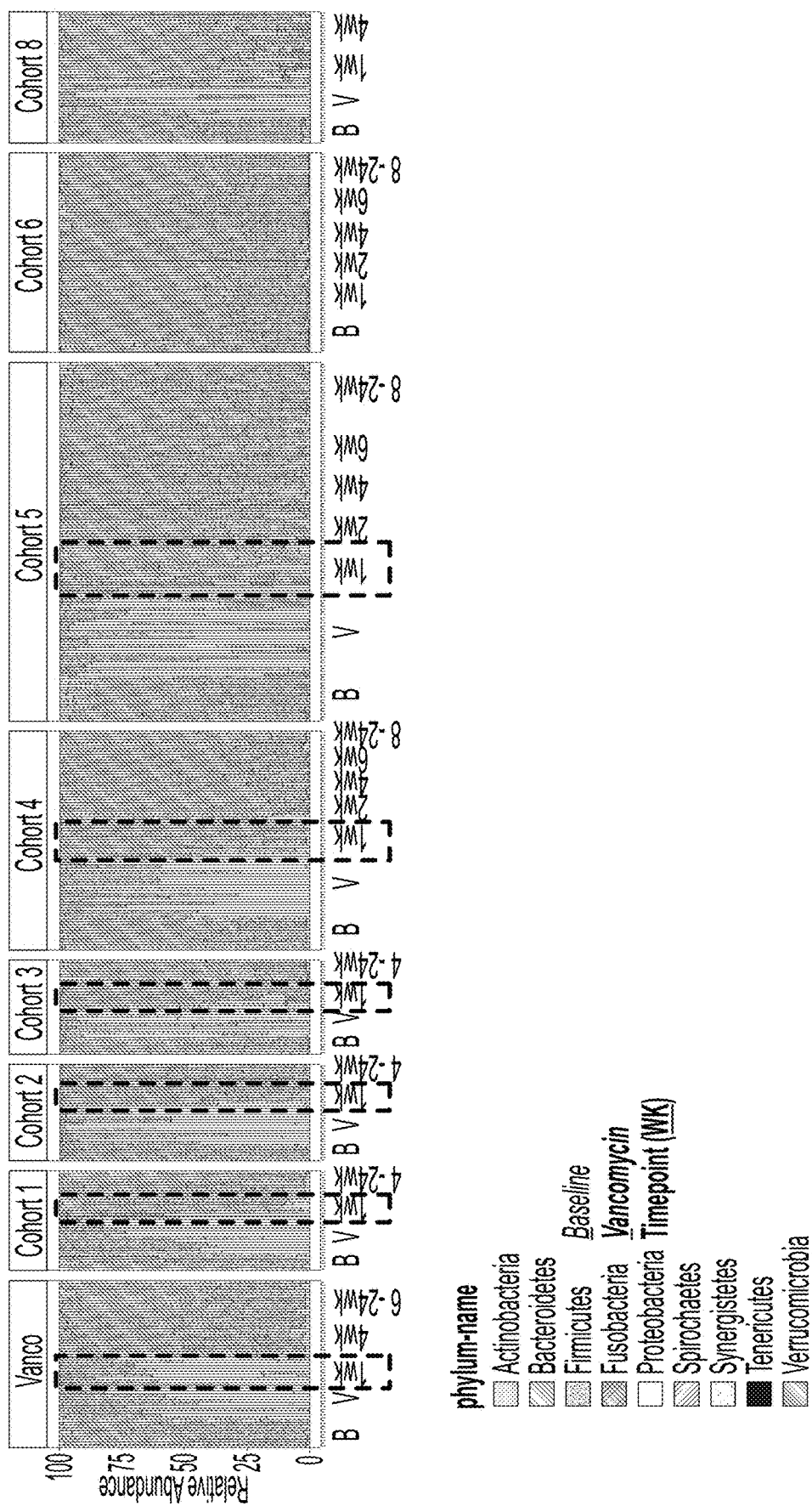
FIG. 25 shows the relative abundance of bacterial phyla prior to (baseline), after administration of vancomycin, and after administration of composition VE303. "B" indicates the number of VE303 composition strains detected at baseline and "V" indicates the number of VE303 composition strains detected during vancomycin treatment.

Additionally, as previously reported by Smilie et al. 2018, subjects having rCDI who were treated with FMT transfer were found to have increased levels of Bacteriodetes and decreased levels of Proteobacteria compared to Bacteriodetes and Proteobacteria levels pre-FMT treatment (FIG. 3A). Administration of vancomycin alters the gastrointestinal microbiota, which then resembles the microbiome during *C. difficile* infection prior to FMT transfer (e.g., high levels of Proteobacteria, low levels of Bacteroidetes). Samples from subjects that were administered composition VE303 following administration of vancomycin treatment were analyzed at baseline, after administration of vancomycin, and after administration of composition VE303 for recovery of the microbiome. Vancomycin significantly reduces the bacterial biomass, but Proteobacteria DNA increases in some subjects (FIG. 15). Interestingly, administration of composition VE303 promoted faster recovery of the microbiome (e.g., return to normal levels of Bacteriodetes and Proteobacteria). The recovery was even faster for the cohorts that received multiple doses of composition VE303 (less than 1 week from the start of VE303 administration (FIGS. 3B-D. FIG. 15, FIG. 16, FIG. 25).

Figure 4A:
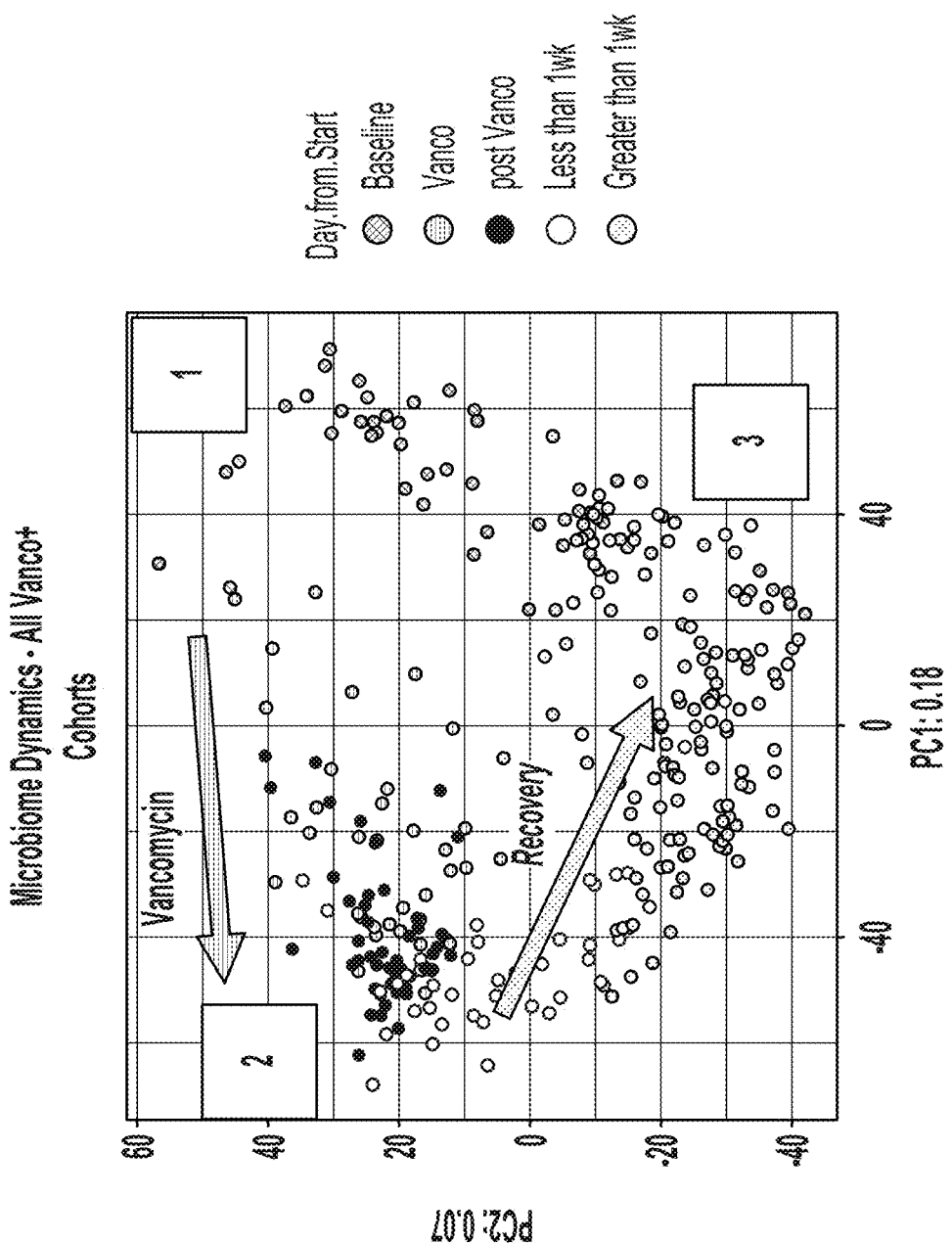
FIGS. 4A-4C illustrate microbiome dynamics following administration of vancomycin and following administration of composition VE303.
Figure 4B:
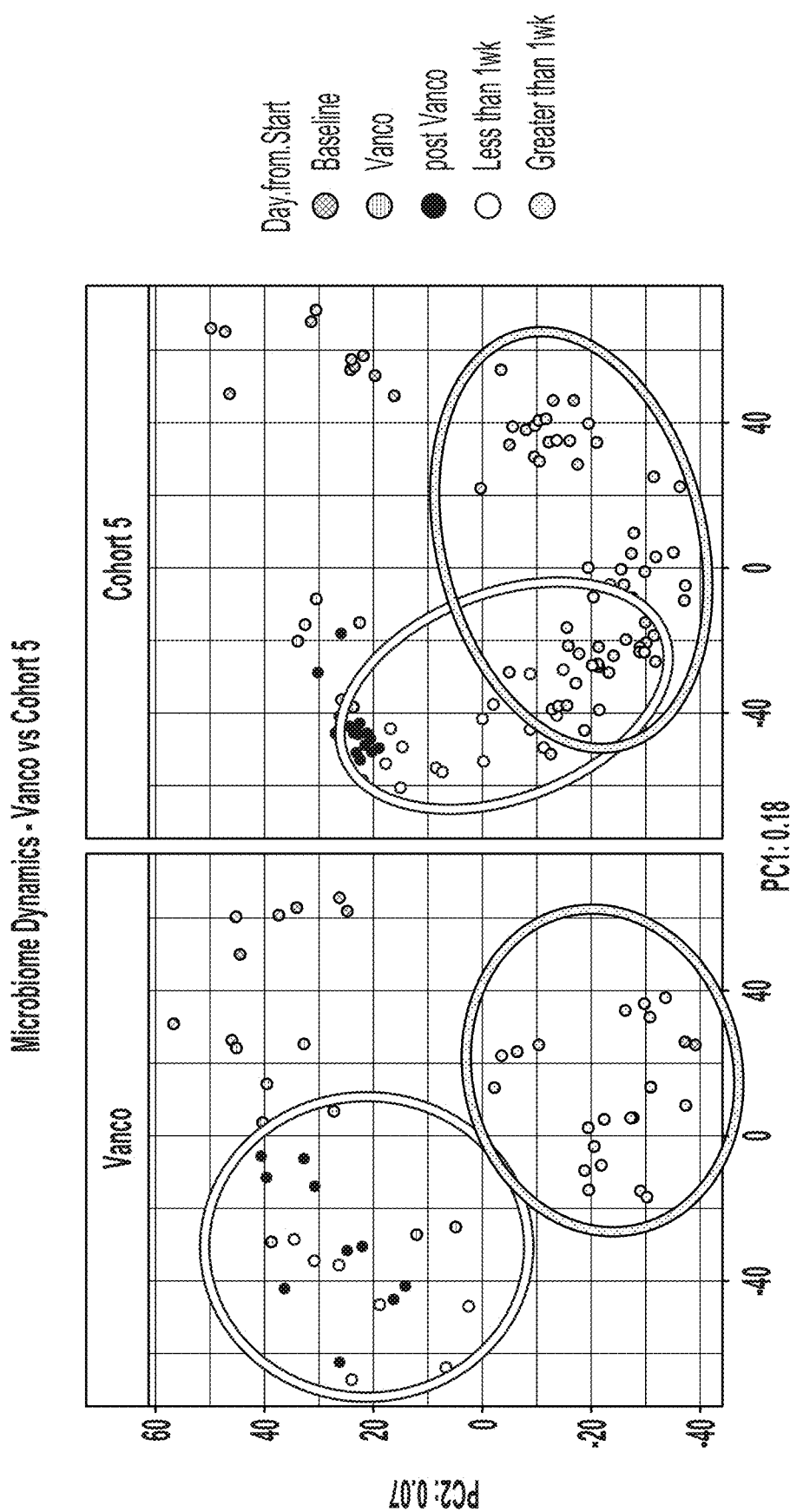
Figure 4C:
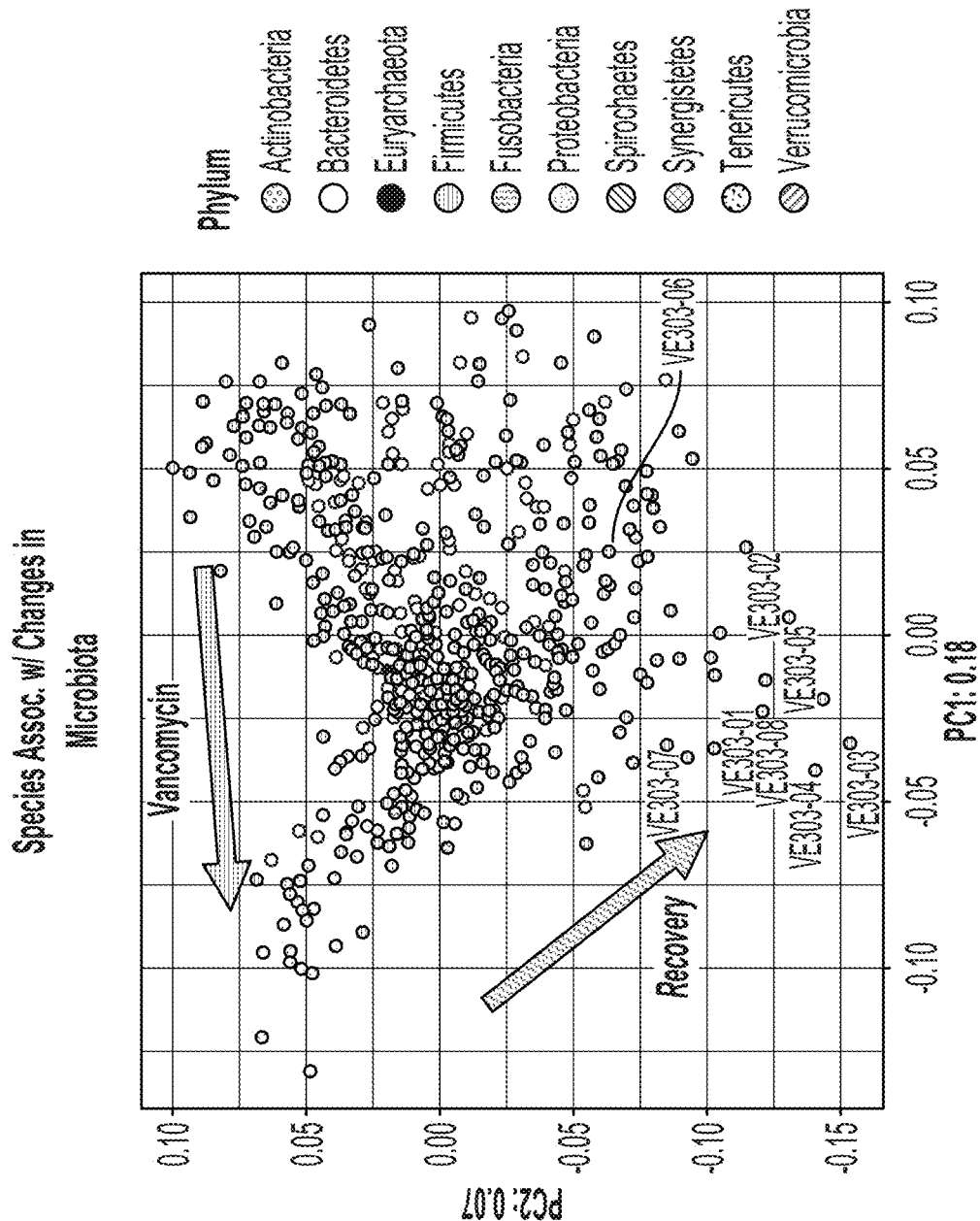
Figure 5:
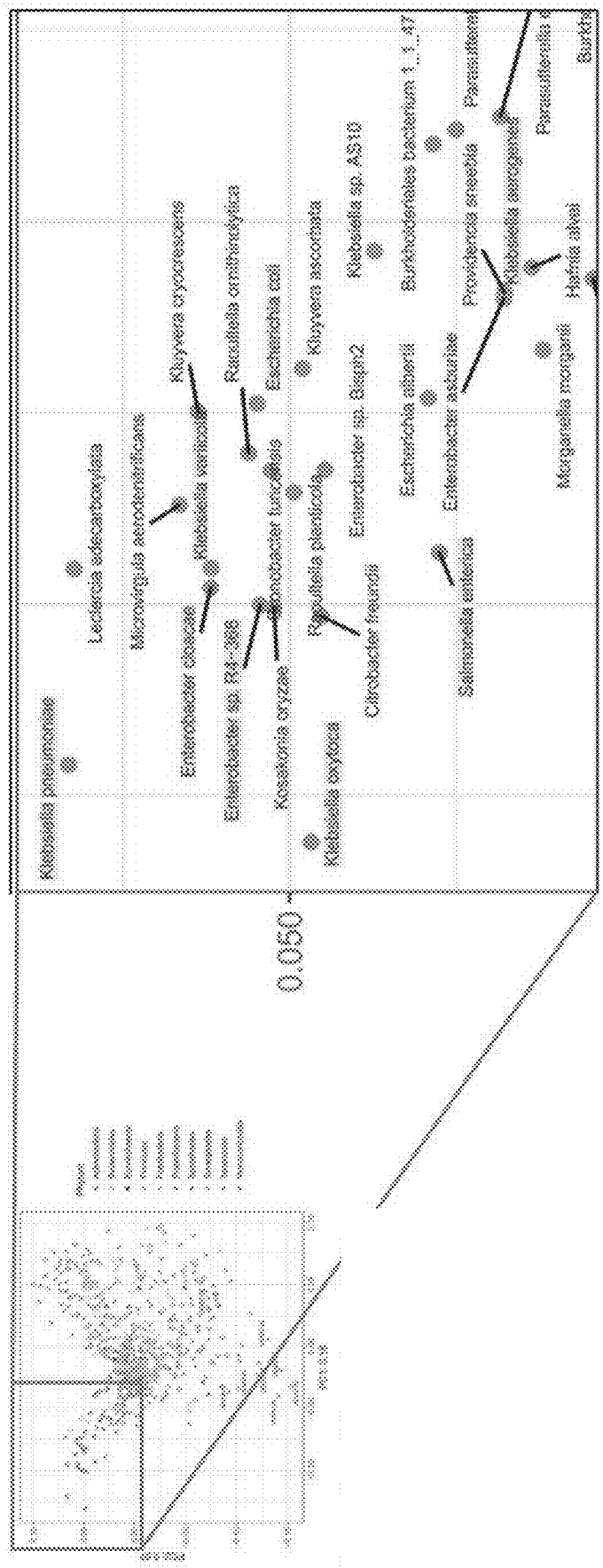
FIG. 5 is a detailed species analysis which highlights the presence of Proteobacteria and other pathogens immediately following administration of vancomycin.
Figure 6A:
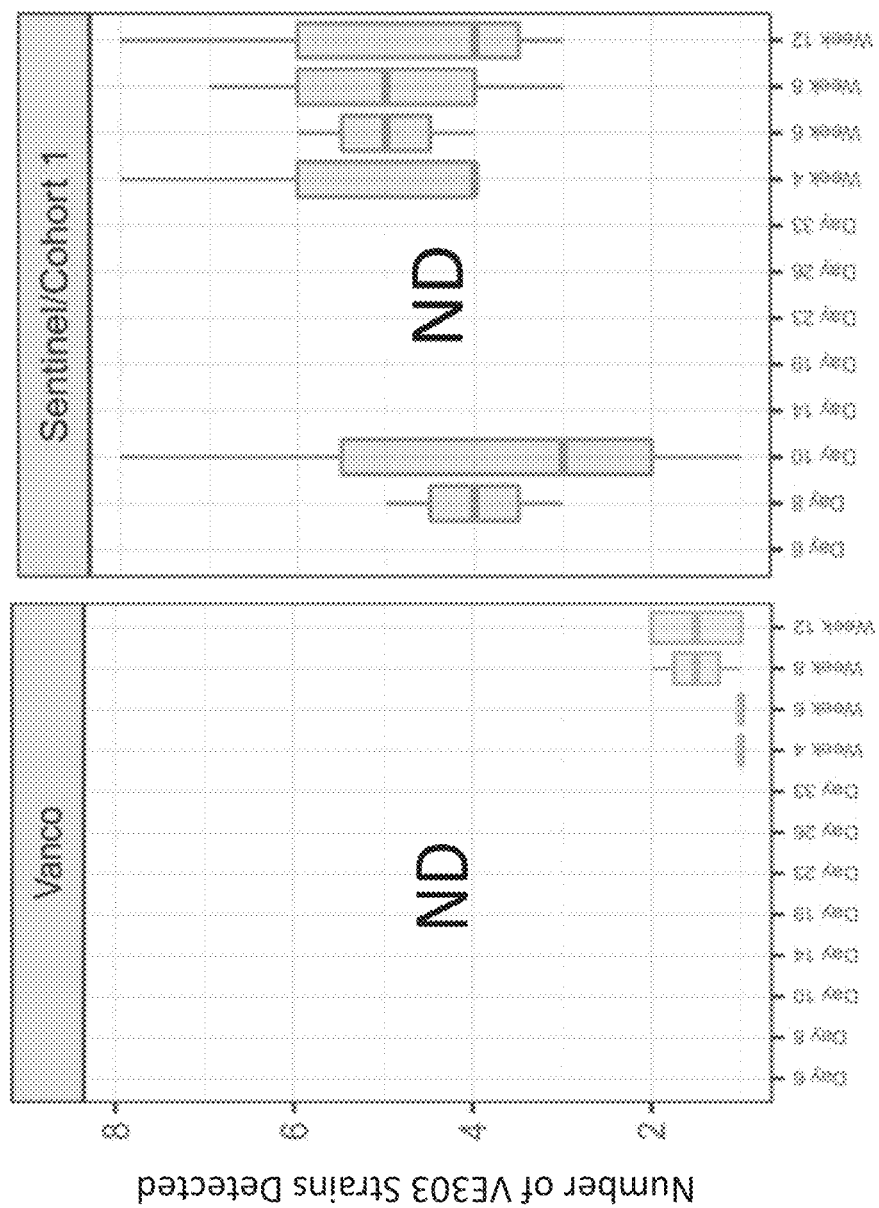
FIGS. 6A-6D present graphs showing colonization data depicted as the number of bacterial strains of composition VE303 detected in the microbiota of the total subject population. ND: data not collected. Vanco: 0 CFU; Cohort 1: $1.6 \times 10^9$ CFU (1 day); Cohort 2: $4.0 \times 10^9$ CFU (1 day); Cohort 3: $8.0 \times 10^9$ CFU (1 day); Cohort 4: $4.0 \times 10^{10}$ CFU (5 days); Cohort 5: $1.1 \times 10^{11}$ CFU (14 days).
Figure 6B:
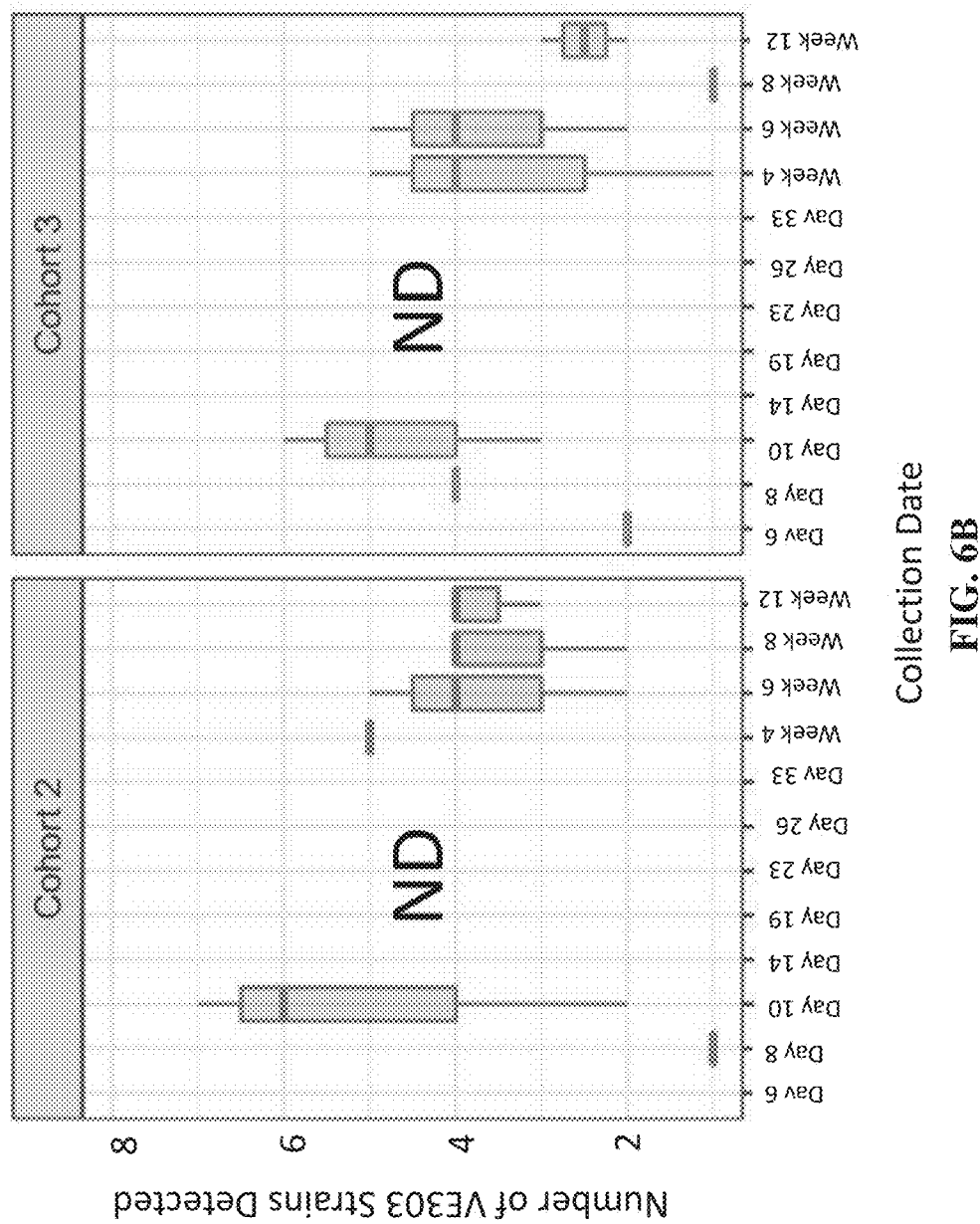
Figure 6C:
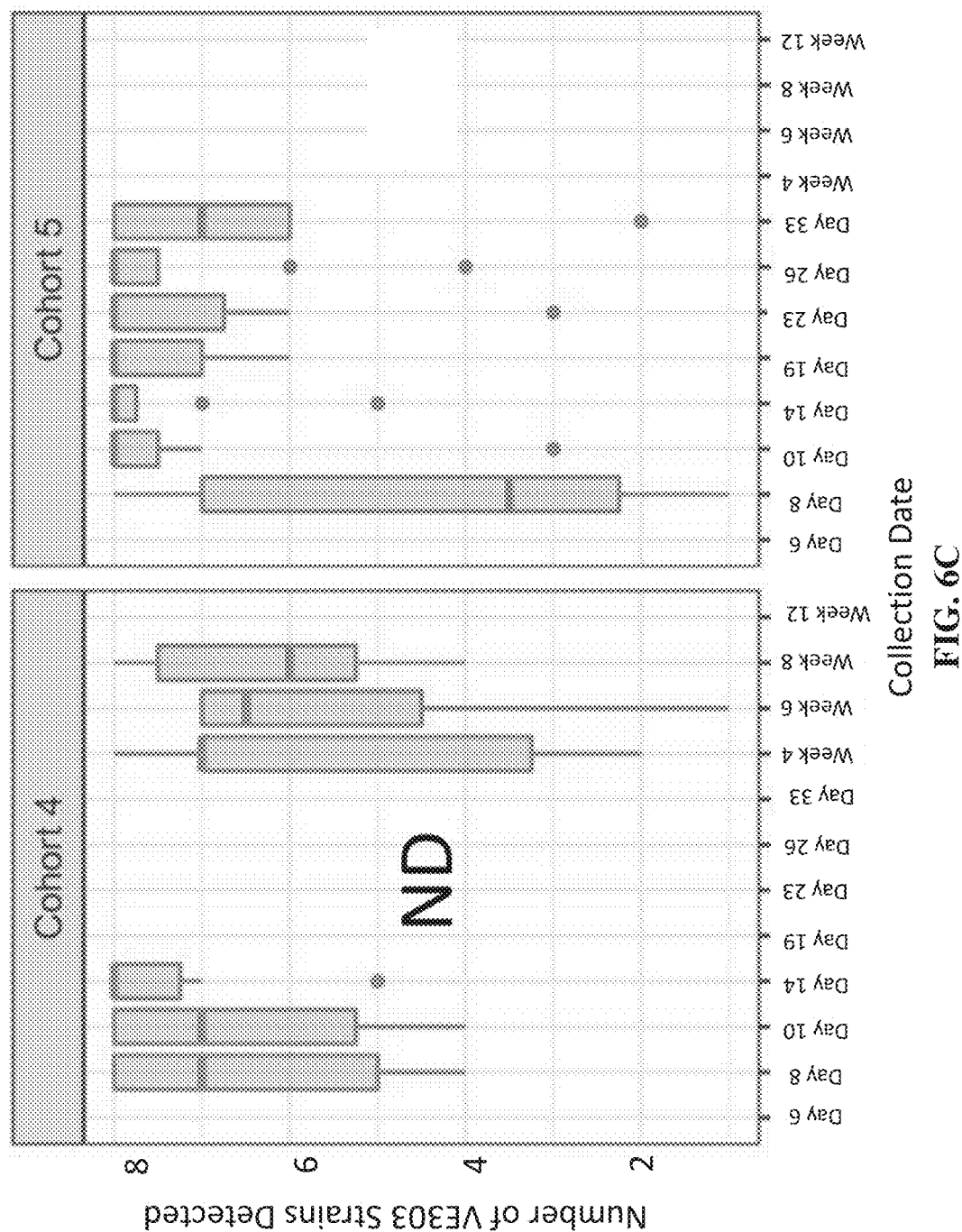
Figure 6D:
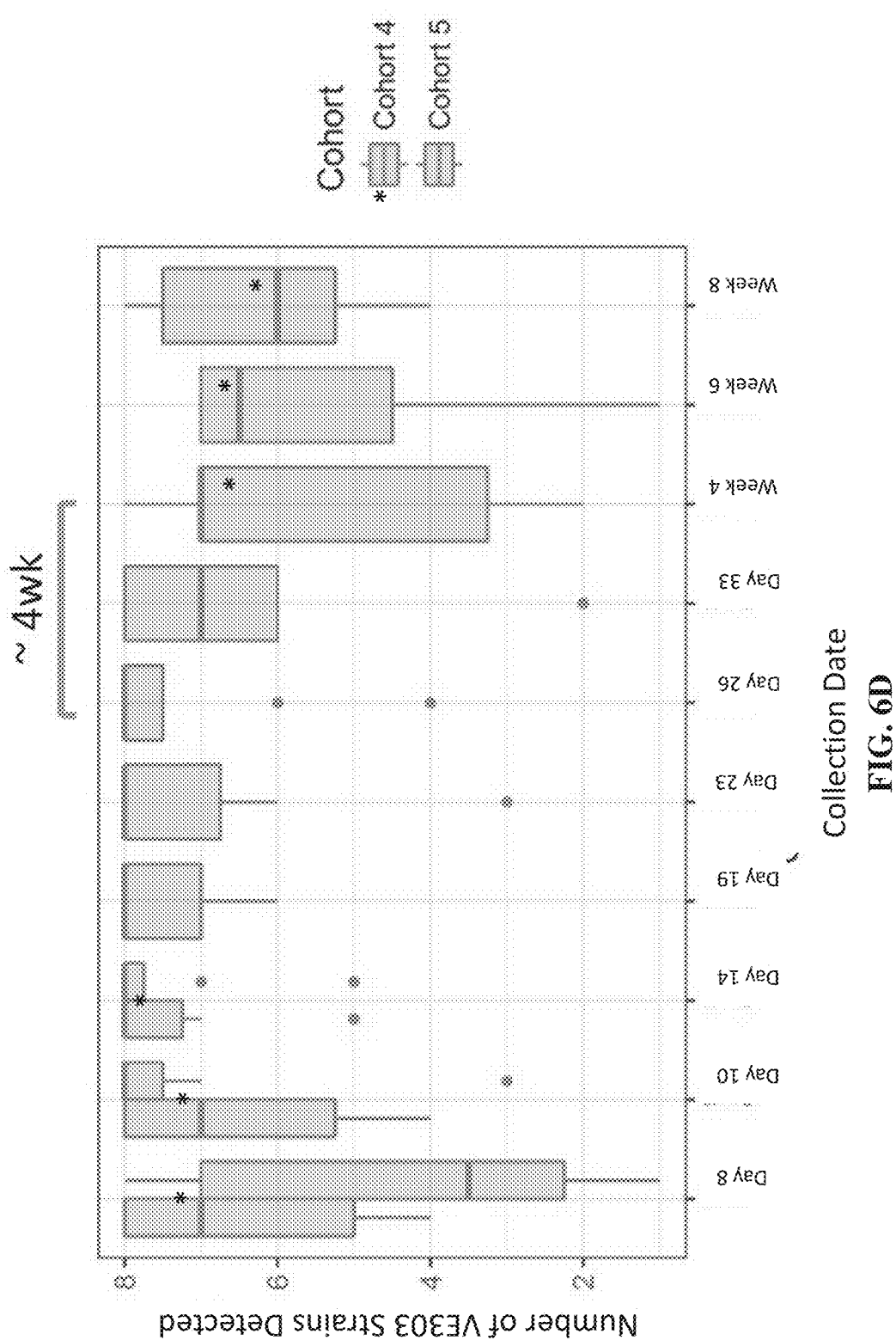

Principal component analysis (PCA) was conducted on the microbiome community composition of each sample to examine the microbiome dynamics following administration of vancomycin and during recovery (see, e.g., Zinkernagel, et al., 2017, Scientific Reports). PCA analysis revealed 3 microbiome community states (FIG. 4A). State 1 corresponded to a baseline microbiome community; State 2 corresponded to a community after administration of vancomycin; and State 3 corresponded to a community after administration of composition VE303. When compared to the vancomycin-only control group, administration of VE303 resulted in a faster recovery of the microbiome. For instance, cohort 5 was found to quickly return to the recovered state within one week of administration of composition VE303, whereas the vancomycin-only control group showed a delayed recovery (FIG. 4B). State 1 was characterized by baseline levels of Firmicutes and Bacteroidetes, state 2 had relatively high levels of Proteobacteria, and state 3 had enhanced levels (abundance) of Bacteroidetes and Firmicutes (including enrichment of bacterial strains of composition VE303) levels compared with state 2 (FIG. 4C). Pathobiont species, including Proteobacteria species, were found to be enriched by administration of vancomycin (e.g., *Klebsiella, Salmonella*, and *Escherichia*) (FIG. 5).

Figure 22A:
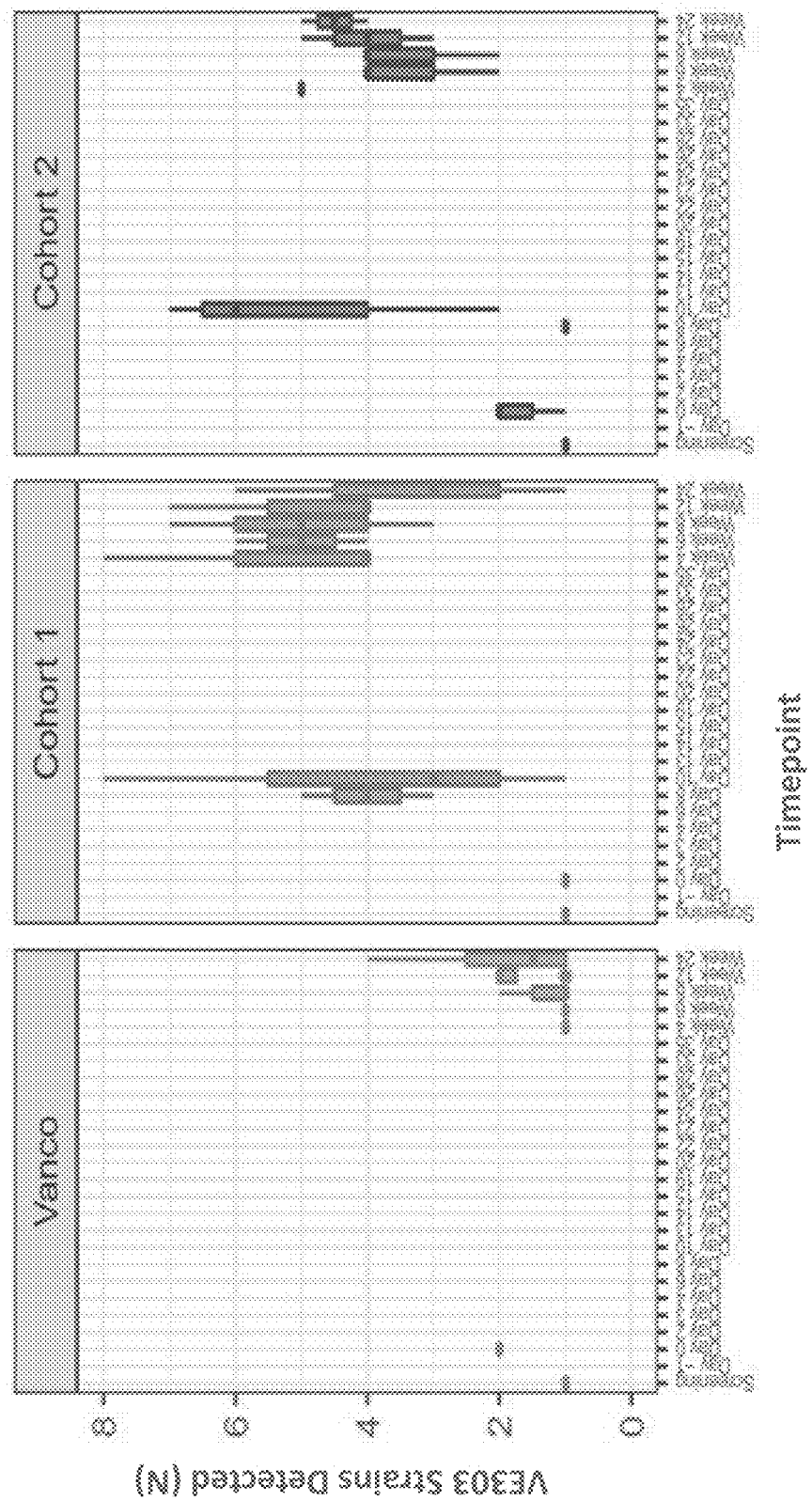
FIGS. 22A-22C present graphs showing colonization data depicted as the number of bacterial strains of composition VE303 detected in the microbiota of the total subject population in Cohorts 1-6 and 8. Samples were taken at the indicated time points up to 24 weeks.
Figure 22B:
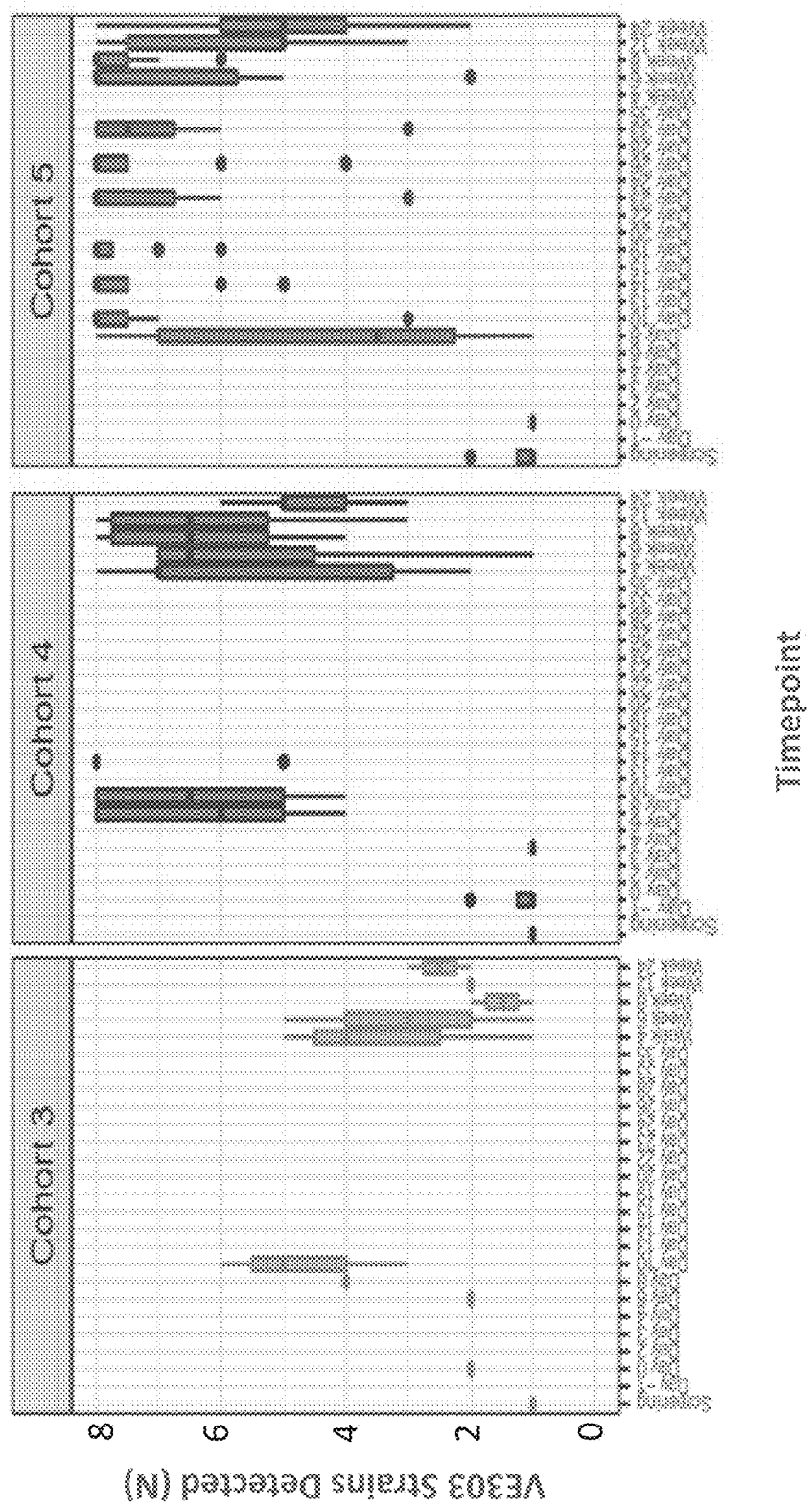
Figure 22C:
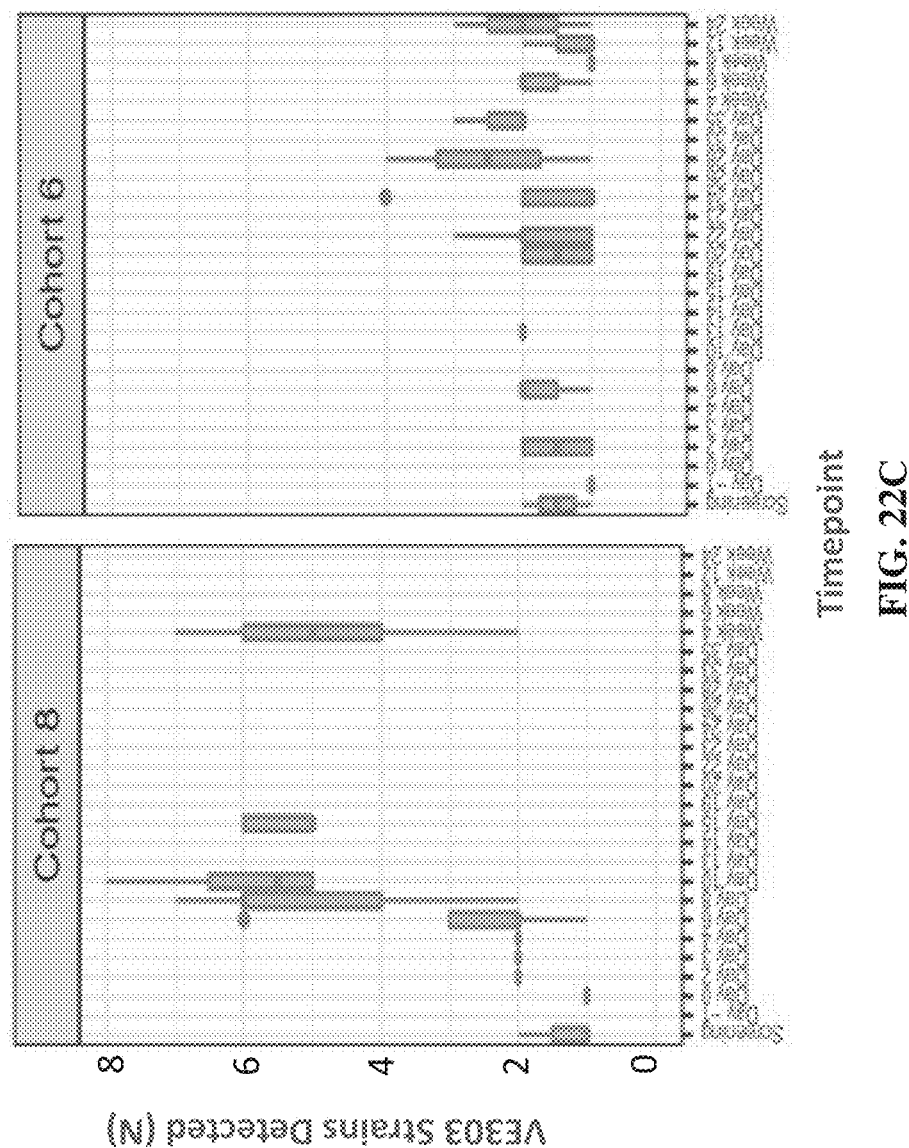
Figure 23:
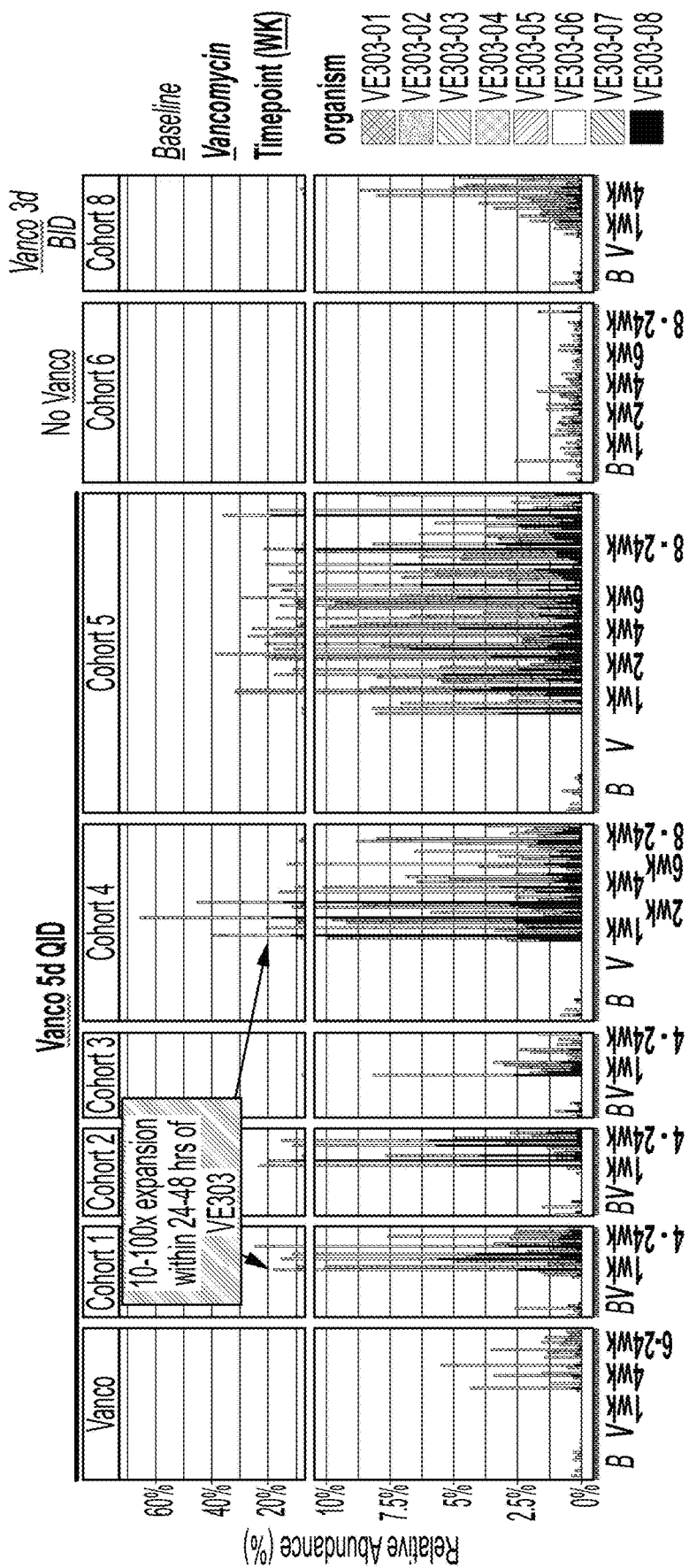
FIG. 23 shows the overall abundance and durability of engraftment of each bacterial strains of composition VE303 in the microbiome of each individual subject in each cohort. For each subject, the bacterial strains of composition VE303 are shown, from top to bottom: VE303-1, VE303-2, VE303-3, VE303-4, VE303-5, VE303-6, VE303-7, VE303-8.
Figure 24A:
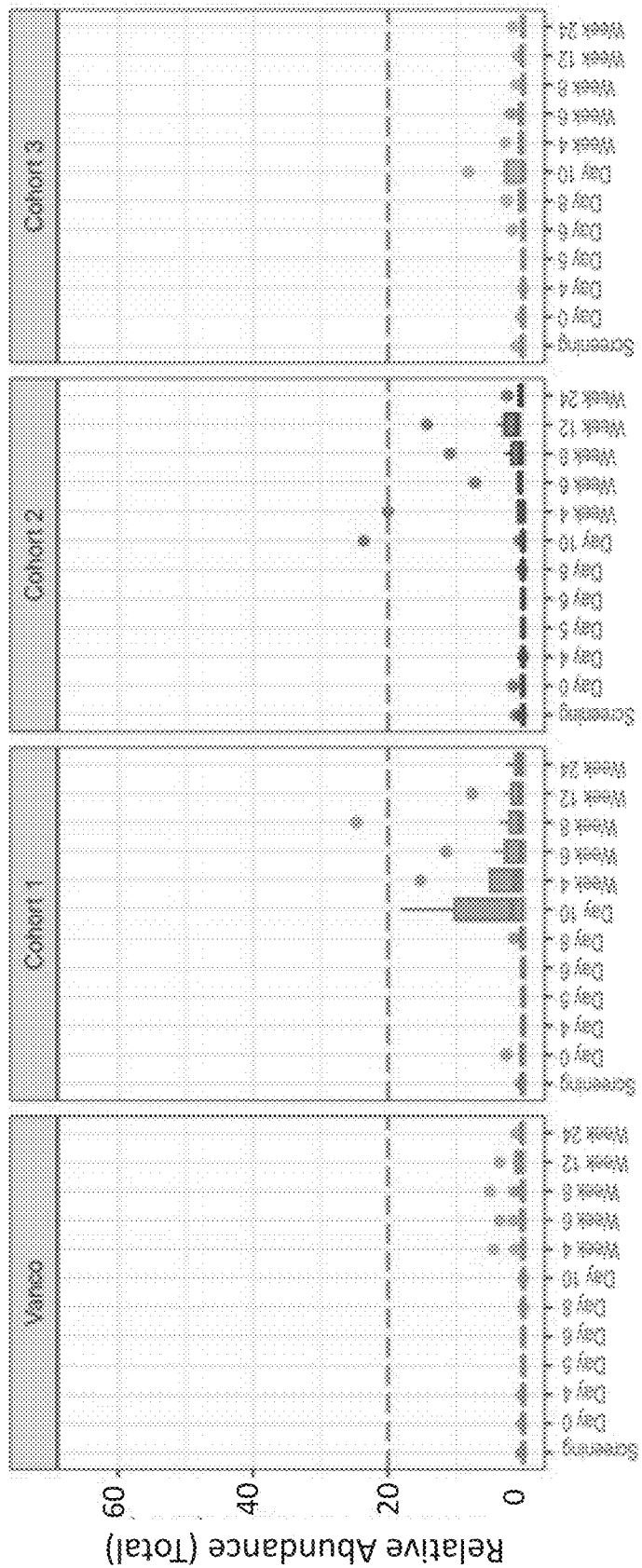
FIGS. 24A-24D show the relative abundance of each bacterial strains of composition VE303 in the microbiome within each of cohorts 1-6 and 8 over time.
Figure 24B:
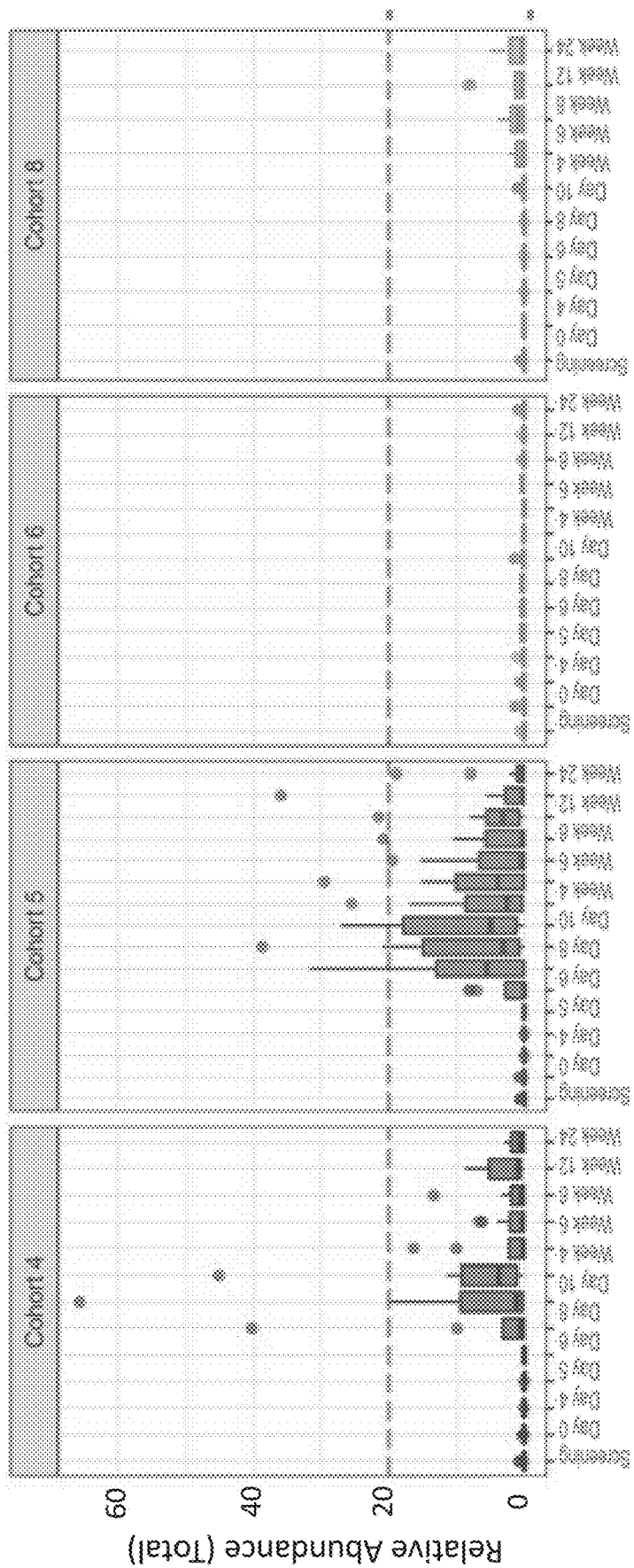
Figure 24C:
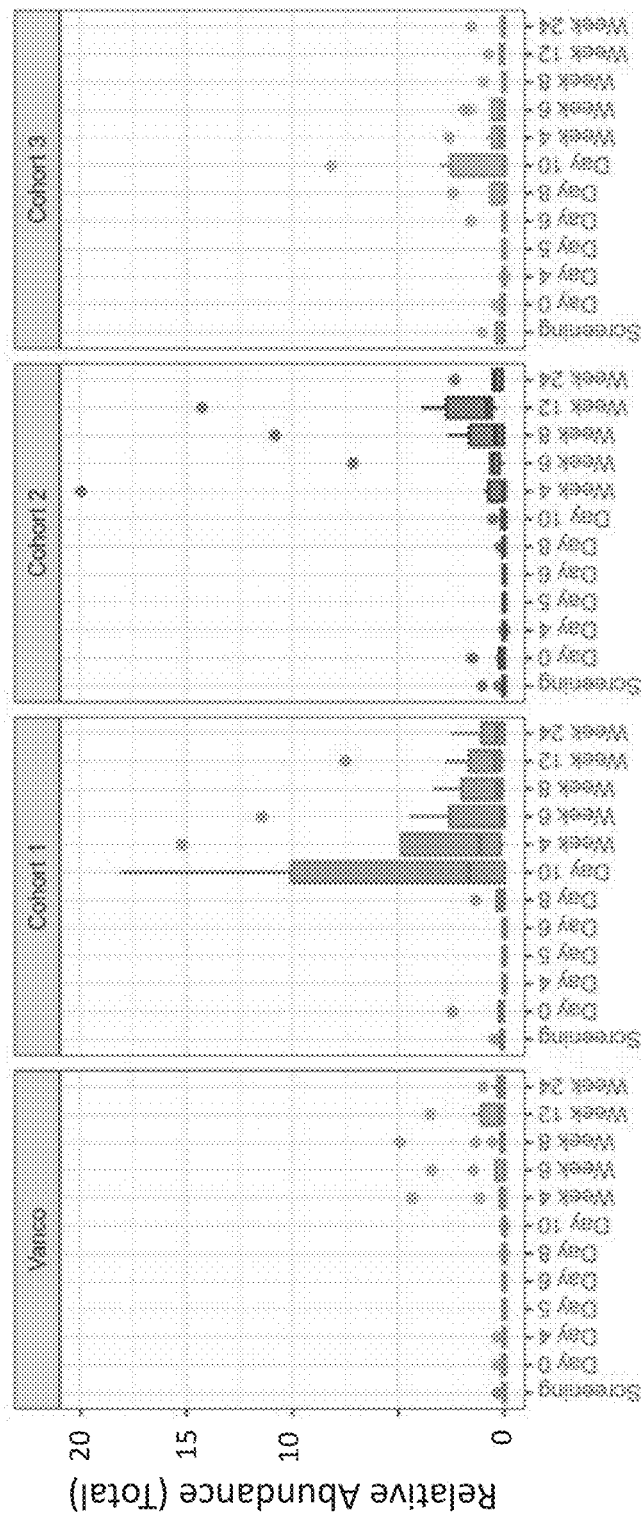
Figure 24D:
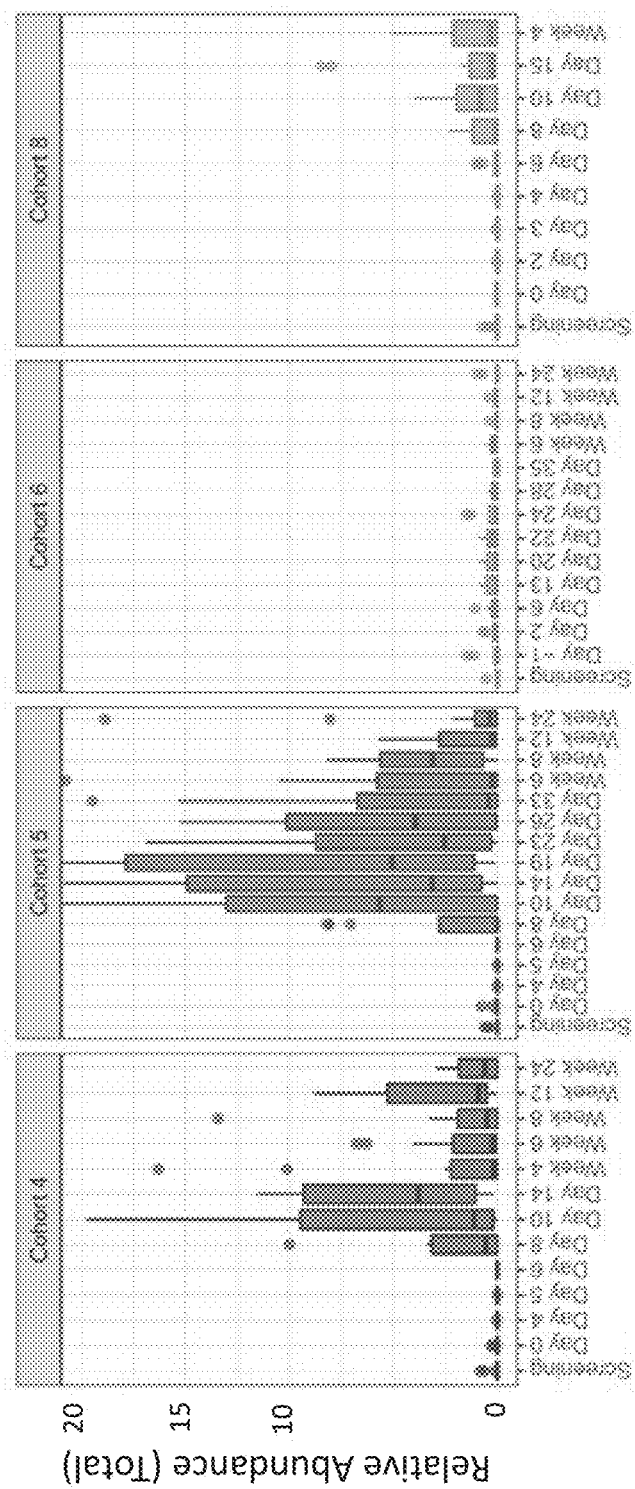

To determine the comparative effectiveness of single versus multiple doses of VE303, samples were obtained from subjects in the vancomycin-only group (control) and each of Cohorts 1-5. Subjects in Cohorts 1-3 were administered a single dose of composition VE303, and subjects in Cohorts 4-5 were administered multiple doses of composition VE303. In sum, multiple doses (over 5 days or 14 days) were found to lead to better overall engraftment (colonization), as expressed by the number of the bacterial strains of composition VE303 observed (FIGS. 6, 8, and 22). A larger number of bacterial strains from composition VE303 engrafted in the multidose cohorts 4, 5, and 8 when compared to the single dose cohorts. Further, the engraftment of bacterial strains from composition VE303 was stable following administration of the composition in most subjects in Cohorts 4, 5, and 8 (FIGS. 7A and 22). In contrast, only engraftment was observed the control group that did not receive vancomycin (FIG. 7B).

Despite the better overall engraftment (colonization) of the bacterial strains of composition VE303 resulting from multiple doses, durable engraftment was observed both in cohorts that received single doses or multiple doses (FIGS. 9A-9C and 23). The vancomycin-only group had a low abundance of bacterial strains from composition VE303 between 3-7 weeks after administration of the composition. The cohorts that received a single dose of composition VE303 showed variable abundance of bacterial strains of composition VE303, with the lower/mid-doses having a higher abundance. The cohorts that received multiple doses of composition VE303 showed a maximal abundance of over 60% of the microbiome (i.e., the bacterial strains of composition VE303 represented over 60% of the microbiome). This abundance decreased at later time points.

Figure 11A:
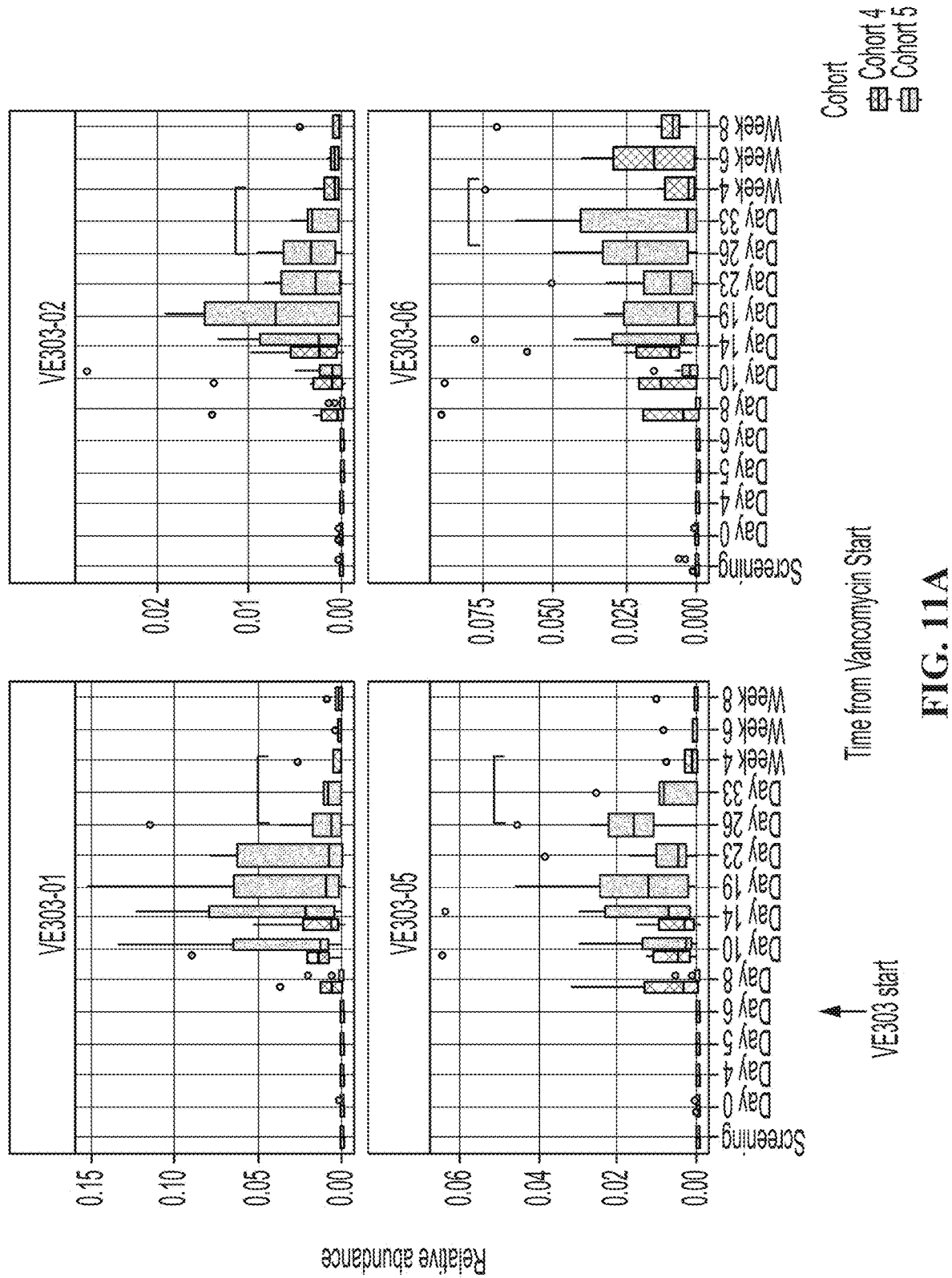
Figure 11B:
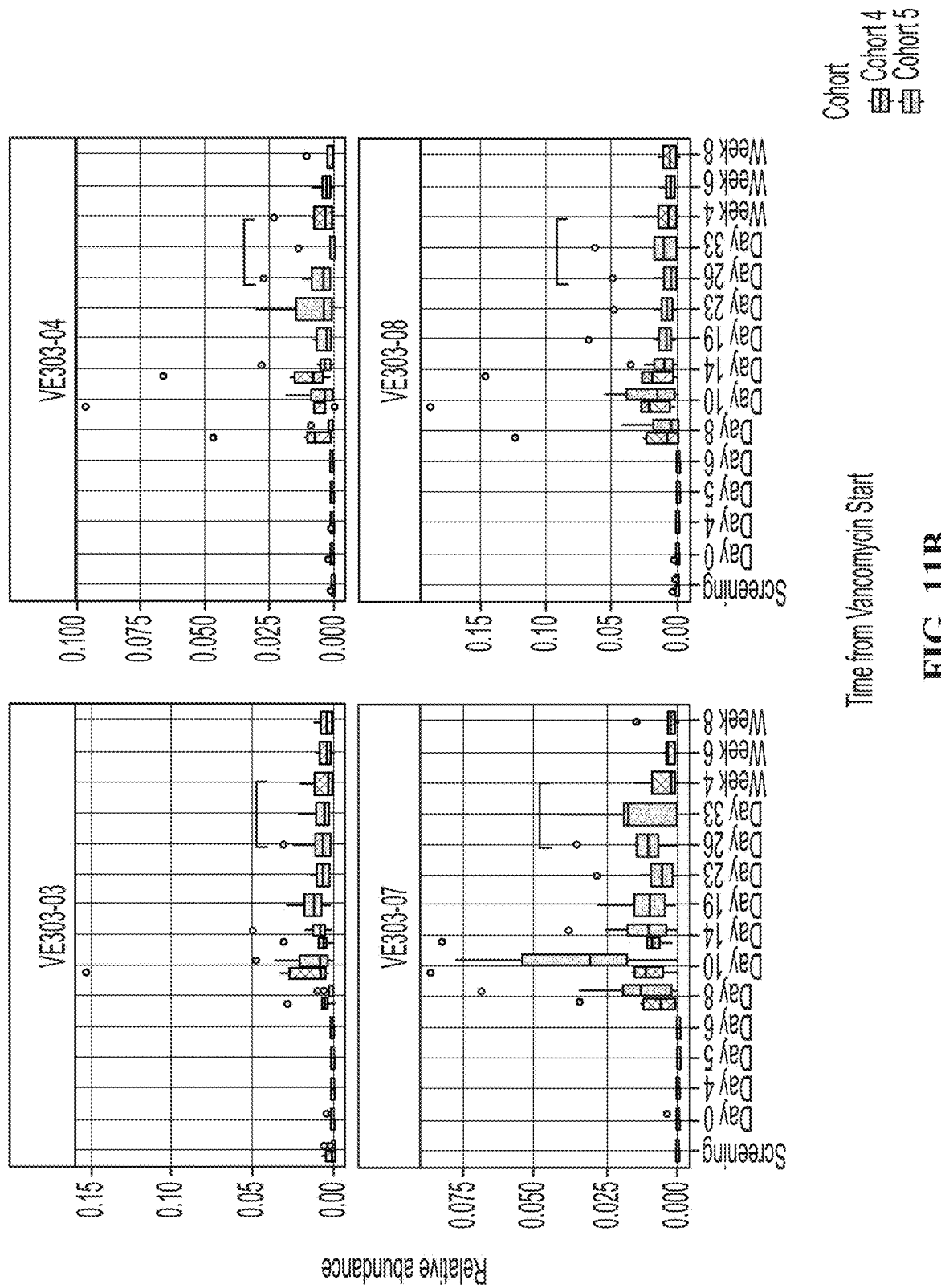
Figure 12:
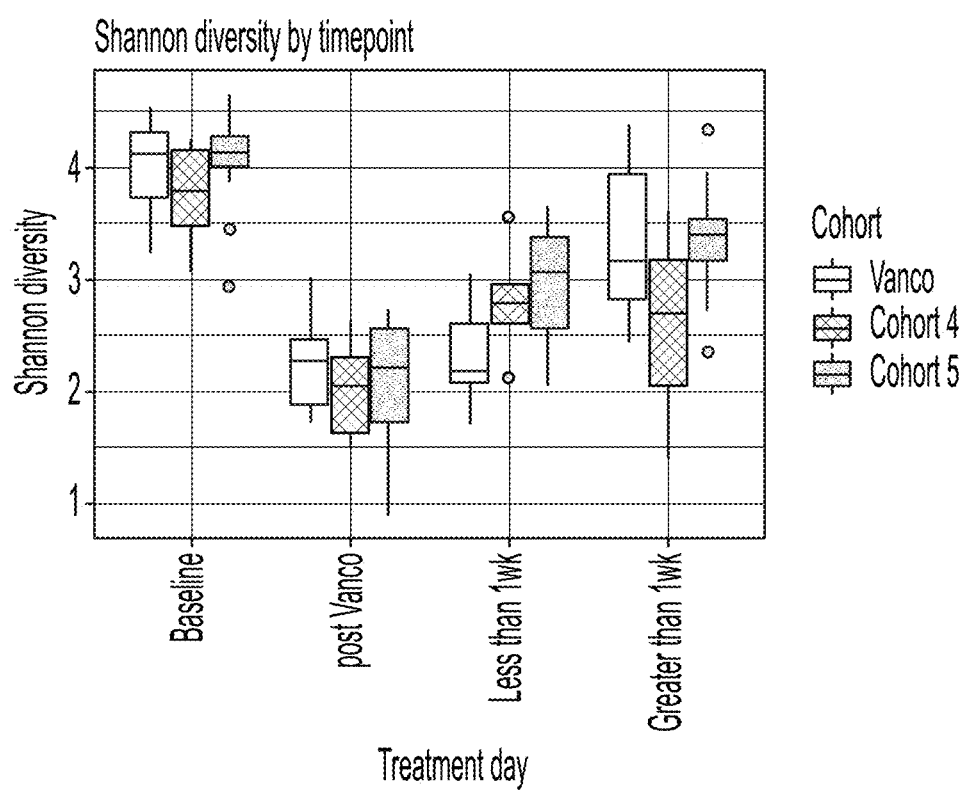
FIG. 12 shows the diversity of the microbiota over time: at baseline, post-administration of vancomycin ("post-Vanco"), less than one week following administration of composition VE303, and greater than one week following administration of composition VE303. For each treatment day, the data are presented, from left to right: vancomycin only ("Vanco"), Cohort 4, and Cohort 5.

The bacterial strains of composition VE303 were estimated to have expanded 10-100-fold within 2 days following administration of the composition based on the dose. FIGS. 10 and 24 show the overall trend in abundance of bacterial strains of composition VE303 across each cohort. In particular, in Cohort 5, the abundance of bacterial strains of composition VE303 increased at about 4 weeks post-administration (FIGS. 11A and 11B). Diversity of bacterial species present in the microbiome may also be a measure of engraftment efficacy and overall recovery, as shown for Cohorts 4, 5, and 8 in FIGS. 12 and 25.

Figure 26A:
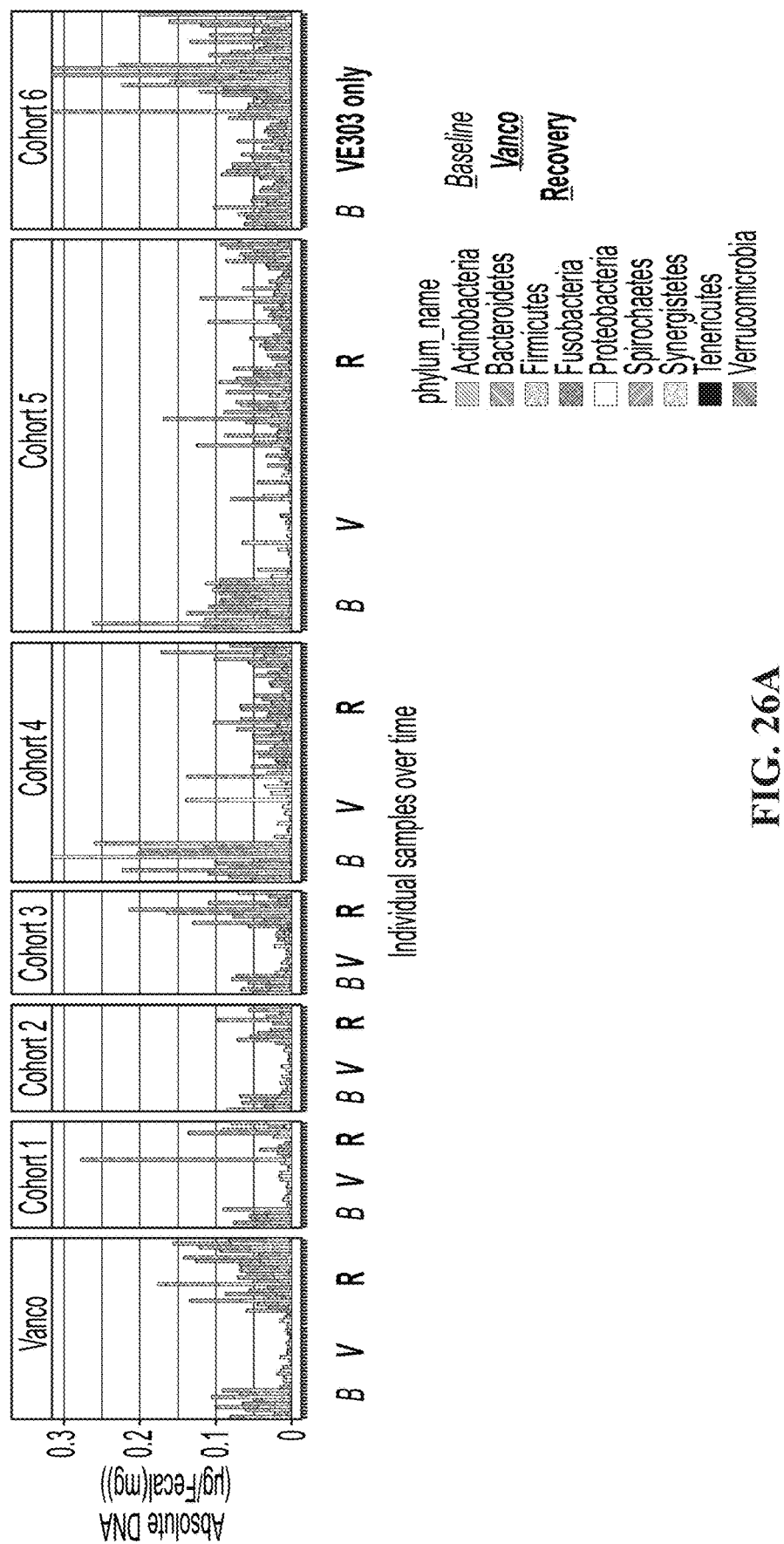
FIGS. 26A-26B show a quantification of the bacterial phyla prior to (baseline), after administration of vancomycin, and after administration of composition VE303. "B" indicates the quantity of each bacterial phyla detected at baseline, "V" indicates the quantity of each bacterial phyla detected during vancomycin treatment, and "R" indicates the quantity of each bacterial phyla detected during recovery from vancomycin treatment.
Figure 26B:
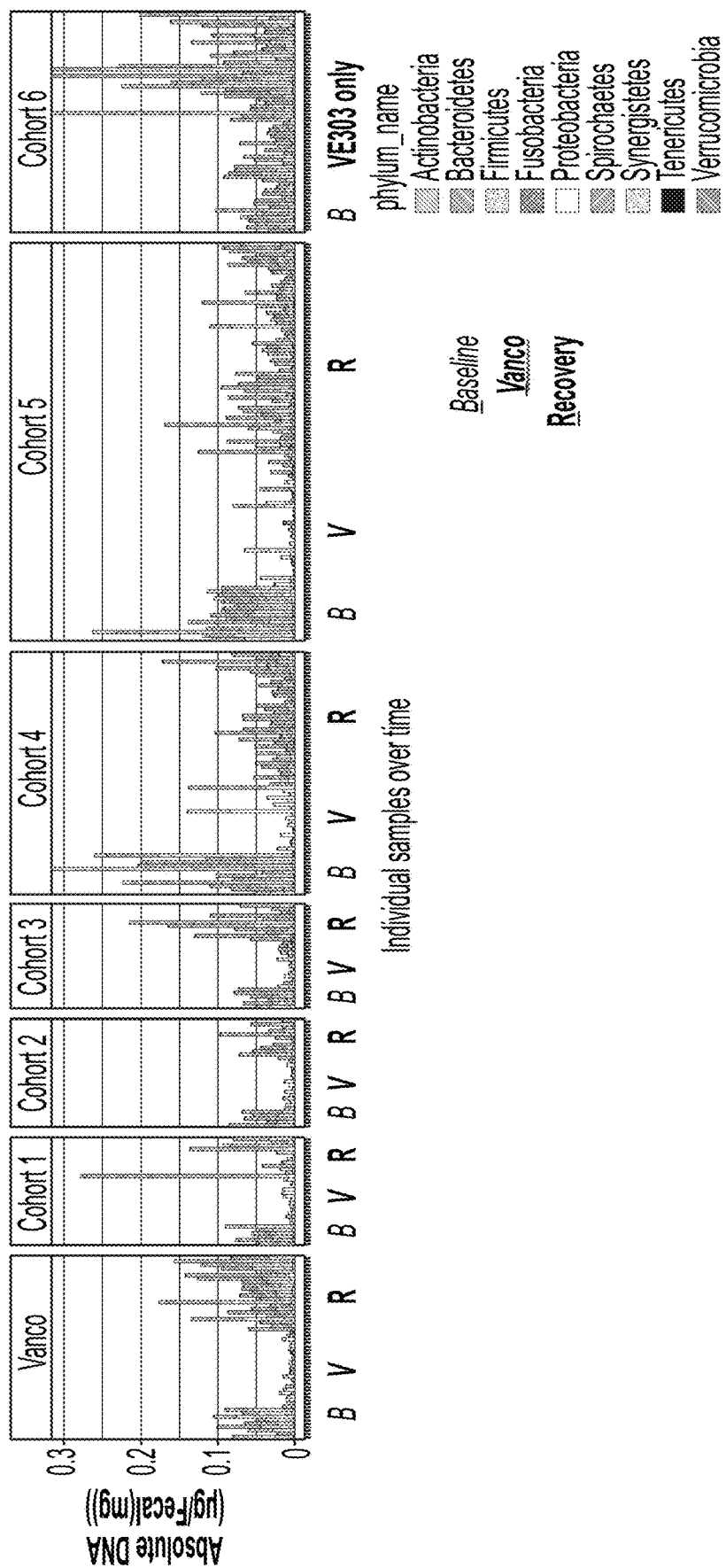
Figure 27:
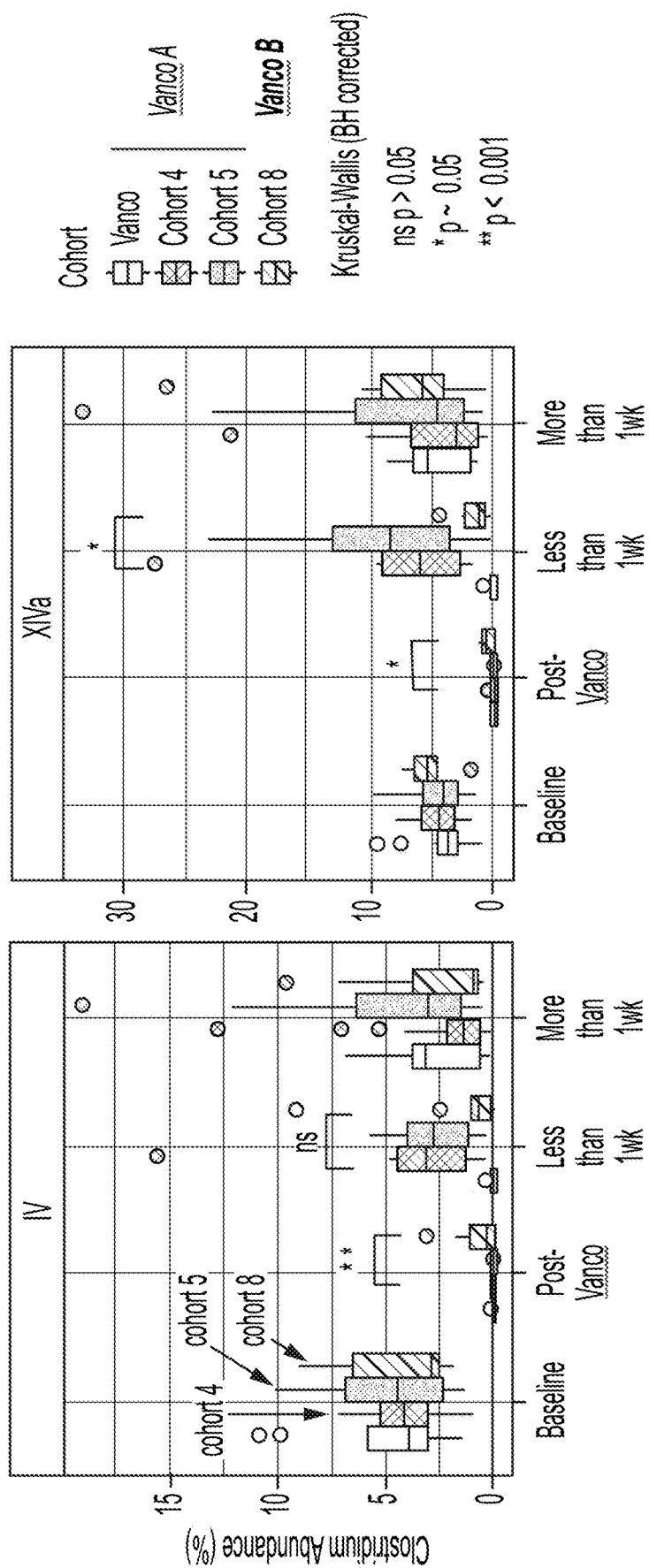
FIG. 27 shows the abundance of *Clostridium* Cluster IV and XIVa bacteria after treatment with vancomycin in cohorts 4, 5, and 8 over time. "ns" denotes p values that are greater than 0.05, "*" denotes p values that are about 0.05, and "**" denotes p values that are less than 0.001 as calculated with the Kruskal-Wallis test.

Vancomycin treatment significantly reduces the absolute abundance of bacteria in the microbiota of a subject (FIG. 26). *Clostridium* cluster IV and XIVa bacterial species levels are more decreased by five days of vancomycin administration QID (Cohorts 4 and 5) compared to three days of vancomycin administration BID (Cohort 8) (FIG. 27). The abundance of bacteria will recover both with and without administration of VE303 once the vancomycin is no longer administered (FIGS. 26 and 27).

Conclusions

In sum, composition VE303 was well-tolerated and safe at all doses. Administration of composition VE303 resulted in early, robust, and durable colonization with early recovery (increased recovery) of a normal microbiota following administration of vancomycin. Furthermore, the robustness of engraftment improved with treatment duration.

Example 1B: Phase 1 Study of Composition VE303 in Healthy Volunteers: Cohorts 7-9

An additional Phase 1 study is conducted to assess the safety and tolerability of composition VE303 in healthy volunteers (HVs) after vancomycin-induced dysbiosis. As shown in Table 1B, HVs were divided into three cohorts that received different doses of vancomycin, prior to receiving the same dose of VE303. Pharmacokinetics, including strain colonization and durability) and pharmacodynamics (e.g., restoration of resident microbiota) were evaluated by metagenomics sequencing of fecal bacteria collected longitudinally.

TABLE 1B

Dosing Regimens for Phase 1 cohorts 7-9

| Group | Vancomycin Dose | | Total Dose Administered |
|---|---|---|---|
| Cohort 7 | 125 mg BID/ 1 day | 10 capsules per day for 2 days; followed by 2 capsules for 3 days | $2.1 \times 10^{10}$ CPU |
| Cohort 8 | 125 mg BID/ 3 days | 10 capsules per day for 2 days; followed by 2 capsules for 3 days | $2.1 \times 10^{10}$ CPU |
| Cohort 9 | 125 mg QID/ 5 days | 10 capsules per day for 2 days; followed by 2 capsules for 3 days | $2.1 \times 10^{10}$ CPU |

Example 1C: Rationally Defined Consortium of Human Bacterial Strains for rCDI

Figure 13A:
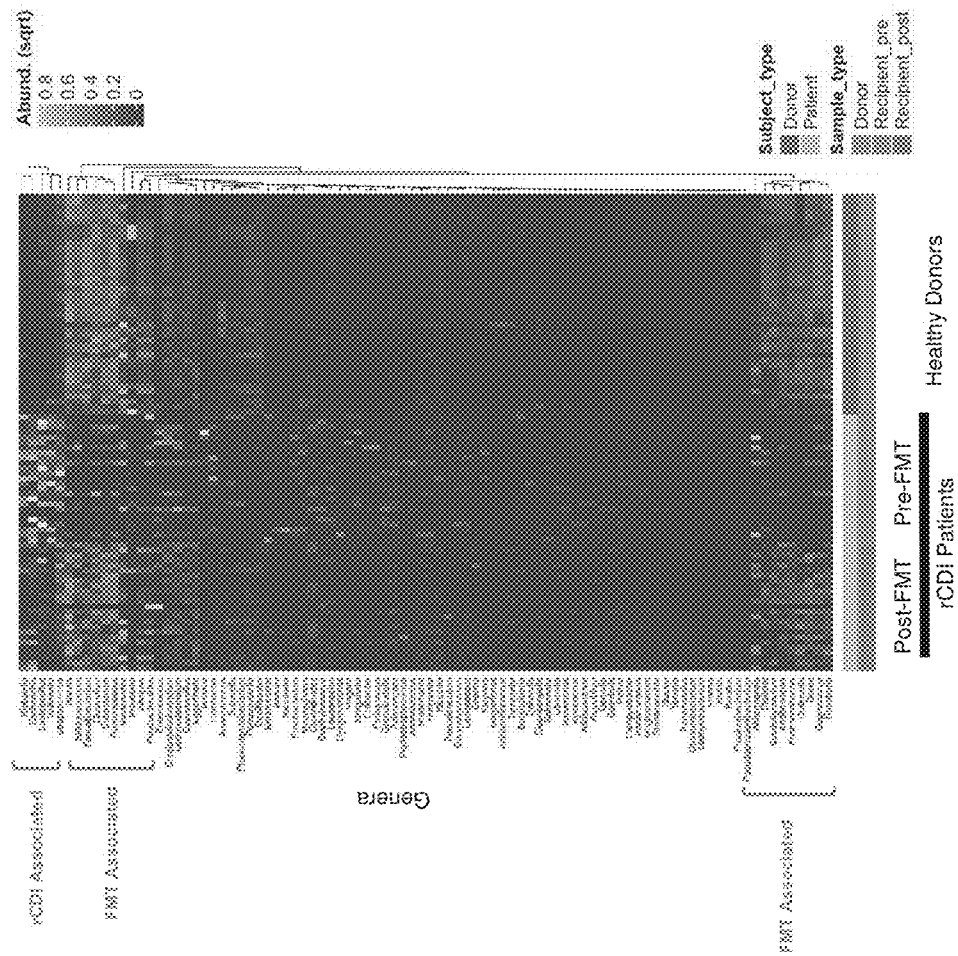
FIGS. 13A and 13B shows a rationally defined consortium of human bacterial strains for rCDI.

Stool samples were collected from healthy donor volunteers and patients with recurrent *Clostridioides difficile* infection (rCDI) in collaboration with Leiden University Medical Center and the Netherlands Donor Feces Bank (NDFB). The abundance in the stool samples of the top bacterial genera associated with recovery from rCDI were analyzed before and after fecal microbiota transplantation (pre-FMT, post-FMT) (FIG. 13A). The response to fecal microbiota transplant (FMT) in rCDI patients is associated with transfer of *Clostridium* clusters IV and XIVa bacteria.

Figure 13B:
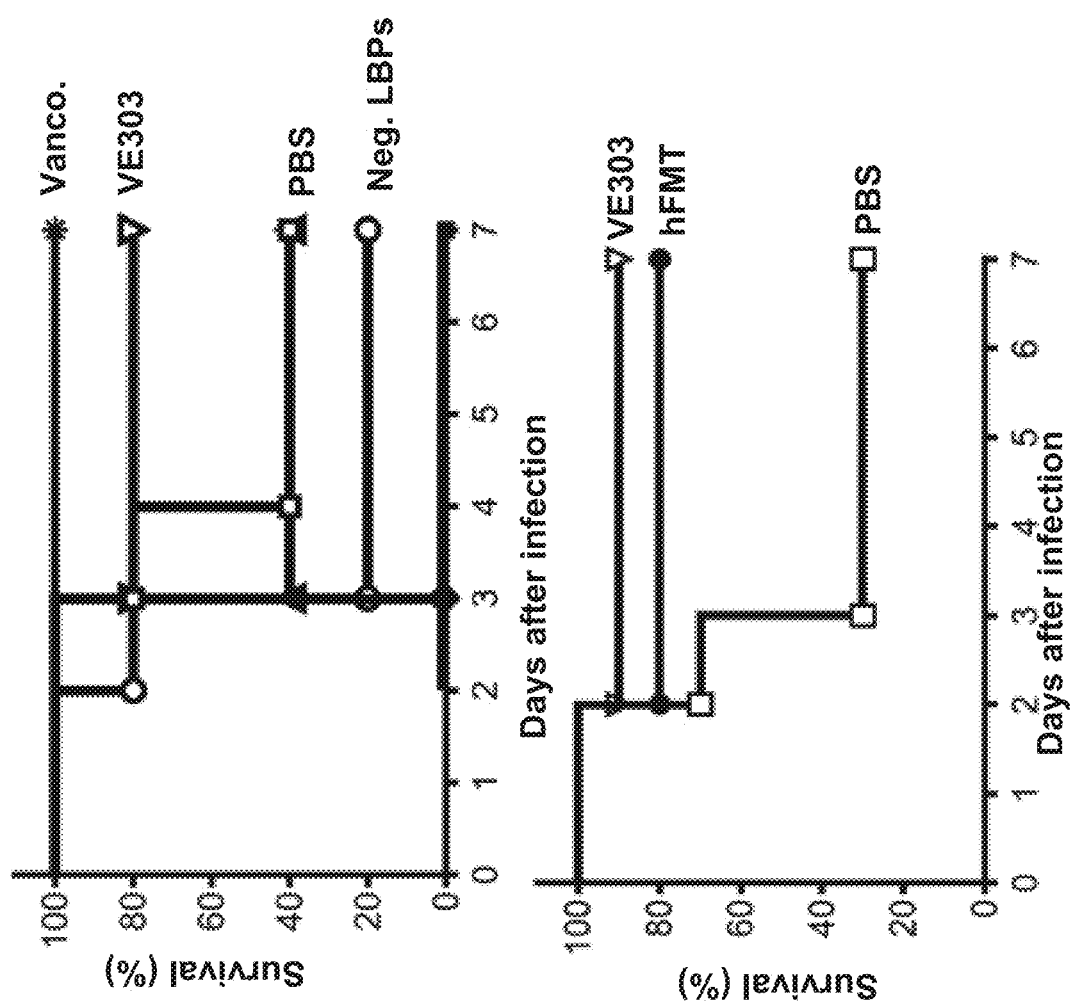

Mice were infected with *Clostridium difficile* (CDI) and administered VE303 or human FMT. Roughly 85% of mice treated with VE303 and roughly 80% of mice treated with human FMT survived to at least 7 days after CDI. In contrast, roughly 30% of mice treated with PBS and roughly 20% of mice treated with negative live biotherapeutic products (LBPs) survived to at least 7 days after CDI (FIG. 13B). Therefore, VE303 uniquely promotes the survival of mice in a model of CDI infection that is comparable to a human FMT.

Example 2: Phase 2 Adaptive, Dose-Finding Study of VE303 to Prevent Recurrent *Clostridium difficile* (rCDI) Infections in Adult Subjects The purpose of this study is to determine the effective therapeutic dose of VE303 in preventing rCDI in adult subjects. VE303 is a rationally defined bacterial composition comprising 8 distinct species of commensal, nonpathogenic, avirulent, clonal bacteria that are associated with response in FMT, suppress *C. difficile* growth in vitro, and improve survival in *C. difficile* infection (CDI) models (Table 1).
Methods A Phase 2 dose-finding analysis is conducted on adult volunteers with at least 2 episodes of rCDI to determine the effective therapeutic dose of VE303 to lessen the recurrence of or prevent rCDI. The dosing regimens are as outlined in Table 2 (below). Prior to administration of the VE303 dose or placebo, subjects were administered vancomycin at any dose described herein or at the standard-of-care dose for rCDI. Stool samples are collected from subjects for *C. difficile* testing (e.g., glutamate dehydrogenase, toxin protein, *C. difficile* PCR, *C. difficile* culture for ribotyping and toxin assay), microbiome composition, VE303 strain detection, antibiotic concentrations, metabolomics, culture, and detection of antibiotic resistant bacteria other than *C. difficile* (e.g., Carbapenem-resistant enterobacteriacea [CRE], extended β-lactamase producing Enterobacteriaceae [ESBL], or vancomycin-resistant *Enterococcus* [VRE]).

TABLE 2

Dosing Regimens for Phase 2 trial

| Group | Dose | Total Dose Administered |
|---|---|---|
| Placebo | 10 capsules per day/14 days | N/A |
| VE303 low dose | 5 capsules per day/7 days | $2.8 \times 10^{10}$ CFU |
| VE303 mid dose | 5 capsules per day/14 days | $5.6 \times 10^{10}$ CFU |
| VE303 high dose | 10 capsules per day/14 days | $1.1 \times 10^{11}$ CFU |
| VE303 very low dose | 2 capsules per day/14 days | $2.2 \times 10^{10}$ CFU |

Example 3: Strain Colonization and Microbiome Dynamics of Healthy Volunteers Administered a Defined Consortium of Commensal Bacterial Isolates Background Alterations of the human gut microbiota are associated with infections by opportunistic pathogens like *Clostridioides difficile* (*C. difficile*). Reduction in *C. difficile* infection recurrence rate has been shown with fecal microbiota transplantation (FMT); however, FMT carries inherent risks and variability. VE303, a live biotherapeutic product (LBP), is being developed for the prevention of recurrent *C. difficile* infection (rCDI). VE303 is a rationally defined bacterial consortium that consists of 8 purified, clonal strains belonging to *Clostridium* clusters IV, XIVa, and XVII. The strains were isolated from the fecal matter of healthy volunteers, banked as pure cultures, and manufactured under cGMP conditions. Safety, tolerability, pharmacokinetics (PK) and pharmacodynamics (PD) of VE303 were assessed in healthy volunteers (N=33). Increasing doses of VE303 were administered with or without a 5-day course of oral vancomycin. Fecal samples were collected longitudinally up to 12 weeks and metagenomic sequencing was performed on the Illumina platform to quantify the colonization of the VE303 strains over time (PK) and their impact on the recovery of the resident microbiota following vancomycin exposure (PD). A scalable bioinformatic method that utilizes unique marker sequences for each VE303 strain was developed to precisely define PK by differentiating the members of the LBP from resident strains. Dosing conditions were identified where the VE303 strains rapidly increased in abundance and were detected at least 12 weeks after administration of the consortium. VE303 also led to an enhancement in the gut microbiota recovery post-vancomycin, demonstrated by an accelerated increase in resident *Clostridium* and Bacteroidetes species and reduced Proteobacteria. Collectively, these data indicate for the first time that LBPs based on rationally defined bacterial consortia are a safe microbiome-based treatment that can durably colonize the gut and modulate the microbiota of human recipients.

Pharmacokinetics of VE303 in Normal, Healthy Volunteers

Figure 17A:
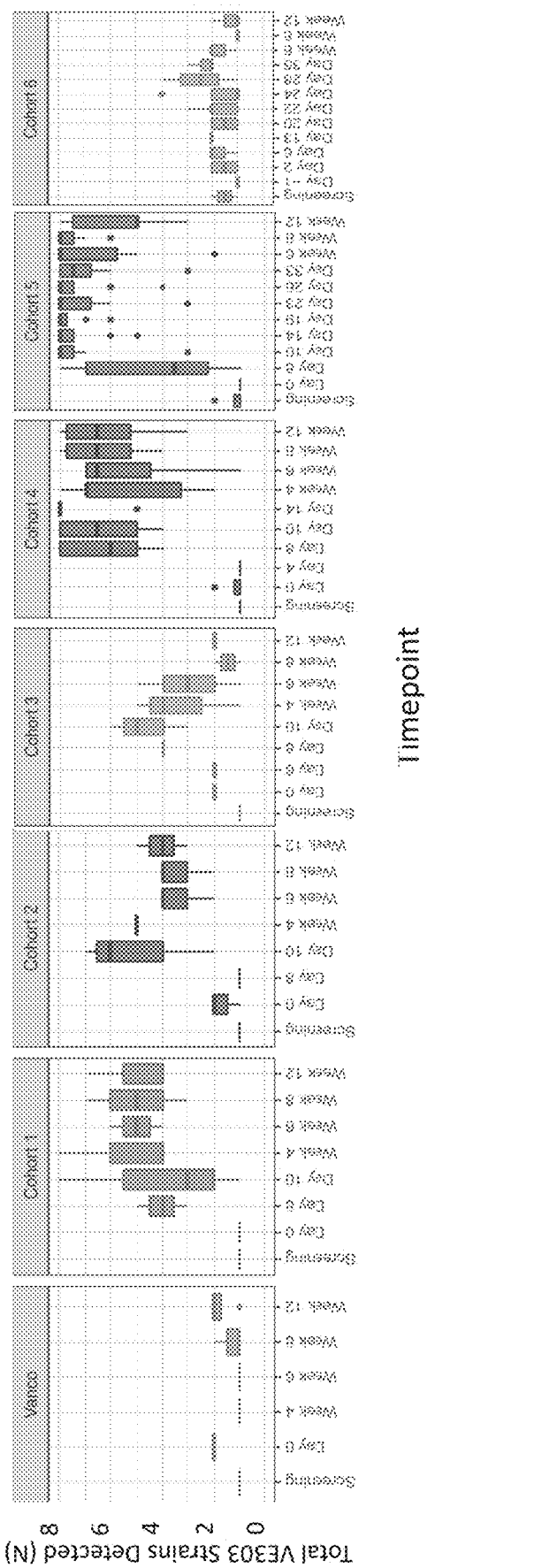

The total numbers of VE303 strains detected in normal, healthy volunteer subject was evaluated following collection of stool samples and Illumina sequencing to identify each VE303 strain using unique 50 base pair (bp) marker sequences (FIGS. 17A-17B). All 8 strains of the VE303 consortium were detected in nearly all Cohort 4 and 5 subjects.

Figure 17C:
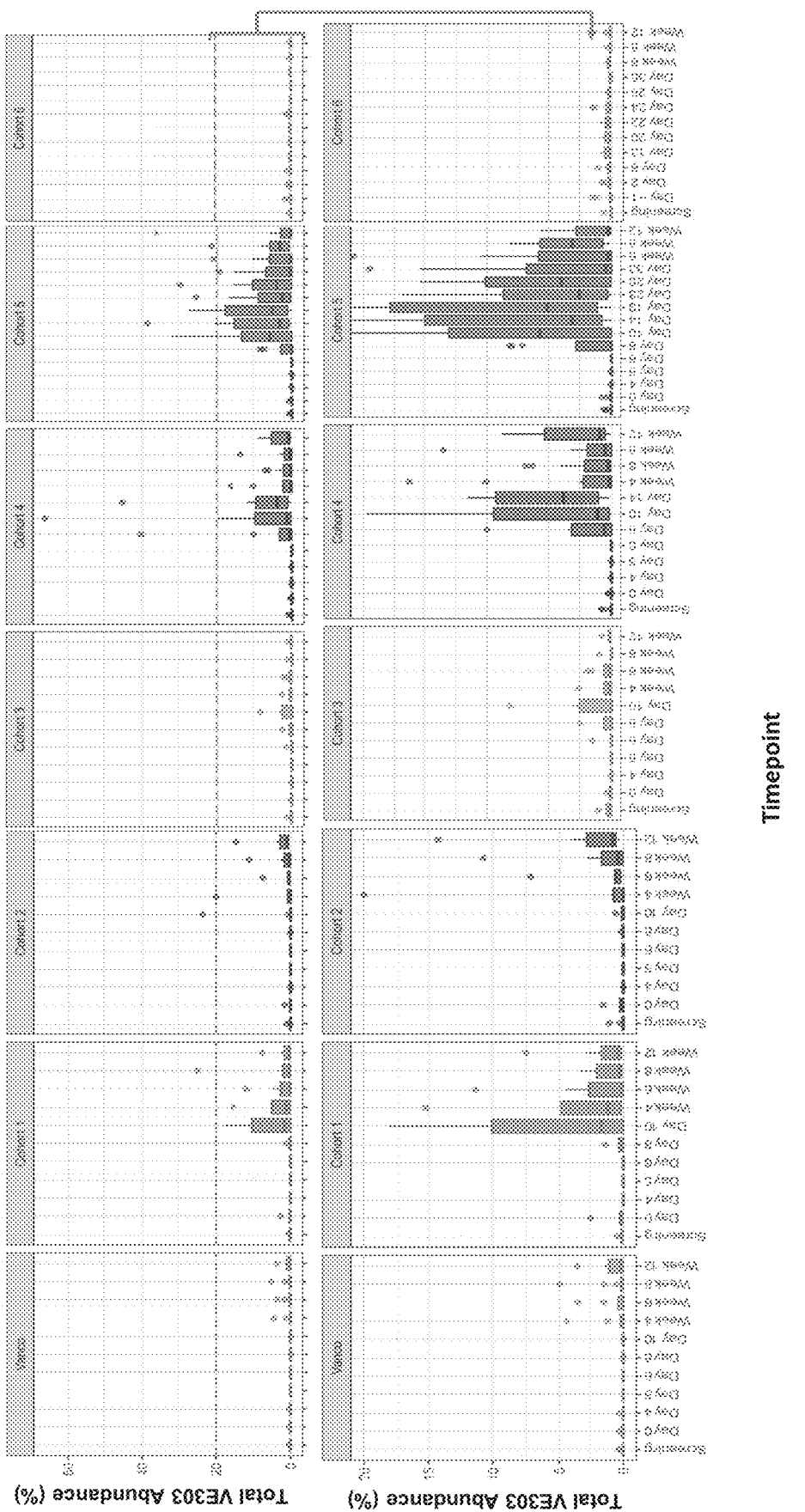

The total abundance of the VE303 consortium in each subject over time was measured (FIG. 17B. The VE303 consortium rapidly expands ~10-100-fold within the first 48 hours after administration and then stabilizes to 5-10% of the microbiome. The VE303 consortium constitutes a significant fraction of the microbiome up to 12 weeks after stopping dosing with VE303. Low abundance VE303-related species were detected in the vancomycin (Vanco) only cohort subjects (FIGS. 17C-17D).

Pharmacodynamics of VE303 in Normal, Healthy Volunteers

Figure 18A:
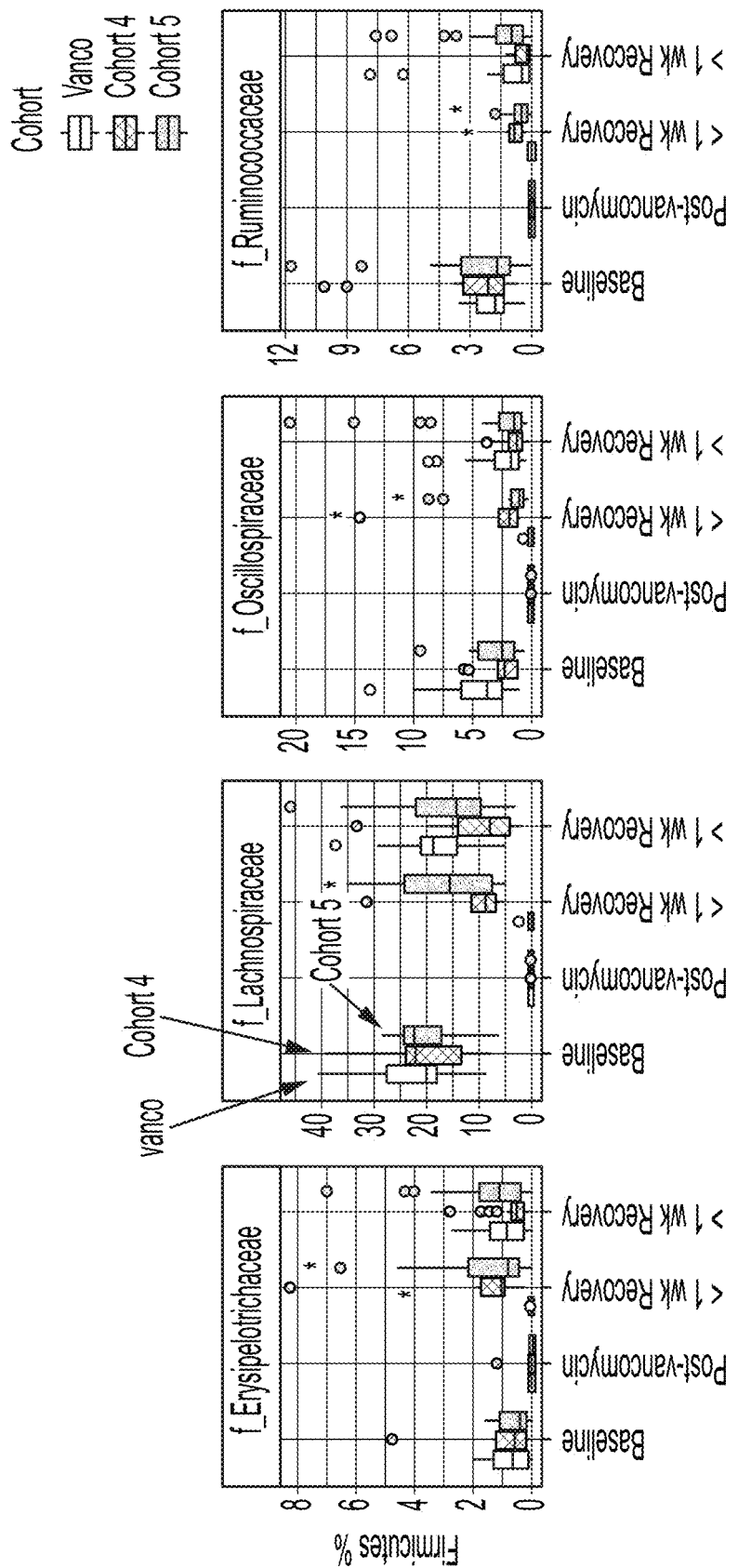
FIGS. 18A-18C show pharmacodynamics (PD) of VE303 in normal healthy volunteers. Changes in the total relative abundance per subject of the most abundant Firmicutes, Bacteroidetes, and Proteobacteria after vancomycin (post-vancomycin), up to 1 week of recovery (<1 wk recovery), or greater than 1 week of recovery (>1 wk recovery). The natural recovery after vancomycin alone is compared to the recovery in the presence of VE303 (Cohorts 4 and 5). Asterisk (*) indicates p<0.05 Kruskal-Wallis, BH corrected.
Figure 18B:
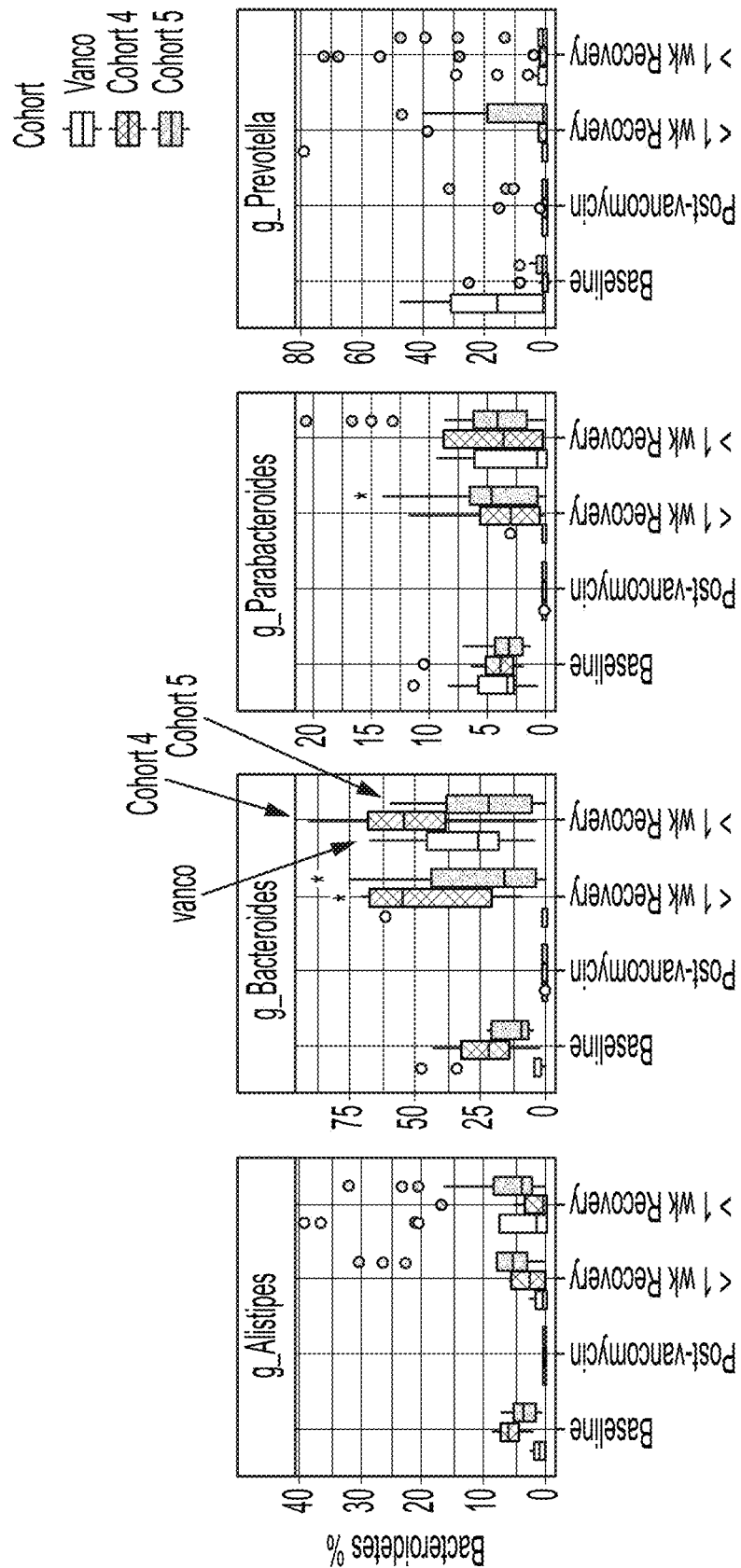
Figure 18C:
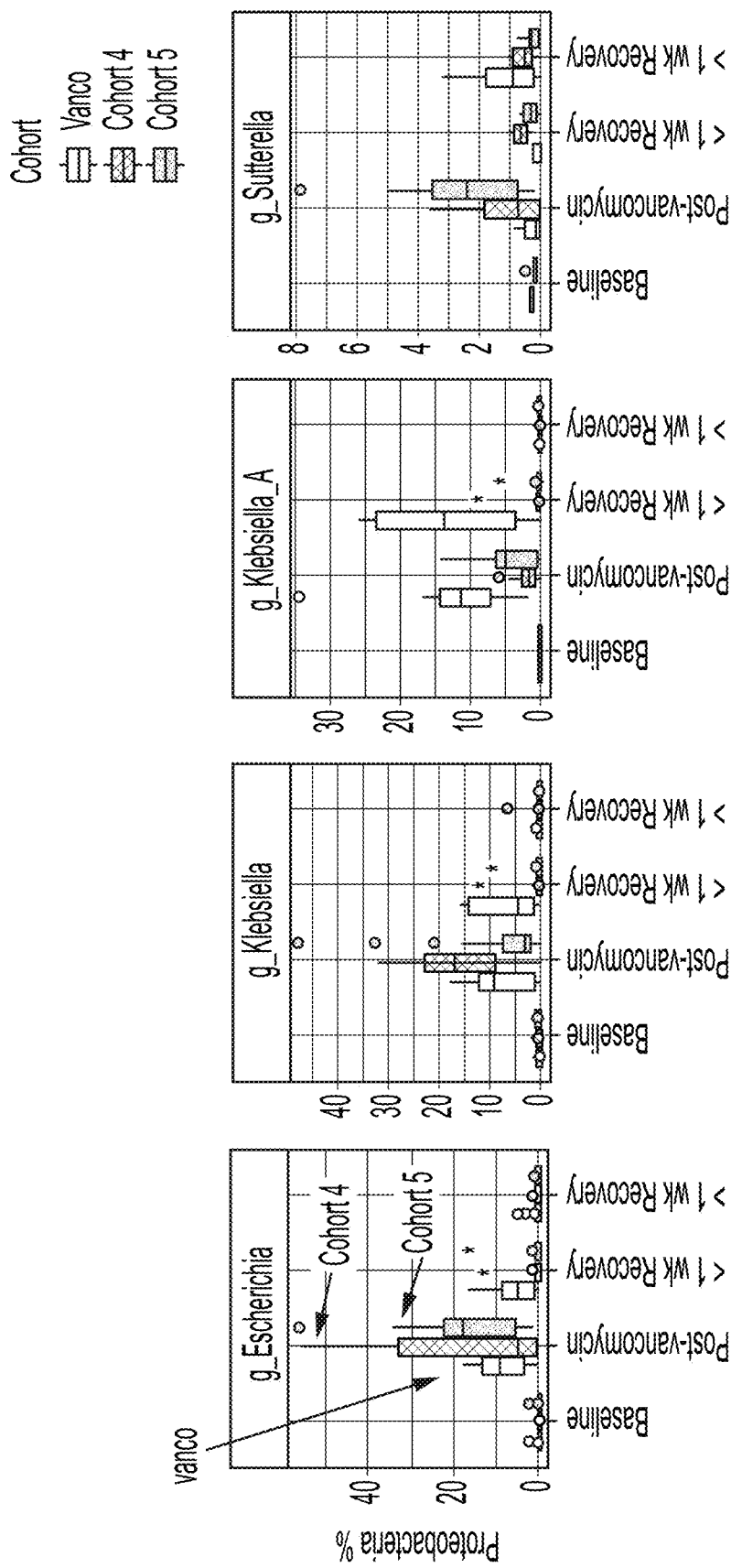

The total relative abundance per subject of the most abundant Firmicutes, Bacteroidetes, and Proteobacteria was measured after vancomycin administration, up to 1 week after recovery from vancomycin administration, and greater than 1 week after recovery from vancomycin administration. VE303 administration enhances the recovery from vancomycin-induced dysbiosis within 1 week after vancomycin treatment (FIG. 18). Specifically, VE303 administration increases Firmicutes families (*Clostridium* clusters IV, XIVa, and XVII), increases Bacteroides and Parabacteroides species, and decreases *Escherichia* species and *Klebsiella* species.

Summary

VE303 is a rationally designed consortium of 8 *Clostridium* cluster IV, XIVa, and XVII strains isolated from healthy human donors that is effective at treating CDI in mice. VE303 is safe and well-tolerated in Normal, Healthy Volunteers (NHV). VE303 strains robustly colonize NHV, expand ~10-100-fold, and persist for up to 12 weeks. Higher doses of VE303 are associated with expedited recovery of vancomycin-induced dysbiosis by promoting the expansion of Bacteriodetes and *Clostridium* cluster IV, XIVa, and XVII species and reducing Proteobacteria species.

Example 4: Preliminary Results of a Phase 1, Open-Label Healthy Volunteers Study of Oral VE303 after Vancomycin Background Gut microbiota alterations are associated with *Clostridioides difficile* infections (CDI). Reduction in recurrent CDI (rCDI) has been shown with fecal microbiota transplantation (FMT), but FMT has limitations for routine use and carries unforeseen risks. VE303 is a first-in-class drug consisting of a rationally defined bacterial consortium manufactured under GMP conditions being developed for prevention of rCDI. VE303 comprises 8 distinct species belonging to *Clostridium* clusters IV, XIVa, and XVII, which are commensal, nonpathogenic, avirulent, clonal bacteria that are associated with clinical response in FMT, suppress *C. difficile* growth in vitro, and improve survival in CDI models.

Methods

A first-in-human Phase 1 dose-escalation study assessed safety and tolerability of VE303 in healthy adult volunteers (HV) after vancomycin (vanco)-induced dysbiosis. Pharmacokinetics (PK) (strain colonization and durability) and pharmacodynamics (PD) (post-antibiotic restoration of the resident microbiota) were evaluated by metagenomics sequencing of fecal bacteria based on the stool samples collected longitudinally.

Results

HV (N=23, 5 cohorts) received oral vanco (125 mg every day for 4 days, followed by VE303 capsules at escalating single then multiple doses) according to the diagram in FIG. 1. VE303-related adverse events (AEs) were all Grade 1 and transient and were observed in 30% of HV. There were no VE303-related higher-grade AE or severe AE (SAE). Most of VE303-related AEs were gastrointestinal (abdominal distention, diarrhea, soft feces, and ALT/AST increase, 8.7% each; discolored or hard feces, constipation, abdominal discomfort or pain, dysgeusia, nausea, flatulence, 4.3% each). The most common Grade 2-3 laboratory abnormalities were increased cholesterol, blood in urine, and increased lipase and amylase.

Figures 19A, 19B:
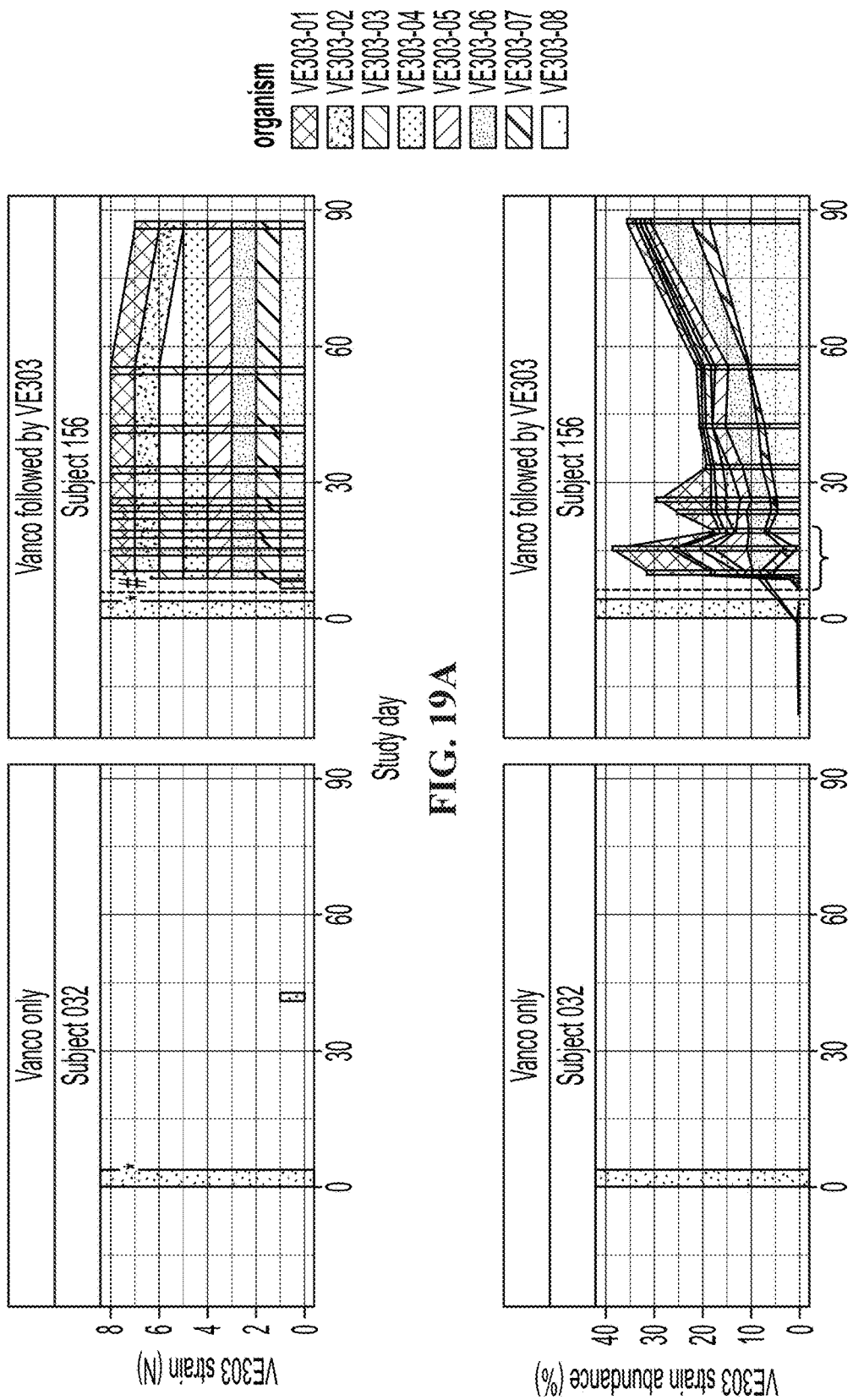
FIGS. 19A-19B show the number and strain abundance of bacterial strains of composition VE303 detected in the microbiota of individual subjects.

Durable, abundant, and dose-dependent colonization was observed in the single- and multi-dose cohorts. Each VE303 component strain was detectable in the stool, and VE303 expanded 10-100-fold within 2 days after dosing; in many HV, VE303 bacteria were abundantly detected at 12 weeks (FIGS. 19A, 19B). VE303 bacteria enhanced subjects; microbiota recovery after vanco treatment. When compared with the vanco-only control cohort, VE303-treated HV had earlier and more complete recovery of potentially beneficial taxa (e.g., Bacteroidetes, Firmicutes) and reduction in potentially inflammatory taxa (e.g., Proteobacteria).

Conclusion

VE303 was well tolerated and safe at all doses and demonstrated early, robust, and durable colonization with early recovery of a normal microbiota following vanco treatment; robustness of colonization improved with treatment duration. A Phase 2 study of VE303 for prevention of rCDI is underway.

Figure 29:
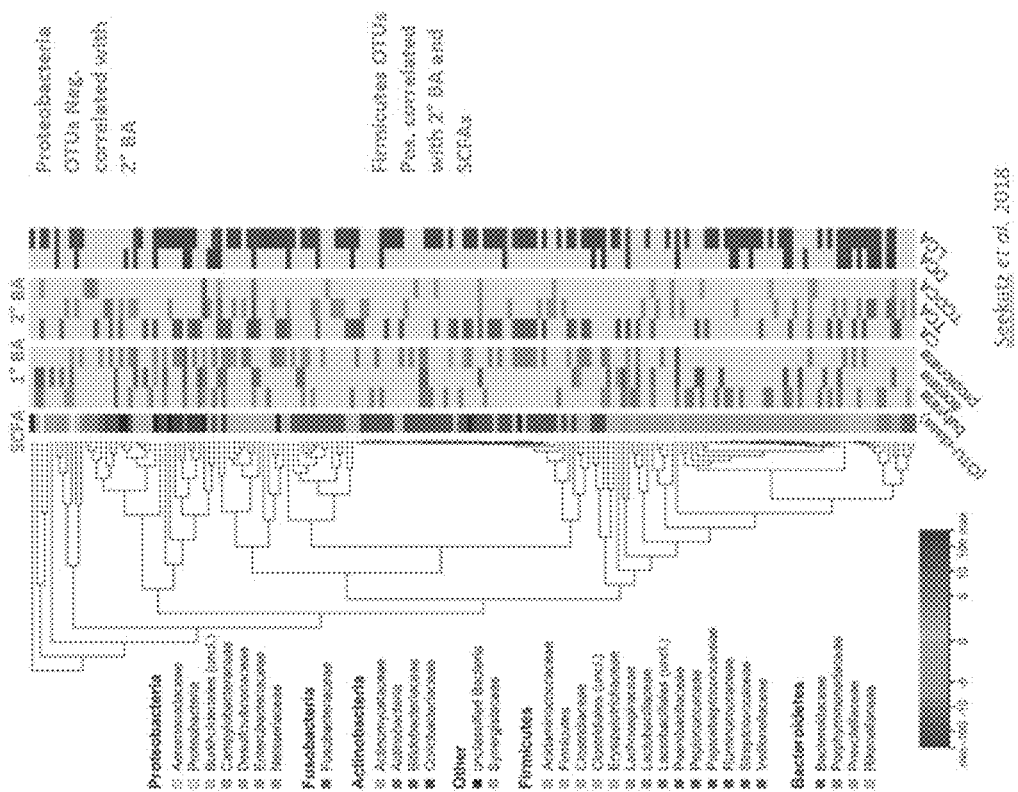
FIG. 29 shows that short chain fatty acids (SCFA) and secondary bile acid recovery is associated with recovery in *Clostridium difficile* infection (CDI) patients (From Seekatz et al., Anaerobe 2018, October, 53: 64-73).
Figure 30A:
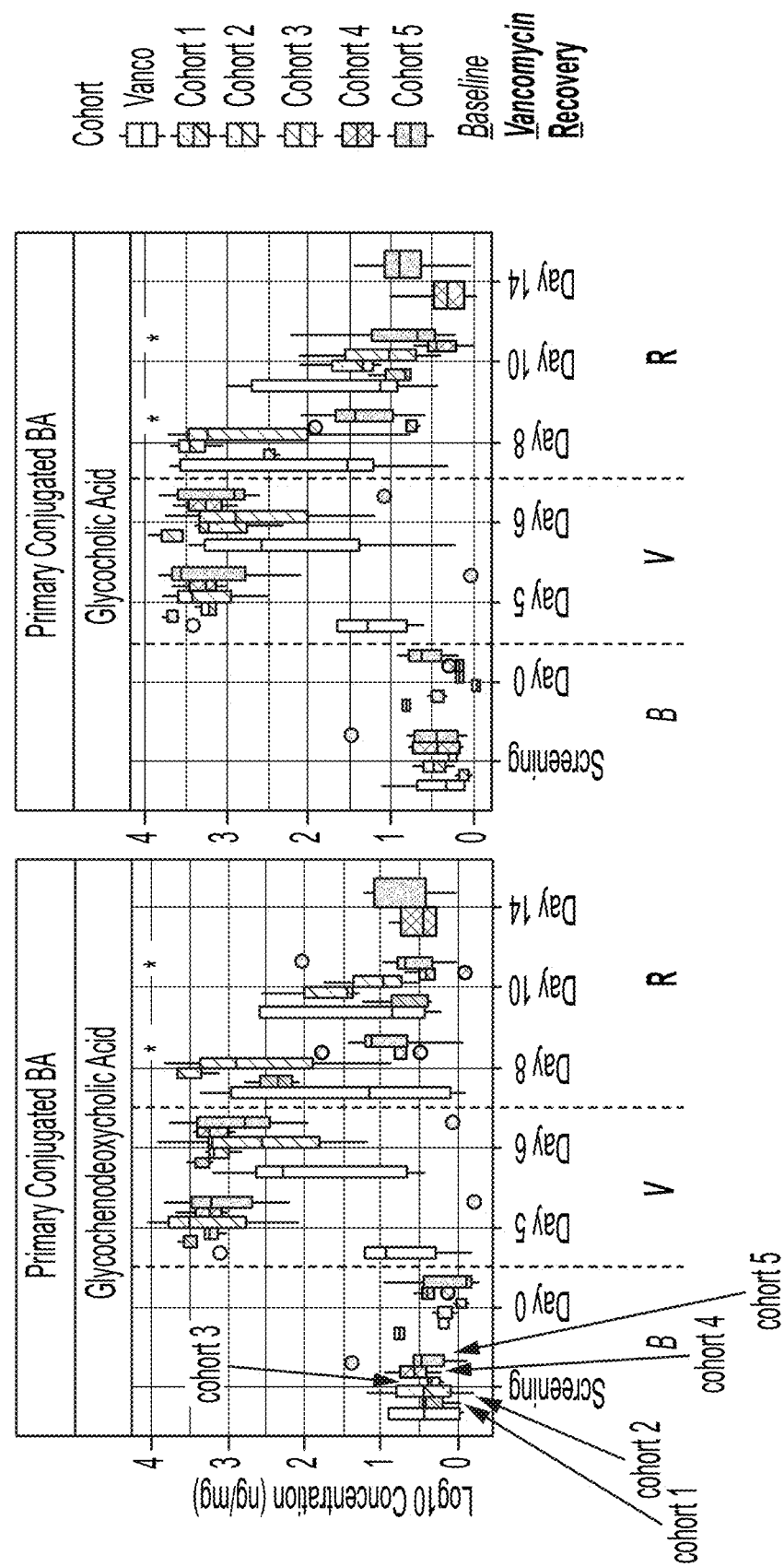
FIGS. 30A-30B show the reduction of primary conjugated bile acids (BA) following treatment with VE303. Different primary bile acids (glycohenodeoxycholic acid, glycoholic acid, taurochenodeoxycholic acid, and taurocholic acid) from subjects in cohorts 1-5 were quantified from samples taken at the indicated time points. "B" indicates the quantity of each primary conjugated BA detected at baseline, "V" indicates the quantity of each primary conjugated BA detected during vancomycin treatment, and "R" indicates the quantity of each primary conjugated BA detected during recovery from vancomycin treatment. "*" denotes interesting trends where VE303 administration is associated with expedited depletion of primary BAs.
Figure 30B:
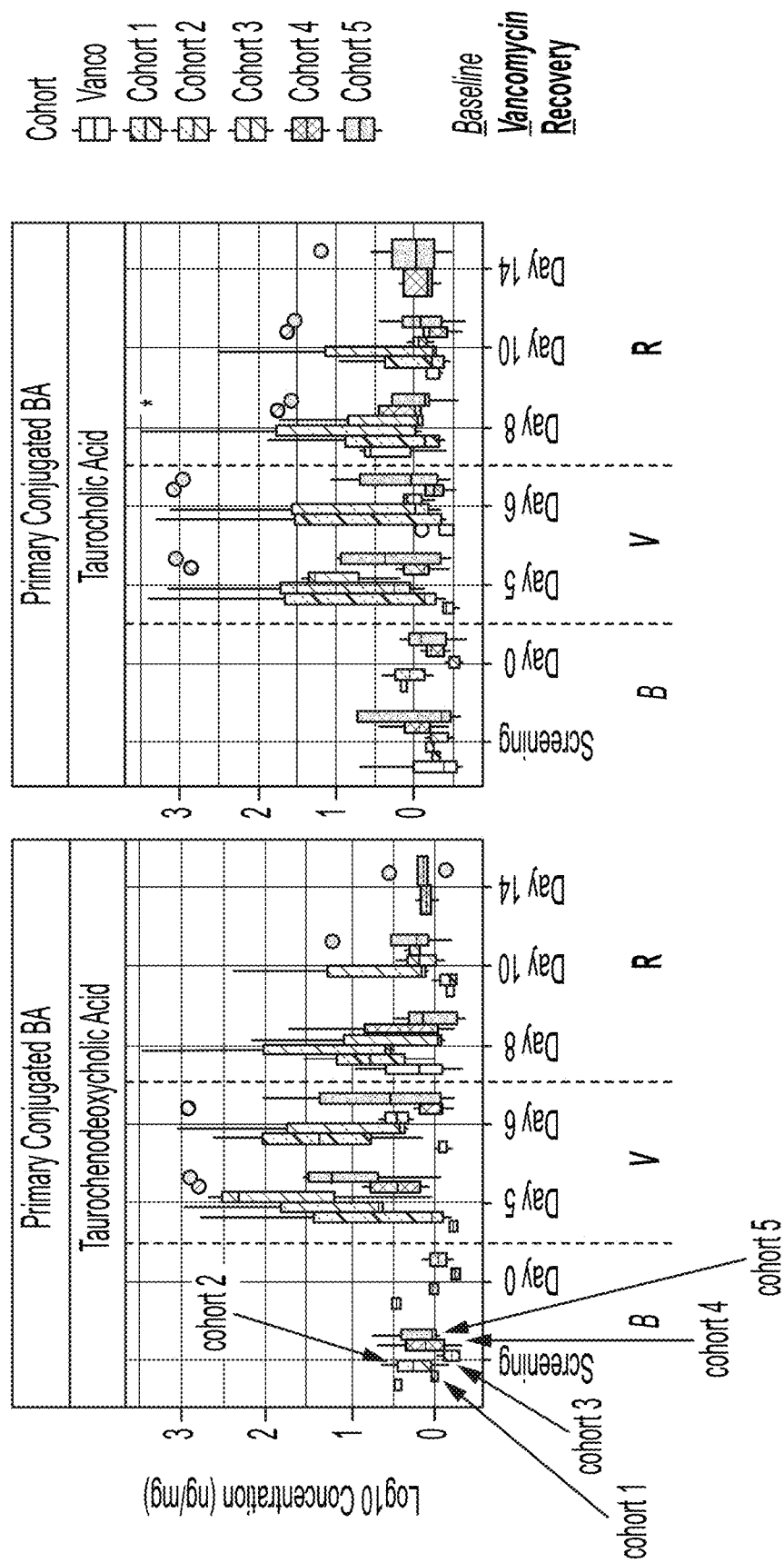

Example 5: VE303 Administration Promotes Recovery of Bile Acid after Antibiotic Treatment Background Treatment with antibiotics (e.g., vancomycin) disrupts host microbiota and the pool of bile acid metabolites (FIG. 28). These bile acids may be either primary bile acids or secondary bile acids. Specifically, antibiotics may, e.g., through reducing the number of beneficial microorganisms, stimulate the production of primary bile acids as opposed to secondary bile acids. Recurrent *Clostridium difficile* infection (rCDI) is associated with increased primary bile acids and decreased secondary bile acids. Fecal matter transplant (FMT) rescues these bile acid deficiencies. Secondary bile acids are positively correlated with Firmicutes abundance post-FMT and negatively correlated with Proteobacteria OTUs, thereby inhibiting rCDI (FIG. 29).

Methods

Feces samples from subjects were lyophilized and pulverized before analysis in order to obtain a homogeneous sample. Approximately 8-12 mg of each sample was weighed and the exact weight was recorded. The samples were then extracted with acidified methanol. After centrifugation, the sample was split with one portion of the clear supernatant set aside undiluted and the other sample diluted 100-fold. Aliquots of the undiluted and diluted sample extract were spiked with a solution of labeled internal standards and were evaporated to dryness in a gentle stream of nitrogen. The dried extracts were reconstituted and injected onto an Agilent 1290/Sciex QTrip 6500 LC-MS/MS system equipped with a C18 reverse phase HPLC column with acquisition in negative ion mode.

The peak area of each bile acid parent (pseudo-MRM mode) or product ion was measured against the peak are of the respective labeled internal standard parents (pseudo-MRM mode) or product ion. Quantitation was performed using a weighted linear least squares regression analysis generated from fortified calibration standards prepared immediately prior to each run. Results were corrected for sample weight (dried lyophilized feces sample) and provided as ng bile acid/mg lyophilized feces.

Results

Figure 31:
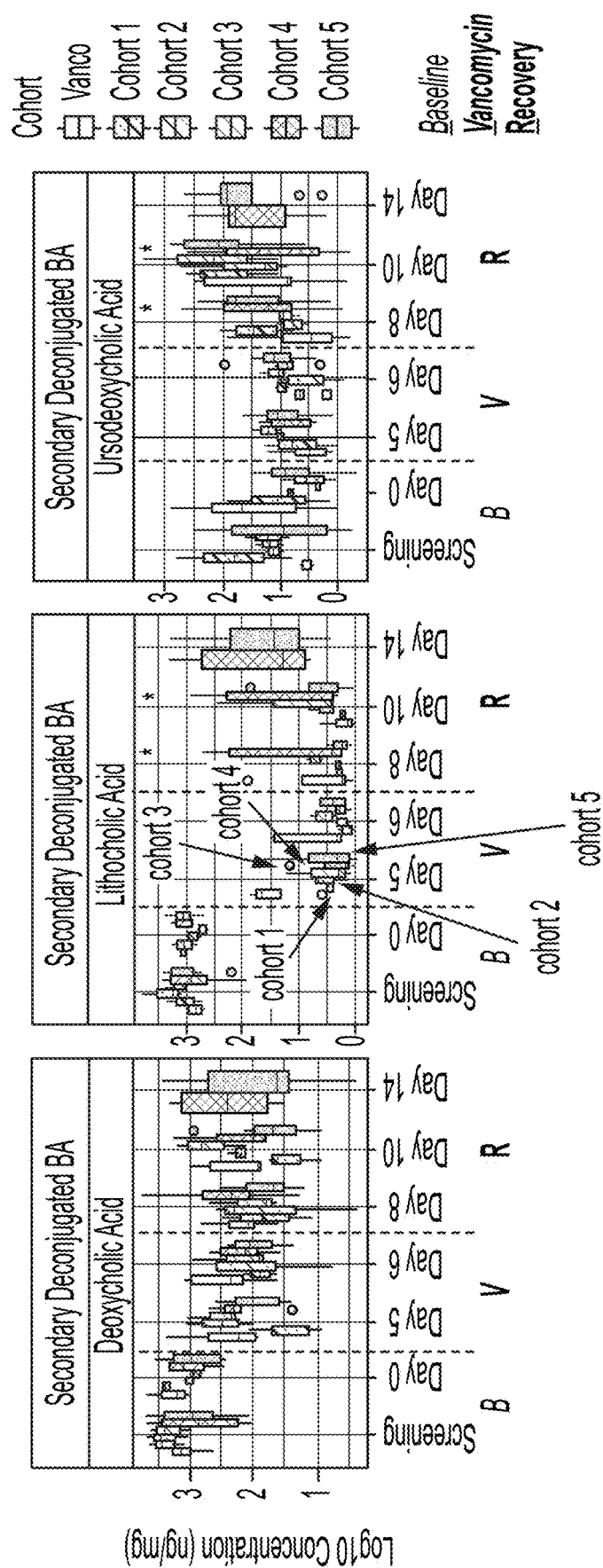
FIG. 31 shows the recovery of secondary deconjugated bile acids (BA) following treatment with VE303. Different secondary bile acids (deoxycholic acid, lithocholic acid, and ursodeoxycholic acid) from subjects in cohorts 1-5 were quantified from samples taken at the indicated time points. "B" indicates the quantity of each secondary deconjugated BA detected at baseline, "V" indicates the quantity of each secondary deconjugated BA detected during vancomycin treatment, and "R" indicates the quantity of each secondary deconjugated BA detected during recovery from vancomycin treatment. "*" denotes interesting trends where VE303 administration is associated with expedited recovery of secondary BAs.
Figure 36A:
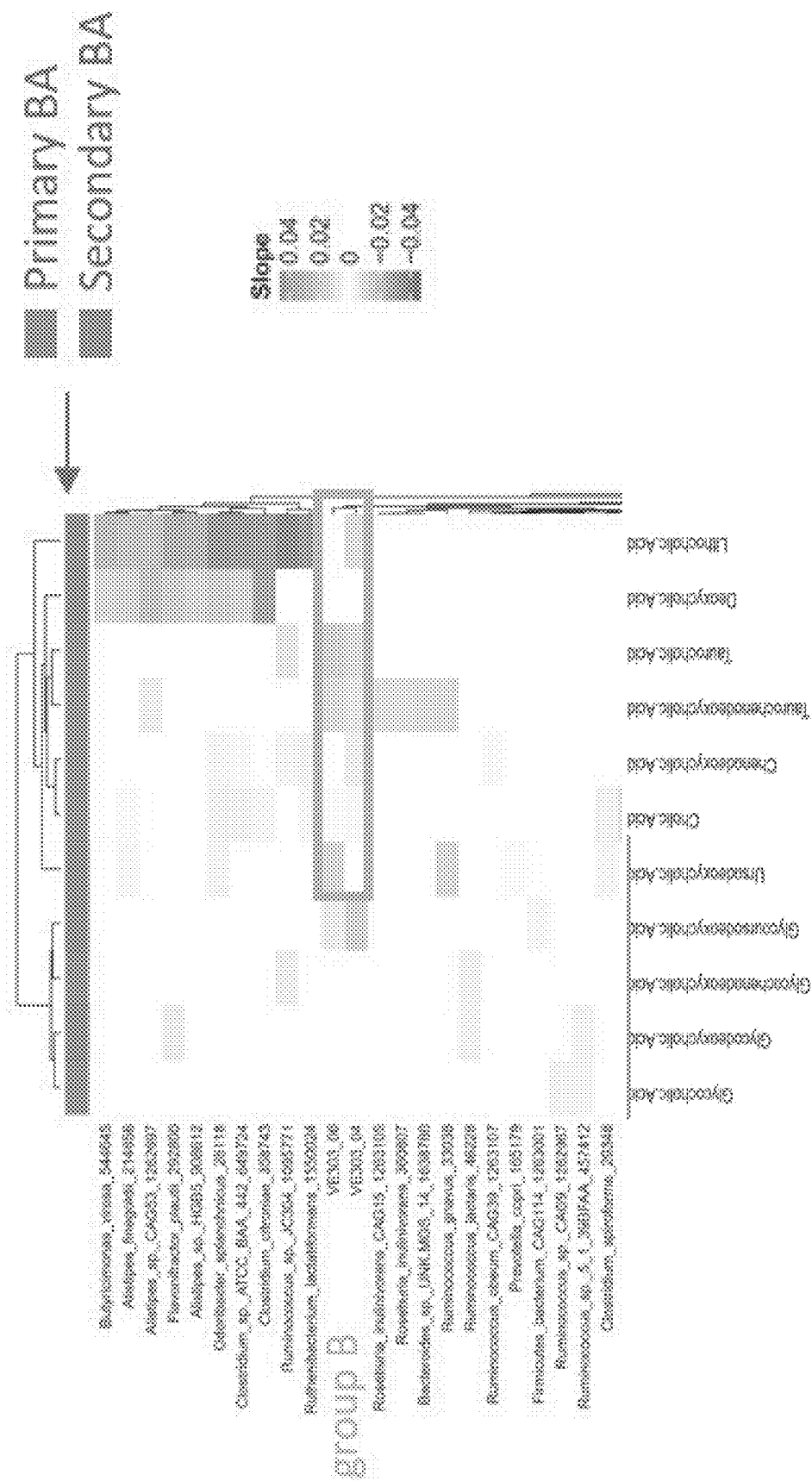
FIGS. 36A-36C show the VE303 species and resident microbes that are important for bile acid (BA) recovery. VE303 group A (VE303-01, VE303-02, VE303-03, VE303-05, VE303-07, VE303-8) strains are negatively associated with primary BA recovery and positively associated with secondary BA recovery. VE303 group B strains (VE303-04, VE303-06), are positively associated with secondary BA recovery.
Figure 36B:
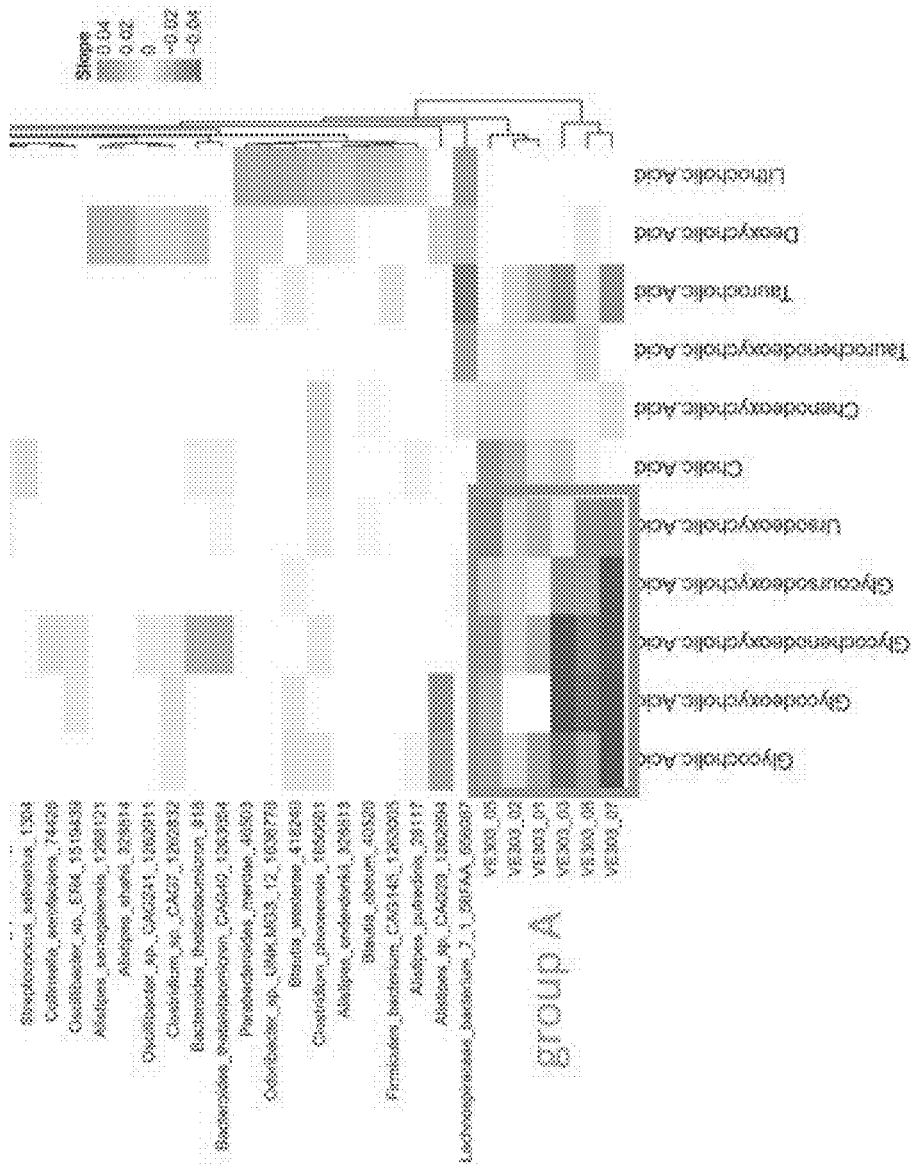
Figure 36C:
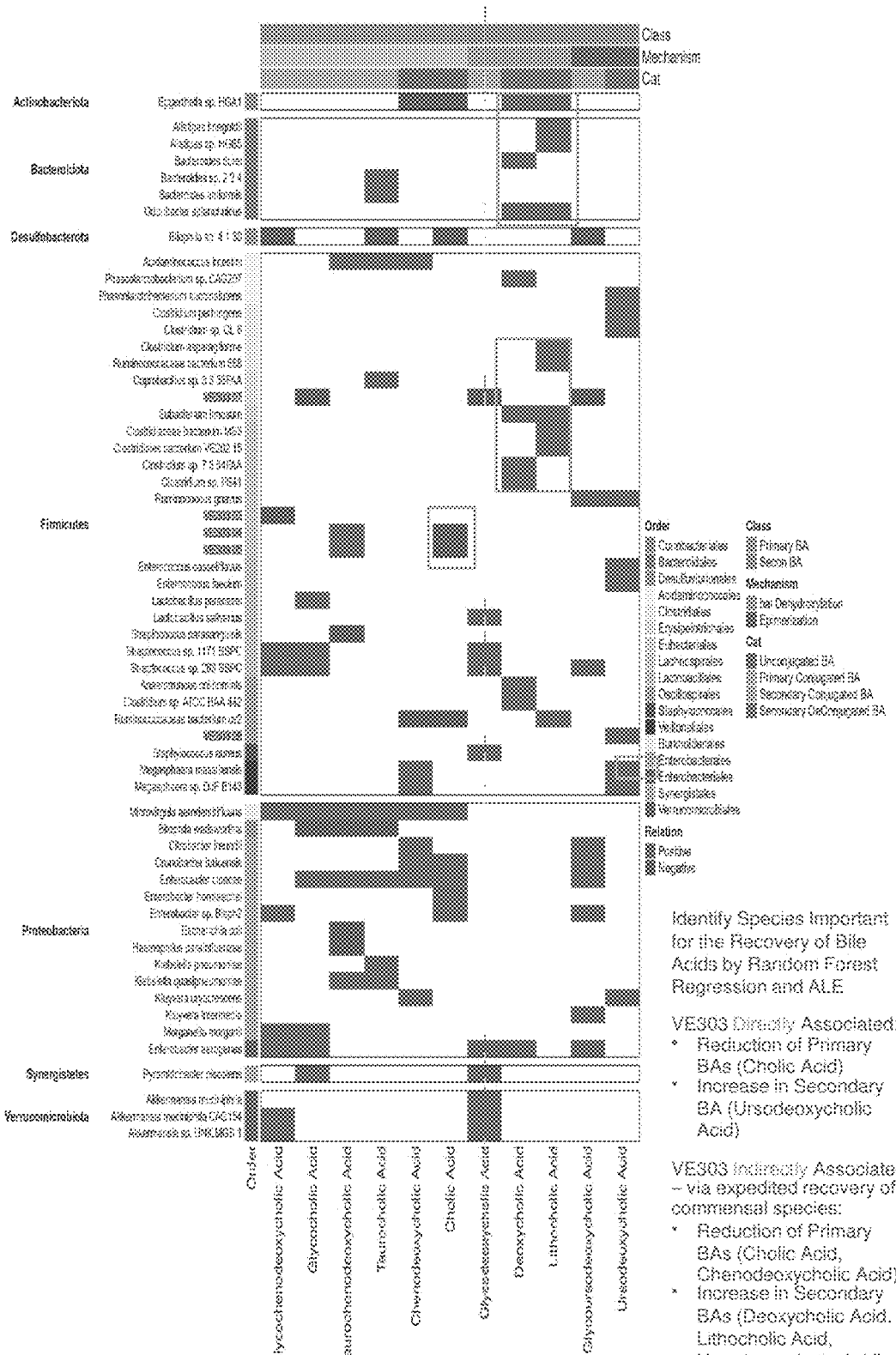

Primary bile acids were low in healthy volunteers and increased up to 3-4 logs upon treatment with vancomycin (FIGS. 31, 33, 34), although the amount varies between Cohorts 1-5. Specifically, the primary conjugated bile acids (BAs) glycochenodeoxycholic acid, glycocholic acid, taurochenodeoxycholic acid, and taurocholic acid were increased (FIGS. 30, 32-34). These primary bile acids decreased upon administration of VE303, with variation among Cohorts 1-5. Interestingly, VE303 administration was associated with expedited depletion of some primary bile acids (FIG. 31, denoted by asterisk). The association of VE303 treatment with the decrease in primary bile acids was confirmed to be significant by Linear Mixed Effects Modeling (FIG. 34) and Random Forest Analysis (FIG. 36). VE303 strains were also found to be among the top 20 most important features for the recovery to baseline levels of primary bile acids (FIG. 35).

Figure 32:
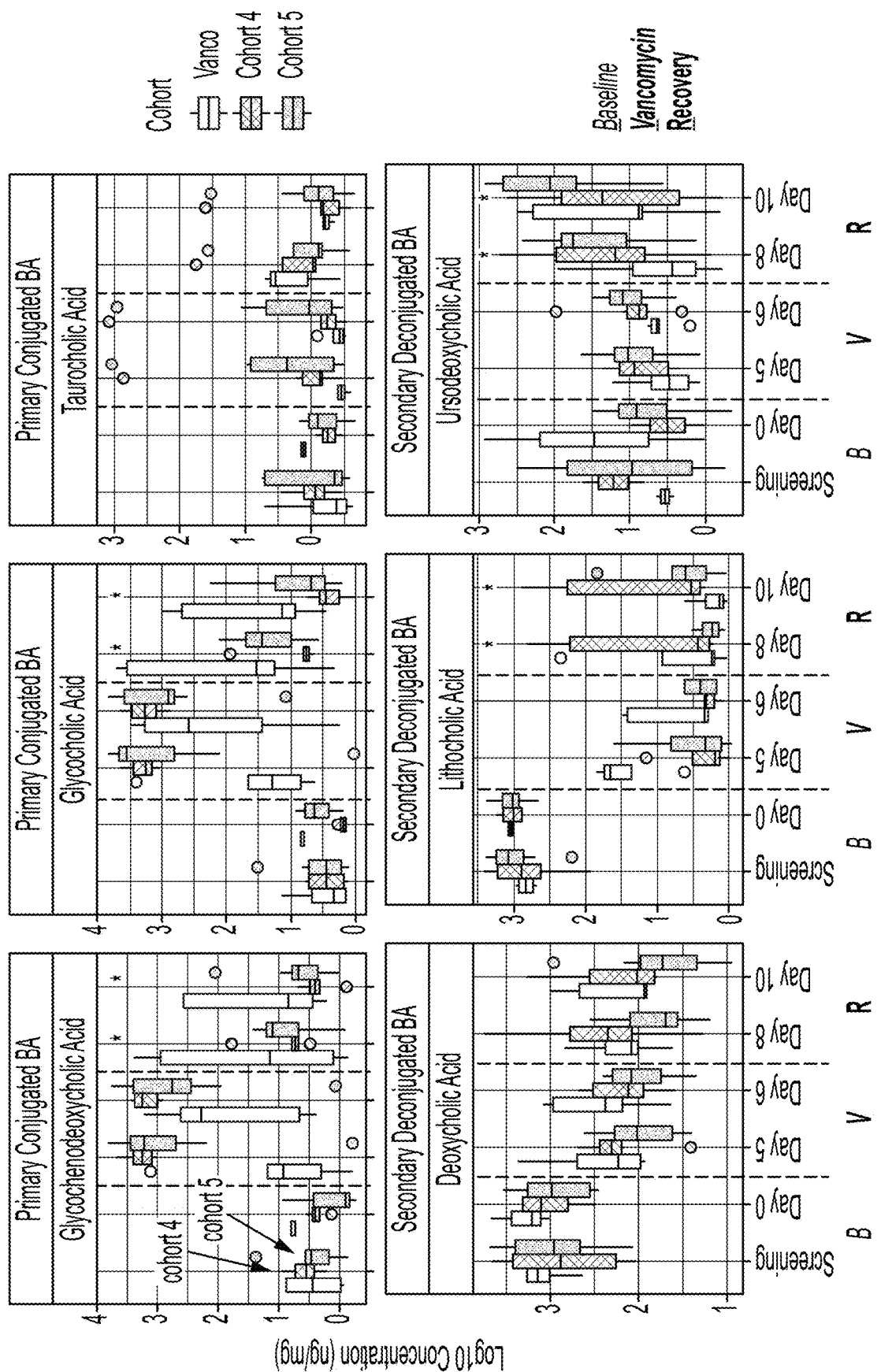
FIG. 32 shows the reduction of primary conjugated BAs and recovery of secondary deconjugated BAs following treatment with VE303. Different primary and secondary BAs (glycohenodeoxycholic acid, glycoholic acid, and taurocholic acid; deoxycholic acid, lithocholic acid, and ursodeoxycholic acid) from subjects in cohorts 4 and 5 were quantified from samples taken at the indicated time points. "B" indicates the quantity of each primary or secondary BA detected at baseline, "V" indicates the quantity of each primary or secondary BA detected during vancomycin treatment, and "R" indicates the quantity of each primary or secondary BA detected during recovery from vancomycin treatment. "*" denotes interesting trends where VE303 administration is associated with expedited depletion of primary BAs or recovery of secondary BAs.
Figure 33A:
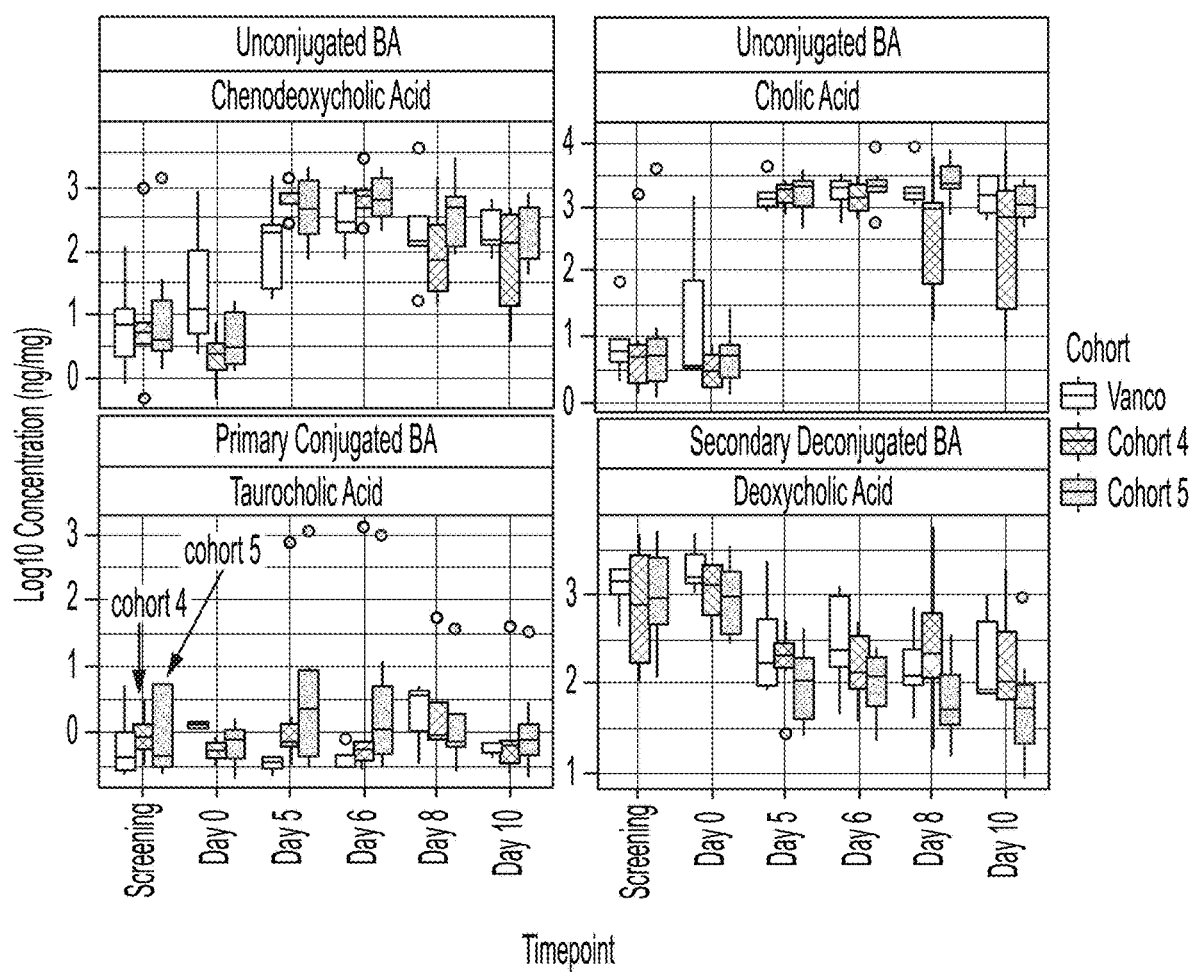
FIGS. 33A-33B show the reduction and recovery of BAs following treatment with antibiotics and administration of VE303. Different primary and secondary BAs (chenodeoxycholic acid, cholic acid, glycochenodeoxycholic acid, glycocholic acid, taurocholic acid, deoxycholic acid, lithocholic acid, and ursodeoxycholic acid) from subjects in cohorts 4 and 5 were quantified from samples taken at the indicated time points.
Figure 33B:
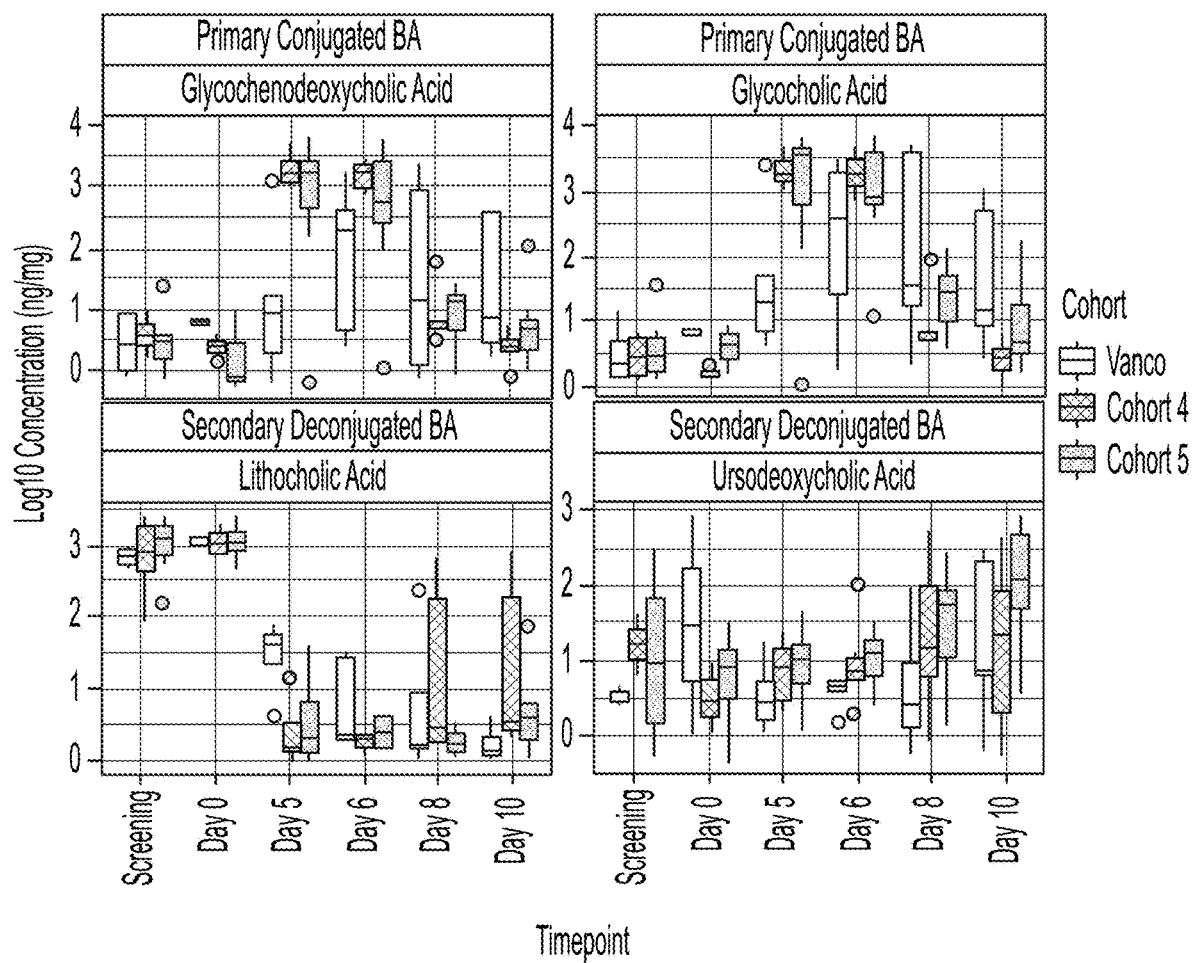
Figure 35A:
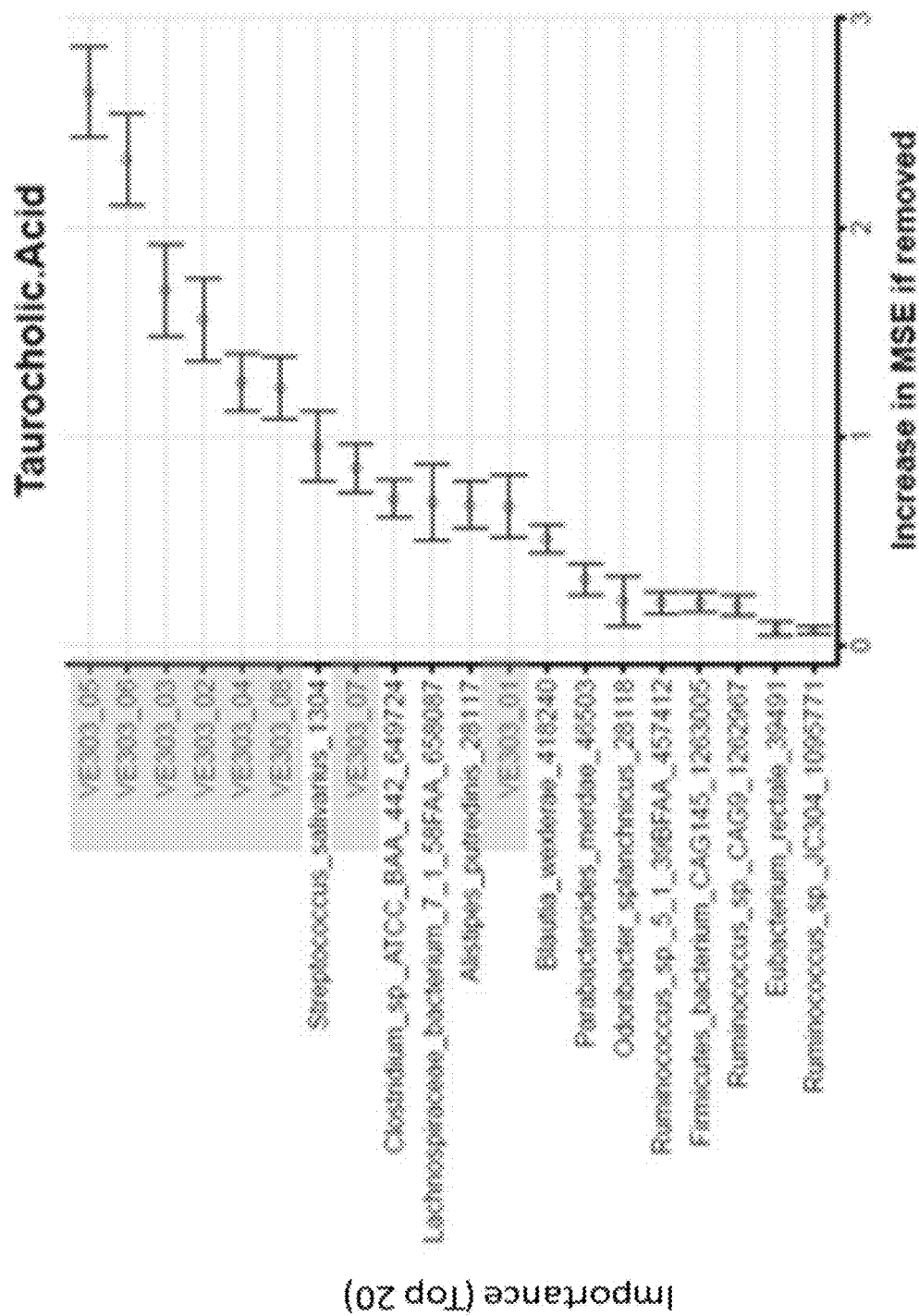
FIGS. 35A-35D show the identity of the top 20 bacterial strains that are important in the metabolism of primary and secondary bile acids. VE303 bacterial strains are important in the metabolism of both primary and secondary bile acids.
Figure 35B:
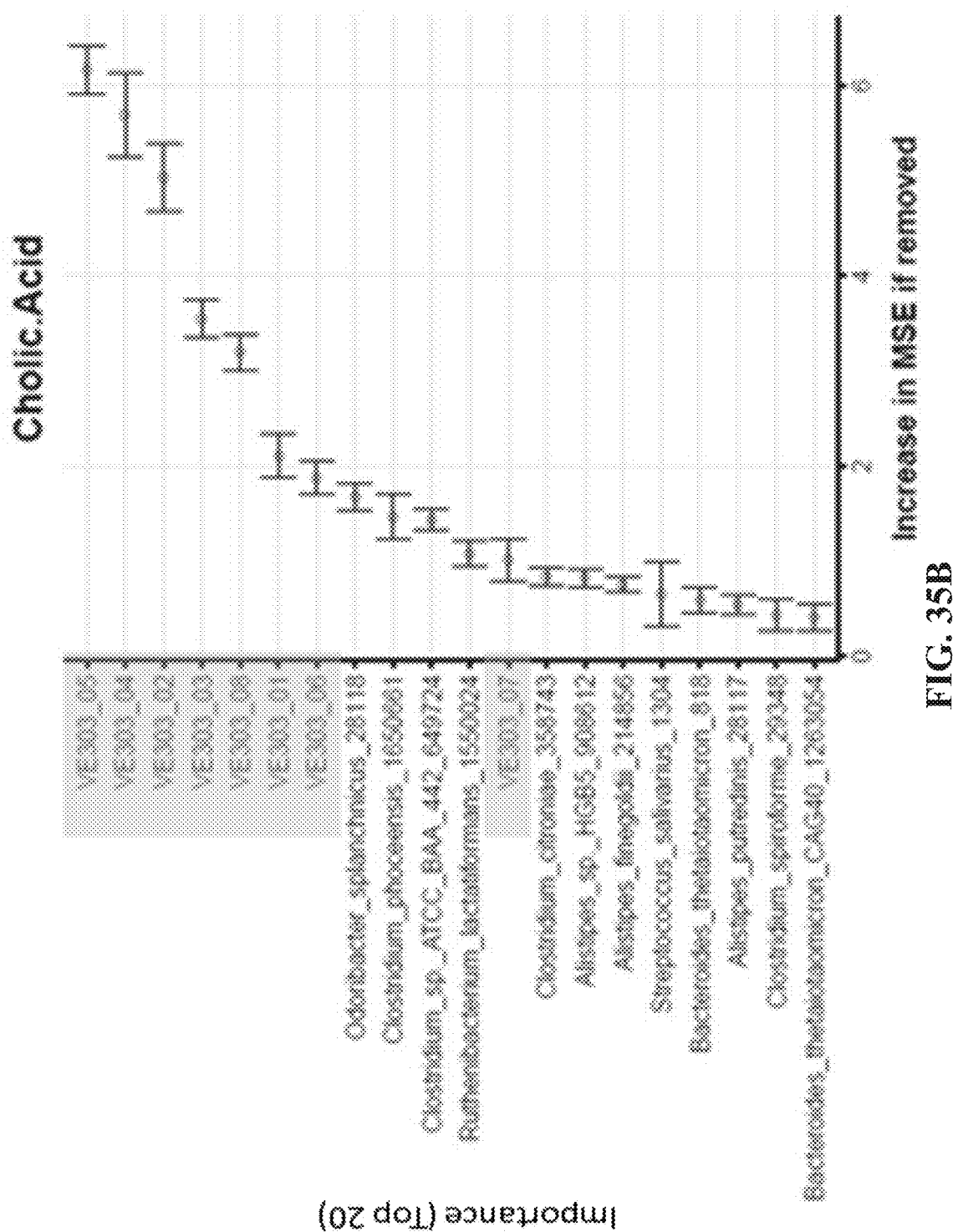
Figure 35C:
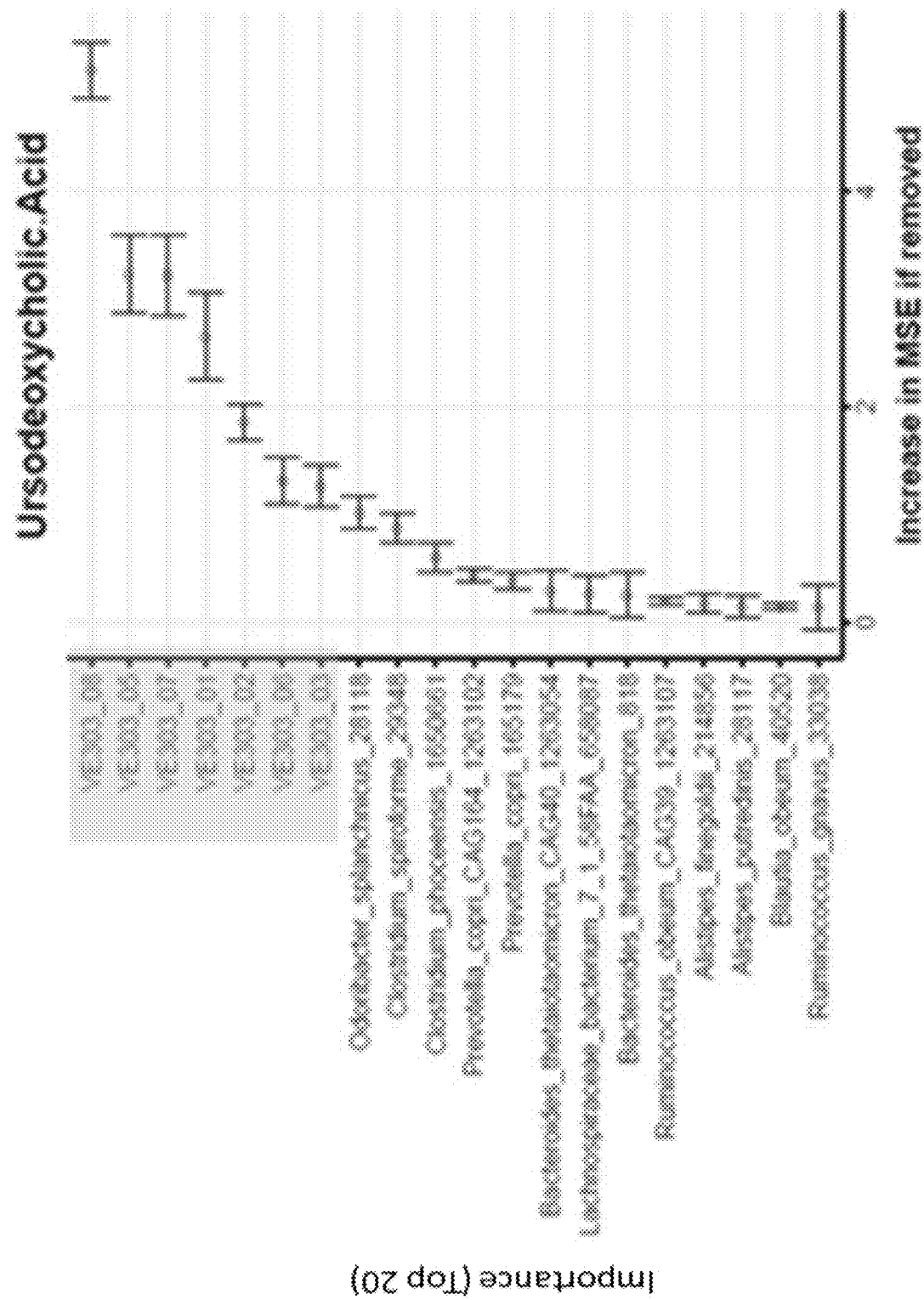
Figure 35D:
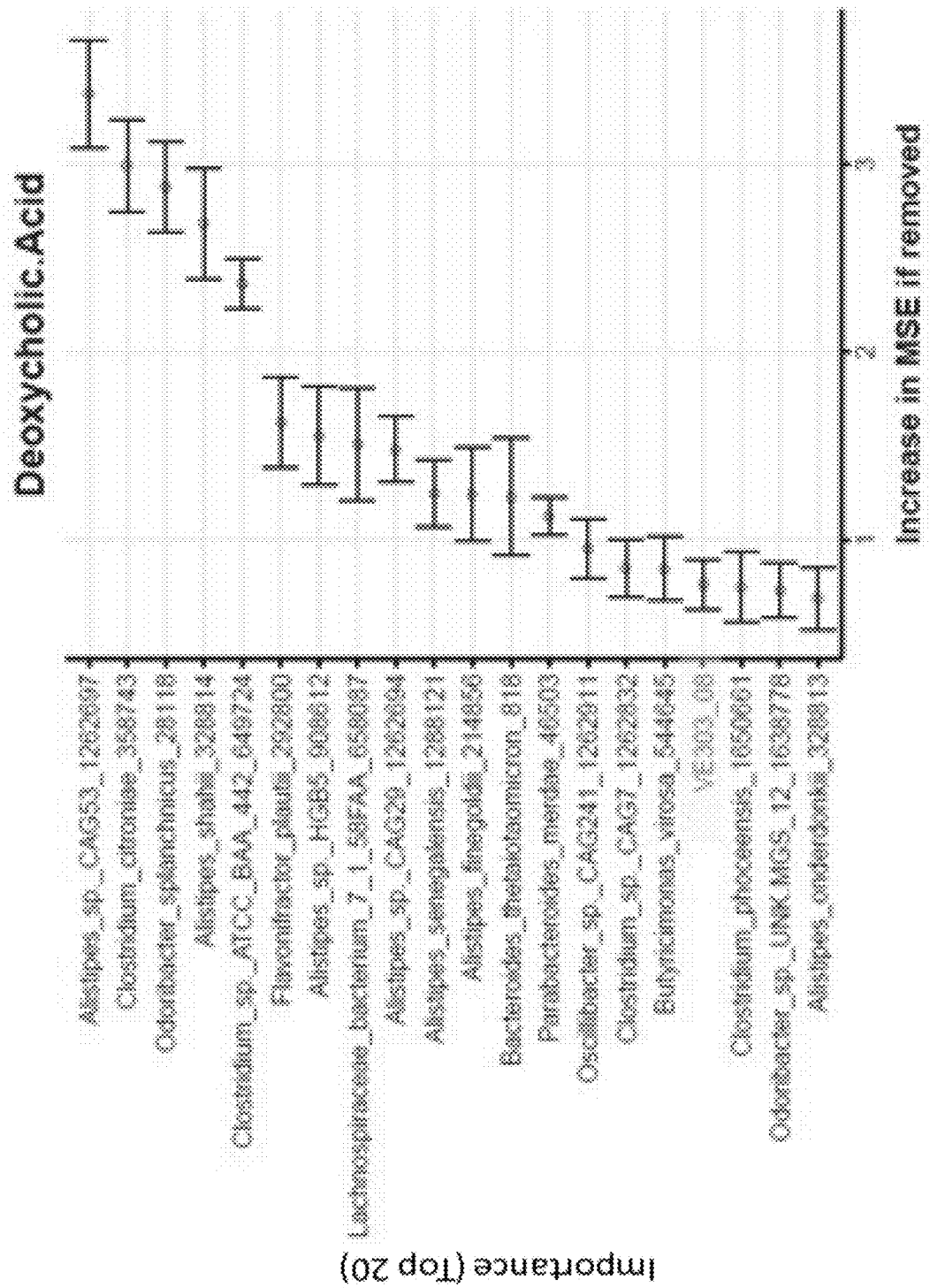

Secondary bile acids were high in healthy volunteers and decreased up to 1-2 logs with vancomycin treatment and increased with administration of VE303 (FIGS. 32-34), although the amount varies between Cohorts 1-5. Specifically, the secondary deconjugated BAs deoxycholic acid, lithocholic acid, and ursodeoxycholic acid (FIGS. 32-34) were decreased. These secondary bile acids were increased upon administration of VE303, with variation among Cohorts 1-5. Interestingly, VE303 administration was associated with expedited recovery of some secondary bile acids (FIG. 32, denoted by asterisk). The association of VE303 treatment with the increase in secondary bile acids was confirmed to be significant by Linear Mixed Effects Modeling (LMEM) (FIG. 34) and Random Forest Analysis (RFA) (FIG. 36). For LME, the below equation was utilized to calculate the significance of the association of VE303 administration with primary bile acid decrease and secondary bile acid increase.

$$BA = 1 + Vanco + Ve303(t) + (Cohort \mid ID) \quad \text{Equation 1}$$

With:

$Vanco = $ Pre, During, Post $$Ve303(t) = \sum_i Ve303_i(t)$$

For RFA, a partial dependence analysis+Linear Model of the top 20 important features was constructed. VE303 group A strains (VE303-01, VE303-02, VE303-3, VE303-05, VE303-07, VE303-8; also described herein as "VE303 group A strains—bile acids") were negatively associated with primary bile acid (BA) abundance and positively associated with the abundance of the secondary bile acid (BA) ursodeoxycholic acid. VE303 group B strains (VE303-04, VE303-06; also described herein as "VE303 group B strains—bile acids") were positively associated with abundance of the secondary BAs lithocholic acid and ursodeoxycholic acid. Additionally, the resident Bacteroidetes and *Clostridium* cluster IV and XIVa species were positively associated with secondary BA deoxycholic acid. VE303 strains were also found to be among the top 20 most important features for the recovery to baseline levels of secondary bile acids (FIG. 35).

Conclusion

The balance of primary and secondary bile acids is altered by vancomycin treatment. Secondary bile acids are reduced in *Clostridium difficile* infection (CDI) and are important for limiting *C. difficile* spore germination. VE303 strains are important for the recovery of secondary bile acids both directly and indirectly. The secondary bile acids deoxycholic acid, lithocholic acid, and ursodeoxycholic acid are all increase following FMT treatment in CDI patients.

Example 6: VE303 Administration Promotes Recovery of Short Chain Fatty Acids after Antibiotic Treatment Background Treatment with antibiotics (e.g., vancomycin) disrupts host microbiota and the pool of short chain fatty acid (SCFA) metabolites (FIG. 28). Specifically, antibiotics may result in decreased levels of SCFAs. Recurrent *Clostridium difficile* infection (rCDI) is associated with decreased levels of the SCFAs butyrate, propionate, and acetate (FIG. 29). Fecal microbiota transplant (FMT) rescues these SCFA deficiencies. SCFAs are positively correlated with Firmicutes abundance post-FMT (FIG. 29).

Methods

Approximately 100 mg of each sample was weighed and the exact weight was recorded. The samples were then spiked with a solution of stable labelled internal standards, and homogenized and extracted with methanol. After centrifugation, an aliquot of the supernatant was derivatized, forming the corresponding short chain fatty acid aryl hydrazides. The reaction mixture was diluted and an aliquot was injected onto an Agilent 1290/AB Sciex Trip Quad 5500 LC-MS/MS system equipped with a C18 reverse phase UHPLC column. The mass spectrometer was operated in negative mode using electrospray ionization (ESI).

The peak area of the individual analyte product ions were measured against the peak area of the product ions of the corresponding internal standards. Quantitation was performed using a weighted linear least squares regression analysis generated from fortified calibration standards prepared immediately prior to each run. Results were corrected for sample weight (dried lyophilized feces sample) and provided as µg SCFA/g fresh feces.

Results

Figure 37:
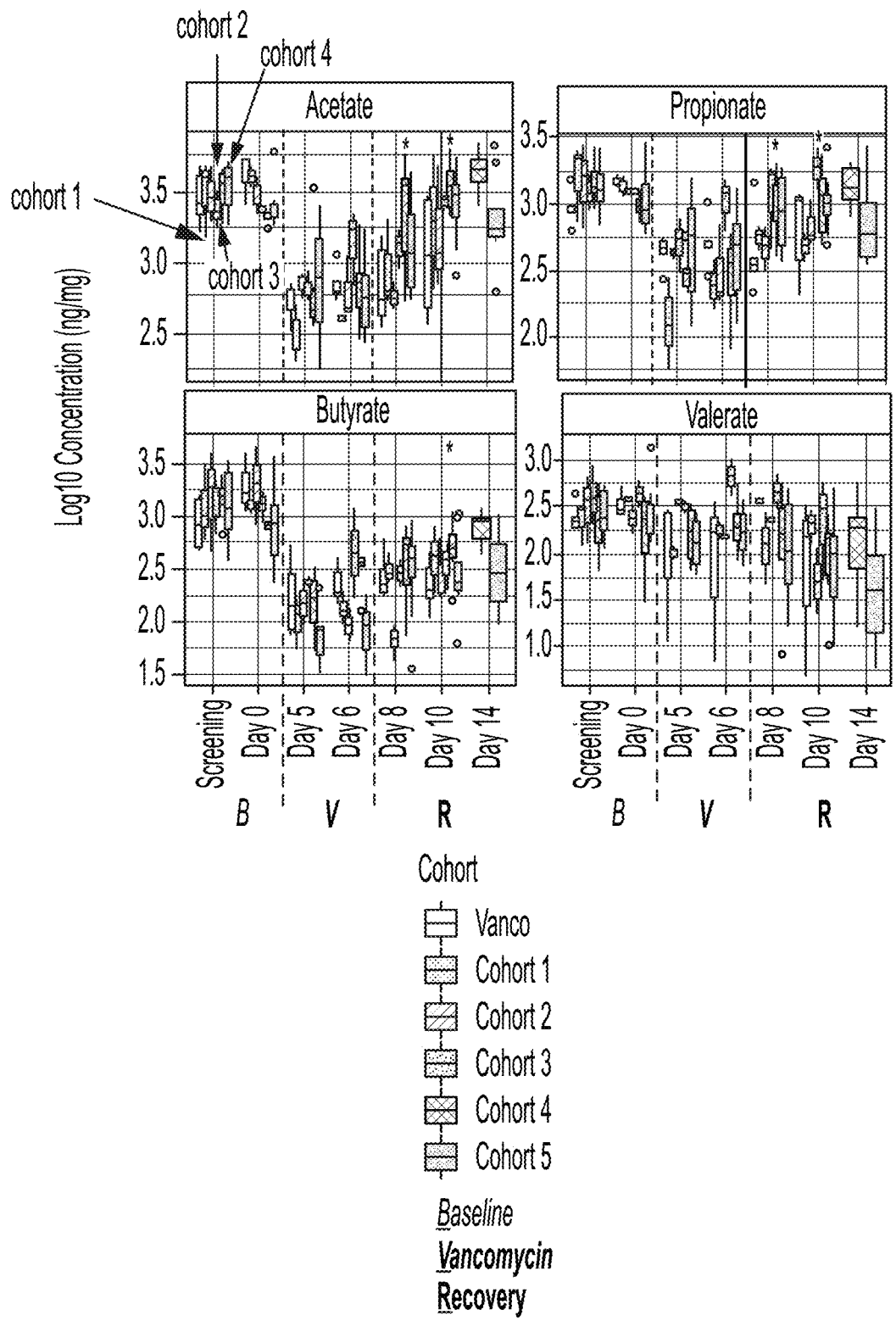
FIG. 37 shows the recovery of short chain fatty acids (SCFAs) following treatment with antibiotics and administration of VE303. Different SCFAs (acetate, propionate, butyrate, and valerate) from subjects in cohorts 1-5 were quantified from samples taken at the indicated time points. "B" indicates the quantity of each SCFA detected at baseline, "V" indicates the quantity of each SCFA detected during vancomycin treatment, and "R" indicates the quantity of each SCFA detected during recovery from vancomycin treatment. "*" denotes interesting trends where VE303 administration is associated with expedited recovery of SCFAs.
Figure 38:
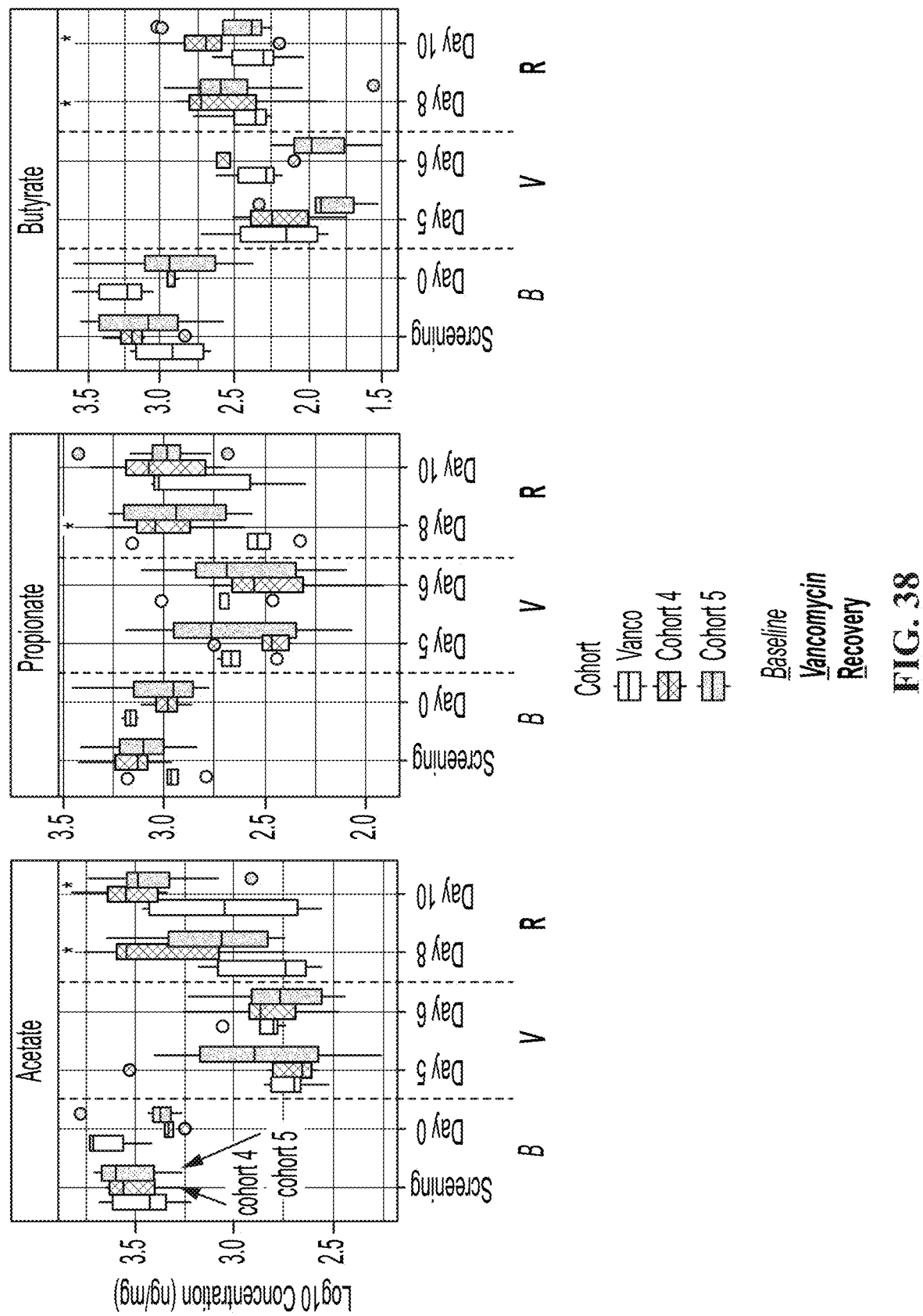
FIG. 38 shows the recovery of short chain fatty acids (SCFAs) following treatment with antibiotics and administration of VE303. Different SCFAs (acetate, propionate, and butyrate) from subjects in cohorts 4 and 5 were quantified from samples taken at the indicated time points. "B" indicates the quantity of each SCFA detected at baseline, "V" indicates the quantity of each SCFA detected during vancomycin treatment, and "R" indicates the quantity of each SCFA detected during recovery from vancomycin treatment. "*" denotes interesting trends where VE303 administration is associated with expedited recovery of SCFAs.
Figure 41A:
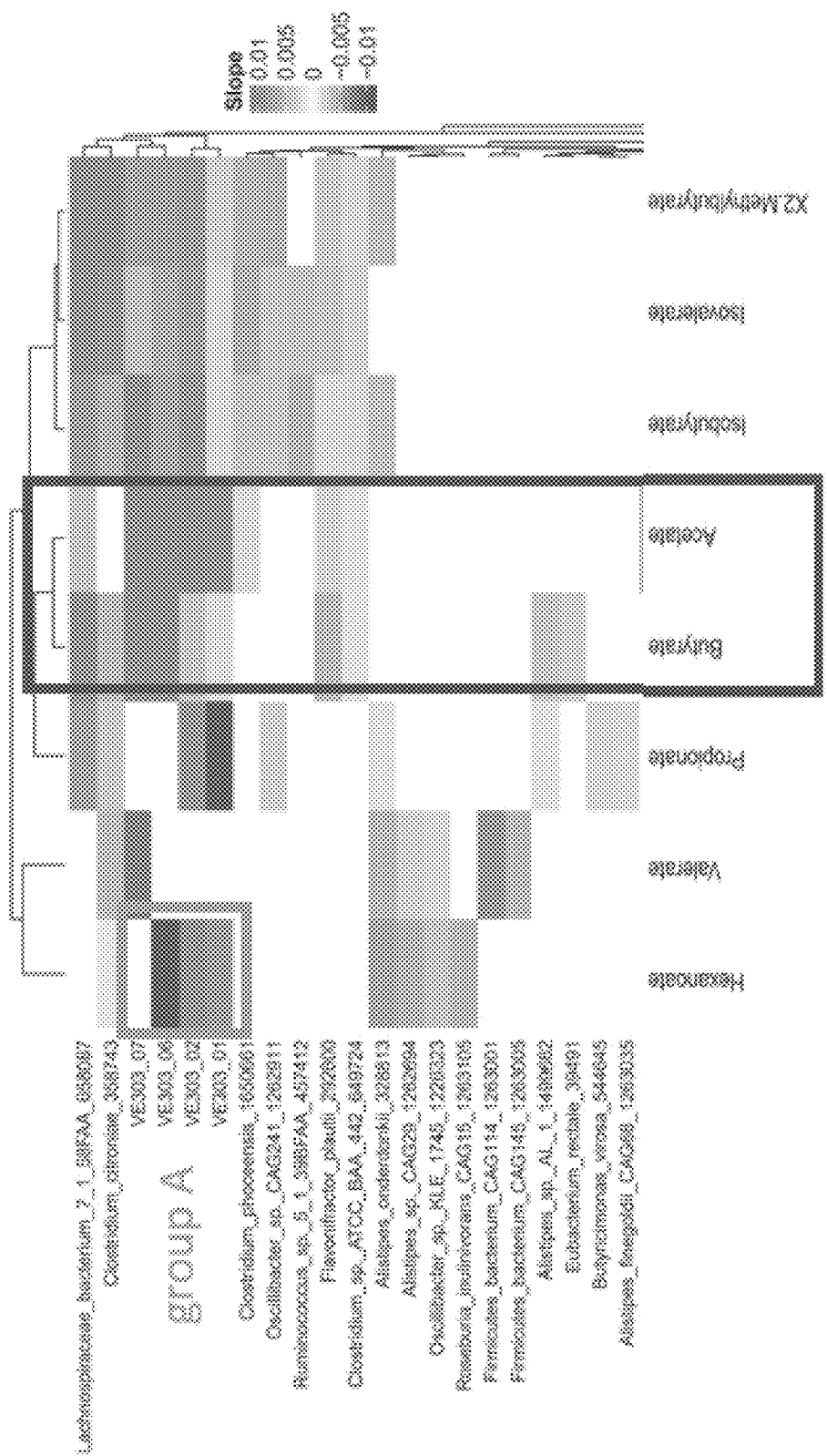
Figure 41B:

SCFAs were high in healthy volunteers and decreased up to 1-1.5 logs with vancomycin treatment and increased with administration of VE303 (FIGS. 37-38), although the amount varies between Cohorts 1-5. Specifically, the SCFAs acetate, propionate, butyrate, and valerate (FIGS. 37 and 38) are decreased. These secondary bile acids are increased upon administration of VE303, with variation among Cohorts 1-5. Interestingly, VE303 administration was associated with expedited recovery of some SCFAs (FIG. 37, denoted by asterisk). The association of VE303 treatment with the increases in SCFAs was confirmed to be significant by Linear Mixed Effects (LME) Modeling (FIG. 39) and Random Forest Analysis (FIG. 41). For LME, the below equation was utilized to calculate the significance of the association of VE303 administration with SCFA recovery.

$$SCFA = 1 + Vanco + Ve303(t) + (Cohort \mid ID) \quad \text{Equation 2}$$

With:

$Vanco = \text{Pre, During, Post}$ $$Ve303(t) = \sum_i Ve303_i(t)$$

Figure 40A:
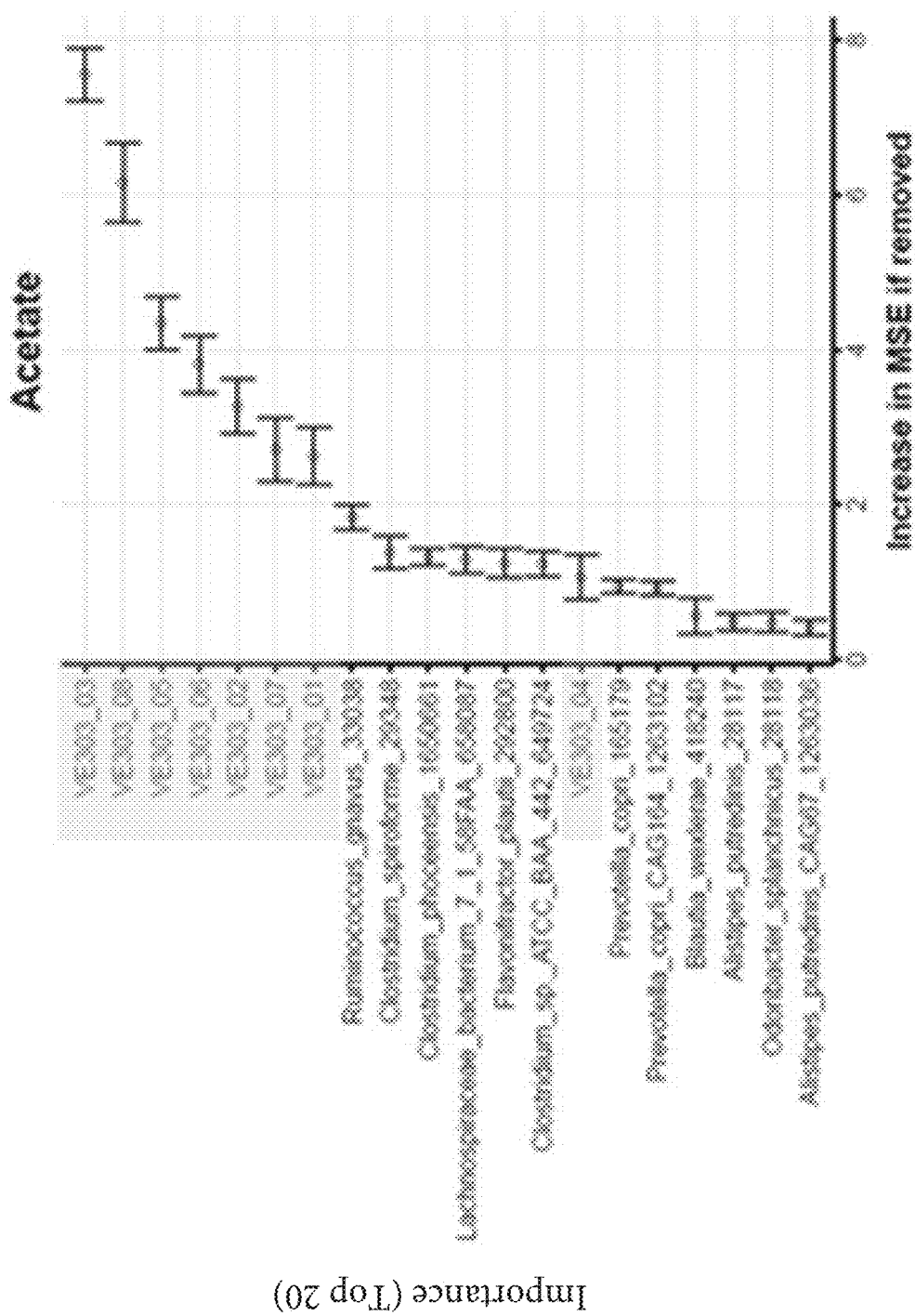
FIGS. 40A-40C show the identity of the top 20 bacterial strains that are important in the recovery of short chain fatty acids (SCFAs) after treatment with antibiotics. VE303 bacterial strains are important in the recovery of SCFAs.
Figure 40B:
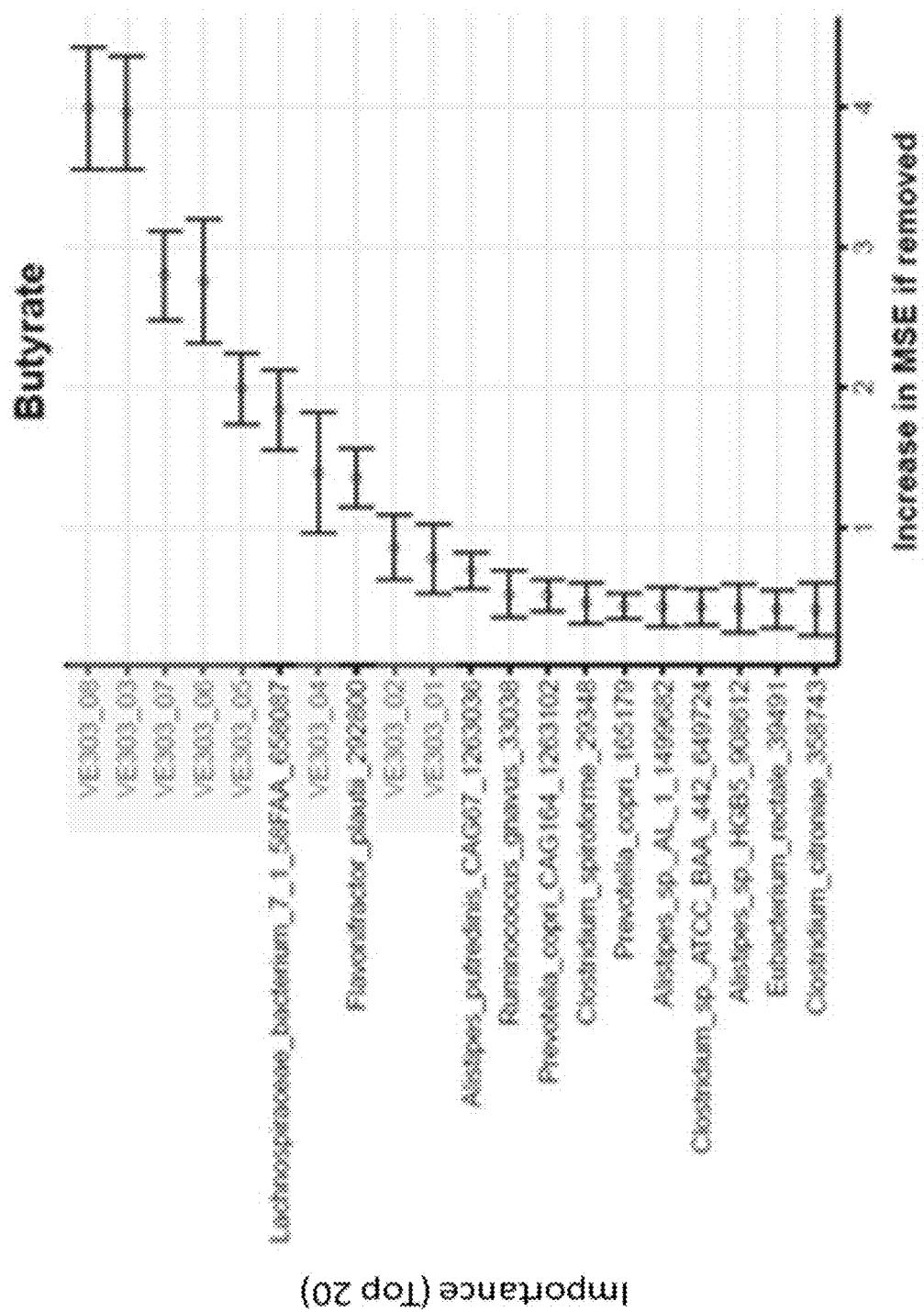
Figure 40C:
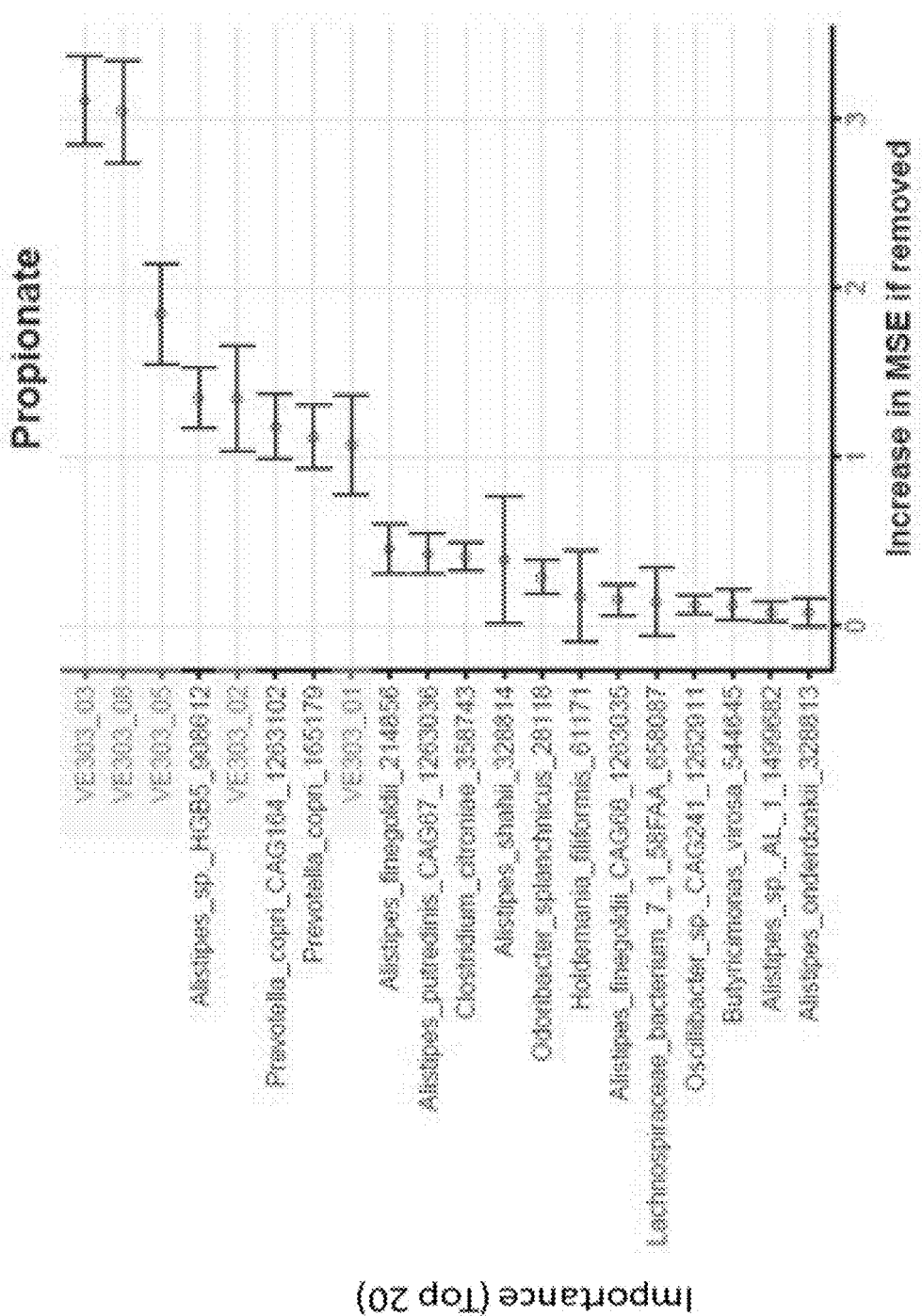

For RFA, a partial dependence analysis+Linear Model of the top 20 important features was constructed. All VE303 strains were positively associated with acetate and butyrate SCFA recovery. VE303 group A and group B strains were clustered according to their association with SCFA recovery. VE303 group A (V303-01, VE303-02, VE303-06, VE303-07; also described herein as "VE303 group A strains—SCFA") is positively associated with hexanoate SCFA levels and VE303 group B (V303-03, VE303-04, VE303-08; also described herein as "VE303 group B strains—SCFA") is positively associated with propionate SCFA levels. VE303 strains were also found to be among the top 20 most important features for the recovery to baseline levels of the SCFAs acetate, propionate, and butyrate (FIG. 40).

Conclusion

The levels of SCFAs are decreased with vancomycin treatment. Acetate, propionate, and butyrate levels are significantly decreased by vancomycin administration. This is consistent in subjects with CDI, in which butyrate levels are decreased. Administration of VE303 and the abundance of VE303 strains is associated with the recovery of SCFA levels. These SCFA levels are also increased following FMT treatment in patients with CDI.

Example 7: Strain Colonization of a Defined Bacterial Consortium and Restoration of the Microbiota and Metabolite Pool of Healthy Volunteers Alterations of the human gut microbiota are associated with infections by opportunistic pathogens like *Clostridium difficile* (*C. difficile*). Reduction in *C. difficile* infection recurrence rate has been shown with fecal microbiota transplantation (FMT); however, FMT carries inherent risks and variability. VE303, a live biotherapeutic product (LBP) for the prevention of recurrent *C. difficile* infection (rCDI). VE303 is a rationally-defined bacterial consortium that consists of 8 purified, clonal strains belonging to *Clostridium* clusters IV, XIVa, and XVII. The strains were isolated from the fecal matter of healthy volunteers, banked as pure cultures, and manufactured under cGMP conditions. Safety, tolerability, pharmacokinetics (PK), and pharmacodynamics (PD) of VE303 were assessed in healthy volunteers (N=33). Increasing doses of VE303 were administered with or without a 5-day course of oral vancomycin. Fecal samples were collected longitudinally up to 6 months and metagenomics sequencing were performed on the Illumina platform to quantify the colonization of the VE303 strains over time (Pharmacokinetics, PK) and their impact on the recovery of the resident gut microbiota and the levels of short chain fatty acids (SCFA) and bile acids (BA) (Pharmacodynamics, PD) following vancomycin exposure. A scalable bioinformatic method that utilizes unique marker sequences for each VE303 strain was developed to precisely define PK by differentiating the members of the LBP from resident strains. VE303 administration post-vancomycin was safe and well-tolerated across all dose levels. Dosing conditions were identified where the VE303 strains rapidly increased in abundance and were detected at least 6 months after administrations of the consortium. VE303 also lead to an enhancement in the gut microbiota recovery post-vancomycin, demonstrated by an accelerated increase in *Clostridium* and Bacteroidetes species and reduced Proteobacteria. VE303 strain colonization was also associated with expedited recovery of SCFAs and secondary BAs measured in the stool post-vancomycin administration. Collectively, these data indicate for the first time that an LBP based on a rationally-defined bacterial consortium is safe, can durably colonize the gut, and is capable of promoting intestinal homeostasis of human recipients.

Example 8: VE303 Stably Restores the Gut Microbiome after Vancomycin-Induced Dysbiosis in Adult Healthy Volunteers (HV)

Gut microbiota alterations and resulting changes in metabolites involved in colonization resistance and host responses, including bile acids (BA) and short chain fatty acids (SCFAs), are hallmarks of *C. difficile* infection (CDI). A reduction in recurrent CDI (rCDI) has been observed with fecal microbiota transplants (FMT), however FMT has limitations for routine use and carries unforeseen risks. VE303 is a first-in-class drug being developed for prevention of rCDI, and consists of a rationally defined bacterial consortium manufactured under good manufacturing principle (GMP) conditions. VE303 comprises 8 distinct species belonging to *Clostridium* clusters IV, XIVa, and XVII, the commensal bacteria associated with clinical response in FMT. VE303 suppresses *C. difficile* growth in vitro and improves survival in vivo.

A first in-human Phase 1 dose-escalation study assessed safety and tolerability of VE303 in healthy volunteers (HV) after vancomycin (vanco)-induced dysbiosis. VE303 pharmacokinetics (PK), including bacterial strain colonization and durability, and pharmacodynamics (PD), including restoration of the resident microbiota, SCFA pool and BA pool were evaluated by metagenomic sequencing and metabolomics analysis of fecal material.

Figure 42:
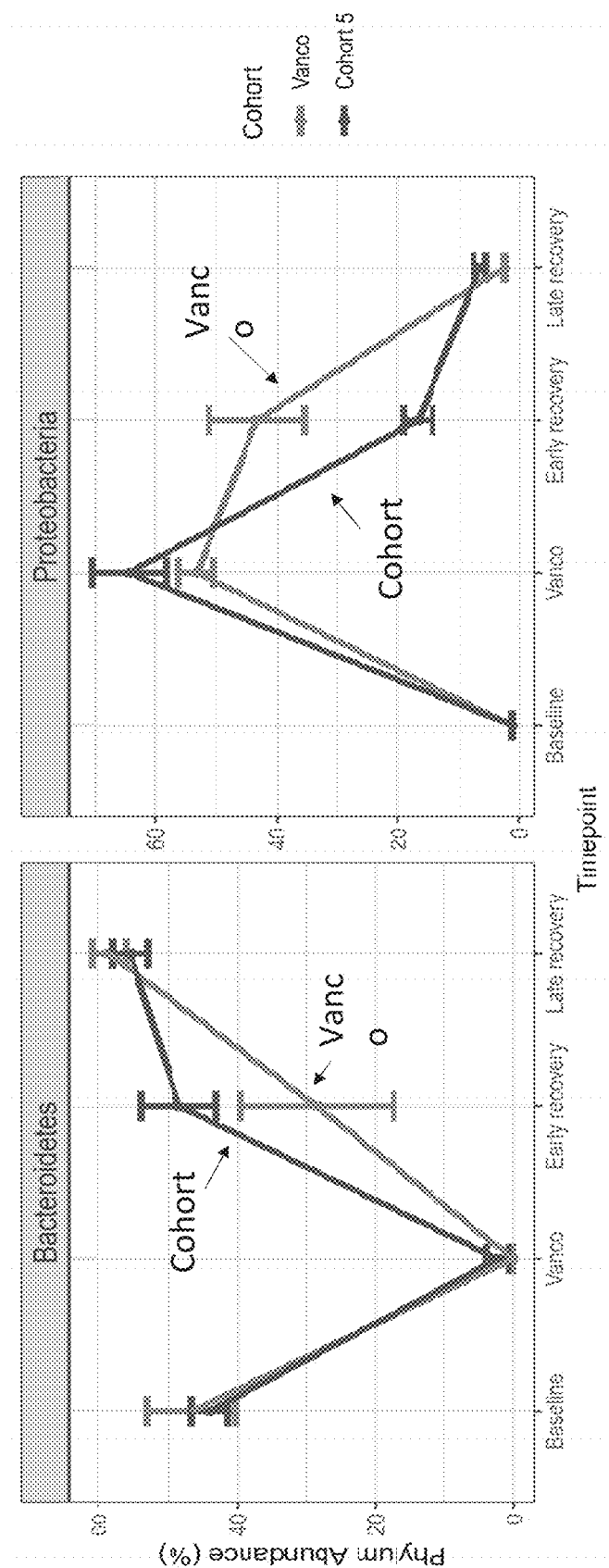
FIG. 42 shows that VE303 enhances the early recovery of the microbiota after vancomycin. The mean relative abundance (+/−SEM) of Bacteroidetes (left panel) and Proteobacteria (right panel) for healthy volunteers (HV) administered vancomycin only (5 days, administered daily) ("Vanco") or VE303 for 14 days ("Cohort 5"). The "Vanco" time points include samples collected during vancomycin administration +24 hrs. The "Early recovery" time points include samples collected within the first 7 days of recovery. The "Late recovery" time points include samples collected after the first 7 days of recovery.

Twenty-three healthy volunteers received 125 mg oral vancomycin every day for 5 days, followed by VE303 capsules at escalating single doses then multiple doses (total dose range $1.6 \times 10^9$ colony forming units (CFUs) to $1.1 \times 10^{11}$ CFUs). VE303-related adverse events (AEs), were observed in 35% of HVs and were mostly gastrointestinal, all Grade 1 and transient. Colonization with VE303 strains was abundant, durable (detected at 24 weeks), and dose-dependent. VE303 rapidly expanded 10-100-fold, and each strain was detectable within 2 days after dosing. VE303 enhanced subjects' microbiota and metabolic recovery after vancomycin treatment. When compared with the vancomycin-only cohort (N=5), VE303 led to earlier and more complete recovery of beneficial taxa (e.g., Bacteroidetes, Firmicutes), reduction in inflammatory taxa (e.g., Proteobacteria), and recovery of the secondary BA and SCFA pools (See e.g., FIG. 42).

VE303, a rationally designed microbial consortium, was safe, well-tolerated, and efficiently restored microbiome composition after antibiotic-induced dysbiosis in a dose dependent manner. VE303 was associated with early recovery of key PD markers of response, including microbiota composition, bile acid, and SCFA pools. A Phase 2 study of VE303 for prevention of rCDI is underway (NCT03788434).

Example 9: Evaluation of Strain Colonization of a Defined Bacterial Consortium and Restoration of the Microbiota of Healthy Volunteers after Antibiotics Exposure Alterations of the human gut microbiota are associated with infections by opportunistic pathogens like Clostridioides difficile (Clostridium difficile, C. difficile). Reduction in C. difficile infection recurrence rate has been shown with fecal microbiota transplantation (FMT); however, FMT carries inherent risks and variability. VE303, a live biotherapeutic product (LBP) for the prevention of C. difficile recurrence (rCDI), is a rationally-defined bacterial consortium that consists of 8 purified, clonal strains belonging to Clostridium clusters IV, XIVa, and XVII. The strains were isolated from the fecal matter of healthy volunteers, banked as pure cultures, and manufactured under cGMP conditions. A Phase 1a/1b study was conducted in healthy volunteers (HV; N=38), in which the primary outcomes were the evaluation of the safety and tolerability of VE303 and to determine doses for testing efficacy against recurrent CDI (rCDI) in a Phase 2 study. The secondary outcomes were to define the pharmacokinetics (PK) and pharmacodynamics (PD) of VE303.

Increasing doses of VE303 were administered to 33 healthy volunteers (HVs) with or without a 5-day course of oral vancomycin. A 5-day course of oral vancomycin (vanco) alone was administered to 5 HV. Fecal samples were collected longitudinally up to 1 year and metagenomic sequencing was performed on the Illumina platform to quantify the colonization of the VE303 strains over time (Pharmacokinetics, PK) and their impact on the recovery of the resident gut microbiota (Pharmacodynamics, PD) following vancomycin exposure. A scalable bioinformatic method that utilizes unique marker sequences for each VE303 strain was developed to precisely characterize VE303 PK by differentiating the members of the VE303 live biotherapeutic product (LBP) from related, endogenous microorganisms. This tool enabled the precise quantification of PK and PD in human stool samples after VE303 administration. VE303 administration post-vancomycin was safe and well-tolerated across all dose levels. Dosing conditions were identified where the VE303 strains rapidly increased in abundance and were detected up to 12 months after administration. VE303 also led to an enhancement in the gut microbiota recovery post-vancomycin, demonstrated by an accelerated increase in Clostridium and Bacteroidetes species and reduced Proteobacteria.

Collectively, these data indicate for the first time that an LBP based on a rationally-defined bacterial consortium is safe, can durably colonize the gut, and expedite the recovery of the resident microbiota after antibiotics exposure. A Phase 2 study is ongoing to assess the efficacy of VE303 in rCDI patients.

Example 10: In Vitro Competition Between VE303 and C. difficile

Bacterial compositions were evaluated for their ability to suppress Clostridium difficile growth by an in vitro mixed culture competition assay. The Dorea longicatena strain 6, VE303 consortium, and VE303 without Dorea longicatena were each assessed. Clostridium bifermentans was used as a positive control.

Eggerth-Gagnon agar plates with horse blood (EG+HB) were prepared according to standard procedures and reduced in an anaerobic environment for at least 6-8 hours prior to use. Liquid BHI medium was obtained from BD Biosciences (Catalog #211059, San Jose, CA), prepared according to the manufacturer's instructions, and reduced in an anaerobic environment for at least 18-24 hours prior to use. Taurocholate-Cycloserine-Cefoxitin-Fructose Agar (TCCFA) plates were prepared according to standard procedures and reduced in an anaerobic environment for at least 6-8 hours prior to use.

Clostridium difficile strain used in the experiments is from the American Type Culture Collection (ATCC), strain ATCC 43255.

Each of the bacterial strains were struck out onto EG+HB agar plates from frozen glycerol stocks inside an anaerobic chamber for 48-72 hours. Single colonies were inoculated into 10 mL of BHI media and grown 24-48 hours at 37° C. in the anaerobic chamber. Turbid cultures were then diluted to an OD of 0.1 and grown for 2-3 hours at 37° C. in the anaerobic chamber. Exponential phase cultures were diluted and combined at equivalent ODs.

For the competition assay, each of the strains of VE303 or VE303 without Dorea longicatena were combined in equal parts, based on OD600, to reach a final consortium OD600 of 0.1. The single strains C. bifermentans and Dorea longicatena were prepared to compete directly with C. difficile individually at an $OD_{600}$ of 0.1. The $OD_{600}$ for C. difficile in each of the mixed culture competition experiments was 0.1. After combination, the cultures were incubated for 2-3 hours at 37° C. in the anaerobic chamber, then prepared for C. difficile enumerations on plates selective for C. difficile growth (TCCFA plates). Inside an anaerobic chamber, a 100 µL sample of each competition culture was collected and serially diluted 1:10 to reach a final dilution of $1\times10^{-6}$. Plates for colony forming unit (CFU) enumeration were prepared by spreading 100 µL of each of the $1\times10^{-4}$ through $1\times10^{-6}$ dilutions using sterile spreading loops on TCCFA plates. The TCCFA plates were incubated for 48-72 hours at 37° C. in the anaerobic chamber.

Figure 43:
FIG. 43 shows that the VE303 consortium and strain 6 (*Dorea longicatena*) reduced *Clostridium difficile* (*C. difficile*) growth in in vitro competition experiments. VE303 without *Dorea longicatena* was not as effective in suppressing VE303 growth. Cultures of *C. difficile* were incubated in the presence of *Clostridium bifermentans* (positive control), VE303, *Dorea longicatena*, VE303 without *Dorea longicatena*, or in the absence of a competing strain(s) (*C. difficile* only). The quantity of *C. difficile* is presented as the percentage of the control (*C. difficile* only).

CFU enumeration was completed by manually counting colonies for the C. difficile only control as well as each of the competition experiments. To determine the effect of competition, the ratio of CFUs for the competition samples as compared to C. difficile alone was calculated and expressed as a percentage of C. difficile alone, which was set at 100%. The results are shown in FIG. 43. Dorea longicatena (VE303 Strain 6) and VE303 significantly suppressed C. difficile growth. VE303 without Dorea longicatena was less effective in suppressing C. difficile growth.

Example 11: Pharmacokinetics and Pharmacodynamics of the Live Biotherapeutic Product VE303 in Normal Healthy Volunteers Alterations of the bacterial microbiome in the human intestine, such as reduced diversity and lower abundance of commensal organisms, are associated with infections by opportunistic pathogens like Clostridioides difficile (previously referred to as C. difficile). Current microbiome-based treatments aimed at restoring a diverse microbiota, such as fecal microbiota transplant (FMT), have demonstrated reduction in the rate of C. difficile recurrence. However, FMT and similar approaches that require the transfer of a large fraction of mostly uncharacterized fecal matter from a donor are inherently variable by nature, poorly defined and have the potential to transmit infectious agents. Although overall changes in the microbiome as a result of FMT have been reported, it is not practical to measure the link between the administered fecal microbiota and the resulting microbiome changes. We have developed a live biotherapeutic product (LBP), called VE303, for the prevention of *C. difficile* recurrence (rCDI). The VE303 consortium is a rationally-designed therapeutic that consists of 8 clonal strains of *Clostridium*. The strains were isolated from the fecal matter of healthy volunteers, fully characterized, and grown individually under GMP conditions. We have initiated a Phase 1a/1b, dose-escalating study to assess the safety, tolerability, and colonization of VE303 in healthy volunteers is ongoing.

Also described herein is a novel bioinformatic method for determining pharmacokinetics (PK) and pharmacodynamics (PD) of a live biotherapeutic product (LBP) is described, and conditions under which the strains durably and robustly colonize the human gut are demonstrated. The VE303 strains rapidly increase in abundance after they are administered and are readily detected at least 12 weeks after administration of the consortium. Strain colonization required displacement of related commensal microbes via pre-treatment with an antibiotic and daily administration of the consortium for upwards of 14 days, a protocol unachievable by FMT. An evaluation of the microbiome recovery post-antibiotics indicated that VE303 administration promoted the recovery of Bacteroidetes species and reduced the presence of Proteobacteria. Additionally, VE303 administration was found to significantly enhance the recovery of a number of Short-Chain Fatty Acids (SCFAs) and the biotransformation of a subset of primary bile acids into secondary bile acids post-antibiotics. Collectively, these data demonstrate for the first time that LBPs are a safe alternative to FMT that can durably colonize the gut and modulate the microbiota of human recipients.

The methods described herein allow for the determination of the PK and PD for live microbial consortia-based therapies. A Phase 1 study was performed as part of an investigational new drug (IND) in normal healthy volunteers (NHVs) to establish the safety of a microbial consortium and to define PK and PD methods. The VE303 drug product was manufactured using standardized, scalable processes compliant with current good manufacturing practice (GMP) regulations and delivered in a lyophilized form. VE30, as described herein, is an LBP consisting of 8 well characterized, non-genetically engineered, clonally-derived, non-pathogenic, nontoxigenic, commensal strains of Clostridia. The VE303 consortium was developed to prevent the recurrence of CDIs. The PK and PD of the VE303 consortium were extensively investigated using a novel bioinformatic algorithm specifically designed to discern VE303 strains from endogenous relatives. Further, the VE303 dose regimen was optimized in healthy volunteers, thus, demonstrating safe, durable, and robust colonization of VE303 strains in the human gut which persisted throughout the year. VE303 also has the capacity to expedite the recovery of the resident microbial community and partial recovery of metabolites, including bile acids (BAs) and short-chain fatty acids (SCFAs), in NHVs after antibiotic induced dysbiosis.

Recurrent *C. difficile* infection is associated with reduced presence of bacteria belonging to *Clostridium* clusters IV and XIVa; FMT has been reported to restore this deficiency. The VE303 live biotherapeutic product (LBP) is a consortium of 8 well-characterized clonally-derived, nonpathogenic, nontoxigenic, commensal strains of Clostridia, including 5 strains from *Clostridium* cluster XIVa, 2 strains from *Clostridium* IV, and 1 strain from *Clostridium* XVII. These strains were originally derived from healthy human donor stool. The VE303 LBP demonstrates superior reproducible protection compared with other LBPs of commensal Clostridia, including consortia containing more than 50 strains, as VE303 produces SCFAs including acetate and butyrate and suppresses *C. difficile* growth both in vitro and in an in vivo murine model. The VE303 consortium was manufactured using good manufacturing practices and formulated into capsules containing a lyophilized mixture of the 8 strains. The individual strains within the VE303 consortium are not engineered or modified in any way relative to their native state in the human gut.

A first-in-human Phase 1 dose-escalation study was designed to assess the safety and the tolerability of VE303 in normal healthy adult volunteers (NHV) after vancomycin (vanco)-induced dysbiosis. The primary objective was to characterize the highest safe and well-tolerated dose regimen of VE303 by assessing adverse events (AEs), including GI symptoms, based on physical examinations, assessment of vital signs, and changes in the clinical laboratory measurements. Secondary objectives included an evaluation of the colonization of the intestinal microbiota with VE303 component bacteria, changes in the intestinal microbiota as a result of VE303 dosing, and metabolomic changes in stool.

Figure 44:
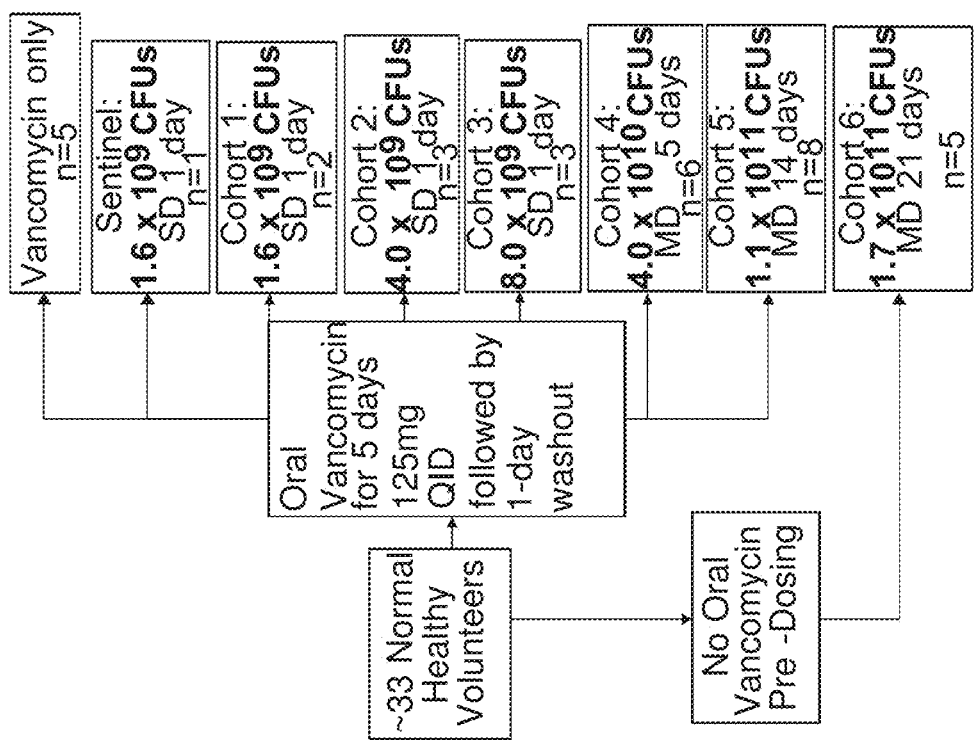
FIG. 44 presents a diagram illustrating the various treatment cohorts for the present disclosure.

Healthy volunteers (N=33) were enrolled in the study (baseline characteristics in Table 4) and received either oral vancomycin (125 mg every day (QID) for 5 days) or vancomycin followed by VE303 at ascending doses, or VE303 at the highest dose without vancomycin pretreatment (total dose range $1.6 \times 10^9$ to $1.1 \times 10^{11}$ CFUs) (FIG. 44). Subjects' disposition is presented in Table 4. Adverse events were observed in 85% of subjects in the study (see Tables 5A and 5B for details). Adverse events (AEs) attributed to either vancomycin or VE303 were observed in 50% of vancomycin-treated subjects and in 35% of VE303-treated subjects. VE303-related AEs were all Grade 1 and transient. Most of these AEs were gastrointestinal in nature and included abdominal distention, diarrhea, soft feces, alanine aminotransferase/aspartate aminotransferase (ALT/AST) increase, discolored or hard feces, constipation, abdominal discomfort or pain, dysgeusia, nausea, and flatulence (see Table 6 for details). The most common Grade 2-3 laboratory abnormalities were increased cholesterol, blood in urine, and increased lipase and amylase.

The detection of unmodified strains in the VE303 drug product and their differentiation from related endogenous strains in stool presented substantial hurdles in accurately determining VE303 pharmacokinetics (PK) in the human gut, especially since all 8 strains share greater than 98% Average Nucleotide Identity (ANI) to their nearest relative (Table 3). Consequently, a novel bioinformatic method was developed that enables the differentiation of the VE303 consortium member strains from highly related, endogenous taxa (described in Methods). Briefly, the detection of VE303 strains in stool metagenomes utilized unique 50 base pair (bp) genomic markers and assessment of the depth of marker recovery (the number of sequence reads matching any marker divided by the total number of markers for each strain) and the coverage of marker recovery (the number of markers with >=1 matching read, divided by the total number of markers for each strain). A strain was considered "Detected" when the mean marker depth exceeded 0.1× and the coverage of markers detected exceeded a minimum threshold of two standard deviations below the mean expected from a multinomial distribution (with 25% zero inflation to account for marker dropout). The 0.1× mean marker depth threshold was standard for all 8 strains, however strain detection events were evaluated post-hoc by comparing subjects with and without VE303 administration for added confidence. A strain was determined to be "Probable", "Insufficient data", or "Not detected" based on less confident marker coverage or depth thresholds (see Methods). The abundance of each strain and of resident bacterial taxa was determined using the One Codex software (one-codex.com) and a proprietary database of genomes assembled by One Codex in combination with bacterial genomes corresponding to bacterial isolates from healthy human stool samples.

TABLE 3

VE303 consortium members

| Strain | Clostridium Cluster | Nearest Relative (Scientific name) | Nearest Relative (NCBI TaxID) | FastANI identity (%) | Genome Length (bp) |
|---|---|---|---|---|---|
| VE303-01 | XIVa | Clostridium bolteae 90A9 | 997894 | 99.7576 | 6071159 |
| VE303-02 | IV | Anaerotrurtcus cotihominis DSM 17241 | 445972 | 99.155 | 3538351 |
| VE303-03 | XIVa | Sellimonas intestinalis | 1653434 | 99.4586 | 3195208 |
| VE303-04 | XIVa | [Clostridium] symbiosum WAL-14163 | 742740 | 99.0591 | 5600243 |
| VE303-05 | XIVa | Clostridia bacterium UC5.1-1D4 | 1697784 | 98.6518 | 5944559 |
| VE303-06 | XIVa | Dorea longicatena CAG:42 | 1263074 | 98.4309 | 3439497 |
| VE303-07 | XVII | Etysipelotrichaceae bacterium 21_3 | 658657 | 99.4812 | 4386760 |
| VE303-08 | IV | Ravonifractor plautii 1_3_50AFAA | 742738 | 98.1231 | 4771756 |

Figure 49A:
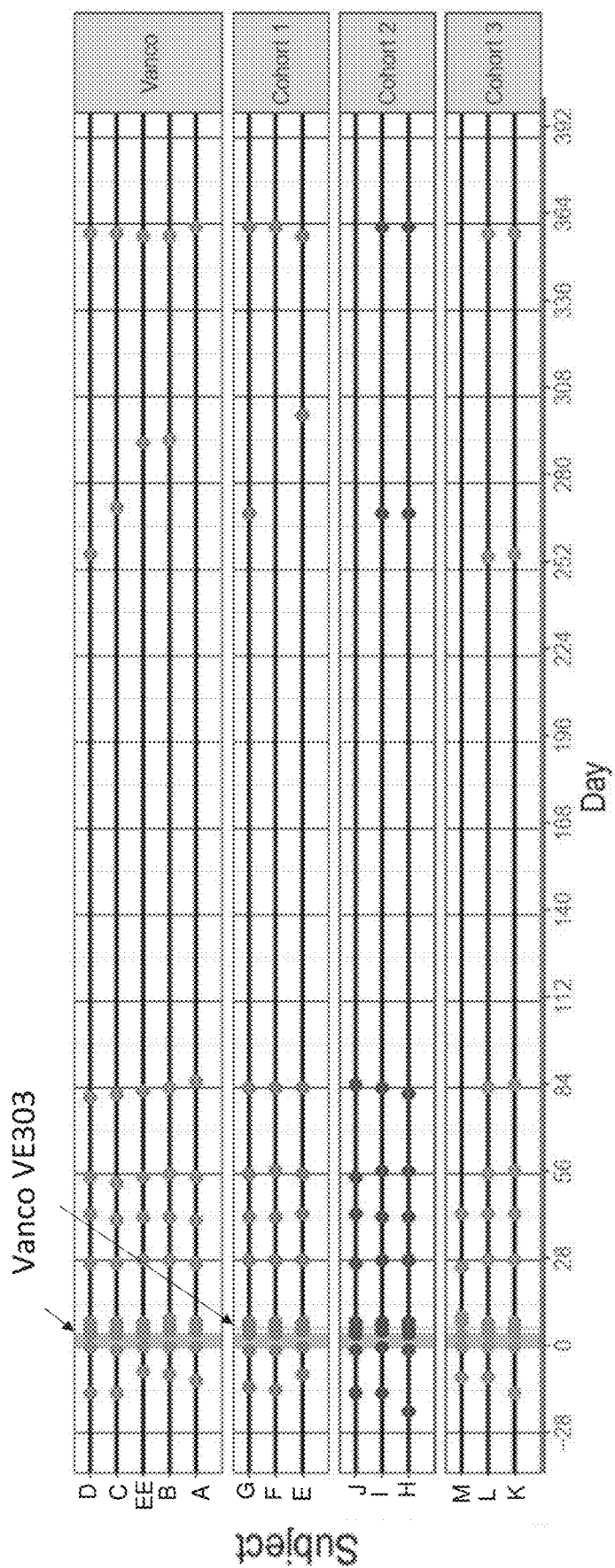
FIGS. 49A-49B show an investigational Phase 1a/b dose escalation study in volunteers. The various cohorts were treated according to the diagram in FIG. 44. Fecal stool samples were collected at the indicated time for each subject and analyzed by Illumina shotgun metagenomics sequencing. The first shaded region (left) indicates a daily vancomycin administration. The second shaded region (right) indicates daily VE303 administration. Each data point represents a fecal stool collection. "Vanco" is vancomycin.
Figure 49B:
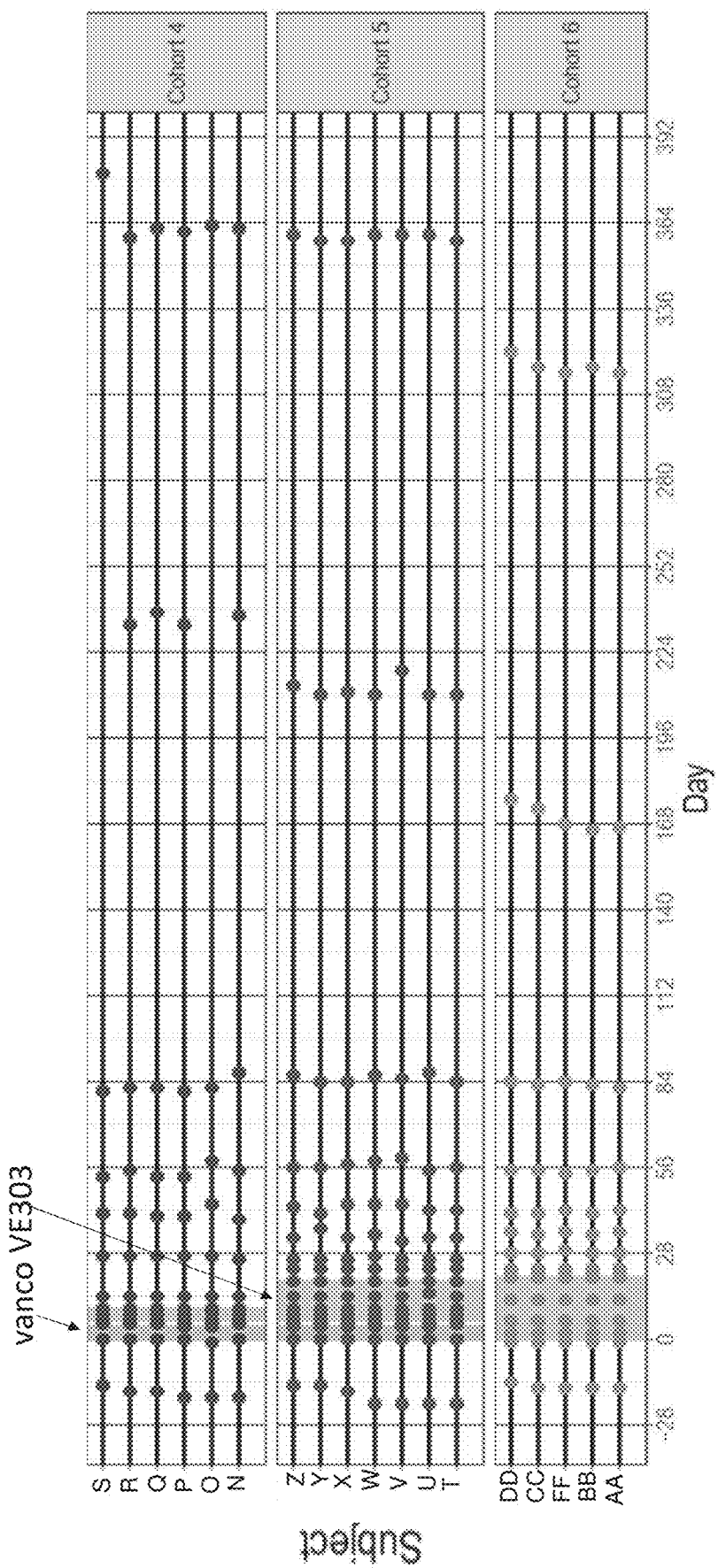
Figure 50A:
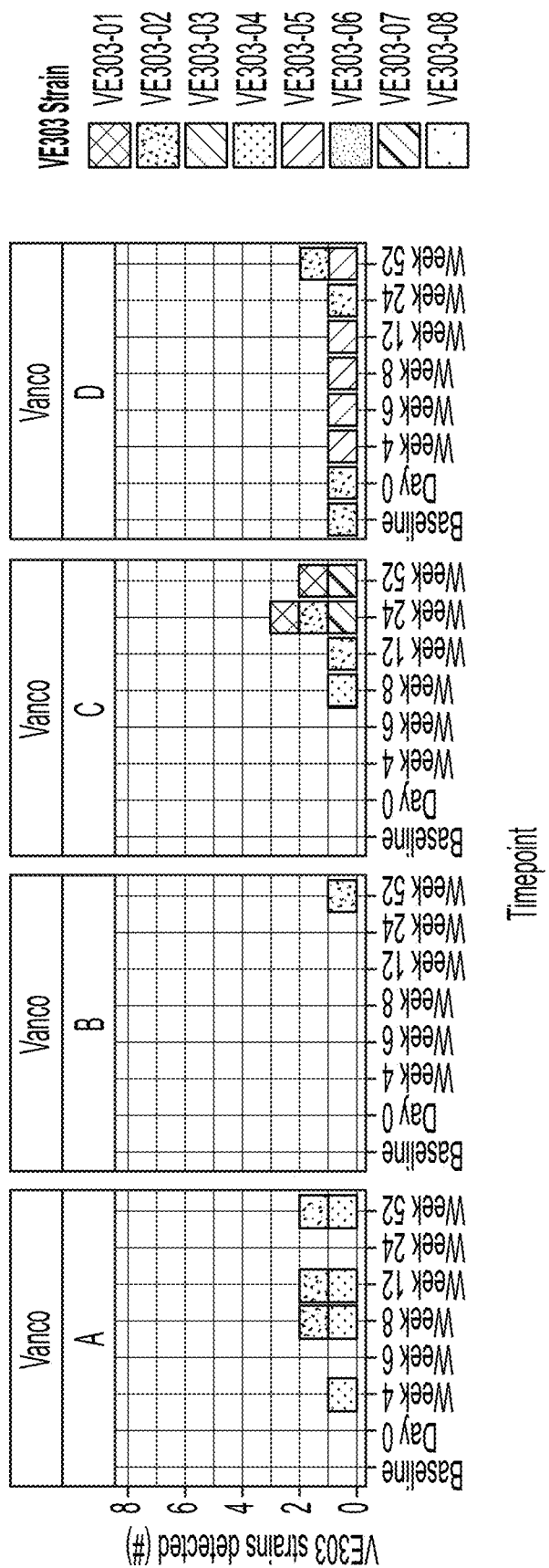
FIGS. 50A-50I present graphs showing the number of bacterial strains of composition VE303 detected in the microbiota of individual subjects.
Figure 50B:
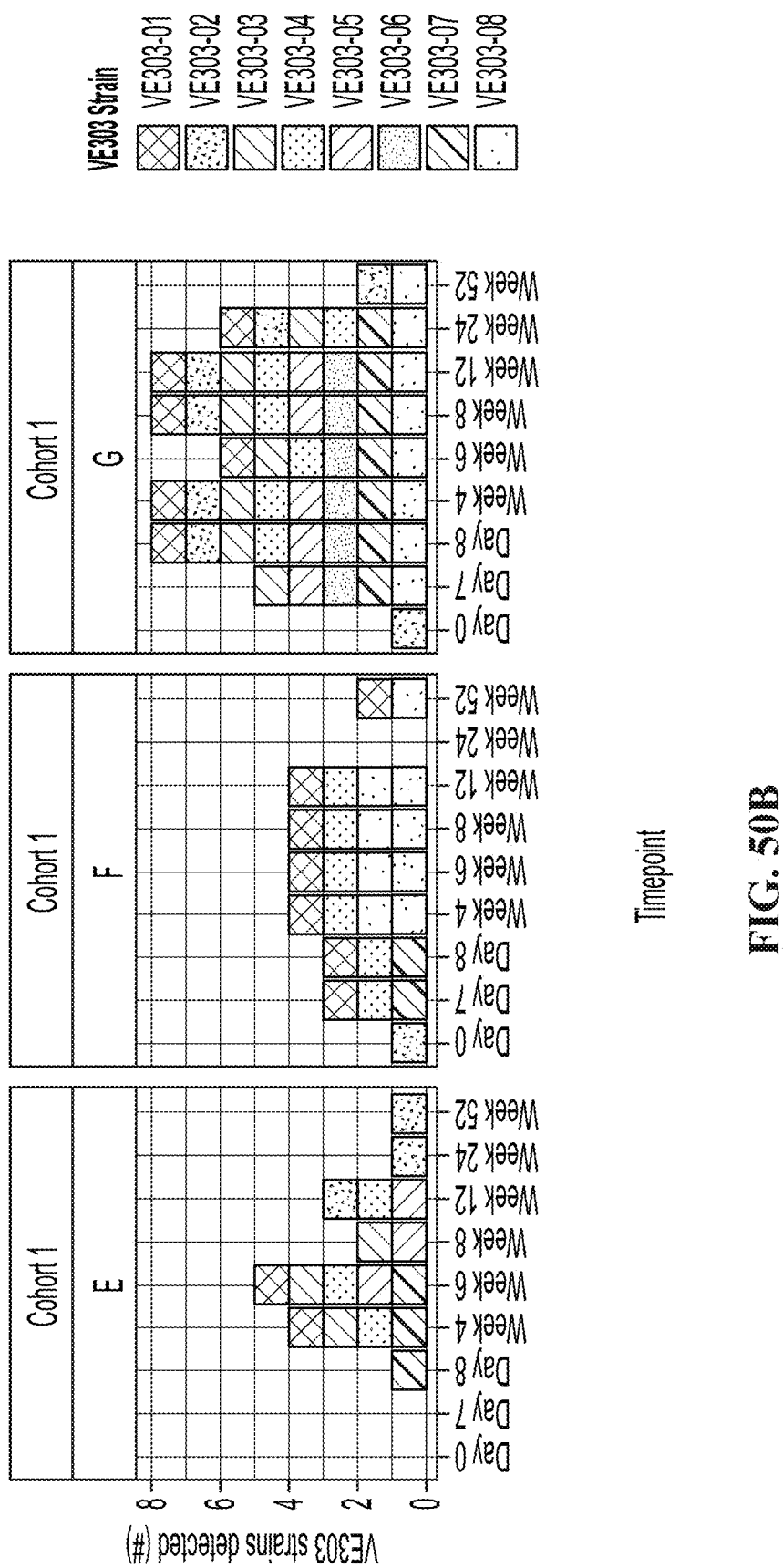
Figure 50C:
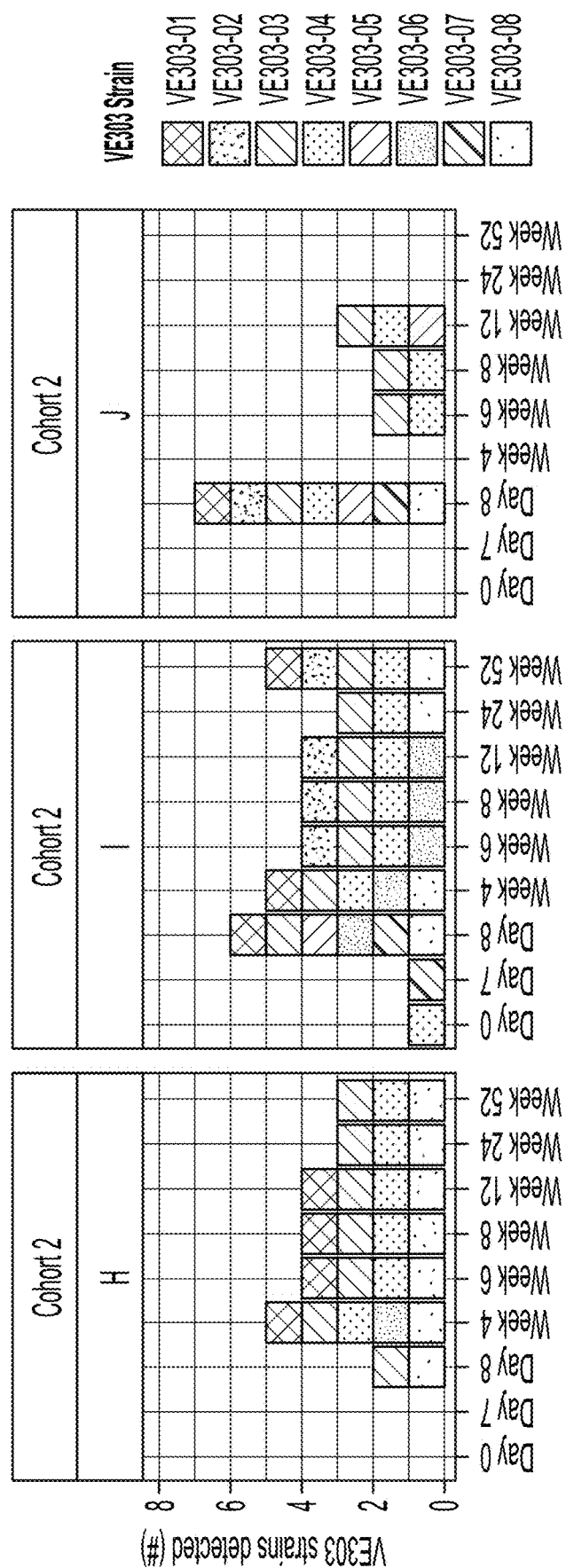
Figure 50D:
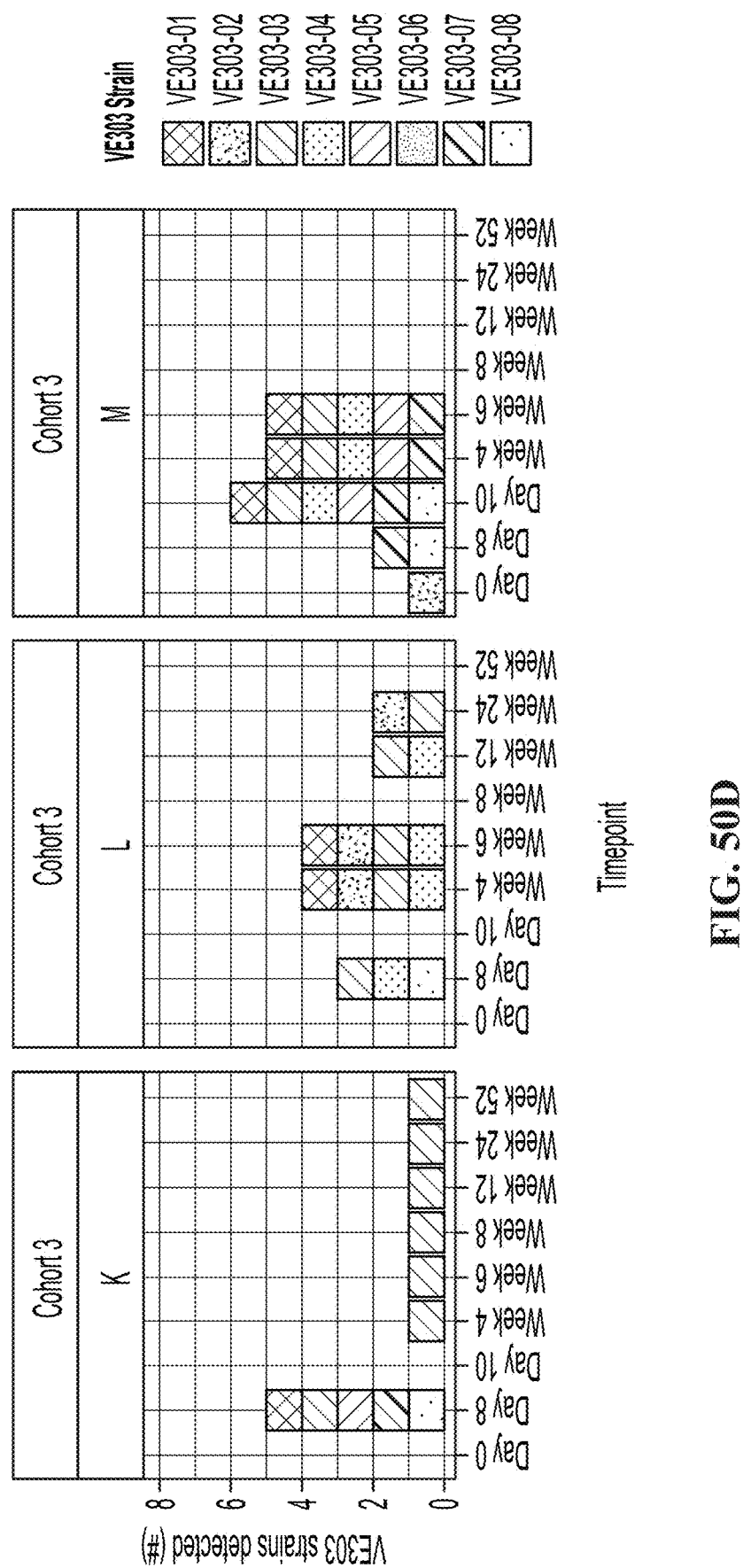
Figure 50E:
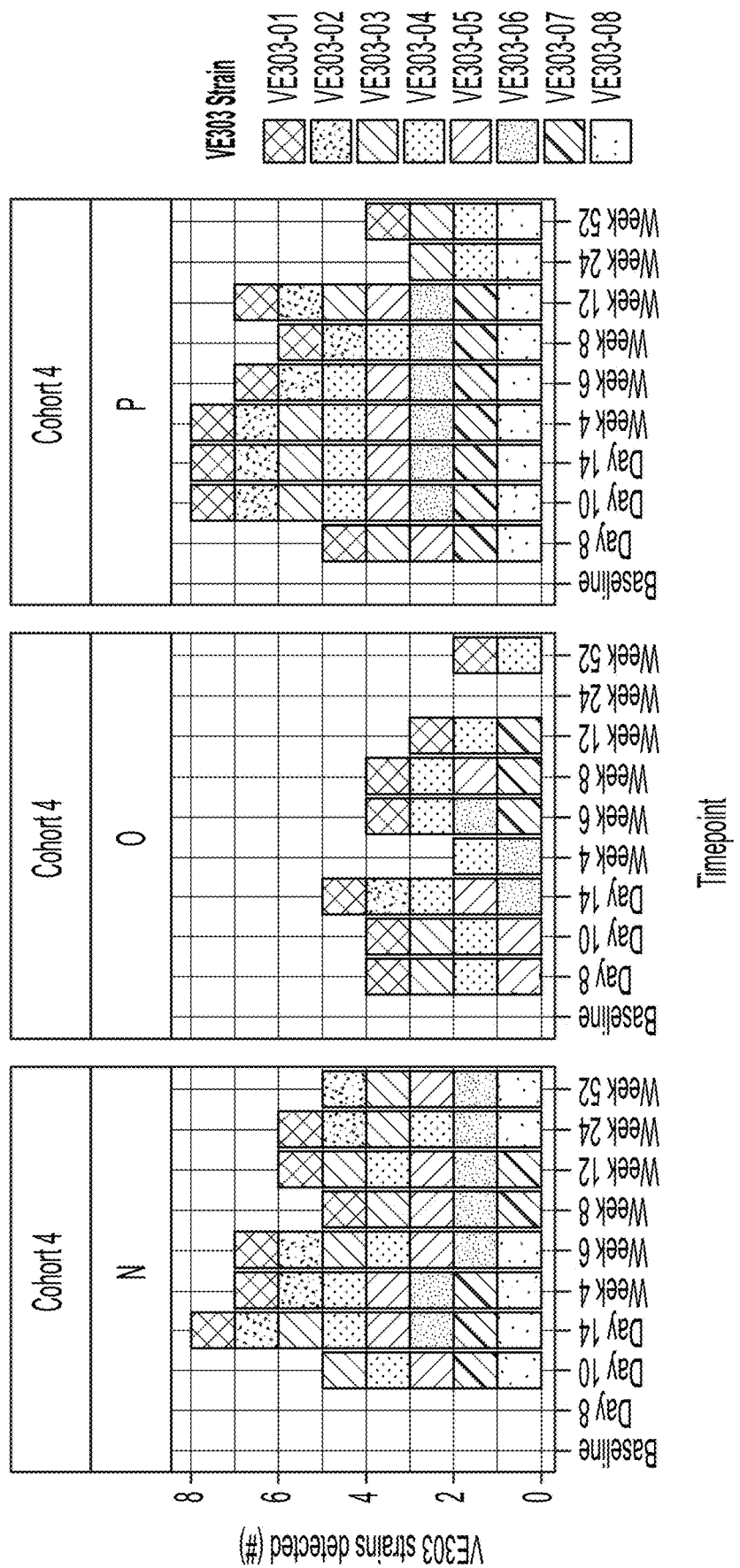
Figure 50F:
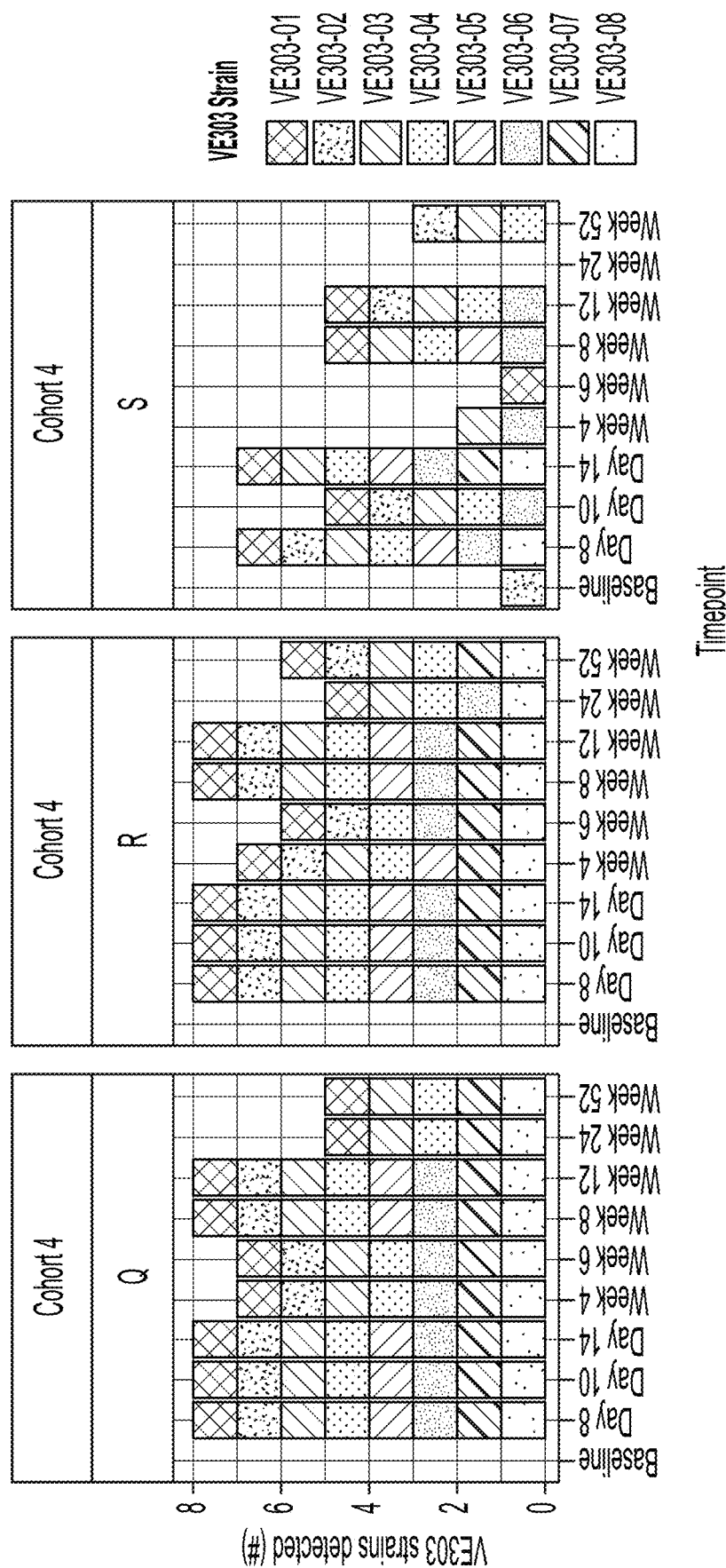
Figure 50G:
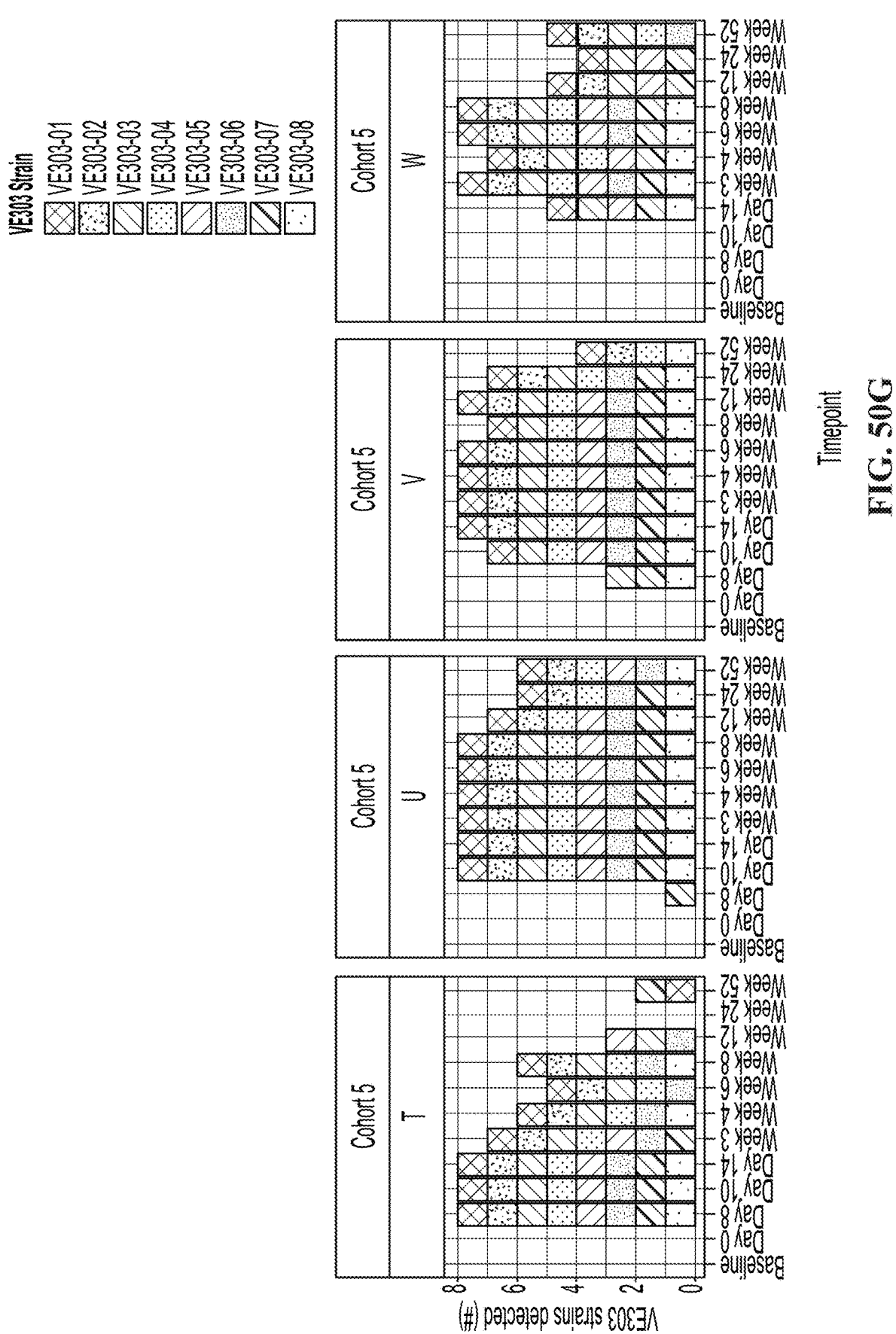
Figure 50H:
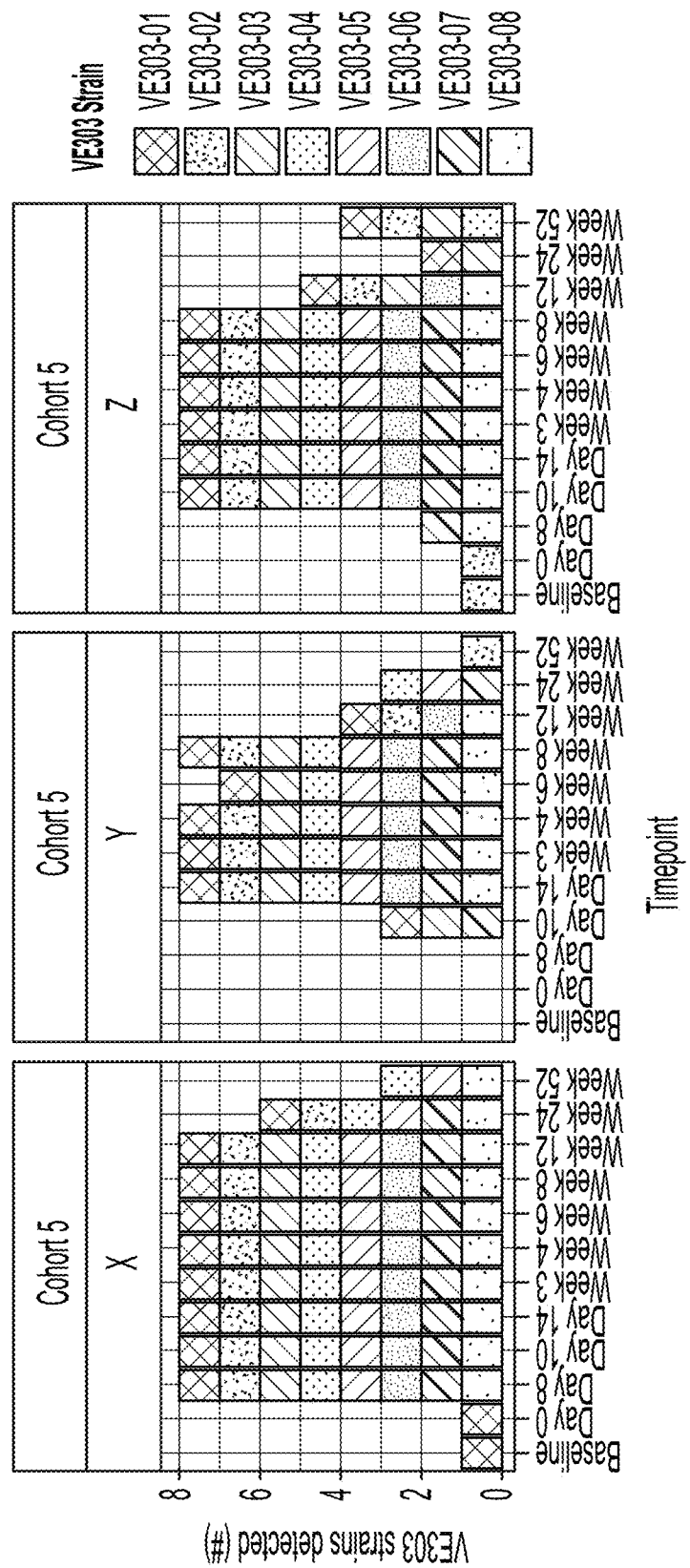
Figure 50I:
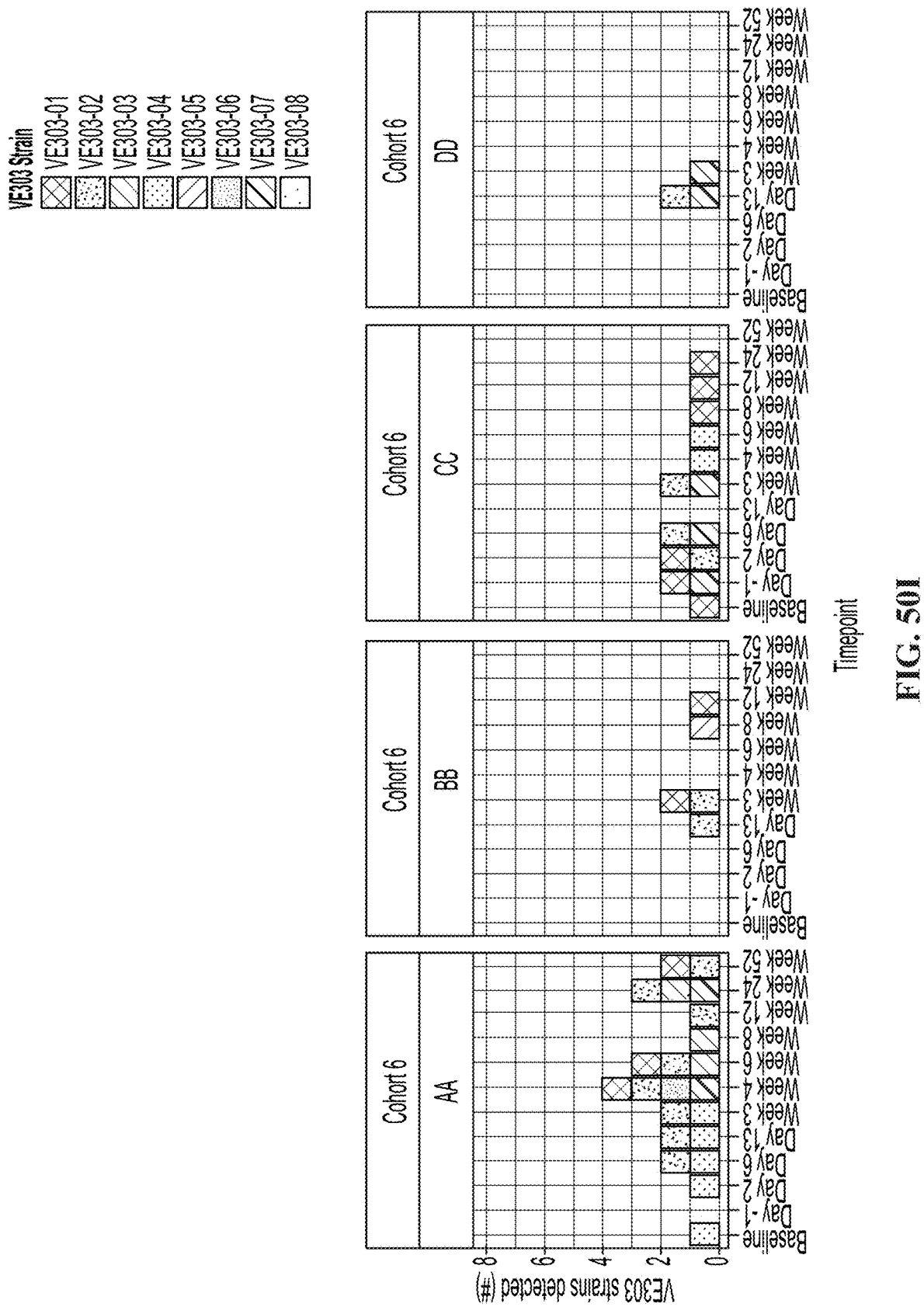
Figure 51A:
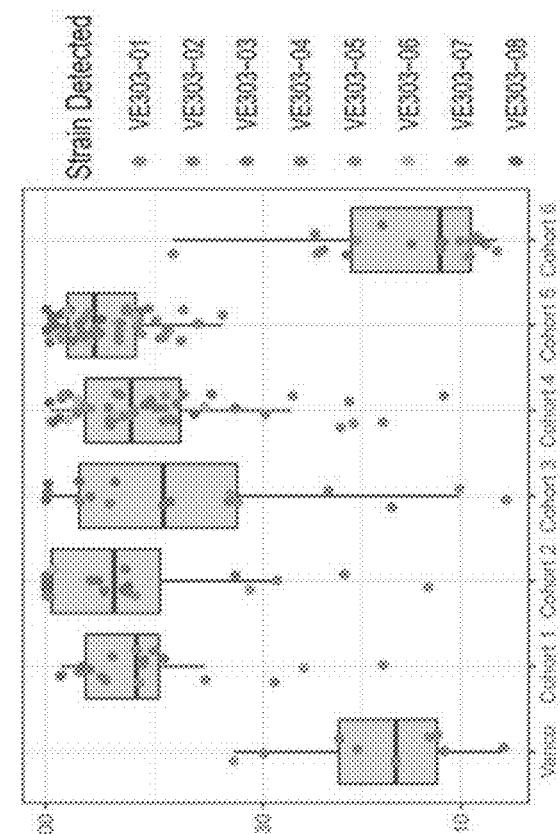
FIGS. 51A and 51B show VE303 marker panel depth and coverage using the detection methods described in Example 11.
Figure 51B:
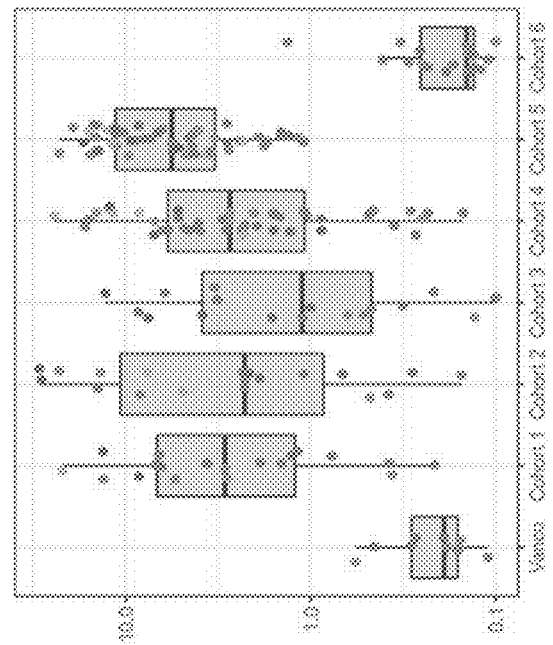
Figure 52A:
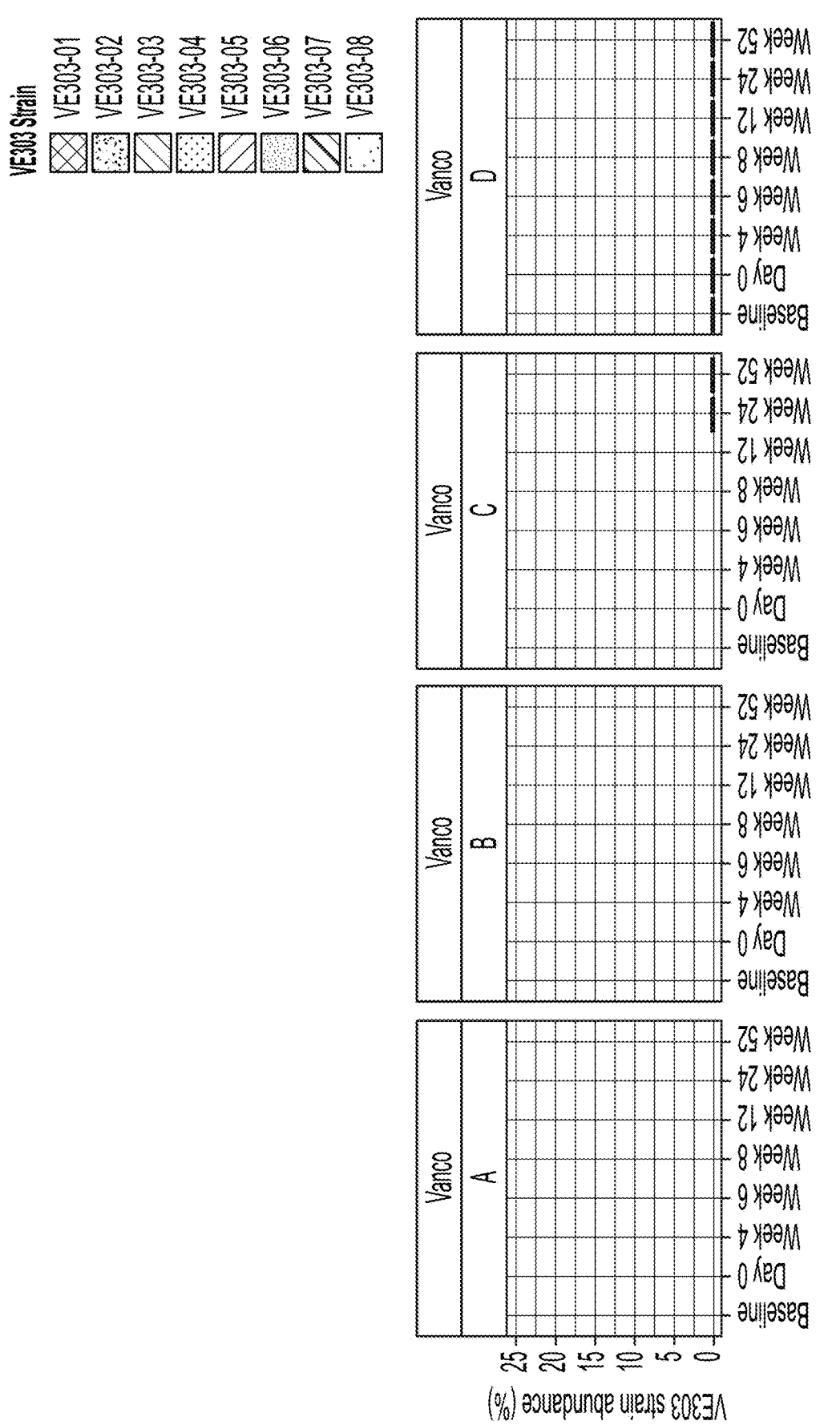
FIGS. 52A-52K present graphs showing the abundance of bacterial strains of composition VE303 detected in the microbiota of individual subjects.
Figure 52B:
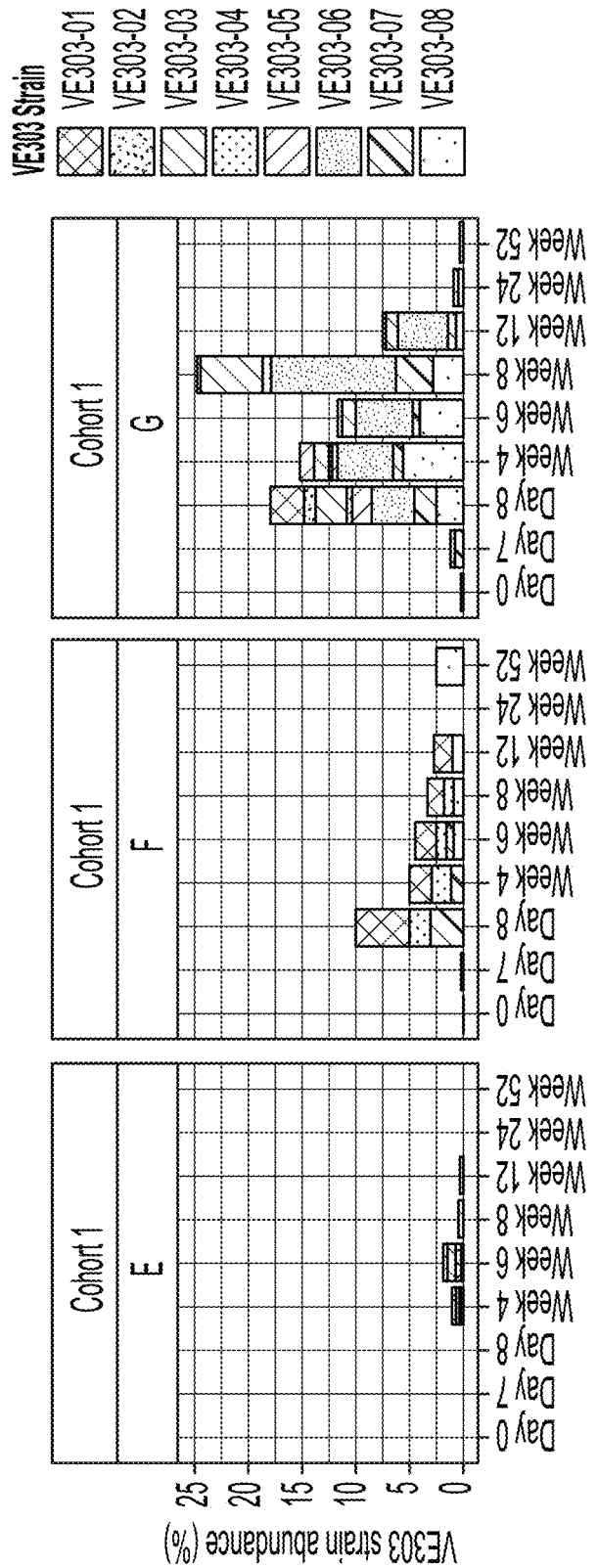
Figure 52C:
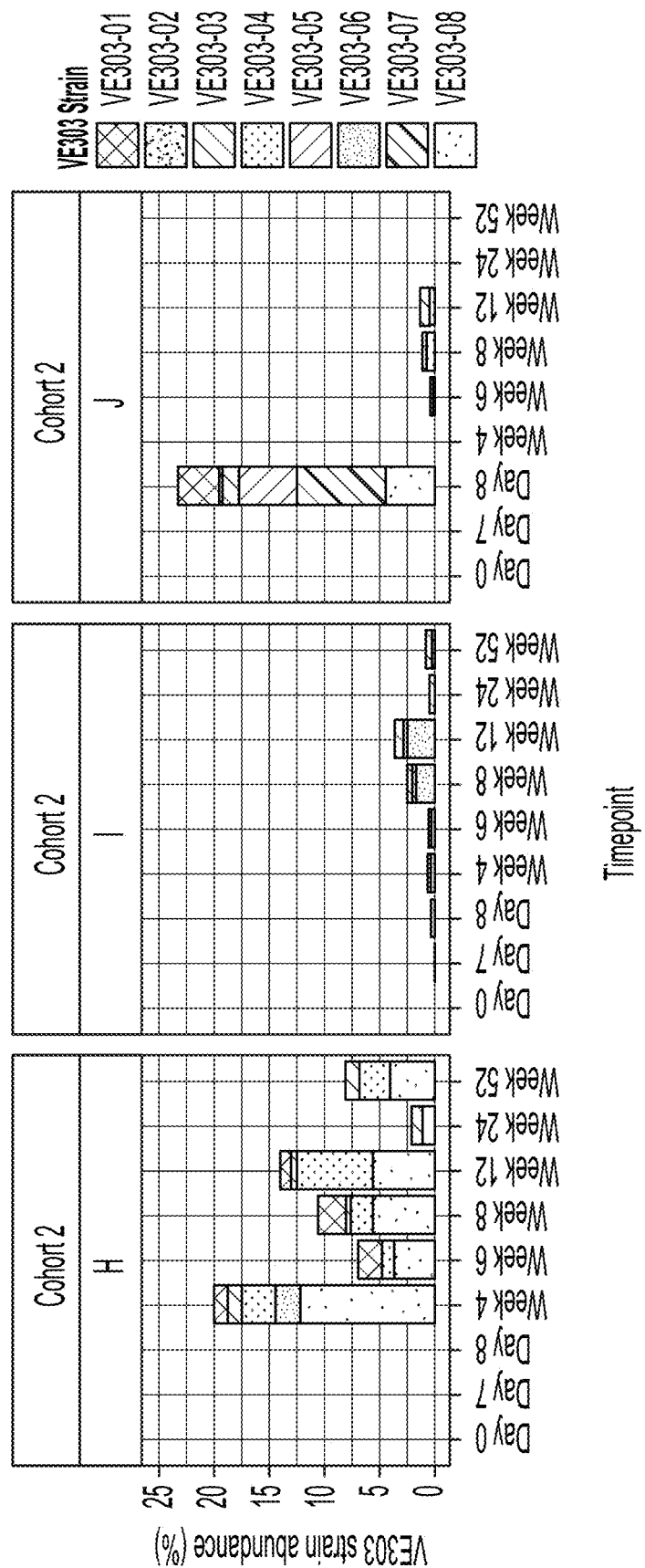
Figure 52D:
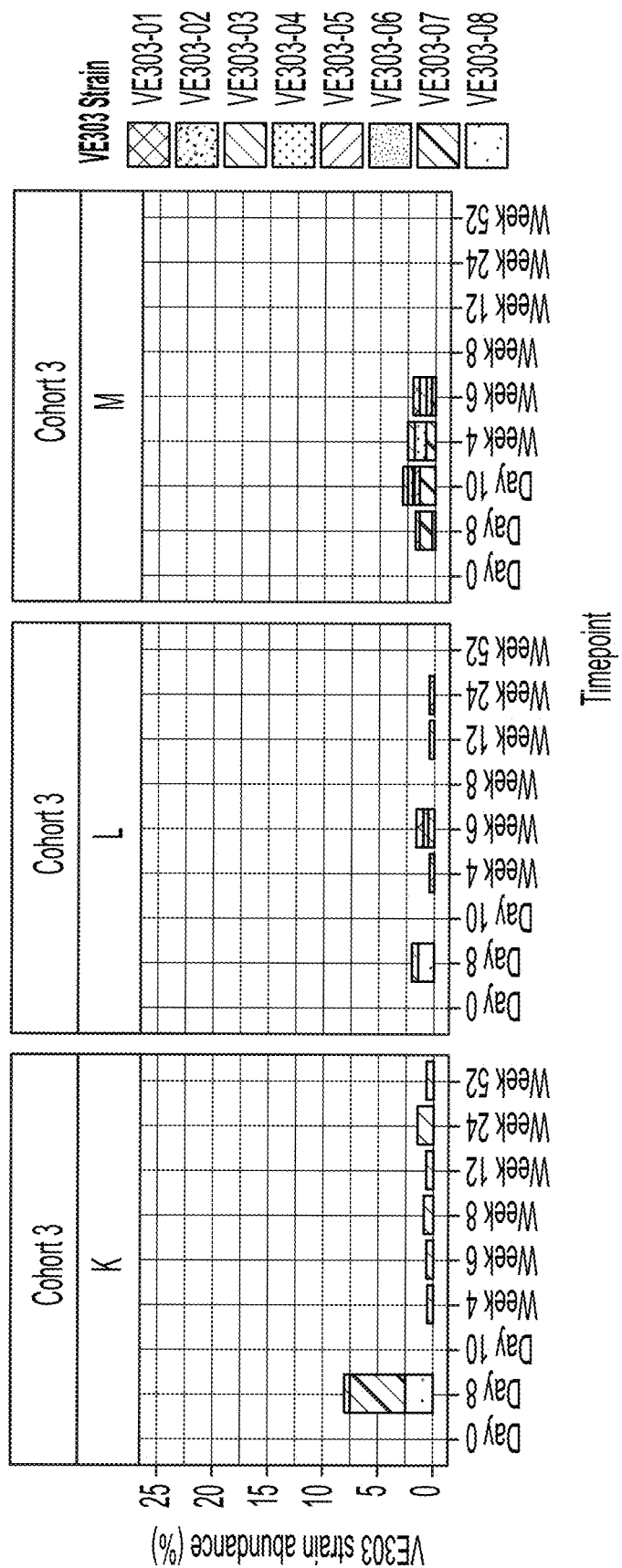
Figure 52E:
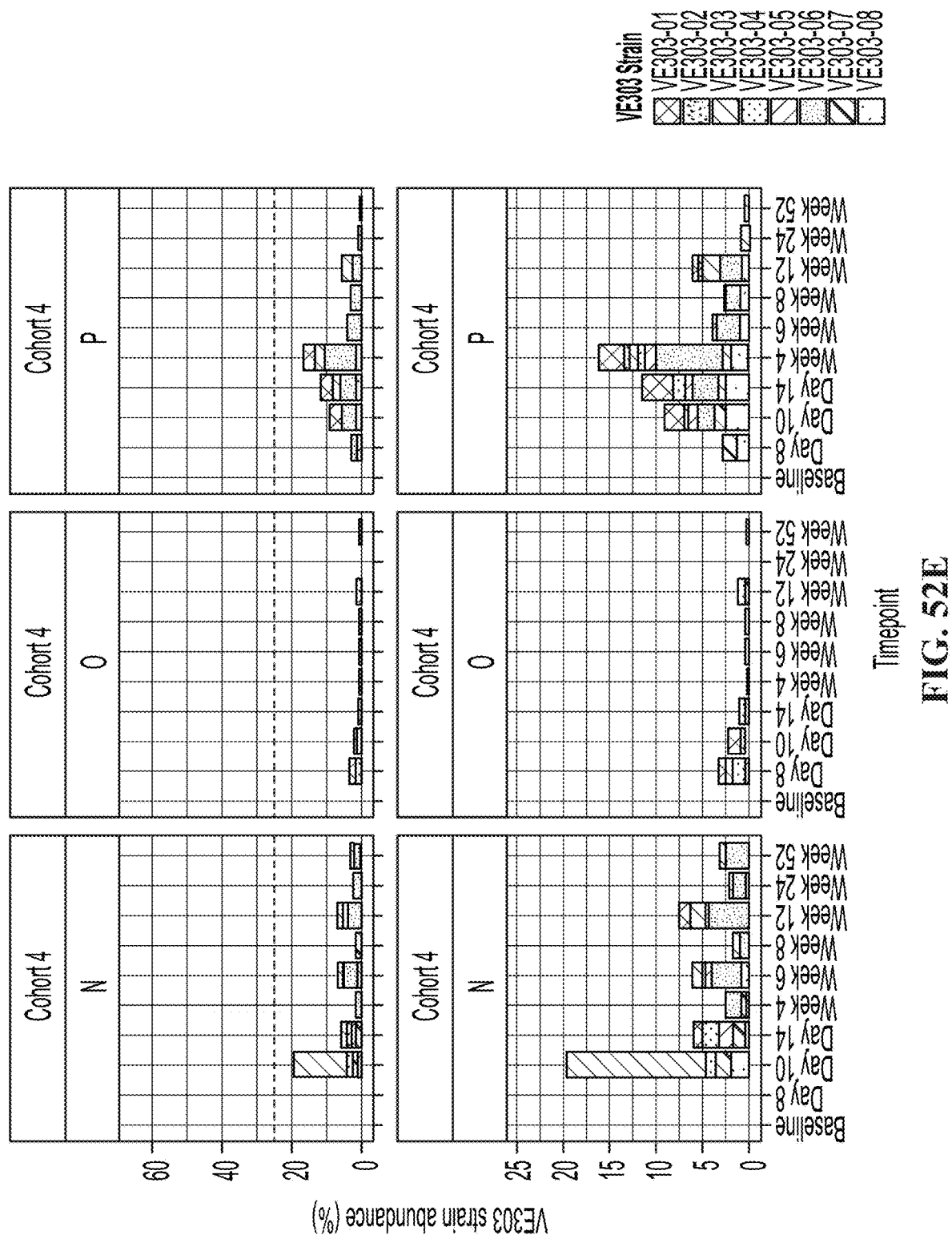
Figure 52F:
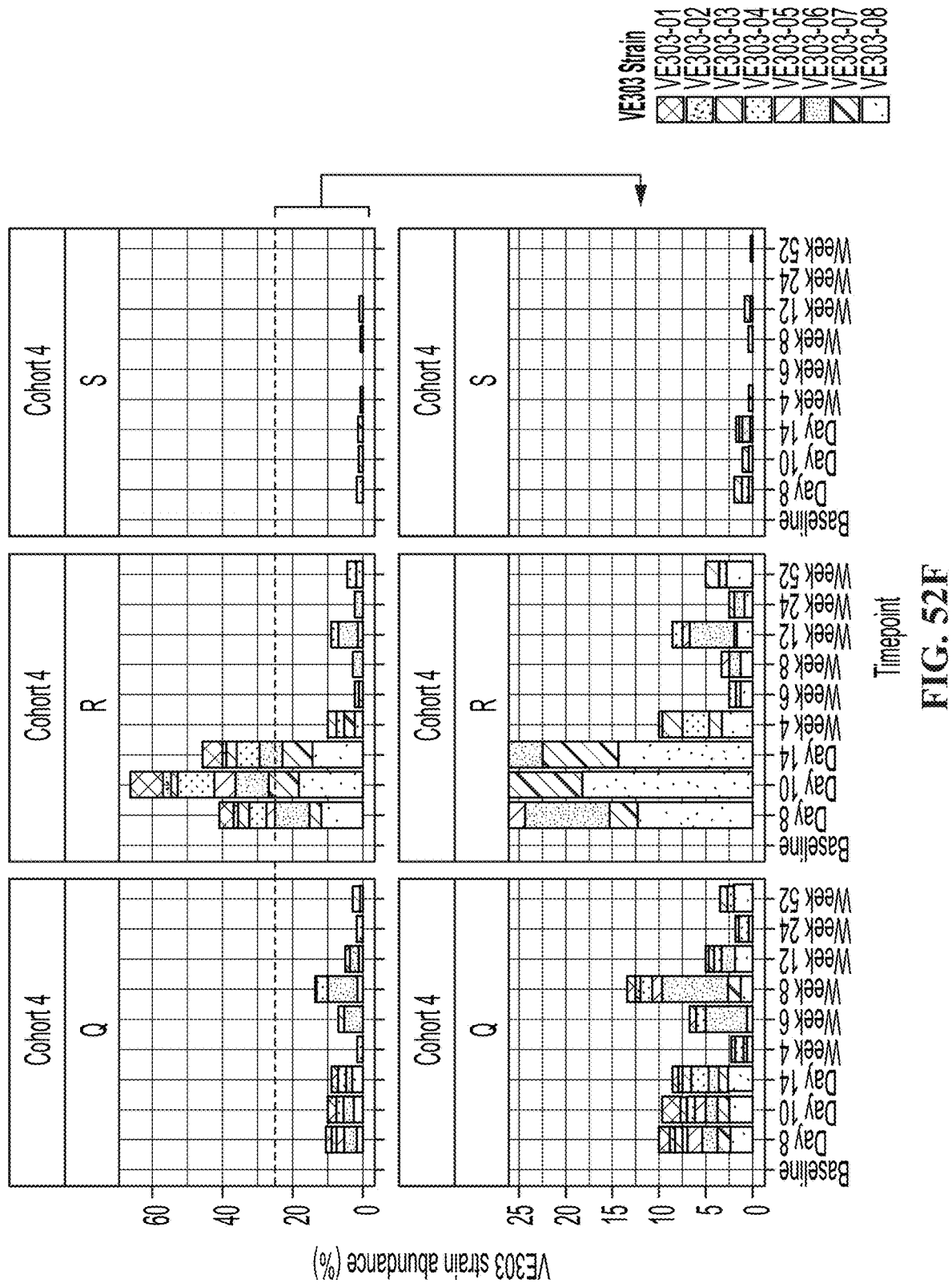
Figure 52G:
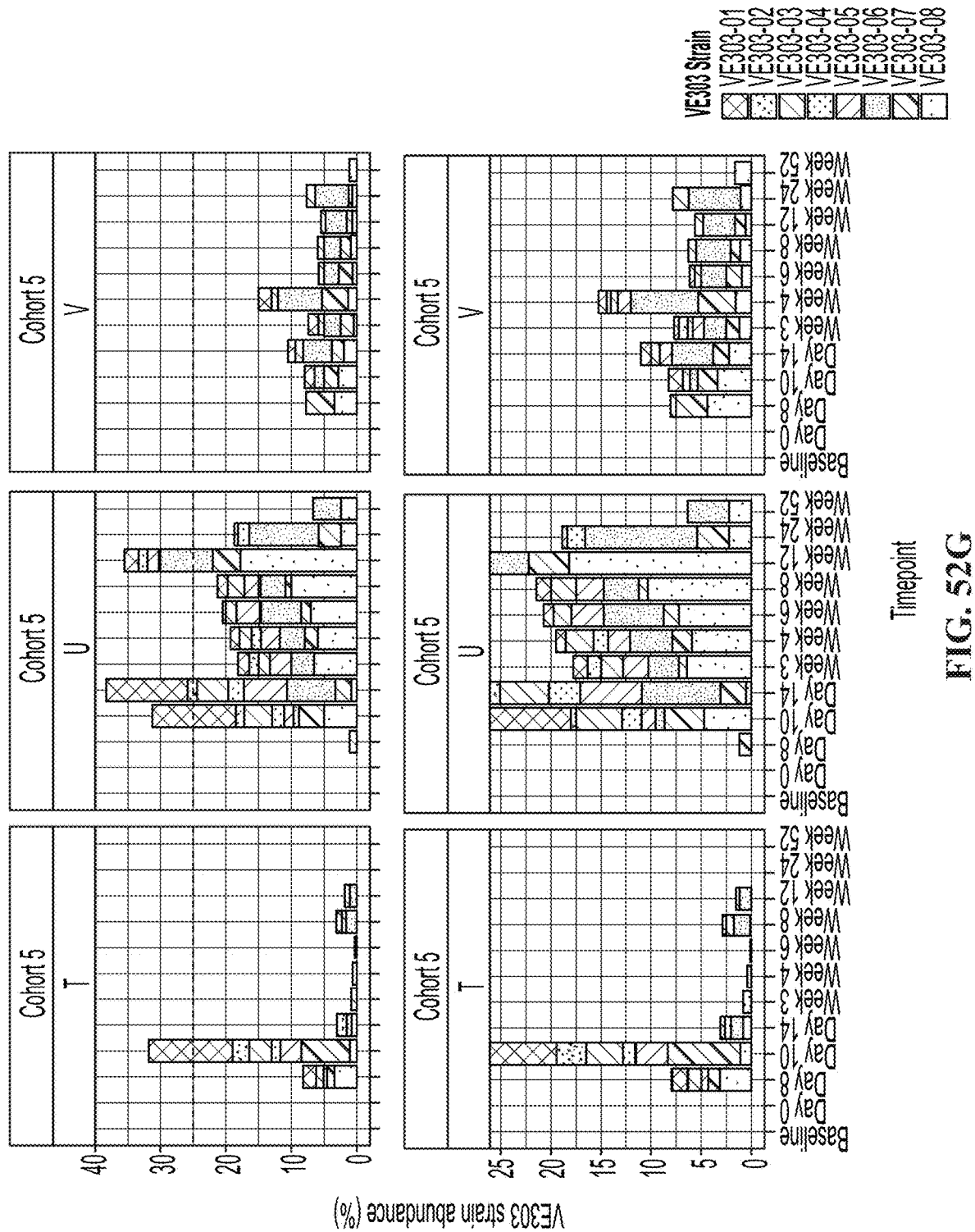
Figure 52H:
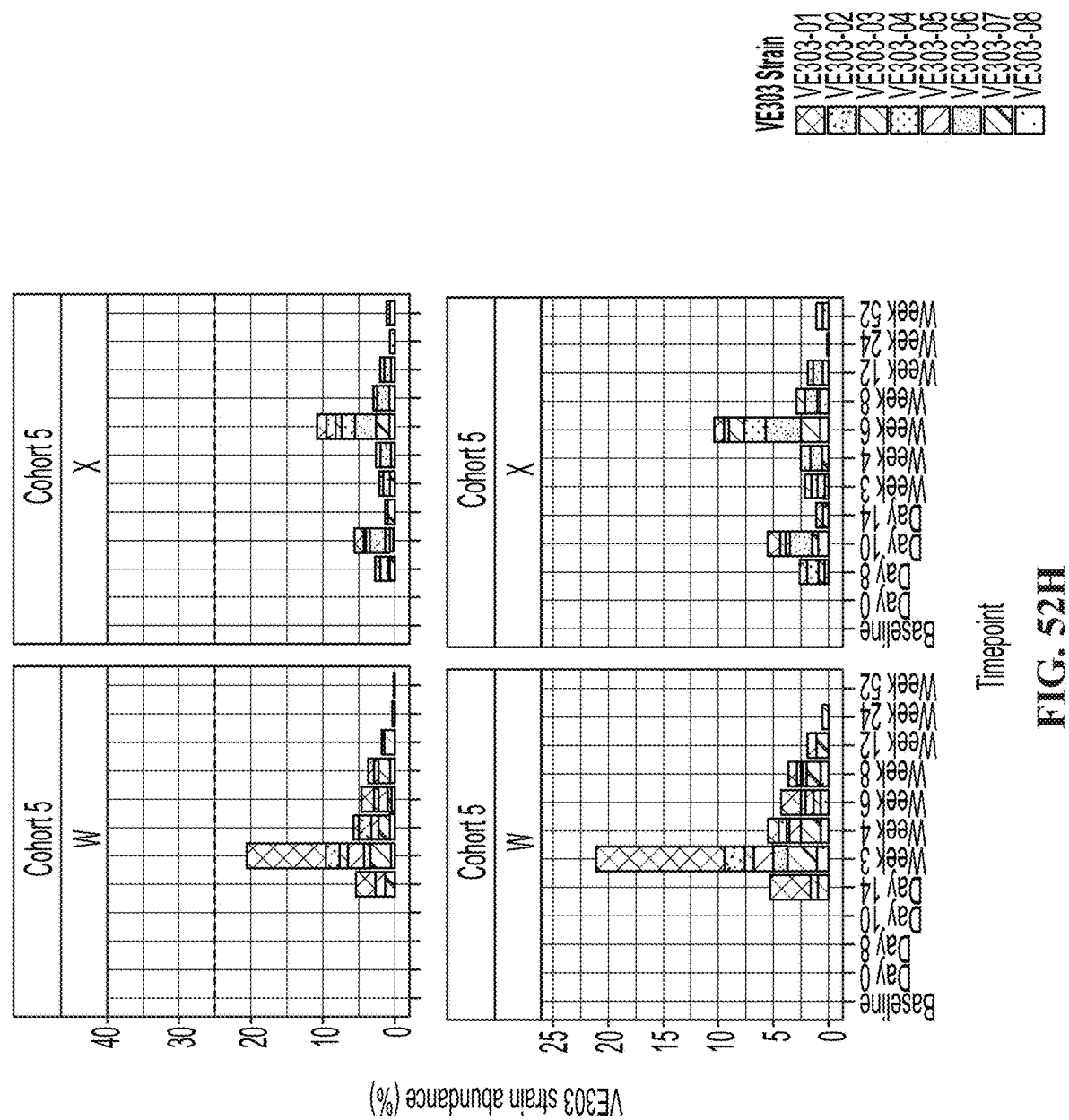
Figure 52I:
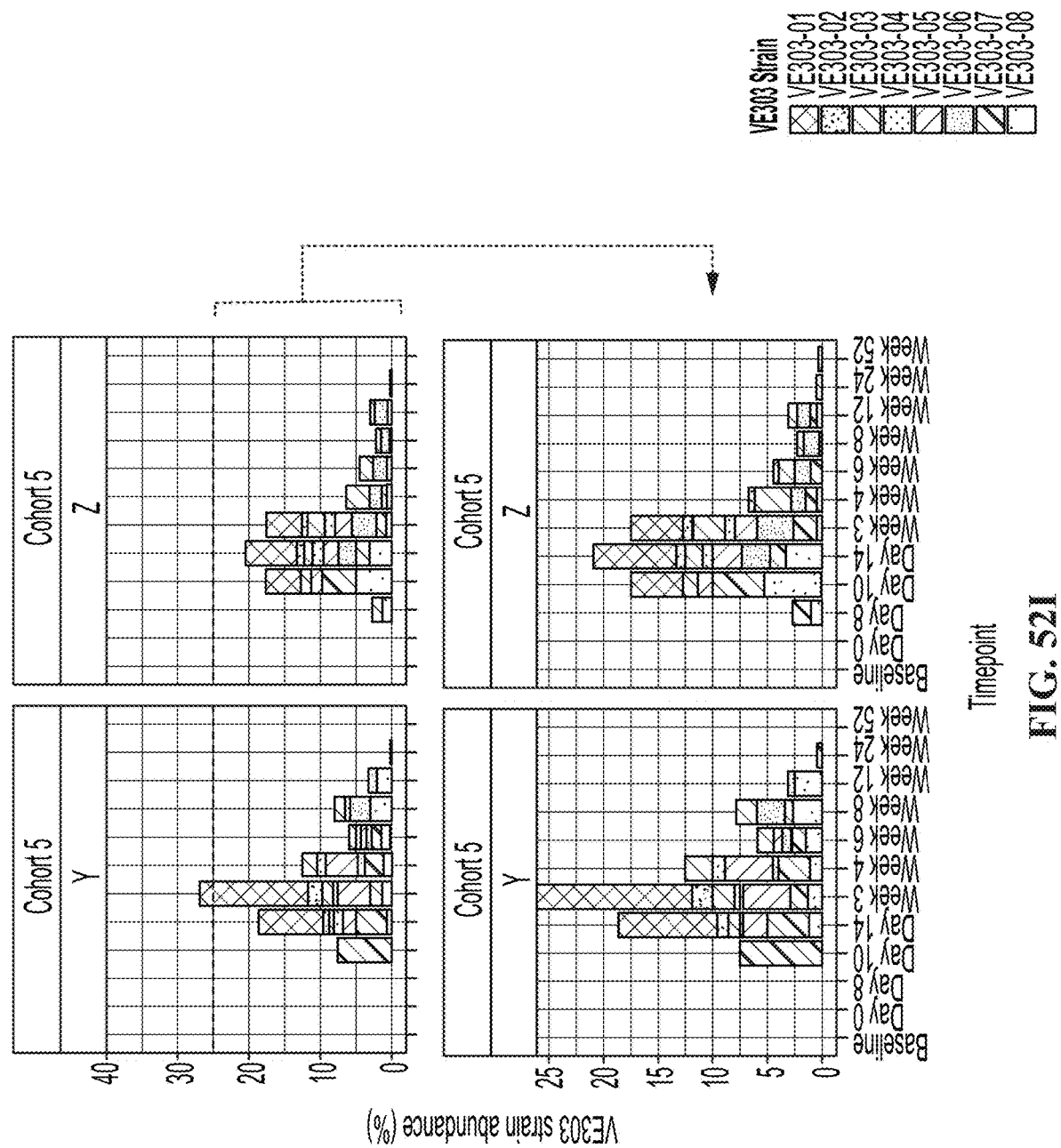
Figure 52J:
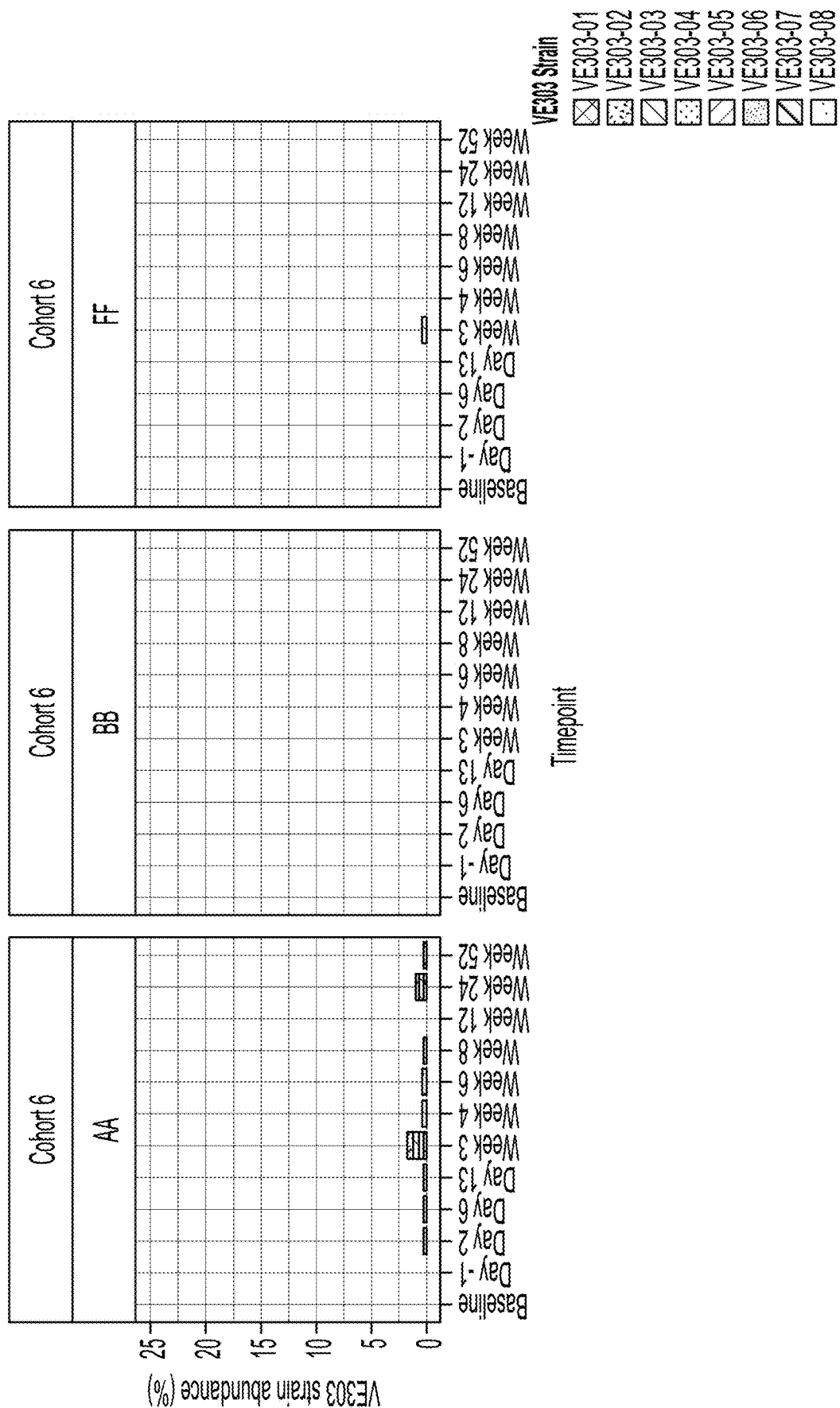
Figure 52K:
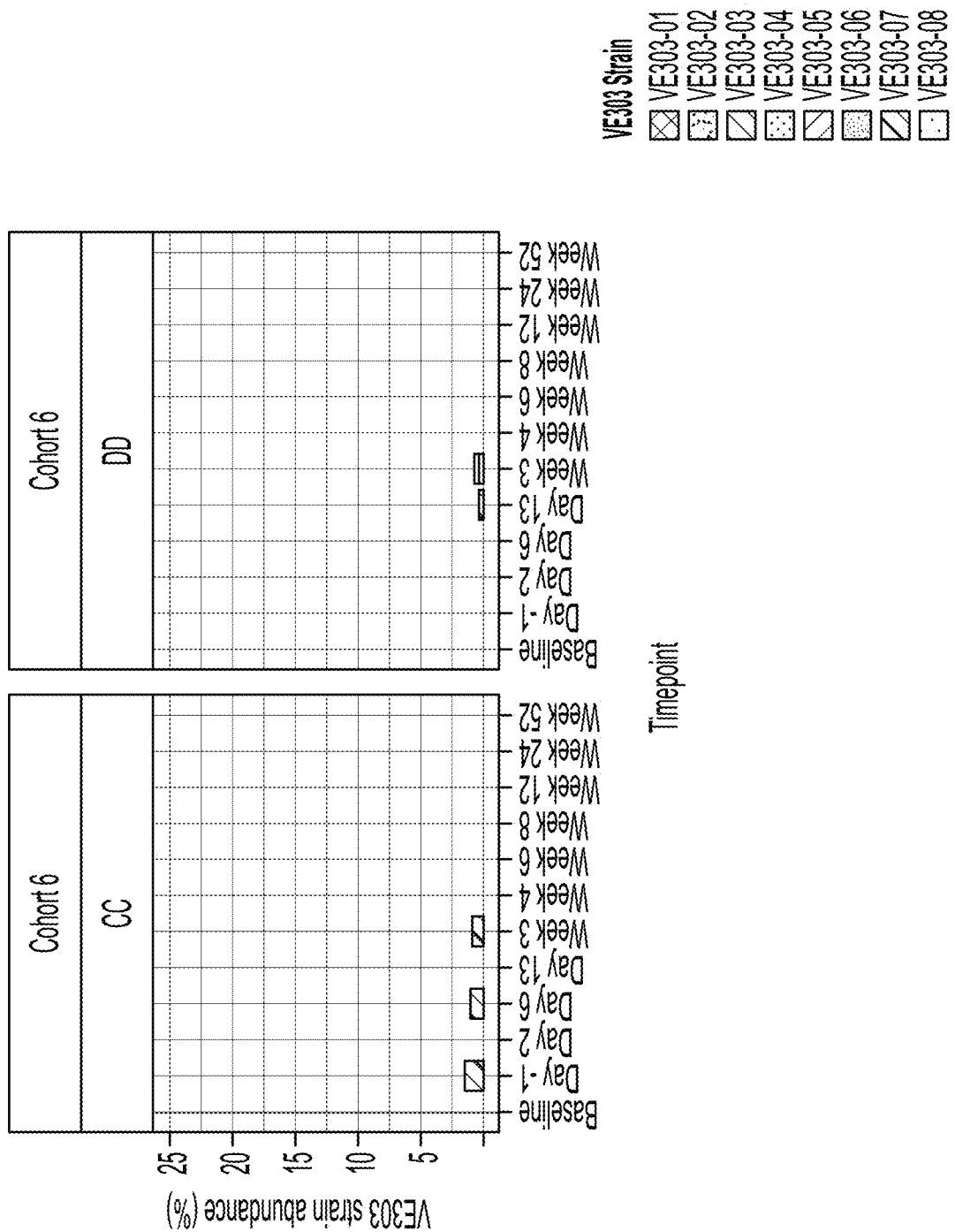

Stool samples were collected longitudinally for each healthy volunteer to determine the baseline microbiome composition, the microbiome after vancomycin administration, and the prevalence and abundance of the VE303 consortium members after LBP administration by metagenomics sequencing (FIG. 49). Each stool sample was sequenced at a target depth of >4 gigabases on the Illumina NextSeq platform, and VE303 strain PK was determined. VE303 strains were detected at low abundance in some subjects at baseline timepoints, and in the vancomycin cohort at weeks 8 and 12 (FIG. 50). A comparison of the mean marker depth and proportion of markers for "Detected" strains in the vancomycin cohort and VE303 cohorts indicated that the strains detected in the vancomycin cohort have reduced genome coverage and are likely close relatives of the VE303 strains (FIG. 51). Strains detected in subjects administered VE303 had a significantly higher proportion of markers detected and at greater depth.

Figure 45A:
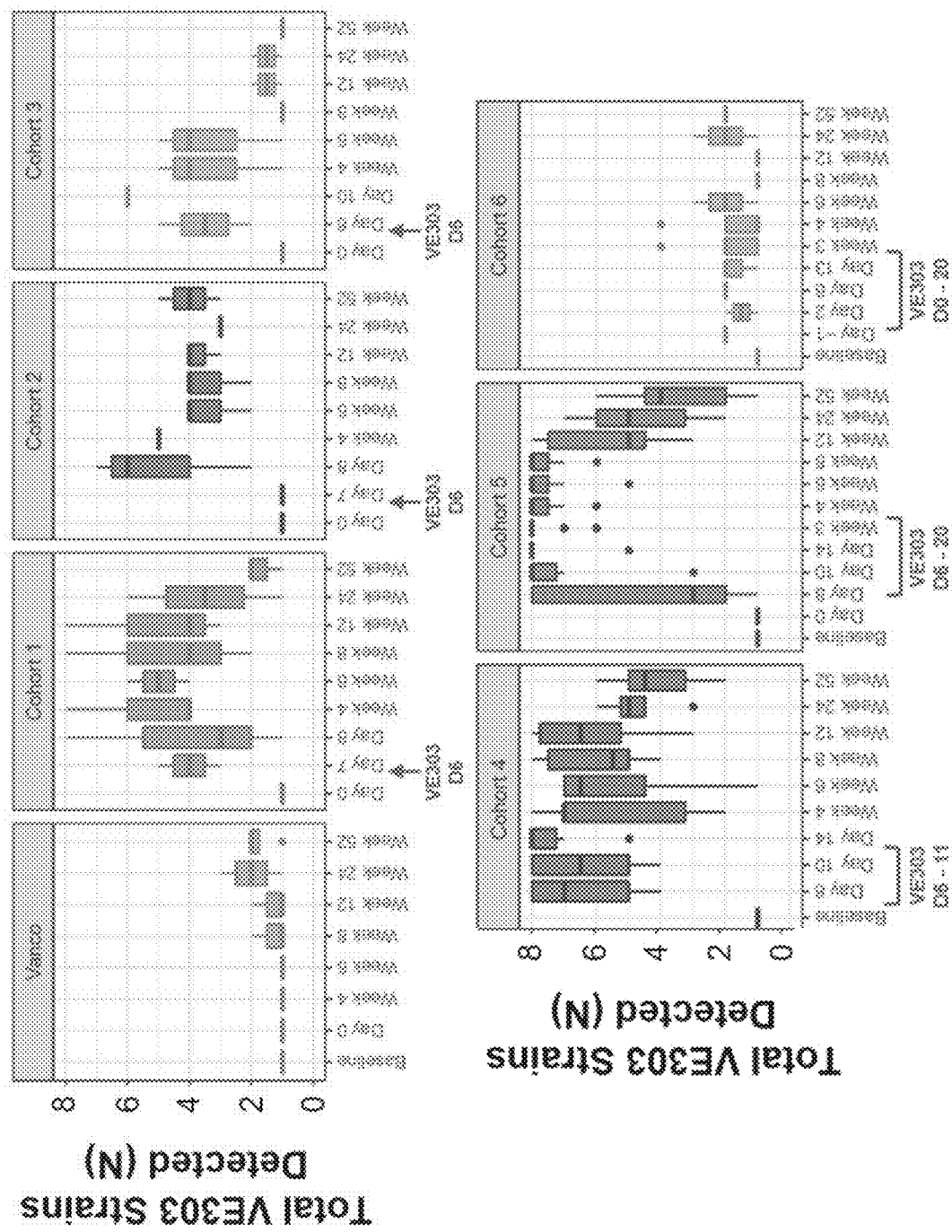
FIGS. 45A and 45B show VE303 colonization.
Figure 45B:
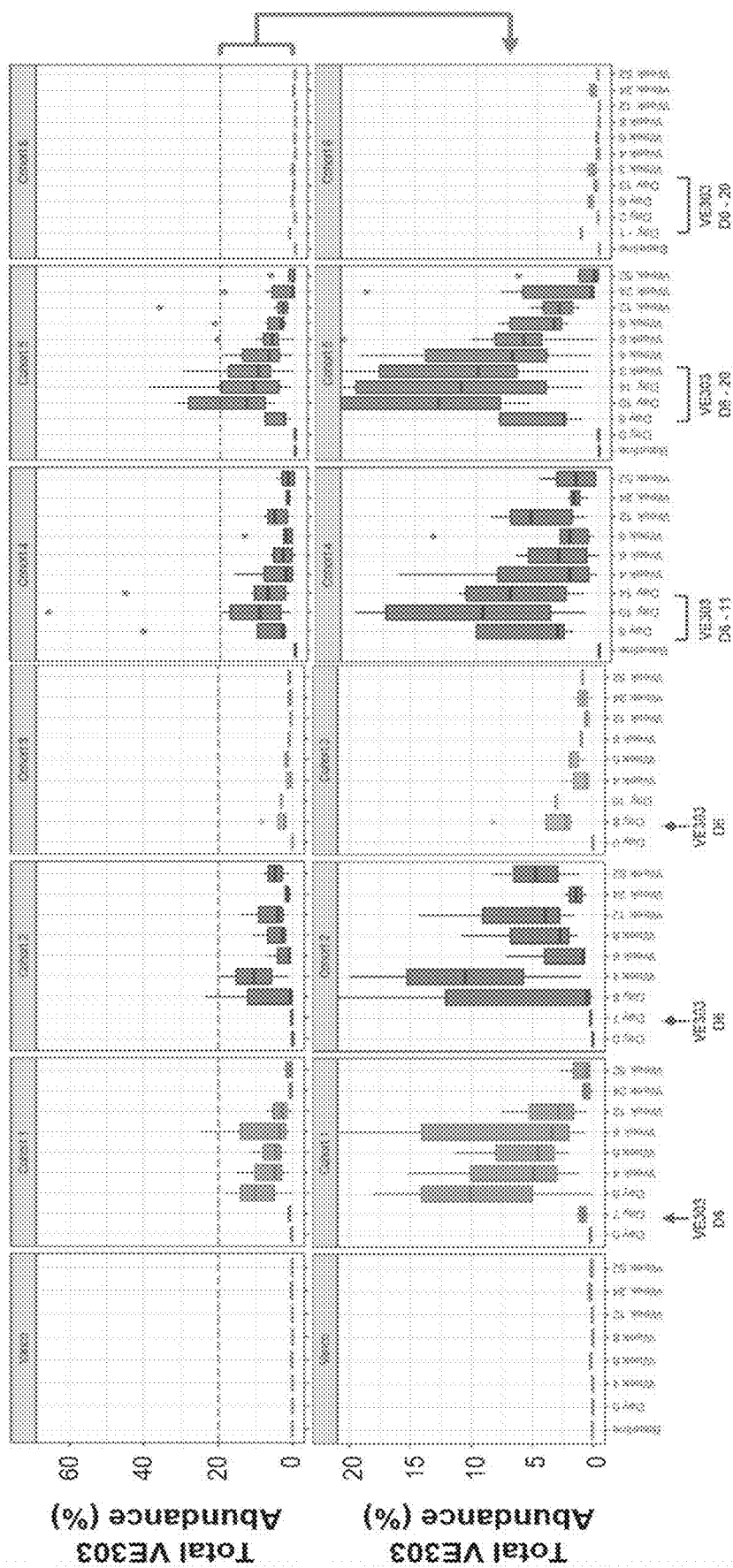

Vancomycin administration is known to eliminate or reduce bacteria that are essential for the biotransformation of primary bile acids to secondary bile acids as well as short chain fatty acid (SCFA) production. Therefore, the ability of VE303 to promote the recovery of a health microbial community and its metabolic state was examined. Vancomycin administration reduced the abundance of Clostridium cluster IV and XIVa species to undetectable levels. These distinguishing features enabled the determination of the PK of the consortium member strains in subjects who had been administered VE303 due to increased confidence that detected strains are likely LBP consortia members and not close relatives. In subjects dosed with VE303 following vancomycin administration (Cohorts 1-5), the bacterial strains of VE303 were rapidly detected within the first 24-48 hours after VE303 administration and then expanded in abundance to occupy the Clostridium cluster IV and XIVa niche (FIG. 45B). After vancomycin and a single dose of VE303 (Cohorts 1-3), a median between 37.5% to 75% of the strains was detected on day 10 (4 days after the start of VE303) (FIG. 45A). There was considerable variability among individuals receiving a single dose of VE303, but the LBP component strains were detected immediately after VE303 administration in all subjects. Notably, all 8 strains were detected in Cohort 1 subject 059, which suggested that robust colonization was achievable even with a single, low dose of VE303 under favorable microbiome conditions (FIG. 50). There was no dose response in the number of VE303 strains detected among the single ascending dose cohorts (Cohorts 1-3); however, the microbiome conditions appeared to be the most favorable in Cohort 1 subjects, as indicated by the greater total VE303 strain abundance in these subjects compared to Cohorts 2 and 3 (FIG. 45B).

In comparison to the single dose cohorts, multiple days of VE303 administration following vancomycin treatment (Cohorts 4-5) resulted in more robust and consistent strain detection. The median percentage of VE303 strains detected on day 10 was between 80-100% (FIG. 45A), with 5 of 6 subjects in Cohort 4 and 7 of 8 subjects in Cohort 5 being colonized by all members of the VE303 consortium at more than one time point (FIG. 50). The total abundance of VE303 strains was highest in Cohort 5 at both early (acute) and late time points, indicating that multiple days of LBP administration achieves the most robust and durable PK. The data also indicated that despite multiple days of VE303 dosing, vancomycin administration allowed for colonization healthy volunteers by VE303 strains (FIG. 45, Cohort 6), suggesting that resident Clostridium strains limited VE303 strain colonization.

Importantly, when vancomycin was used to reduce bacterial diversity and VE303 was administered over multiple days, the LBP strains were able to rapidly, robustly, and durably colonize subjects for at least 12 weeks. In the cohorts with the greatest colonization (Cohorts 1, 4, and 5), the relative abundance of VE303 strains expanded within the first few days after the start of VE303 dosing to about 5-10% of the total microbiome (FIG. 45B) and reached upwards of 60% of the total microbiota in one subject (FIG. 51). After this initial expansion, the relative abundance of the VE303 strains declined to 1-5% of the microbiome, but remained stable for at least 12 weeks. These data, coupled with clinical observations, clearly demonstrate that under optimal microbiome and dosing conditions, the VE303 consortium strains are safe and able to robustly and durably colonize the human gut.

Figure 46A:
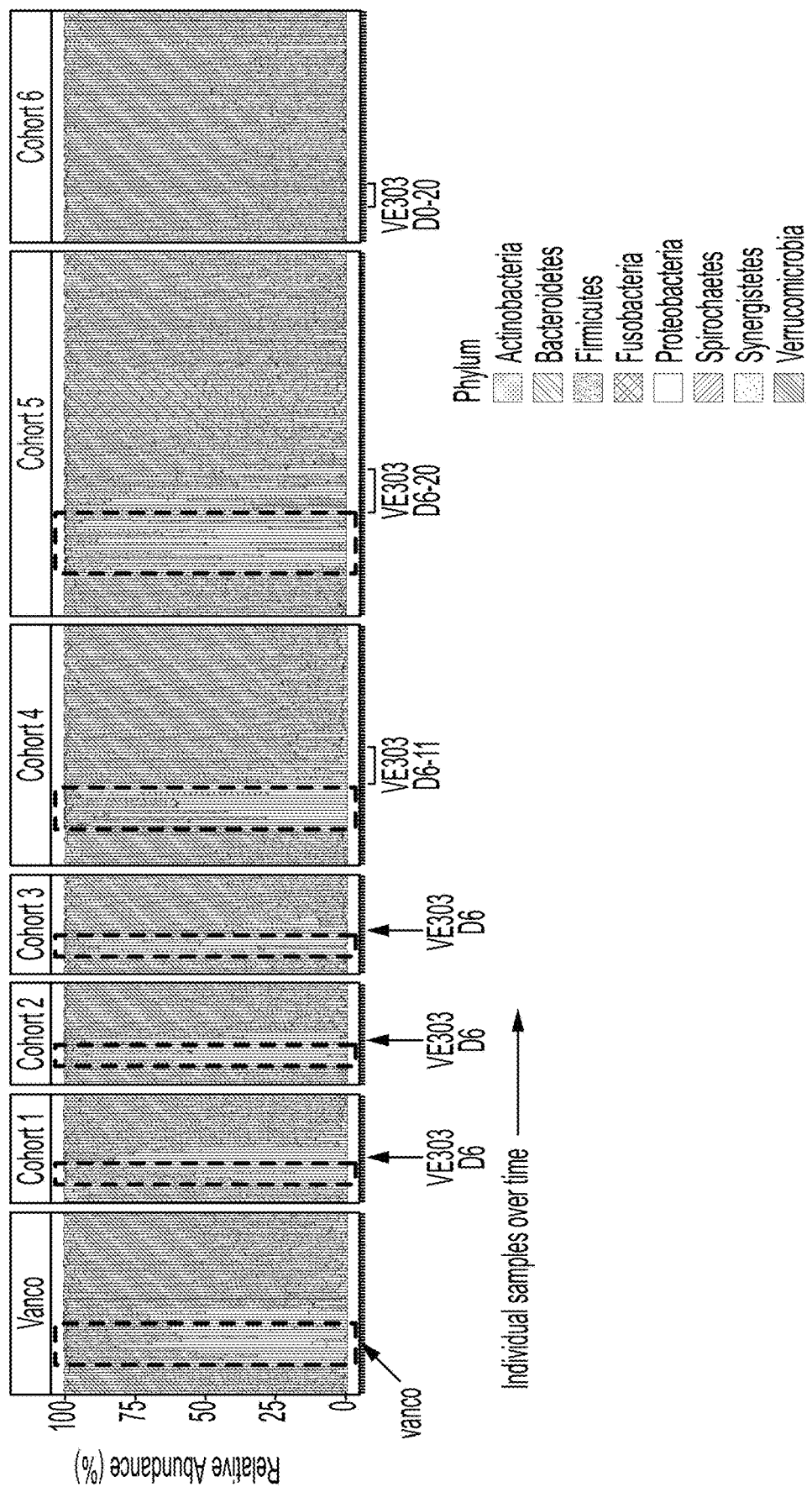
Figure 53A:
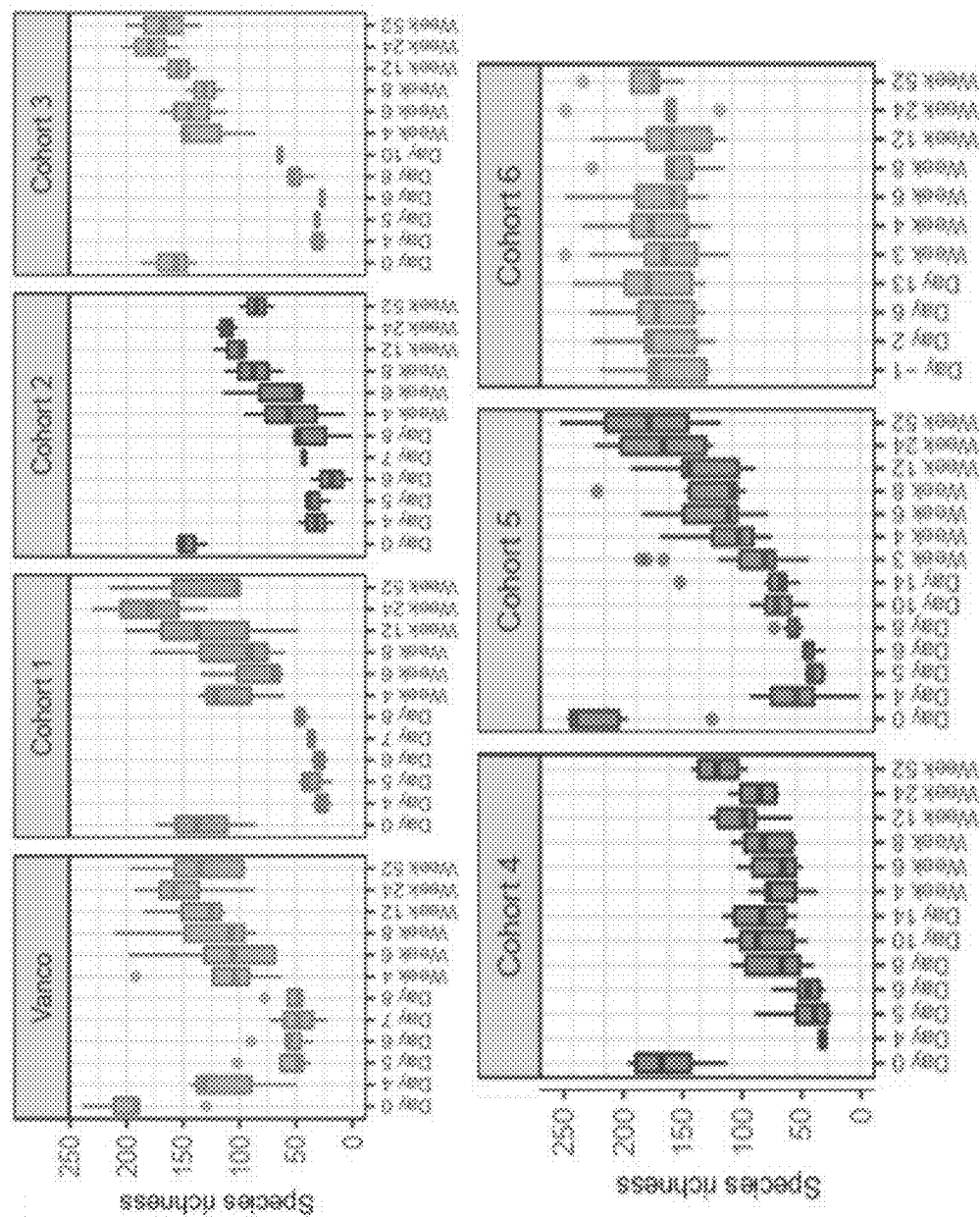
FIGS. 53A-53C show species richness and diversity in the stool microbiota of subjects.
Figure 53B:
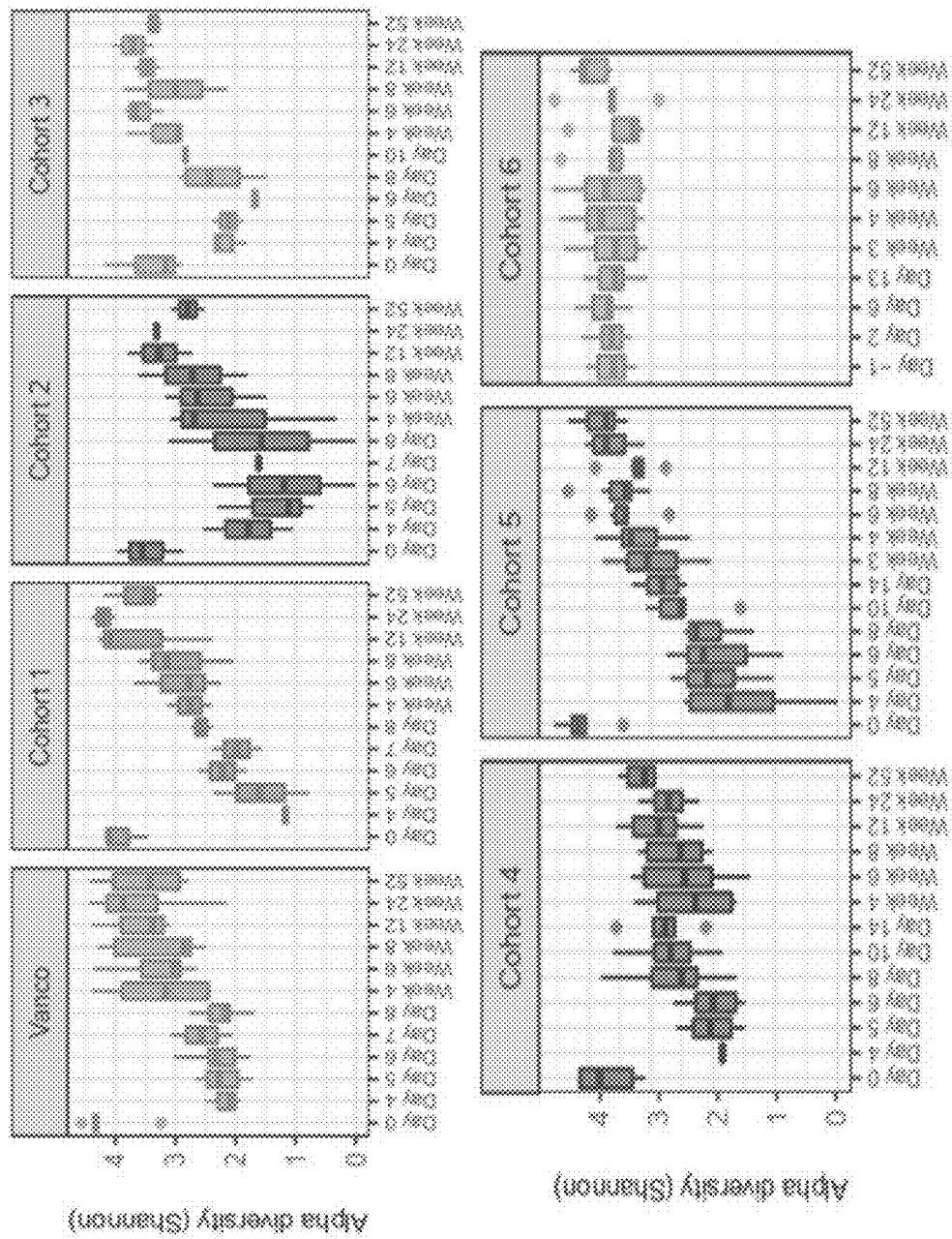
Figure 53C:
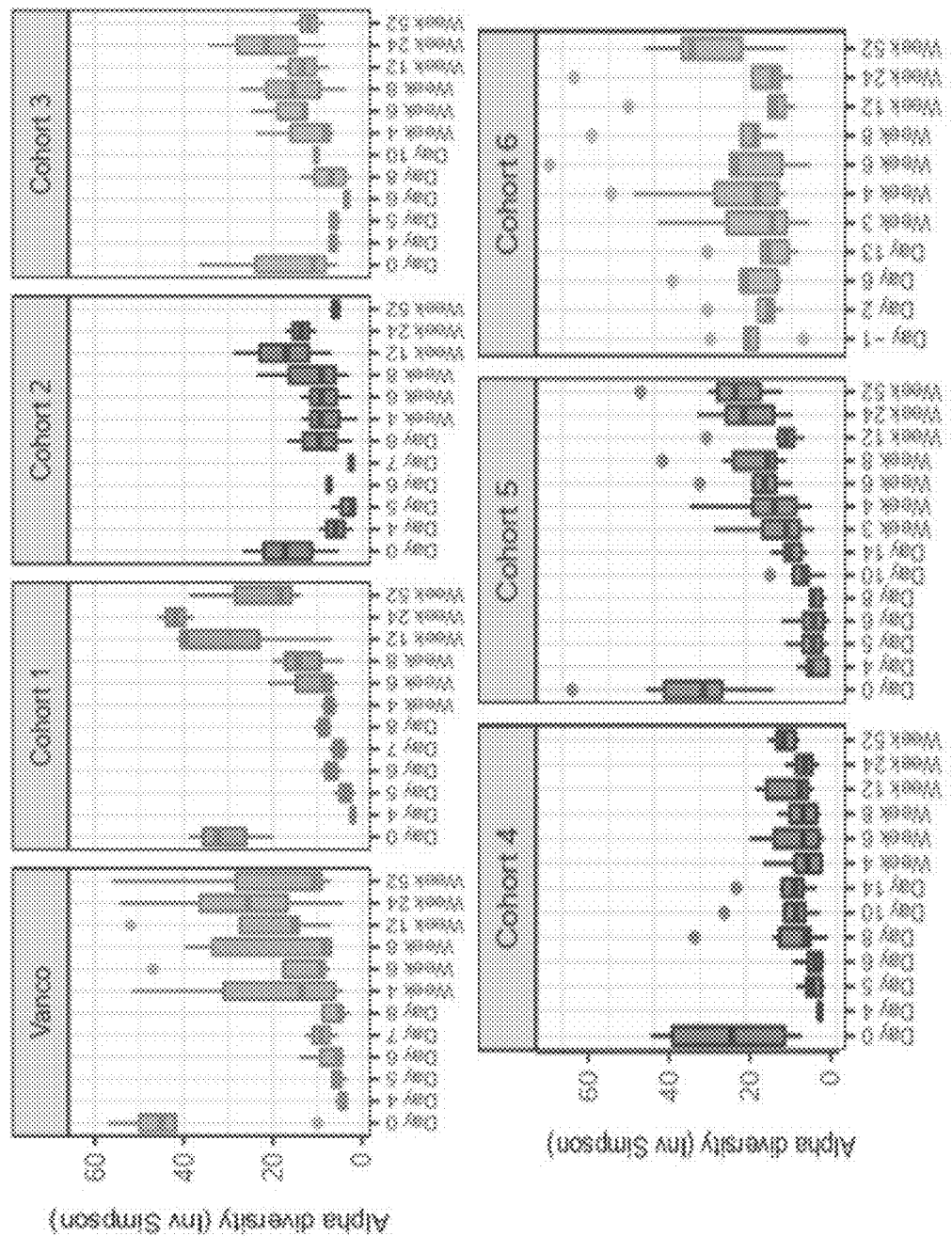
Figure 54A:
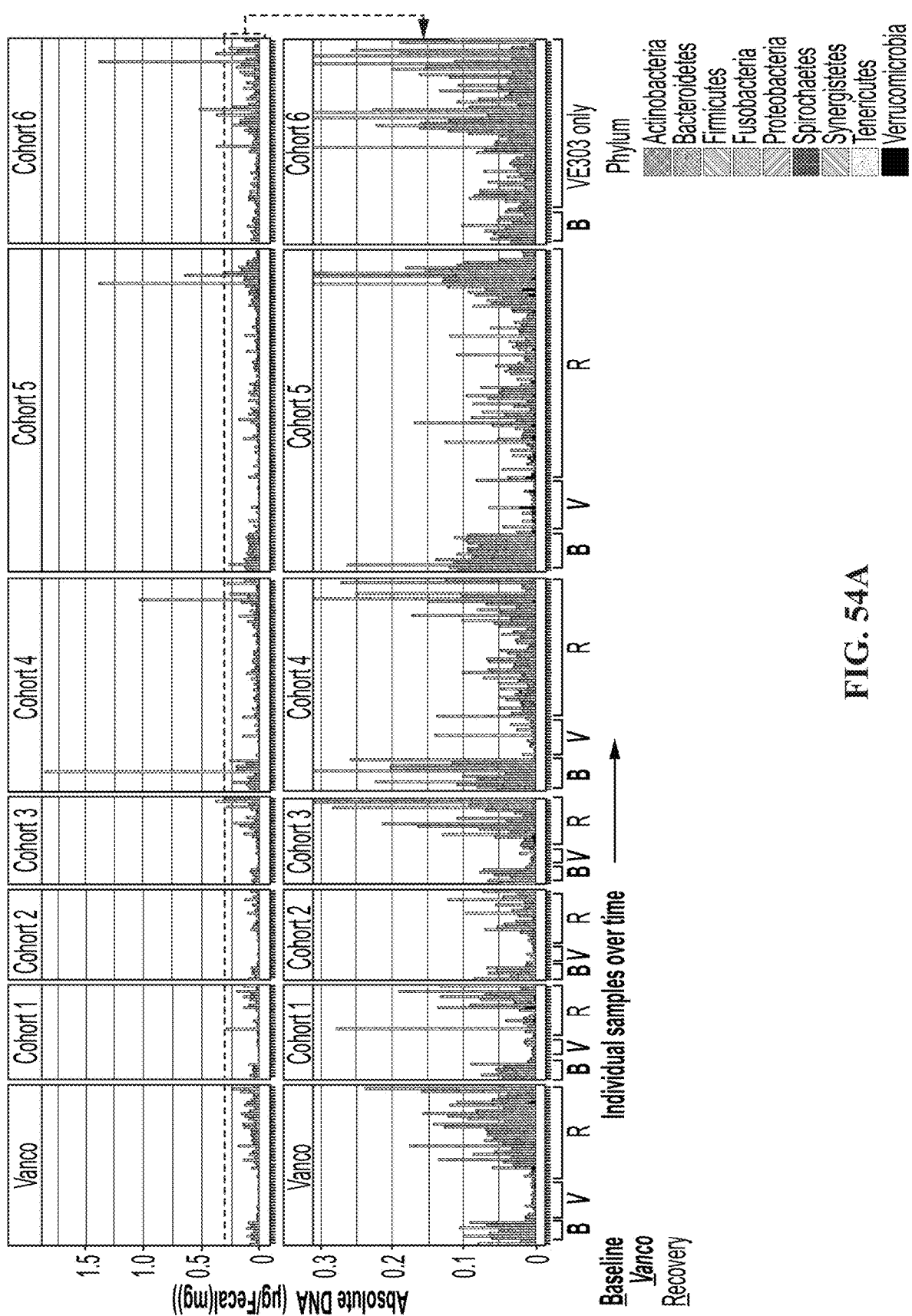
FIGS. 54A-54B show the absolute bacterial abundance.
Figure 54B:
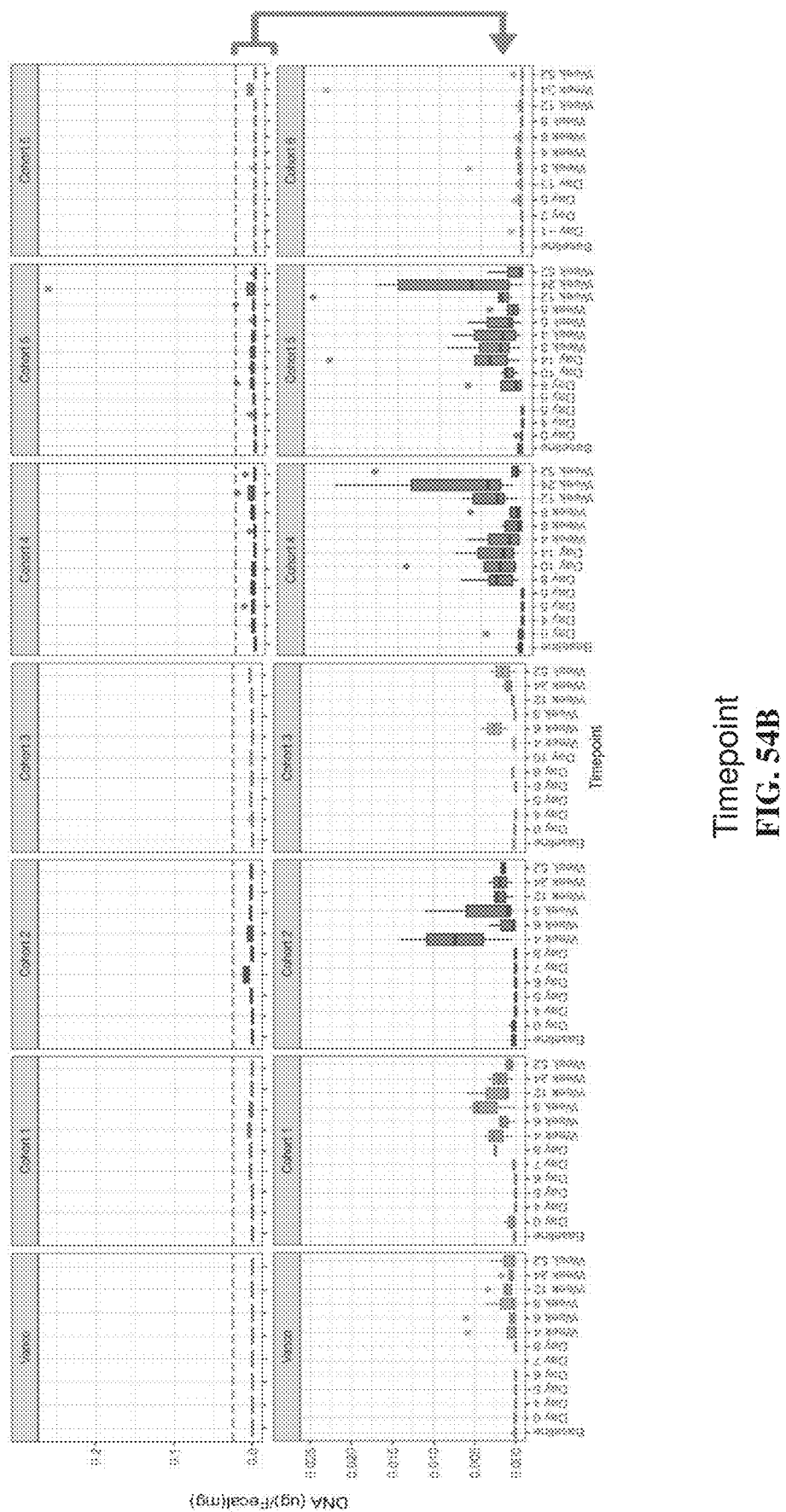

The shotgun metagenomics data collected at baseline, after vancomycin administration, and during the recovery phase both in the presence and absence of VE303 strains were used to assess the dynamics of the stool microbiota in healthy volunteers and the role of VE303 in the recovery from antibiotic-induced dysbiosis. As expected, the baseline microbiota had high diversity (FIG. 52) and was dominated by Bacteroidetes and Firmicutes species in all subjects (FIG. 46A). Vancomycin administration greatly reduced the bacterial biomass (FIG. 54) and diversity (FIG. 53) and led to a shift in the composition of the microbiota, indicated by the reduced Bacteroidetes and Firmicutes and the expanded Proteobacteria (FIG. 46A). Notably, the post-vancomycin microbial community of healthy volunteers resembled the community of rCDI subjects[2] (and unpublished observations). The microbial community of healthy volunteers only given vancomycin recovered to baseline levels of Bacteroidetes and Firmicutes species within 1 month of being given antibiotics (FIG. 46A) and the diversity of the microbiota partially recovered within 12 weeks (FIG. 53). These community-level observations are consistent with clinical safety observations. The recovery of Bacteroidetes species to baseline levels occurred within 1 week in subjects that were given higher doses of VE303 (FIGS. 46A and 46C). No significant microbial community changes were observed in the absence of vancomycin (FIG. 46A, Cohort 6).

Figure 46B:
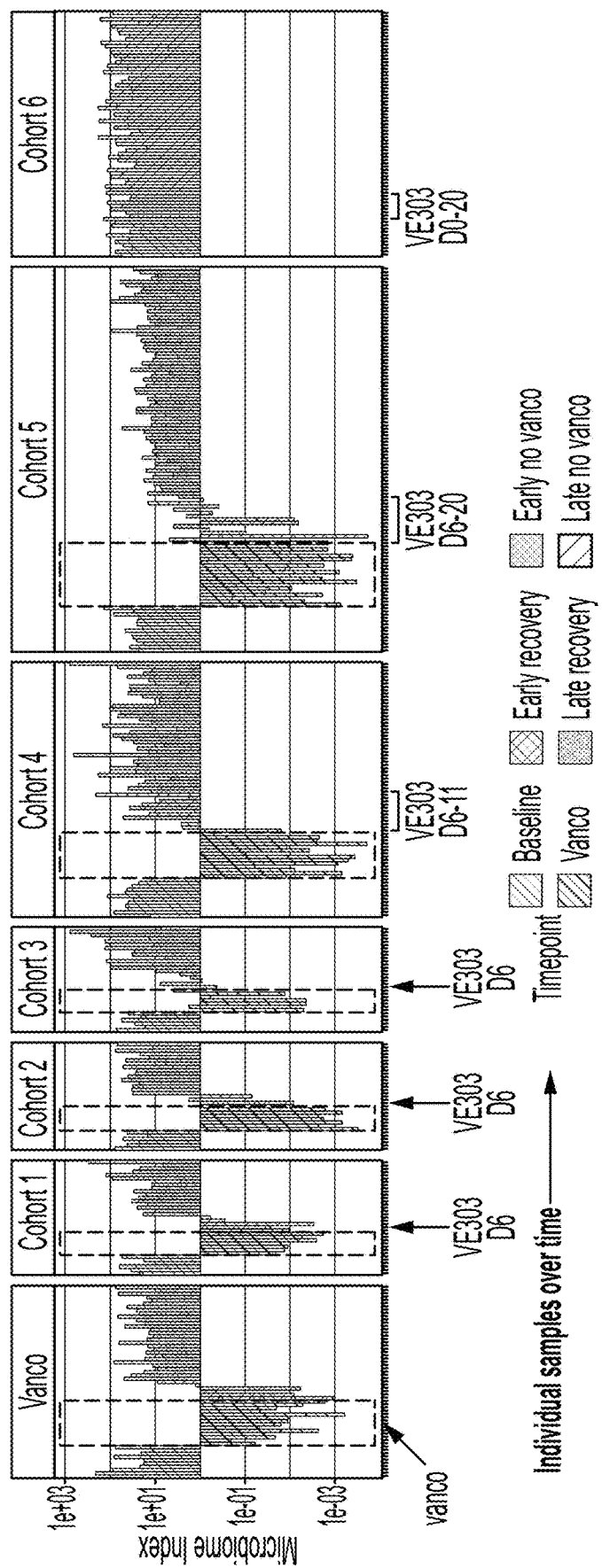

To quantify the overall microbiota health, the ratio of bacterial classes that were dominant at baseline (Bacteroidia, Clostridia, Actinobacteria, and Coriobacteriia) to the bacterial classes that were dominant after vancomycin and often associated with disease (Bacilli, Gammaproteobacteria, and Negativicutes) was calculated (FIG. 54) (rebiotix.com/scientific-evidence/microbiota-restoration-therapy-posters/microbiome-rehabilitation-biomarkers-clostridium-difficile-infections-prototype-microbiome-health-index/).
This "microbiota index" (MI) was high at baseline, significantly reduced by vancomycin administration, and recovered to baseline levels within 1 month in subjects only receiving vancomycin (FIG. 46B). However, in subjects receiving VE303, the MI increased within 1 week of starting the LBP administration (FIG. 46B) and this increase in MI was dose-dependent (FIG. 46D). No changes in the MI were observed in subjects receiving VE303 in the absence of vancomycin pretreatment (FIG. 46B), which is consistent with the clinical safety results. These data suggest that not only does VE303 rapidly colonize the gut, but that it can also promote the partial recovery of the microbial community, suggesting that it would boost resistance to pathogens, like C. difficile, after antibiotic therapy.

Figure 47A:
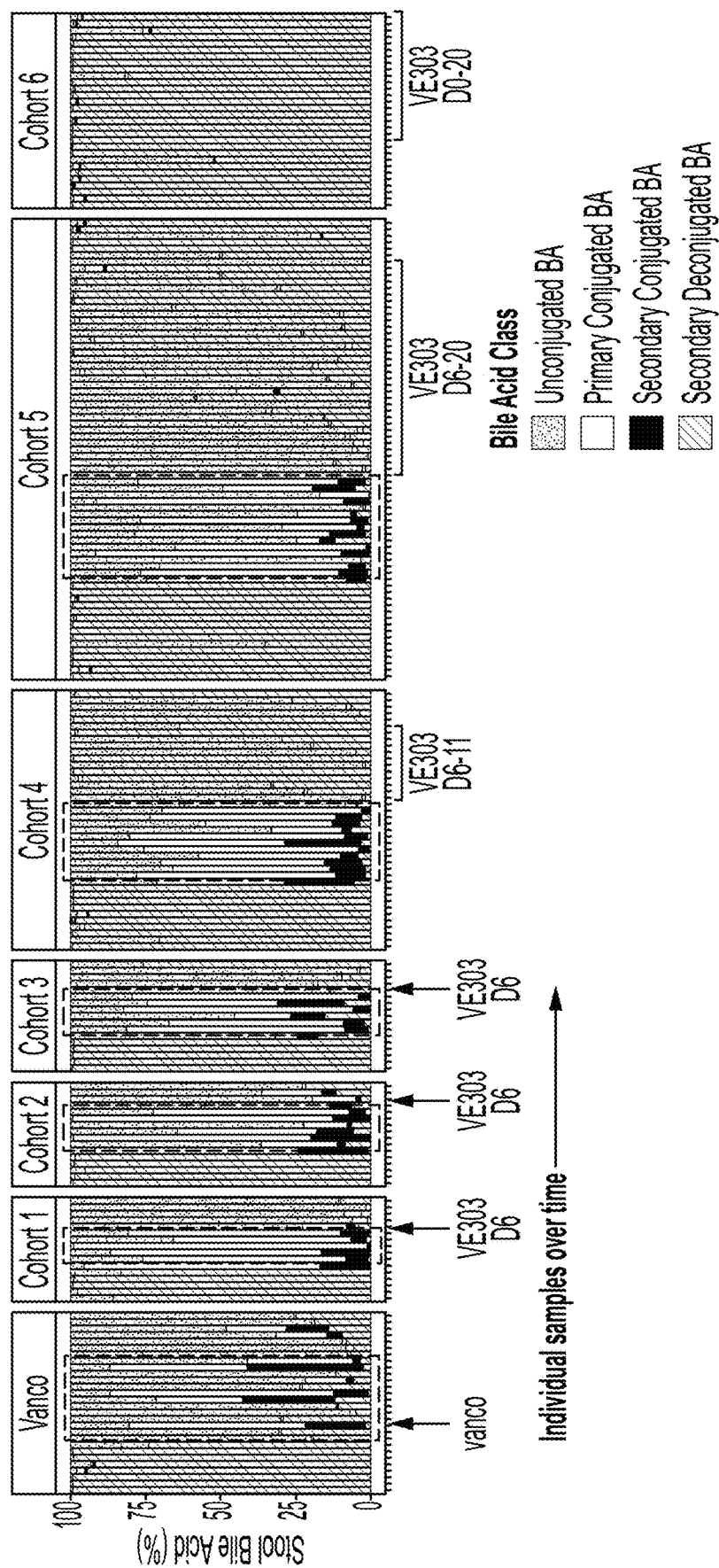
FIGS. 47A-47K show the bile acid pharmacodynamics of VE303 administration.

To determine the effect of vancomycin on bile acid concentrations and measure the pharmacodynamics of VE303, primary and secondary bile acid concentrations were measured in the stool of subjects at baseline, during vancomycin administration, and during the recovery phase after vancomycin with and without VE303 administration (Table 6). Sample collection hurdles limited the metabolite profiling to periods of acute (early) recovery post vancomycin in all cohorts. Bile acids are traditionally considered important in the digestion of fats, however there is growing evidence for a broader role of secondary bile acids in promoting gut health and inhibiting CDI. Primary bile acids (Cholic Acid and Chenodeoxycholic Acid) and the glycine and taurine conjugated forms (Glycocholic Acid, Taurocholic Acid, Glycochenodeoxycholic Acid, and Taurochenodeoxycholic Acid) were detected at low concentrations at baseline and make up a small fraction of the total bile acid pool in the stool (FIG. 47A and FIG. 57). Most of the bile acid pool at baseline consisted of deconjugated secondary bile acids (Deoxycholic Acid, Lithocholic Acid, and Ursodeoxycholic Acid). The glycine and taurine conjugated forms of the secondary bile acids (Glycodeoxycholic Acid, Taurodeoxycholic Acid, Glycolithocholic Acid, Taurolithocholic Acid, Glycoursodeoxycholic Acid, and Tauroursodeoxycholic Acid) had low baseline levels. Vancomycin treatment led to an increase in the proportion of primary bile acids and a decrease in deconjugated secondary bile acids. This observation is consistent with vancomycin-mediated reduction of bacterial species capable of promoting the deconjugation and the biotransformation of primary bile acids. After vancomycin treatment and as the microbial community recovered, very early signs of recovery in the bile acid pool in subjects only receiving vancomycin is observed. This recovery was incomplete on day 9 when the final sample was collected.

Figure 47B:
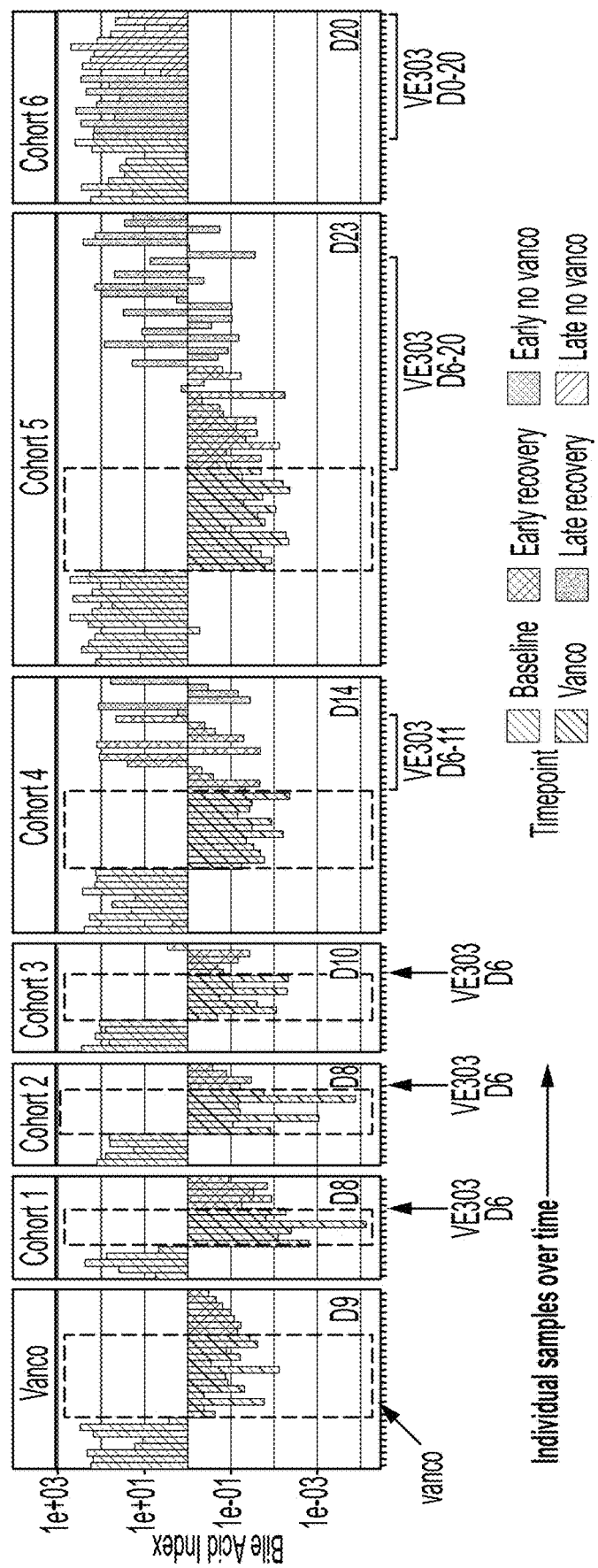

To quantify the overall change in bile acids, the ratio of deconjugated secondary bile acids (dominant at baseline) to primary bile acids (elevated by vancomycin) was calculated. This "bile acid index" (BAI), was high at baseline, then drastically reduced by vancomycin administration and demonstrated very early signs of recovery in subjects only receiving vancomycin (FIG. 47B). However, in subjects receiving multiple doses of VE303 (Cohorts 4 and 5), there was an increase in the BAI within 1-2 weeks of VE303 administration (FIG. 47B). No changes in the overall bile acid profile (FIG. 47A) or BAI (FIG. 47B) were observed in subjects only receiving VE303. These data suggest that higher doses of VE303 can promote the early recovery of the bile acid pool.

Linear mixed effects modeling was developed to test whether bile acid abundances were altered by vancomycin and whether total VE303 abundance significantly affected their post-antibiotics dynamics. When looking at each individual primary bile acid, antibiotic administration caused a significant increase in their abundance compared to pre-antibiotics, while the total abundance of VE303 was found to predict a significant decrease in the levels of the majority of primary bile acids (all apart from Taurocholic Acid and Taurodeoxycholic Acid) (Tables 7A and 7B). In contrast, vancomycin treatment was found to cause a significant decrease in the levels of BAI-dependent 7a Dehydroxylated Secondary Bile Acids, Litocholic and Deoxycholic Acids, while total VE303 abundance was found to enhance their recovery post-vancomycin administration. Additionally, even though vancomycin did not seem to significantly affect ursodeoxycholic acid, VE303 was found to significantly enhance its abundance post-antibiotic treatment.

Figure 47C:
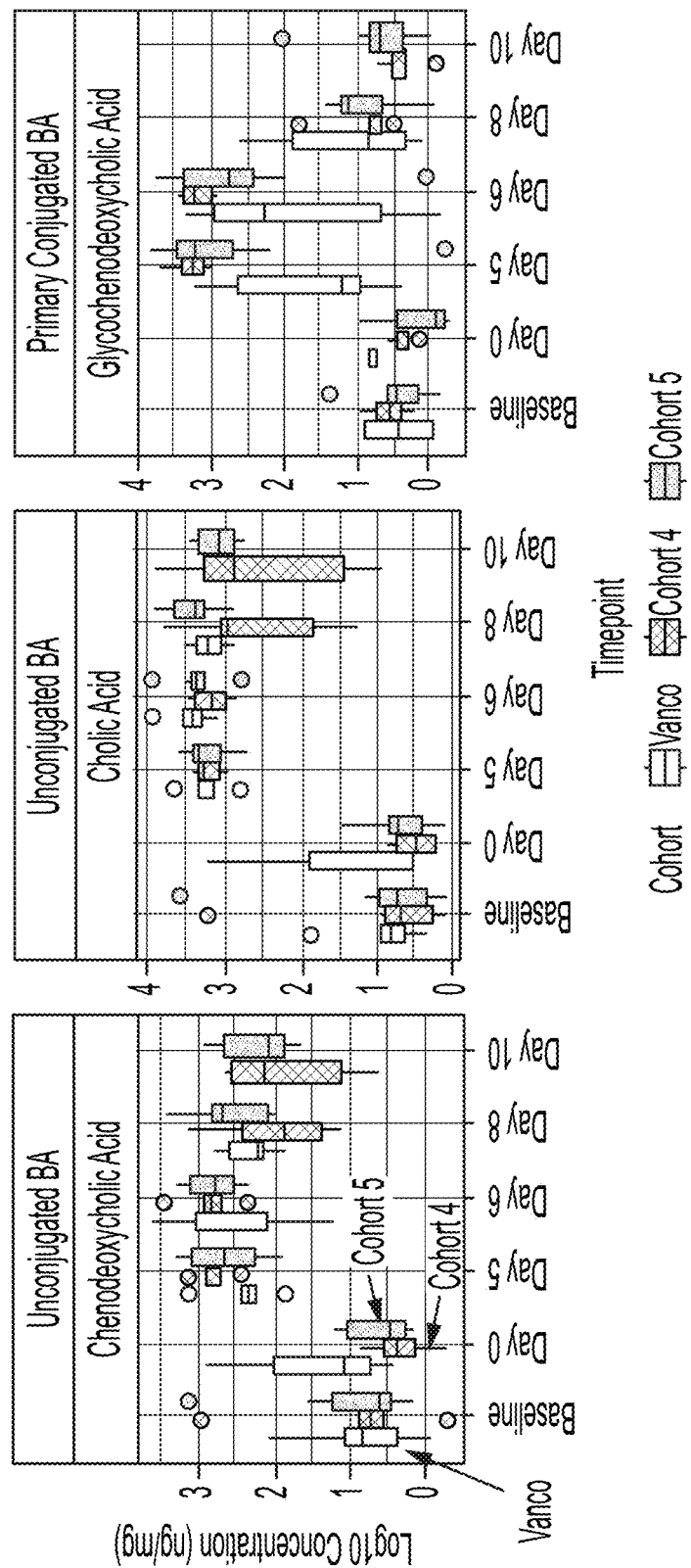
Figure 47D:
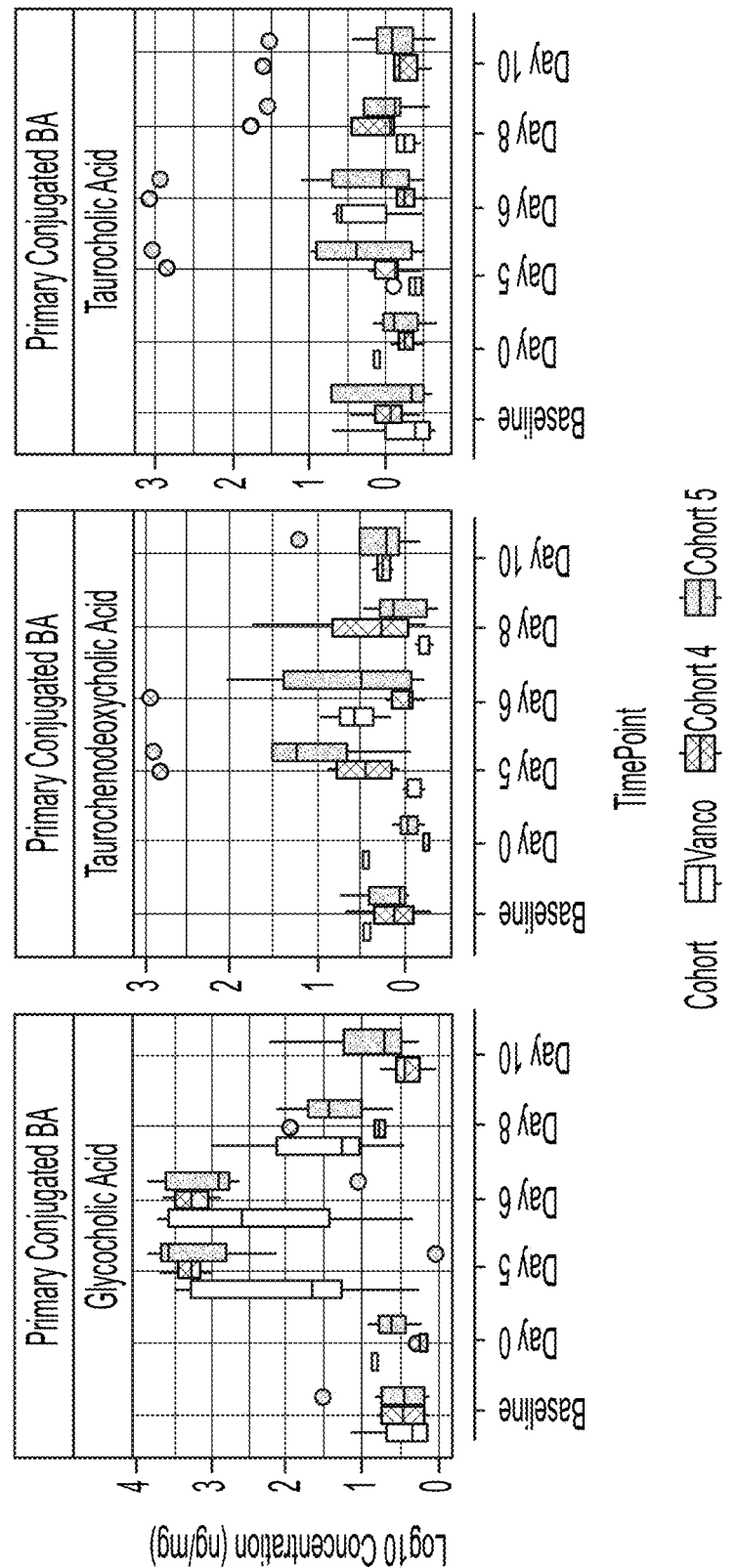
Figure 47E:
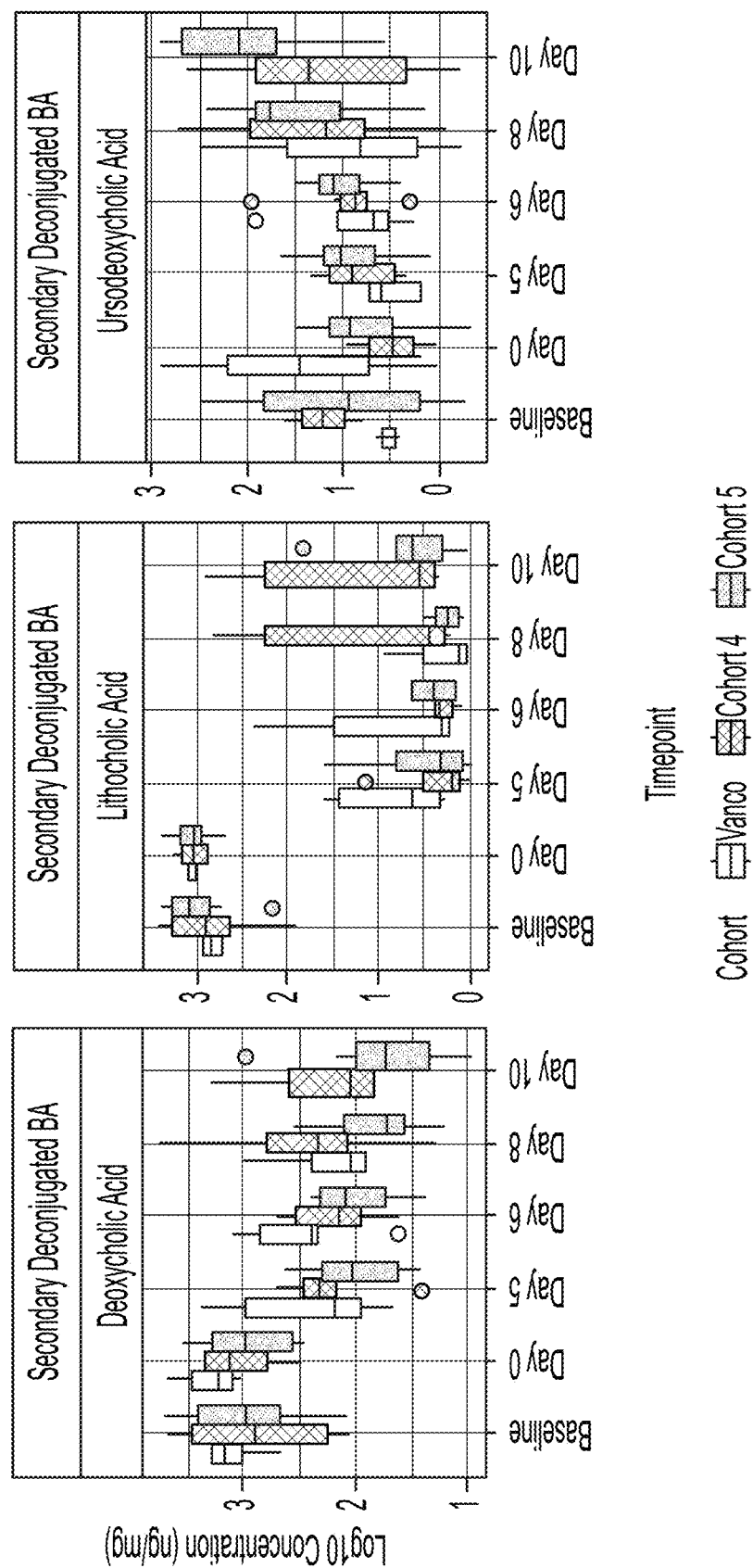
Figure 47F:
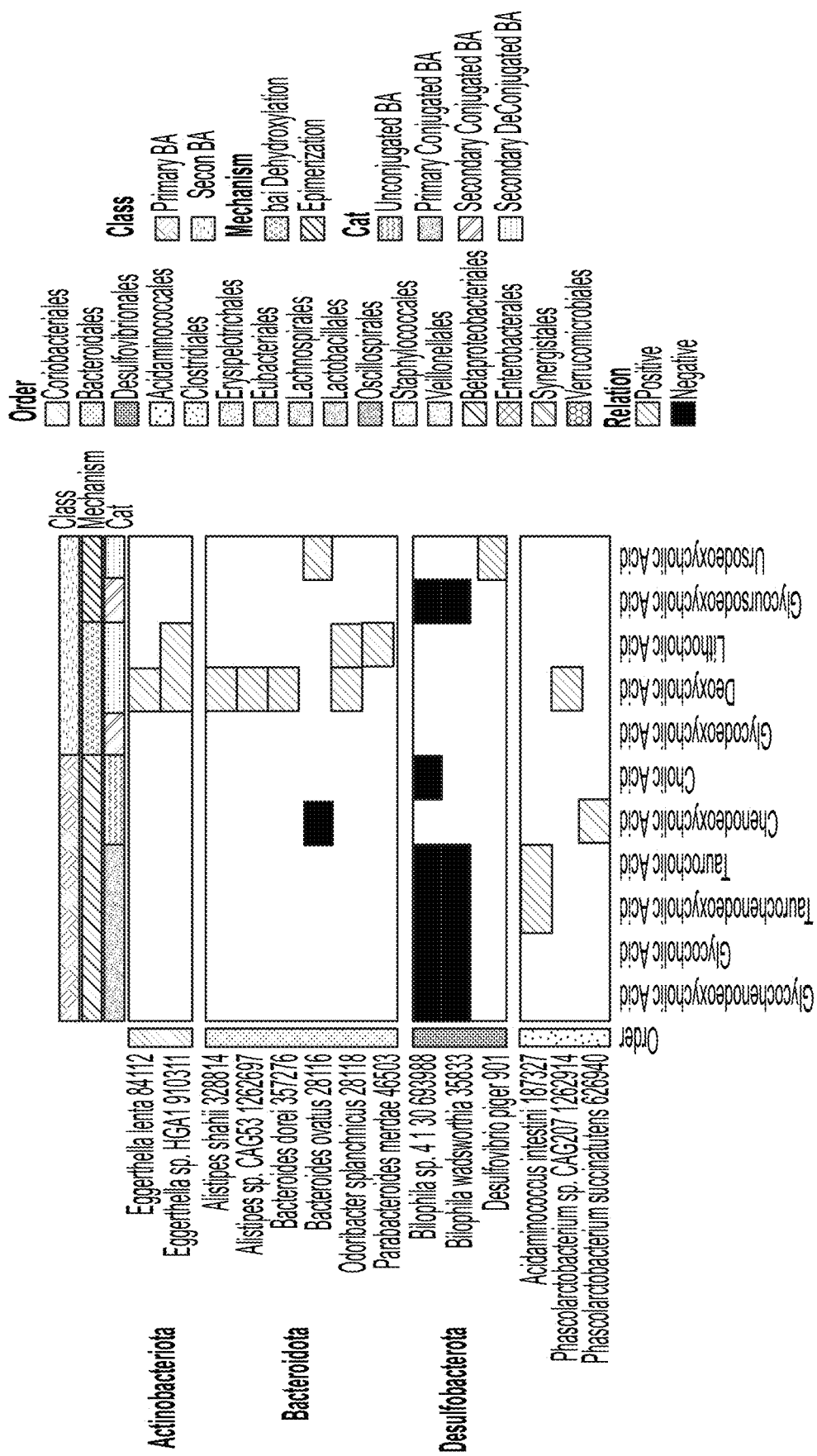
Figure 47G:
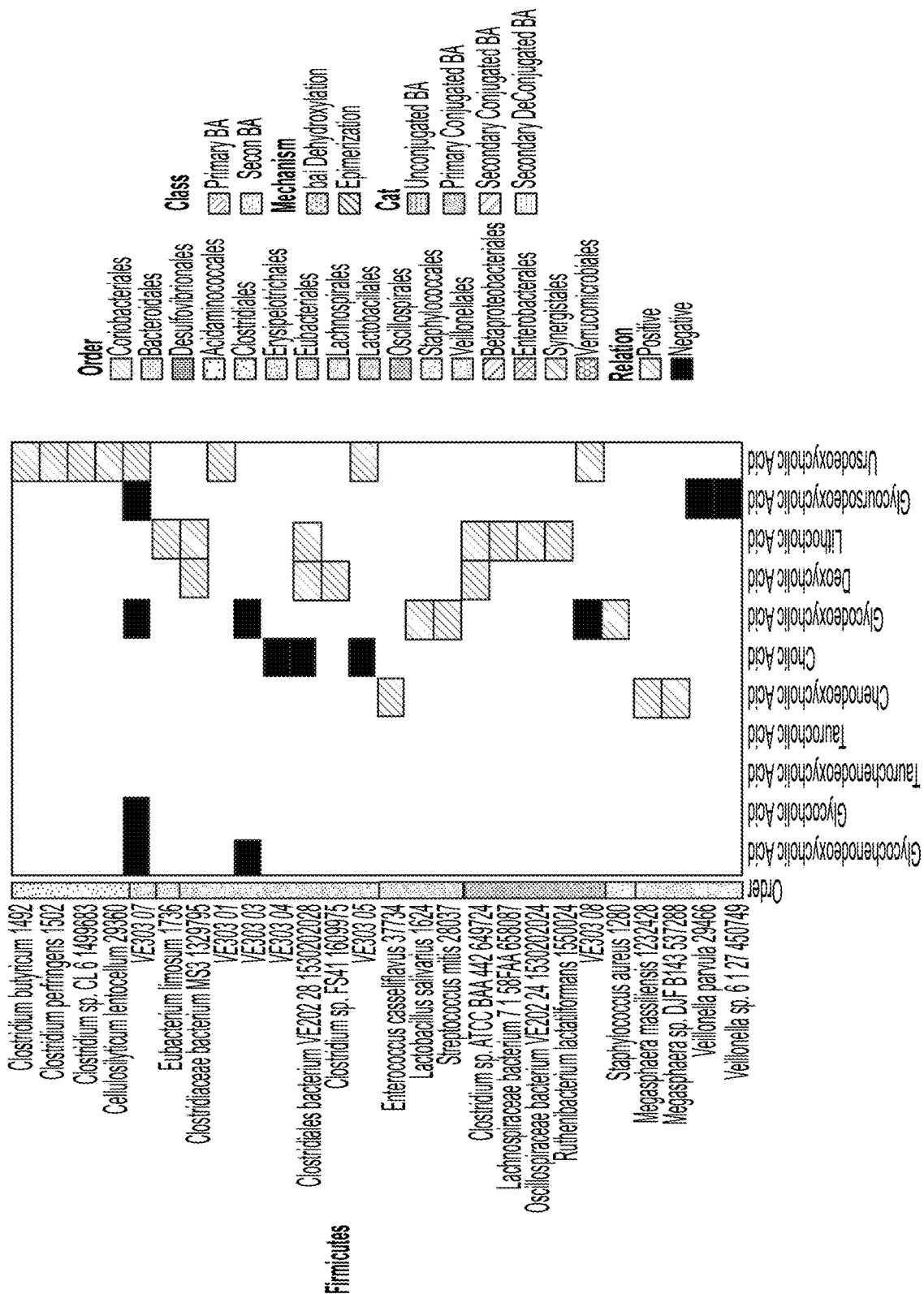
Figure 47H:
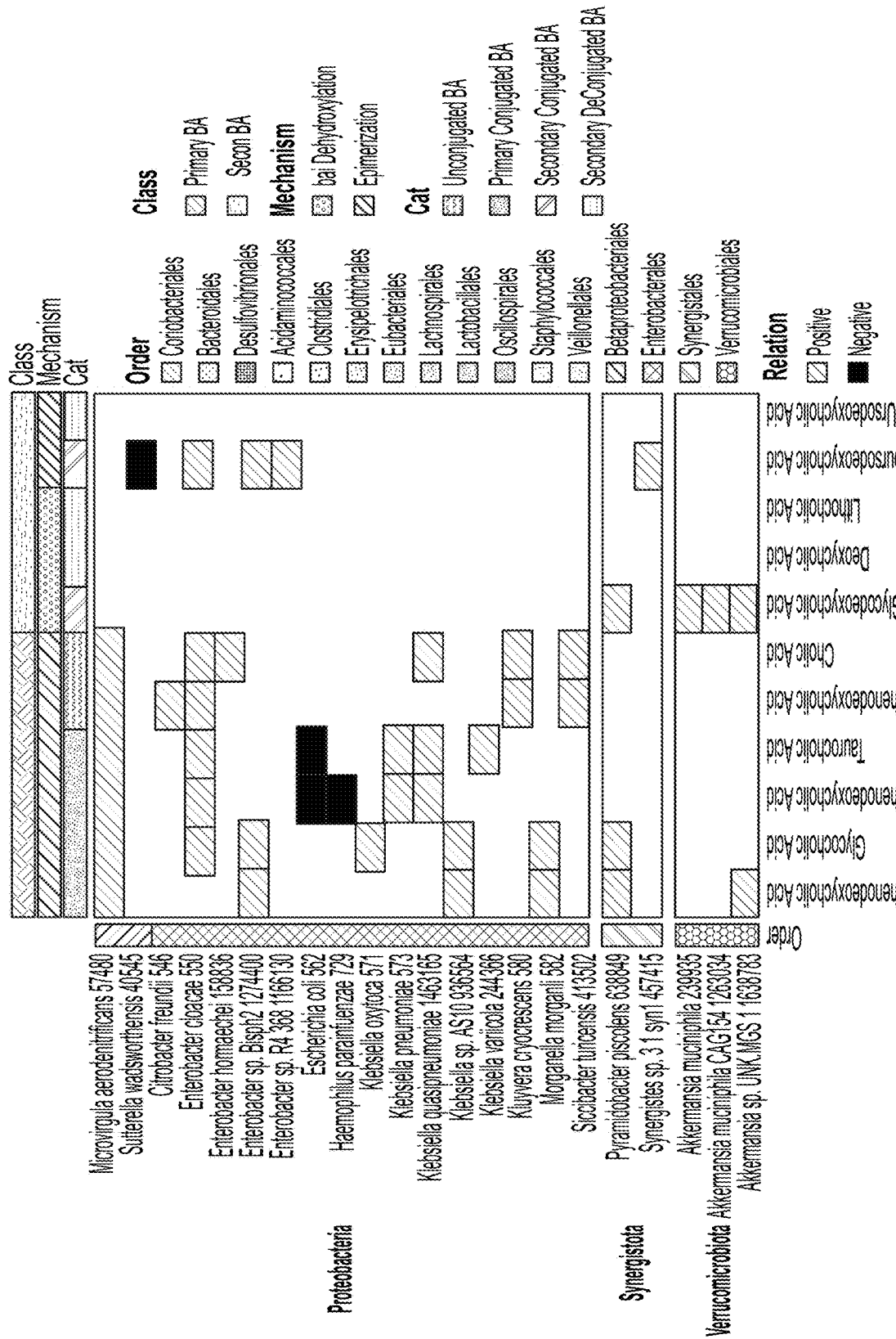
Figure 47I:
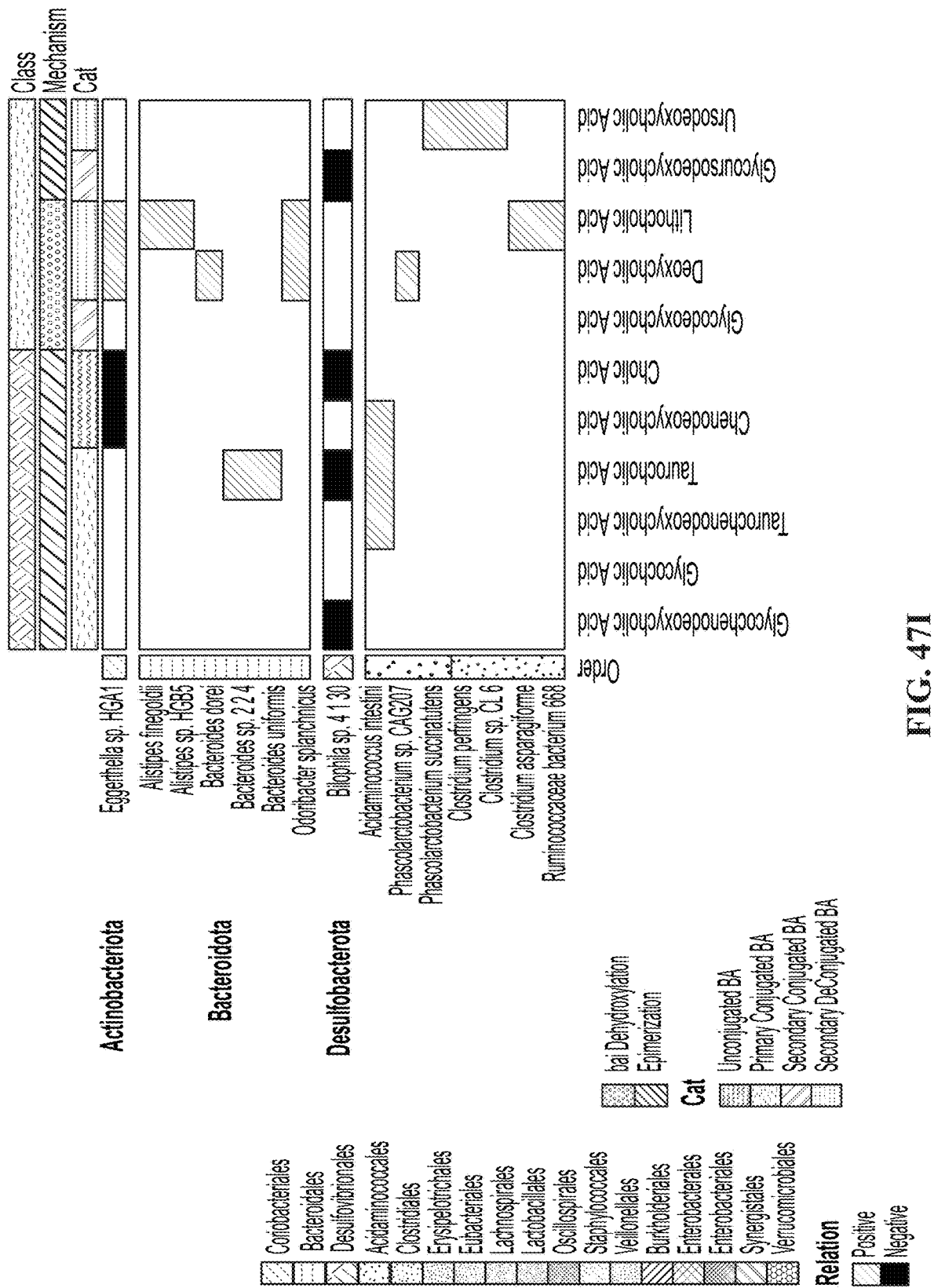
Figure 47J:
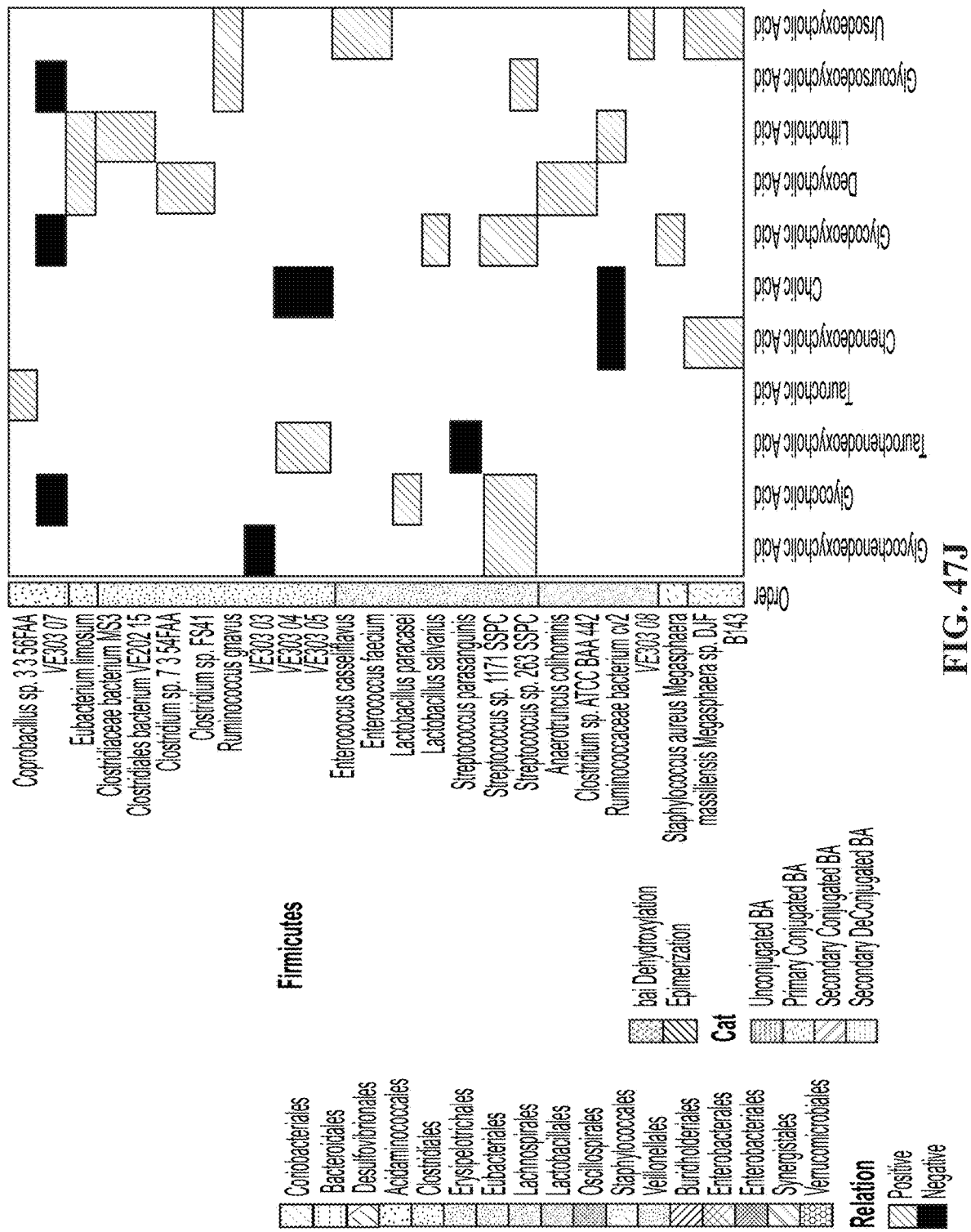
Figure 47K:
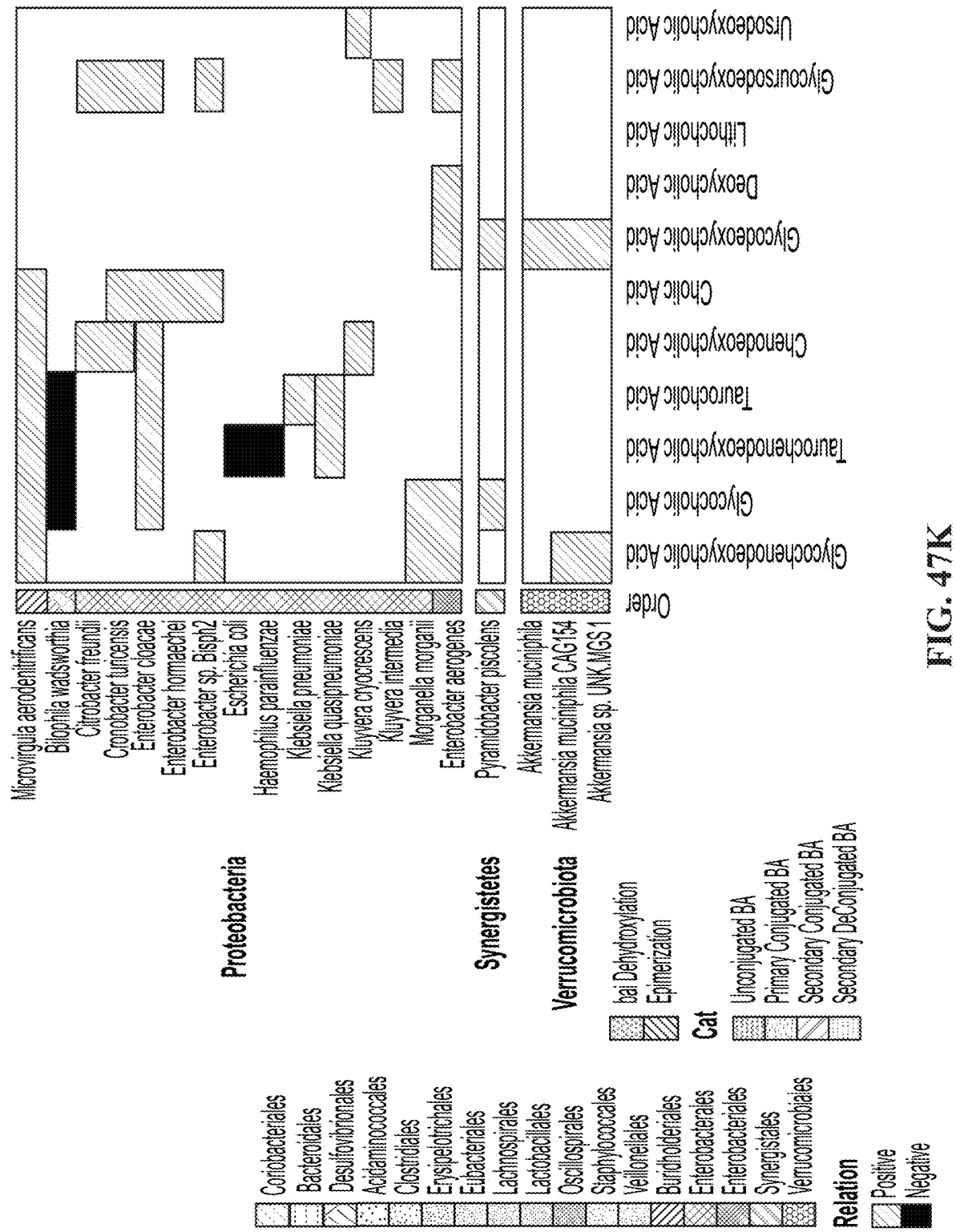

The effects of individual VE303 consortium members and resident bacterial species on bile acids dynamics after vancomycin administration was decoupled by Random Forest Regression (RFR). RFR was chosen due to the fact that it does not assume any underlying model structure, and because it performs implicit feature selection, thus allowing detection of the best contributors to each metabolite's abundance from a large pool of possible predictors (FIG. 47C). RFR identified several of the VE303 strains to be within the top 20 most important species influencing bile acids dynamics (FIG. 47D). Specifically, primary bile acids (both conjugated and unconjugated) decrease in abundance gradually over time after vancomycin is withdrawn, and RFR indicated that VE303 species are amongst the top 20 important species associated with this decline (FIG. 47D, FIG. 55).

Figure 55A:
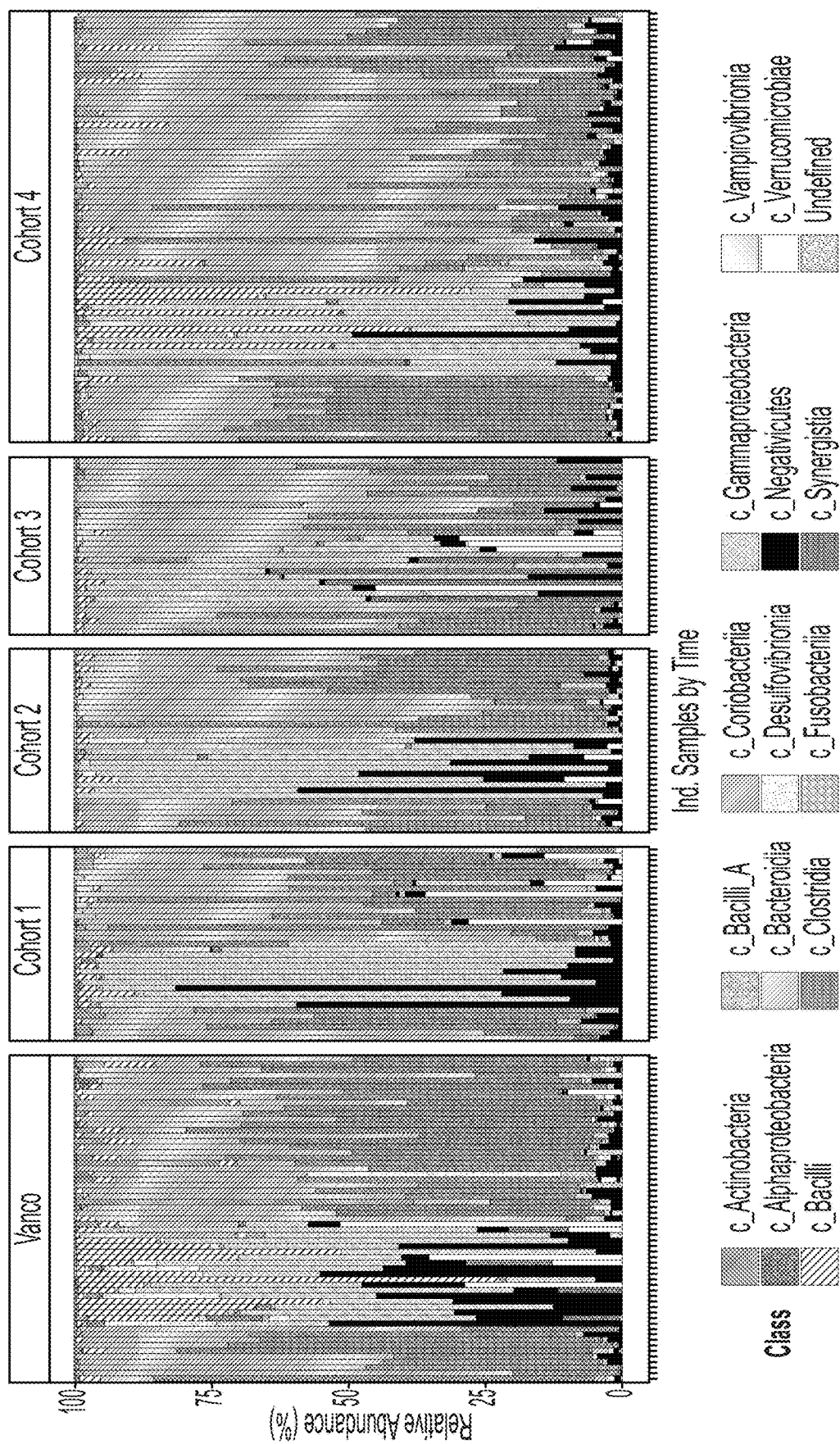
FIGS. 55A-55B shows the relative abundance of each of the indicated bacterial classes based on individual sample by time in each of the indicated cohorts.
Figure 55B:
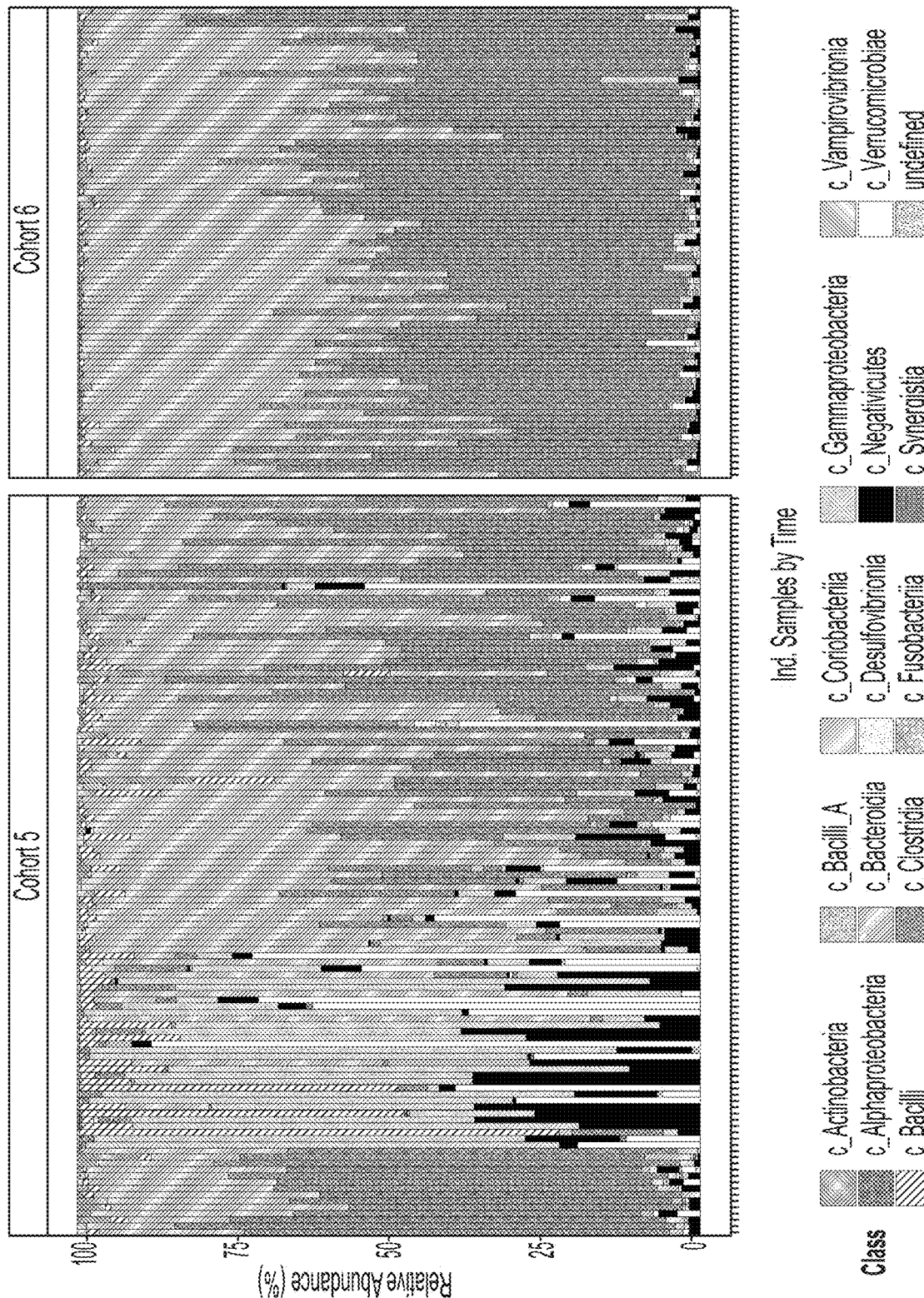

Furthermore, RFR indicated the VE303 species are associated with the observed increase in secondary bile acids (FIG. 47D, FIG. 55). The role of VE303 was more consistent in the recovery of ursodeoxycholic acid (also referred to as ursodiol), which is the biproduct of an epimerization reaction of chenodeoxycholic acid.

Microbiome-produced Short Chain Fatty Acids (SCFAs) are known to positively affect host physiology in the gut by promoting gut barrier function as well as in peripheral tissues, by providing anti-inflammatory, antitumorigenic, and antimicrobial functions. Reduction in SCFAs levels and in the abundance of SCFAs-producing bacteria have been associated with increased risk of multiple diseases including metabolic disease, cardiovascular disease (See e.g., Chambers et l. *Current Nutrition Reports* (2018) 7(4), 198-206), NAFLD (See e.g., Rau et al, *United European Gastroenterology Journal* (2018) Dec. 6 (10), 1496), IBD (See e.g., Venegas et al. Front Immunology 11 Mar. 2019), GvHD (Matthewson et al., *Nat Immunology* (2016) May 17 (5) 505-513), and food allergy (See e.g., Roduit et al., *Allergy* (2019), April 74 (4) 799).

Figure 48A:
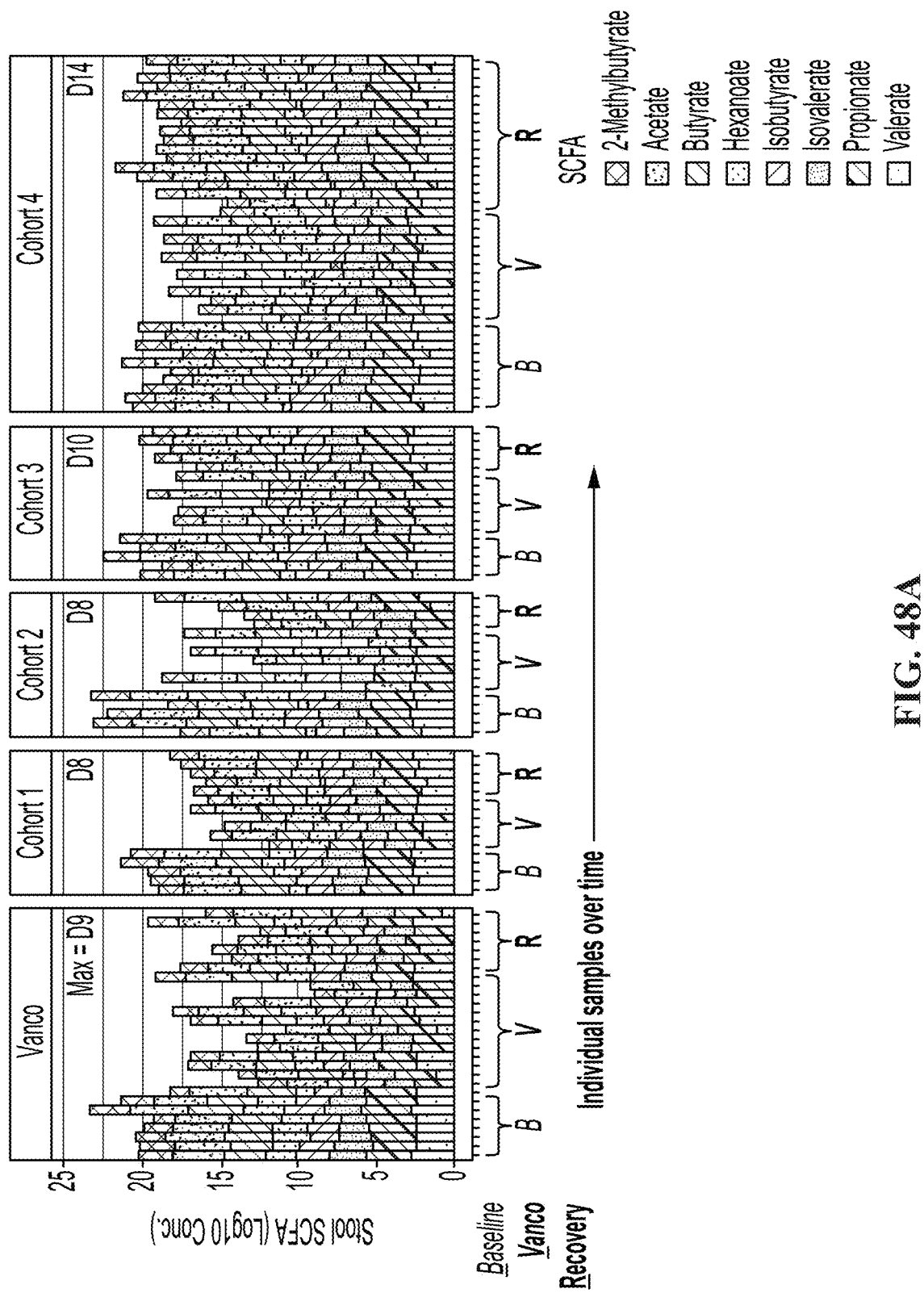
FIGS. 48A-48G show the short chain fatty acid (SCFA) pharmacodynamics of VE303 administration.

To determine the effect of vancomycin and VE303 on SCFAs concentrations, SCFAs were measured in the stool of subjects at baseline, during vancomycin administration, and during the recovery phase after vancomycin with and without VE303 (Table 6, FIG. 48A). Linear mixed effect modeling was performed to test whether the SCFAs were altered by vancomycin and whether total VE303 abundance significantly affected their post-antibiotic dynamics (Tables 8A and 8B). All measured SCFAs levels (with the exception of hexanoate) were reduced by vancomycin treatment and remained below pre-antibiotic levels in the absence of VE303. More importantly, all SCFA levels affected by vancomycin were also found to significantly increase in response to VE303 administration, suggesting a beneficial effect of VE303 in SCFAs recovery.

Figure 48B:
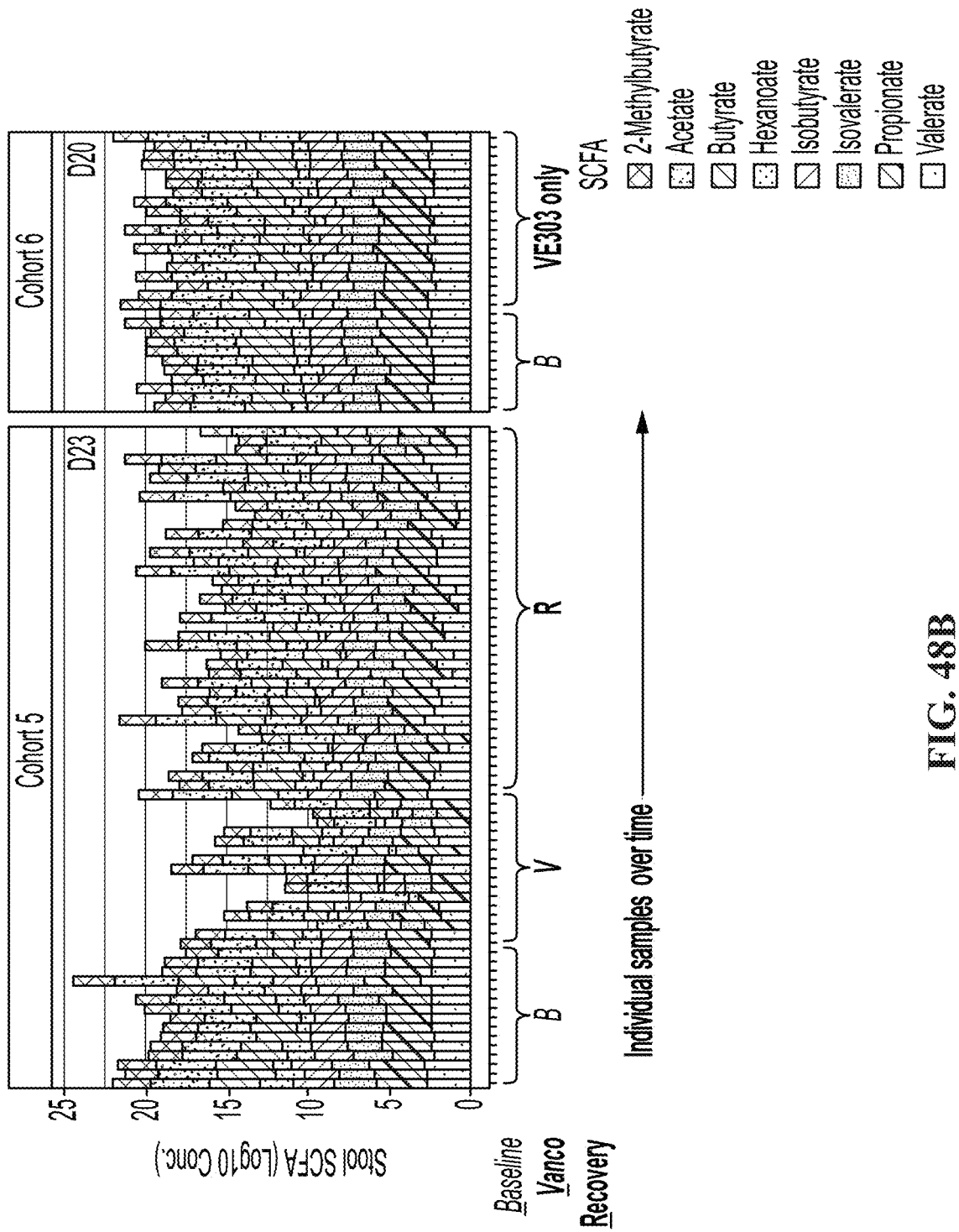
Figure 48C:
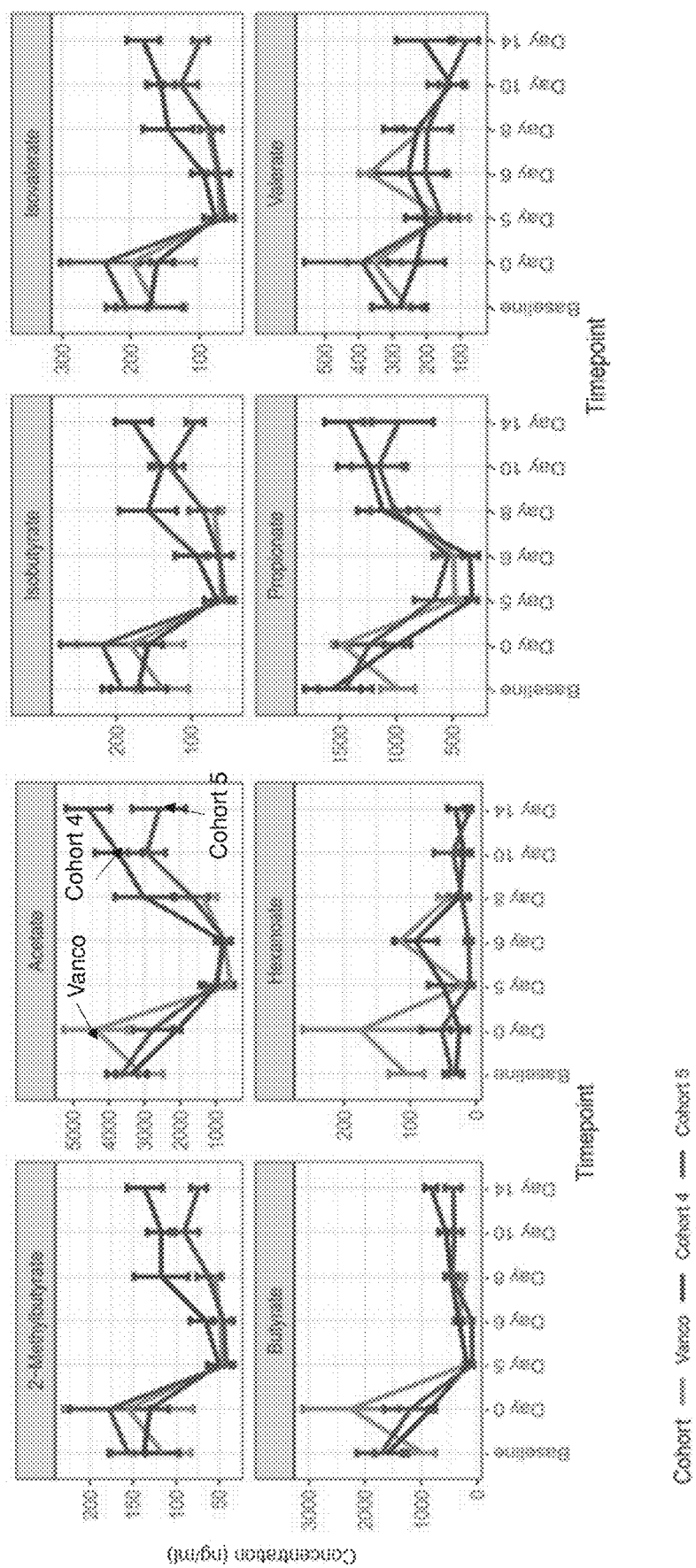
Figure 48D:
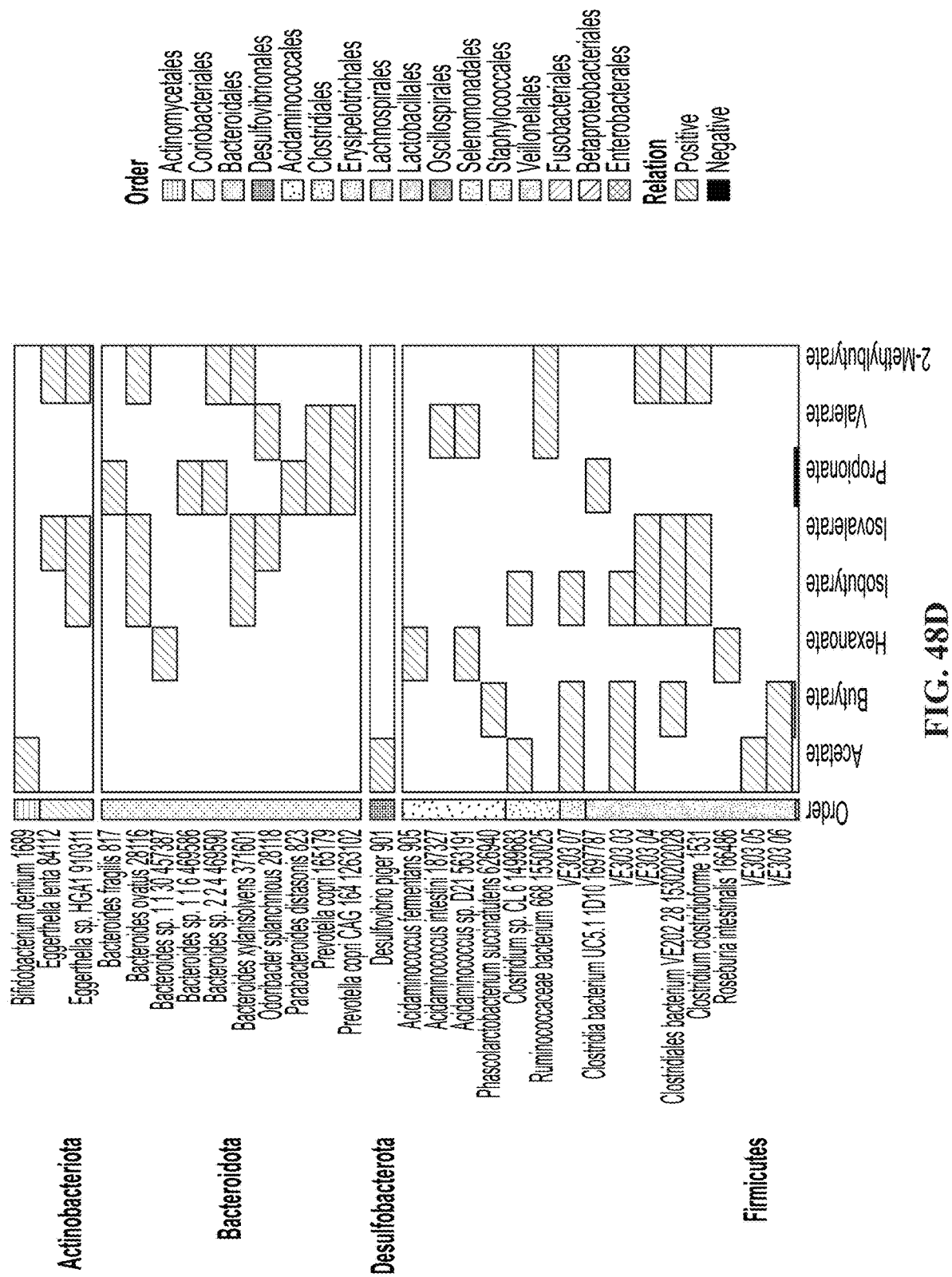
Figure 48E:
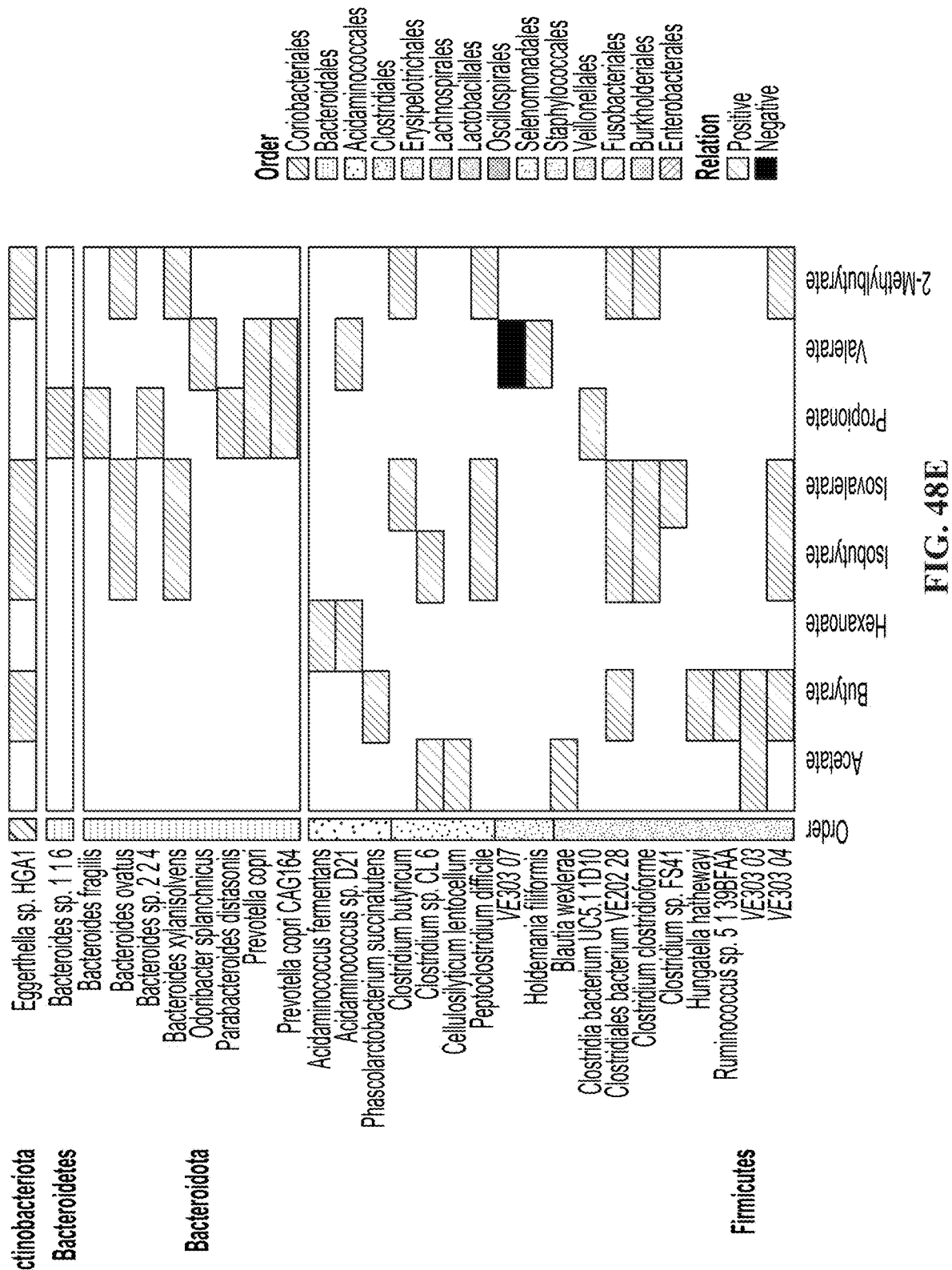
Figure 48F:
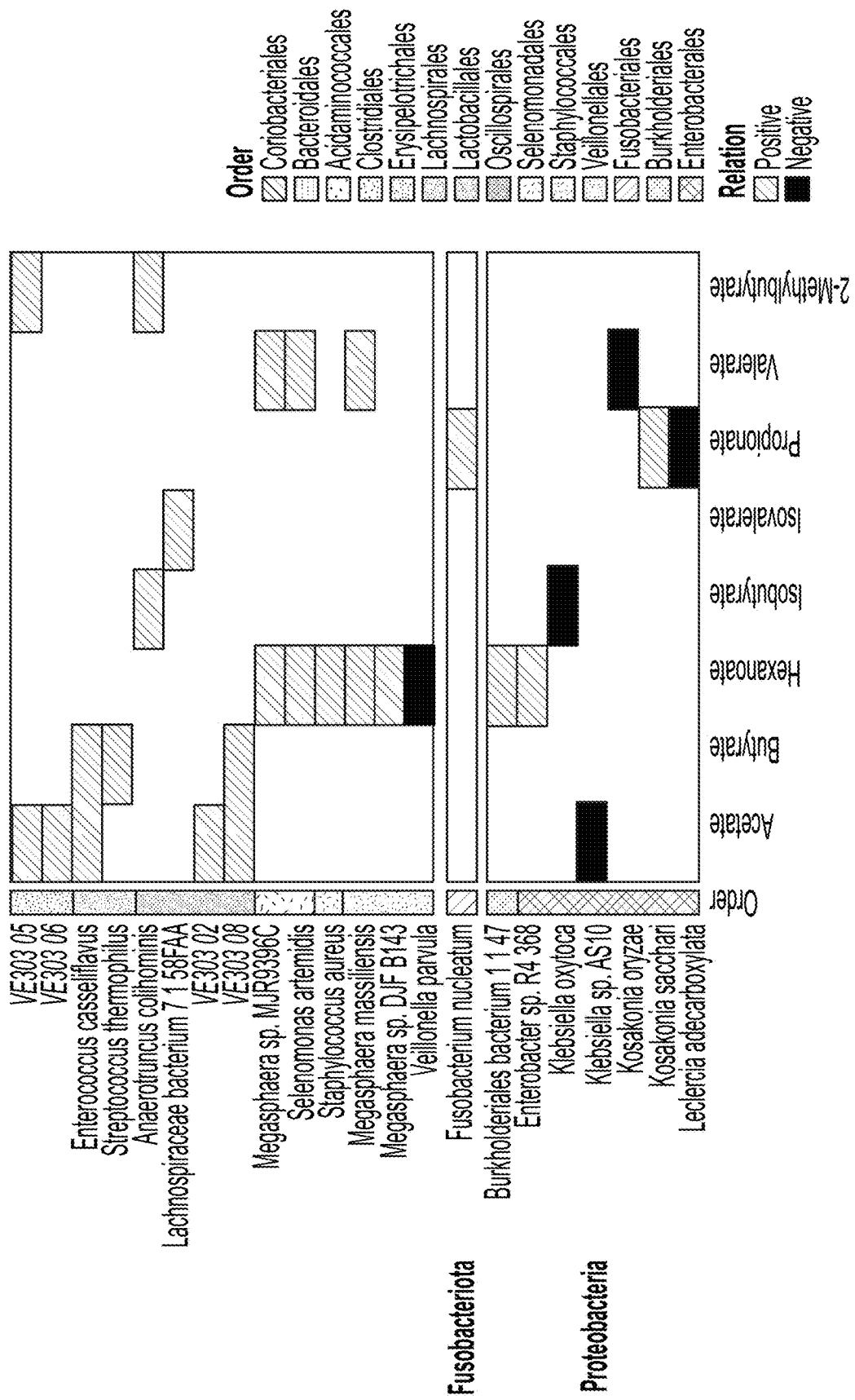
Figure 48G:
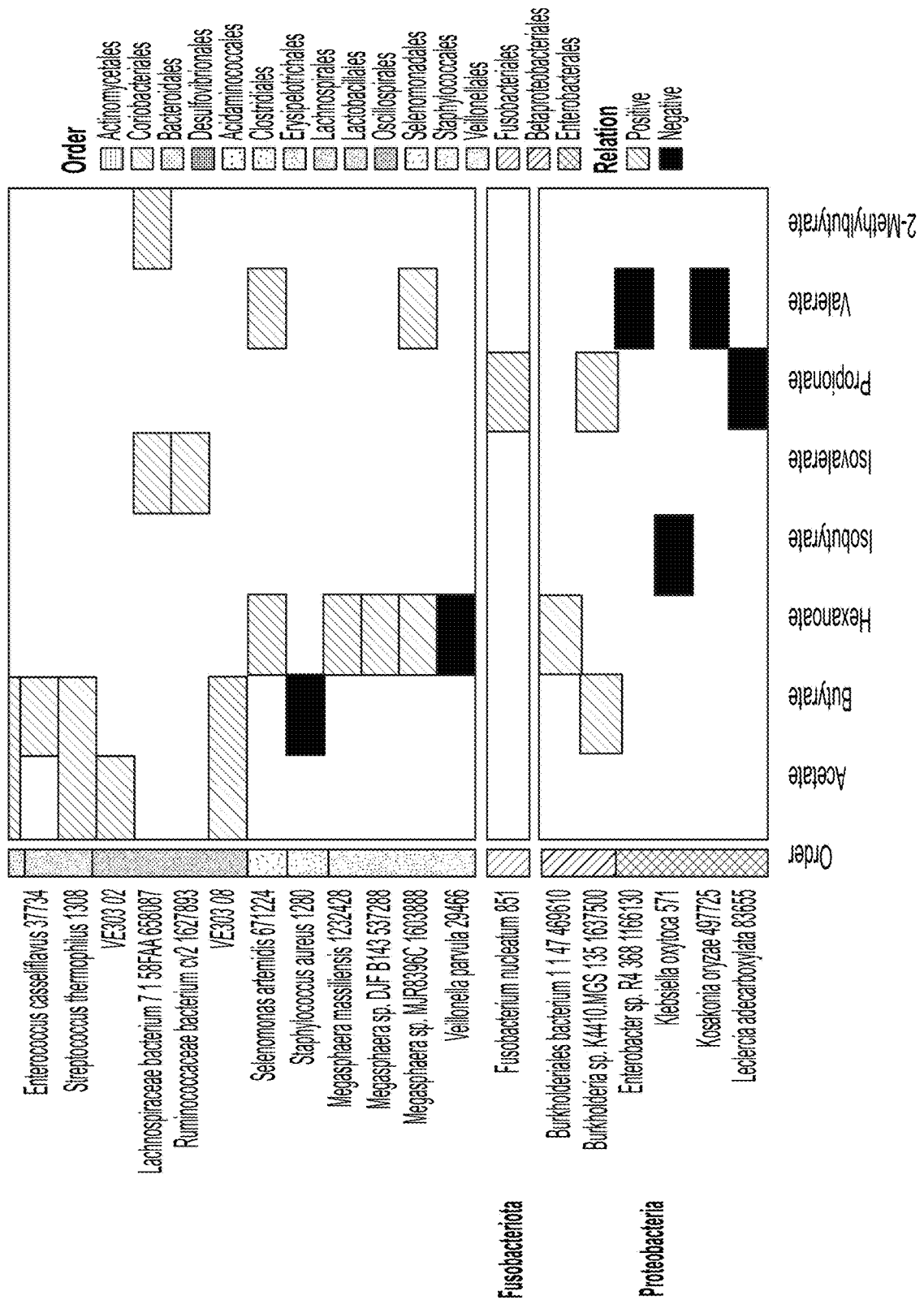
Figure 56:
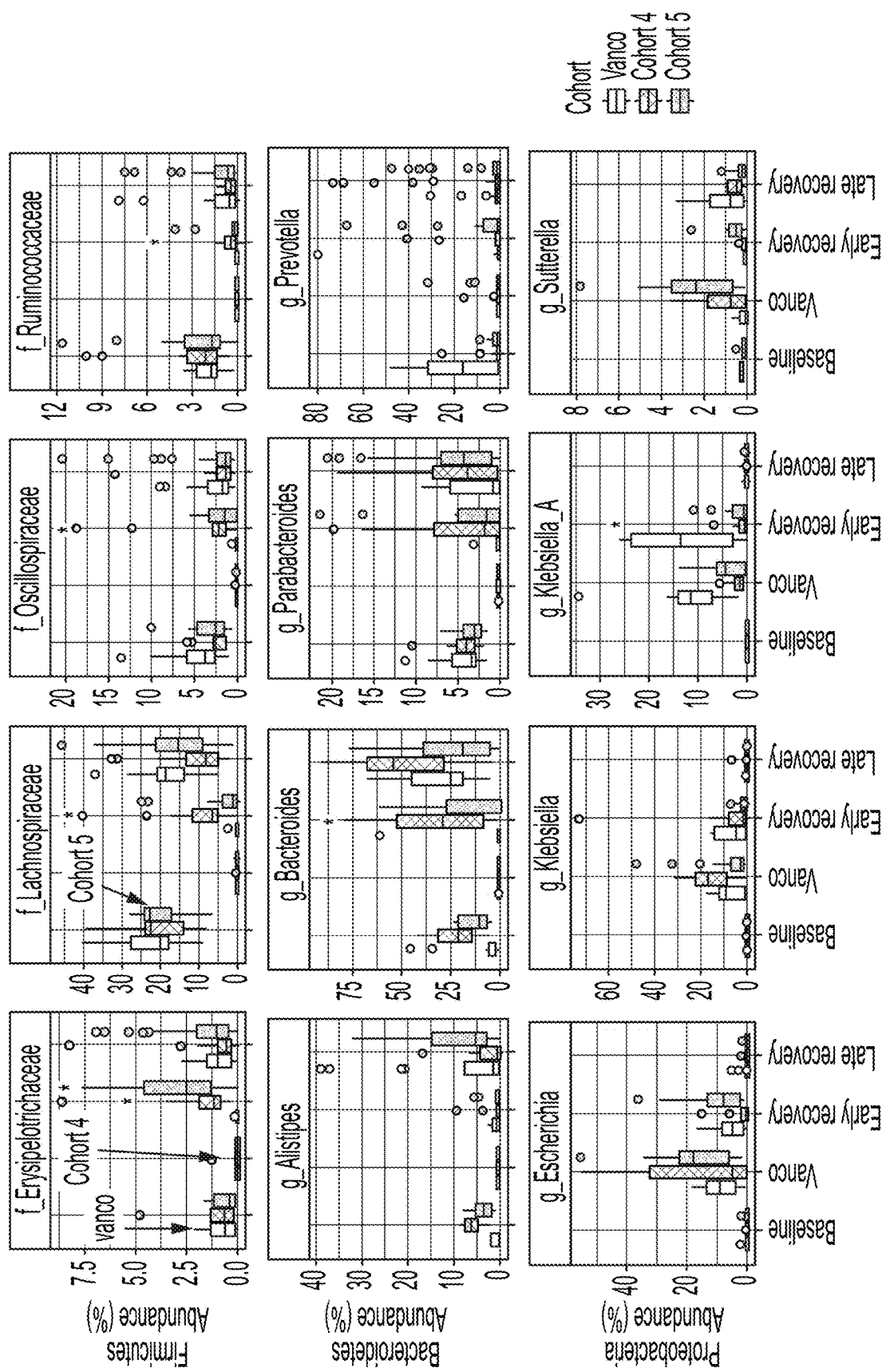
FIG. 56 shows pharmacodynamics (PD) of the microbiota in each of the cohorts. The relative abundance of each of the most abundant Firmicutes (top row), Bacteroidetes (middle row) and Proteobacteria (bottom row) are shown at baseline, after vancomycin administration ("Vanco"), up to 1 week of recovery ("Early recovery"), and greater than 1 week of recovery ("Late recovery"). For each time point, the cohorts are, from left to right, vancomycin only ("vanco"), cohort 4, and cohort 5. The natural recovery after vancomycin alone is compared to the recovery in the presence of VE303 (Cohorts 4 and 5). Asterisk (*) indicates $p<0.05$ Kruskal-Wallis, BH corrected.
Figure 57A:
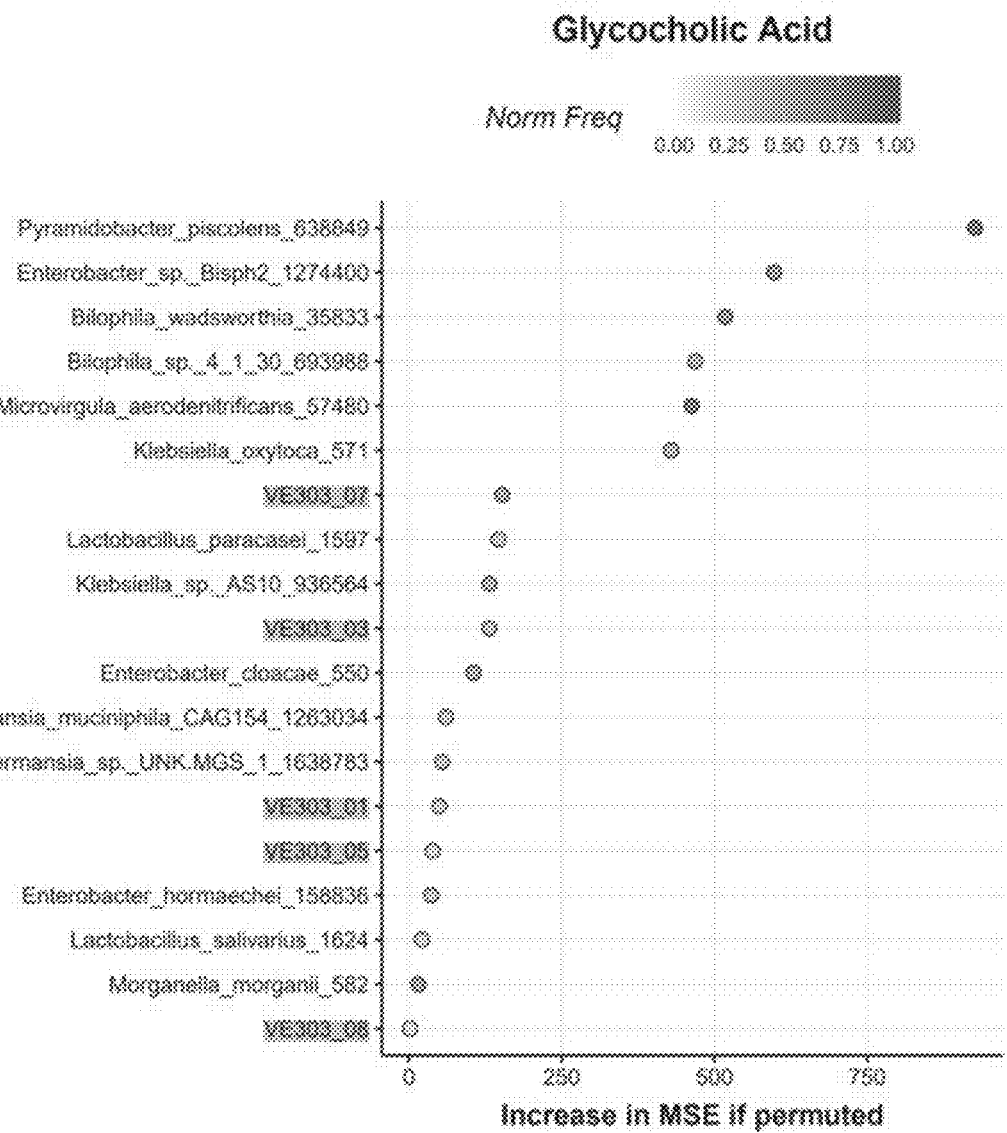
FIGS. 57A-57T show the bacterial strains associated with recovery of the indicated conjugated primary bile acids ("Conjugated 1° BA": glycocholic acid, taurocholic acid, glycochenodeoxycholic acid, taurochenodeoxycholic acid), unconjugated primary bile acids ("Unconjugated 1° BA": cholic acid; chenodeoxycholic acid), secondary bile acids ("Secondary BA": deoxycholic acid, lithocholic acid, ursodeoxycholic acid), and conjugated secondary bile acids ("Conjugated 2° BA": glycodeoxycholic acid, glycoursodeoxycholic acid). The bacterial strains were identified based on the permutated importance analysis and ranked on increase in mean squared prediction error when permutated. Each panel display bacteria that were found significant (permutated p-value <0.05) in at least one iteration. Shading of the dots indicates the frequency of being statistically significant calculated over the total number of Random Forest iterations. Each of the VE303 strains that are deemed important are indicated with an arrow. Species identified by this analysis may be positively or negatively affecting the bile acids abundance.
Figure 57B:
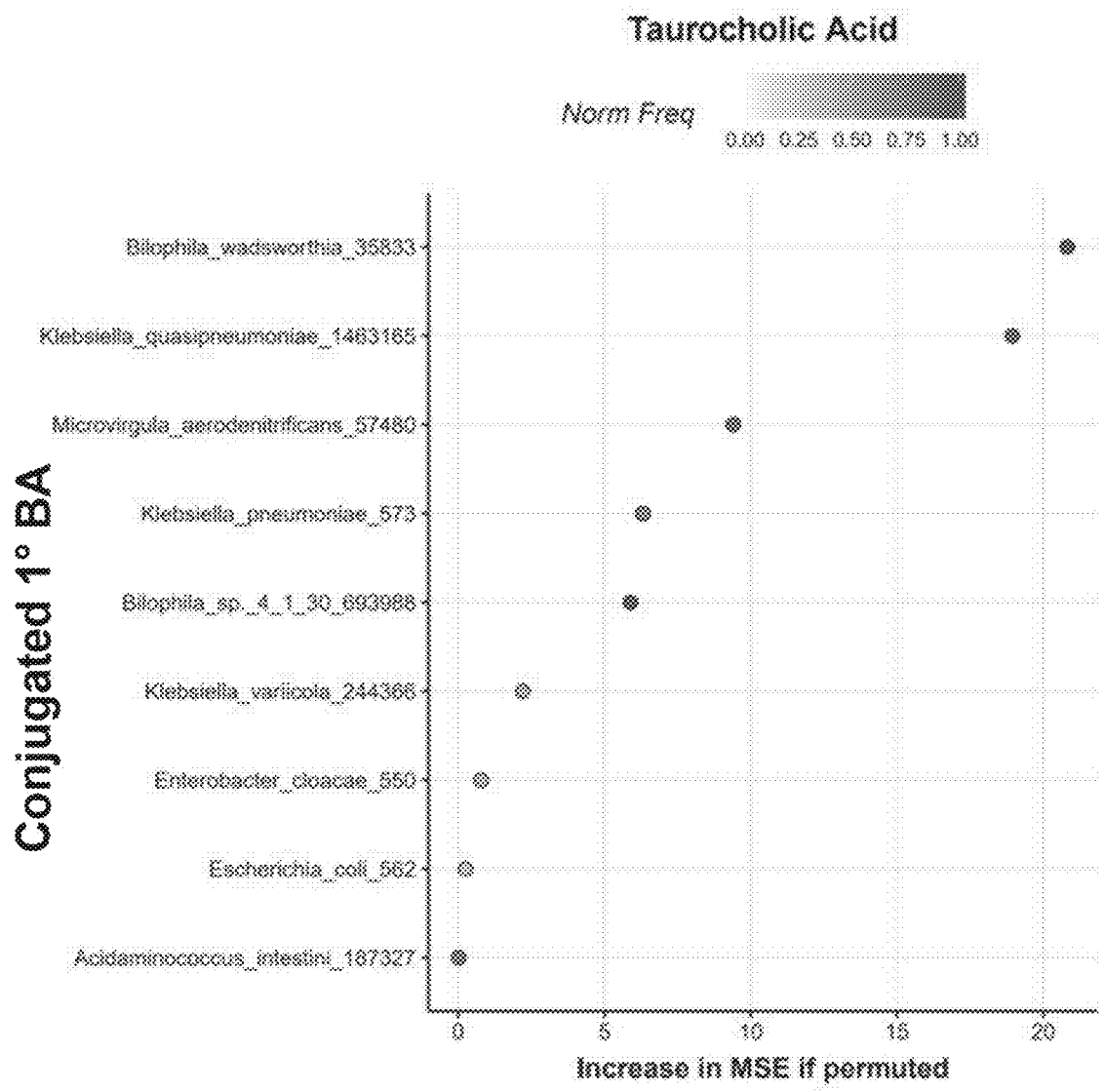
Figure 57C:
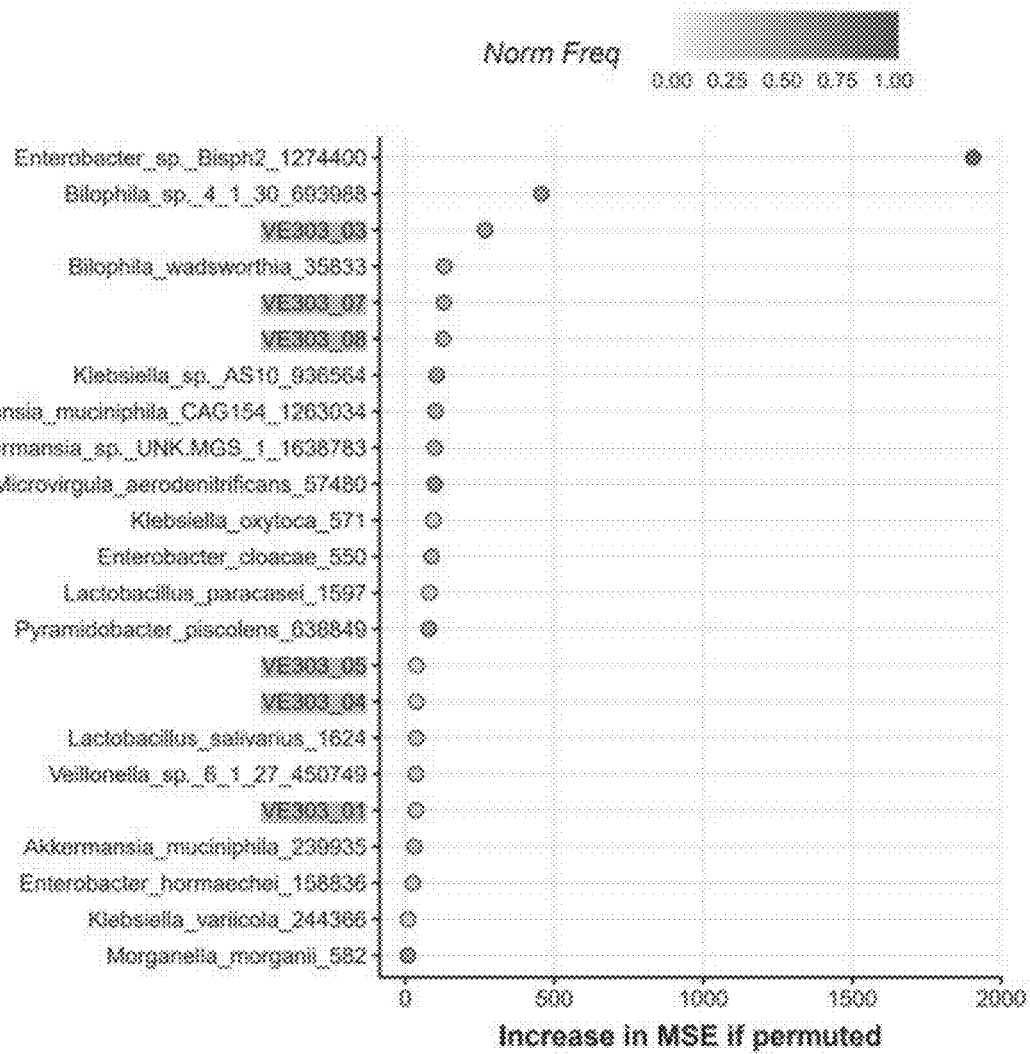
Figure 57D:
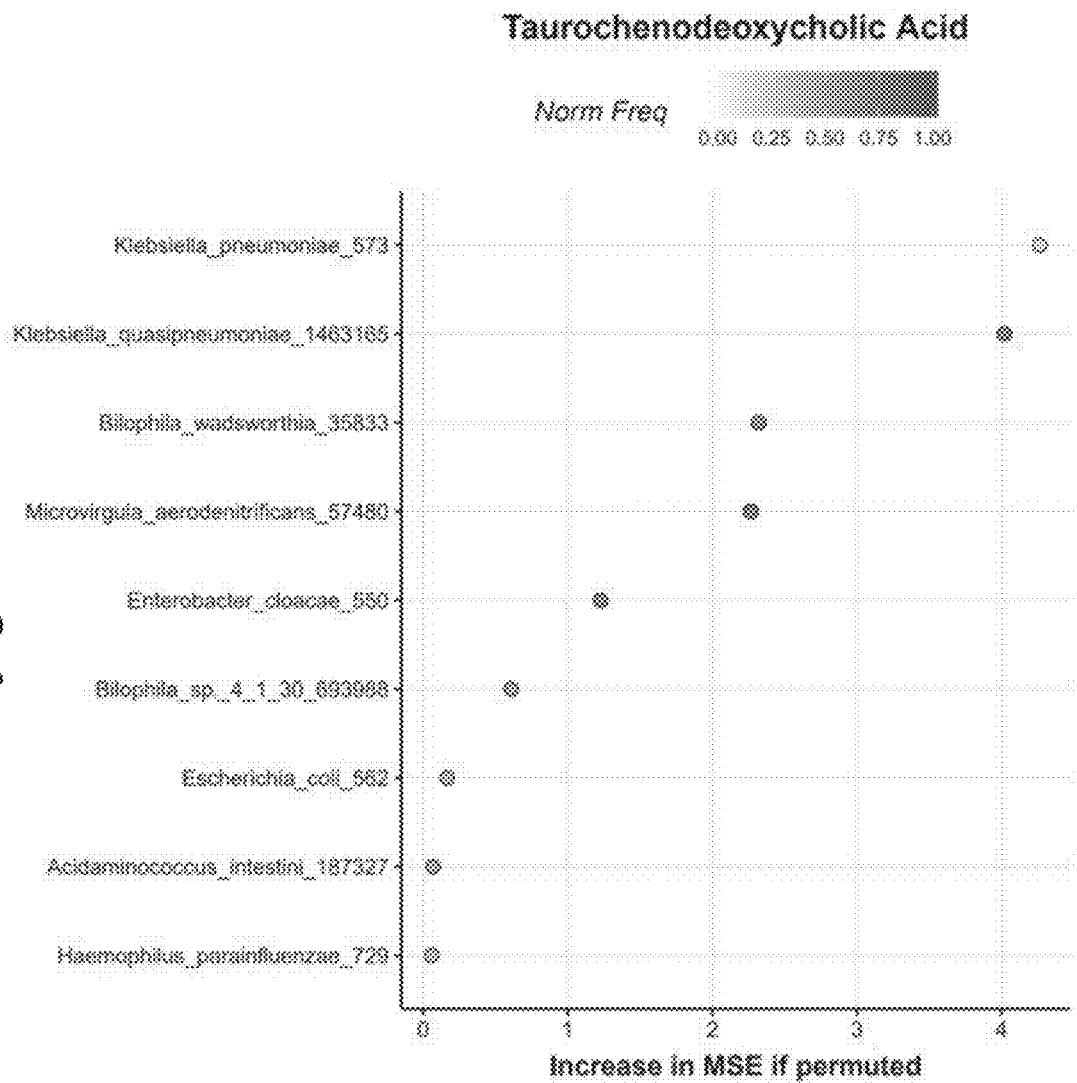
Figure 57E:
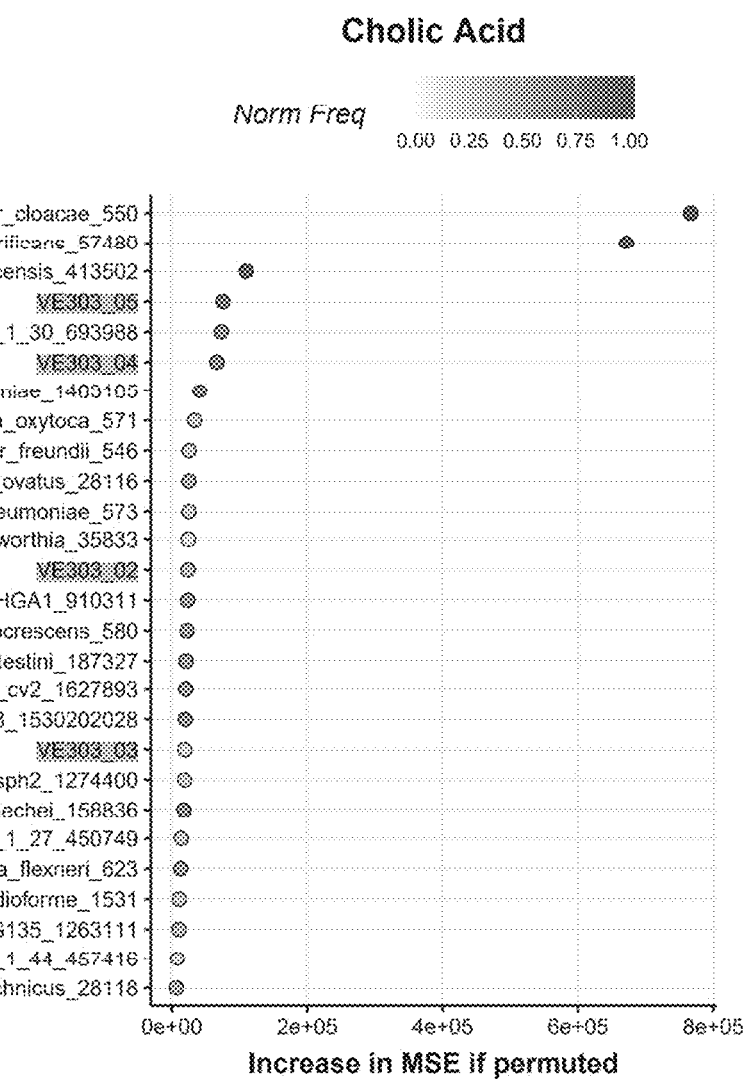
Figure 57F:
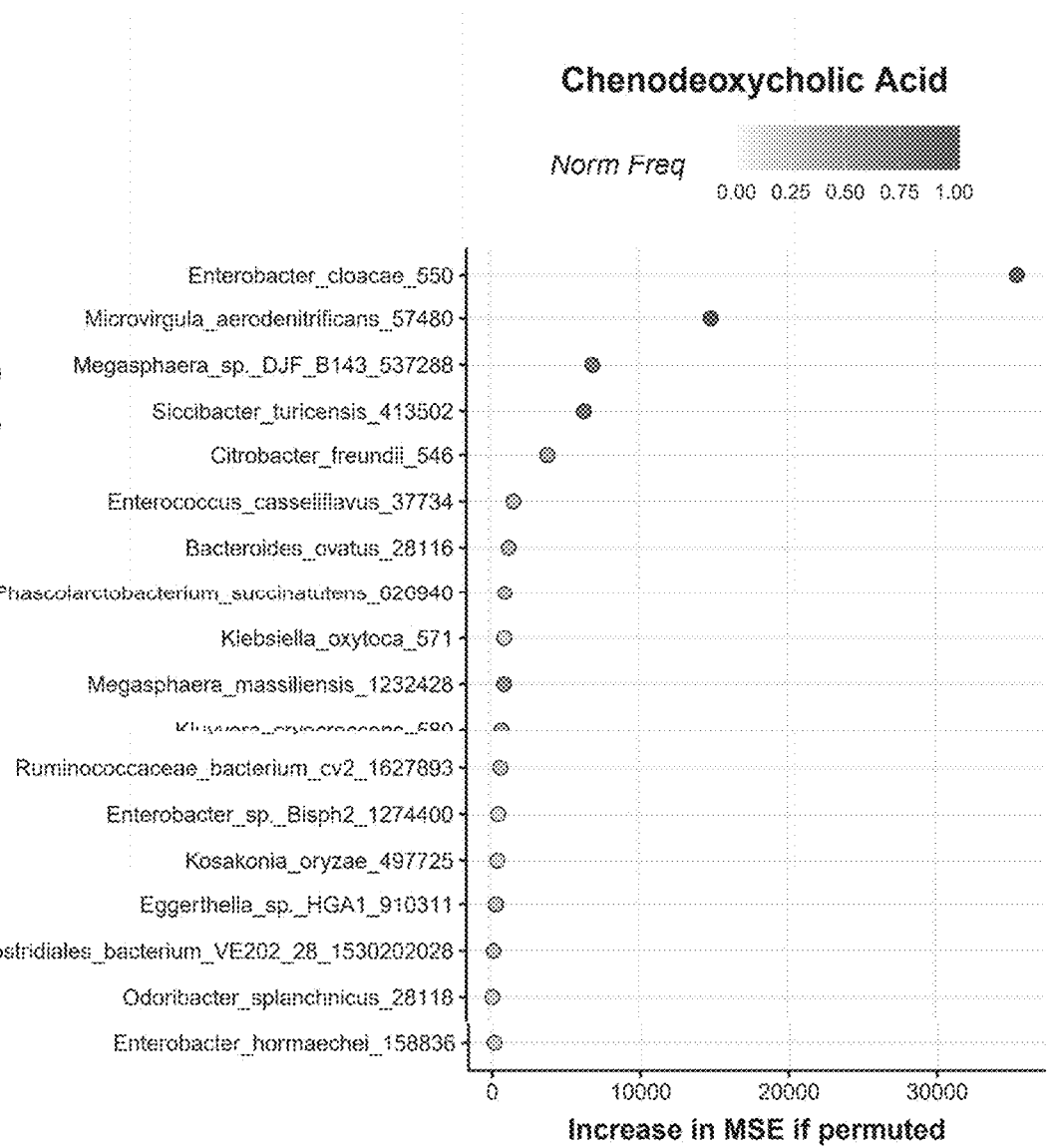
Figure 57H:
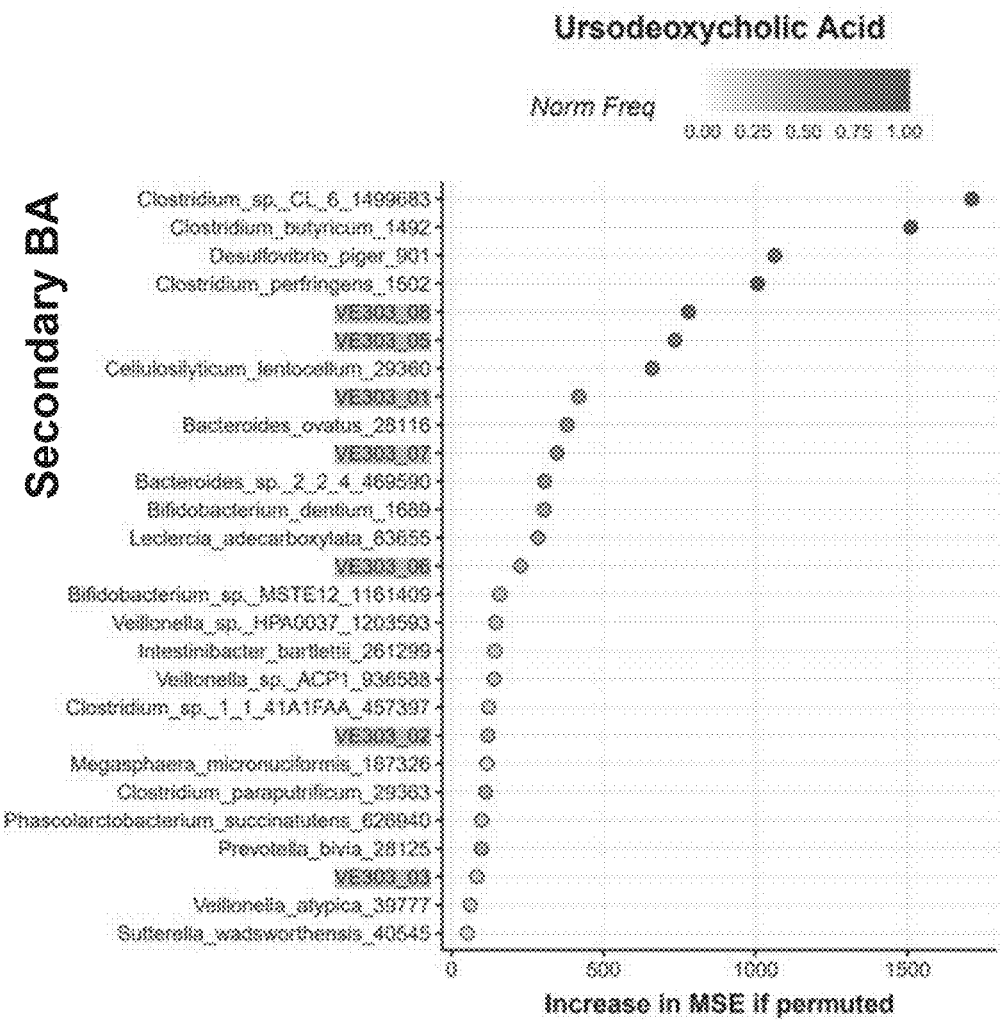
Figure 57I:
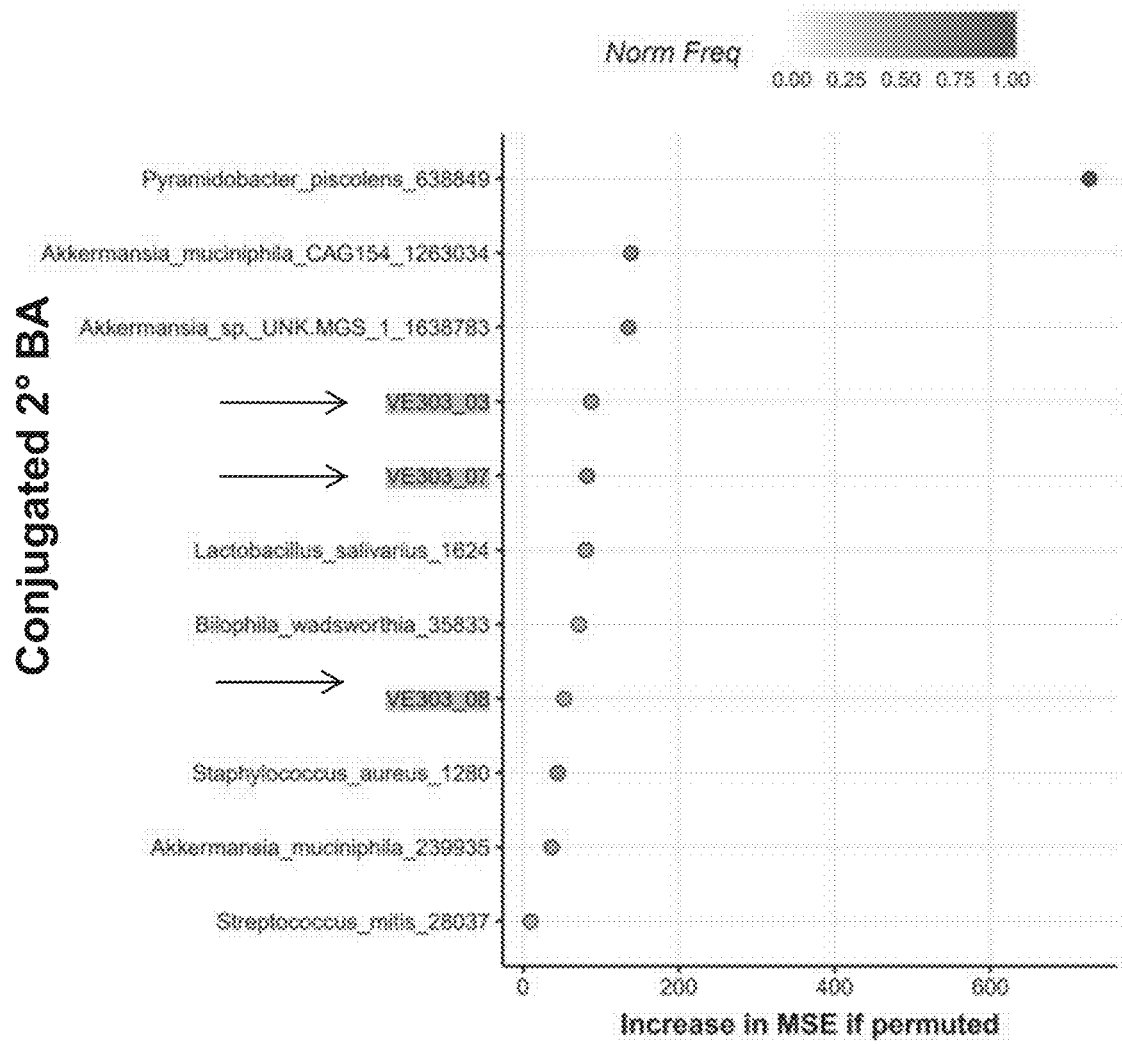
Figure 57J:
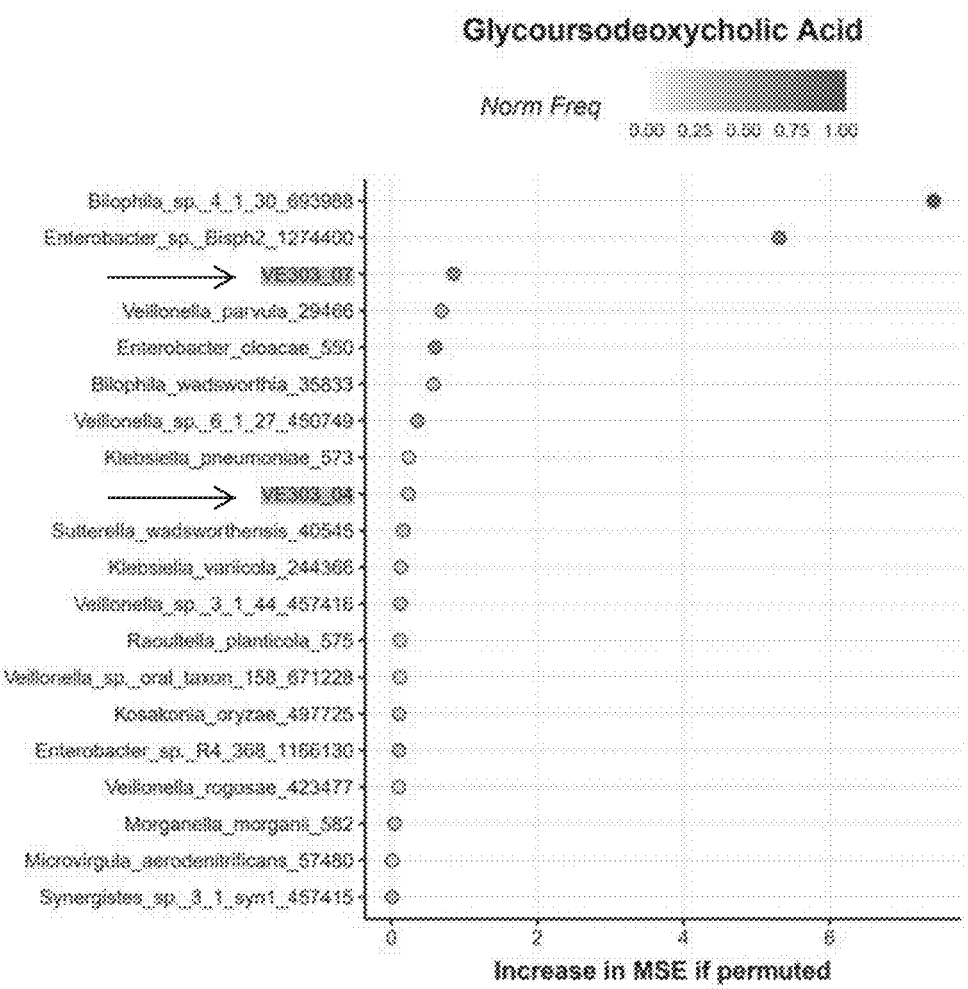
Figure 57K:
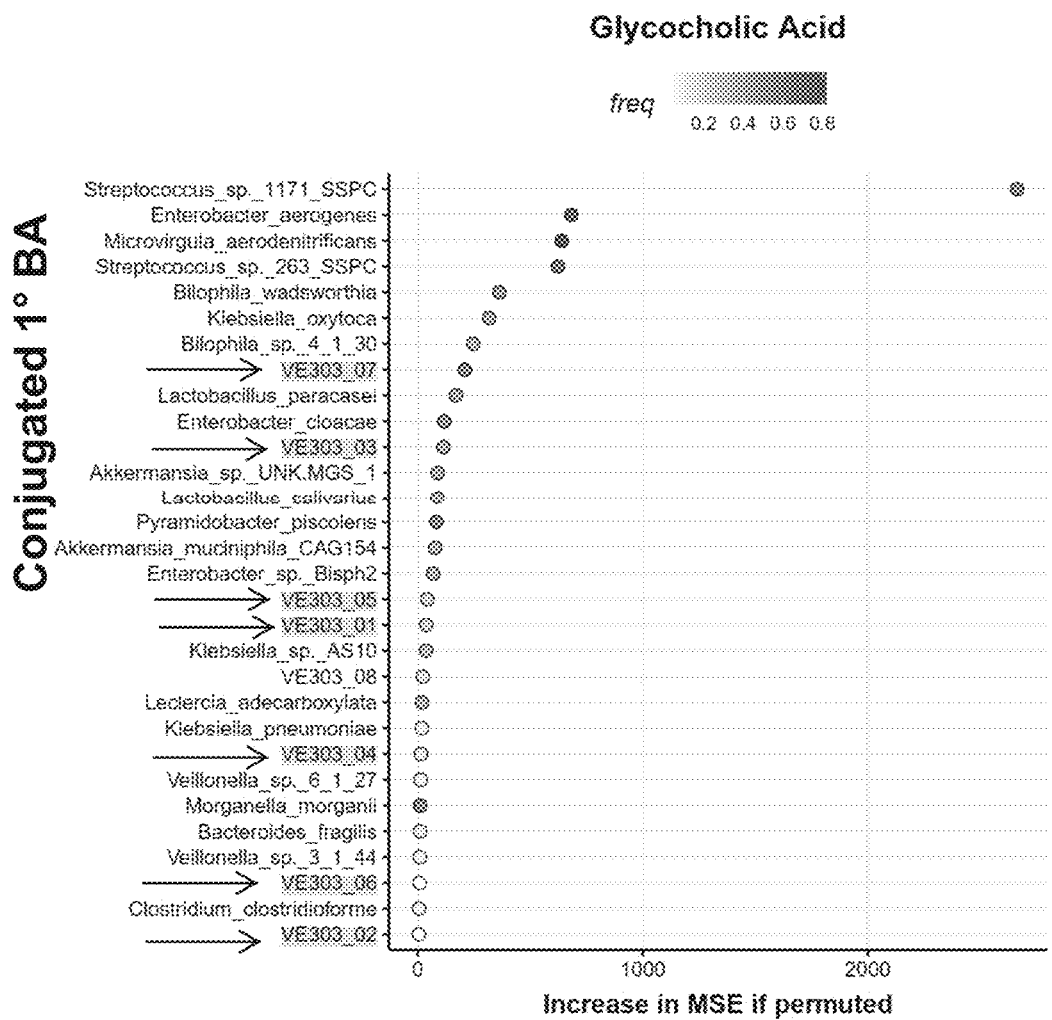
Figure 57L:
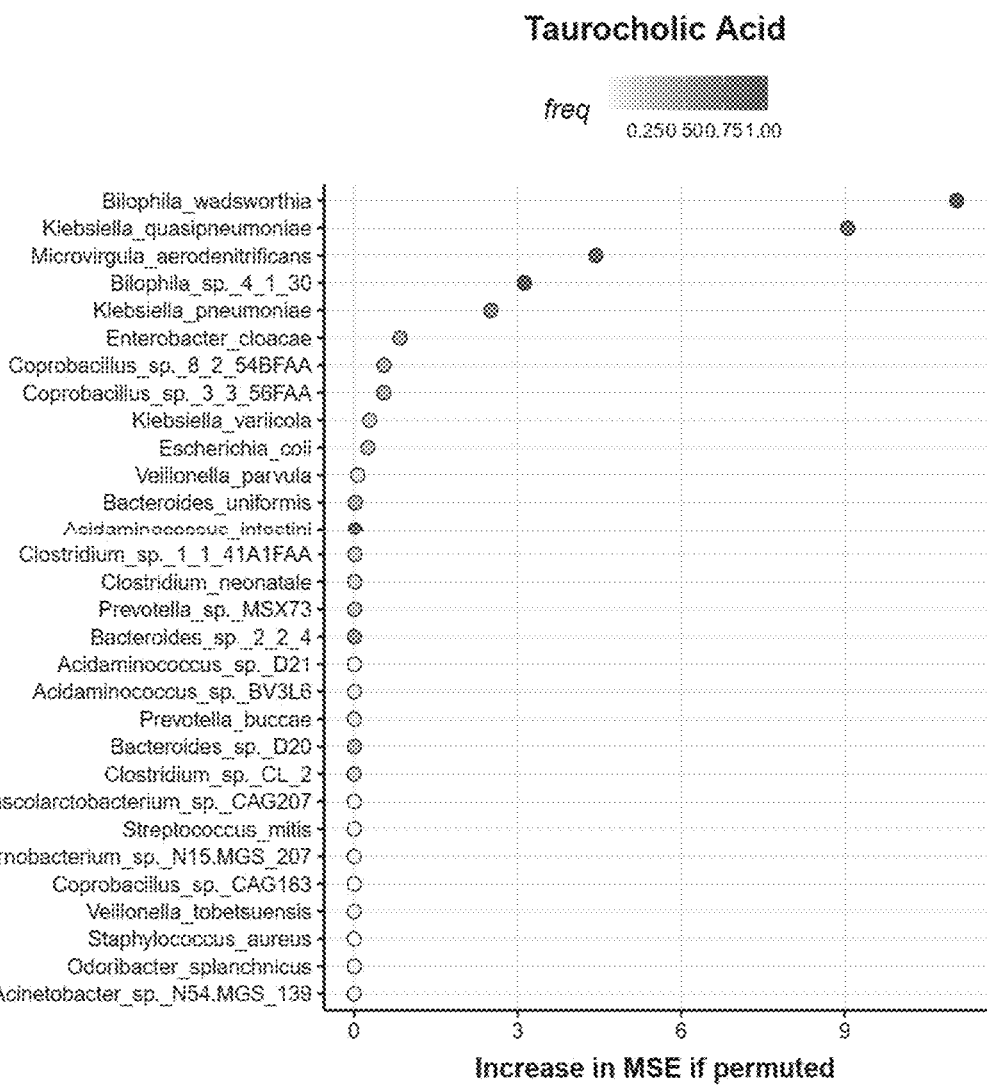
Figure 57M:
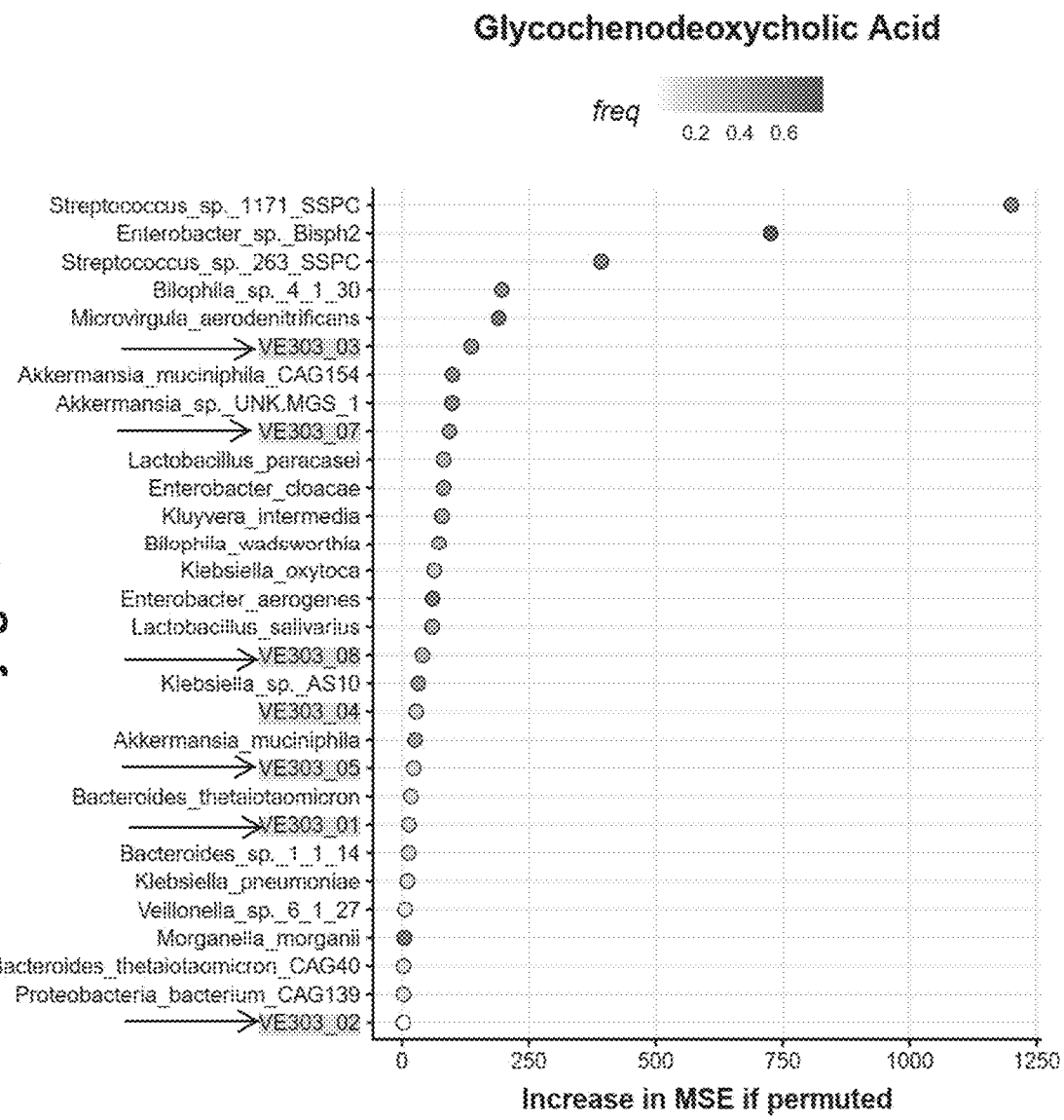
Figure 57N:
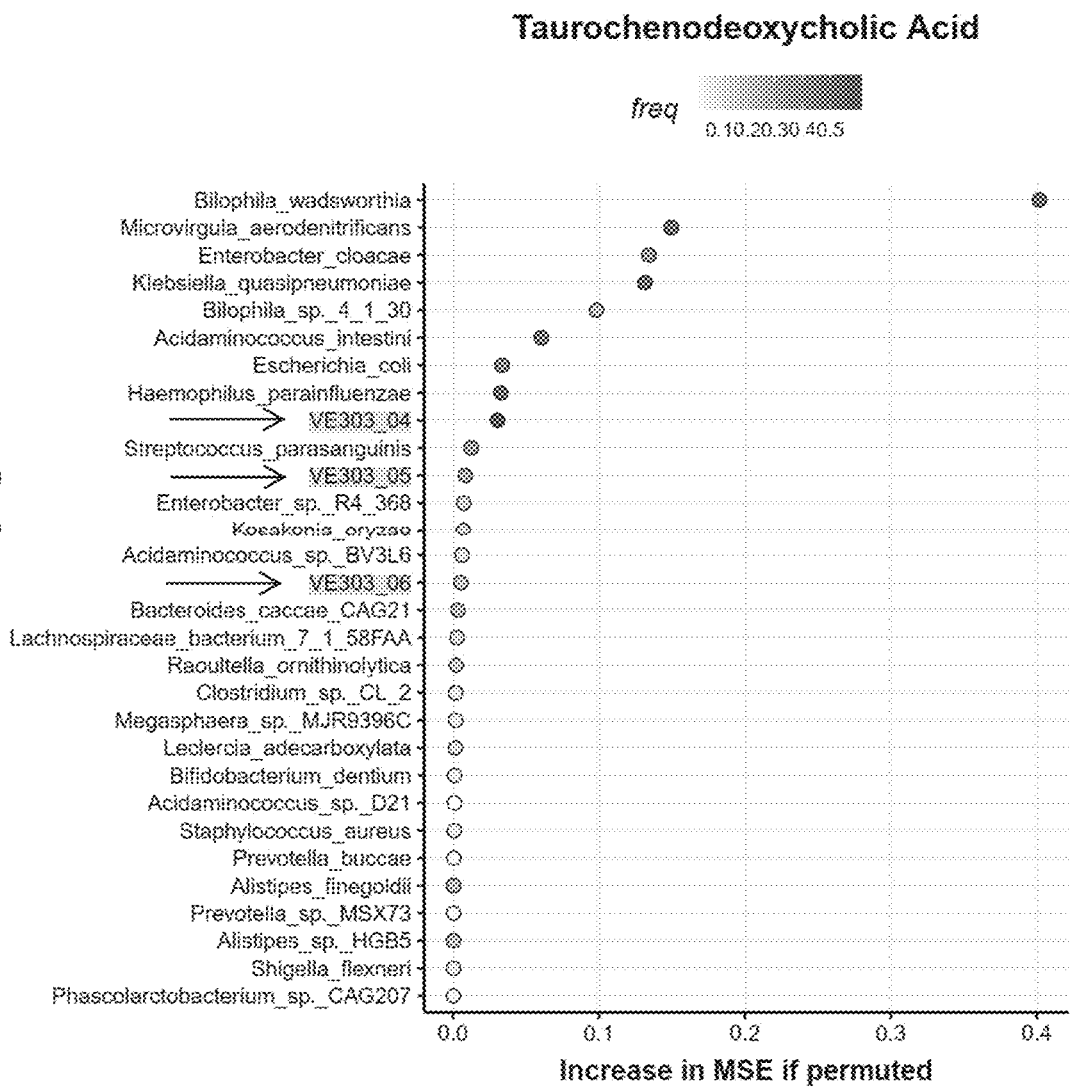
Figure 57O:
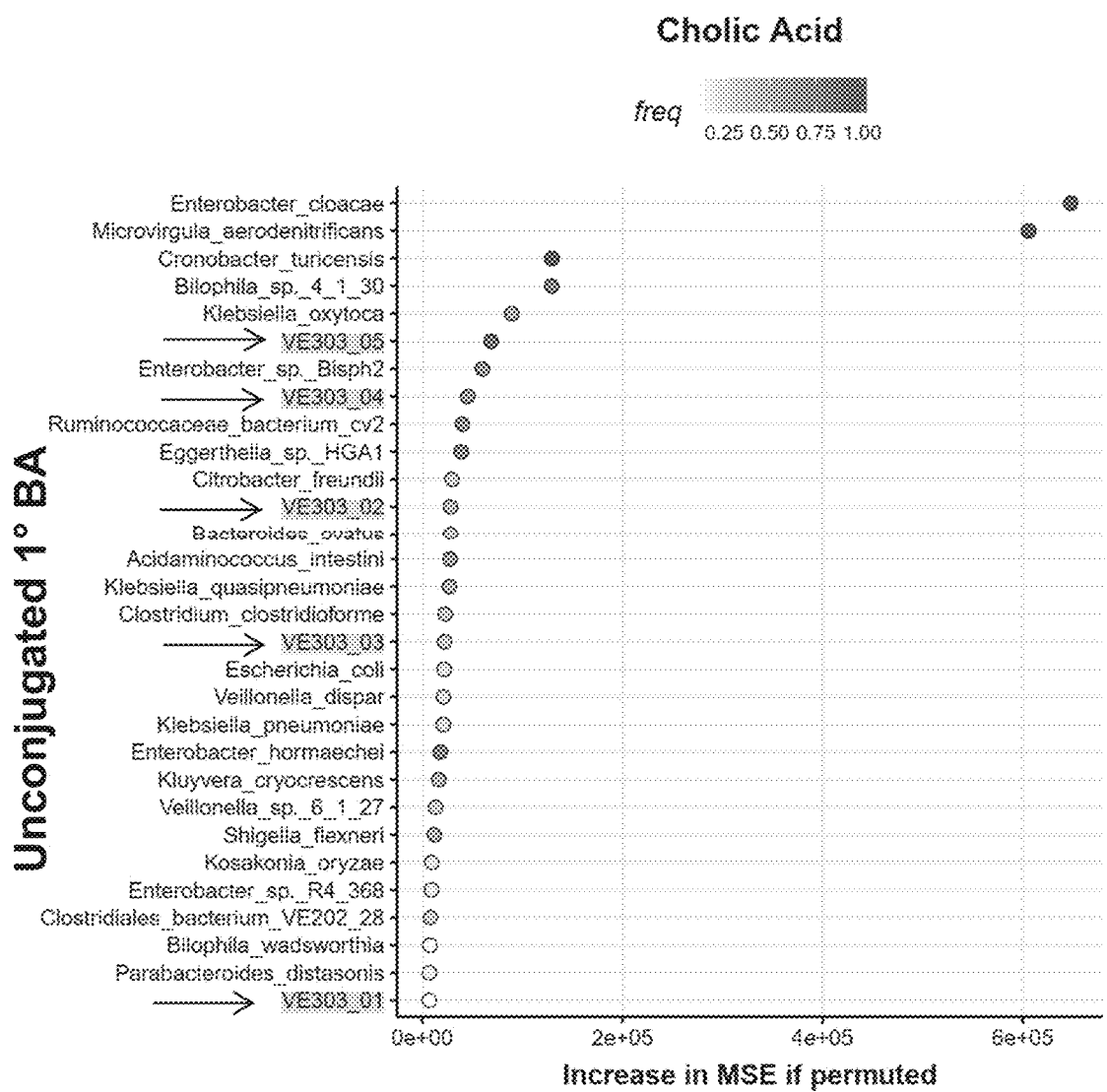
Figure 57P:
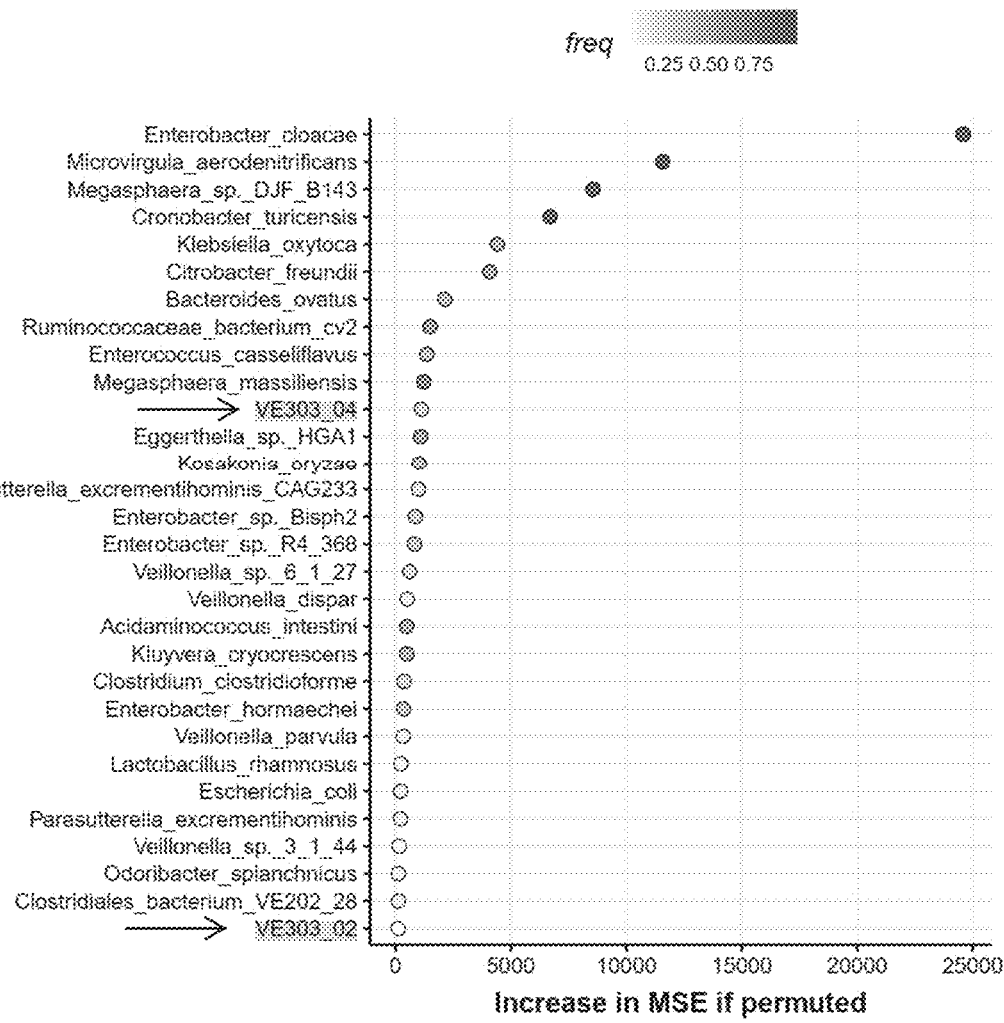
Figure 57R:
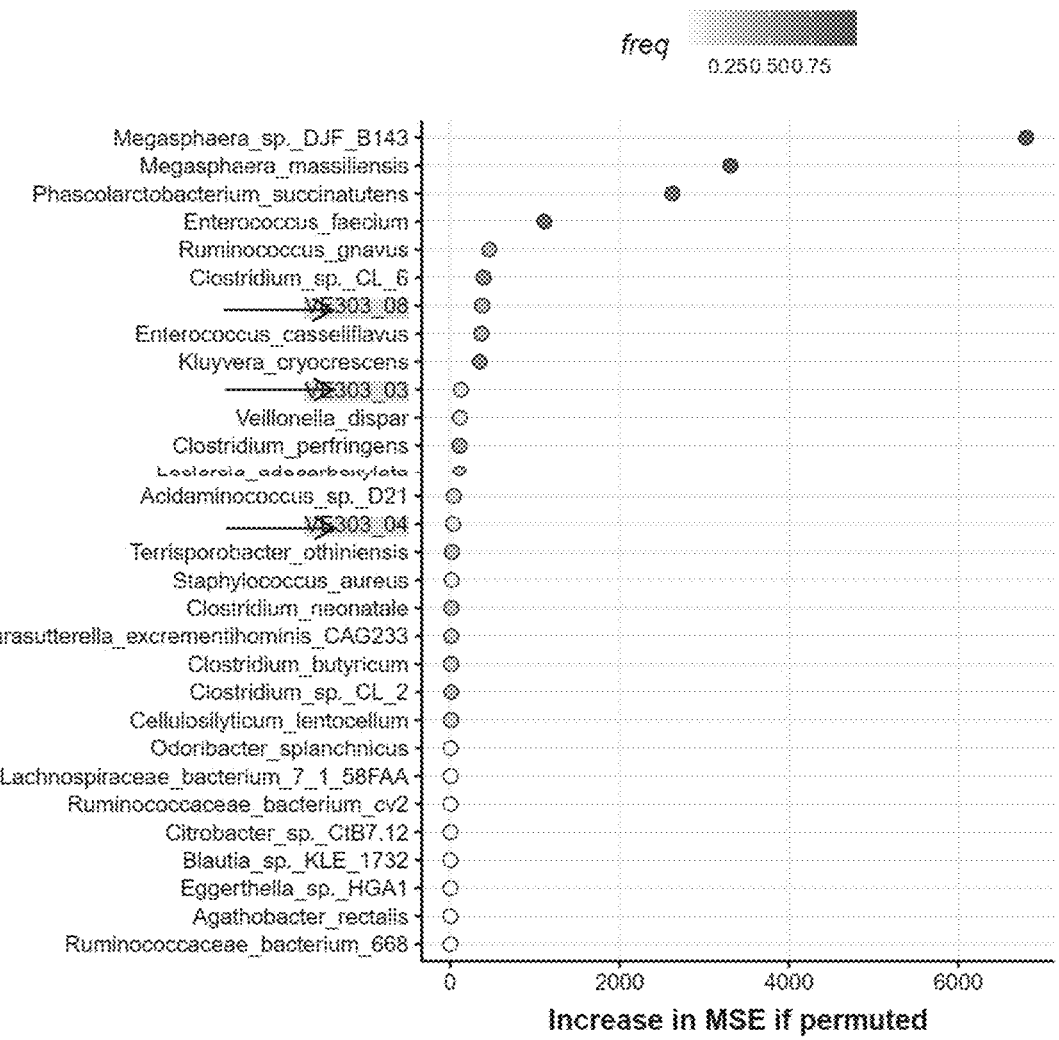
Figure 57S:
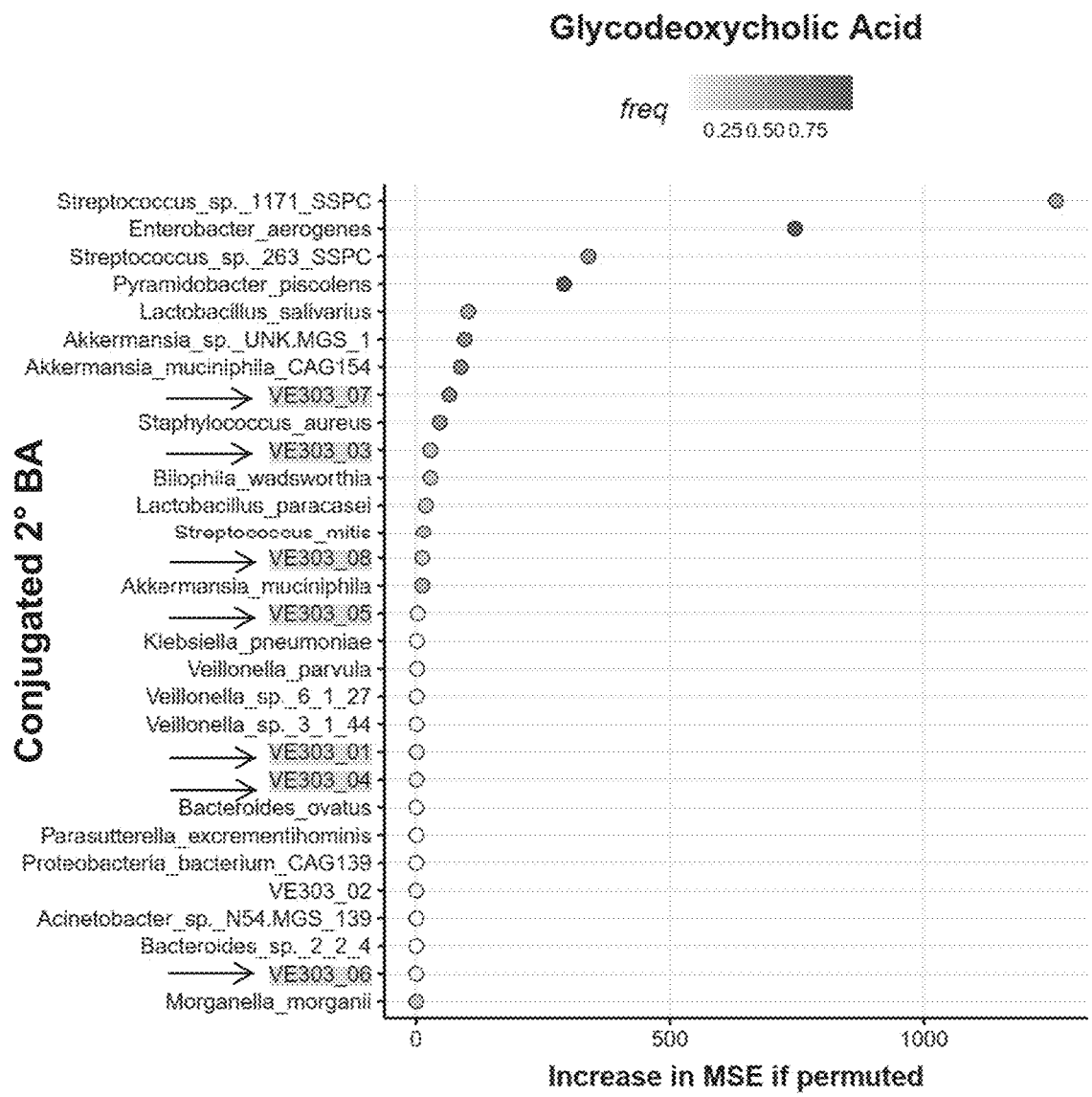
Figure 57T:
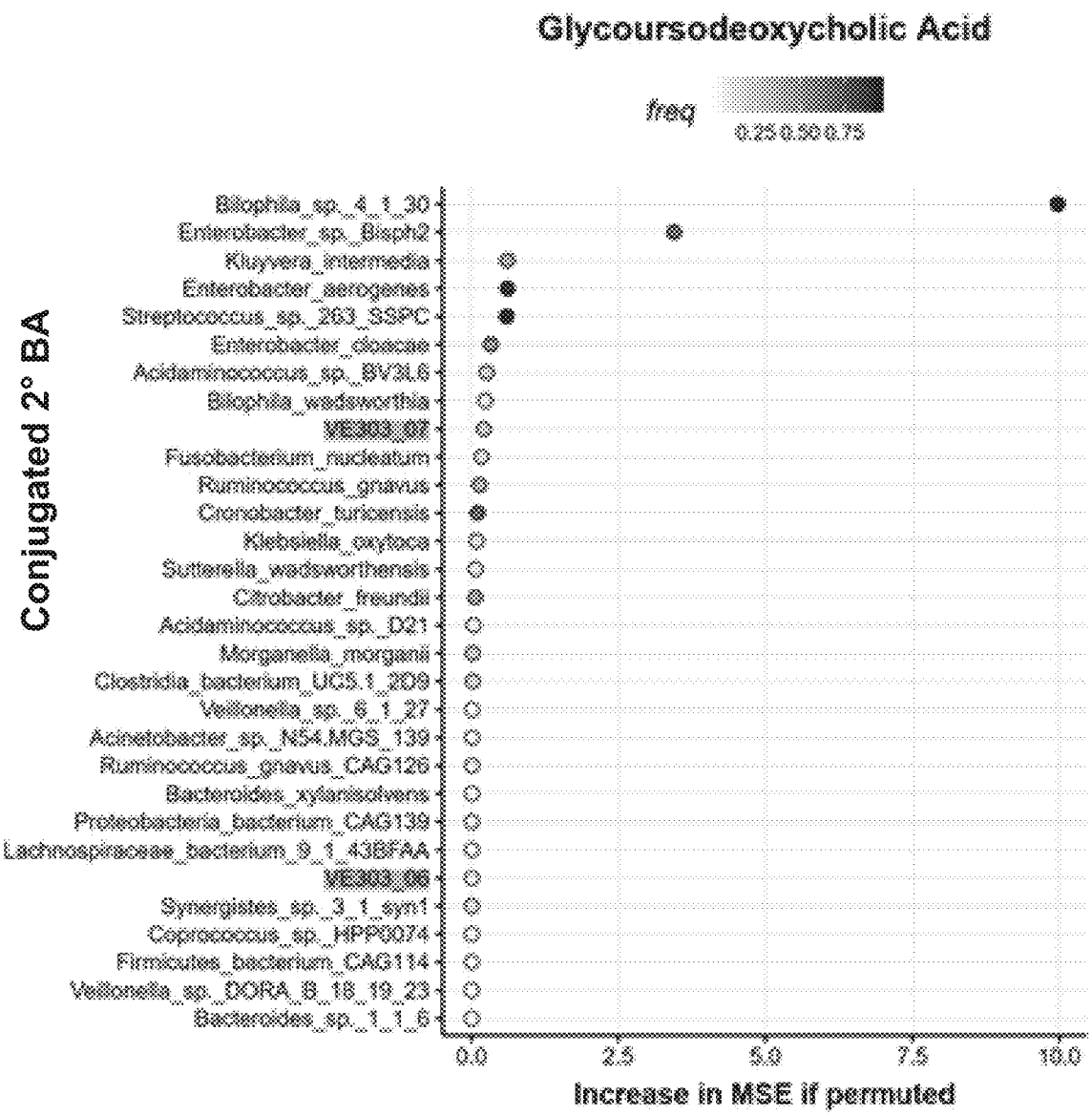
Figure 58A:
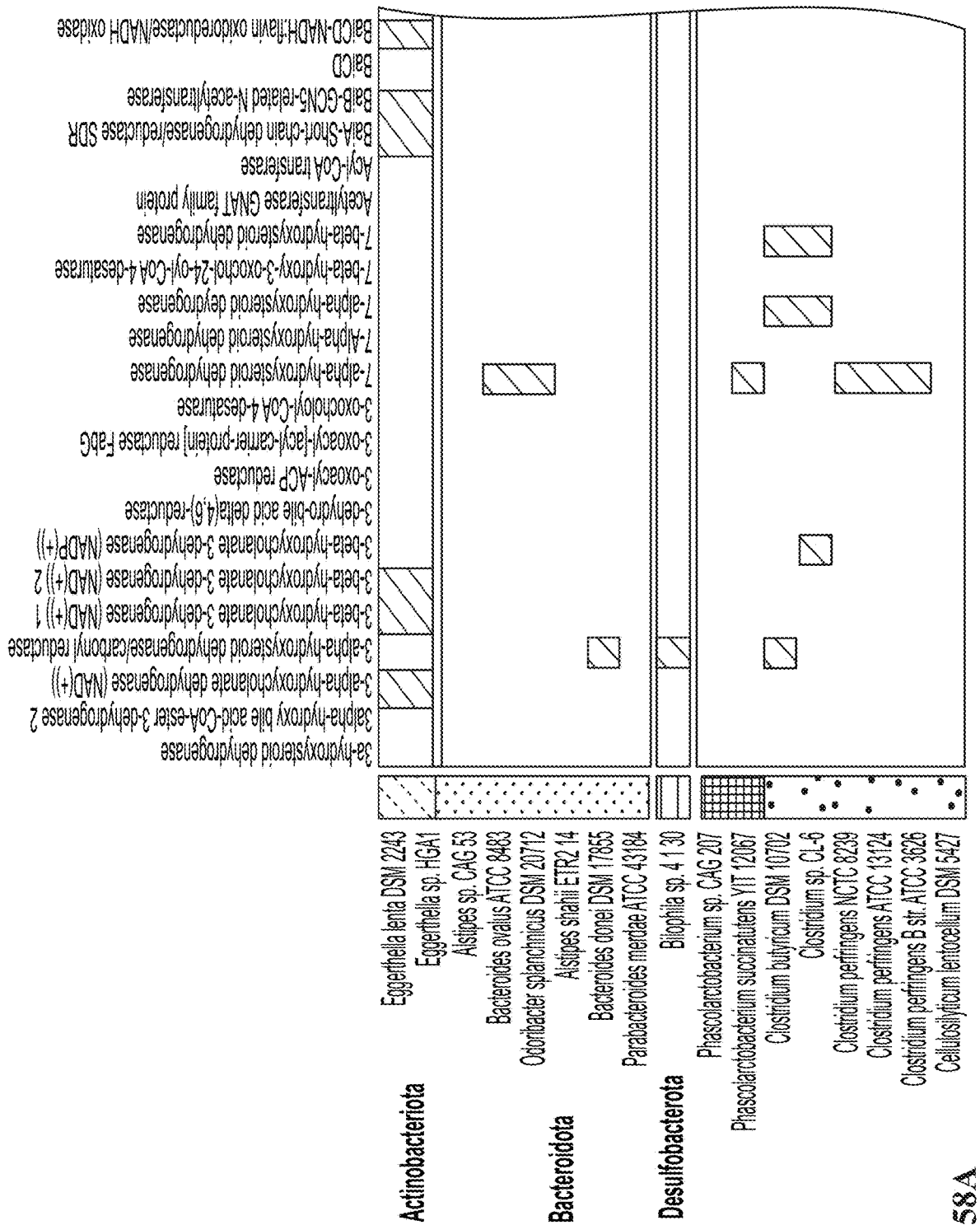
FIGS. 58A-58J are heat maps depicting the percent identity of VE303 bacterial strain open reading frames (ORFs) (or control reference genome ORFs) to known bile acid deconjugation, epimerization, and dihydroxylation genes.
Figure 58B:
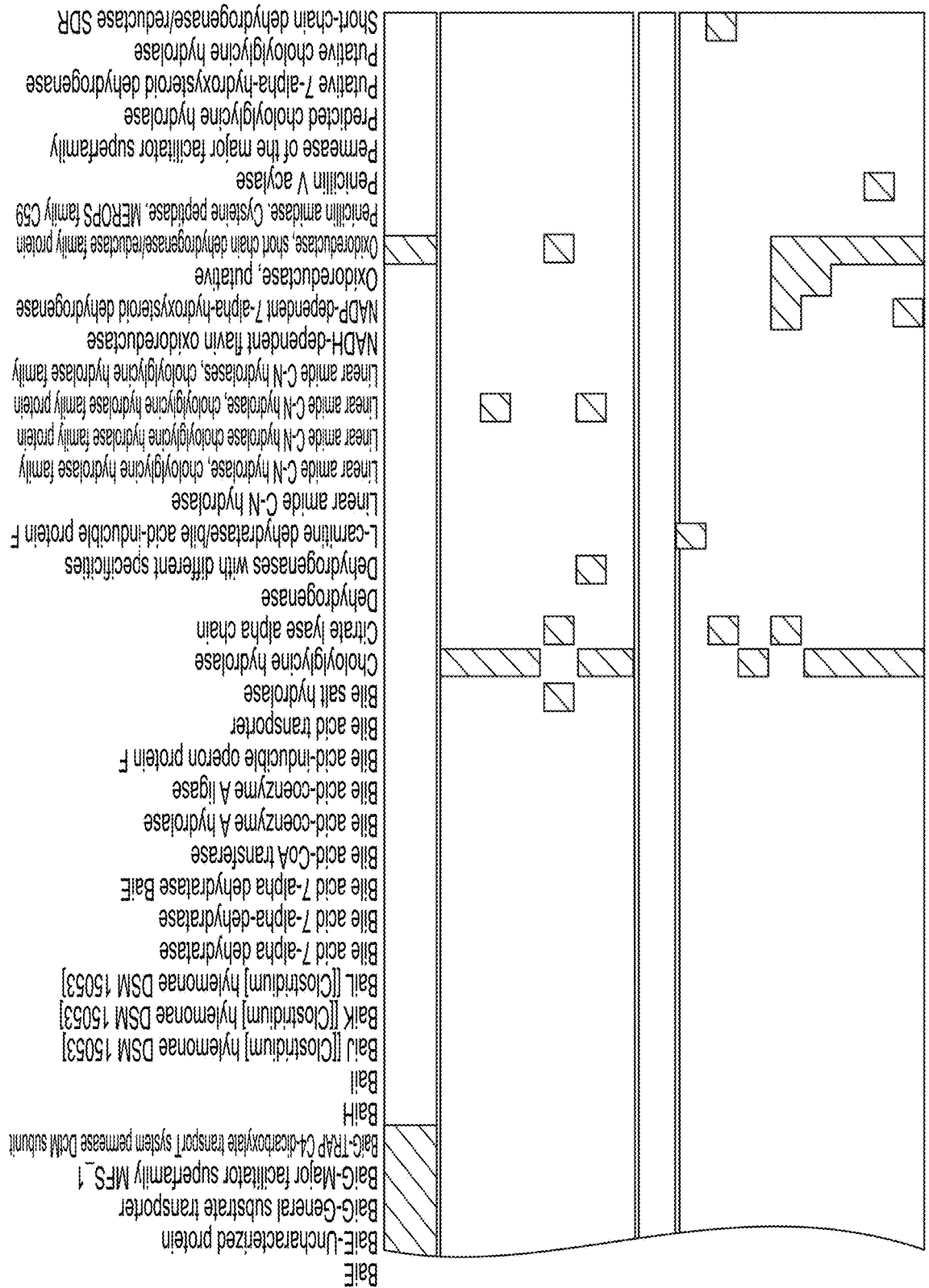
Figure 58C:
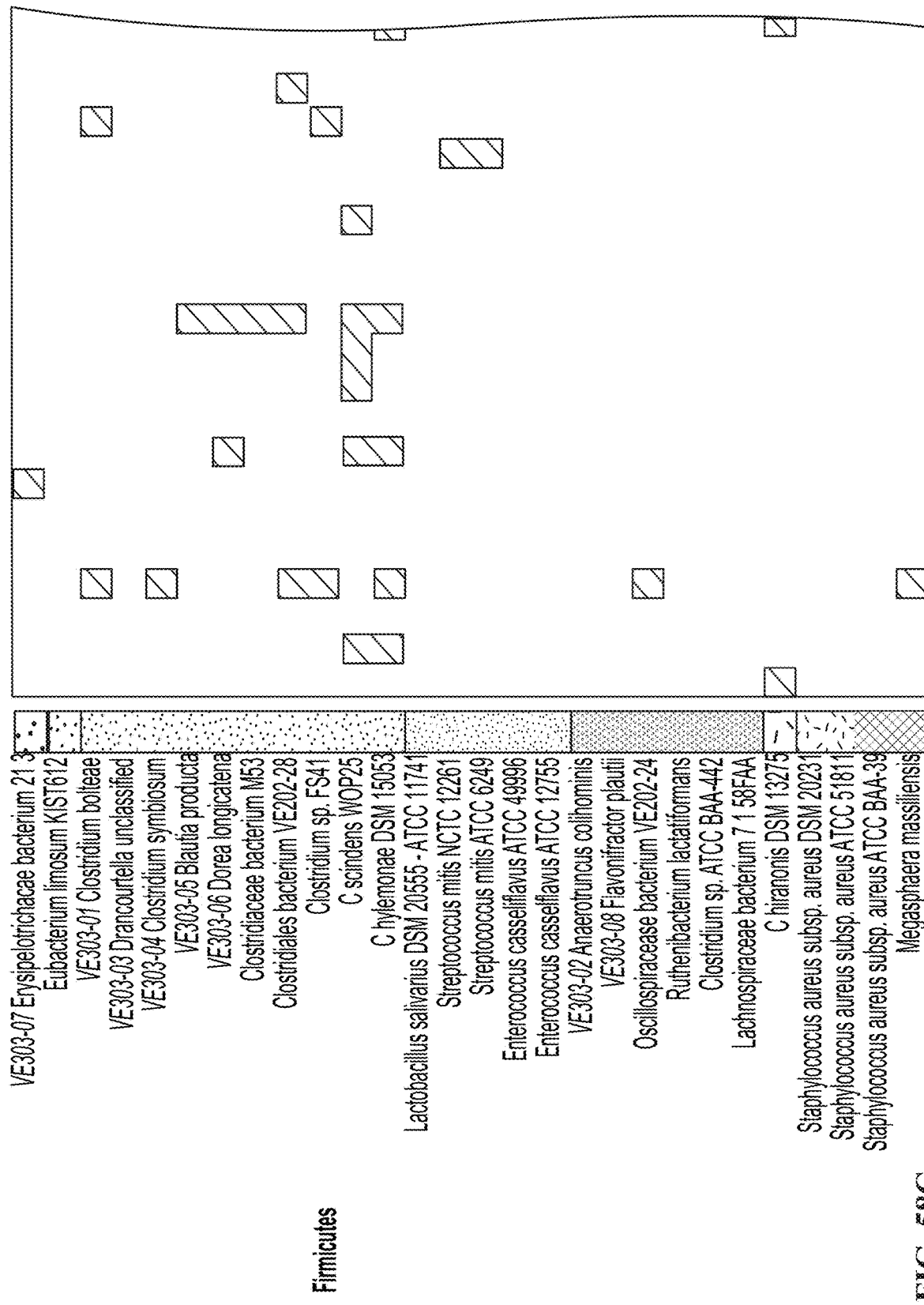
Figure 58D:
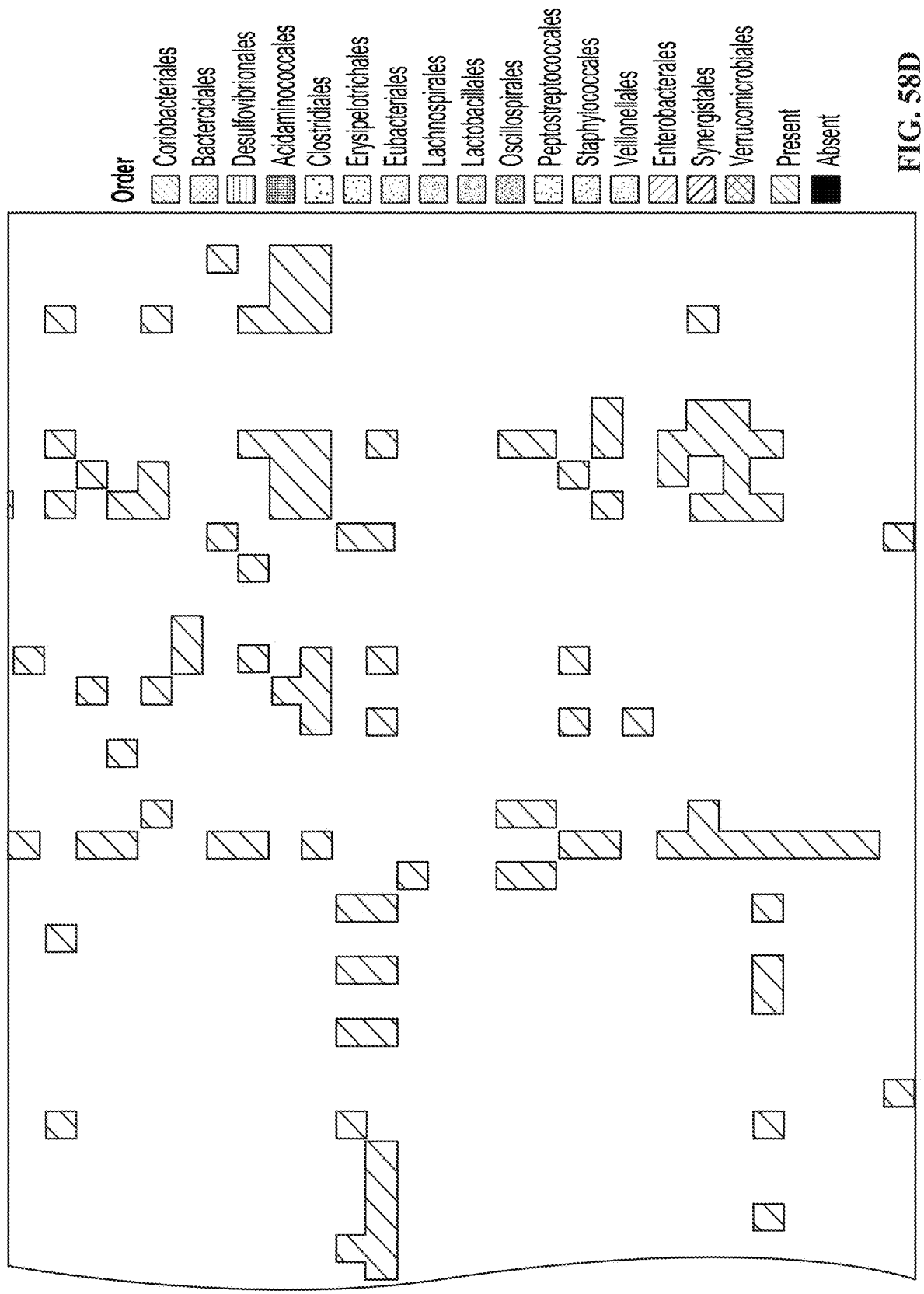
Figure 58E:
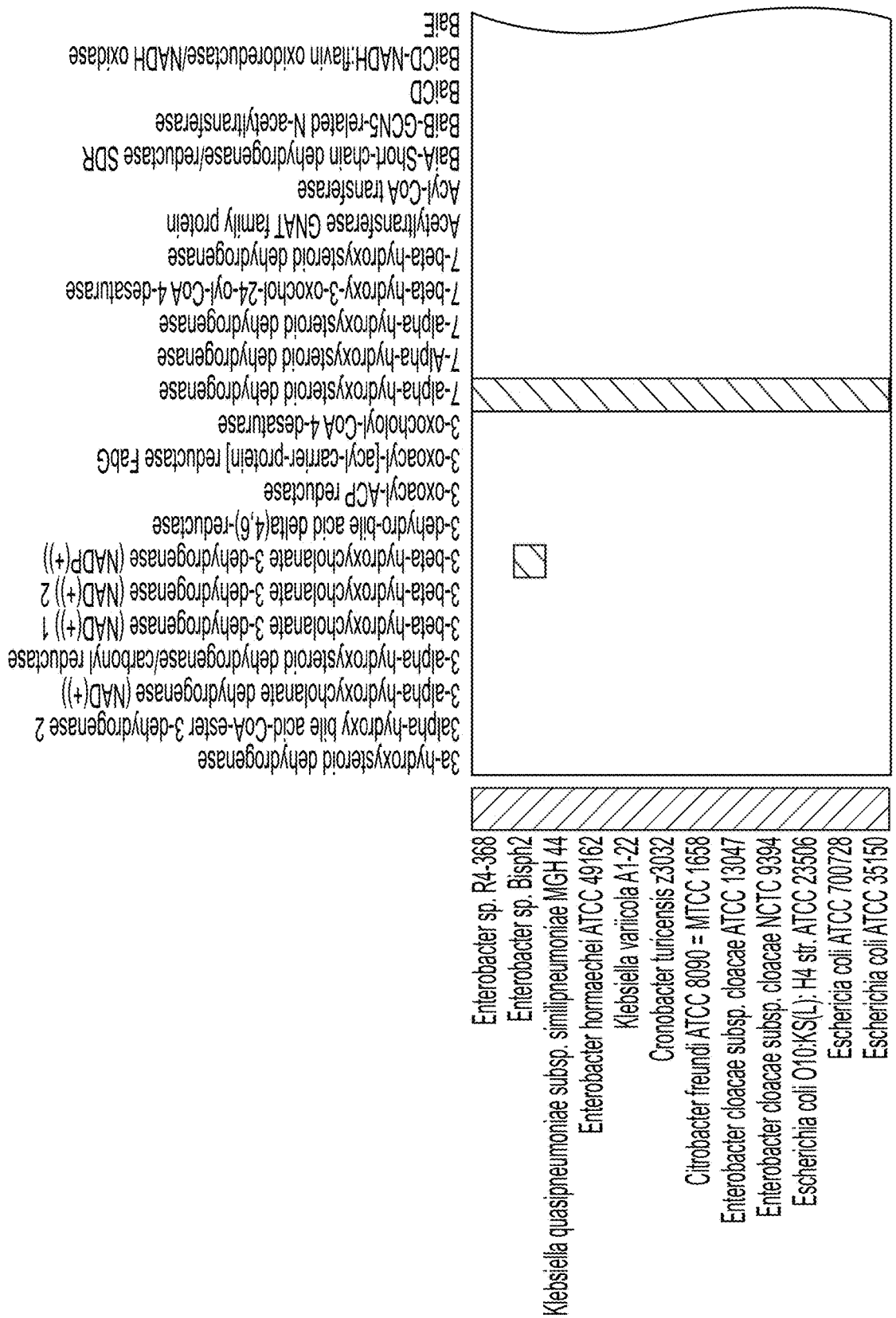
Figure 58F:
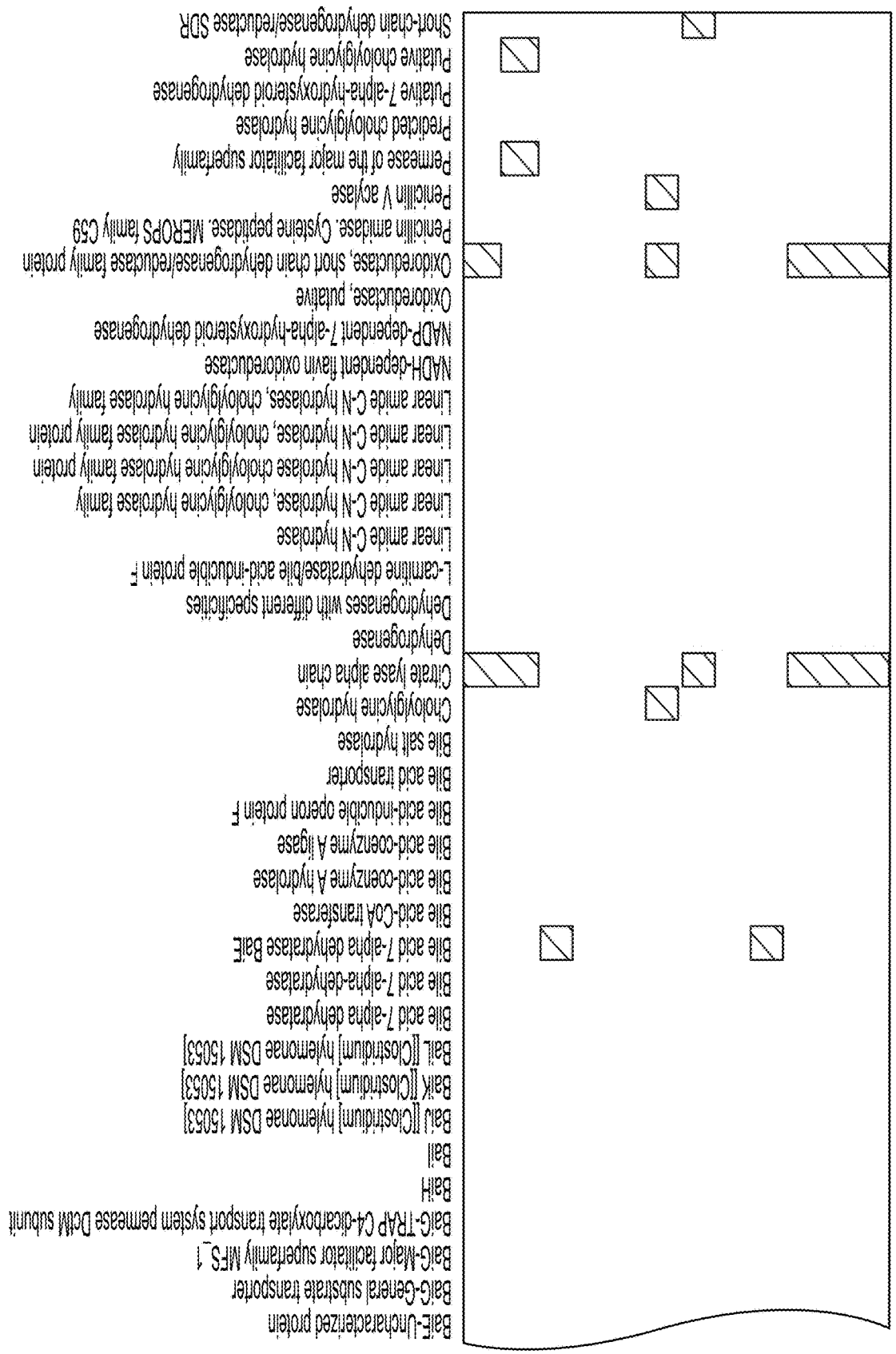
Figure 58G:
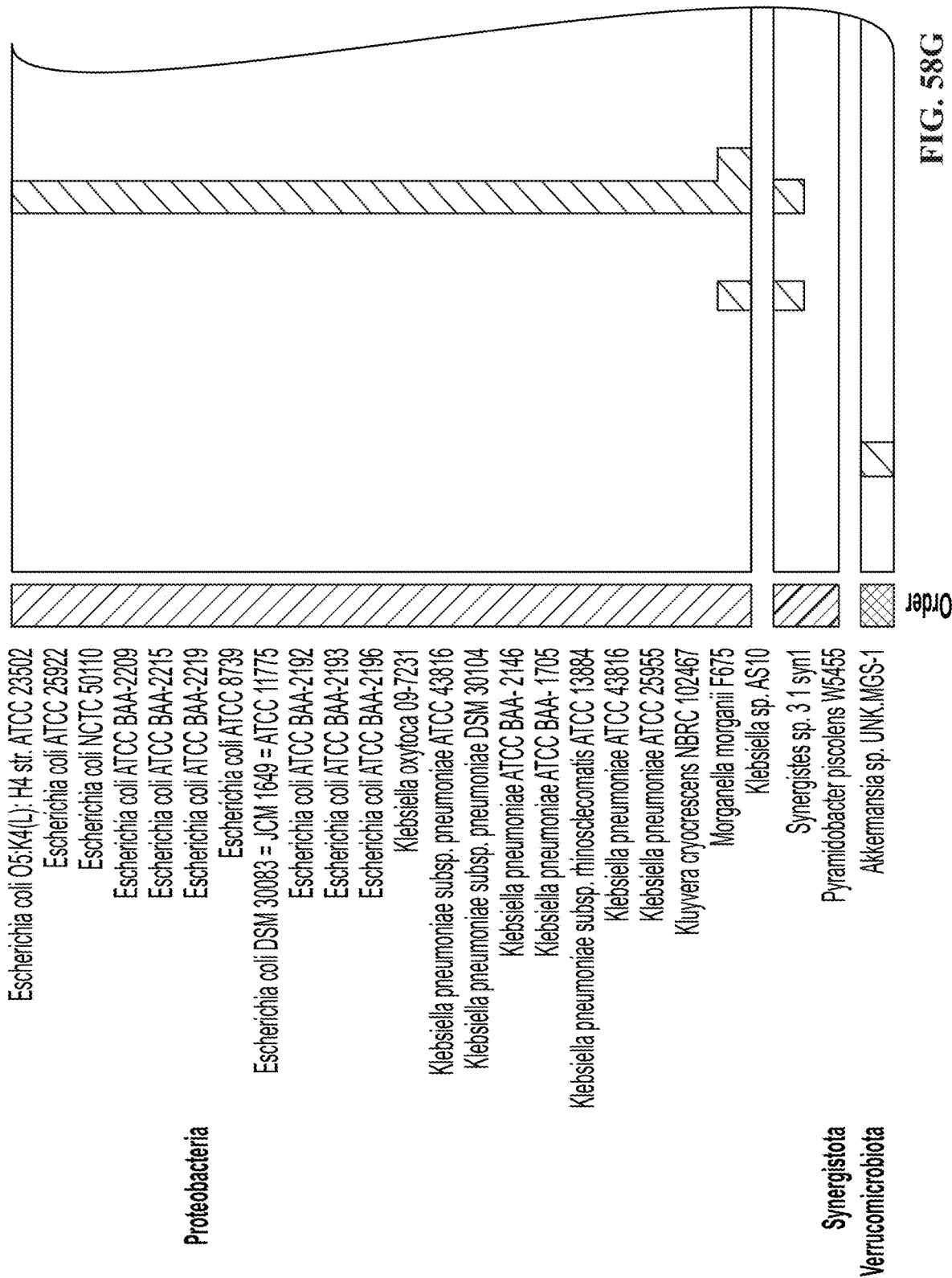
Figure 58H:
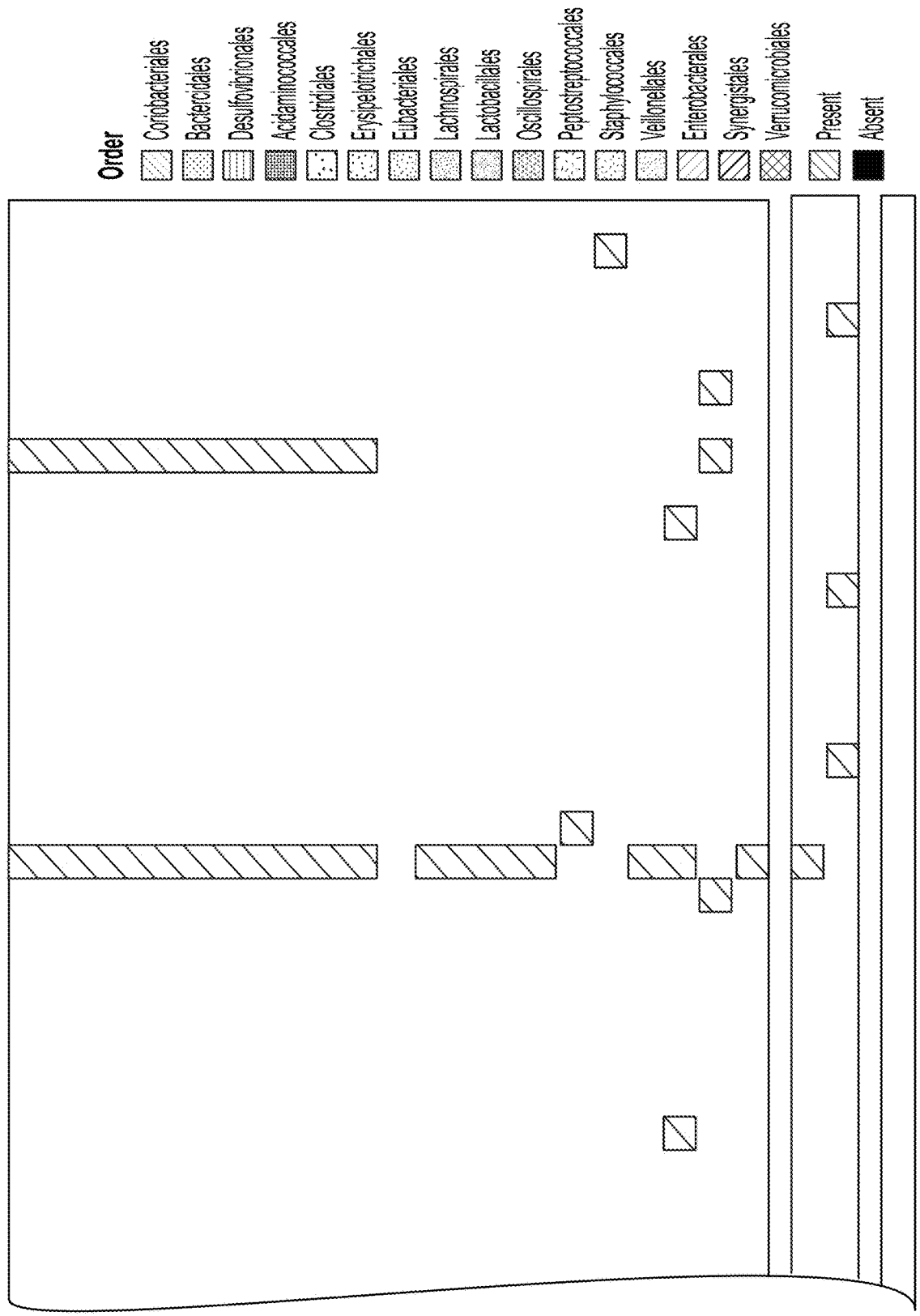
Figure 58I:
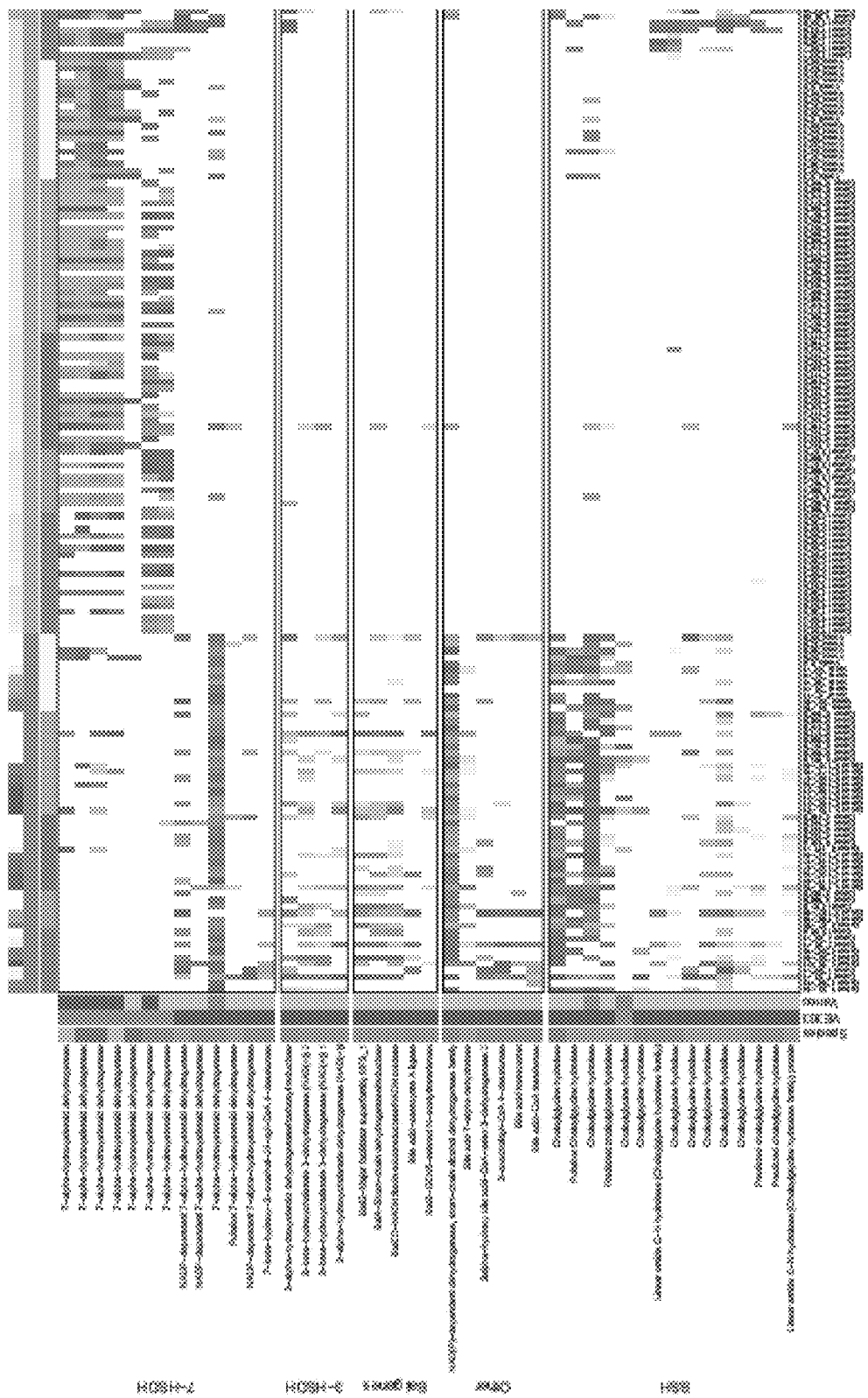
Figure 58J:
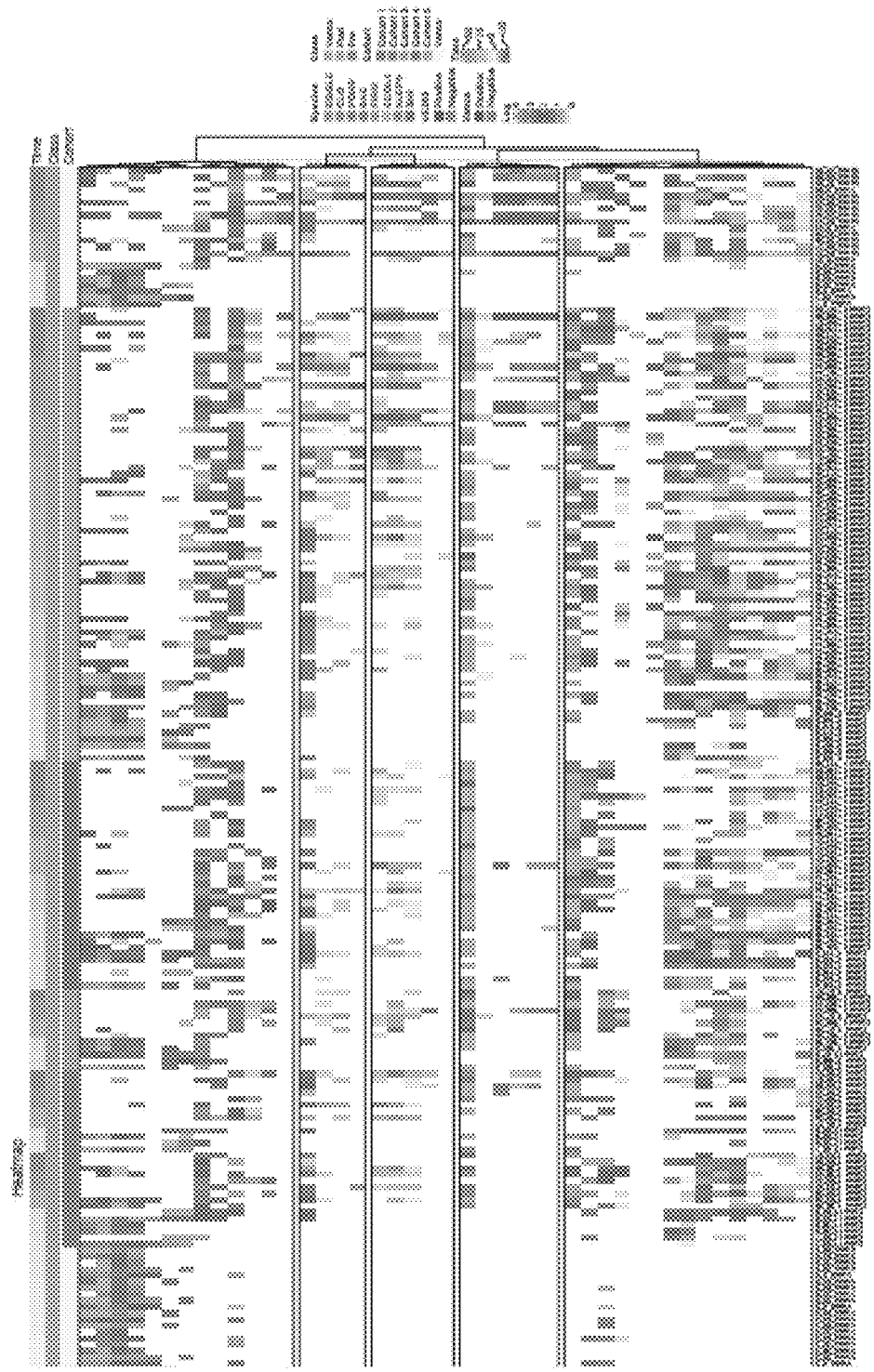
Figure 59A:
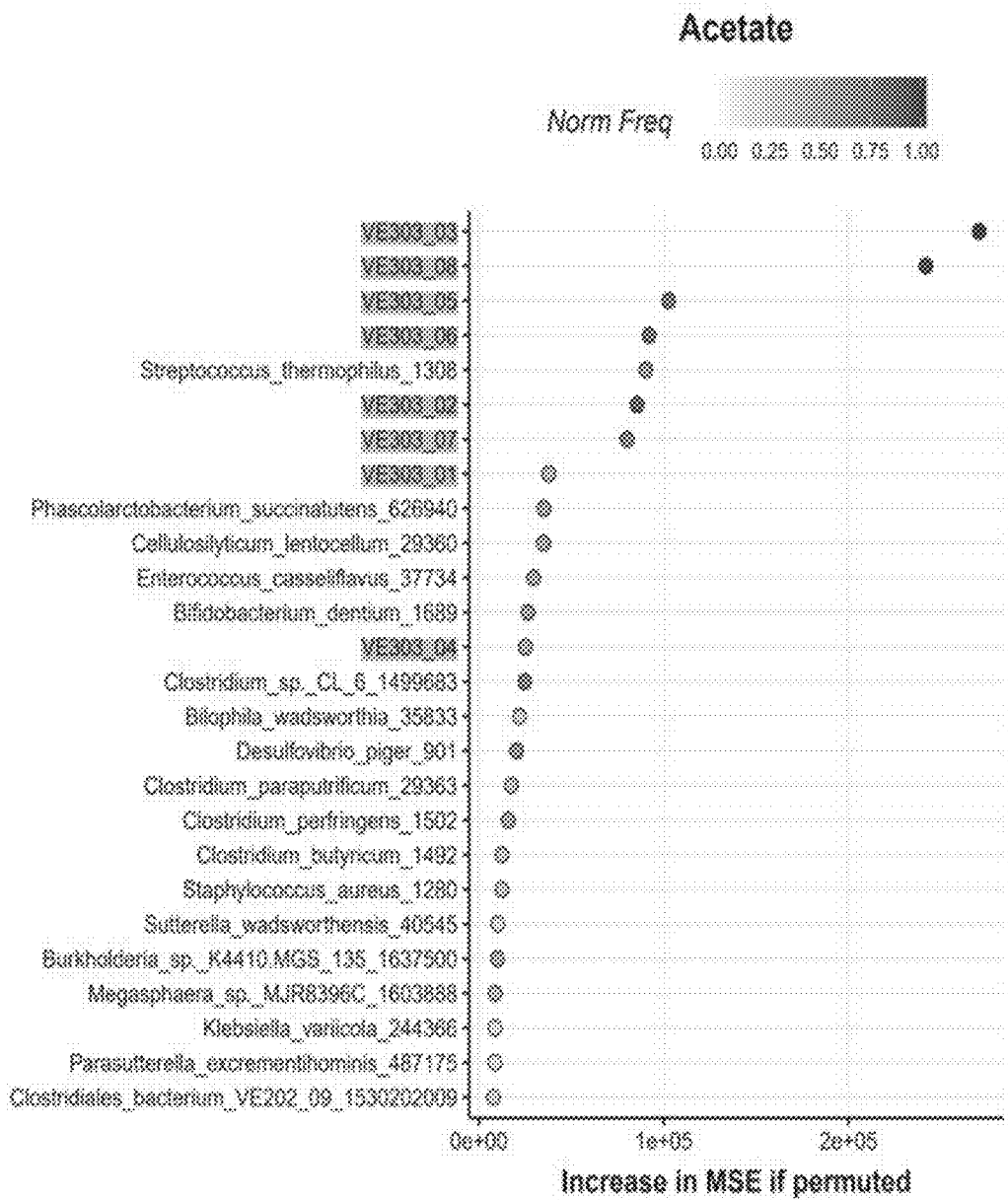
FIGS. 59A-59P show the bacterial strains associated with the recovery of short chain fatty acids (SCFAs: acetate, butyrate, propionate, hexanoate, isobutyrate, isovalerate, valerate, and 2 methylbutyrate) after treatment with antibiotics. The bacterial strains were identified based on the permutated importance analysis and ranked on increase in mean squared prediction error when permutated. Each panel display bacteria that were found significant (permutated p-value <0.05) in at least one iteration. Shading of the dots indicates the frequency of being statistically significant calculated over the total number of Random Forest iterations. Each of the VE303 strains that are deemed important are indicated with an arrow. Species identified by this analysis may be positively or negatively affecting the SCFA abundance.
Figure 59B:
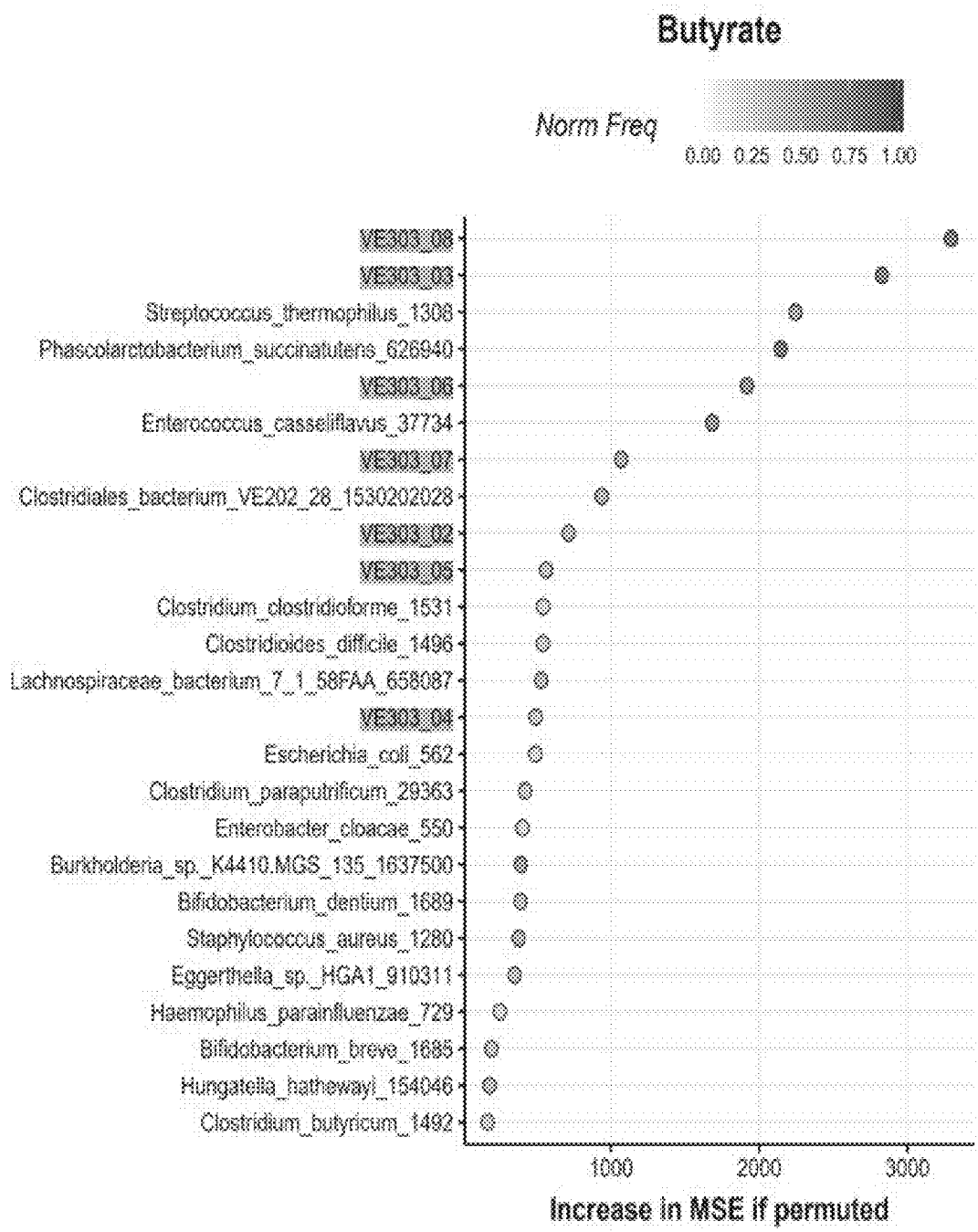
Figure 59C:
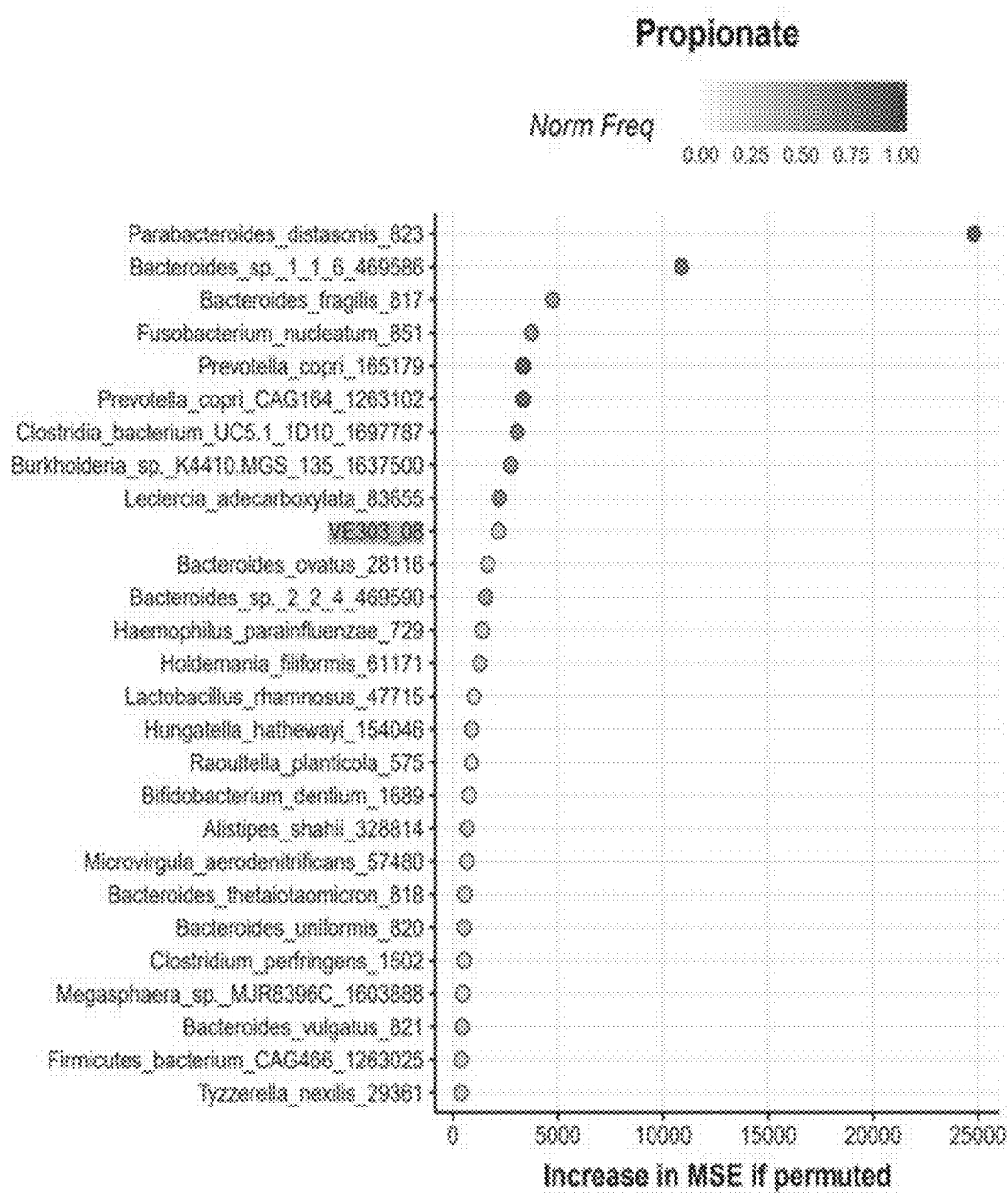
Figure 59D:
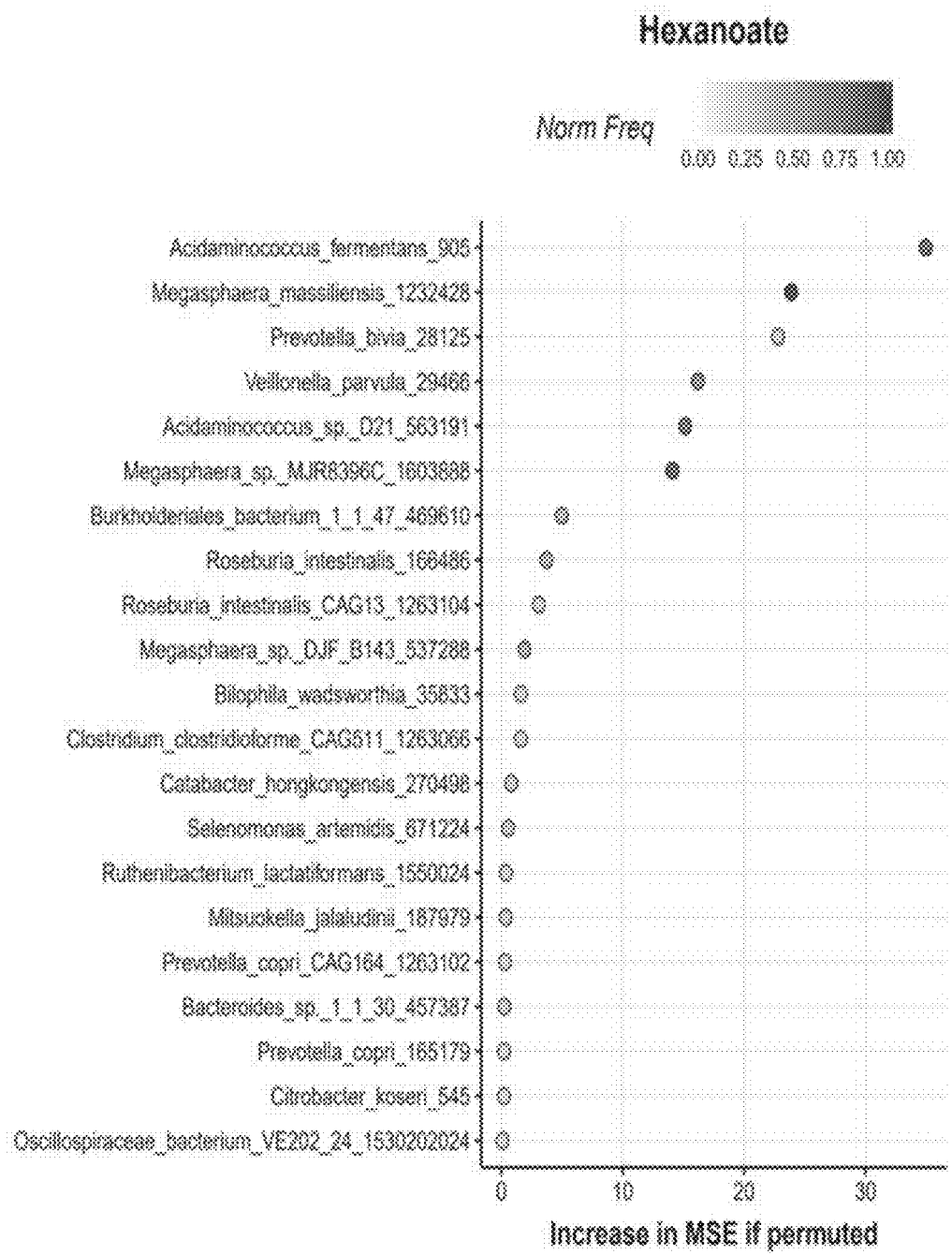
Figure 59E:
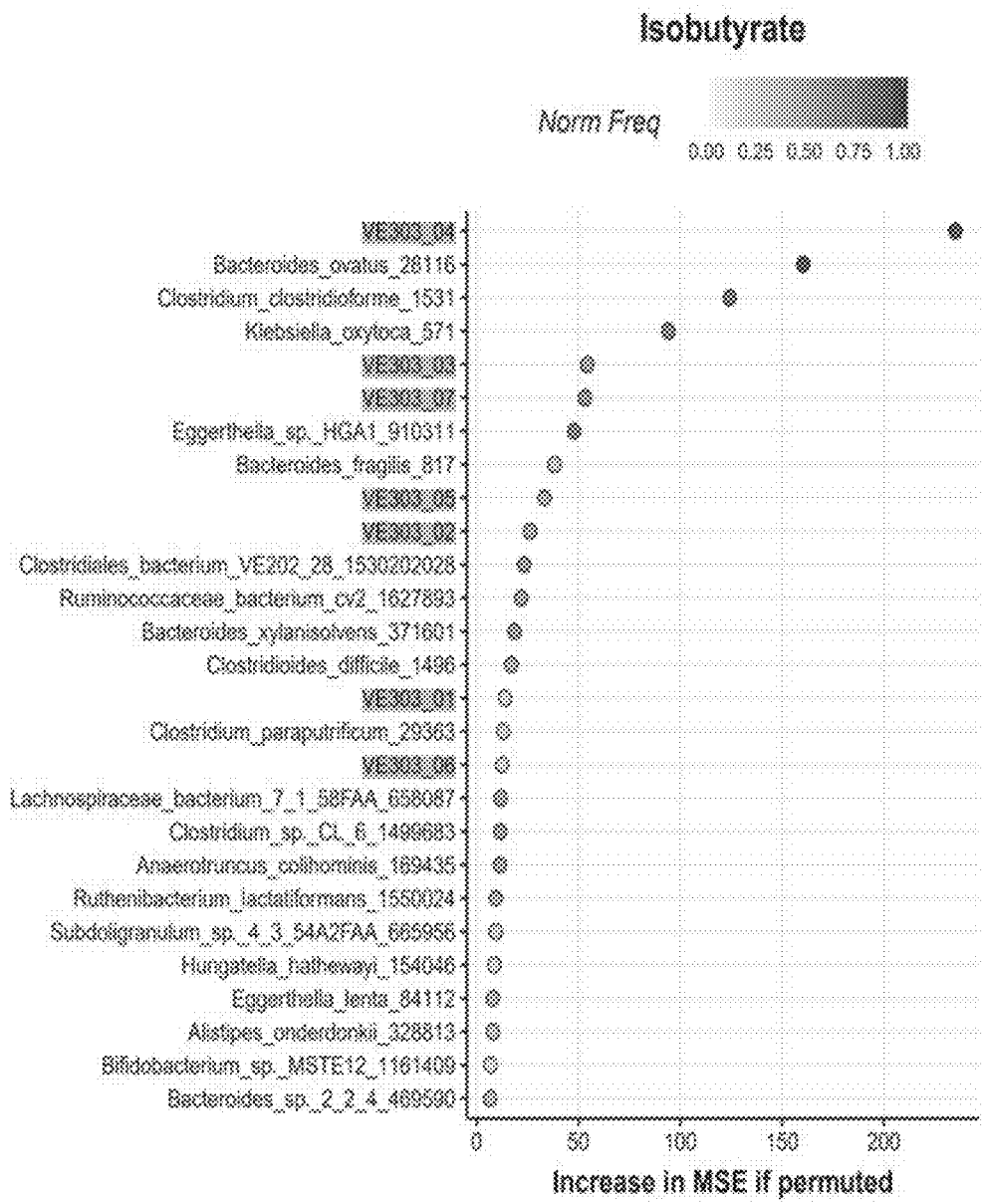
Figure 59F:
Figure 59G:
Figure 59H:
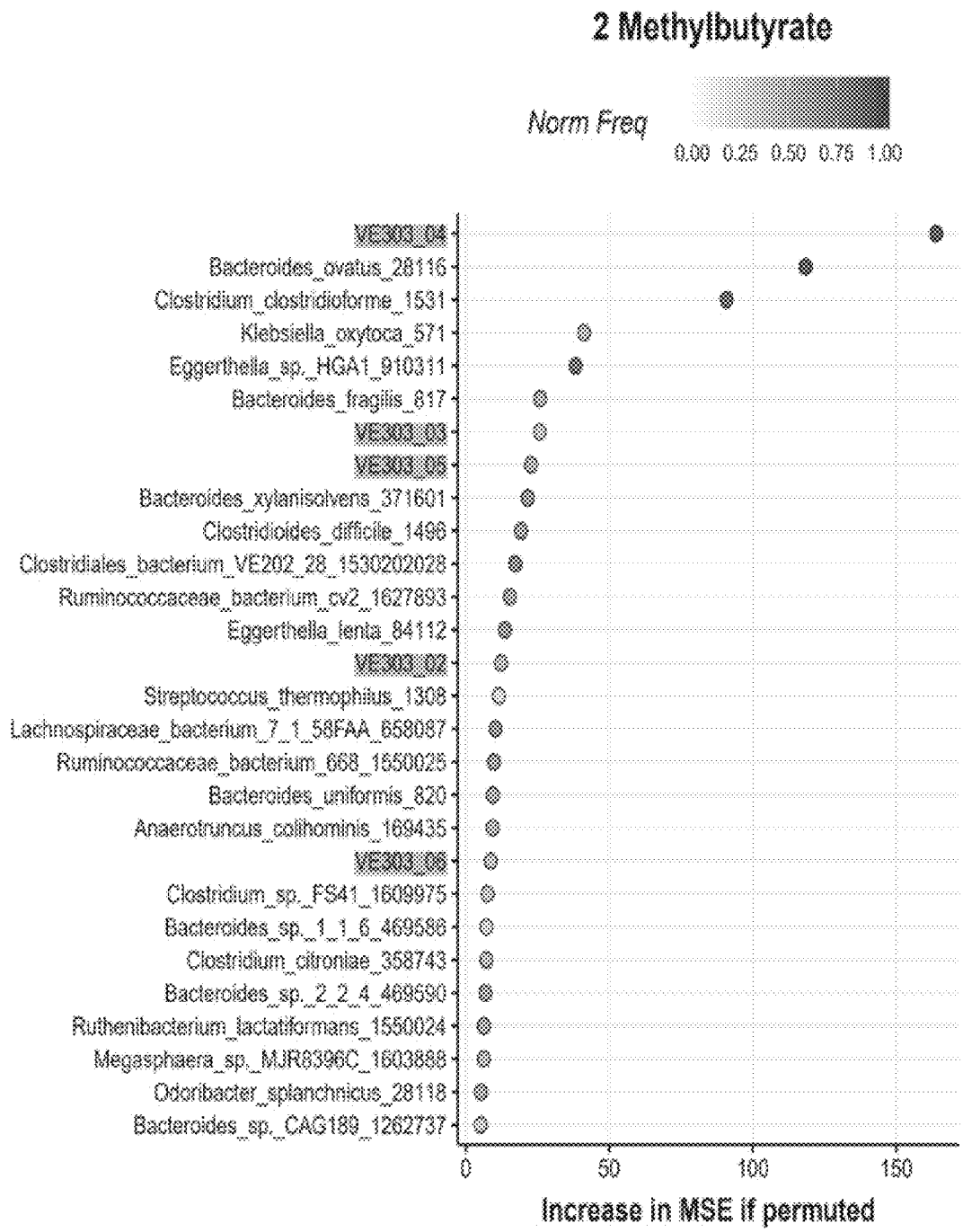
Figure 59I:
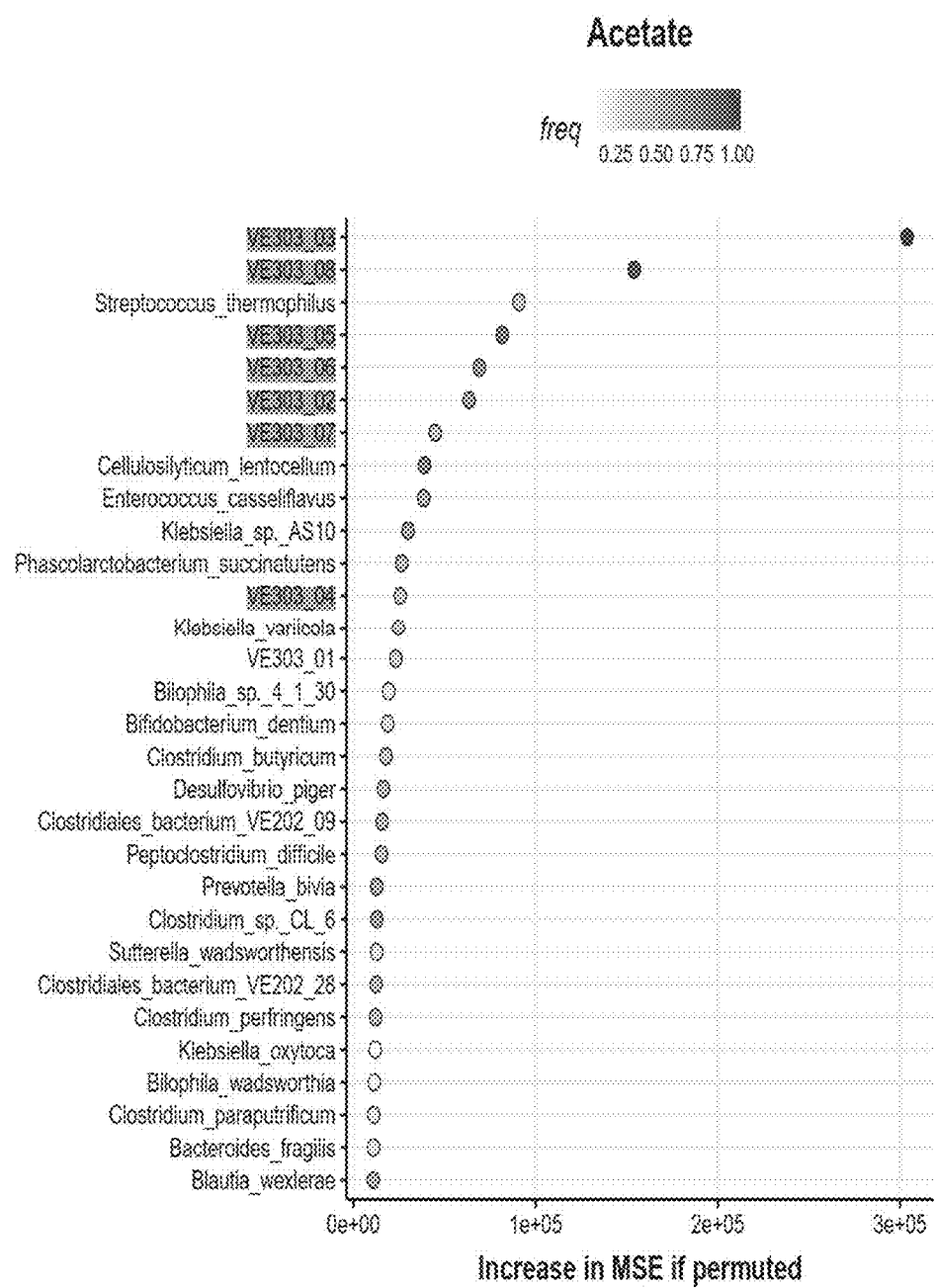
Figure 59J:
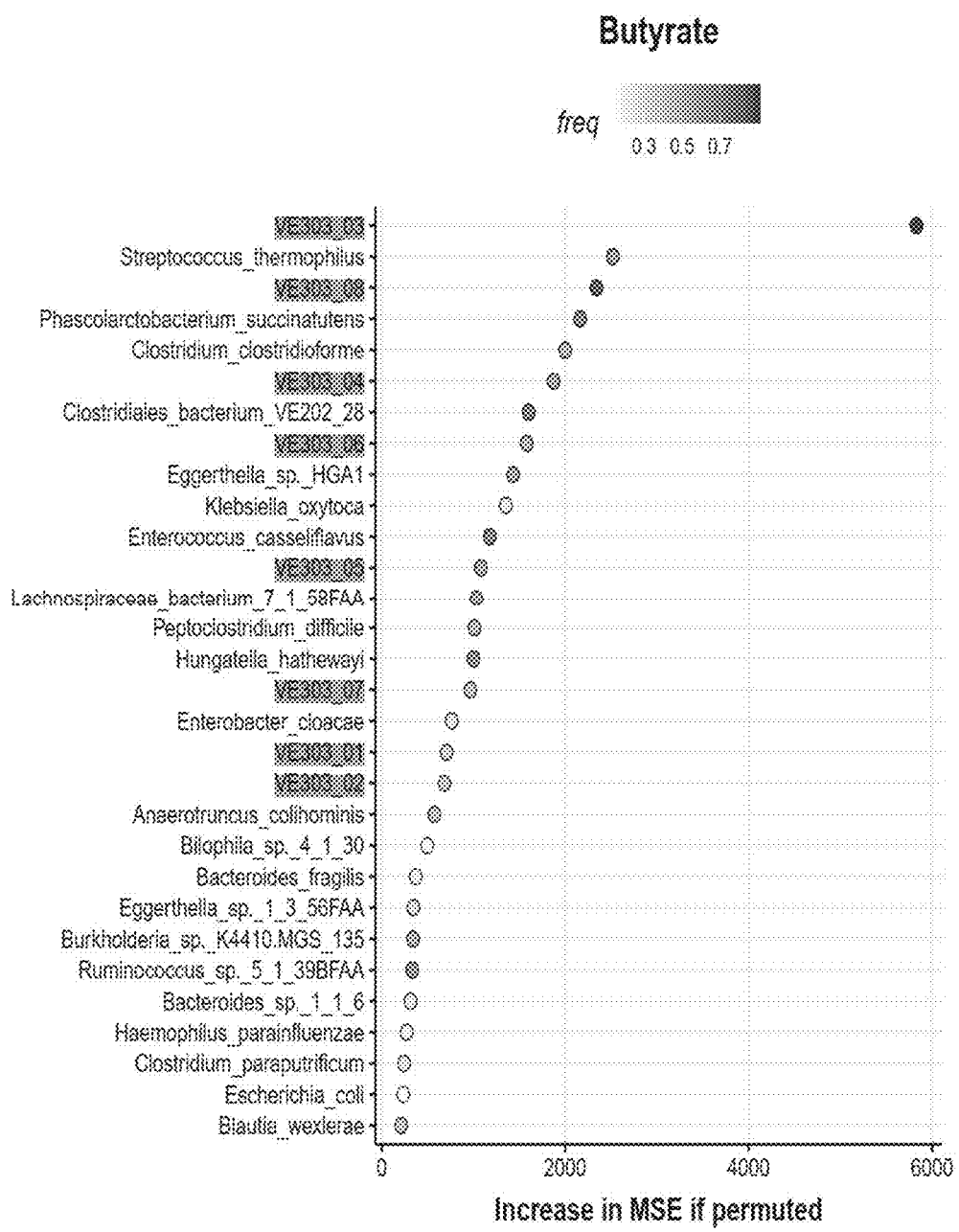
Figure 59K:
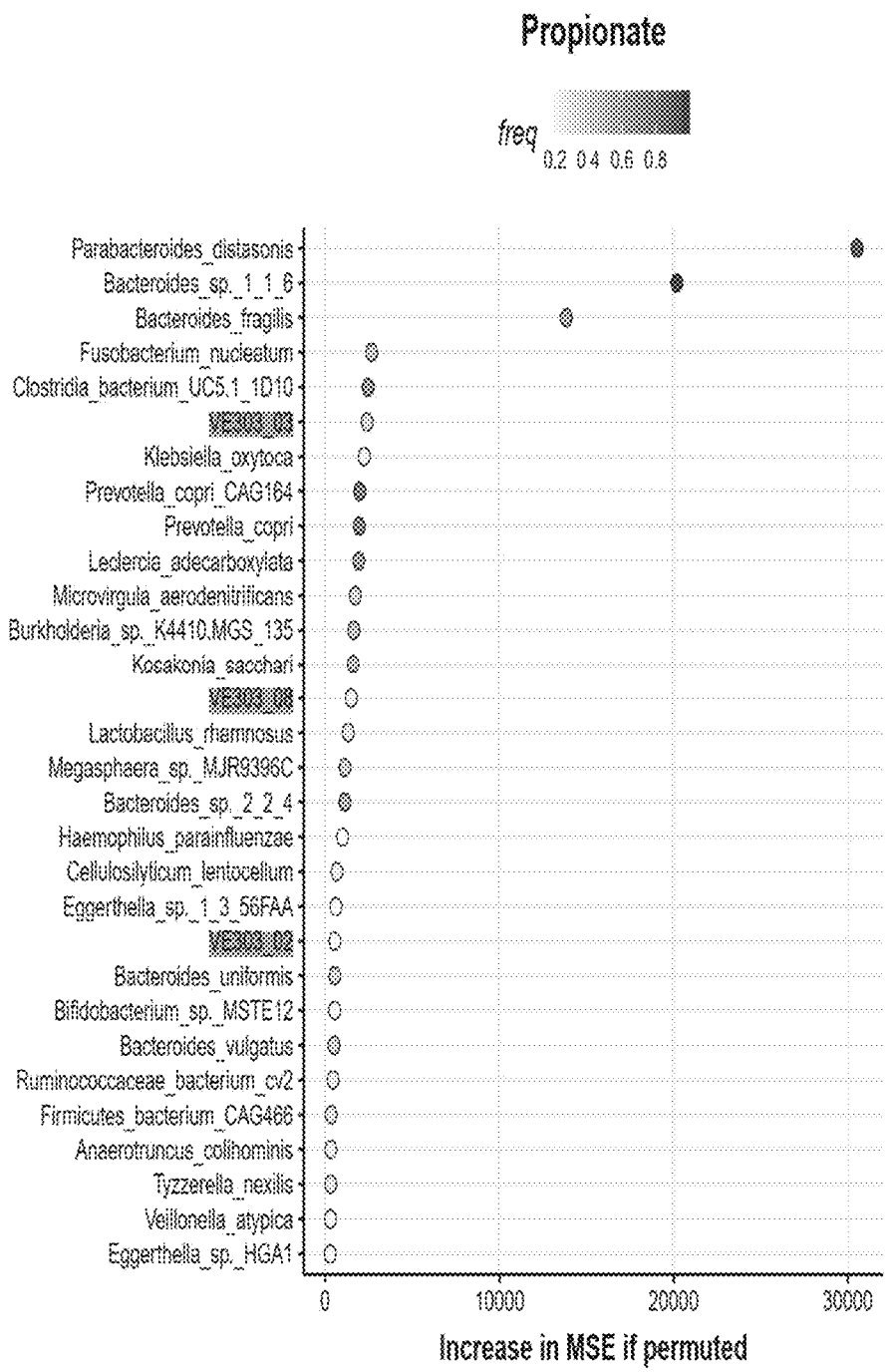
Figure 59L:
Figure 59M:
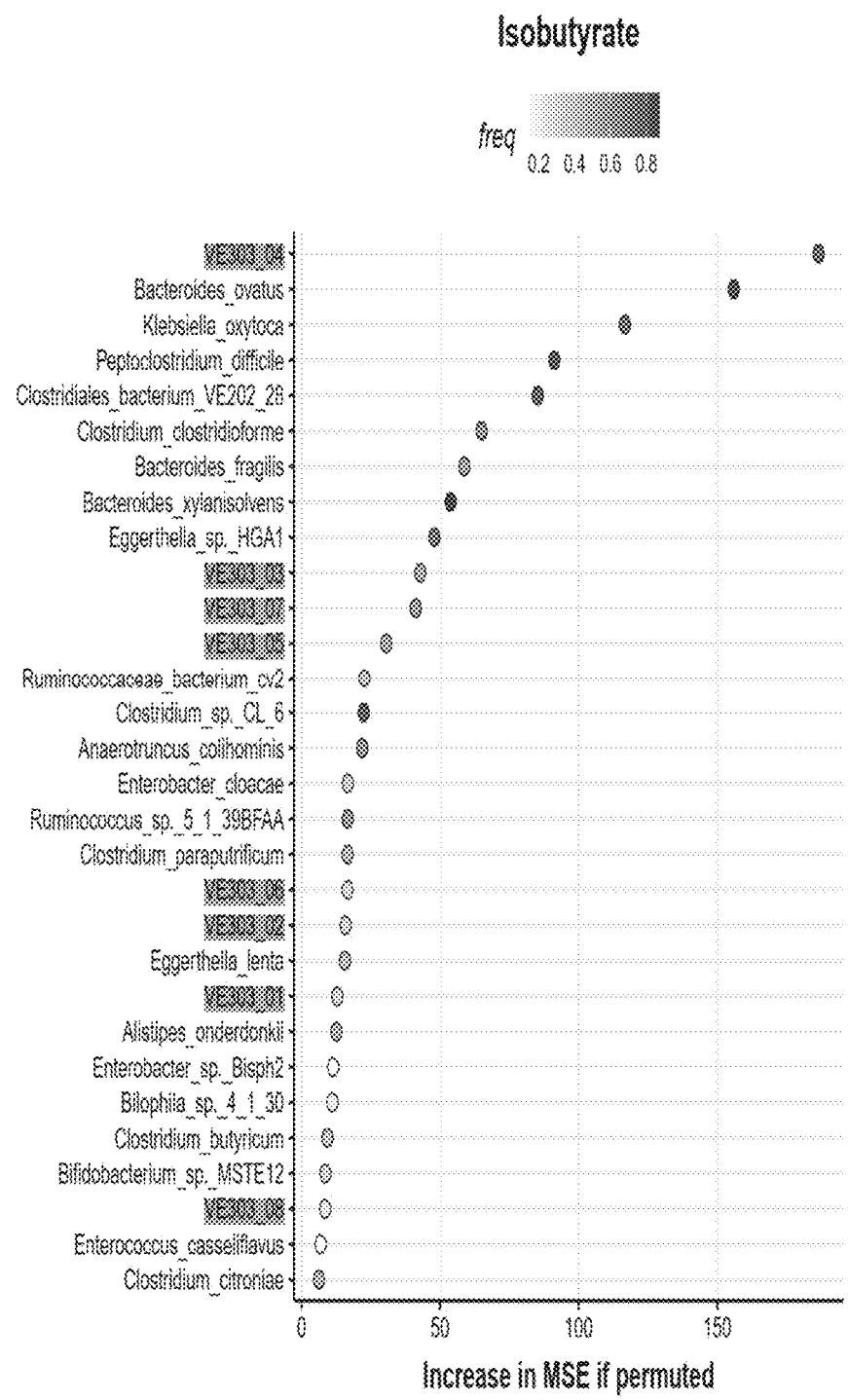
Figure 59N:
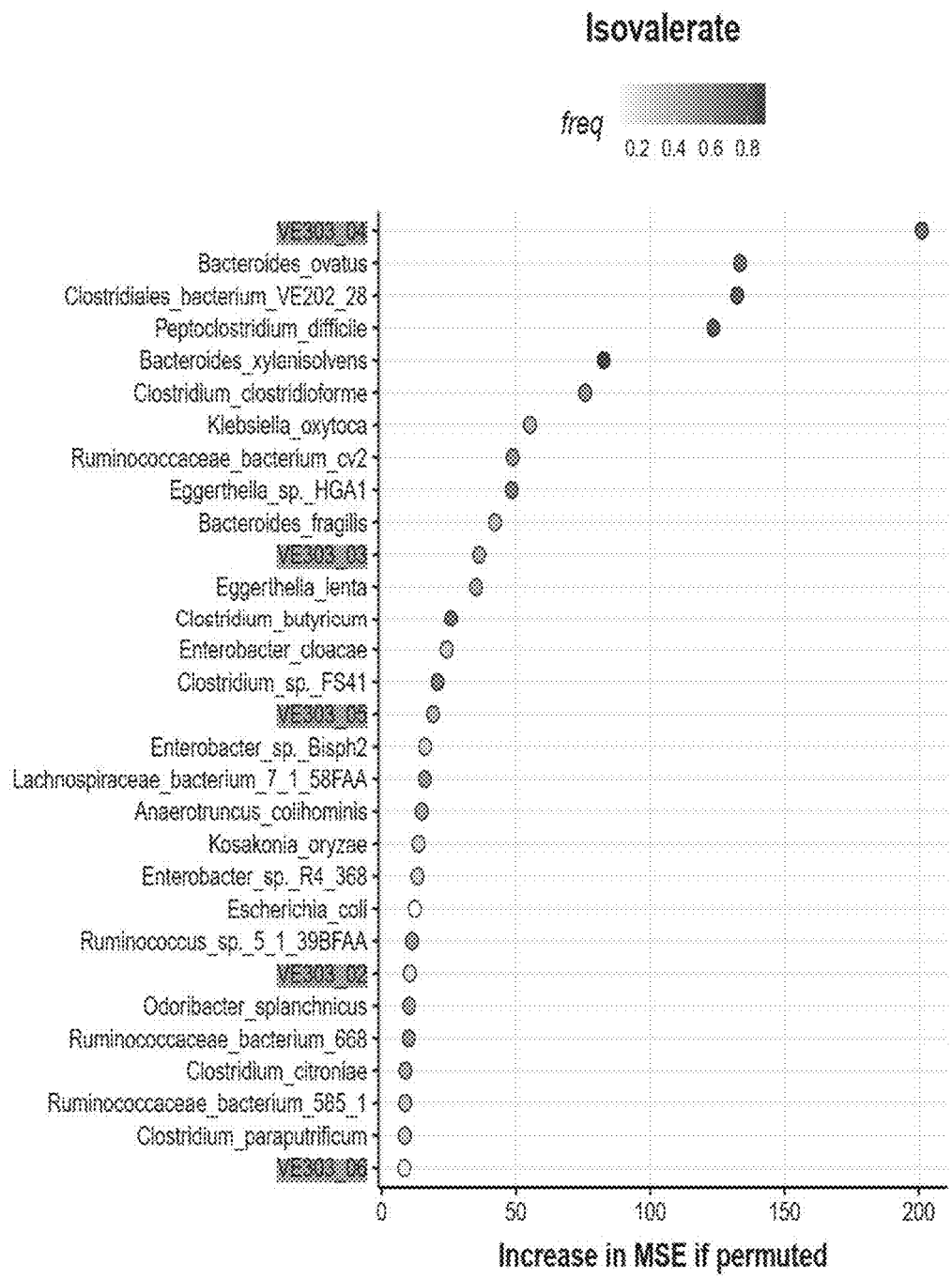
Figure 59O:
Figure 59P:
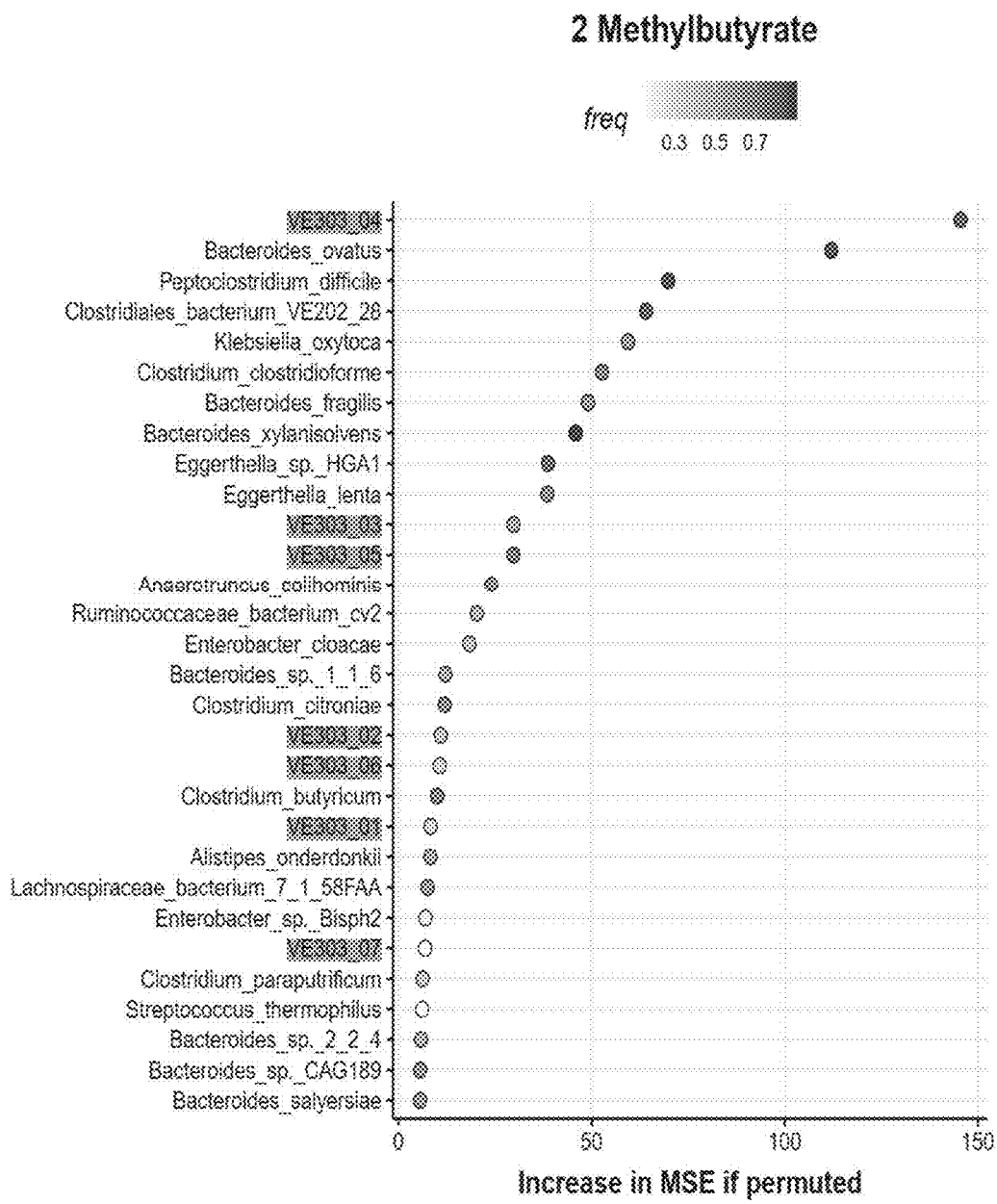

To decouple the effect of VE303 from that of the recovering microbiota on the SCFAs post-antibiotic dynamics, Random Forest Regression (RFR) was again performed. As expected, RFR identified several of the VE303 strains to be within the top 20 most important species associated with SCFAs level dynamics, with different VE303 strains predicted to be associated with increases in the levels of acetate, butyrate, propionate, isobutyrate, methylbutyrate, and isovalerate (FIG. 48C, FIG. 56). Taken together these data suggest not only that VE303 affects the recovery of SCFAs after antibiotic perturbation but it is the major driver of the observed recovery.

VE303 was developed to prevent the recurrence of CDIs and demonstrated safe, robust, and durable colonization of its strains. Without being limited to any particular theory, a predicted mechanism by which VE303 achieves therapeutic effects is illustrated in FIG. 61. The optimal dosing region, including the highest safe dose, of VE303 was also determined. It was further established that antibiotic-mediated perturbation of the host microbiome is necessary for colonization by VE303.

Additionally, pharmacokinetic (PK) and pharmacodynamic (PD) methods were developed to monitor the colonization and durability of LBP strains, as well as changes in the host microbial community. These first-in-class methods may be utilized to monitor future LBPs (FIG. 60). Further, methods have been developed to allow for the monitoring the recovery of the microbial community and metabolite pools, including short chain fatty acids and bile acids, following administration of antibiotics (e.g., vancomycin).

REFERENCES

1. Minot, S. S., Krumm, N. & Greenfield, N. B. One Codex: A Sensitive and Accurate Data Platform for Genomic Microbial Identification. *BioRxiv* (2015). doi:10.1101/027607
2. Smillie, C. S. et al. Strain tracking reveals the determinants of bacterial engraftment in the human gut following fecal microbiota transplantation. *Cell Host Microbe* 23, 229-240.e5 (2018).
3. Berlin, K. et al. Assembling large genomes with single-molecule sequencing and locality-sensitive hashing. *Nat. Biotechnol.* 33, 623-630 (2015).
4. Cock, P. J. A. et al. Biopython: freely available Python tools for computational molecular biology and bioinformatics. *Bioinformatics* 25, 1422-1423 (2009).
5. Lessa, F. C. et al. Burden of *Clostridium difficile* infection in the United States. *N. Engl. J. Med.* 372, 825-834 (2015).
6. Leffler, D. A. & Lamont, J. T. *Clostridium difficile* infection. *N. Engl. J. Med.* 372, 1539-1548 (2015).
7. Cohen, S. H. et al. Clinical practice guidelines for *Clostridium difficile* infection in adults: 2010 update by the society for healthcare epidemiology of America (SHEA) and the infectious diseases society of America (IDSA). *Infect. Control Hosp. Epidemiol.* 31, 431-455 (2010).
8. Kyne, L. & Kelly, C. P. Recurrent *Clostridium difficile* diarrhoea. *Gut* 49, 152-153 (2001).
9. Pothoulakis, C. Effects of *Clostridium difficile* toxins on epithelial cell barrier. *Ann. N. Y. Acad. Sci.* 915, 347-356 (2000).
10. Tonna, I. & Welsby, P. D. Pathogenesis and treatment of *Clostridium difficile* infection. *Postgrad. Med. J.* 81, 367-369 (2005).
11. Gough, E., Shaikh, H. & Manges, A. R. Systematic review of intestinal microbiota transplantation (fecal bacteriotherapy) for recurrent *Clostridium difficile* infection. *Clin. Infect. Dis.* 53, 994-1002 (2011).

Methods

Strain Genome and Stool Metagenomic Sequencing

The VE303 bacterial gDNA were sequenced on both the Illumina and Pacific Biosciences platforms. Illumina libraries were built using the TruSeq DNA PCR-Free Library Prep and sequenced on the MiSeq sequencer. Pacific Biosciences (PacBio) libraries for each of the VE303 strains were prepared using the SMRTbell Template Preparation kit and sequenced on the RS II (Pacific Biosciences, Menlo Park, CA) at the University of Maryland Institute for Genome Sciences (Baltimore, MD, USA). VE303 genome assemblies were generated using the PacBio sequences using HGAP assembler (SMRTAnalysis 2.3.0) and Celera Assembler v.8.2$^3$ and assessed for quality by the University of Maryland Institute for Genome Sciences bioinformatics core. Stool samples were collected fresh and approximately 250 mg was transferred to an OMNIgene-GUT tube (DNAgenotek, Ottawa, CAN) and resuspended in preservation buffer according to the manufacturer's instructions. Preserved stool suspensions were then extracted and sequenced on the Illumina NextSeq platform at DNAgenotek using standard operating procedures.

Establishment of the Strain Detection Algorithm

Figure 63:
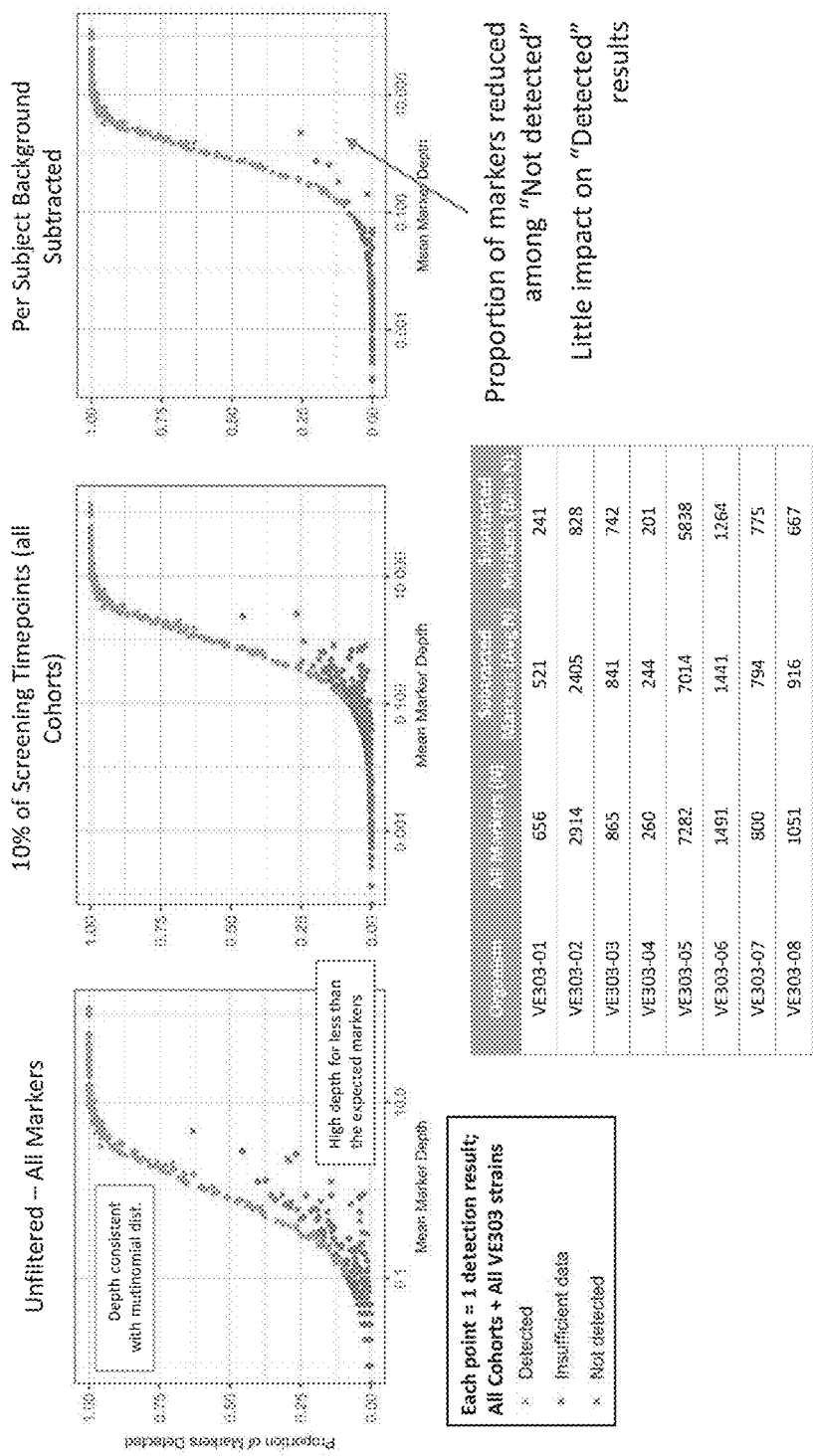
FIG. 63 shows optimization of the assay to detect the presence of bacterial strains of a bacterial composition in the microbiome of a subject.
Figure 64:
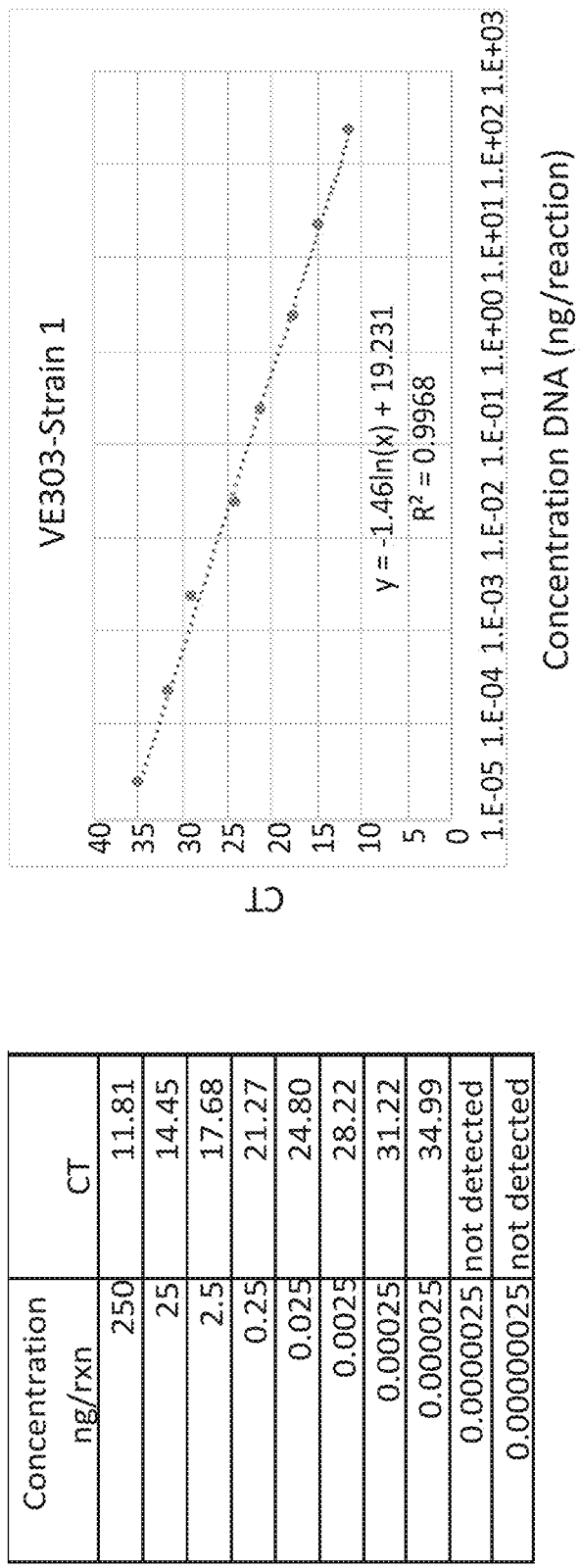
FIG. 64 shows qPCR amplification of DNA isolated from VE303 strain 1 bacteria. CT is the number of qPCR cycles at which the amount of amplified DNA is detectable above background. ng/rxn is the amount of DNA in nanograms that is present at the beginning of each qPCR reaction. The slope of the line correlates with the efficiency of qPCR amplification.
Figure 65:
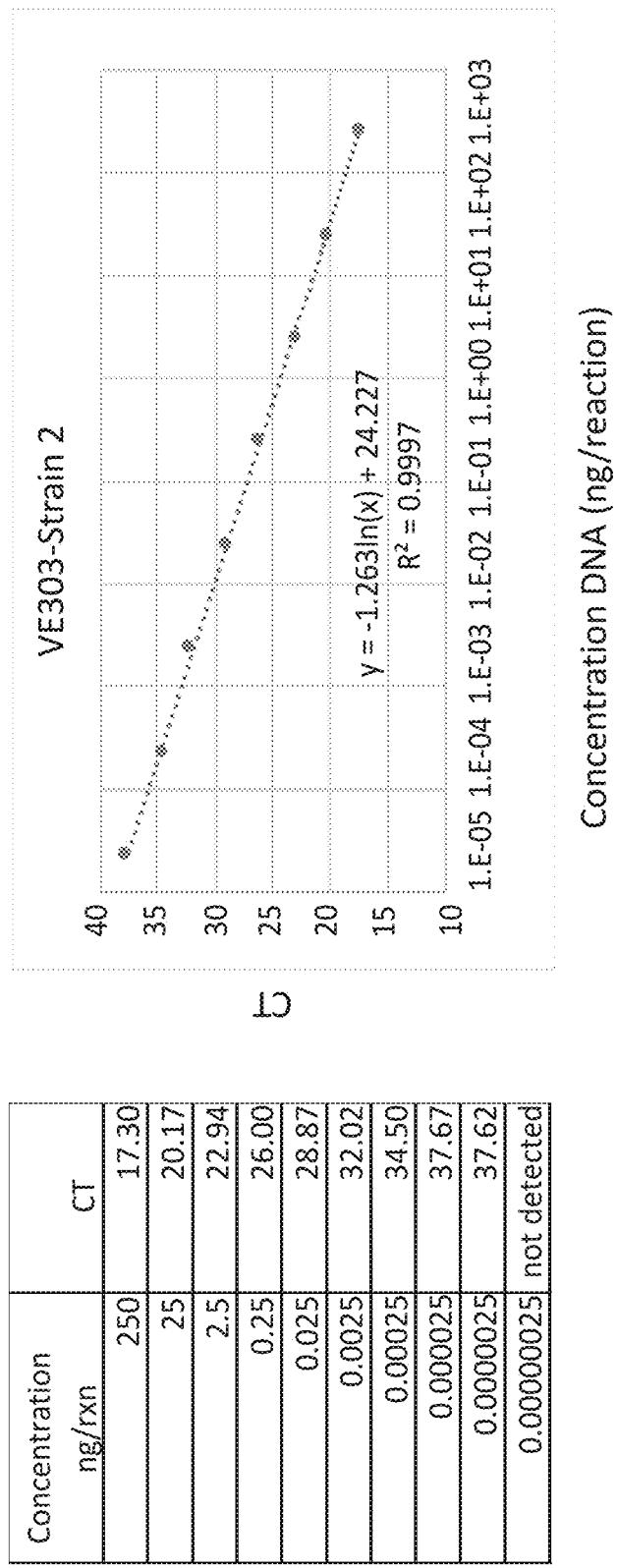
FIG. 65 shows qPCR amplification of DNA isolated from VE303 strain 2 bacteria. CT is the number of qPCR cycles at which the amount of amplified DNA is detectable above background. ng/rxn is the amount of DNA in nanograms that is present at the beginning of each qPCR reaction. The slope of the line correlates with the efficiency of qPCR amplification.
Figure 66:
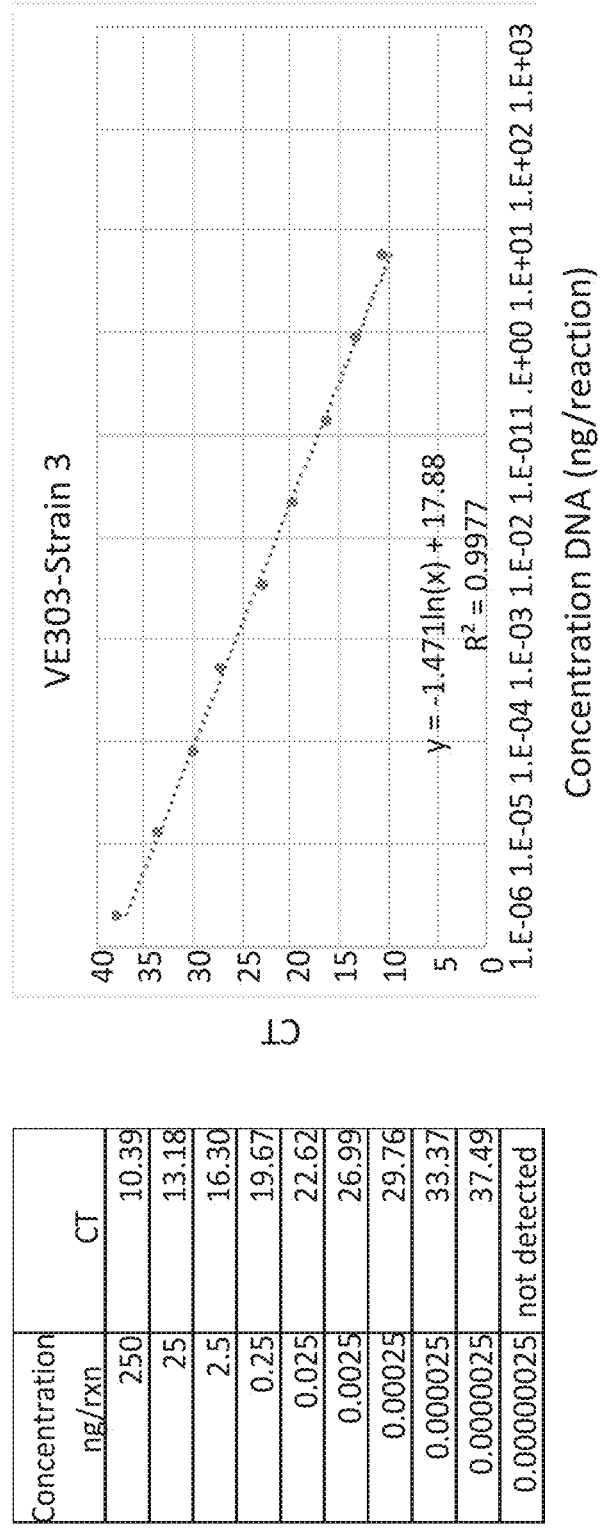
FIG. 66 shows qPCR amplification of DNA isolated from VE303 strain 3 bacteria. CT is the number of qPCR cycles at which the amount of amplified DNA is detectable above background. ng/rxn is the amount of DNA in nanograms that is present at the beginning of each qPCR reaction. The slope of the line correlates with the efficiency of qPCR amplification.
Figure 67:
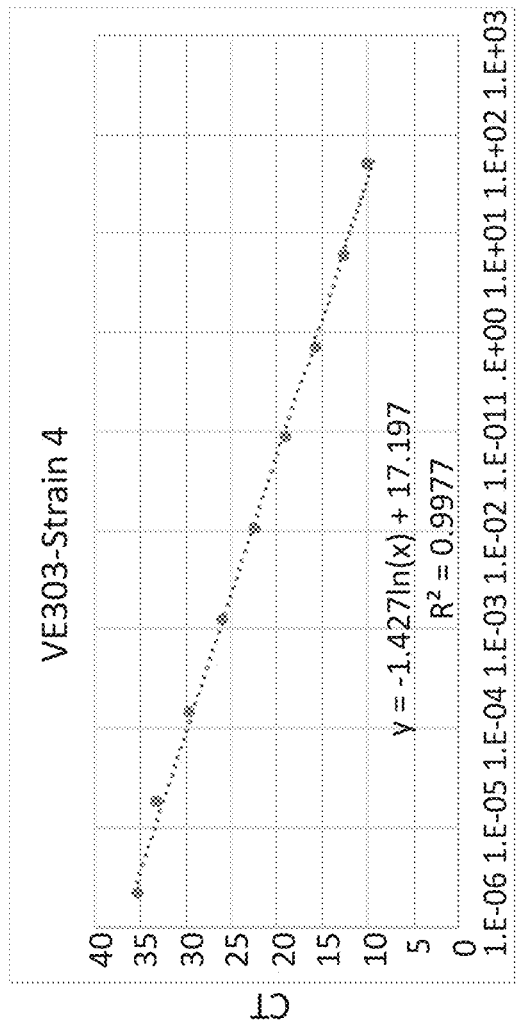
FIG. 67 shows qPCR amplification of DNA isolated from VE303 strain 4 bacteria. CT is the number of qPCR cycles at which the amount of amplified DNA is detectable above background. ng/rxn is the amount of DNA in nanograms that is present at the beginning of each qPCR reaction. The slope of the line correlates with the efficiency of qPCR amplification.
Figure 68:
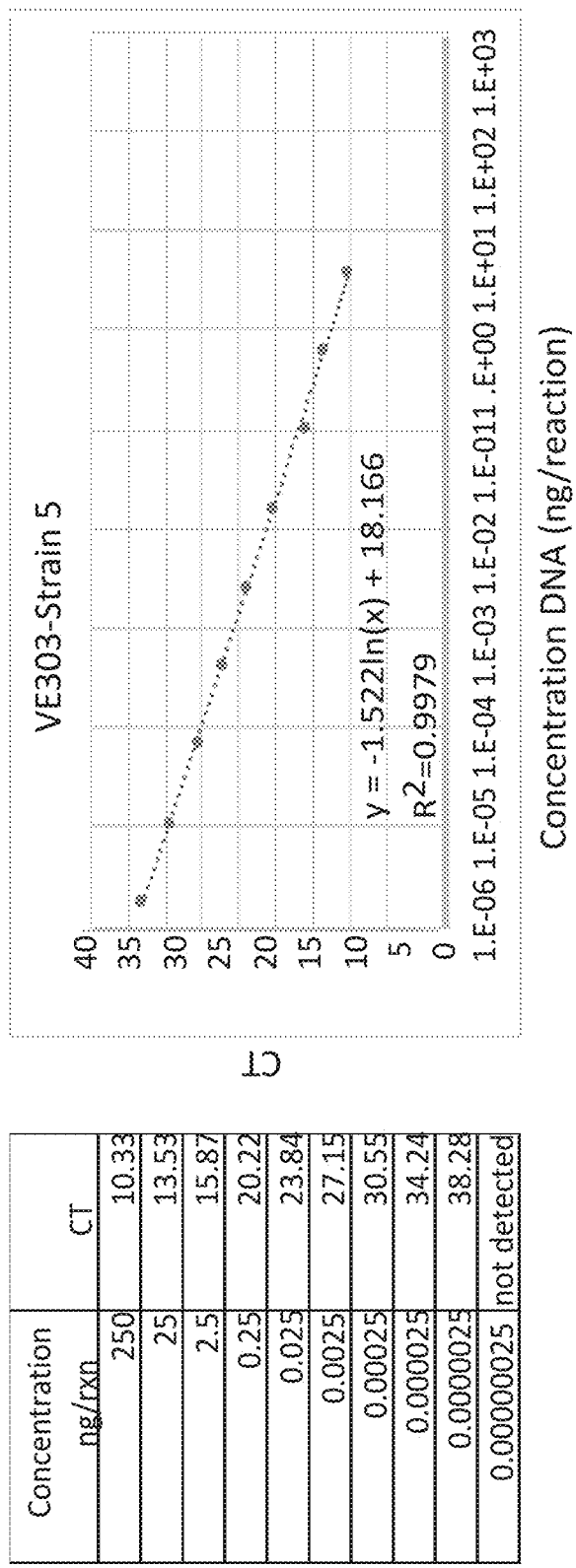
FIG. 68 shows qPCR amplification of DNA isolated from VE303 strain 5 bacteria. CT is the number of qPCR cycles at which the amount of amplified DNA is detectable above background. ng/rxn is the amount of DNA in nanograms that is present at the beginning of each qPCR reaction. The slope of the line correlates with the efficiency of qPCR amplification.
Figure 69:
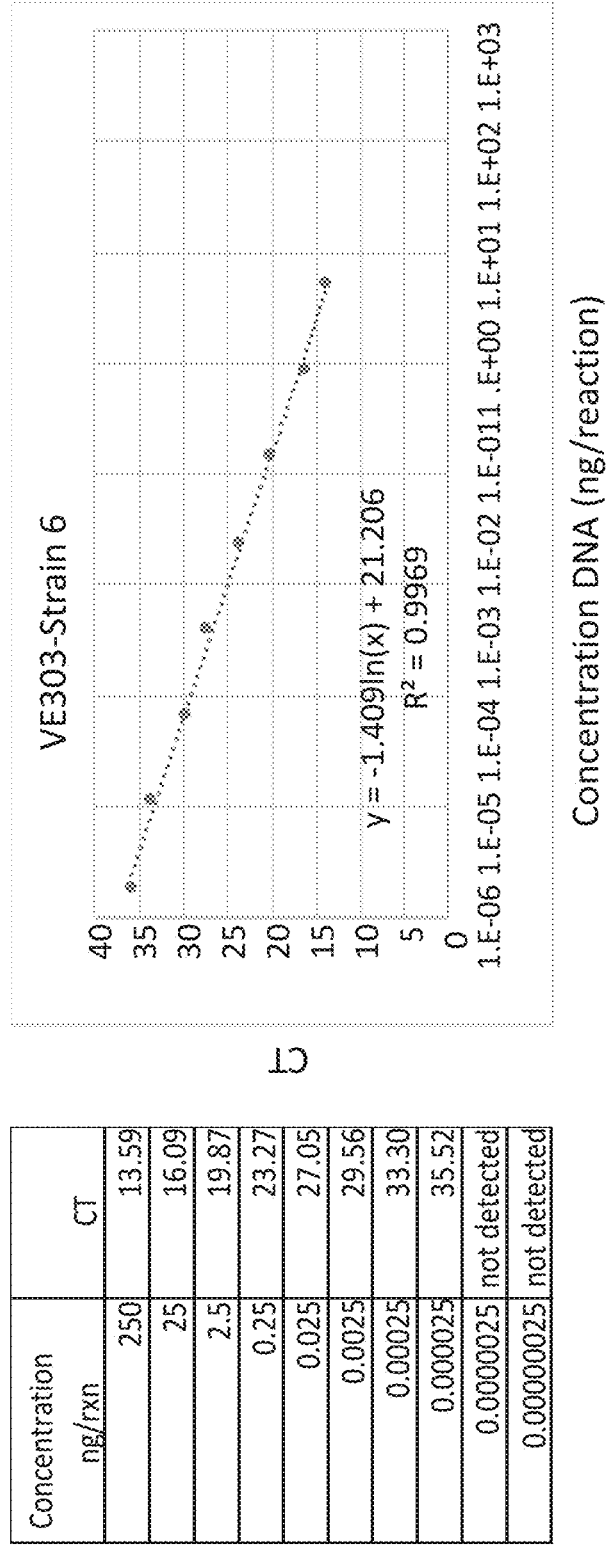
FIG. 69 shows qPCR amplification of DNA isolated from VE303 strain 6 bacteria. CT is the number of qPCR cycles at which the amount of amplified DNA is detectable above background. ng/rxn is the amount of DNA in nanograms that is present at the beginning of each qPCR reaction. The slope of the line correlates with the efficiency of qPCR amplification.
Figure 70:
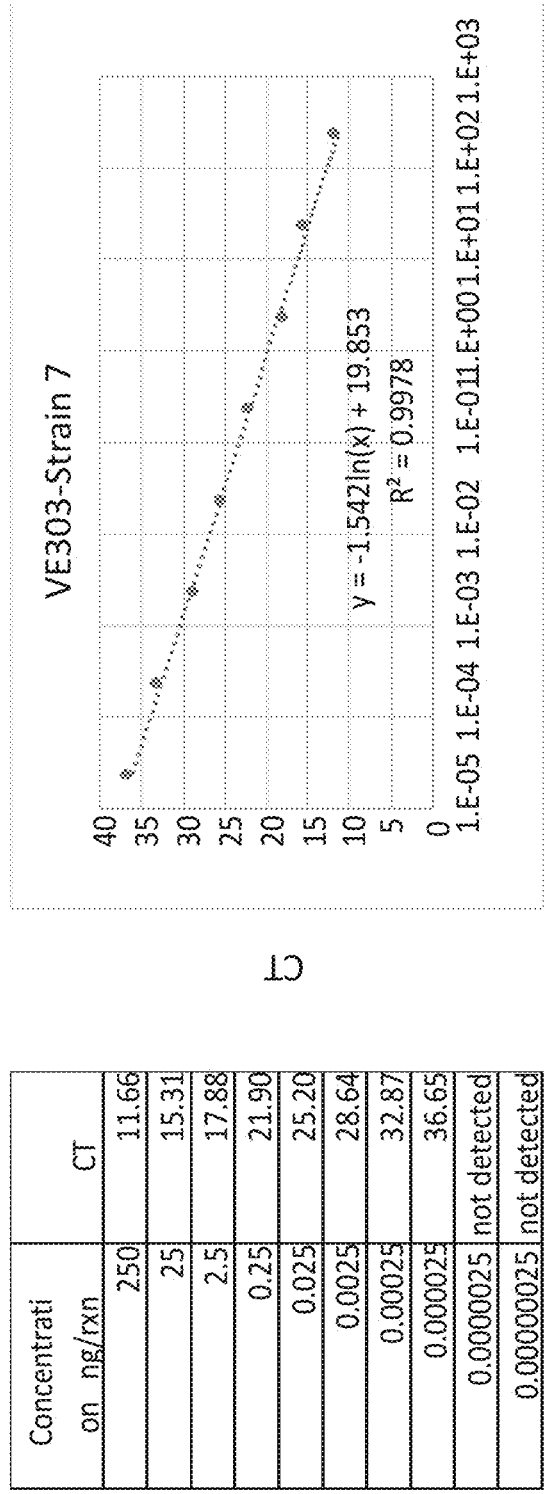
FIG. 70 shows qPCR amplification of DNA isolated from VE303 strain 7 bacteria. CT is the number of qPCR cycles at which the amount of amplified DNA is detectable above background. ng/rxn is the amount of DNA in nanograms that is present at the beginning of each qPCR reaction. The slope of the line correlates with the efficiency of qPCR amplification.
Figure 71:
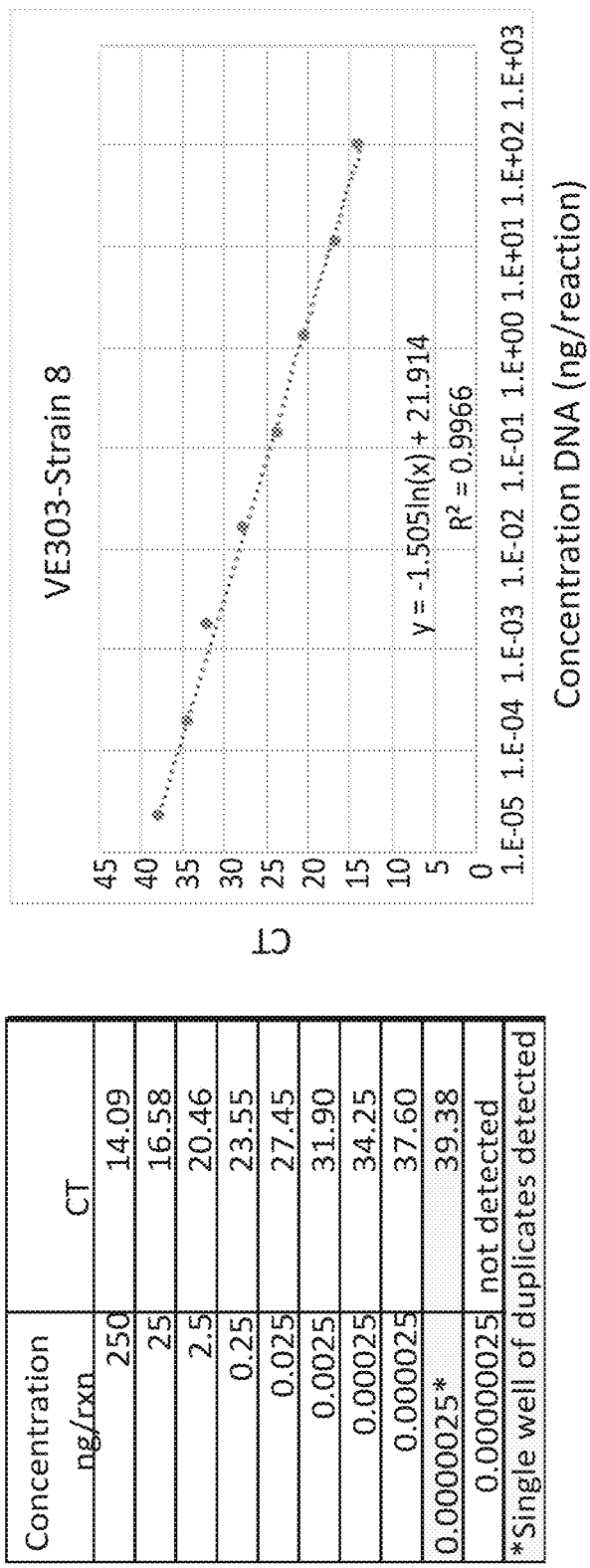
FIG. 71 shows qPCR amplification of DNA isolated from VE303 strain 8 bacteria. CT is the number of qPCR cycles at which the amount of amplified DNA is detectable above background. ng/rxn is the amount of DNA in nanograms that is present at the beginning of each qPCR reaction. The slope of the line correlates with the efficiency of qPCR amplification.

Unique genomic regions for each of the VE303 organisms were identified by: 1) identifying a candidate set of overlapping k-mers (k=31 bp) for each VE303 strain genome that are absent in the One Codex microbial genomes database, and 2) identifying a final set of unique genomic regions (50 base pair (bp) windows) that were not found in any other reference genome in the One Codex database, were not found in any other VE303 strain genome, and did not share a 17 bp subsequence with other candidate genomic regions. A total of 43,955 genomic regions satisfied these criteria, ranging from 1,539-10,847 per VE303 strain. This initial set of genomic regions was further refined by excluding those regions that were detected in a set of 249 healthy human stool metagenomic sequencing datasets and any regions that were recovered at a low rate in whole genome shotgun sequence datasets from pure cultures of the VE303 strains. Following this exclusivity testing step, a final set of 14,319 genomic markers were identified, ranging from 260-7,282 per VE303 strain (FIG. 63). Detection of the VE303 strains from Illumina whole genome metagenomic sequencing datasets relied on the unique genomic marker regions. Each of the 50 bp genomic regions is shorter than the sequence fragments ("reads") generated through the whole genome metagenomic sequencing process. Therefore, the unique genomic regions were detected as subsequences within any of the metagenomic reads. The unique genomic regions were considered detected if 1) the sequence fragment contained at least 1 perfect alignment >=17 bp to the target genomic region; and 2) the entire 50 bp genomic region aligned against the sequence fragment with no more than 3 mismatches. Detection of the exact 17 bp alignment was executed using a k-mer alignment approach. Sensitive alignment of the entire 50 bp genome sequence was conducted using the pairwise alignment module implemented in BioPython[4]. Each of the target genomic regions was considered present if there is at least one read in the input dataset that satisfies these criteria.

Figure 62:
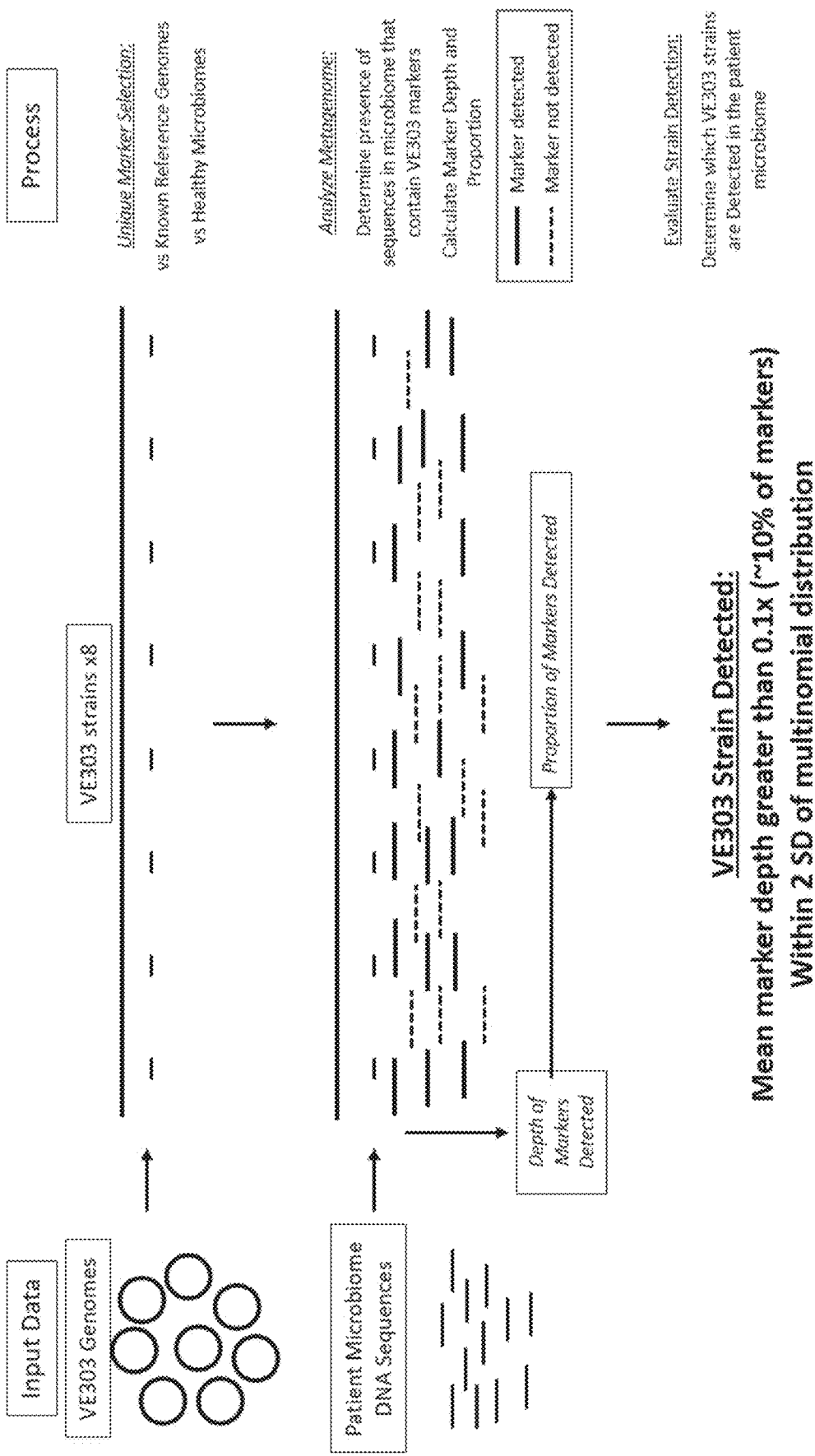
FIG. 62 shows a schematic of the development of an assay to detect the presence of bacterial strains of a bacterial composition in the microbiome of a subject. The top schematic shows identification of unique genomic markers for each bacterial strain of bacterial composition. The bottom schematic shows detection of the unique genomic markers in DNA sequences obtained from a microbiome sample of a subject to determine the presence of the bacterial strain in the microbiome of the subject.

The presence or absence of each VE303 strain in each patient sample was determined by analyzing the number of unique genomic markers that were detected, as well as the relative abundance of each marker (FIG. 62). Two key metrics were used to detect each VE303 strain: 1) Depth of marker recovery: the number of sequence fragments matching any marker, divided by the total number of markers; and 2) Coverage of marker recovery: the number of markers with >=1 matching sequence fragment, divided by the total number of markers. The detection of each VE303 strain was determined as follows:

"Detected" when the mean marker depth exceeded 0.1× and the coverage of markers detected exceeded a minimum threshold of two standard deviations below the mean expected from a multinomial distribution (with 25% zero inflation to account for marker dropout).

"Probable" when the mean marker depth exceeded 0.1× and the coverage of markers detected was between 2-4 standard deviations below the mean.

"Insufficient data" when the mean marker depth fell between 0.01×-0.1×.

"Not detected" when the mean marker depth did not exceed 0.01× or the number of markers was less than four standard deviations below the expected mean.

These methods were determined to robustly and specifically detect each VE303 strain using two approaches: 1) human stool samples spiked with increasing colony forming units (CFU) of each VE303 strain prior to DNA extraction and metagenomic sequence analysis, and 2) the ability to detect the VE303 strain genomes in the original host donor stool and not in unrelated control stool samples.

Bacterial Community Abundance and Microbiome Index

The estimated relative abundance of bacterial species in the microbial community (including VE303 strains) was determined using the standard One Codex algorithm from quality filtered metagenomic sequence reads after removal of reads that map to the human host. At higher taxonomic levels (e.g. Phylum or Class level) the relative abundance was calculated for each sample as the ratio of sequence reads assigned at the desired taxonomic level (plus all reads assigned below) to the total number of assigned reads. We then calculated the absolute abundance of DNA for each species in the microbial community according to Equation (3), below:

$$\text{Abs} = RA \times \frac{DNA_{\mu g}}{\text{Stool}_{mg}} \times \frac{V_B}{V_S}. \qquad \text{Equation (3)}$$

In this Equation, RA equals estimated relative abundance of the bacterial taxa. $DNA_{\mu g}$ is the total DNA yield. $\text{Stool}_{mg}$ is the mass of stool collected (final mass of Omnigene gut tube—average weight of Omnigene gut tube). $V_B$ is the volume of buffer in the Omnigene gut tube. $V_s$ is the volume of sample in the DNA extraction.

The microbiome index was calculated according to Equation (4) using the Class-level relative abundance of sequences in each metagenomic sample, as described previously (rebiotix.com/scientific-evidence/microbiota-restoration-therapy-posters/microbiome-rehabilitation-biomarkers-clostridium-difficile-infections-prototype-microbiome-health-index/).

$$MI = \frac{(RA_{Bacteroidia} + RA_{Clostridia} + RA_{Actinobacteria} + RA_{Coriobacteria})}{(RA_{Bacilli} + RA_{\gamma Proteobacteria} + RA_{Negativicutes})} \qquad \text{Equation (4)}$$

$$BAI_{Stool} = \frac{(RA_{Sec.Deconj.})}{(RA_{Unconj.} + RA_{Pri.} + RA_{Sec.Conj.})} \qquad \text{Equation (5)}$$

Linear Mixed Effect Modeling to Determine Analytes Significantly Affected by Total VE303 Abundance Linear mixed effect modeling was conducted to identify how different analytes (Bile Acids and Short Chain Fatty Acids) are affected by VE303 administration according to Equation (6):

$$\text{analyte} \sim \text{Treatment} + ve303 + \left(\frac{pID}{CohortID}\right). \qquad \text{Equation (6)}$$

Here, analyte corresponds to the SCFA or BA measured density in a certain individual at a certain time point (day), Treatment is a categorical variable to describe if the measurement is taken before, during or after vancomycin treatment, and ve303 corresponds to the total abundance of VE303 (µg DNA/mg Stool) in a certain sample after vancomycin administration. For Treatment the pre-vancomycin samples are used as the baseline. Because data are repeated samples from different patients that are subdivided in different cohorts, we used patient ID (pID)/CohortID is used as nested random effect. Metabolites with p-value associated to Treatment: during—vancomycin smaller than 0.05 are considered significantly affected by vancomycin treatment. Metabolites with p-value associated to Treatment: post-vancomycin smaller than 0.05 are considered significantly affected by vancomycin post-treatment and in the absence of VE303 (e.g., only vancomycin cohort). Metabolites with p-value associated to ve303 smaller than 0.05 are significantly affected by total VE303 abundance post treatment.

Random Forest Regression to Decouple Effect of VE303 and Recovering Resident Microbiota on Metabolites Dynamics Post-VE303 Administration To determine the contribution of the different VE303 strains to the SCFAs and BAs post-vancomycin dynamics and to decouple the effect on these metabolites of VE303 strains from the one of the recovering resident microbiota, Random Forest Regression (RFR) was conducted to predict each metabolite abundance as a function of the abundance of resident bacteria and VE303 abundances (FIGS. 58 and 59). A previously-validated approach was adopted to address the repeated sampling nature of the data (See Haran J P, Bhattarai S K, Foley S E, Dutta P, Ward D V, Bucci V, McCormick B A. (2019) Alzheimer's disease microbiome is associated with dysregulation of the anti-inflammatory P-glycoprotein pathway. *mBio* 10:e00632-19) in which RFR is run on 100 different subsets of randomly-selected samples (after choosing one sample per individual) and repeated starting from 30 different random number seeds. Microbes (both resident bacteria and VE303) were ranked based on their permutated variable importance value across the 30×100 RFR realizations. For all the top important predictors Accumulated Local Effects (ALE) Plots were generated to determine how each metabolite is affected by change in microbial feature abundance. A regression line was fitted to the log-log transformed ALE plots, and the results are summarized as a clustered heatmap of these inferred coefficients.

Reciprocal BLAST Analysis to Identify Bacteria with the Ability to Biotransform Primary Bile Acids Biotransformation of primary BAs to secondary BAs was recently identified to be a 'community task', requiring concerted efforts by several members of the gastrointestinal (GI) microbiome. Genomic datasets were used to identify secondary bile acid genes of commensal resident bacteria identified as lithocholic acid (LCA) and deoxycholic (DCA) inducers and VE303 strains as ursodeoxycholic acid (UDCA) inducers to further examine the metabolic potential of the recovered microbiota. For the commensals, representative genomes were downloaded either from the OneCodex database or from the NCBI Taxonomy database. BLAST Reciprocal Best Hits (doi.org/10.1186/s13742-015-0080-7) were used to map the commensal genomes, the VE303 genomes as well as the genomes of bacteria known to perform bile acid (BA) transformations (positive controls) (Heinken et al. *Microbiome* (2019) 7(1): 75) against a reference database of secondary bile acids biosynthesis proteins. This database was built in-house from UNIPROT using parameters stated by Heinken et al. Hits from these genomes against the built database were displayed as a similarity heatmap (FIG. 58).

TABLE 4

Percent of Subjects Colonized

| | Day 10 | | Week 4 | | Week 12 | |
|---|---|---|---|---|---|---|
| | Cohort 4 | Cohort 5 | Cohort 4 | Cohort 5 | Cohort 4 | Cohort 5 |
| VE303-01 | 83.3 | 87.5 | 66.7 | 87.5 | 100 | 87.5 |
| VE303-02 | 66.7 | 75 | 66.7 | 87.5 | 66.7 | 75 |
| VE303-03 | 100 | 87.5 | 66.7 | 100 | 83.3 | 62.5 |
| VE303-04 | 100 | 75 | 83.3 | 100 | 83.3 | 37.5 |
| VE303-05 | 83.3 | 75 | 50 | 75 | 66.7 | 62.5 |
| VE303-06 | 66.7 | 62.5 | 83.3 | 75 | 83.3 | 75 |
| VE303-07 | 66.7 | 87.5 | 66.7 | 75 | 83.3 | 50 |
| VE303-08 | 66.7 | 75 | 66.7 | 87.5 | 50 | 62.5 |

TABLE 5A

Median VE303 Strain Abundance

| | Day 10 | | Week 4 | | Week 12 | |
|---|---|---|---|---|---|---|
| | Cohort 4 | Cohort 5 | Cohort 4 | Cohort 5 | Cohort 4 | Cohort 5 |
| VE303-01 | 1.43% | 1.17% | 0.26% | 0.78% | 0.11% | 0.02% |
| VE303-02 | 0.10% | 0.08% | 0.07% | 0.31% | 0.04% | 0.11% |
| VE303-03 | 0.62% | 0.62% | 0.11% | 0.48% | 0.56% | 0.19% |
| VE303-04 | 0.58% | 0.24% | 0.29% | 0.52% | 0.58% | 0.00% |
| VE303-05 | 0.51% | 0.35% | 0.13% | 1.60% | 0.05% | 0.00% |
| VE303-06 | 0.61% | 0.10% | 0.26% | 2.02% | 1.55% | 1.28% |
| VE303-07 | 1.19% | 3.16% | 0.18% | 1.12% | 0.48% | 0.20% |
| VE303-08 | 2.37% | 1.37% | 0.67% | 0.48% | 0.51% | 0.89% |

TABLE 5B

Median VE303 Strain Abundance

| | Day 10 | | Week 4 | | Week 12 | |
|---|---|---|---|---|---|---|
| | Cohort 4 | Cohort 5 | Cohort 4 | Cohort 5 | Cohort 4 | Cohort 5 |
| VE303-01 | 1.70% | 2.98% | 0.48% | 0.12% | 0.11% | 0.02% |
| VE303-02 | 0.26% | 0.34% | 0.16% | 0.34% | 0.02% | 0.11% |
| VE303-03 | 0.62% | 0.97% | 0.77% | 1.01% | 0.60% | 0.19% |
| VE303-04 | 0.58% | 0.45% | 0.45% | 0.12% | 0.62% | 0.00% |
| VE303-05 | 0.74% | 1.32% | 0.34% | 0.92% | 0.20% | 0.00% |
| VE303-06 | 1.59% | 0.36% | 0.31% | 1.19% | 1.86% | 1.28% |
| VE303-07 | 1.43% | 4.31% | 0.68% | 1.81% | 0.47% | 0.20% |
| VE303-08 | 2.59% | 3.53% | 1.24% | 0.95% | 1.72% | 0.89% |

TABLE 6

Stool Samples (N) Analyzed for SCFA and BA

| Cohort ID | Base-line | Day 2 | Day 4 | Day 5 | Day 6 | Day 7 | Day 8 | Day 9 | Day 10 | Day 13 | Day 14 | Day 15 | Day 19 | Day 20 | Day 23 |
|---|---|---|---|---|---|---|---|---|---|---|---|---|---|---|---|
| Vanco | 8 | —* | 3* | 5* | 5@ | 2 | 4 | 1 | — | — | — | — | — | — | — |
| Cohort 1 | 5 | —* | 1* | 3* | 2@ | 2 | 3 | — | — | — | — | — | — | — | — |

TABLE 6-continued

Stool Samples (N) Analyzed for SCFA and BA

| Cohort ID | Baseline | Day 2 | Day 4 | Day 5 | Day 6 | Day 7 | Day 8 | Day 9 | Day 10 | Day 13 | Day 14 | Day 15 | Day 19 | Day 20 | Day 23 |
|---|---|---|---|---|---|---|---|---|---|---|---|---|---|---|---|
| Cohort 2 | 5 | —* | 2* | 3* | 2@ | 1 | 3 | — | — | — | — | — | — | — | — |
| Cohort 3 | 5 | —* | 3* | 2* | 2@ | — | 3 | 1 | 1 | — | — | — | — | — | — |
| Cohort 4 | 10 | —* | —* | 6* | 6@ | —@ | 5@ | 1@ | 6@ | — | 6 | — | — | — | — |
| Cohort 5 | 15 | —* | —* | 8* | 8@ | —@ | 8@ | —@ | 8@ | —@ | 7@ | 1@ | 8@ | — | 8 |
| Cohort 6 | 10 | 5@ | —@ | —@ | 5@ | —@ | —@ | —@ | -@ | 5@ | -@ | -@ | -@ | 5@ | — |

— = No samples collected
* = Samples during Vancomycin administration or washout
@ = Samples during VE303 administration (Cohorts 1-5 started on Day 6, Started on Day 0 Cohort 6)

TABLE 7A

Bile Acid LME Results

| | During Vancomycin | | Post Vancomycin (no VE303) | | Post Vancomycin (with VE303) | |
|---|---|---|---|---|---|---|
| | δ | p | δ | p | β | p |
| Primary Bile Acids | | | | | | |
| Cholic Acid | 5.592E+02 | 1.921E-01 | 1.941E+03 | 2.165E-06 | -4.168E+02 | 2.090E-05 |
| Glycochenodeoxycholic Acid | 7.492E+02 | 7.932E-03 | 2.750E+02 | 3.351E-01 | -3.882E+02 | 2.165E-06 |
| Glycocholic Acid | 1.398E+03 | 1.390E-04 | 2.856E+02 | 4.089E-01 | -3.943E+02 | 2.093E-05 |
| Chenodeoxycholic Acid | 2.603E+02 | 1.095E-01 | 4.154E+02 | 5.100E-03 | -1.419E+02 | 6.668E-05 |
| Taurocholic Acid | 9.505E+01 | 9.122E-03 | 9.505E+01 | 1.884E-01 | -2.837E+01 | 1.884E-01 |
| Taurochenodeoxycholic Acid | 2.347E+01 | 3.462E-02 | 2.347E+01 | 6.347E-01 | -1.280E+01 | 3.785E-01 |
| Secondary Bile Acids-bai 7α Dehydroxylation | | | | | | |
| Lithocholic Acid | -6.865E+02 | 5.096E-05 | -1.206E+03 | 5.527E-13 | 1.611E+02 | 2.093E-05 |
| Taurolithocholic Acid | — | NA | — | NA | -3.606E-01 | 4.519E-02 |
| Glycolithocholic Acid | -6.194E-01 | 1.884E-01 | -7.816E-01 | 2.465E-01 | -7.799E-04 | 9.944E-01 |
| Deoxycholic Acid | -9.983E+02 | 3.786E-05 | -1.677E+03 | 6.951E-12 | 2.044E+02 | 3.108E-04 |
| Glycodeoxycholic Acid | 6.748E+01 | 6.403E-03 | 6.748E+01 | 5.447E-01 | -1.160E+02 | 7.080E-05 |
| Taurodeoxycholic Acid | 1.036E+02 | 1.884E-01 | 3.010E+01 | 7.110E-01 | -1.054E+01 | 6.347E-01 |
| Secondary Bile Acids-Epimerization | | | | | | |
| Ursodeoxycholic Acid | 4.705E+00 | 9.295E-01 | 4.539E+01 | 3.470E-01 | 2.240E+01 | 4.519E-02 |
| Glycoursodeoxycholic Acid | 3.919E+01 | 1.574E-01 | 7.391E+00 | 7.547E-01 | -1.126E+01 | 4.519E-02 |
| Tauroursodeoxycholic Acid | 3.929E+00 | 9.946E-02 | -2.082E+00 | 3.785E-01 | 1.115E+00 | 7.085E-02 |

δ—distance from baseline (pre vancomycin)
β—regression coefficient
p—p value

TABLE 7B

Bile Acid LME Results

| | During Vancomycin | | Post Vancomycin (No VE303) | | VE303 | |
|---|---|---|---|---|---|---|
| | δ | p | δ | p | β | p |
| Primary Bile Acids | | | | | | |
| Cholic Acid | 6.453E+02 | 1.476E-01 | 1.914E+03 | 1.875E-06 | -3.833E+02 | 1.109E-04 |
| Glycochenadeoxycholic Acid | 8.523E+02 | 1.054E-02 | 4.011E+02 | 2.007E-01 | -3.546E+02 | 1.497E-05 |
| Glycocholic Acid | 1.357E+03 | 7.775E-04 | 2.973E+02 | 4.135E-01 | -3.848E+02 | 4.340E-05 |
| Chenodeoxycholic Acid | 2.716E+02 | 9.926E-02 | 3.935E+02 | 6.567E-03 | -1.308E+02 | 3.992E-04 |
| Taurocholic Acid | 1.587E+02 | 1.374E-01 | 6.966E+01 | 4.343E-01 | -3.328E+01 | 1.824E-01 |

TABLE 7B-continued

Bile Acid LME Results

| | During Vancomycin | | Post Vancomycin (No VE303) | | VE303 | |
|---|---|---|---|---|---|---|
| | δ | p | δ | p | β | p |
| Taurochenodeoxycholic Acid | 7.431E+01 | 2.878E−01 | 2.219E+01 | 7.271E−01 | −2.177E+01 | 1.904E−01 |
| Secondary Bile Acids-bai Dehydroxyation | | | | | | |
| Glycodeoxycholic Acid | 3.268E+02 | 5.980E−03 | 1.355E+02 | 2.419E−01 | −1.156E+02 | 1.109E−04 |
| Lithocholic Acid | −6.119E+02 | 3.512E−04 | −1.150E+03 | 1.326E−11 | 1.739E+02 | 1.795E−05 |
| Deoxycholic Acid | −9.509E+02 | 2.344E−04 | −1.578E+03 | 1.815E−10 | 2.015E+02 | 7.540E−04 |
| Secondary Bile Acids-Epimerization | | | | | | |
| Glycoursodeoxycholic Acid | 5.441E+01 | 8.691E−02 | 2.687E+01 | 3.385E−01 | −9.978E+00 | 1.033E−01 |
| Ursodeoxycholic Acid | 8.403E+00 | 9.413E−01 | 8.975E+01 | 2.700E−01 | 2.276E+01 | 2.127E−01 |
| Secondary Bile Acids-Other | | | | | | |
| Taurolithocholic Acid | 2.117E−01 | 7.969E−01 | NA | NA | −2.085E−01 | 2.878E−01 |
| Glycolithocholic Acid | −6.368E−01 | 1.930E−01 | −6.477E−01 | 4.135E−01 | −1.316E−02 | 9.413E−01 |
| Tauroursodeoxycholic Acid | 2.059E+00 | 4.205E−01 | 2.171E−01 | 9.413E−01 | 2.147E−01 | 8.197E−01 |
| Taurodeoxycholic Acid | 4.977E+01 | 5.894E−01 | −2.120E+01 | 8.696E−01 | −3.956E+01 | 1.476E−01 |

δ—distance from baseline (pre vancomycin)
β—regression coefficient

TABLE 8A

SCFA LME Results

| | During Vancomycin | | Post Vancomycin (no VE303) | | Post Vancomycin (with VE303) | |
|---|---|---|---|---|---|---|
| SCFA | δ | p | δ | p | β | p |
| Butyrate | −6.620E+02 | 3.769E−04 | −1.158E+03 | 6.806E−10 | 1.480E+02 | 5.432E−04 |
| Acetate | −1.080E+03 | 1.413E−03 | −9.804E+02 | 2.300E−03 | 4.588E+02 | 3.254E−08 |
| Isobutyrate | −3.131E+01 | 1.095E−01 | −7.973E+01 | 1.397E−05 | 1.860E+01 | 2.232E−05 |
| Methylbutyrate | −2.186E+01 | 1.914E−01 | −6.892E+01 | 1.637E−05 | 1.631E+01 | 2.389E−05 |
| Isovalerate | −2.728E+01 | 1.921E−01 | −8.555E+01 | 2.093E−05 | 1.942E+01 | 6.518E−05 |
| Propionate | −5.686E+02 | 4.512E−05 | −5.178E+02 | 8.156E−05 | 1.285E+02 | 1.006E−04 |
| Valerate | −2.236E+01 | 6.449E−01 | −1.637E+02 | 3.682E−04 | 2.233E+01 | 1.038E−01 |
| Hexanoate | 1.566E+01 | 2.963E−01 | −2.844E+01 | 6.275E−02 | 6.297E+00 | 1.884E−01 |

δ—distance from baseline (pre vancomycin)
β—regression coefficient
p—p value

TABLE 8B

SCFA LME Results

| | During Vancomycin | | Post Vancomycin (No VE303) | | VE303 | |
|---|---|---|---|---|---|---|
| SCFAs | δ | p | δ | p | β | p |
| Butyrate | −8.035E+02 | 2.328E−05 | −1.185E+03 | 5.238E−11 | 1.274E+02 | 2.540E−03 |
| Acetate | −1.104E+03 | 9.789E−04 | −8.988E+02 | 3.314E−03 | 4.186E+02 | 3.283E−07 |
| Isobutyrate | −4.929E+01 | 3.314E−03 | −8.278E+01 | 3.283E−07 | 1.531E+01 | 1.109E−04 |
| Methylbutyrate | −4.088E+01 | 6.913E−03 | −7.183E+01 | 7.473E−07 | 1.305E+01 | 2.359E−04 |
| Isovalerate | −5.583E+01 | 3.314E−03 | −8.838E+01 | 9.983E−07 | 1.392E+01 | 1.392E−03 |
| Propionate | −5.768E+02 | 3.349E−05 | −4.661E+02 | 2.320E−04 | 1.094E+02 | 7.006E−04 |
| Valerate | −7.774E+01 | 6.220E−02 | −1.588E+02 | 3.349E−05 | 9.636E+00 | 3.953E−01 |
| Hexanoate | −5.165E−01 | 9.722E−01 | −4.137E+01 | 6.702E−03 | 6.148E+00 | 1.730E−01 | d—distance from baseline (pre vancomycin)
b—regression coefficient

Example 12: New Methods to Assess the Engraftment of a Live Microbial Consortium in Normal Healthy Volunteers Alterations of the bacterial microbiome in the human intestine, such as reduced diversity and lower abundance of commensal organisms, are associated with infections by opportunistic pathogens like *Clostridium difficile*. Current microbiome-based treatments aimed at restoring a diverse microbiota, such as fecal microbiota transfer (FMT), have proven successful in reducing the rate of *C. difficile* recurrence. However, FMT and similar approaches that require the transfer of a large fraction of mostly uncharacterized fecal matter from a donor have the potential to transmit infectious agents. A live biotherapeutic product (called VE303) is being developed for the treatment of recurrent *C. difficile* infection (rCDI). The VE303 consortium is a rationally designed therapeutic that consists of purified, clonal bacterial strains. The strains were isolated from the fecal matter of healthy volunteers, fully characterized and grown individually under GMP conditions. A Phase 1a/1b, dose-escalating study has been initiated to assess the safety, tolerability, and colonization of VE303 in healthy volunteers. The primary outcomes of the study are the evaluation of the safety and tolerability of VE303 and to determine doses for testing rCDI efficacy in a Phase 2 study. The secondary outcomes include the kinetics of intestinal colonization by the bacterial strains in VE303 and restoration of the resident microbiota after vancomycin-induced dysbiosis. Here, recent findings and new methodology to assess the colonization by the bacterial strains in VE303 are presented. Novel bioinformatic tools were developed to differentiate VE303 from related, endogenous microorganisms. These tools enable precise quantification of pharmacokinetics and pharmacodynamics in human stool samples after VE303 administration.

Example 13: Selection of Oligonucleotide DNA Primers and Protocol Parameters for Detection of VE303 Strains Oligonucleotide DNA primers were designed to target specific sequences of less than 150 base pairs of each of Strains 1-8 of VE303 (Table 1). Oligonucleotide DNA probes with 5'-/56-FAM fluorescent dye and a ZEN moiety and 3IABkFQ/-3' quencher were designed to selectively identify the specific bacterial species in the VE303 consortia. The primer and DNA probe sequences are listed in Table 9.

TABLE 9 qPCR Oligonucleotide Primer and Probe Sequences

| Strain Number | | Primers |
|---|---|---|
| 1 | Forward Primer: | 5'-TGCAGCCGGTATTCTGATTT-3' (SEQ ID NO: 9) |
|   | Reverse Primer: | 5'-GCGAATGGTAGTCCGGTATAAT-3' (SEQ ID NO: 10) |
|   | Probe: | 5'-/56-FAM/TGGGCTGAT/ZEN/CCCGTTCCGTTT/EIABkFQ/-3' (SEQ ID NO: 11) |
|   | Forward Primer: | 5'-GAAATCTTACACACCTATTCAGACC-3' (SEQ ID NO: 33) |
|   | Reverse Primer: | 5'-ATCATCCATCTGCTGTTCCAGGCTC-3' (SEQ ID NO: 34) |
|   | Probe: | 5'-/56-FAM/CATAATTAT/ZEN/CCGCGTGGCC/3IABkFQ/-3' (SEQ ID NO: 35) |
|   | Forward Primer: | 5'-GGCTTGTGAGCCCTGATTA-3' (SEQ ID NO: 36) |
|   | Reverse Primer: | 5'-GCTATTTGGGAGAATGTCCTTTG-3' (SEQ ID NO: 37) |
|   | Probe: | 5'-/56-FAM/AATCTCCAC/ZEN/ACTTTCCGCAGGTCA/3IABkFQ/-3' (SEQ ID NO: 38) |
|   | Forward Primer: | 5'-TTTAATCCATGGGCCTCCTTAG-3' (SEQ ID NO: 39) |
|   | Reverse Primer: | 5'-ATGAGGCAGAGACGGAAATG-3' (SEQ ID NO: 40) |
|   | Probe: | 5'-/56-FAM/CCCTTTCTG/ZEN/GCCTGTTCTATTGCCT/3IABkFQ/-3' (SEQ ID NO: 41) |
| 2 | Forward Primer: | 5'-TTGTACTGTTCCCAATGAGTATCAA-3' (SEQ ID NO: 12) |
|   | Reverse Primer: | 5'-GAATATAATCAAGATCCTCCAGCGG-3' (SEQ ID NO: 13) |
|   | Probe: | 5'-/56-FAM/AAAAATATT/ZEN/TGGGTTATGCAACC/3IABkFQ/-3' (SEQ ID NO: 14) |
| 3 | Forward Primer: | 5'-CGAACCCTTAAACCTCTTCCTT-3' (SEQ ID NO: 15) |
|   | Reverse Primer: | 5'-TCCGGCTTGTGATGTCTTGT-3' (SEQ ID NO: 16) |
|   | Probe: | 5'-/56-FAM/CCCTCCTTC/ZEN/TTGATATTCGGTTGTTCCA/3IABkFQ-3' (SEQ ID NO: 17) |
|   | Forward Primer: | 5'-CTGATAGACGAAGAAGGCGCATACT-3' (SEQ ID NO: 42) |
|   | Reverse Primer: | 5'-TTCTCCATTTTCCATCATCCTTTCA-3' (SEQ ID NO: 43) |
|   | Probe: | 5'-/56-FAM/CTGTATGGA/ZEN/AGGGCTGTT/3IABkFQ/3' (SEQ ID NO: 44) |
|   | Forward Primer: | 5'CTGATAGACGAAGAAGGCGCATACT-3' (SEQ ID NO: 45) |
|   | Reverse Primer: | 5'-TTCTCCATTTTCCATCATCCTTTCA-3' (SEQ ID NO: 46) |
|   | Probe: | 5'-FAM/CTGTATGGA/ZEN/AGGGCTGTT/3IABkFQ/-3' (SEQ ID NO: 47) |
|   | Forward Primer: | 5'-CCAAAGCAAATGTTAACGGAACTA-3' (SEQ ID NO: 48) |
|   | Reverse Primer: | 5'-TACAGCAGGAGTTTGTGTGATT-3' (SEQ ID NO: 49) |
|   | Probe: | 5'-/56-FAM/ACTGCCAAT/ZEN/CTCCAATCAATGCCA/3IABkFQ/-3' (SEQ ID NO: 50) |
|   | Forward Primer: | 5'-GTTAACGGAACTACAATGCTAGAAA-3' (SEQ ID NO: 51) |
|   | Reverse Primer: | 5'-TGTGGAATCTCAGACCATTAACT-3' (SEQ ID NO: 52) |
|   | Probe: | 5'/56-FAM/ACTGCCAAT/ZEN/CTCCAATCAATGCCA/3IABkFQ/-3' (SEQ ID NO: 53) |
|   | Forward Primer: | 5'-ATCAATCCCATGACTCTCTCCC-3' (SEQ ID NO: 54) |
|   | Reverse Primer: | 5'-CCTACTGATGAAATAATAGAAGGAACTC-3' (SEQ ID NO: 55) |
|   | Probe: | 5'-/56-FAM/TCCTCCACG/ZEN/TAAGTCATGACTAAGAAGCT/3IABkFQ/-3' (SEQ ID NO: 56) |

TABLE 9-continued qPCR Oligonucleotide Primer and Probe Sequences

| Strain Number | | Primers |
|---|---|---|
| 4 | Forward Primer: | 5'-CCCGAAACCCTTTGATTTACTG-3' (SEQ ID NO: 18) |
| | Reverse Primer: | 5'-CTTGGCCGGTGGATATGTT-3' (SEQ ID NO: 19) |
| | Probe: | 5'-/56-FAM/AGCAACACC/ZEN/ACCGTTTCAACATGC/3IABkFQ/-3' (SEQ ID NO: 20) |
| | Forward Primer: | 5'-ATCATCCGCTACTCCAAACCCGATT-3' (SEQ ID NO: 57) |
| | Reverse Primer: | 5'-GTGCGATGGGGAGGACGATTATGCC-3' (SEQ ID NO: 58) |
| | Probe: | 5'-/56-FAM/CCCGCATAA/ZEN/TTGC/3IABkFQ/-3' (SEQ ID NO: 59) |
| | Forward Primer: | 5'-CTACCTTCTTTCCGCCTATTGT-3' (SEQ ID NO: 60) |
| | Reverse Primer: | 5'-TTGAGGCGGTTCTCGTAAATAA-3' (SEQ ID NO: 61) |
| | Probe: | 5'-/56-FAM/TCTGATTCG/ZEN/GAATAACGGCTGGCC/3IABkFQ/-3' (SEQ ID NO: 62) |
| | Forward Primer: | 5'-CTGGTTCCGTGGGCATTTA-3' (SEQ ID NO: 63) |
| | Reverse Primer: | 5'-CGATGCCTACCATATCACATCC-3' (SEQ ID NO: 64) |
| | Probe: | 5'-/56-FAM/CGGCATCGT/ZEN/TCATCGCAAATTCCA/3IABkFQ/-3' (SEQ ID NO: 65) |
| | Forward Primer: | 5'-CTGCGTTCTGGGTCAGATAAA-3' (SEQ ID NO: 66) |
| | Reverse Primer: | 5'-CCAAAGCAGTAAGAGGAGGATAAA-3' (SEQ ID NO: 67) |
| | Probe: | 5'-/56-FAM/TGTTTCGCC/ZEN/AGGCTGTTCTGTACT/3IABkFQ/-3' (SEQ ID NO: 68) |
| 5 | Forward Primer: | 5'-ACACGCATATCGTTTGACACTGTT-3' (SEQ ID NO: 21) |
| | Reverse Primer: | 5'-CAATTATGATTGCCGTTCT-3' (SEQ ID NO: 22) |
| | Probe: | 5'-/56-FAM/ACGGAACTT/ZEN/ATGAACCC/3IABkFQ/-3' (SEQ ID NO: 23) |
| 6 | Forward Primer: | 5'-TATTCAGATCGTATTTGGATGTACC-3' (SEQ ID NO: 24) |
| | Reverse Primer: | 5'-CCCTTGCAAGCTCTGTCGTCATAAG-3' (SEQ ID NO: 25) |
| | Probe: | 5'-/56-FAM/ACTGCTCGC/ZEN/TTCAGG/3IABkFQ/-3' (SEQ ID NO: 26) |
| 7 | Forward Primer: | 5'-AATGCCAGAAAGCATGTGATCCGTC-3' (SEQ ID NO: 27) |
| | Reverse Primer: | 5'-TCCTGCCATTCCGTGATGTAAGGT-3' (SEQ ID NO: 28) |
| | Probe: | 5-/56-FAM/CATTGAAAG/ZEN/ATATCCGGAACT/3IABkFQ/-3' (SEQ ID NO: 29) |
| 8 | Forward Primer: | 5'-CTCTGTAACCAGACAGGAGTTG-3' (SEQ ID NO: 30) |
| | Reverse Primer: | 5'-CCGGTGATACCCAAAGAAGAA-3' (SEQ ID NO: 31) |
| | Probe: | 5'-/56-FAM/CGTCGTGCT/ZEN/GGATCGGTTGAATCT/3IABkFQ/-3' (SEQ ID NO: 32) |
| | Forward Primer: | 5'-AGGGTGAAGTCCAATGAAGATCTCC-3' (SEQ ID NO: 69) |
| | Reverse Primer: | 5'-ATACCTCCAGAAGCACACAAGGGCC-3' (SEQ ID NO: 70) |
| | Probe: | 5'-/56-FAM/ATCATGGCT/ZEN/CTGCTACC/3IABkFQ/-3' (SEQ ID NO: 71) |
| | Forward Primer: | 5'-CCGAATATTGCGTCCGTAGTT-3' (SEQ ID NO: 72) |
| | Reverse Primer: | 5'-TAGGTATATCACAGCCGTCTCTC-3' (SEQ ID NO: 73) |
| | Probe: | 5'-/56-FAM/TGTTAATCA/ZEN/CTCTTGCGCTCGGCT/3IABkFQ/-3' (SEQ ID NO: 74) |

DNA was isolated from bacterial pellets containing a single bacterial strain (VE303 Strains 1-8) to test the specificity of the primers listed in Table 9. The concentration of isolated DNA was quantified using a fluorometer (e.g., Qubit 3.0, ThermoFisher). The isolated DNA was used to produce standard curves by qPCR using the primers listed in Table 9. These standard curves were used to determine linearity of the reaction, determine the reaction efficiency, and examine the limits of detection. The results of these qPCR assays are shown in FIGS. 64-71.

The CT in a qPCR reaction is the number of cycles at which the signal for a target DNA (e.g., VE303 strains 1-8) is distinguishable above background. All 8 VE303 strains were detectable by the end of 18 qPCR cycles with 250 ng of DNA in the qPCR reaction (FIGS. 64-71). None of VE303 strains 1-8 were detected above background in qPCR reactions that contained 2.5E-7 ng of DNA (FIGS. 64-71).

The amplification efficiency of the qPCR assays for each of VE303 strains 1-8 were also calculated. qPCR amplification efficiency is 100% if the number of target sequence molecules (e.g., VE303 strains 1-8) doubles during each replication cycle. If the efficiency is less than 100%, the number of target sequence molecules is not doubling during each replication cycle, and if the efficiency is greater than 100%, the number of target sequence molecules is more than doubling during each replication cycle. The average amplification efficiency for qPCR of VE303 strains 1-8 are shown in Table 10 below. All qPCR assays were at least 94% efficient.

TABLE 10 qPCR Amplification Efficiencies

| VE303 Strain | Efficiency Plate 1 | Efficiency Plate 2 | Average Efficiency |
|---|---|---|---|
| 1 | 98.34% | — | 98.34% |
| 2 | 105.60% | 120.67% | 113.13% |
| 3 | 97.35% | — | 97.35% |
| 4 | 101.50% | — | 101.50% |
| 5 | 96.38% | 92.93% | 94.65% |
| 6 | 100.68% | 103.39% | 102.03% |
| 7 | 100.23% | 91.27% | 95.75% |
| 8 | 94.32% | — | 94.32% |

The limit of detection of the qPCR assays for each of VE303 strains 1-8 was also calculated. qPCR limit of detection is the lowest concentration of DNA that can be detected above background signal after the final amplification cycle (in this case, 40 cycles). The limits of detection of VE303 strains 1-8 were between 2.5E-4 ng/reaction to 2.5E-6 ng/reaction.

The cross-reactivity of the primers in Table 9 was evaluated against non-target VE303 strains (e.g., not the bacterial strain to which the primer was designed to target). A consortium of VE303 bacterial strains, excluding the strain to which the primers were designed to target, were amplified using the primers in Table 9. Cross-reactivity was determined by evaluating CT, and a primer was considered to cross-react with non-target VE303 strains if there was a detectable signal above background by the end of the qPCR reaction (e.g., 40 cycles). Results of cross-reactivity experiments are shown in Table 11 below. The primers designed to amplify VE303 strains 1-4 and 7 were cross-reactive with at least one other VE303 species, although the amplified DNA was not detected until qPCR cycle 34 at the earliest.

TABLE 11

Cross-reactivity

| Primers Against VE303 Strain | Cross-Reactive with VE303 Strain | DNA (ng/rxn) | CT1 | CT2 |
|---|---|---|---|---|
| 1 | 4 | 2.5 | 36.43 | — |
| 2 | 1 | 2.5E-3 | 36.75 | — |
| 3 | 6 | 2.5E-3 | 35.86 | — |
| 3 | 7 | 2.5 | 34.59 | — |
| 4 | 1 | 2.5 | 37.12 | — |
| 4 | 7 | 2.5E-3 | 35.59 | — |
| 7 | 2 | 2.5 | 39.52 | — |
| 7 | 6 | 2.5 | 34.48 | 34.92 |

Example 14: Detection of VE303 Strains in Fecal Samples

The oligonucleotide primers selected in Example 13 were tested for efficacy in detecting bacterial strains of the VE303 compositions in fecal samples. Briefly, fecal samples were obtained from human subjects to determine baseline samples and at day 0, both of which time points were prior to administration of the VE303 composition, to assess the level of false positives. The individuals were administered vancomycin, and fecal samples were collected on day 5. Additional fecal samples were collected following administration of VE303 compositions on day 14, week 3, week 8, and week 12.

DNA was extracted from fecal samples using a modified QIAamp PowerFecal DNA Isolation Protocol for Stool Extraction Kit (Qiagen). Double stranded DNA was quantified using the Qubit 3.0 Fluorometer. Two microliters of extracted DNA was added per well, tested in duplicate by qPCR, for each primer/probe set.

PCR reaction components, for each reaction:
10 µl of Taqman Fast Universal PCR Master Mix (2×)
0.3 µl 20 uM Forward Primer
0.3 µl 20 uM Reverse Primer
0.4 µl 20 uM Probe
7 µl Nuclease Free Water
2 µl extracted DNA
for a total volume of 20 ul per well.
The following PCR reaction parameters were used:
50° C. Hold for 2 minutes
95° C. Hold for 20 seconds
40 cycles of:
  95° C. for 3 seconds
  60° C. for 30 seconds (* Acquisition in this stage)
A ramp rate of 2.63° C./second was used across the entire run.

Once all runs were complete, and the CT values (number of PCR cycles required for the fluorescent signal to cross the threshold) were obtained, and the amount of DNA per well (ng per reaction) was interpolated using GraphPad Prism software using a standard curve. These interpolated DNA amounts were then normalized to DNA concentration by deriving the percent of the total DNA represented by the Target DNA, using the following formula: (Interpolated DNA[ng]/((Total Qubit Concentration[ng/µl]*2 ul))*100.

Figure 72A:
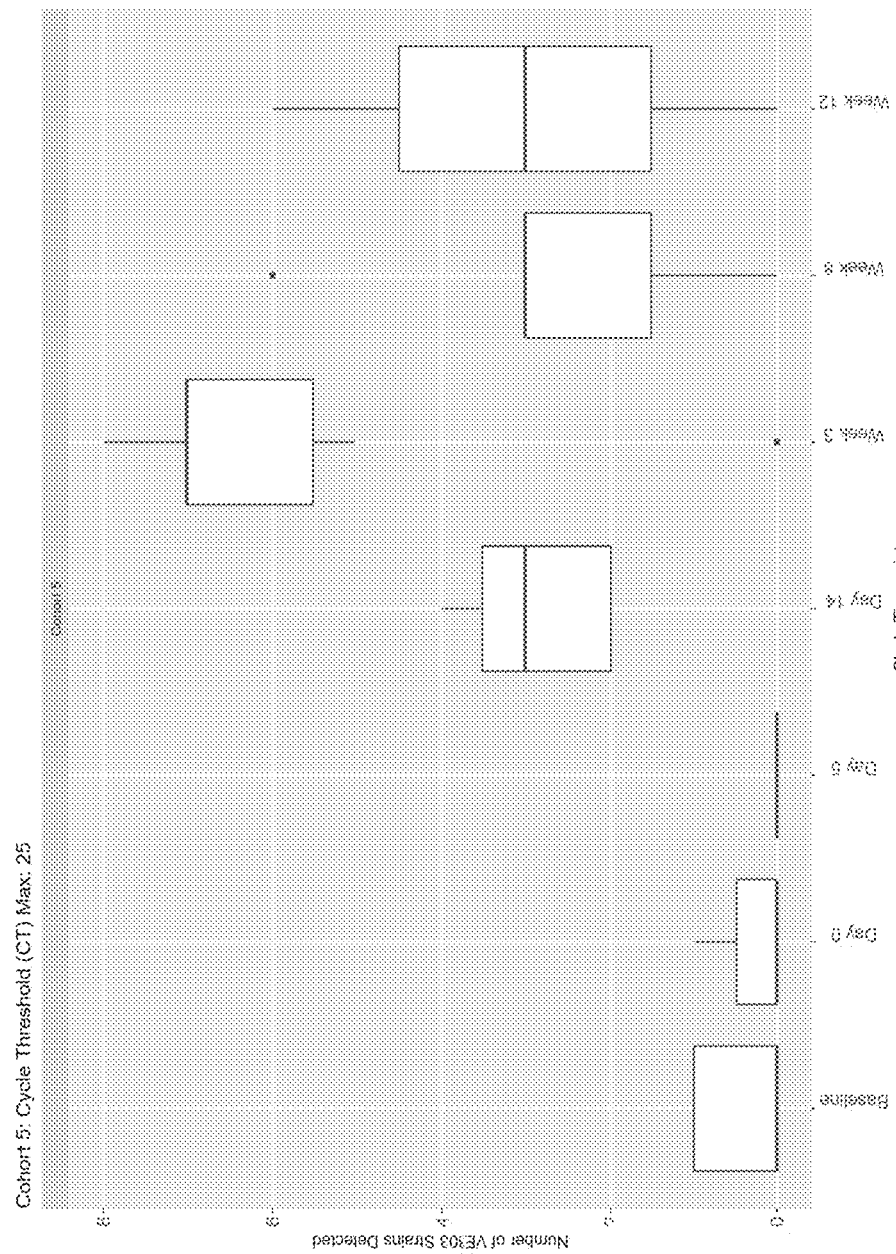
FIGS. 72A-72C show the number of VE303 strains detected in fecal samples from individuals in a cohort at the indicated time-point following administration of the bacterial composition.
Figure 72B:
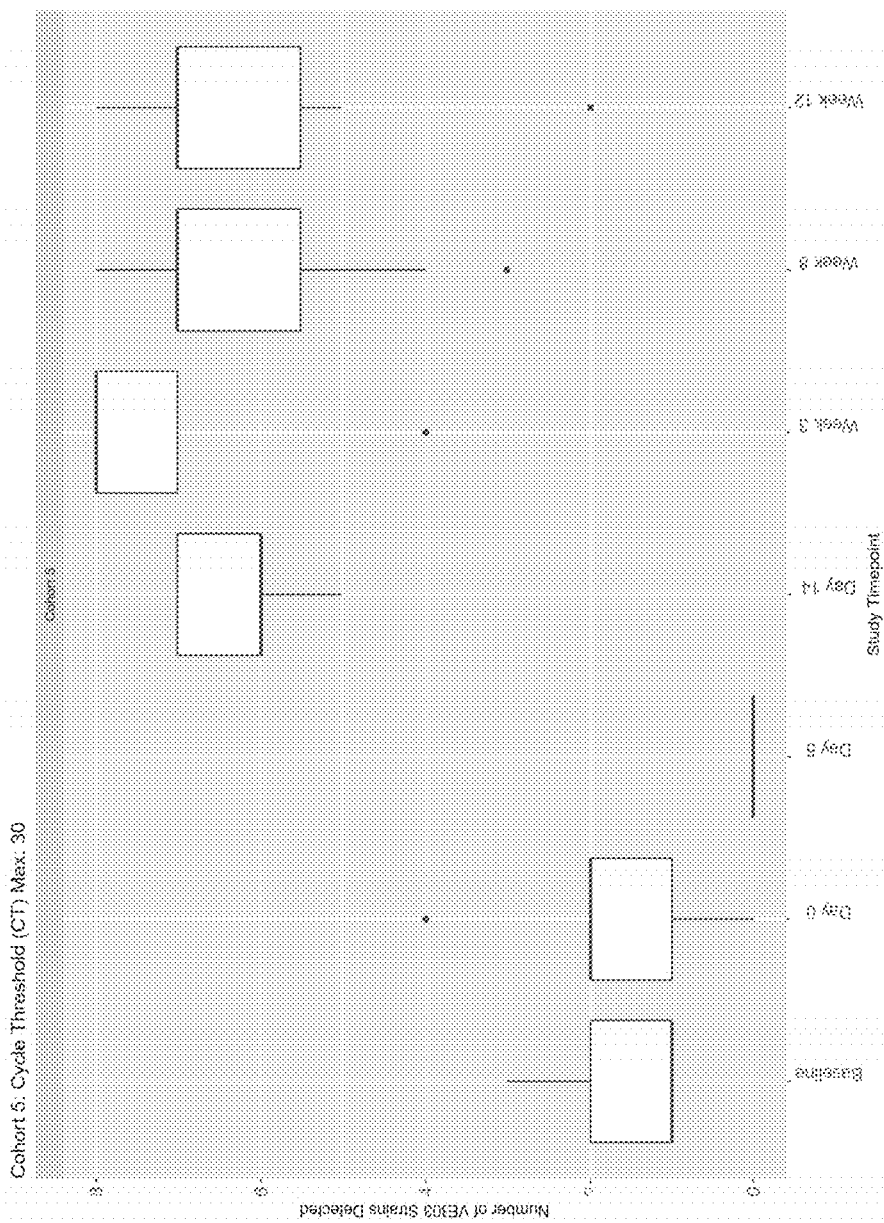
Figure 72C:
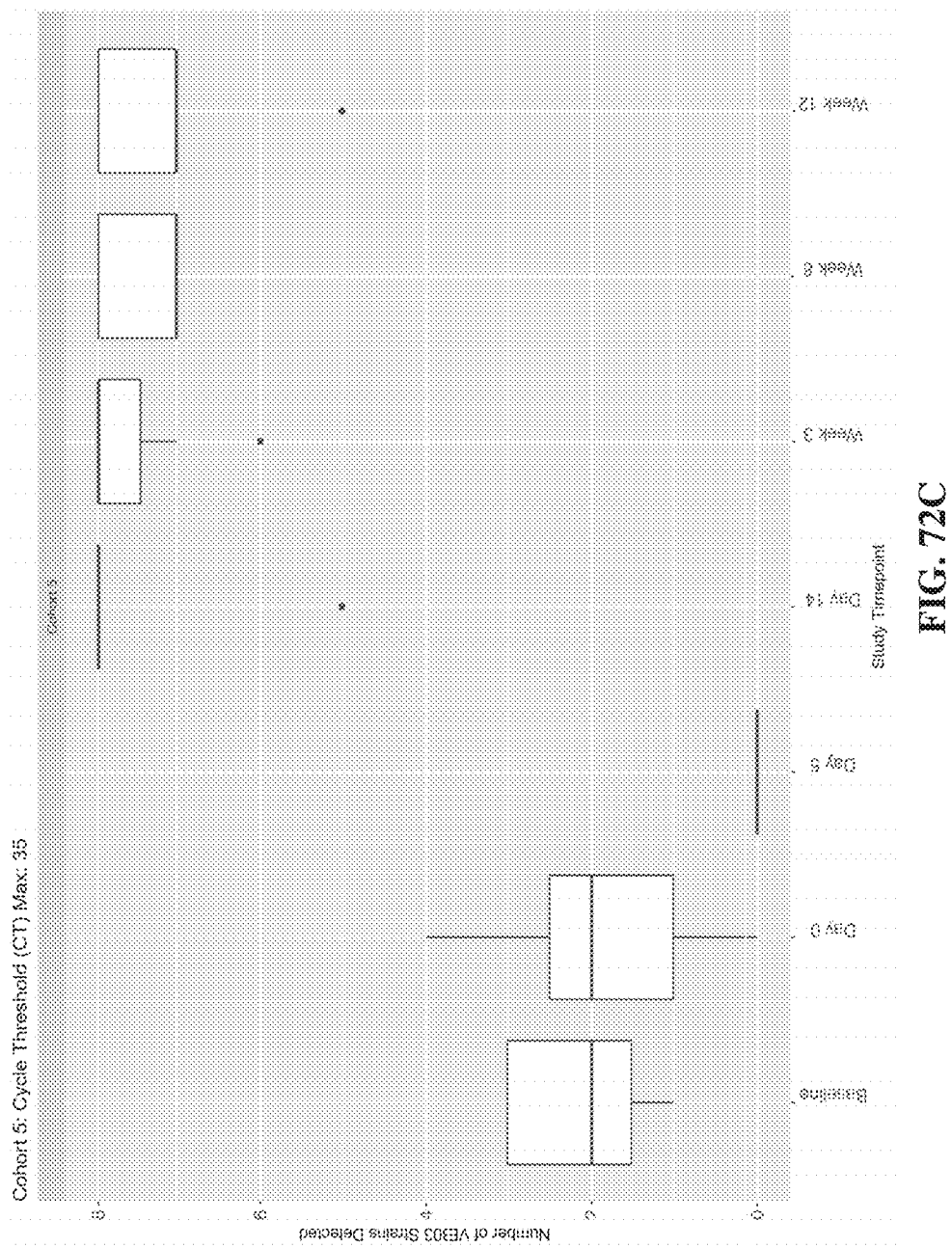
Figure 73A:
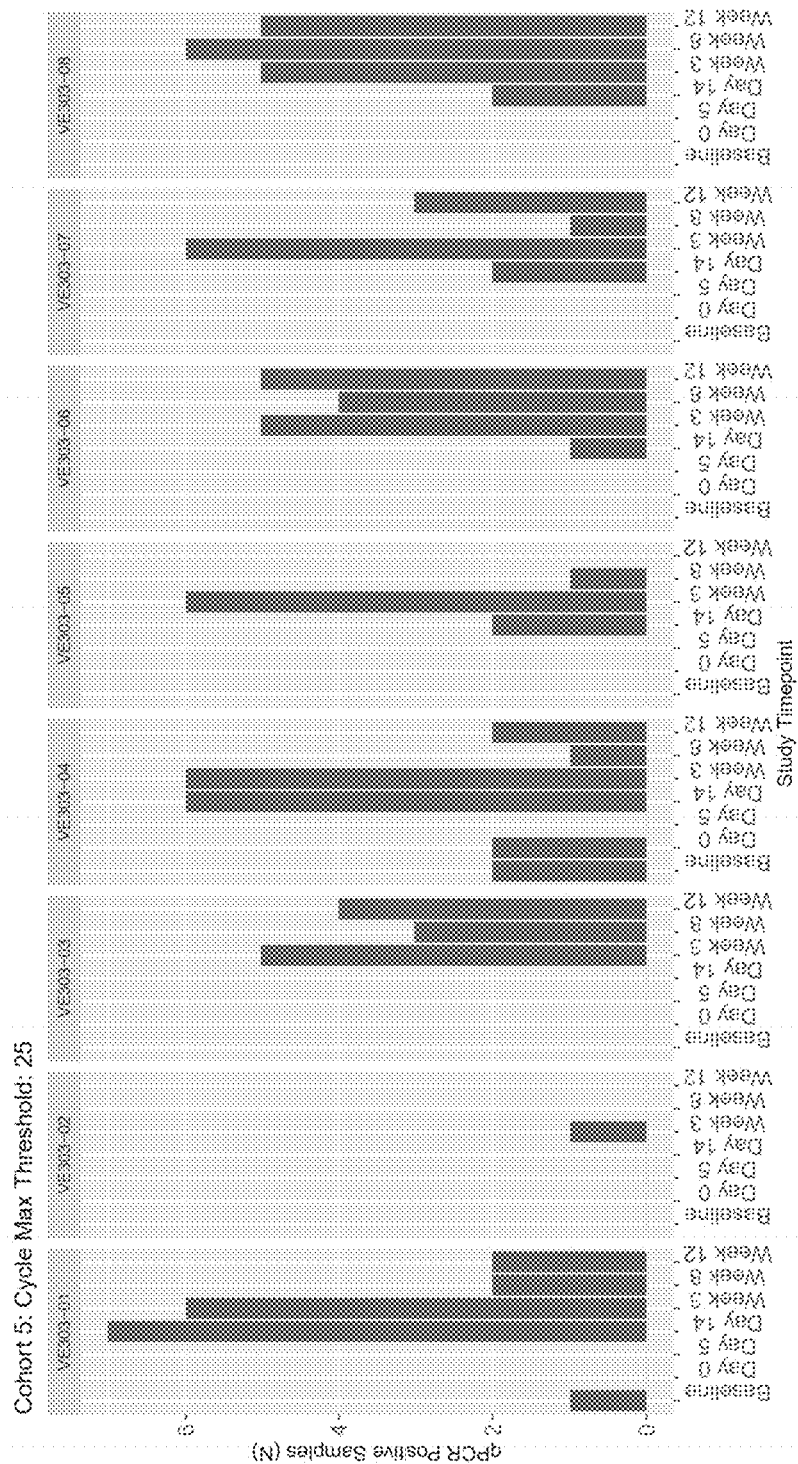
FIGS. 73A-73C show the number of qPCR positive samples for each strain in composition VE303 strains detected in fecal samples from individuals in a cohort at the indicated time-points following administration of the bacterial composition.
Figure 73B:
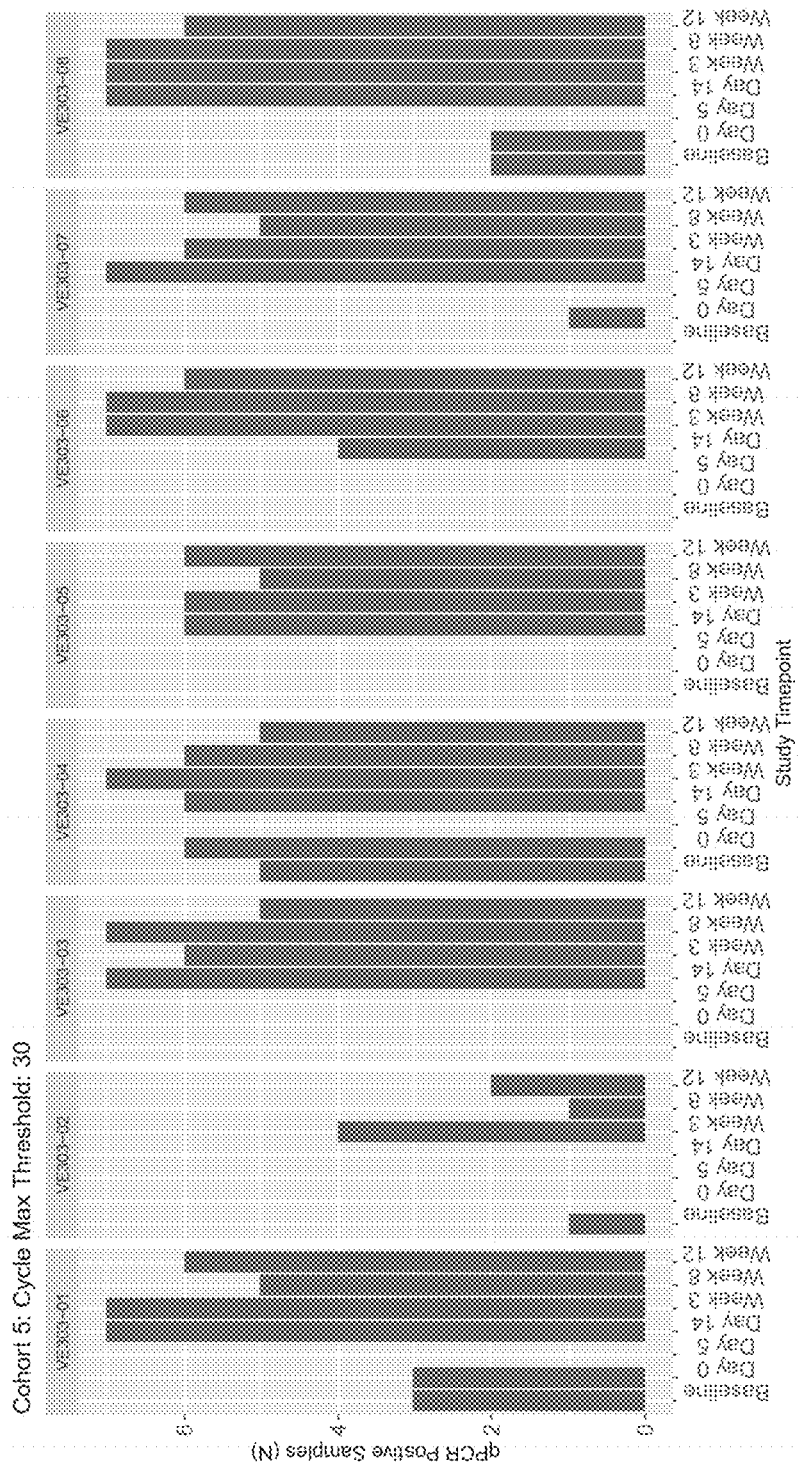
Figure 73C:
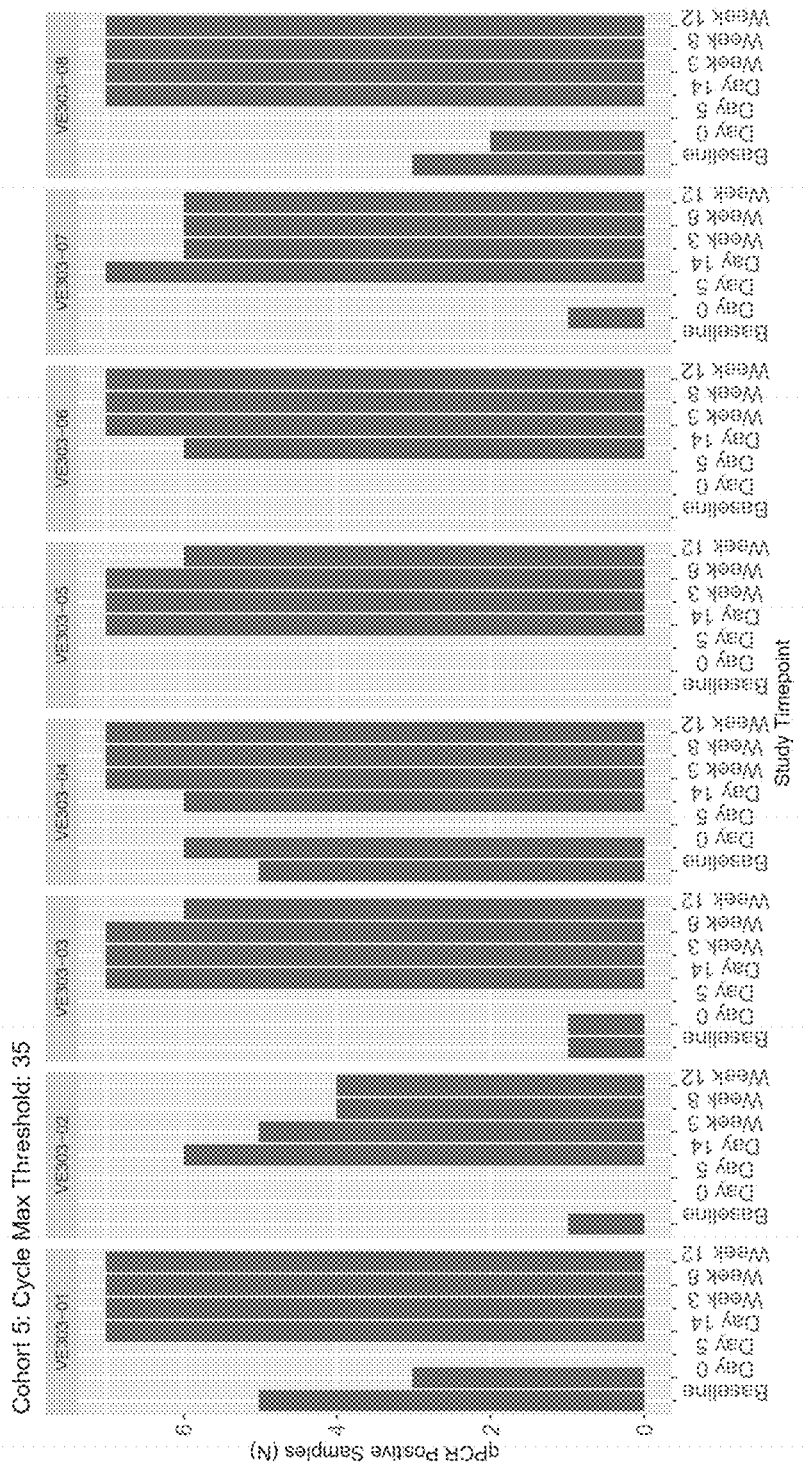

The number of VE303 strains detected per individual were evaluated at each of PCR cycles 25, 30, and 35. FIGS. 72A-72C. The number of qPCR samples that were positive for each of the VE303 strains was also determined at each time point, also at each of PCR cycles 25, 30, and 35. FIGS. 73A-73C. Detection at cycle 30 was selected for analysis based on level of detection and low false positive rate.

Example 15: Pharmacokinetics and Pharmacodynamics of VE303 in Normal Healthy Volunteers Alterations of the bacterial microbiome in the human intestine, such as reduced diversity and lower abundance of commensal organisms, are associated with infections by opportunistic pathogens like Clostridioides difficile (C. difficile). Current microbiome-based treatments aimed at restoring a diverse microbiota, such as fecal microbiota transplant (FMT), have demonstrated reduction in the rate of C. difficile recurrence. However, FMT and similar approaches that require the transfer of a large fraction of mostly uncharacterized fecal matter from a donor are inherently variable by nature, poorly defined and have the potential to transmit infectious agents. Although overall changes in the microbiome as a result of FMT have been reported, it is not practical to measure the link between the administered fecal microbiota and the resulting microbiome changes.

A live biotherapeutic product (LBP), called VE303, has been developed for the prevention of C. difficile recurrence (rCDI). The VE303 consortium is a rationally-designed therapeutic that consists of 8 clonal strains of Clostridium. The strains were isolated from the fecal matter of healthy volunteers, fully characterized, and grown individually under GMP conditions. A Phase 1a/1b, dose-escalating study has been initiated to assess the safety, tolerability, and colonization of VE303 in healthy volunteers. Herein, a novel bioinformatic method is described for determining pharmacokinetics and pharmacodynamics of a live biotherapeutic product (LBP) and demonstrate conditions where the strains durably and robustly colonize the human gut. The VE303 strains rapidly increase in abundance after they are administered and are readily detected at least 1 year after administration of the consortium. Strain colonization required displacement of related commensal microbes via pre-treatment with an antibiotic and daily administration of the consortium for upwards of 14 days, a protocol unachievable by FMT. An evaluation of the microbiome recovery post-antibiotics indicated that VE303 administration promoted the recovery of Bacteroidetes species and reduced Proteobacteria. Additionally, VE303 administration was found to significantly enhance the recovery of a number of Short-Chain Fatty Acids and the biotransformation of a subset of primary into secondary bile acids post-antibiotics. Collectively, these data demonstrate for the first time that LBPs are a safe alternative to FMT that can durably colonize the gut and modulate the microbiota of human recipients.

Given its complexity and comprehensive role in the maintenance of health, the human microbiota has provided a myriad of microbiome-based therapeutic modalities for the prevention or treatment of pathologies or infections associated with altered gut homeostasis. Nonetheless, we are as yet to observe a pharmacological evaluation of these modalities through investigational studies that define the pharmacokinetics (PK) and pharmacodynamics (PD). Microbiome-based modalities include fecal microbiota transplantation (FMT), that involves the transfer of fecal material by nasoduodenal tube or rectal enema, nutraceutical probiotics, and live biotherapeutic products (LBPs) that involve the administration of a single or many live microbial strains. Whilst being increasingly popular in recent years, there is little evidence to support the efficacy of nutraceutical probiotics or their role in compositional or functional microbiome modulation or in treating recurrent *Clostridioides difficile* infection (CDI; formerly *Clostridium difficile*). Clinical experience with FMT indicates that the procedure can be effective against treating rCDI. However, FMT is limited by the need to screen healthy donors for transmissible agents and this procedure lacks standardization, as evidenced by recent deaths associated with the delivery of multidrug resistant organisms (MDROs) by FMT. Conversely, the use of LBPs may offer several advantages including the standardized, scalable production of microbial strains containing no antimicrobial resistance genes or virulence factors. In addition, stable engraftment can offer a long-term treatment option delivering physiological concentrations of metabolites directly to other members of the microbiota or the host or promote the recovery of resident microbial taxa. Regardless of the modality, there is a need for increased scrutiny and rigorous evaluation of microbiome-based therapies to thoroughly establish their safety, optimal dosing strategies and predict outcomes on the microbial community and host health.

Here, a "road map" is provided to determine PK and PD for live microbial consortia-based therapies. A Phase 1 study is performed as part of an investigational new drug (IND) in normal healthy volunteers (NHVs) to establish the safety of a microbial consortium and to define PK and PD methods. The VE303 drug product was manufactured using standardized, scalable processes compliant with current good manufacturing practice (GMP) regulations and delivered in a lyophilized form. VE303 is an LBP consisting of 8 well characterized, non-genetically engineered, clonally-derived, nonpathogenic, nontoxigenic, commensal strains of Clostridia. It was developed to prevent the recurrence of CDIs. The PK and PD of the VE303 consortium was thoroughly investigated using a novel bioinformatic algorithm specifically designed to discern VE303 strains from endogenous relatives. The VE303 dose and regimen was optimized in healthy volunteers, thus, demonstrating safe, durable, and robust colonization of VE303 strains in the human gut which persisted throughout the year. VE303 also has the capacity to expedite the recovery of the resident microbial community and partial recovery of metabolites, including bile acids (BAs) and short-chain fatty acids (SCFAs), in NHVs after antibiotic induced dysbiosis.

A first-in-human Phase 1 dose-escalation study was designed to assess the safety and the tolerability of VE303 in normal healthy adult volunteers (NHV) after vancomycin (vanco)-induced shifts in gut homeostasis. The primary objective was to characterize the highest safe and well-tolerated dose regimen of VE303 for subsequent administration in a Phase 2 trial for the prevention of CDI recurrence. For this adverse events (AEs) were assessed, including GI symptoms, based on physical examinations, assessment of vital signs, and changes in the clinical laboratory measurements. Secondary objectives included an evaluation of the colonization of the intestinal microbiota with VE303 component bacteria, changes in the intestinal microbiota as a result of VE303 dosing, and metabolomic changes in stool.

Healthy volunteers (N=33) were enrolled in the study and received either oral vancomycin (125 mg every for 5 days) or vancomycin followed by VE303 at ascending doses, or VE303 at the highest dose without vancomycin pretreatment (total dose range $1.6 \times 10^9$ to $1.1 \times 10^{11}$ CFUs) (FIG. 44). Vancomycin was chosen as it is routinely administered as a first line treatment of CDI. One volunteer was withdrawn from the study after completion of the vancomycin course because of an inability to swallow capsules without chewing. Adverse events were observed in 85% of subjects in the study. Adverse events attributed to either vancomycin or VE303 were observed in 50% of vancomycin-treated subjects and in 35% of VE303-treated subjects. VE303-related AEs were all Grade 1 and transient. Most of these AEs were gastrointestinal in nature and included abdominal distention, diarrhea, soft feces, alanine aminotransferase/aspartate aminotransferase (ALT/AST) increase, discolored or hard feces, constipation, abdominal discomfort or pain, dysgeusia, nausea, and flatulence. The most common Grade 2-3 laboratory abnormalities were increased cholesterol, blood in urine, and increased stool lipase and amylase.

A novel bioinformatic method was developed that enables the differentiation of the VE303 consortium member strains from highly related, endogenous taxa (described in Methods). The detection of these strains and their differentiation from related endogenous strains in stool presented substantial hurdles in accurately determining VE303 PK in the human gut, especially since all 8 strains share greater than 98% average nucleotide identity (ANI) to their nearest relative. The detection of VE303 strains in stool metagenomes utilized unique 50 bp genomic markers and assessment of the depth of marker recovery (the number of sequence reads matching any marker divided by the total number of markers for each strain) and the coverage of marker recovery (the number of markers with >=1 matching read, divided by the total number of markers for each strain). A strain was considered "Detected" when the mean marker depth exceeded 0.1× and the coverage of markers detected exceeded a minimum threshold of two standard deviations below the mean expected from a multinomial distribution (with 25% zero inflation to account for marker dropout) (FIG. 51). The 0.1× mean marker depth threshold was standard for all 8 strains, however strain detection events were evaluated post-hoc by comparing subjects with and without VE303 administration for added confidence. A strain was determined as "Probable", "Insufficient data", or "Not detected" based on less confident marker coverage or depth thresholds (see Methods). The abundance of each strain and of resident bacterial taxa was determined using the One Codex software (onecodex.com) and a proprietary database of genomes assembled by One Codex in combination with bacterial genomes corresponding to bacterial isolates from healthy human stool samples was generated. These methods were validated as described in the Supplemental Information.

Stool samples were collected longitudinally for each healthy volunteer to determine the baseline microbiome composition, the microbiome after vancomycin administration, and the prevalence and abundance of the VE303 consortium members after LBP administration by metagenomics sequencing (FIG. 49). Each stool sample was sequenced at a target depth of >4 gigabases on the Illumina NextSeq platform (an average of $4.4 \times 10^7 +/- 1.1 \times 10^7$ reads) and VE303 strain PK was determined. VE303 strains were detected at very low abundance in some subjects at baseline timepoints and in the vancomycin cohort (FIG. 50). A comparison of the mean marker depth and proportion of markers for "Detected" strains in the vancomycin cohort and VE303 cohorts indicated that the strains categorized in the vancomycin cohort have reduced genome coverage and are either close relatives of the VE303 strains or are detected at low abundance (FIG. 51). Strains classified in VE303 administered subjects had a considerably higher proportion of markers detected and at a greater depth.

These distinguishing features enabled us to determine the PK of the consortium member strains in VE303 administered subjects due to increased confidence that detected strains are very likely LBP consortia members and not close relatives. In subjects dosed with VE303 following vancomycin administration (Cohorts 1-5), the VE303 component strains were rapidly detected within the first 24-48 hours after VE303 administration and they considerably expanded in abundance (FIG. 45). After vancomycin and a single dose of VE303 (Cohorts 1-3), a median of 33.3% to 66.6% of the strains were detected per subject on day 8 (2 days after the start of VE303) (FIG. 45A) There was considerable variability among individuals receiving a single dose of VE303, but the LBP component strains were detected immediately after VE303 administration in all subjects. Notably, all 8 strains were detected in Cohort 1 subject 059, which suggests robust colonization is achievable even with a single, low dose of VE303 under favorable microbiome conditions (FIG. 50). There was no dose response in the number of VE303 strains detected among the single ascending dose cohorts (Cohorts 1-3); however, the microbiome conditions appeared to be the most favorable in Cohort 1 subjects, as indicated by the greater total VE303 strain abundance in these subjects compared to Cohorts 2 and 3 (FIG. 45B).

In comparison to the single dose cohorts, multiple days of VE303 administration after vancomycin (Cohorts 4-5) resulted in a more robust and consistent strain detection. The median percentage of VE303 strains detected per subject on day 14 was between 91.6-100% (FIG. 45A), with 3 of 6 subjects in Cohort 4 and all 8 subjects in Cohort 5 being colonized by all members of the VE303 consortium at more than one timepoint (FIG. 50C). The total abundance of VE303 strains was highest in Cohort 5 at both acute and late timepoints, indicating that multiple days of LBP administration is needed to achieve the most robust and durable PK (FIG. 45A). The data also indicates that despite multiple days of VE303 dosing, vancomycin administration was necessary for VE303 strains to colonize healthy volunteers (FIG. 45, Cohort 6), suggesting that resident *Clostridium* strains limited VE303 strain colonization. Importantly, when vancomycin was used to reduce bacterial diversity and VE303 was administered over multiple days, the LBP strains were able to rapidly, robustly, and durably colonize subjects for at least 1 year. In the cohorts with the greatest colonization (Cohorts 1, 4, and 5), the relative abundance of VE303 strains expanded within the first few days after the start of VE303 dosing to 9.5-19.5% of the total microbiome (FIG. 45B) and reached upwards of 60% of the total microbiota in one subject (FIG. 51). After this initial expansion, the relative abundance of the VE303 strains declined to 1.6-4.6% of the total microbiome at 1 year. These data coupled with clinical observations clearly demonstrate that under optimal microbiome and dosing conditions, the VE303 consortium strains are safe and able to robustly and durably colonize the human gut for at least 1 year.

The metagenomics data collected at baseline, after vancomycin administration, and during the recovery phase both in the presence and absence of VE303 strains were used to assess the dynamics of the stool microbiota in healthy volunteers and the role of VE303 in the recovery from antibiotic-induced shifts in homeostasis. As expected, the baseline microbiota had high diversity (FIG. 52) and was dominated by Bacteroidetes and Firmicutes species in all subjects (FIG. 46A). Vancomycin administration greatly reduced the bacterial biomass (FIG. 54) and diversity (FIG. 53) and led to a shift in the composition of the microbiota, indicated by the reduced Bacteroidetes and Firmicutes and the expanded Proteobacteria (FIG. 46A). Notably, the post-vancomycin microbial community of healthy volunteers resembled the community of rCDI subjects[2] (and unpublished observations). We observed that the microbial community of healthy volunteers only given vancomycin recovered to baseline levels of Bacteroidetes and Firmicutes species within 1 month of being given antibiotics (FIG. 53). The diversity of the microbiota recovered to baseline levels within 12 weeks in cohorts 1-3 and partially recovered in cohorts 4-5 (FIG. 53). These community-level observations are consistent with our clinical safety observations. The recovery of Bacteroidetes and Proteobacteria species to baseline levels occurred within 1 week in subjects that were given higher doses of VE303 (FIGS. 46A and 46C). No significant microbial community changes were observed in the absence of vancomycin (FIG. 46A, Cohort 6).

To quantify the overall microbiota health, we calculated the ratio of bacterial classes that were dominant at baseline (Bacteroidia, Clostridia, Actinobacteria, and Coriobacteriia) to the bacterial classes that were dominant after vancomycin and often associated with disease (Bacilli, Gammaproteobacteria, and Negativicutes) (FIG. 54) (rebiotix.com/scientific-evidence/microbiota-restoration-therapy-posters/microbiome-rehabilitation-biomarkers-clostridium-difficile-infections-prototype-microbiome-health-index/). This "microbiome index" (MI), was high at baseline, significantly reduced by vancomycin administration, and recovered to baseline levels within 1 month in subjects only receiving vancomycin (FIG. 46B). However, in subjects receiving multiple doses of VE303 the MI increased within 1 week of LBP administration (FIG. 46B) and this increase in MI was dose-dependent (FIG. 46D). A similar trend was observed during the late recovery phase with subjects receiving VE303 effectively recovered to baseline levels (FIG. 46D).

No changes in the MI were observed in subjects receiving VE303 in the absence of vancomycin pretreatment (FIG. 46B), which is consistent with the clinical safety results. These data suggest that not only does VE303 rapidly colonize the gut but also promote the partial recovery of the microbial community, suggesting that it would boost resistance to pathogens, like *C. difficile*, after antibiotic therapy.

To determine the effect of vancomycin on bile acid concentrations and measure the PD of VE303, primary and secondary bile acid concentrations were measured in the stool of subjects at baseline, during vancomycin administration, and during the recovery phase after vancomycin with and without VE303 administration. Sample collection hurdles limited the metabolite profiling to periods of acute recovery post vancomycin in all cohorts. Bile acids are traditionally considered important in the digestion of fats, however there is growing evidence for a broader role of secondary BAs in promoting gut health and inhibiting CDI. Primary BAs (Cholic Acid and Chenodeoxycholic Acid) and the glycine and taurine conjugated forms (Glycocholic Acid, Taurocholic Acid, Glycochenodeoxycholic Acid, and Taurochenodeoxycholic Acid) were detected at low concentrations at baseline and make up a small fraction of the total BA pool in the stool (FIG. 47A). Most of the BA pool at baseline consisted of deconjugated secondary BAs including Deoxycholic Acid, Lithocholic Acid, and Ursodeoxycholic Acid. Vancomycin treatment led to an increase in the proportion of primary BAs and a decrease in deconjugated secondary BAs. This observation is consistent with vancomycin-mediated elimination or reduction of bacterial species capable of promoting the deconjugation and the biotransformation of primary BAs. After vancomycin treatment and as the microbial community recovered, we observed little recovery in the BA pool in subjects only receiving vancomycin. This recovery was incomplete on day 9 when the final sample was collected. Notwithstanding the limited sampling, in subjects receiving multiple doses of VE303 (Cohorts 4 and 5), we observed increases in the levels of deconjugated secondary BAs by 0.5 to 2-logs in some subjects (FIG. 47C).

To quantify the overall change in BAs, the ratio of deconjugated secondary BAs (dominant at baseline) to primary BAs (elevated by vancomycin) was calculated. The "bile acid index" (BAI), was high at baseline, then drastically reduced by vancomycin administration and demonstrated few signs of recovery in subjects only receiving vancomycin during the sampling period (FIG. 47B). However, in subjects receiving multiple doses of VE303 (Cohorts 4 and 5), we observed an increase in the BAI within 1-2 weeks of VE303 administration (FIG. 47B). No changes in the overall BA profile (FIG. 47A) or BAI (FIG. 47B) were observed in subjects only receiving VE303. These data suggest that higher doses of VE303 can promote the early recovery of the BA pool.

Linear mixed effects modeling was developed to determine if BA abundances were altered by vancomycin and if VE303 abundance significantly affected their post-antibiotic recovery. Antibiotic administration was associated with a significant increase in the abundance of each primary BA and a significant decrease in the abundances of secondary BAs including Lithocholic Acid and Deoxycholic Acid as compared to baseline levels. Conversely, the total abundance of VE303 was associated with a significant decrease in the abundances of most primary BAs (with the exception of Taurocholic Acid and Taurodeoxycholic Acid). VE303 abundance was also associated with the post-vancomycin recovery of Lithocholic Acid, Deoxycholic Acid, and Ursodeoxycholic Acid.

Linear mixed effects modeling was also performed to predict changes in the relative abundance of secondary BA coding genes in response to vancomycin treatment and/or VE303 administration (FIG. 56). These changes were measured after mapping sequence reads to a custom secondary BA biosynthesis enzyme database. Vancomycin treatment reduced the abundance of several BA metabolism genes including bile salt hydrolases (BSHs), genes in the BA induced (bai) operon, and 3/7-hydroxysteroid dehydrogenases (HSDHs). These secondary BA-biosynthesis genes are largely observed in anaerobes such as Clostridia and Eggerthella whose relative abundances were also negatively impacted by vancomycin treatment. During vancomycin treatment we observed an increase in 7-HSDH genes encoded by Proteobacteria such *E. coli* and *Klebsiella*, an observation that was also consistent with their expansion. Conversely, VE303 administration is positively associated with the enhanced recovery of BSH genes, bai operon genes, and 3/7-HSDH genes and negatively associated with the reduction of Proteobacteria encoded 7-HSDH genes.

Random forest regression (RFR) was chosen to decouple the effects of individual VE303 consortium members and the resident bacterial species on BA recovery after vancomycin administration. RFR was chosen as it does not assume any underlying model structure, and because it performs implicit feature selection, thus allowing us to determine the best contributors to each metabolite's abundance from a large pool of possible predictors. RFR identified several VE303 strains as among the top 20 most important taxa influencing BA recovery (FIG. 47D). Specifically, primary BAs (both conjugated and unconjugated) gradually decrease in abundance over time after vancomycin is withdrawn and RFR indicated that VE303 strains are among the top 20 most important taxa associated with this decline (FIG. 47D, FIG. 55). RFR also indicated that VE303 strains were associated with the observed increase in secondary BAs (FIG. 76D, FIG. 55). The role of VE303 was more consistent in the recovery of Ursodeoxycholic Acid, which is the biproduct of an epimerization reaction of Chenodeoxycholic Acid.

To determine the effect of vancomycin and VE303 on SCFA concentrations, SCFAs were measured in the stool of subjects at baseline, during vancomycin administration, and during the recovery phase after vancomycin with and without VE303 (FIG. 48A). Microbiome-produced SCFAs are known to positively affect host physiology in the gut by promoting gut barrier function as well as in peripheral tissues, by providing anti-inflammatory, antitumorigenic, and antimicrobial functions. Reduction in SCFA levels and in the abundance of SCFA-producing bacteria have been associated with several autoimmune, allergic, and metabolic diseases. Linear mixed effect modeling was performed to determine if SCFAs were altered by vancomycin and if total VE303 abundance significantly affected their post-antibiotic dynamics. All measured SCFA levels (with the exception of Hexanoate) were reduced by vancomycin treatment and remained below baseline levels in the absence of VE303 (FIG. 48B). More importantly, all SCFA levels affected by vancomycin were also found to increase in response to VE303 administration suggesting a beneficial role of VE303 in SCFA recovery.

RFR was performed to decouple the effects of VE303 strains from that of the recovering microbiota on SCFA post-antibiotic dynamics. This analysis identified several VE303 strains as among the top 20 most important taxa associated with SCFA level dynamics. VE303 strains were associated with increases in the levels of Acetate, Butyrate, Isobutyrate, Methyl butyrate, and Isovalerate (FIG. 48C, FIG. 56). These data also indicated that commensal Bacteriodetes species were associated with the observed increase in Propionate. Taken together these data suggest that VE303 affects the recovery of SCFAs after antibiotic perturbation and is the major driver of the observed recovery.

VE303 was developed to prevent the recurrence of CDIs and have demonstrated safe, robust, and durable colonization of its strains that persisted for an entire year. The VE303 dose and regimen was optimized, thus determining the highest safe dose. It was also determined that antibiotic-mediated perturbation of the microbiota was essential for the robust colonization of VE303 strains. A novel bioinformatic approach was also developed to assess the PK and PD of VE303 strains and the changes occurring in the host microbial community, respectively. The recovery of the microbial community and the metabolic pool comprising BAs and SCFAs was also monitored to baseline levels across all cohorts. An initial dose-dependent expansion of VE303 strains followed by a steady decline to approximately 3% of the total microbiome at 1 year post administration was observed. VE303 strains were associated with the expedited recovery of Bacteroidetes and Proteobacteria to baseline levels within one week following vancomycin treatment. VE303 strains also promoted the early recovery of secondary BAs and SCFAs.

Herein, the pharmacokinetics (PK) of an LBP as the prevalence and abundance dynamics of each component strain are defined. Traditionally, PK is defined as the study of the time course of drug absorption, distribution, bioavailability, metabolism, and excretion. Unlike small-molecule drugs, the administration and dosage of an LBP does not follow these traditional PK principles, thus posing novel challenges in its definition. One formidable challenge includes the differentiation of LBP component strains from highly related, endogenous taxa also present in the gastrointestinal tract. Recent improvements in molecular techniques such as quantitative PCR (qPCR) and high-throughput sequencing technologies have enabled the reliable detection of LBP component strains within complex microbial ecosystems. Quantitative PCR is a well-established, fast, high-throughput, and potentially cost-effective molecular technique for the detection and quantification of target DNA in different matrices. Other advantages of this technique include high sensitivity as it offers a wide dynamic range for quantification and multiplexing of amplification of several targets into a single reaction. Whilst largely beneficial, designing an assay that can accurately distinguish LBP component strains from highly-related endogenous taxa constitute a substantial challenge, thus resulting in poor specificity. Moreover, as more strains and their genomic DNA are deposited in publicly available databases, developed assays may no be longer be specific to its target. Assay design is a crucial component of qPCR result interpretation, thus requiring that special care be taken to include appropriate controls. The metagenomic sequencing approach for strain detection offers several advantages over qPCR as it employs a detection panel comprising hundreds of marker sequences that span the length of the genome, thus resulting in an assay with improved specificity. It also requires no prior knowledge about the microbial diversity or composition. A detection panel comprising hundreds-to-thousands of markers can be systematically tested against all publicly available bacterial genomes and healthy human gut metagenomes to remove non-specific markers. Assay specificity can be repeatedly improved as newer versions of public datasets become available without the need to repeat and validate the assay. It is noteworthy to mention that neither methods can distinguish among viable and dead bacterial cells. To address this, multiple timepoints for up to 1 year after LBP dosing are included to demonstrate robust engraftment of VE303 strains.

Similar to PK, the pharmacodynamics (PD) of an LBP was defined as its impact on the host microbial community and metabolites. Traditionally, PD is the study of the biochemical, physiologic, molecular effects of drugs on the body. As the VE303 drug product was designed for the prevention of CDI recurrence, we measured the rate of change in the gut microbiota as well as the rate of recovery of the gut microbiota and key, beneficial metabolites including BAs and SCFAs to baseline levels following vancomycin-mediated perturbation and/or VE303 administration. It should be noted that vancomycin is routinely administered to CDI patients and is known to emulate the microbiota of CDI patients by depleting host beneficial bacteria, lowering diversity and thereby altering the metabolic state. For other microbiome-mediated clinical indications such as food allergy or response to cancer immunotherapy, it would be important to customize the PD readouts to fit the indication. Unlike PK, assessing the PD of an LBP requires whole microbial community analyses. In addition to the PK readout, metagenomic sequences also offer an insight into the taxonomic composition and functional potential of an entire microbial community. Importantly, it allows us to examine changes in the relative abundance of important pathways and genes such as antimicrobial resistance genes, virulence factors, and bile acid transformation genes that may occur after vancomycin administration and/or VE303 administration. 16S amplicon sequencing is an alternative approach to examine whole bacterial communities. While being more cost-efficient and simpler to analyze, 16S amplicon sequencing provides limited taxonomic resolution and is not appropriate for assessing functional potential of the microbiome.

As part of the PD, the recovery of the host microbial community was also measured and compared to baseline levels. For this, the relative abundances of key bacterial phyla including Proteobacteria and Bacteroidetes and the 'Microbiome Index' were examined. The 'Microbiome Index' is a semi-quantitative, unidimensional prototype biomarker proposed to effectively distinguish a recovered or a restored microbiota from one that is perturbed by disease or antibiotic treatment. It was designed to simplify and provide the field with a clear interpretation of LBP activity and its efficacy in restoring a disease-mediated perturbed state. Scores closer to 100.0 are indicative of complete recovery or restoration to baseline levels.

Finally, early signs of dose-dependent recovery of key, beneficial metabolites including BAs and SCFAs were observed following vancomycin and VE303 administration. The restoration of the microbial community together with the metabolic pool comprising secondary BAs represent key mechanisms for the prevention of CDI recurrence. Recent investigations have particularly built a compelling case for the central role of secondary BAs including Lithocholic Acid, Deoxycholic Acid, and Ursodeoxycholic Acid in inhibiting *C. difficile* spore germination. VE303 strains were also associated with the recovery of secondary BA producing genes and associated taxa including members of Clostridia and Eggerthella. It is also noteworthy to mention that early signs of SCFA recovery were observed. SCFAs are known for their role in promoting gut barrier integrity which in turn is crucial for the maintenance of an anaerobic environment necessary to sustain a 'healthy' microbiome. These metabolites also play an important role in lowering inflammation, thus alleviating symptoms of a CDI.

*Clostridioides difficile* infection (CDI; formerly *Clostridium difficile*) remains the most frequently reported hospital- and community-acquired infection in the developed world, with an estimated incidence of 453,000 cases and approximately 29,000 deaths in the US in 2011. A prerequisite for developing disease in all infected individuals is the disruption of the normal gastrointestinal (GI) microbiota that provides natural colonization resistance against *C. difficile* strains. Here, the development of a safe, well-tolerated LBP using novel PK and PD methods is described. A dose regimen is also established that yields robust colonization of VE303 strains for at least 1 year. Early signs of BA and SCFA recovery are observed together with the recovery of the microbiota to baseline levels, thus mirroring observations also true for the FMT procedure. A Phase 2 study is ongoing to determine efficacy (NCT03788434).

REFERENCES

1. Minot, S. S., Krumm, N. & Greenfield, N. B. One Codex: A Sensitive and Accurate Data Platform for Genomic Microbial Identification. *BioRxiv* (2015). doi:10.1101/027607
2. Smillie, C. S. et al. Strain tracking reveals the determinants of bacterial engraftment in the human gut following fecal microbiota transplantation. *Cell Host Microbe* 23, 229-240.e5 (2018).

3. Berlin, K. et al. Assembling large genomes with single-molecule sequencing and locality-sensitive hashing. *Nat. Biotechnol.* 33, 623-630 (2015).
4. Cock, P. J. A. et al. Biopython: freely available Python tools for computational molecular biology and bioinformatics. *Bioinformatics* 25, 1422-1423 (2009).
5. Lessa, F. C. et al. Burden of *Clostridium difficile* infection in the United States. *N. Engl. J. Med.* 372, 825-834 (2015).
6. Leffler, D. A. & Lamont, J. T. *Clostridium difficile* infection. *N. Engl. J. Med.* 372, 1539-1548 (2015).
7. Cohen, S. H. et al. Clinical practice guidelines for *Clostridium difficile* infection in adults: 2010 update by the society for healthcare epidemiology of America (SHEA) and the infectious diseases society of America (IDSA). *Infect. Control Hosp. Epidemiol.* 31, 431-455 (2010).
8. Kyne, L. & Kelly, C. P. Recurrent *Clostridium difficile* diarrhoea. *Gut* 49, 152-153 (2001).
9. Pothoulakis, C. Effects of *Clostridium difficile* toxins on epithelial cell barrier. *Ann. N. Y. Acad. Sci.* 915, 347-356 (2000).
10. Tonna, I. & Welsby, P. D. Pathogenesis and treatment of *Clostridium difficile* infection. *Postgrad. Med. J.* 81, 367-369 (2005).
11. Gough, E., Shaikh, H. & Manges, A. R. Systematic review of intestinal microbiota transplantation (fecal bacteriotherapy) for recurrent *Clostridium difficile* infection. *Clin. Infect. Dis.* 53, 994-1002 (2011).

Methods

Strain Genome and Stool Metagenomic Sequencing

The VE303 bacterial gDNA were sequenced on both the Illumina and Pacific Biosciences platforms. Illumina libraries were built using the TruSeq DNA PCR-Free Library Prep and sequenced on the MiSeq sequencer. Pacific Biosciences (PacBio) libraries for each of the VE303 strains were prepared using the SMRTbell Template Preparation kit and sequenced on the RS II (Pacific Biosciences, Menlo Park, CA) at the University of Maryland Institute for Genome Sciences (Baltimore, MD, USA). VE303 genome assemblies were generated using the PacBio sequences using HGAP assembler (SMRTAnalysis 2.3.0) and Celera Assembler v.8.2[3] and assessed for quality by the University of Maryland Institute for Genome Sciences bioinformatics core. Stool samples were collected fresh and approximately 250 mg was transferred to an OMNIgene-GUT tube (DNAgenotek, Ottawa, CAN) and resuspended in preservation buffer according to the manufacturer's instructions. Preserved stool suspensions were then extracted and sequenced on the Illumina NextSeq platform at DNAgenotek using standard operating procedures.

Establishment of the Strain Detection Algorithm

Unique genomic regions for each of the VE303 organisms were identified by: 1) identifying a candidate set of overlapping k-mers (k=31 bp) for each VE303 strain genome that are absent in the One Codex microbial genomes database, and 2) identifying a final set of unique genomic regions (50 base pair (bp) windows) that were not found in any other reference genome in the One Codex database, were not found in any other VE303 strain genome, and did not share a 17 bp subsequence with other candidate genomic regions. A total of 43,955 genomic regions satisfied these criteria, ranging from 1,539-10,847 per VE303 strain. This initial set of genomic regions was further refined by excluding those regions that were detected in a set of 249 healthy human stool metagenomic sequencing datasets and any regions that were recovered at a low rate in whole genome shotgun sequence datasets from pure cultures of the VE303 strains. Following this exclusivity testing step, a final set of 14,319 genomic markers were identified, ranging from 260-7,282 per VE303 strain (FIG. 63). Detection of the VE303 strains from Illumina whole genome metagenomic sequencing datasets relied on the unique genomic marker regions. Each of the 50 bp genomic regions is shorter than the sequence fragments ("reads") generated through the whole genome metagenomic sequencing process. Therefore, the unique genomic regions were detected as subsequences within any of the metagenomic reads. The unique genomic regions were considered detected if 1) the sequence fragment contained at least 1 perfect alignment >=17 bp to the target genomic region; and 2) the entire 50 bp genomic region aligned against the sequence fragment with no more than 3 mismatches. Detection of the exact 17 bp alignment was executed using a k-mer alignment approach. Sensitive alignment of the entire 50 bp genome sequence was conducted using the pairwise alignment module implemented in BioPython[4]. Each of the target genomic regions was considered present if there is at least one read in the input dataset that satisfies these criteria.

The presence or absence of each VE303 strain in each patient sample was determined by analyzing the number of unique genomic markers that were detected, as well as the relative abundance of each marker (FIG. 62). Two key metrics were used to detect each VE303 strain: 1) Depth of marker recovery: the number of sequence fragments matching any marker, divided by the total number of markers; and 2) Coverage of marker recovery: the number of markers with >=1 matching sequence fragment, divided by the total number of markers. The detection of each VE303 strain was determined as follows:

"Detected" when the mean marker depth exceeded 0.1× and the coverage of markers detected exceeded a minimum threshold of two standard deviations below the mean expected from a multinomial distribution (with 25% zero inflation to account for marker dropout).

"Probable" when the mean marker depth exceeded 0.1× and the coverage of markers detected was between 2-4 standard deviations below the mean.

"Insufficient data" when the mean marker depth fell between 0.01×-0.1×.

"Not detected" when the mean marker depth did not exceed 0.01× or the number of markers was less than four standard deviations below the expected mean.

These methods were determined to robustly and specifically detect each VE303 strain using two approaches: 1) human stool samples spiked with increasing colony forming units (CFU) of each VE303 strain prior to DNA extraction and metagenomic sequence analysis, and 2) the ability to detect the VE303 strain genomes in the original host donor stool and not in unrelated control stool samples.

Bacterial Community Abundance and Microbiome Index

The estimated relative abundance of bacterial species in the microbial community (including VE303 strains) was determined using the standard One Codex algorithm from quality filtered metagenomic sequence reads after removal of reads that map to the human host. At higher taxonomic levels (e.g. Phylum or Class level) the relative abundance was calculated for each sample as the ratio of sequence reads assigned at the desired taxonomic level (plus all reads assigned below) to the total number of assigned reads. We then calculated the absolute abundance of DNA for each species in the microbial community according to Equation (3), below:

$$\text{Abs} = RA \times \frac{DNA_{\mu g}}{\text{Stool}_{mg}} \times \frac{V_B}{V_S}. \qquad \text{Equation (3)}$$

In this Equation, RA equals estimated relative abundance of the bacterial taxa. $DNA_{\mu g}$ is the total DNA yield. $\text{Stool}_{mg}$ is the mass of stool collected (final mass of Omnigene gut tube–average weight of Omnigene gut tube). $V_B$ is the volume of buffer in the Omnigene gut tube. $V_s$ is the volume of sample in the DNA extraction.

The microbiome index was calculated according to Equation (4) using the Class-level relative abundance of sequences in each metagenomic sample, as described previously (rebiotix.com/scientific-evidence/microbiota-restoration-therapy-posters/microbiome-rehabilitation-biomarkers-*clostridium-difficile*-infections-prototype-microbiome-health-index/).

$$MI = \frac{(RA_{Bacteroidia} + RA_{Clostridia} + RA_{Actinobacteria} + RA_{Coriobacteria})}{(RA_{Bacilli} + RA_{\gamma Proteobacteria} + RA_{Negativicutes})} \qquad \text{Equation (4)}$$

$$BAI_{Stool} = \frac{(RA_{Sec.Deconj.})}{(RA_{Unconj.} + RA_{Pri.} + RA_{Sec.Conj.})} \qquad \text{Equation (5)}$$

Linear Mixed Effect Modeling to Determine Analytes Significantly Affected by Total VE303 Abundance Linear mixed effect modeling was conducted to identify how different analytes (Bile Acids and Short Chain Fatty Acids) are affected by VE303 administration according to Equation (6):

$$\text{analyte} \sim \text{Treatment} + ve303 + \left(\frac{pID}{CohortID}\right). \qquad \text{Equation (6)}$$

Here, analyte corresponds to the SCFA or BA measured density in a certain individual at a certain time point (day), Treatment is a categorical variable to describe if the measurement is taken before, during or after vancomycin treatment, and ve303 corresponds to the total abundance of VE303 (μg DNA/mg Stool) in a certain sample after vancomycin administration. For Treatment the pre-vancomycin samples are used as the baseline. Because data are repeated samples from different patients that are subdivided in different cohorts, we used patient ID (pID)/CohortID is used as nested random effect. Metabolites with p-value associated to Treatment: during—vancomycin smaller than 0.05 are considered significantly affected by vancomycin treatment. Metabolites with p-value associated to Treatment: post-vancomycin smaller than 0.05 are considered significantly affected by vancomycin post-treatment and in the absence of VE303 (e.g., only vancomycin cohort). Metabolites with p-value associated to ve303 smaller than 0.05 are significantly affected by total VE303 abundance post treatment.

Random Forest Regression to Decouple Effect of VE303 and Recovering Resident Microbiota on Metabolites Dynamics Post-VE303 Administration To determine the contribution of the different VE303 strains to the SCFAs and BAs post-vancomycin dynamics and to decouple the effect on these metabolites of VE303 strains from the one of the recovering resident microbiota, Random Forest Regression (RFR) was conducted to predict each metabolite abundance as a function of the abundance of resident bacteria and VE303 abundances (FIGS. 58 and 59). A previously-validated approach was adopted to address the repeated sampling nature of the data (See Haran J P, Bhattarai S K, Foley S E, Dutta P, Ward D V, Bucci V, McCormick B A. (2019) Alzheimer's disease microbiome is associated with dysregulation of the anti-inflammatory P-glycoprotein pathway. mBio 10:e00632-19) in which RFR is run on 100 different subsets of randomly-selected samples (after choosing one sample per individual) and repeated starting from 30 different random number seeds. Microbes (both resident bacteria and VE303) were ranked based on their permutated variable importance value across the 30×100 RFR realizations. For all the top important predictors Accumulated Local Effects (ALE) Plots were generated to determine how each metabolite is affected by change in microbial feature abundance. A regression line was fitted to the log-log transformed ALE plots, and the results are summarized as a clustered heatmap of these inferred coefficients.

---

The invention claimed is:

1. A method for treating or preventing *Clostridium difficile* infection in a subject, comprising
administering vancomycin to the subject, and
administering to the subject a therapeutically effective amount of a pharmaceutical composition comprising a purified bacterial mixture, the purified bacterial mixture comprising:
(i) a bacterial strain comprising a 16S rDNA sequence with at least 99% sequence identity to the nucleotide sequence of SEQ ID NO: 1;
(ii) a bacterial strain comprising a 16S rDNA sequence with at least 99% sequence identity to the nucleotide sequence of SEQ ID NO: 2;
(iii) a bacterial strain comprising a 16S rDNA sequence with at least 99% sequence identity to the nucleotide sequence of SEQ ID NO: 3;
(iv) a bacterial strain comprising a 16S rDNA sequence with at least 99% sequence identity to the nucleotide sequence of SEQ ID NO: 4;
(v) a bacterial strain comprising a 16S rDNA sequence with at least 99% sequence identity to the nucleotide sequence of SEQ ID NO: 5;
(vi) a bacterial strain comprising a 16S rDNA sequence with at least 99% sequence identity to the nucleotide sequence of SEQ ID NO: 6;
(vii) a bacterial strain comprising a 16S rDNA sequence with at least 99% sequence identity to the nucleotide sequence of SEQ ID NO: 7; and
(viii) a bacterial strain comprising a 16S rDNA sequence with at least 99% sequence identity to the nucleotide sequence of SEO ID NO: 8,
wherein the vancomycin is administered in multiple doses prior to administering the pharmaceutical composition; wherein the pharmaceutical composition is administered in multiple doses, and wherein a total of at least $4.0 \times 10^{10}$ CFUs (colony forming units) or $1.1 \times 10^{11}$ CFUs of bacteria are administered to the subject.

2. The method of claim 1, wherein the multiple doses comprise administering the pharmaceutical composition to the subject at least 4 times and/or wherein the multiple doses are administered at regular intervals.

3. The method of claim 1, wherein the multiple doses of the pharmaceutical composition comprise a total of at least $4.0 \times 10^{10}$ CFUs of bacteria and are administered in five doses.

4. The method of claim 1, wherein the multiple doses of the pharmaceutical composition comprise a total of at least $1.1 \times 10^{11}$ CFUs of bacteria and are administered in fourteen doses.

5. The method of claim 1, wherein each of the multiple doses of the pharmaceutical composition is administered on consecutive days.

6. The method of claim 1, wherein each of the multiple doses is administered in 10 capsules comprising the pharmaceutical composition.

7. The method of claim 1, wherein the method is for preventing recurrence of *C. difficile* infection.

8. The method of claim 1, wherein the purified bacterial mixture consists of the bacterial strains of (i)-(viii).

9. The method of claim 1, wherein the vancomycin is administered at 500 mg per day or 250 mg per day.

10. The method of claim 9, wherein the vancomycin is administered in 4 doses of 125 mg per day or 2 doses of 125 mg per day.

11. The method of claim 1, wherein the vancomycin is administered on five consecutive days up to two days prior to the day of administration of the pharmaceutical composition, and wherein the method includes a washout day prior to administration of the pharmaceutical composition.

12. The method of claim 1, wherein one or more of the bacterial strains are lyophilized or spray-dried.

13. The method of claim 1, wherein one or more of the bacterial strains are in spore form and/or one or more of the bacterial strains are in vegetative form.

14. The method of claim 1, wherein each of the one or more bacterial strains are in spore form or each of the bacterial strains are in vegetative form.

15. The method of claim 1, wherein the pharmaceutical composition further comprises one or more enteric polymers.

16. The method of claim 1, wherein the administration is oral administration.

17. The method of claim 1, wherein the pharmaceutical composition is formulated for oral delivery or rectal delivery; and/or the pharmaceutical composition is formulated for delivery to the intestine, optionally for delivery to the colon.

18. The method of claim 1, wherein one or more of the bacterial strains are detected in the microbiome at least four weeks after initial administration of the pharmaceutical composition.

19. The method of claim 1, further comprising assessing colonization of one or more bacterial strains of the pharmaceutical composition in a microbiome of the subject, optionally wherein the assessing comprises:
(i) isolating nucleic acid from a sample of the microbiome of the subject;
sequencing the isolated nucleic acid to obtain a plurality of nucleotide sequences of the isolated nucleic acid; and
determining the presence of at least one bacterial strain of the bacterial composition by comparing the plurality of nucleotide sequences to a plurality of genomic markers for each bacterial strain of the bacterial composition;
wherein if a genomic marker for a bacterial strain is present in the plurality of nucleotide sequences, the microbiome is colonized with the bacterial strain; or (ii) isolating nucleic acid from a sample of the microbiome of the subject; and determining the presence of at least one bacterial strain of the bacterial composition by amplifying a nucleotide sequence of a genomic marker for the at least one the bacterial strains in the isolated nucleic acid;

wherein if a genomic marker for a bacterial strain is present in the amplified nucleotide sequences, the microbiome is colonized with the bacterial strain.

20. The method of claim 19, wherein if the genomic marker for the bacterial strain is absent in the plurality of nucleotide sequences or absent in the amplified nucleotide sequences, the method further comprises administering one or more additional doses of the pharmaceutical composition to the subject.

\* \* \* \* \*

UNITED STATES PATENT AND TRADEMARK OFFICE
CERTIFICATE OF CORRECTION

| | |
|---|---|
| PATENT NO. | : 12,161,680 B2 |
| APPLICATION NO. | : 17/268781 |
| DATED | : December 10, 2024 |
| INVENTOR(S) | : Jason Norman et al. |

Page 1 of 1

It is certified that error appears in the above-identified patent and that said Letters Patent is hereby corrected as shown below:

In the Claims

At Column 201, Claim 1, Line 46:
"SEO ID NO: 8,"
Should read:
-- SEQ ID NO. 8, --

Signed and Sealed this
First Day of April, 2025

Coke Morgan Stewart
*Acting Director of the United States Patent and Trademark Office*